United States Patent
Shoichet et al.

(10) Patent No.: US 10,702,498 B2
(45) Date of Patent: Jul. 7, 2020

(54) MU OPIOID RECEPTOR MODULATORS

(71) Applicants: THE REGENTS OF THE UNIVERSITY OF CALIFORNIA, Oakland, CA (US); FRIEDRICH-ALEXANDER-UNIVERSITÄT ERLANGEN-NÜRNBERG, Erlangen (DE); THE BOARD OF TRUSTEES OF THE LELAND STANFORD JUNIOR UNIVERSITY, Stanford, CA (US); THE UNIVERSITY OF NORTH CAROLINA AT CHAPEL HILL, Chapel Hill, NC (US)

(72) Inventors: Brian K. Shoichet, Kentfield, CA (US); Henry Lin, Dresher, PA (US); Peter Gmeiner, Buckenhof (DE); Aashish Manglik, Menlo Park, CA (US); Brian Kobilka, Palo Alto, CA (US); Bryan L. Roth, Durham, NC (US); Daniela Gisela Dengler, Erlangen (DE)

(73) Assignees: THE REGENTS OF THE UNIVERSITY OF CALIFORNIA, Oakland, CA (US); FRIEDRICH-ALEXANDER-UNIVERSITAT ERLANGEN-NÜRNBERG, Erlangen (DE); THE BOARD OF TRUSTEES OFTHE LELAND STANFORD JUNIOR UNIVERSITY, Stanford, CA (US); THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 0 days.

(21) Appl. No.: 15/743,079

(22) PCT Filed: Jun. 30, 2016

(86) PCT No.: PCT/US2016/040553
§ 371 (c)(1),
(2) Date: Jan. 9, 2018

(87) PCT Pub. No.: WO2017/007695
PCT Pub. Date: Jan. 12, 2017

(65) Prior Publication Data
US 2019/0076398 A1    Mar. 14, 2019

Related U.S. Application Data

(60) Provisional application No. 62/190,390, filed on Jul. 9, 2015.

(51) Int. Cl.
| | | |
|---|---|---|
| C07C 275/26 | (2006.01) |
| A61K 31/381 | (2006.01) |
| C07D 401/12 | (2006.01) |
| C07C 275/24 | (2006.01) |
| C07D 207/452 | (2006.01) |
| C07D 233/16 | (2006.01) |
| C07D 498/18 | (2006.01) |
| C07D 333/16 | (2006.01) |
| C07D 249/04 | (2006.01) |
| C07D 409/12 | (2006.01) |
| C07D 471/04 | (2006.01) |
| C07D 333/20 | (2006.01) |
| C07D 295/125 | (2006.01) |
| C07D 333/58 | (2006.01) |
| C07D 495/04 | (2006.01) |
| A61P 25/36 | (2006.01) |
| A61K 31/165 | (2006.01) |
| A61K 31/17 | (2006.01) |

(52) U.S. Cl.
CPC .......... *A61K 31/381* (2013.01); *A61K 31/165* (2013.01); *A61K 31/17* (2013.01); *A61P 25/36* (2018.01); *C07C 275/24* (2013.01); *C07C 275/26* (2013.01); *C07D 207/452* (2013.01); *C07D 233/16* (2013.01); *C07D 249/04* (2013.01); *C07D 295/125* (2013.01); *C07D 333/16* (2013.01); *C07D 333/20* (2013.01); *C07D 333/58* (2013.01); *C07D 401/12* (2013.01); *C07D 409/12* (2013.01); *C07D 471/04* (2013.01); *C07D 495/04* (2013.01); *C07D 498/18* (2013.01); *C07C 2602/08* (2017.05)

(58) Field of Classification Search
None
See application file for complete search history.

(56) References Cited

U.S. PATENT DOCUMENTS

| | | |
|---|---|---|
| 6,593,348 B2 | 7/2003 | Carroll et al. |
| 2005/0277674 A1 | 12/2005 | Hinze et al. |
| 2014/0288077 A1 * | 9/2014 | Fujii .................... A61K 31/535 514/237.5 |

FOREIGN PATENT DOCUMENTS

| | | | |
|---|---|---|---|
| CN | 101 823 987 B | 6/2014 | |
| WO | WO-9817636 A1 * | 4/1998 | ........... C07C 275/28 |

(Continued)

OTHER PUBLICATIONS

2010:1139374 CAPLUS.*
(Continued)

*Primary Examiner* — Heidi Reese
(74) *Attorney, Agent, or Firm* — Mintz, Levin, Cohn, Ferris, Glovsky and Popeo, P.C.; Irina E. Britva

(57) ABSTRACT

Described herein, inter alia, are compositions and methods for modulating mu opioid receptor activity.

28 Claims, 20 Drawing Sheets

(56) References Cited

FOREIGN PATENT DOCUMENTS

WO  WO-2005/090315 A1  9/2005
WO  WO-2013/068467 A1  5/2013

OTHER PUBLICATIONS

Extended European Search Report dated Jan. 2, 2019, for EP Patent Application No. 16821843.6, 6 pages.
International Search Report dated Dec. 12, 2016 for PCT Application No. PCT/US2016/040553, filed Jun. 30, 2016, 4 pages.
PubChem CID 18589025, date created: Dec. 4, 2007, date accessed: Nov. 8, 2016, 9 pages.
PubChem CID 63120296, date created: Oct. 22, 2012, date accessed Nov. 8, 2016, 10 pages.
Written Opinion dated Dec. 12, 2016 for PCT Application No. PCT/US2016/040553, filed Jun. 30, 2016, 6 pages.

* cited by examiner

| Cmpd | A | a | b | pK$_i$ (nM) | G$_i$ (Glosensor) pEC$_{50}$ | E$_{max}$ |
|---|---|---|---|---|---|---|
| 12 | -H | S,R | S,R | 7.37 ± 0.06 | 6.75 ± 0.06 | 0.88 ± 0.03 |
| (S,S)-12 | -H | S | S | 8.32 ± 0.03 | 7.19 ± 0.10 | 0.85 ± 0.04 |
| (S,R)-12 | -H | S | R | 7.34 ± 0.04 | 6.63 ± 0.27 | 0.38 ± 0.06 |
| (R,S)-12 | -H | R | S | 6.59 ± 0.03 | 6.28 ± 0.18 | 0.68 ± 0.09 |
| (R,R)-12 | -H | R | R | 7.05 ± 0.03 | 5.51 ± 0.45 | 0.82 ± 0.48 |
| (S,S)-21 | -OH | S | S | 8.97 ± 0.03 | 8.34 ± 0.07 | 0.76 ± 0.02 |
| (S,R)-21 | -OH | S | R | 8.02 ± 0.03 | 9.92 ± 0.26 | 0.18 ± 0.02 |
| (R,S)-21 | -OH | R | S | 6.12 ± 0.07 | 6.28 ± 0.14 | 0.63 ± 0.07 |
| (R,R)-21 | -OH | R | R | 6.07 ± 0.07 | 5.88 ± 0.24 | 0.53 ± 0.13 |

FIG. 4 - cont.
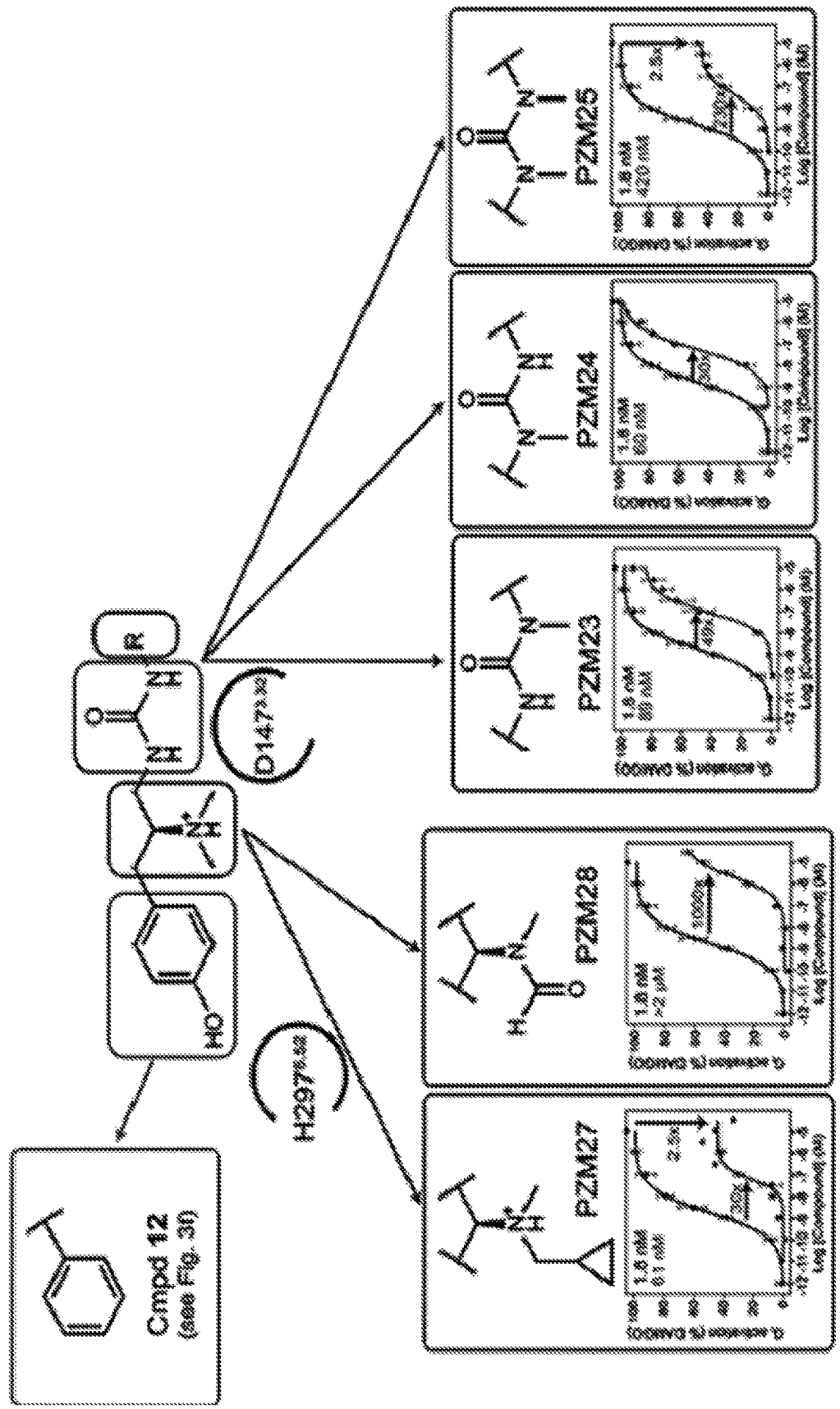

FIG. 5 - cont.
Agonist mode
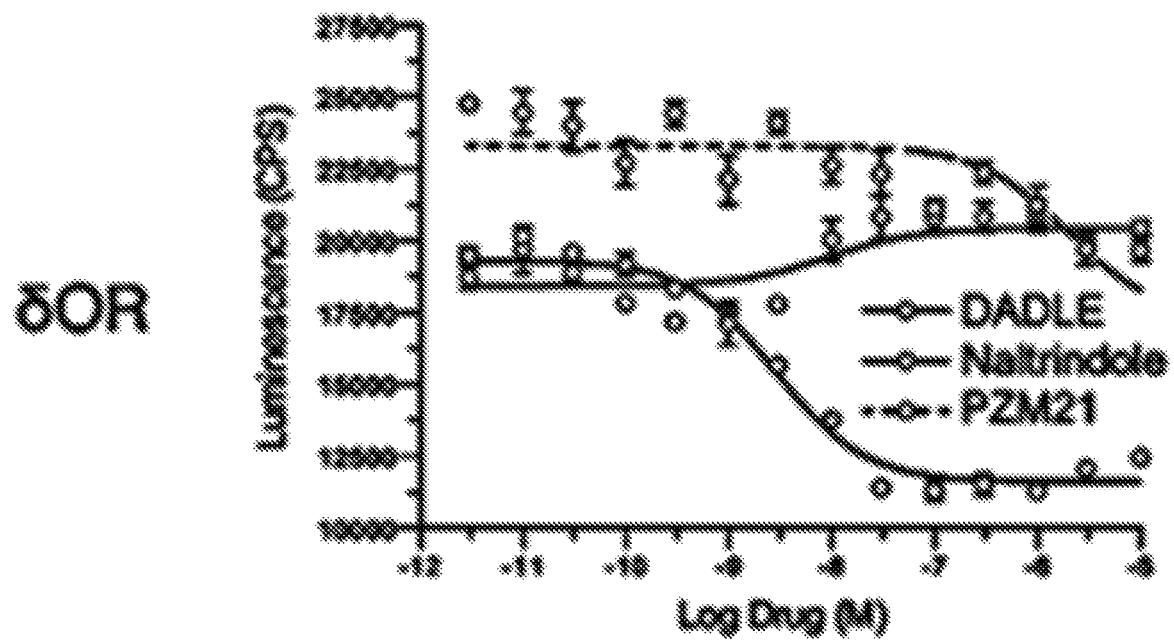
Antagonist mode
(+ 50 nM agonist)
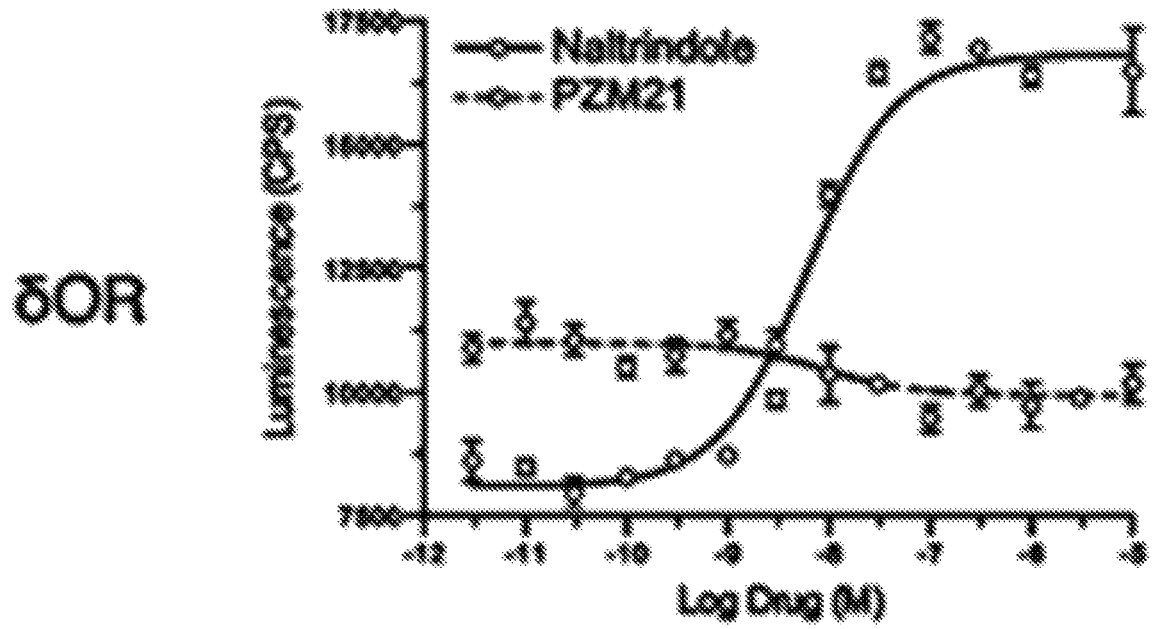

FIG. 5 - cont.
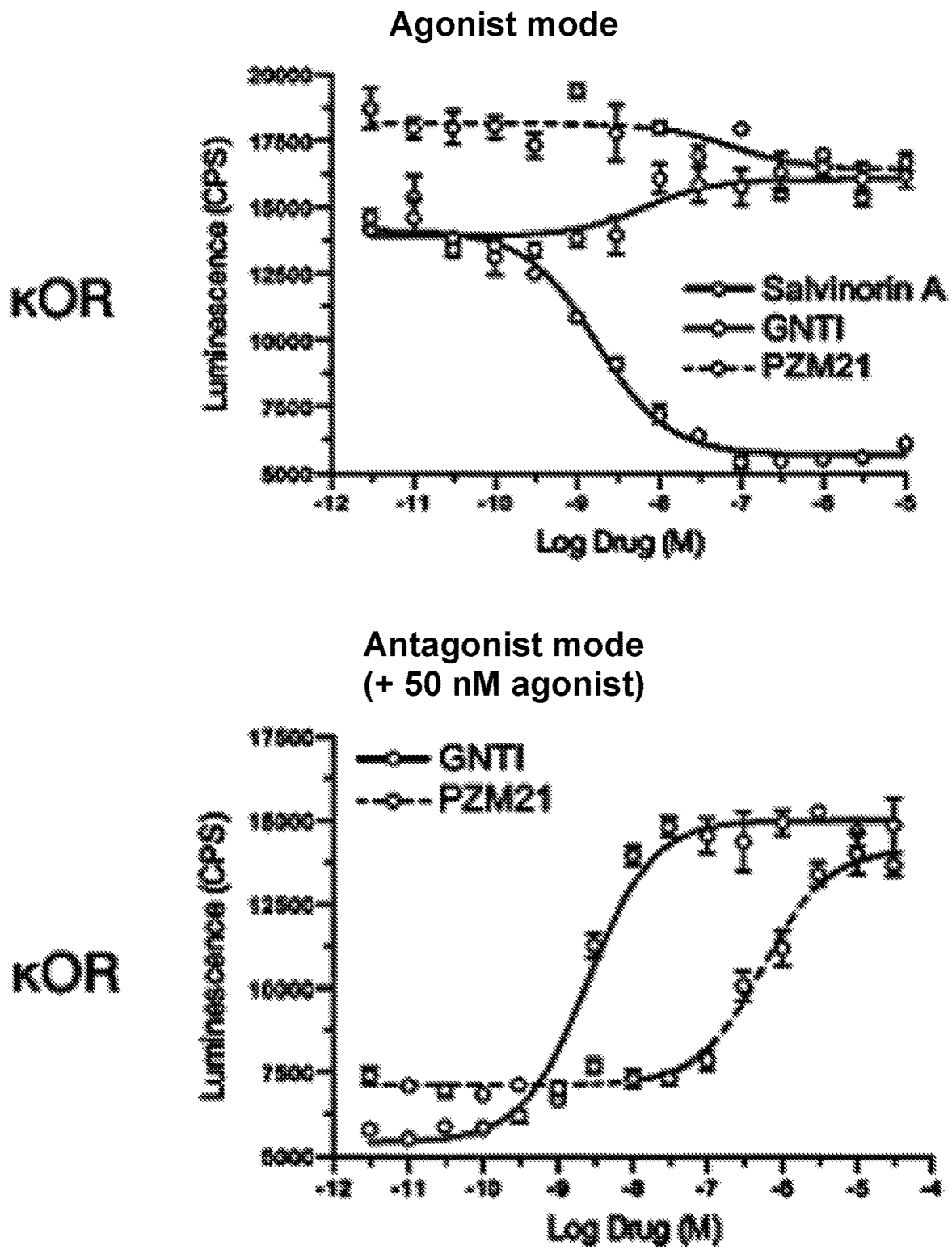

FIG. 5 - cont.
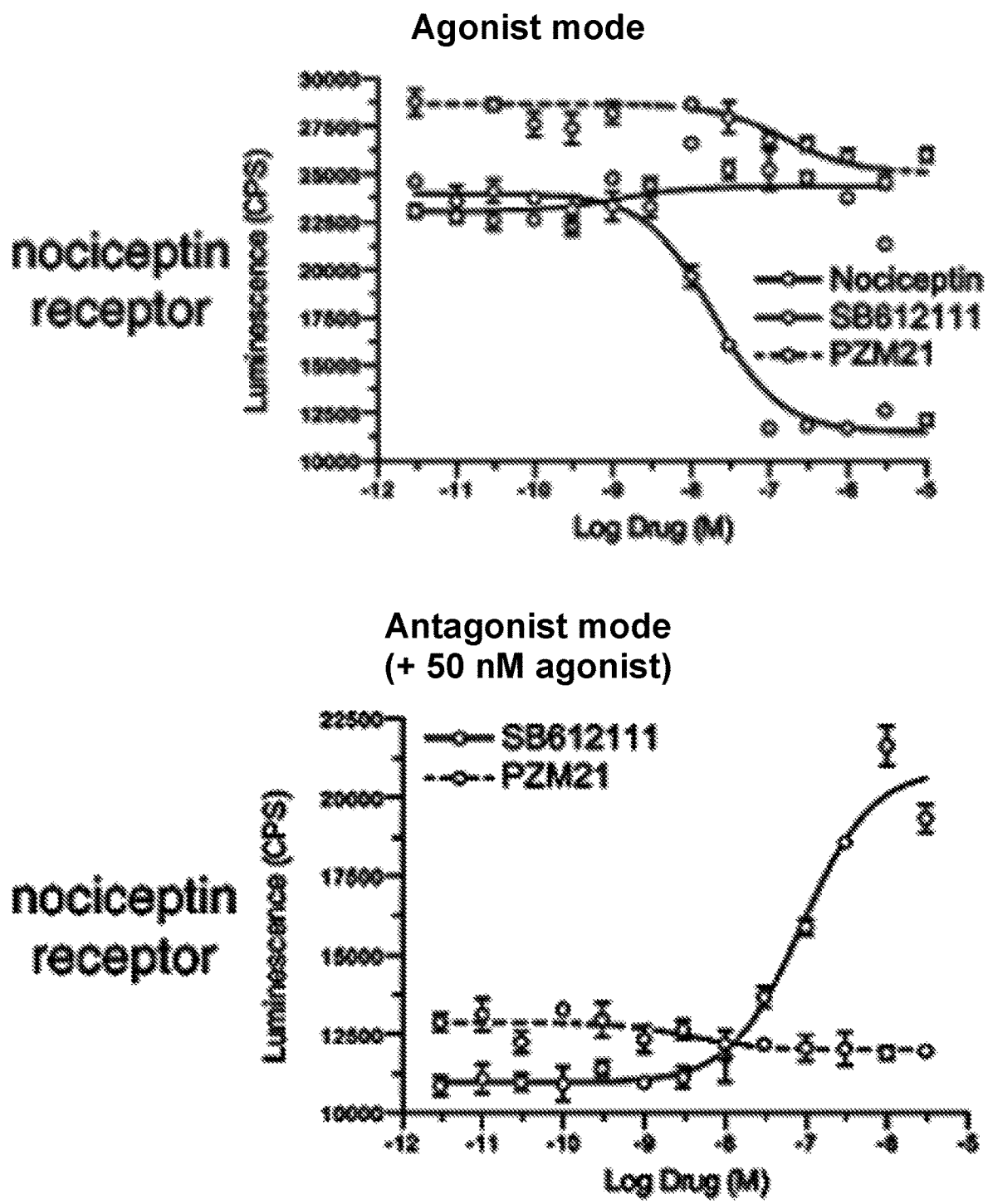

MU OPIOID RECEPTOR MODULATORS

CROSS-REFERENCES TO RELATED APPLICATIONS

This application is a US national stage under 35 U.S.C. § 371 of the International Application No. PCT/US2016/040553, filed on Jun. 30, 2016, and entitled "MU OPIOID RECEPTOR MODULATORS", which claims the benefit of U.S. Provisional Patent Application No. 62/190,390, filed on Jul. 9, 2015, and entitled "MU OPIOID RECEPTOR MODULATORS", the entirety of which is hereby incorporated by reference herein.

STATEMENT AS TO RIGHTS TO INVENTIONS MADE UNDER FEDERALLY SPONSORED RESEARCH AND DEVELOPMENT

This invention was made with government support under grant nos. GM059957, GM106990, DA036246 and DA017204, awarded by the National Institutes of Health. The government has certain rights in the invention.

BACKGROUND

The use of opioids in therapy dates to the Neolithic, and their effectiveness for pain treatment, as euphoragens, and their addictiveness has made them central to medicine, commerce, and conflict ever since. Their addictiveness and potentially lethal side effects, such as respiratory depression, have driven campaigns to improve them since the 19$^{th}$ century, with the purification of morphine and codeine and the synthesis of heroin. Recently, molecular studies have in fact suggested that the CNS-based analgesia relates to μ opioid receptor signaling through the $G_i$-protein pathway, while many of the pathophysiologies of the opioid drugs, including respiratory depression and constipation, is conferred via arrestin pathway signaling. Identifying agonists specific to μ opioid receptors and biased toward the $G_i$-protein pathway have thus far remained elusive. Disclosed herein, inter alia, are solutions to these and other problems in the art.

BRIEF SUMMARY OF THE INVENTION

In an aspect is provided a compound having the formula:

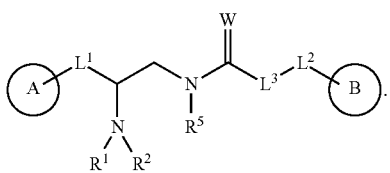

W is O or S. Ring A is independently substituted or unsubstituted aryl or substituted or unsubstituted heteroaryl. Ring B is independently substituted or unsubstituted cycloalkyl, substituted or unsubstituted heterocycloalkyl, substituted or unsubstituted aryl, or substituted or unsubstituted heteroaryl. $L^1$ and $L^2$ are independently a bond, substituted or unsubstituted ($C_1$-$C_5$) alkylene, or substituted or unsubstituted 2 to 5 membered heteroalkylene. $R^1$ and $R^2$ are independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, $OCF_3$, —$OCHF_2$, substituted or unsubstituted ($C_1$-$C_5$) alkyl, substituted or unsubstituted 2 to 5 membered heteroalkyl, substituted or unsubstituted ($C_3$-$C_6$) cycloalkyl, or substituted or unsubstituted 3 to 6 membered heterocycloalkyl. $R^1$ and $R^2$ may optionally be joined to form a substituted or unsubstituted 3 to 6 membered heterocycloalkyl or substituted or unsubstituted 5 to 6 membered heteroaryl. $L^1$ and $R^1$ may optionally be joined to form a substituted or unsubstituted 4 to 8 membered heterocycloalkyl. $L^1$ and $R^2$ may optionally be joined to form a substituted or unsubstituted 4 to 8 membered heterocycloalkyl. $L^3$ is a bond, —O—, —N($R^6$)—, or —$CH_2$—. $R^5$ is hydrogen, —$CF_3$, —CN, —COOH, —$CONH_2$, —$CHF_2$, —$CH_2F$, substituted or unsubstituted ($C_1$-$C_5$) alkyl, or substituted or unsubstituted 2 to 5 membered heteroalkyl; and $R^6$ is hydrogen, —$CF_3$, —CN, —COOH, —$CONH_2$, —$CHF_2$, —$CH_2F$, substituted or unsubstituted ($C_1$-$C_5$) alkyl, or substituted or unsubstituted 2 to 5 membered heteroalkyl.

In another aspect is provided a pharmaceutical composition including a pharmaceutically acceptable excipient and a compound, as described herein.

In an aspect is provided a method of treating pain in a subject in need of the treatment, the method including administering an effective amount of a compound as described herein, to the subject. In embodiments, the method does not include an increased risk of respiratory depression or constipation.

In an aspect is provided a method of treating opioid overdose in a subject in need of the treatment, the method including administering an effective amount of a compound as described herein, to the subject.

In another aspect is provided a method of treating addiction in a subject in need of the treatment, the method including administering an effective amount compound as described herein, to the subject.

In an aspect is provided a method of treating a psychiatric disorder in a subject in need of the treatment, the method including administering an effective amount of a compound as described herein, to the subject.

In another aspect is provided a method of modulating the activity of an opioid receptor protein, the method including contacting the opioid receptor protein with an effective amount of a compound as described herein.

DETAILED DESCRIPTION

Figure 1:
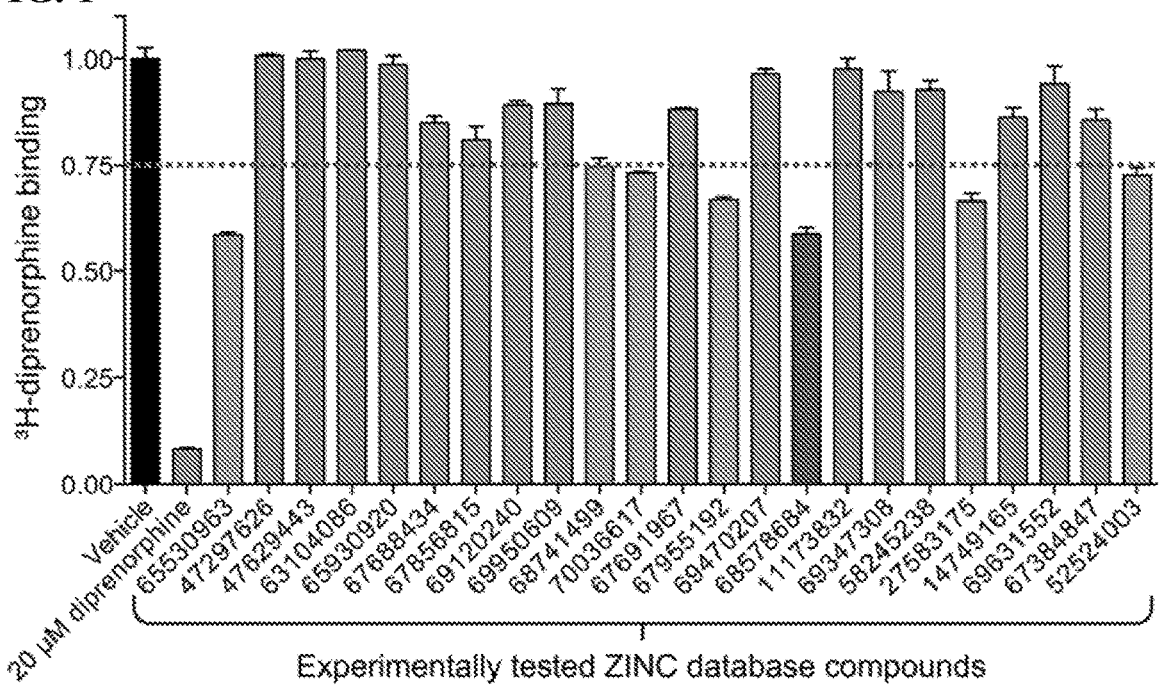
FIG. 1. Initial docking screen. Single point competition binding assay of 23 candidate molecules against the μOR antagonist radioligand $^3$H-diprenorphine. Each ligand was tested at 20 μM and those showing >25% inhibition were further tested by full displacement curves to determine affinity; data represent mean±s.e.m. (n=3 measurements).
Figure 2A:
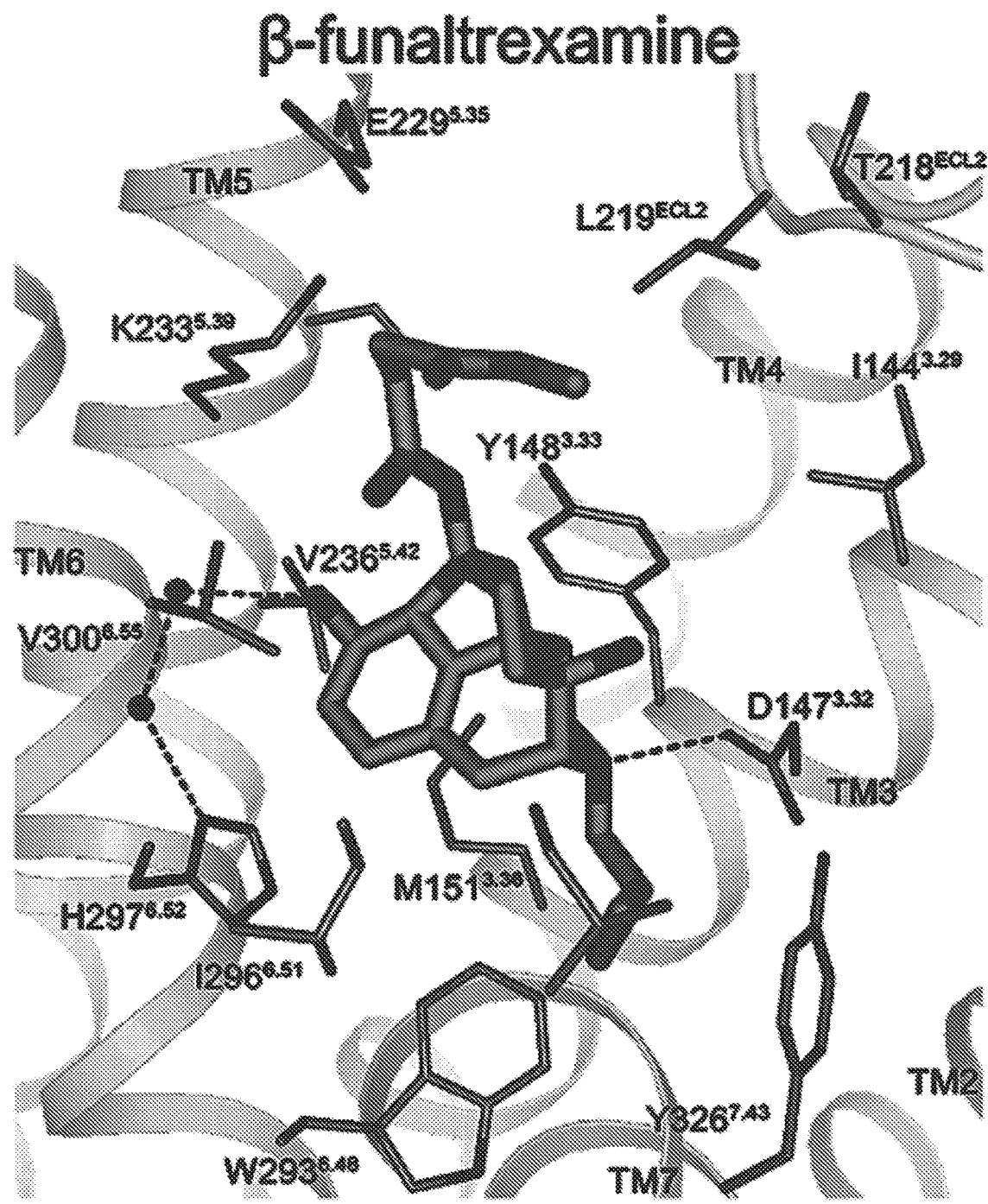
FIGS. 2A-2H. Predicted binding poses and dose response curves of initial hits from the docking screen against the μ-Opioid Recpetor. All figures visualized with Pymol.
Figure 2B:
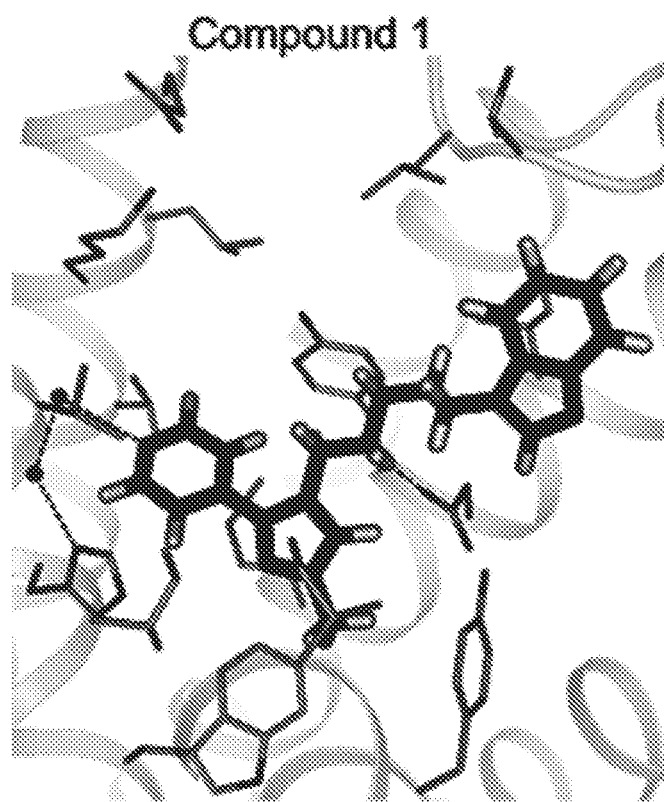
Figure 2C:
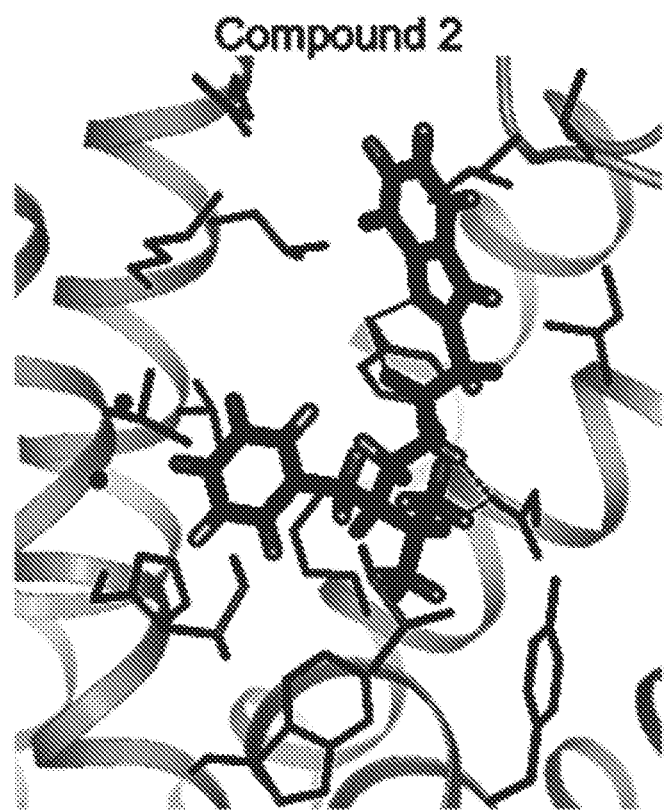
Figure 2D:
Figure 2E:
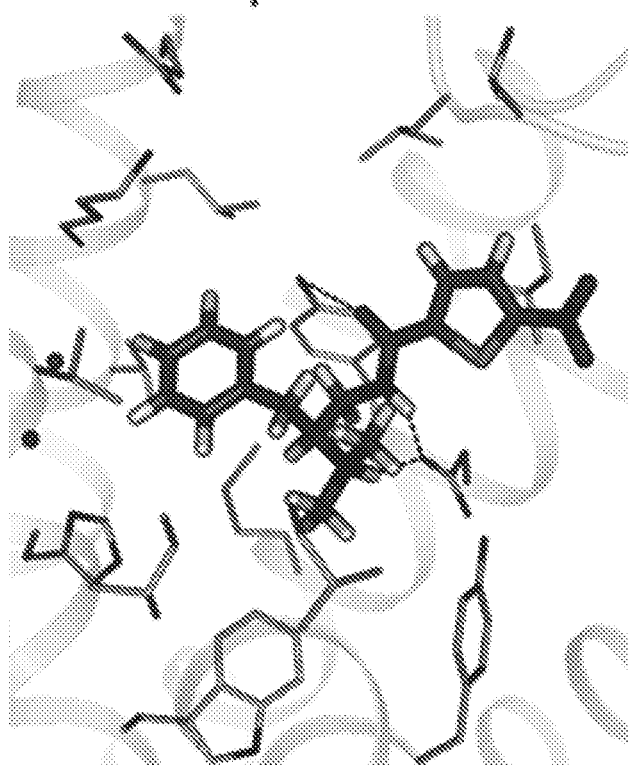
Figure 2F:
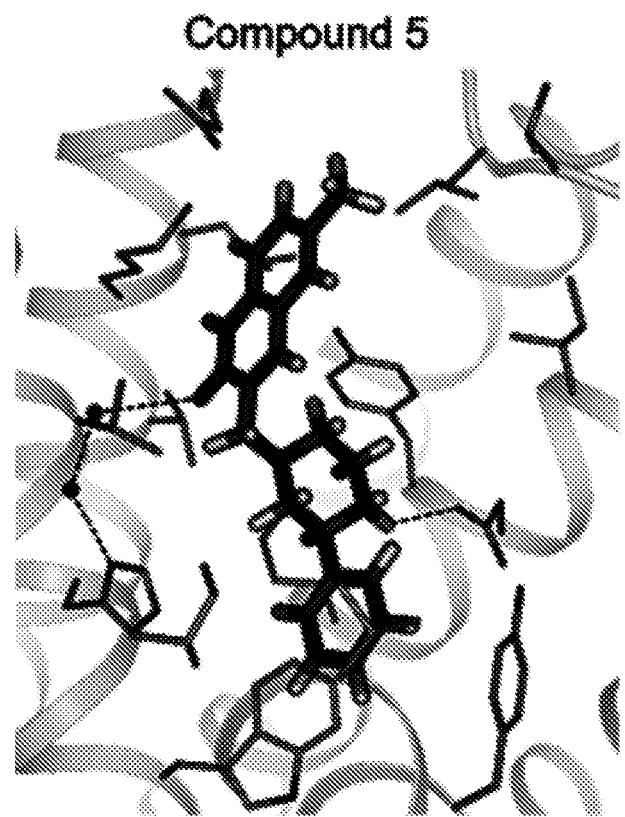
Figure 2G:
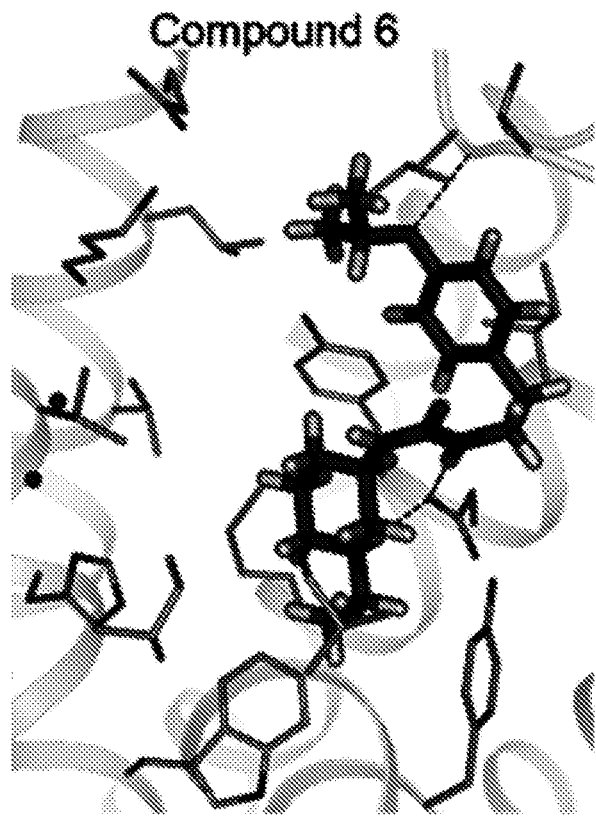
Figure 2H:
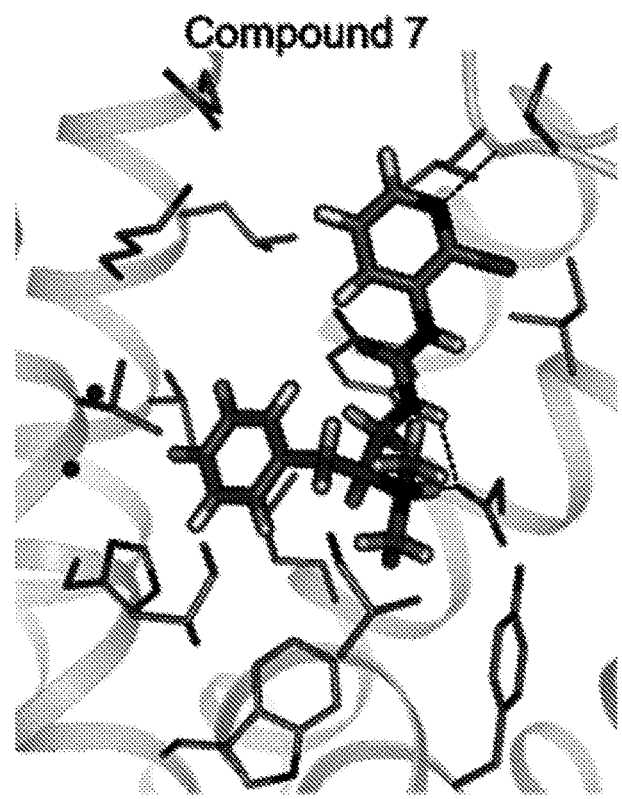

Structure-based optimization led to the identification of an agonist, PZM21, with an $EC_{50}$ for $G_{i/o}$ activation of 5 nM ($K_i$ 1 nM) and with selectivity for µOR activity as compared to the three other opioid receptors (δ, κ, and nociceptin). Consistent with its novel scaffold, PZM21 has unique signaling properties with minimal recruitment of β-arrestin2. Compounds disclosed herein in embodiments, reduce the affective component of pain, without detectably altering reflexive behaviors. Unlike the respiratory depression observed with morphine, an equianalgesic dose of compounds described herein had little effect on respiration.

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds (alkenyl) or triple bonds (alkynyl). An alkenyl may include more than one double bond and/or one or more triple bonds in addition to the one or more double bonds. An alkynyl may include more than one triple bond and/or one or more double bonds in addition to the one or more triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene. The term "alkynylene," by itself or as part of another substituent, means, unless otherwise stated, a divalent radical derived from an alkyne.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like. The term "heteroalkenylene," by itself or as part of another substituent, means, unless otherwise stated, a divalent radical derived from heteroalkenyl. The term "heteroalkynylene," by itself or as part of another substituent, means, unless otherwise stated, a divalent radical derived from heteroalkynyl The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. The terms "cycloalkenyl" and "cycloalkynyl," by themselves or in combination with other terms, mean, unless otherwise stated, cyclic versions of "alkenyl" and "alkynyl," respectively. The terms "heterocycloalkenyl" and "heterocycloalkynyl," by themselves or in combination with other terms, mean, unless otherwise stated, cyclic versions of "heteroalkenyl" and "heteroalkynyl," respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different.

Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "⤳" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

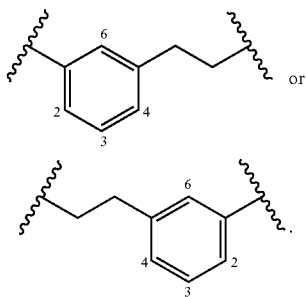

An alkylarylene moiety may be substituted (e.g. with a substituent group) on the alkylene moiety or the arylene linker (e.g. at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$— SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl", "heteroalkyl", "cycloalkyl", "heterocycloalkyl", "aryl", and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C(O)NR"NR'''R'''', —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C(O)NR"NR'''R'''', —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R''', and R'''' groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, claims, or tables below.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol or number may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc. (or $R^{13.1}$, $R^{13.2}$, $R^{13.3}$, $R^{13.4}$, etc.), wherein each of $R^{13A}$, $R^{13B}$, $R^{13C}$, $R^{13D}$, etc. (or $R^{13.1}$, $R^{13.2}$, $R^{13.3}$, $R^{13.4}$, etc.) is defined within the scope of the definition of $R^{13}$ and optionally differently.

A "detectable moiety" as used herein refers to a moiety that can be covalently or noncovalently attached to a compound or biomolecule that can be detected for instance, using techniques known in the art. In embodiments, the detectable moiety is covalently attached. The detectable moiety may provide for imaging of the attached compound or biomolecule. The detectable moiety may indicate the contacting between two compounds. Exemplary detectable moieties are fluorophores, antibodies, reactive dies, radiolabeled moieties, magnetic contrast agents, and quantum dots. Exemplary fluorophores include fluorescein, rhodamine, GFP, coumarin, FITC, Alexa fluor, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of an active agent to and absorption by a subject and can be included in the compositions of the compounds described herein without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds described herein. One of skill in the art will recognize that other pharmaceutical excipients are useful in combination with the compounds described herein.

Pharmaceutical compositions may include compositions wherein the active ingredient (e.g. compounds described herein) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds described herein. Adjustment and manipulation of established dosages (e.g., frequency and duration) are well within the ability of those skilled in the art.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

A "mu opioid receptor modulator" or "mu opioid receptor compound" or "P opioid receptor modulator" refers to a compound (e.g. compounds described herein) that reduce the activity of opioid receptor when compared to a control, such as absence of the compound or a compound with known inactivity.

A "specific," "specifically", "specificity", or the like of a compound refers to the compound's ability to discriminate between particular molecular targets to a significantly greater extent than other proteins in the cell (e.g. a compound having specificity towards µ opioid receptor ("µ opioid receptor—specific compound" or a compound including a "µ opioid receptor—specific moiety") binds to µ opioid receptor whereas the same compound displays little-to-no binding to other opioid receptors such as kappa opioid receptor or delta opioid receptor, or nociceptin receptor). A "µ opioid receptor–specific compound" refers to a compound (e.g. compounds described herein) having specificity towards µ opioid receptor (e.g., over one or more other opioid receptors).

The terms "selective," or "selectivity" or the like of a compound refers to the compound's ability to cause a particular action in a particular molecular target (e.g. a compound having selectivity toward opioid receptor would inhibit only opioid receptor). A "µ opioid receptor–selective compound" or a compound including a "µ opioid receptor–selective moiety" refers to a compound (e.g. compounds described herein) having selectivity towards opioid receptor.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A polypeptide, or a cell is "recombinant" when it is artificial or engineered, or derived from or contains an artificial or engineered protein or nucleic acid (e.g. non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "activation", "activate", "activating" and the like in reference to a protein-activator interaction means positively affecting (e.g. increasing) the activity or function of the protein relative to the activity or function of the protein in the absence of the activator. In embodiments inhibition refers means positively affecting (e.g. increasing) the concentration or levels of the protein relative to the concentration or level of the protein in the absence of the activator. In embodiments, activation refers to an increase in the activity of a particular protein target (mu opioid receptor). Thus, activation includes, at least in part, partially or totally increasing stimulation or activation, or activating, sensitizing, or up-regulating signal transduction or enzymatic activity or the amount of a protein. In embodiments, activation refers to an increase of activity of a target protein resulting from a direct interaction (e.g. an activator binds to the target protein). In embodiments, activation refers to an increase of activity of a target protein from an indirect interaction (e.g. an activator binds to a protein that inhibits the target protein, thereby causing target protein activation).

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition refers means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

Opioid receptors are a group of inhibitory G-protein coupled receptors that bind opioids (e.g., endogenous opioids are dynorphins, enkephalins, endorphins, endomorphins, and nociception).

The terms "μ opioid receptor" and "mu opioid receptor" or "MOR" refer to a subtype of opioid receptor and is used according to its common, ordinary meaning. "μ opioid receptor" refers to proteins of the same or similar names, homologs, isoforms, and functional fragments thereof, so long as such fragments retain μ opioid receptor activity. The term includes any recombinant or naturally-occurring form of μ opioid receptor, or variants thereof that maintain opioid receptor activity (e.g. within at least 30%, 40%, 50%, 60%, 70%, 80%, 90%, 95%, or 100% activity compared to wildtype opioid receptor). In embodiments, the μ opioid receptor protein encoded by the OPRM1 gene has the amino acid sequence set forth in RefSeq (mRNA) NM_000914, NM_001008503, NM_001008504, NM_001008505, NM_001145279, NM_001145280, NM_001145281, NM_001145282, NM_001145283, NM_001145284, NM_001145285, NM_001145286, NM_001145287, NM_001285522, NM_001285523, NM_001285524, NM_001285526, NM_001285527, or NM_001285528. In embodiments, the μ opioid receptor protein encoded by the OPRM1 gene has the amino acid sequence set forth in RefSeq (protein) NP_000905.3, NP_001008503.2, NP_001008504.2, NP_001008505.2, NP_001138751.1, NP_001138752.1, NP_001138753.1, NP_001138754.1, NP_001138755.1, NP_001138756.1, NP_001138757.1, NP_001138758.1, NP_001138759.1, NP_001272452.1, NP_001272453.1, NP_001272455.1, NP_001272456.1, or NP_001272457.1.

In embodiments, the μ opioid receptor protein encoded by the OPRM1 gene has the amino acid sequence set forth in Entrez 4988, UniProt P35372, RefSeq (mRNA) NM_000914, or RefSeq (protein) NP_000905. In embodiments, the μ opioid receptor protein is a human protein. In embodiments, the μ opioid receptor protein is a wildtype protein. In embodiments, the μ opioid receptor protein is a mutant protein. In embodiments, the μ opioid receptor protein corresponds to GI: 117940060. In embodiments, the μ opioid receptor protein corresponds to NP_000905.3. In embodiments, the μ opioid receptor protein corresponds to GI:550822366. In embodiments, the μ opioid receptor protein corresponds to NM_000914.4.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The terms "disease" or "condition" refer to a state of being or health status of a patient or subject capable of being treated with the compounds or methods provided herein. The disease may be pain, such as for example, nociceptive pain, inflammatory pain which is associated with tissue damage and/or the infiltration of immune cells, or pathological pain, for example a disease state caused by damage to the nervous system (neuropathic pain) or by its abnormal function (dysfunctional pain (e.g., fibromyalgia, irritable bowel syndrome, tension type headache)). In embodiments, the pain may be acute pain. In embodiments, the pain may be chronic pain. In embodiments, the nociceptive pain may be associated with ischemia. In embodiments, the nociceptive pain may be associated with inflammation. In embodiments, the nociceptive pain may be deep somatic pain (e.g., due to damage to ligaments, tendons, bonds, blood vessels, fasciae, or muscles). In embodiments, the nociceptive pain may be associated with skin. In embodiments, the nociceptive pain may be associated with a burn. In embodiments, the pain may be psychogenic (e.g., associated with headache, back pain, stomach pain). In embodiments, the pain may be breakthrough pain. In embodiments, the pain may be breakthrough pain not treated by standard pain management. In embodiments, the pain may be breakthrough pain associated with cancer. In embodiments, the pain may be a pain capable of being treated with an opioid. The disease may be a drug addiction (e.g., addiction to an opioid, tobacco, narcotic, heroin, morphine, opiate, alcohol, cocaine, amphetamine, methamphetamine, MDMA, GHB, LSD, PCP, hydrocodone, oxycodone, fentanyl, or marijuana, methadone, hydromorphone, or a derivative thereof). The disease may be opioid poisoning (e.g., overdose), for example poisoning with heroin, fentanyl, or morphine.

The terms "treating", or "treatment" refer to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment of symptoms can be based on objective or subjective parameters; including the results of a physical examination, neuropsychiatric exams, and/or a psychiatric evaluation. The terms treatment, therapy and the like include, but are not limited to, methods and manipulations to produce beneficial changes in a recipient's health status. The changes can be either subjective or objective and can relate to features such as symptoms or signs of the disease, disorder or condition being treated. For example, if the patient notes decreased pain, then successful treatment of pain has occurred. The term "treating" and conjugations thereof, include prevention of an injury, pathology, condition, or disease.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal) compatible with the preparation. Parenteral administration includes, e.g., intravenous, intramuscular, intraarteriole, intradermal, subcutaneous, intraperitoneal, intraventricular, and intracranial. Other modes of delivery include, but are not limited to, the use of liposomal formulations, intravenous infusion, transdermal patches, etc.

"Co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulator" refers to a composition that increases or decreases the level of a target molecule or the function of a target molecule or the physical state of the target of the molecule relative to the absence of the modulator. In some embodiments, a μ opioid receptor disease modulator is a compound that reduces the severity of one or more symptoms of a disease associated with μ opioid receptor (e.g. pain or drug addiction). A μ opioid receptor modulator is a compound that increases or decreases the activity or function or level of activity or level of function of μ opioid receptor or level of μ opioid receptor in a particular physical state.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "associated" or "associated with" in the context of a substance or substance activity or function associated with a disease (e.g. a protein associated disease, a pain associated with μ opioid receptor activity, μ opioid receptor associated pain, μ opioid receptor associated disease, μ opioid receptor associated drug addiction. For example, a pain associated with μ opioid receptor activity or function may be a pain that results (entirely or partially) from aberrant μ opioid receptor function (e.g. enzyme activity, protein-protein interaction, signaling pathway) or a pain wherein a particular symptom of the disease is caused (entirely or partially) by aberrant μ opioid receptor activity or function. As used herein, what is described as being associated with a disease, if a causative agent, could be a target for treatment of the disease. For example, a pain associated with μ opioid receptor activity or function or a μ opioid receptor associated pain, may be treated with a μ opioid receptor modulator or μ opioid receptor activator, in the instance where decreased μ opioid receptor activity or function (e.g. signaling pathway activity) causes the pain. For example, a drug addiction associated with increased μ opioid receptor activity or function or a μ opioid receptor associated addiction, may be treated with a μ opioid receptor modulator or μ opioid receptor inhibitor, in the instance where increased (e.g., due to the addictive drug) μ opioid receptor activity or function (e.g. signaling pathway activity) causes the drug addiction.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propogated to other signaling pathway components. For example, binding of a μ opioid receptor with a compound as described herein may result in a change in one or more protein-protein interactions of the opioid receptor or interactions between the μ opioid receptor and downstream effectors or signaling pathway components, resulting in changes in cell function.

II. Compounds

In an aspect is provided herein, a compound having the formula:

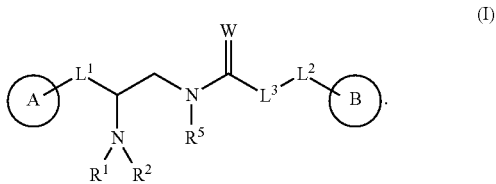

(I)

The symbol W is O or S. Ring A is independently substituted or unsubstituted cycloalkyl, substituted or unsubstituted heterocycloalkyl, substituted or unsubstituted aryl or substituted or unsubstituted heteroaryl. Ring B is independently substituted or unsubstituted cycloalkyl, substituted or unsubstituted heterocycloalkyl, substituted or unsubstituted aryl, or substituted or unsubstituted heteroaryl. $L^1$ and $L^2$ are independently a bond, substituted or unsubstituted alkylene, or substituted or unsubstituted heteroalkylene. $R^5$ is hydrogen, —$CF_3$, —CN, —COOH, —$CONH_2$, —$CHF_2$, —$CH_2F$, substituted or unsubstituted alkyl, or substituted or unsubstituted heteroalkyl.

$R^1$ and $R^2$ are independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)OH, —NHOH, —$CHF_2$, —$CH_2F$, $OCF_3$, —$OCHF_2$, substituted or unsubstituted alkyl, substituted or unsubstituted heteroalkyl, substituted or unsubstituted cycloalkyl, or substituted or unsubstituted heterocycloalkyl, substituted or unsubstituted aryl or substituted or unsubstituted heteroaryl. $R^1$ and $R^2$ may optionally be joined to form a substituted or unsubstituted heterocycloalkyl or substituted or unsubstituted heteroaryl. $L^1$ and $R^1$ may optionally be joined to form a substituted or unsubstituted heterocycloalkyl. $L^1$ and $R^2$ may optionally be joined to form a substituted or unsubstituted heterocycloalkyl.

$L^3$ is a bond, —O—, —N($R^6$)—, —CH($R^6$)—, or —$CH_2$—. $R^6$ is hydrogen, —$CF_3$, —CN, —COOH, —$CONH_2$, —$CHF_2$, —$CH_2F$, substituted or unsubstituted alkyl, or substituted or unsubstituted heteroalkyl. In embodiments, $L^3$ is a bond, substituted or unsubstituted alkylene, or substituted or unsubstituted heteroalkylene. In embodiments, Ring A is independently substituted or unsubstituted aryl or substituted or unsubstituted heteroaryl. In embodiments, $L^1$ and $L^2$ are independently a bond, substituted or unsubstituted alkylene, or substituted or unsubstituted 2 to 5 membered heteroalkylene. In embodiments, $R^6$ is hydrogen, —$CF_3$, —CN, —COOH, —$CONH_2$, —$CHF_2$, —$CH_2F$, substituted or unsubstituted ($C_1$-$C_5$) alkyl, or substituted or unsubstituted 2 to 5 membered heteroalkyl. In embodiments, $R^6$ is hydrogen. In embodiments, $R^6$ is an unsubstituted methyl.

In embodiments, $L^1$ and $L^2$ are independently a bond, substituted or unsubstituted ($C_1$-$C_5$) alkylene, or substituted or unsubstituted 2 to 5 membered heteroalkylene. In embodiments, L and $L^2$ are independently a bond, substituted or unsubstituted ($C_2$-$C_5$) alkylene, or substituted or unsubstituted 2 to 5 membered heteroalkylene.

In embodiments, $R^1$ and $R^2$ are independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)OH, —NHOH, —$CHF_2$, —$CH_2F$, $OCF_3$, —$OCHF_2$, substituted or unsubstituted ($C_1$-$C_5$) alkyl, substituted or unsubstituted 2 to 5 membered heteroalkyl, substituted or unsubstituted ($C_3$-$C_6$) cycloalkyl, or substituted or unsubstituted 3 to 6 membered heterocycloalkyl. In embodiments, $R^1$ and $R^2$ may optionally be joined to form a substituted or unsubstituted 3 to 6 membered heterocycloalkyl or substituted or unsubstituted 5 to 6 membered heteroaryl. In embodiments, $L^1$ and $R^1$ may optionally be joined to form a substituted or unsubstituted 4 to 8 membered heterocycloalkyl. In embodiments, $L^1$ and $R^2$ may optionally be joined to form a substituted or unsubstituted 4 to 8 membered heterocycloalkyl.

In embodiments, $R^5$ is hydrogen, —$CF_3$, —CN, —COOH, —$CONH_2$, —$CHF_2$, —$CH_2F$, substituted or unsubstituted ($C_1$-$C_5$) alkyl, or substituted or unsubstituted 2 to 5 membered heteroalkyl. In embodiments, $R^5$ is hydrogen. In embodiments, $R^5$ is an unsubstituted methyl. In embodiments, $R^5$ is an unsubstituted ethyl. In embodiments, $R^5$ is an unsubstituted isopropyl. In embodiments, $R^5$ is an unsubstituted propyl. In embodiments, $R^5$ is an unsubstituted t-butyl. In embodiments, $R^5$ is an unsubstituted ethenyl. In embodiments, $R^5$ is an unsubstituted propenyl.

In embodiments, $R^5$ is independently hydrogen, oxo, halogen, —$CX^5_3$, —$CHX^5_2$, —$OCH_2X^5$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$OCX^5_3$, —$OCHX^5_2$, $R^{42}$-substituted or unsubstituted alkyl, $R^{42}$-substituted or unsubstituted heteroalkyl, $R^{42}$-substituted or unsubstituted cycloalkyl, $R^{42}$ substituted or unsubstituted heterocycloalkyl, $R^{42}$-substituted or unsubstituted aryl, or $R^{42}$-substituted or unsubstituted heteroaryl. $X^5$ is independently halogen. In embodiments, $X^5$ is independently F or Cl.

$R^{42}$ is independently oxo, halogen, —$CX^{42}_3$, —$CHX^{42}_2$, —$OCH_2X^{42}$, —$OCHX^{42}_2$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$OCX^{42}_3$, —$OCHX^{42}_2$, $R^{43}$-substituted or unsubstituted alkyl, $R^{43}$-substituted or unsubstituted heteroalkyl, $R^{43}$-substituted or unsubstituted cycloalkyl, $R^{43}$-substituted or unsubstituted heterocycloalkyl, $R^{43}$-substituted or unsubstituted aryl, or $R^{43}$-substituted or unsubstituted heteroaryl. $X^{42}$ is independently halogen. In embodiments, $X^{42}$ is independently F or Cl.

$R^{43}$ is independently oxo, halogen, —$CX^{43}_3$, —$CHX^{43}_2$, —$OCH_2X^{43}$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$OCX^{43}_3$, —$OCHX^{43}_2$, $R^{44}$-substituted or unsubstituted alkyl, $R^{44}$-substituted or unsubstituted heteroalkyl, $R^{44}$-substituted or unsubstituted cycloalkyl, $R^{44}$-substituted or unsubstituted heterocycloalkyl, $R^{44}$-substituted or unsubstituted aryl, or $R^{44}$-substituted or unsubstituted heteroaryl. $X^{43}$ is independently halogen. In embodiments, $X^{43}$ is independently F or Cl.

In embodiments, W is O. In embodiments, W is S. Ring A is independently substituted or unsubstituted aryl or substituted or unsubstituted heteroaryl; Ring B is independently substituted or unsubstituted cycloalkyl, substituted or unsubstituted heterocycloalkyl, substituted or unsubstituted aryl, or substituted or unsubstituted heteroaryl. $L^1$ and $L^2$ are independently a bond, substituted or unsubstituted ($C_1$-$C_5$) alkylene, or substituted or unsubstituted 2 to 5 membered heteroalkylene.

$R^1$ and $R^2$ are independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)OH, —NHOH, —$CHF_2$, —$CH_2F$, $OCF_3$, —$OCHF_2$, substituted or unsubstituted ($C_1$-$C_5$) alkyl, substituted or unsubstituted 2 to 5 membered heteroalkyl, substituted or unsubstituted ($C_3$-$C_6$) cycloalkyl, or substituted or unsubstituted 3 to 6 membered heterocycloalkyl; $R^1$ and $R^2$ may optionally be joined to form a substituted or unsubstituted 3 to 6 membered heterocycloalkyl or substituted or unsubstituted 5 to 6 membered heteroaryl.

$L^1$ and $R^1$ may optionally be joined to form a substituted or unsubstituted 4 to 8 membered heterocycloalkyl. $L^1$ and $R^2$ may optionally be joined to form a substituted or unsubstituted 4 to 8 membered heterocycloalkyl. $L^3$ is a bond, —O—, —N($R^6$)—, or —$CH_2$—. $R^5$ is hydrogen, —$CF_3$, —CN, —COOH, —$CONH_2$, —$CHF_2$, —$CH_2F$, substituted or unsubstituted ($C_1$-$C_5$) alkyl, or substituted or unsubstituted 2 to 5 membered heteroalkyl. $R^6$ is hydrogen, —$CF_3$, —CN, —COOH, —$CONH_2$, —$CHF_2$, —$CH_2F$, substituted or unsubstituted ($C_1$-$C_5$) alkyl, or substituted or unsubstituted 2 to 5 membered heteroalkyl. In embodiments, $L^3$ is a bond, —N($R^6$)—, or —O—. In embodiments, $L^3$ is a bond, —NH—, or —O—.

In embodiments, the compound has the formula:

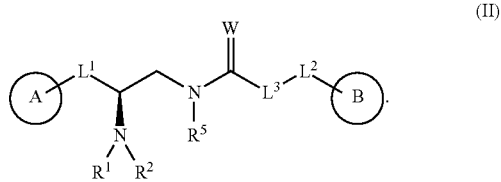

(II)

$R^1$, $R^2$, $R^5$, $L^1$, $L^2$, $L^3$, W, Ring A, and Ring B are as described herein (e.g., including in formula I, and embodiments).

In embodiments, the compound has the formula:

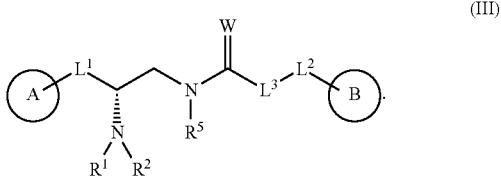

(III)

$R^1$, $R^2$, $R^5$, $L^1$, $L^2$, $L^3$, W, Ring A, and Ring B are as described herein (e.g., including in formula I, and embodiments thereof).

In embodiments, Ring A is substituted or unsubstituted ($C_6$-$C_{10}$) aryl or substituted or unsubstituted 5 to 10 membered heteroaryl. In embodiments, Ring A is substituted or unsubstituted ($C_6$-$C_{10}$) aryl or substituted or unsubstituted 5 to 10 membered heteroaryl. Ring A may be substituted or unsubstituted ($C_6$-$C_{10}$) aryl. Ring A may be substituted or unsubstituted phenyl. Ring A may be substituted or unsubstituted napthyl. Ring A may be substituted or unsubstituted 5 to 10 membered heteroaryl. Ring A may be substituted or unsubstituted 5 to 6 membered heteroaryl. Ring A may be substituted or unsubstituted thienyl. Ring A may be substituted or unsubstituted furanyl. Ring A may be substituted or unsubstituted pyrrolyl. Ring A may be substituted or unsubstituted imidazolyl. Ring A may be substituted or unsubstituted pyrazolyl. Ring A may be substituted or unsubstituted oxazolyl. Ring A may be substituted or unsubstituted isoxazolyl. Ring A may be substituted or unsubstituted thaizolyl. Ring A may be substituted or unsubstituted pyridinyl. Ring A may be substituted or unsubstituted pyridyl. Ring A may be substituted or unsubstituted pyrazinyl. Ring A may be substituted or unsubstituted pyrimidinyl. Ring A may be substituted or unsubstituted pyridazinyl. Ring A may be substituted or unsubstituted 1,2,3-triazinyl. Ring A may be substituted or unsubstituted 1,2,4-triazinyl. Ring A may be substituted or unsubstituted 1,3,5-triazinyl. In embodiments, Ring A is substituted ($C_6$-$C_{10}$) aryl or substituted 5 to 10 membered heteroaryl. In embodiments, Ring A is substituted ($C_6$-$C_{10}$) aryl or substituted 5 to 10 membered heteroaryl. Ring A may be substituted ($C_6$-$C_{10}$) aryl. Ring A may be substituted phenyl. Ring A may be substituted napthyl. Ring A may be substituted 5 to 10 membered heteroaryl. Ring A may be substituted 5 to 6 membered heteroaryl. Ring A may be substituted thienyl. Ring A may be substituted furanyl. Ring A may be substituted pyrrolyl. Ring A may be substituted imidazolyl. Ring A may be substituted pyrazolyl. Ring A may be substituted oxazolyl. Ring A may be substituted isoxazolyl. Ring A may be substituted thaizolyl. Ring A may be substituted pyridinyl. Ring A may be substituted pyridyl. Ring A may be substituted pyrazinyl. Ring A may be substituted pyrimidinyl. Ring A may be substituted pyridazinyl. Ring A may be substituted 1,2,3-triazinyl. Ring A may be substituted 1,2,4-triazinyl. Ring A may be substituted 1,3,5-triazinyl. In embodiments, Ring A is unsubstituted ($C_6$-$C_{10}$) aryl or unsubstituted 5 to 10 membered heteroaryl. In embodiments, Ring A is unsubstituted ($C_6$-$C_{10}$) aryl or unsubstituted 5 to 10 membered heteroaryl. Ring A may be unsubstituted ($C_6$-$C_{10}$) aryl. Ring A may be unsubstituted phenyl. Ring A may be unsubstituted napthyl. Ring A may be unsubstituted 5 to 10 membered heteroaryl. Ring A may be unsubstituted 5 to 6 membered heteroaryl.

Ring A may be unsubstituted thienyl. Ring A may be unsubstituted furanyl. Ring A may be unsubstituted pyrrolyl. Ring A may be unsubstituted imidazolyl. Ring A may be unsubstituted pyrazolyl. Ring A may be unsubstituted oxazolyl. Ring A may be unsubstituted isoxazolyl. Ring A may be unsubstituted thaizolyl. Ring A may be unsubstituted pyridinyl. Ring A may be unsubstituted pyridyl. Ring A may be unsubstituted pyrazinyl. Ring A may be unsubstituted pyrimidinyl. Ring A may be unsubstituted pyridazinyl. Ring A may be unsubstituted 1,2,3-triazinyl. Ring A may be unsubstituted 1,2,4-triazinyl. Ring A may be unsubstituted 1,3,5-triazinyl.

In embodiments, Ring A is $R^3$-substituted or unsubstituted ($C_6$-$C_{10}$) aryl or $R^3$-substituted or unsubstituted 5 to 10 membered heteroaryl. Ring A may be $R^3$-substituted or unsubstituted ($C_6$-$C_{10}$) aryl. Ring A may be $R^3$-substituted or unsubstituted phenyl. Ring A may be $R^3$-substituted or unsubstituted napthyl. Ring A may be $R^3$-substituted or unsubstituted 5 to 10 membered heteroaryl. Ring A may be $R^3$-substituted or unsubstituted 5 to 6 membered heteroaryl. Ring A may be $R^3$-substituted or unsubstituted thienyl. Ring A may be $R^3$-substituted or unsubstituted furanyl. Ring A may be $R^3$-substituted or unsubstituted pyrrolyl. Ring A may be $R^3$-substituted or unsubstituted imidazolyl. Ring A may be $R^3$-substituted or unsubstituted pyrazolyl. Ring A may be $R^3$-substituted or unsubstituted oxazolyl. Ring A may be $R^3$-substituted or unsubstituted isoxazolyl. Ring A may be $R^3$-substituted or unsubstituted thaizolyl. Ring A may be $R^3$-substituted or unsubstituted pyridinyl. Ring A may be $R^3$-substituted or unsubstituted pyridyl. Ring A may be $R^3$-substituted or unsubstituted pyrazinyl. Ring A may be $R^3$-substituted or unsubstituted pyrimidinyl. Ring A may be $R^3$-substituted or unsubstituted pyridazinyl. Ring A may be $R^3$-substituted or unsubstituted 1,2,3-triazinyl. Ring A may be $R^3$-substituted or unsubstituted 1,2,4-triazinyl. Ring A may be $R^3$-substituted or unsubstituted 1,3,5-triazinyl. In embodiments, Ring A is $R^3$-substituted ($C_6$-$C_{10}$) aryl or $R^3$ substituted 5 to 10 membered heteroaryl. Ring A may be $R^3$-substituted ($C_6$-$C_{10}$) aryl. Ring A may be $R^3$-substituted phenyl. Ring A may be $R^3$-substituted napthyl. Ring A may be $R^3$-substituted 5 to 10 membered heteroaryl. Ring A may be $R^3$-substituted 5 to 6 membered heteroaryl. Ring A may be $R^3$-substituted thienyl. Ring A may be $R^3$-substituted furanyl. Ring A may be $R^3$-substituted pyrrolyl. Ring A may be $R^3$-substituted imidazolyl. Ring A may be $R^3$-substituted pyrazolyl. Ring A may be $R^3$-substituted oxazolyl. Ring A may be $R^3$-substituted isoxazolyl. Ring A may be $R^3$-substituted thaizolyl. Ring A may be $R^3$-substituted pyridinyl. Ring A may be $R^3$-substituted pyridyl. Ring A may be $R^3$-substituted pyrazinyl. Ring A may be $R^3$-substituted pyrimidinyl. Ring A may be $R^3$-substituted pyridazinyl. Ring A may be $R^3$-substituted 1,2,3-triazinyl. Ring A may be $R^3$-substituted 1,2,4-triazinyl. Ring A may be $R^3$-substituted 1,3,5-triazinyl. Ring A may be substituted with one $R^3$. Ring A may be substituted with two optionally different $R^3$ substituents. Ring A may be substituted with three optionally different $R^3$ substituents. Ring A may be substituted with four optionally different $R^3$ substituents. Ring A may be substituted with five optionally different $R^3$ substituents. Ring A may be substituted with six optionally different $R^3$ substituents. Ring A may be substituted with seven optionally different $R^3$ substituents. Ring A may be substituted with eight optionally different $R^3$ substituents. Ring A may be substituted with nine optionally different $R^3$ substituents. Ring A may be substituted with ten optionally different $R^3$ substituents.

$R^3$ is independently hydrogen, halogen, —$CX_3$, —CN, —$SO_nR^{10}$, —$SO_nNR^7R^8$, —$NHNR^7R^8$, —$ONR^7R^8$, —NHC=(O)NHNR$^7R^8$, —NHC=(O)NR$^7R^8$, —N(O)$_m$, —NR$^7R^8$, —C(O)R$^9$, —C(O)—OR$^9$, —C(O)NR$^7R^8$, —OR$^{10}$, —NR$^7$SO$_2$R$^{10}$, —NR$^7$C=(O)R$^9$, —NR$^7$C(O) OR$^9$, —NR$^7$OR$^9$, —CHX$_2$, —CH$_2$X, —OCX$_3$, —OCHX$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Where multiple $R^3$ substituents are present, the multiple $R^3$ substituents may be referred to as $R^{3A}$, $R^{3B}$, $R^{3C}$, $R^{3D}$ and $R^{3E}$ as set forth, for example, in formulae provided herein such as Formulae (IV), (IVa) and (IVb). In embodiments where Ring A is a six-membered cyclic substituent, $R^{3A}$ is at the para position, $R^{3B}$ and $R^{3C}$ are at the meta positions and $R^{3D}$ and $R^{3E}$ are at the ortho positions, wherein $R^{3D}$ is adjacent to $R^{3B}$ and $R^{3E}$ is adjacent to $R^{3C}$. Two adjacent $R^3$ substituents (e.g., $R^{3B}$ and $R^{3D}$, $R^{3B}$ and $R^{3A}$, $R^{3A}$ and $R^{3C}$, $R^{3C}$ and $R^{3E}$) may optionally be joined to form a substituted or unsubstituted cycloalkyl, substituted or unsubstituted heterocycloalkyl, substituted or unsubstituted aryl, or substituted or unsubstituted heteroaryl.

In embodiments, $R^3$ is independently hydrogen, oxo, halogen, —$CX^3{}_3$, —$CHX^3{}_2$, —$OCH_2X^3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^3{}_3$, —$OCHX^3{}_2$, $R^{36}$-substituted or unsubstituted alkyl, $R^{36}$-substituted or unsubstituted heteroalkyl, $R^{36}$-substituted or unsubstituted cycloalkyl, $R^{36}$-substituted or unsubstituted heterocycloalkyl, $R^{36}$-substituted or unsubstituted aryl, or $R^{36}$-substituted or unsubstituted heteroaryl. $X^3$ is independently halogen. In embodiments, $X^3$ is independently F or Cl.

$R^{36}$ is independently oxo, halogen, —$CX^{36}{}_3$, —$CHX^{36}{}_2$, —$OCH_2X^{36}$, —$OCHX^{36}{}_2$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{36}{}_3$, —$OCHX^{36}{}_2$, $R^{37}$-substituted or unsubstituted alkyl, $R^{37}$-substituted or unsubstituted heteroalkyl, $R^{37}$-substituted or unsubstituted cycloalkyl, $R^{37}$-substituted or unsubstituted heterocycloalkyl, $R^{37}$-substituted or unsubstituted aryl, or $R^{37}$-substituted or unsubstituted heteroaryl. $X^{36}$ is independently halogen. In embodiments, $X^{36}$ is independently F or Cl.

$R^{37}$ is independently oxo, halogen, —$CX^{37}{}_3$, —$CHX^{37}{}_2$, —$OCH_2X^{37}$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{37}{}_3$, —$OCHX^{37}{}_2$, $R^{38}$-substituted or unsubstituted alkyl, $R^{38}$-substituted or unsubstituted heteroalkyl, $R^{38}$-substituted or unsubstituted cycloalkyl, $R^{38}$ substituted or unsubstituted heterocycloalkyl, $R^{38}$-substituted or unsubstituted aryl, or $R^{38}$-substituted or unsubstituted heteroaryl. $X^{37}$ is independently halogen. In embodiments, $X^{37}$ is independently F or Cl.

$R^3$ may independently be halogen, —$CX_3$, —CN, —$SO_nR^{10}$, —$SO_vNR^7R^8$, —$NHNR^7R^8$, —$ONR^7R^8$, —NHC=(O)$NHNR^7R^8$, —NHC=(O)$NR^7R^8$, —N(O)$_m$, —$NR^7R^8$, —C(O)$R^9$, —C(O)—$OR^9$, —C(O)$NR^7R^8$, —$OR^{10}$, —$NR^7SO_2R^{10}$, —$NR^7C$=(O)$R^9$, —$NR^7C(O)OR^9$, —$NR^7OR^9$, —$CHX_2$, —$CH_2X$, —$OCX_3$, —$OCHX_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^3$ is hydrogen. In embodiments, $R^3$ is independently halogen. In embodiments, $R^3$ is —$CX_3$. In embodiments, $R^3$ is —CN. In embodiments, $R^3$ is —$SO_nR^{10}$. In embodiments, $R^3$ is —$SO_vNR^7R^8$. In embodiments, $R^3$ is —$NHNR^7R^8$. In embodiments, $R^3$ is —$ONR^7R^8$. In embodiments, $R^3$ is —NHC=(O)$NHNR^7R^8$. In embodiments, $R^3$ is —NHC=(O)$NR^7R^8$. In embodiments, $R^3$ is —N(O)$_m$. In embodiments, $R^3$ is —$NR^7R^8$. In embodiments, $R^3$ is —C(O)$R^9$. In embodiments, $R^3$ is —C(O)—$OR^9$. In embodiments, $R^3$ is —C(O)$NR^7R^8$. In embodiments, $R^3$ is —$OR^{10}$. In embodiments, $R^3$ is —$NR^7SO_2R^{10}$. In embodiments, $R^3$ is —$NR^7C$=(O)$R^9$. In embodiments, $R^3$ is —$NR^7C(O)OR^9$. In embodiments, $R^3$ is —$NR^7OR^9$. In embodiments, $R^3$ is —$CHX_2$. In embodiments, $R^3$ is —$CH_2X$. In embodiments, $R^3$ is —$OCX_3$. In embodiments, $R^3$ is —$OCHX_2$. In embodiments, $R^3$ is substituted or unsubstituted alkyl. In embodiments, $R^3$ is substituted or unsubstituted heteroalkyl. In embodiments, $R^3$ is substituted or unsubstituted cycloalkyl. In embodiments, $R^3$ is substituted or unsubstituted heterocycloalkyl. In embodiments, $R^3$ is substituted or unsubstituted aryl. In embodiments, $R^3$ is substituted or unsubstituted heteroaryl. In embodiments, $R^3$ is substituted alkyl. In embodiments, $R^3$ is substituted heteroalkyl. In embodiments, $R^3$ is substituted cycloalkyl. In embodiments, $R^3$ is substituted heterocycloalkyl. In embodiments, $R^3$ is substituted aryl. In embodiments, $R^3$ is substituted heteroaryl. In embodiments, $R^3$ is unsubstituted alkyl. In embodiments, $R^3$ is unsubstituted heteroalkyl. In embodiments, $R^3$ is unsubstituted cycloalkyl. In embodiments, $R^3$ is unsubstituted heterocycloalkyl. In embodiments, $R^3$ is unsubstituted aryl. In embodiments, $R^3$ is unsubstituted heteroaryl.

In embodiments, $R^3$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, $OCF_3$, —$OCHF_2$, substituted or unsubstituted ($C_1$-$C_5$) alkyl, or substituted or unsubstituted 2 to 5 membered heteroalkyl. In embodiments, $R^3$ is independently halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, $OCF_3$, —$OCHF_2$, substituted or unsubstituted ($C_1$-$C_5$) alkyl, or substituted or unsubstituted 2 to 5 membered heteroalkyl.

In embodiments, $R^3$ is independently halogen. In embodiments, $R^3$ is independently —$CF_3$. In embodiments, $R^3$ is independently —CN. In embodiments, $R^3$ is independently —OH. In embodiments, $R^3$ is independently —$NH_2$. In embodiments, $R^3$ is independently —COOH. In embodiments, $R^3$ is independently —$CONH_2$. In embodiments, $R^3$ is independently —$NO_2$. In embodiments, $R^3$ is independently —SH. In embodiments, $R^3$ is independently —$SO_3H$. In embodiments, $R^3$ is independently —$SO_4H$. In embodiments, $R^3$ is independently —$SO_2NH_2$. In embodiments, $R^3$ is independently —$NHNH_2$. In embodiments, $R^3$ is independently —$ONH_2$. In embodiments, $R^3$ is independently —NHC=(O)$NHNH_2$. In embodiments, $R^3$ is independently —NHC=(O)$NH_2$. In embodiments, $R^3$ is independently —$NHSO_2H$. In embodiments, $R^3$ is independently —NHC=(O)H. In embodiments, $R^3$ is independently —NHC(O)OH. In embodiments, $R^3$ is independently —NHOH. In embodiments, $R^3$ is independently —$CHF_2$. In embodiments, $R^3$ is independently —$CH_2F$. In embodiments, $R^3$ is independently —$OCF_3$. In embodiments, $R^3$ is independently —$OCHF_2$. In embodiments, $R^3$ is independently substituted or unsubstituted ($C_1$-$C_5$) alkyl. In embodiments, $R^3$ is independently substituted or unsubstituted 2 to 5 membered heteroalkyl. In embodiments, $R^3$ is independently substituted ($C_1$-$C_5$) alkyl. In embodiments, $R^3$ is independently substituted 2 to 5 membered heteroalkyl. In embodiments, $R^3$ is independently unsubstituted ($C_1$-$C_5$) alkyl. In embodiments, $R^3$ is independently unsubstituted 2 to 5 membered heteroalkyl. In embodiments, $R^3$ is independently substituted or unsubstituted butyl. In embodiments, $R^3$ is independently substituted or unsubstituted butoxy. In embodiments, $R^3$ is independently substituted butyl. In embodiments, $R^3$ is independently substituted butoxy. In embodiments, $R^3$ is independently unsubstituted butyl. In embodiments, $R^3$ is independently unsubstituted butoxy. In embodiments, $R^3$ is independently substituted or unsubstituted propyl. In embodiments, $R^3$ is independently substituted or unsubstituted propoxy. In embodiments, $R^3$ is independently substituted propyl. In embodiments, $R^3$ is independently substituted propoxy. In embodiments, $R^3$ is independently unsubstituted propyl. In embodiments, $R^3$ is independently unsubstituted propoxy. In embodiments, $R^3$ is independently substituted or unsubstituted ethyl. In embodiments, $R^3$ is independently substituted or unsubstituted ethoxy. In embodiments, $R^3$ is independently substituted ethyl. In embodiments, $R^3$ is independently substituted ethoxy. In embodiments, $R^3$ is independently unsubstituted ethyl. In embodiments, $R^3$ is independently unsubstituted ethoxy. In embodiments, $R^3$ is independently substituted or unsubstituted methyl. In embodiments, $R^3$ is independently substituted or unsubstituted methoxy. In embodiments, $R^3$ is independently substituted methyl. In embodiments, $R^3$ is independently substituted methoxy. In embodiments, $R^3$ is independently unsubstituted methyl. In embodiments, $R^3$ is independently unsubstituted methoxy. In embodiments, $R^3$ is independently hydrogen.

In embodiments, $R^{3D}$ and $R^{3B}$ may optionally be joined to form a substituted or unsubstituted cycloalkyl, substituted or unsubstituted heterocycloalkyl, substituted or unsubstituted aryl, or substituted or unsubstituted heteroaryl. In embodiments, $R^{3B}$ and $R^{3A}$ may optionally be joined to form a substituted or unsubstituted cycloalkyl, substituted or unsubstituted heterocycloalkyl, substituted or unsubstituted aryl, or substituted or unsubstituted heteroaryl. In embodiments, $R^{3A}$ and $R^{3C}$ may optionally be joined to form a substituted or unsubstituted cycloalkyl, substituted or unsubstituted heterocycloalkyl, substituted or unsubstituted aryl, or substituted or unsubstituted heteroaryl. In embodiments, $R^{3C}$ and $R^{3E}$ may optionally be joined to form a substituted or unsubstituted cycloalkyl, substituted or unsubstituted heterocycloalkyl, substituted or unsubstituted aryl, or substituted or unsubstituted heteroaryl.

$R^{3A}$ is independently hydrogen, halogen, $-CX_3$, $-CN$, $-SO_nR^{10}$, $-SO_vNR^7R^8$, $-NHNR^7R^8$, $-ONR^7R^8$, $-NHC=(O)NHNR^7R^8$, $-NHC=(O)NR^7R^8$, $-N(O)_m$, $-NR^7R^8$, $-C(O)R^9$, $-C(O)-OR^9$, $-C(O)NR^7R^8$, $-OR^{10}$, $-NR^7SO_2R^{10}$, $-NR^7C=(O)R^9$, $-NR^7C(O)OR^9$, $-NR^7OR^9$, $-CHX_2$, $-CH_2X$, $-OCX_3$, $-OCHX_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{3A}$ is hydrogen, halogen, $-CX^{3A}_3$, $-CHX^{3A}_2$, $-OCH_2X^{3A}$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{3A}_3$, $-OCHX^{3A}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{3A}$ is independently hydrogen, oxo, halogen, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-CHF_2$, $-CH_2F$, $OCF_3$, $-OCHF_2$, substituted or unsubstituted $(C_1-C_5)$ alkyl, or substituted or unsubstituted 2 to 5 membered heteroalkyl. In embodiments, $R^{3A}$ is independently halogen, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-CHF_2$, $-CH_2F$, $OCF_3$, $-OCHF_2$, substituted or unsubstituted $(C_1-C_5)$ alkyl, or substituted or unsubstituted 2 to 5 membered heteroalkyl.

In embodiments, $R^{3A}$ is independently halogen. In embodiments, $R^{3A}$ is independently $-CF_3$. In embodiments, $R^{3A}$ is independently $-CN$. In embodiments, $R^{3A}$ is independently $-OH$. In embodiments, $R^{3A}$ is independently $-NH_2$. In embodiments, $R^{3A}$ is independently $-COOH$. In embodiments, $R^{3A}$ is independently $-CONH_2$. In embodiments, $R^{3A}$ is independently $-NO_2$. In embodiments, $R^{3A}$ is independently $-SH$. In embodiments, $R^{3A}$ is independently $-SO_3H$. In embodiments, $R^{3A}$ is independently $-SO_4H$. In embodiments, $R^{3A}$ is independently $-SO_2NH_2$. In embodiments, $R^{3A}$ is independently $-NHNH_2$. In embodiments, $R^{3A}$ is independently $-ONH_2$. In embodiments, $R^{3A}$ is independently $-NHC=(O)NHNH_2$. In embodiments, $R^{3A}$ is independently $-NHC=(O)NH_2$. In embodiments, $R^{3A}$ is independently $-NHSO_2H$. In embodiments, $R^{3A}$ is independently $-NHC=(O)H$. In embodiments, $R^{3A}$ is independently $-NHC(O)OH$. In embodiments, $R^{3A}$ is independently $-NHOH$. In embodiments, $R^{3A}$ is independently $-CHF_2$. In embodiments, $R^{3A}$ is independently $-CH_2F$. In embodiments, $R^{3A}$ is independently $-OCF_3$. In embodiments, $R^{3A}$ is independently $-OCH_{F2}$.

In embodiments, $R^{3A}$ is independently substituted or unsubstituted $(C_1-C_5)$ alkyl. In embodiments, $R^{3A}$ is independently substituted or unsubstituted 2 to 5 membered heteroalkyl. In embodiments, $R^{3A}$ is independently substituted $(C_1-C_5)$ alkyl. In embodiments, $R^{3A}$ is independently substituted 2 to 5 membered heteroalkyl. In embodiments, $R^{3A}$ is independently unsubstituted $(C_1-C_5)$ alkyl. In embodiments, $R^{3A}$ is independently unsubstituted 2 to 5 membered heteroalkyl. In embodiments, $R^{3A}$ is independently substituted or unsubstituted butyl. In embodiments, $R^{3A}$ is independently substituted or unsubstituted butoxy. In embodiments, $R^{3A}$ is independently substituted butyl. In embodiments, $R^{3A}$ is independently substituted butoxy. In embodiments, $R^{3A}$ is independently unsubstituted butyl. In embodiments, $R^{3A}$ is independently unsubstituted butoxy. In embodiments, $R^{3A}$ is independently substituted or unsubstituted propyl. In embodiments, $R^{3A}$ is independently substituted or unsubstituted propoxy. In embodiments, $R^{3A}$ is independently substituted propyl. In embodiments, $R^{3A}$ is independently substituted propoxy. In embodiments, $R^{3A}$ is independently unsubstituted propyl. In embodiments, $R^{3A}$ is independently unsubstituted propoxy. In embodiments, $R^{3A}$ is independently substituted or unsubstituted ethyl. In embodiments, $R^{3A}$ is independently substituted or unsubstituted ethoxy. In embodiments, $R^{3A}$ is independently substituted ethyl. In embodiments, $R^{3A}$ is independently substituted ethoxy. In embodiments, $R^{3A}$ is independently unsubstituted ethyl. In embodiments, $R^{3A}$ is independently unsubstituted ethoxy. In embodiments, $R^{3A}$ is independently substituted or unsubstituted methyl. In embodiments, $R^{3A}$ is independently substituted or unsubstituted methoxy. In embodiments, $R^{3A}$ is independently substituted methyl. In embodiments, $R^{3A}$ is independently substituted methoxy. In embodiments, $R^{3A}$ is independently unsubstituted methyl. In embodiments, $R^{3A}$ is independently unsubstituted methoxy. In embodiments, $R^{3A}$ is independently hydrogen.

In embodiments, $R^{3A}$ is independently hydrogen, halogen, $-CX^{3A}_3$, $-CHX^{3A}_2$, $-OCH_2X^{3A}$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, —NHC═(O)H, —NHC(O)—OH, —NHOH, —OCX$^{3A}_3$, —OCHX$^{3A}_2$, R$^{36A}$-substituted or unsubstituted alkyl, R$^{36A}$-substituted or unsubstituted heteroalkyl, R$^{36A}$-substituted or unsubstituted cycloalkyl, R$^{36A}$-substituted or unsubstituted heterocycloalkyl, R$^{36A}$-substituted or unsubstituted aryl, or R$^{36A}$-substituted or unsubstituted heteroaryl. X$^{3A}$ is independently halogen. In embodiments, X$^{3A}$ is independently F or Cl.

R$^{36A}$ is independently oxo, halogen, —CX$^{36A}_3$, —CHX$^{36A}_2$, —OCH$_2$X$^{36A}$, —OCHX$^{36A}_2$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCX$^{36}_3$, —OCHX$^{36}_2$, R$^{37A}$-substituted or unsubstituted alkyl, R$^{37A}$-substituted or unsubstituted heteroalkyl, R$^{37A}$-substituted or unsubstituted cycloalkyl, R$^{37A}$-substituted or unsubstituted heterocycloalkyl, R$^{37A}$-substituted or unsubstituted aryl, or R$^{37A}$-substituted or unsubstituted heteroaryl. X$^{36A}$ is independently halogen. In embodiments, X$^{36A}$ is independently F or Cl.

R$^{37A}$ is independently oxo, halogen, —CX$^{37A}_3$, —CHX$^{37A}_2$, —OCH$_2$X$^{37A}$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCX$^{37A}_3$, —OCHX$^{37A}_2$, R$^{38A}$-substituted or unsubstituted alkyl, R$^{38A}$-substituted or unsubstituted heteroalkyl, R$^{38A}$-substituted or unsubstituted cycloalkyl, R$^{38A}$-substituted or unsubstituted heterocycloalkyl, R$^{38A}$-substituted or unsubstituted aryl, or R$^{38A}$-substituted or unsubstituted heteroaryl. X$^{37A}$ is independently halogen. In embodiments, X$^{37A}$ is independently F or Cl.

R$^{3B}$ is independently hydrogen, halogen, —CX$_3$, —CN, —SO$_n$R$^{10}$, —SO$_v$NR$^7$R$^8$, —NHNR$^7$R$^8$, —ONR$^7$R$^8$, —NHC═(O)NHNR$^7$R$^8$, —NHC═(O)NR$^7$R$^8$, —N(O)$_m$, —NR$^7$R$^8$, —C(O)R$^9$, —C(O)—OR$^9$, —C(O)NR$^7$R$^8$, —OR$^{10}$, —NR$^7$SO$_2$R$^{10}$, —NR$^7$C═(O)R$^9$, —NR$^7$C(O)OR$^9$, —NR$^7$OR$^9$, —CHX$_2$, —CH$_2$X, —OCX$_3$, —OCHX$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, R$^{3B}$ is hydrogen, oxo, halogen, —CX$^{3B}_3$, —CHX$^{3B}_2$, —OCH$_2$X$^{3B}$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCX$^{3B}_3$, —OCHX$^{3B}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, R$^{3B}$ is independently hydrogen, halogen, —CX$^{3B}_3$, —CHX$^{3B}_2$, —OCH$_2$X$^{3B}$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCX$^{3B}_3$, —OCHX$^{3B}_2$, R$^{36B}$-substituted or unsubstituted alkyl, R$^{36B}$-substituted or unsubstituted heteroalkyl, R$^{36B}$-substituted or unsubstituted cycloalkyl, alkyl, R$^{36B}$-substituted or unsubstituted heterocycloalkyl, R$^{36B}$-substituted or unsubstituted aryl, or R$^{36B}$-substituted or unsubstituted heteroaryl. X$^{3B}$ is independently halogen. In embodiments, X$^{3B}$ is independently F or Cl.

R$^{36B}$ is independently oxo, halogen, —CX$^{36B}_3$, —CHX$^{36B}_2$, —OCH$_2$X$^{36B}$, —OCHX$^{36B}_2$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCX$^{36B}_3$, —OCHX$^{36B}_2$, R$^{37B}$-substituted or unsubstituted alkyl, R$^{37B}$-substituted or unsubstituted heteroalkyl, R$^{37B}$-substituted or unsubstituted cycloalkyl, R$^{37B}$-substituted or unsubstituted heterocycloalkyl, R$^{37B}$-substituted or unsubstituted aryl, or R$^{37B}$-substituted or unsubstituted heteroaryl. X$^{36B}$ is independently halogen. In embodiments, X$^{36B}$ is independently F or Cl.

R$^{37B}$ is independently oxo, halogen, —CX$^{37B}_3$, —CHX$^{37B}_2$, —OCH$_2$X$^{37B}$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCX$^{37B}_3$, —OCHX$^{37B}_2$, R$^{38B}$-substituted or unsubstituted alkyl, R$^{38B}$-substituted or unsubstituted heteroalkyl, R$^{38B}$-substituted or unsubstituted cycloalkyl, R$^{38B}$-substituted or unsubstituted heterocycloalkyl, R$^{38B}$-substituted or unsubstituted aryl, or R$^{38B}$-substituted or unsubstituted heteroaryl. X$^{37B}$ is independently halogen. In embodiments, X$^{37B}$ is independently F or Cl.

In embodiments, R$^{3B}$ is independently hydrogen, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)OH, —NHOH, —CHF$_2$, —CH$_2$F, OCF$_3$, —OCHF$_2$, substituted or unsubstituted (C$_1$-C$_5$) alkyl, or substituted or unsubstituted 2 to 5 membered heteroalkyl. In embodiments, R$^{3B}$ is independently halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)OH, —NHOH, —CHF$_2$, —CH$_2$F, OCF$_3$, —OCHF$_2$, substituted or unsubstituted (C$_1$-C$_5$) alkyl, or substituted or unsubstituted 2 to 5 membered heteroalkyl. In embodiments, R$^{3B}$ is independently halogen. R$^{3B}$ is independently —CF$_3$. In embodiments, R$^{3B}$ is independently —CN. In embodiments, R$^{3B}$ is independently —OH. In embodiments, R$^{3B}$ is independently —NH$_2$. In embodiments, R$^{3B}$ is independently —COOH. In embodiments, R$^{3B}$ is independently —CONH$_2$. In embodiments, R$^{3B}$ is independently —NO$_2$. In embodiments, R$^{3B}$ is independently —SH. In embodiments, R$^{3B}$ is independently —SO$_3$H. In embodiments, R$^{3B}$ is independently —SO$_{4H}$. In embodiments, R$^{3B}$ is independently —SO$_2$NH$_2$. In embodiments, R$^{3B}$ is independently —NHNH$_2$. In embodiments, R$^{3B}$ is independently —ONH$_2$. In embodiments, R$^{3B}$ is independently —NHC═(O)NHNH$_2$. In embodiments, R$^{3B}$ is independently —NHC═(O)NH$_2$. In embodiments, R$^{3B}$ is independently —NHSO$_2$H. In embodiments, R$^{3B}$ is independently —NHC═(O)H. In embodiments, R$^{3B}$ is independently —NHC(O)OH. In embodiments, R$^{3B}$ is independently —NHOH. In embodiments, R$^{3B}$ is independently —CHF$_2$. In embodiments, R$^{3B}$ is independently —CH$_2$F. In embodiments, R$^{3B}$ is independently —OCF$_3$. In embodiments, R$^{3B}$ is independently —OCHF$_2$. In embodiments, R$^{3B}$ is independently substituted or unsubstituted (C$_1$-C$_5$)

alkyl. In embodiments, $R^{3B}$ is independently substituted or unsubstituted 2 to 5 membered heteroalkyl.

In embodiments, $R^{3B}$ is independently substituted $(C_1-C_5)$ alkyl. In embodiments, $R^{3B}$ is independently substituted 2 to 5 membered heteroalkyl. In embodiments, $R^{3B}$ is independently unsubstituted $(C_1-C_5)$ alkyl. In embodiments, $R^{3B}$ is independently unsubstituted 2 to 5 membered heteroalkyl. In embodiments, $R^{3B}$ is independently substituted or unsubstituted butyl. In embodiments, $R^{3B}$ is independently substituted or unsubstituted butoxy. In embodiments, $R^{3B}$ is independently substituted butyl. In embodiments, $R^{3B}$ is independently substituted butoxy. In embodiments, $R^{3B}$ is independently unsubstituted butyl. In embodiments, $R^{3B}$ is independently unsubstituted butoxy. In embodiments, $R^{3B}$ is independently substituted or unsubstituted propyl. In embodiments, $R^{3B}$ is independently substituted or unsubstituted propoxy. In embodiments, $R^{3B}$ is independently substituted propyl. In embodiments, $R^{3B}$ is independently substituted propoxy. In embodiments, $R^{3B}$ is independently unsubstituted propyl. In embodiments, $R^{3B}$ is independently unsubstituted propoxy. In embodiments, $R^{3B}$ is independently substituted or unsubstituted ethyl. In embodiments, $R^{3B}$ is independently substituted or unsubstituted ethoxy. In embodiments, $R^{3B}$ is independently substituted ethyl. In embodiments, $R^{3B}$ is independently substituted ethoxy. In embodiments, $R^{3B}$ is independently unsubstituted ethyl. In embodiments, $R^{3B}$ is independently unsubstituted ethoxy. In embodiments, $R^{3B}$ is independently substituted or unsubstituted methyl. In embodiments, $R^{3B}$ is independently substituted or unsubstituted methoxy. In embodiments, $R^{3B}$ is independently substituted methyl. In embodiments, $R^{3B}$ is independently substituted methoxy. In embodiments, $R^{3B}$ is independently unsubstituted methyl. In embodiments, $R^{3B}$ is independently unsubstituted methoxy. In embodiments, $R^{3B}$ is independently hydrogen.

$R^{3C}$ is independently hydrogen, halogen, —CX$_3$, —CN, —SO$_n$R$^{10}$, —SO$_v$NR$^7$R$^8$, —NHNR$^7$R$^8$, —ONR$^7$R$^8$, —NHC=(O)NHNR$^7$R$^8$, —NHC=(O)NR$^7$R$^8$, —N(O)$_m$, —NR$^7$R$^8$, —C(O)R$^9$, —C(O)—OR$^9$, —C(O)NR$^7$R$^8$, —OR$^{10}$, —NR$^7$SO$_2$R, —NR$^7$C=(O)R$^9$, —NR$^7$C(O)OR$^9$, —NR$^7$OR$^9$, —CHX$_2$, —CH$_2$X, —OCX$_3$, —OCHX$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{3C}$ is hydrogen, oxo, halogen, —CX$^{3C}_3$, —CHX$^{3C}_2$, —OCH$_2$X$^{3C}$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{3C}_3$, —OCHX$^{3C}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{3C}$ is independently hydrogen, halogen, —CX$^{3C}_3$, —CHX$^{3C}_2$, —OCH$_2$X$^{3C}$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{3C}_3$, —OCHX$^{3C}_2$, R$^{36C}$-substituted or unsubstituted alkyl, R$^{36C}$-substituted or unsubstituted heteroalkyl, R$^{36C}$-substituted or unsubstituted cycloalkyl, R$^{36C}$-substituted or unsubstituted heterocycloalkyl, R$^{36C}$-substituted or unsubstituted aryl, or R$^{36C}$-substituted or unsubstituted heteroaryl. X$^{3C}$ is independently halogen. In embodiments, X$^{3C}$ is independently F or Cl.

$R^{36C}$ is independently oxo, halogen, —CX$^{36C}_3$, —CHX$^{36C}_2$, —OCH$_2$X$^{36C}$, —OCHX$^{36C}_2$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{36C}_3$, —OCHX$^{36C}_2$, R$^{37C}$ substituted or unsubstituted alkyl, R$^{37C}$-substituted or unsubstituted heteroalkyl, R$^{37C}$-substituted or unsubstituted cycloalkyl, R$^{37C}$-substituted or unsubstituted heterocycloalkyl, R$^{37C}$-substituted or unsubstituted aryl, or R$^{37C}$-substituted or unsubstituted heteroaryl. X$^{36C}$ is independently halogen. In embodiments, X$^{36C}$ is independently F or Cl.

$R^{37C}$ is independently oxo, halogen, —CX$^{37C}_3$, —CHX$^{37C}_2$, —OCH$_2$X$^{37C}$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{37C}_3$, —OCHX$^{37C}_2$, R$^{38C}$-substituted or unsubstituted alkyl, R$^{38C}$-substituted or unsubstituted heteroalkyl, R$^{38C}$-substituted or unsubstituted cycloalkyl, R$^{38C}$-substituted or unsubstituted heterocycloalkyl, R$^{38C}$-substituted or unsubstituted aryl, or R$^{38C}$-substituted or unsubstituted heteroaryl. X$^{37C}$ is independently halogen. In embodiments, X$^{37C}$ is independently F or Cl.

In embodiments, $R^{3C}$ is independently hydrogen, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —CHF$_2$, —CH$_2$F, OCF$_3$, —OCHF$_2$, substituted or unsubstituted $(C_1-C_5)$ alkyl, or substituted or unsubstituted 2 to 5 membered heteroalkyl. In embodiments, $R^{3C}$ is independently halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —CHF$_2$, —CH$_2$F, OCF$_3$, —OCHF$_2$, substituted or unsubstituted $(C_1-C_5)$ alkyl, or substituted or unsubstituted 2 to 5 membered heteroalkyl. In embodiments, $R^{3C}$ is independently halogen. In embodiments, $R^{3C}$ is independently —CF$_3$. In embodiments, $R^{3C}$ is independently —CN. In embodiments, $R^{3C}$ is independently —OH. In embodiments, $R^{3C}$ is independently —NH$_2$. In embodiments, $R^{3C}$ is independently —COOH. In embodiments, $R^{3C}$ is independently —CONH$_2$. In embodiments, $R^{3C}$ is independently —NO$_2$. In embodiments, $R^{3C}$ is independently —SH. In embodiments, $R^{3C}$ is independently —SO$_3$H. In embodiments, $R^{3C}$ is independently —SO$_{4H}$. In embodiments, $R^{3C}$ is independently —SO$_2$NH$_2$. In embodiments, $R^{3C}$ is independently —NHNH$_2$. In embodiments, $R^{3C}$ is independently —ONH$_2$. In embodiments, $R^{3C}$ is independently —NHC=(O)NHNH$_2$. In embodiments, $R^{3C}$ is independently —NHC=(O)NH$_2$. In embodiments, $R^{3C}$ is independently —NHSO$_2$H. In embodiments, $R^{3C}$ is independently —NHC=(O)H. In embodiments, $R^{3C}$ is independently —NHC(O)OH. In embodiments, $R^{3C}$ is independently —NHOH. In embodiments, $R^{3C}$ is independently —CHF$_2$. In embodiments, $R^{3C}$ is independently —CH$_2$F. In embodiments, $R^{3C}$ is independently —OCF$_3$. In embodiments, $R^{3C}$ is independently —OCHF$_2$.

In embodiments, $R^{3C}$ is independently substituted or unsubstituted $(C_1-C_5)$ alkyl. In embodiments, $R^{3C}$ is independently substituted or unsubstituted 2 to 5 membered heteroalkyl. In embodiments, $R^{3C}$ is independently substituted ($C_1$-$C_5$) alkyl. In embodiments, $R^{3C}$ is independently substituted 2 to 5 membered heteroalkyl. In embodiments, $R^{3C}$ is independently unsubstituted ($C_1$-$C_5$) alkyl. In embodiments, $R^{3C}$ is independently unsubstituted 2 to 5 membered heteroalkyl. In embodiments, $R^{3C}$ is independently substituted or unsubstituted butyl. In embodiments, $R^{3C}$ is independently substituted or unsubstituted butoxy. In embodiments, $R^{3C}$ is independently substituted butyl. In embodiments, $R^{3C}$ is independently substituted butoxy. In embodiments, $R^{3C}$ is independently unsubstituted butyl. In embodiments, $R^{3C}$ is independently unsubstituted butoxy. In embodiments, $R^{3C}$ is independently substituted or unsubstituted propyl. In embodiments, $R^{3C}$ is independently substituted or unsubstituted propoxy. In embodiments, $R^{3C}$ is independently substituted propyl. In embodiments, $R^{3C}$ is independently substituted propoxy. In embodiments, $R^{3C}$ is independently unsubstituted propyl. In embodiments, $R^{3C}$ is independently unsubstituted propoxy. In embodiments, $R^{3C}$ is independently substituted or unsubstituted ethyl. In embodiments, $R^{3C}$ is independently substituted or unsubstituted ethoxy. In embodiments, $R^{3C}$ is independently substituted ethyl. In embodiments, $R^{3C}$ is independently substituted ethoxy. In embodiments, $R^{3C}$ is independently unsubstituted ethyl. In embodiments, $R^{3C}$ is independently unsubstituted ethoxy. In embodiments, $R^{3C}$ is independently substituted or unsubstituted methyl. In embodiments, $R^{3C}$ is independently substituted or unsubstituted methoxy. In embodiments, $R^{3C}$ is independently substituted methyl. In embodiments, $R^{3C}$ is independently substituted methoxy. In embodiments, $R^{3C}$ is independently unsubstituted methyl. In embodiments, $R^{3C}$ is independently unsubstituted methoxy. In embodiments, $R^{3C}$ is independently hydrogen.

$R^{3D}$ is independently hydrogen, halogen, —$CX_3$, —CN, —$SO_nR^{10}$, —$SO_vNR^7R^8$, —$NHNR^7R^8$, —$ONR^7R^8$, —NHC=(O)NHNR$^7$R$^8$, —NHC=(O)NR$^7$R$^8$, —N(O)$_m$, —NR$^7$R$^8$, —C(O)R$^9$, —C(O)—OR$^9$, —C(O)NR$^7$R$^8$, —OR$^{10}$, —NR$^7$SO$_2$R$^{10}$, —NR$^7$C=(O)R$^9$, —NR$^7$C(O)OR$^9$, —NR$^7$OR$^9$, —$CHX_2$, —$CH_2X$, —$OCX_3$, —$OCHX_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{3D}$ is hydrogen, oxo, halogen, —$CX^{3D}_3$, —$CHX^{3D}_2$, —$OCH_2X^{3D}$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, —$OCX^{3D}_3$, —$OCHX^{3D}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{3D}$ is independently hydrogen, halogen, —$CX^{3D}_3$, —$CHX^{3D}_2$, —$OCH_2X^{3D}$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, —$OCX^{3D}_3$, —$OCHX^{3D}_2$, $R^{36D}$-substituted or unsubstituted alkyl, $R^{36D}$-substituted or unsubstituted heteroalkyl, $R^{36D}$-substituted or unsubstituted cycloalkyl, $R^{36D}$-substituted or unsubstituted heterocycloalkyl, $R^{36D}$-substituted or unsubstituted aryl, or $R^{36D}$-substituted or unsubstituted heteroaryl. $X^{3D}$ is independently halogen. In embodiments, $X^{3D}$ is independently F or Cl.

$R^{36D}$ is independently oxo, halogen, —$CX^{36D}_3$, —$CHX^{36D}_2$, —$OCH_2X^{36D}$, —$OCHX^{36D}_2$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, —$OCX^{36D}_3$, —$OCHX^{36D}_2$, $R^{37D}$-substituted or unsubstituted alkyl, $R^{37D}$-substituted or unsubstituted heteroalkyl, $R^{37D}$-substituted or unsubstituted cycloalkyl, $R^{37D}$-substituted or unsubstituted heterocycloalkyl, $R^{37D}$-substituted or unsubstituted aryl, or $R^{37D}$-substituted or unsubstituted heteroaryl. $X^{36D}$ is independently halogen. In embodiments, $X^{36D}$ is independently F or Cl.

$R^{37D}$ is independently oxo, halogen, —$CX^{37D}_3$, —$CHX^{37D}_2$, —$OCH_2X^{37D}$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, —$OCX^{37D}_3$, —$OCHX^{37D}_2$, $R^{38D}$-substituted or unsubstituted alkyl, $R^{38D}$-substituted or unsubstituted heteroalkyl, $R^{38D}$-substituted or unsubstituted cycloalkyl, $R^{38D}$-substituted or unsubstituted heterocycloalkyl, $R^{38D}$-substituted or unsubstituted aryl, or $R^{38D}$-substituted or unsubstituted heteroaryl. $X^{37D}$ is independently halogen. In embodiments, $X^{37D}$ is independently F or Cl.

In embodiments, $R^{3D}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)OH, —NHOH, —$CHF_2$, —$CH_2F$, $OCF_3$, —$OCHF_2$, substituted or unsubstituted ($C_1$-$C_5$) alkyl, or substituted or unsubstituted 2 to 5 membered heteroalkyl. In embodiments, $R^{3D}$ is independently halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)OH, —NHOH, —$CHF_2$, —$CH_2F$, $OCF_3$, —$OCHF_2$, substituted or unsubstituted ($C_1$-$C_5$) alkyl, or substituted or unsubstituted 2 to 5 membered heteroalkyl. In embodiments, $R^{3D}$ is independently halogen. In embodiments, $R^{3D}$ is independently —$CF_3$. In embodiments, $R^{3D}$ is independently —CN. In embodiments, $R^{3D}$ is independently —OH. In embodiments, $R^{3D}$ is independently —$NH_2$. In embodiments, $R^{3D}$ is independently —COOH. In embodiments, $R^{3D}$ is independently —$CONH_2$. In embodiments, $R^{3D}$ is independently —$NO_2$. In embodiments, $R^{3D}$ is independently —SH. In embodiments, $R^{3D}$ is independently —$SO_3H$. In embodiments, $R^{3D}$ is independently —$SO_{4H}$. In embodiments, $R^{3D}$ is independently —$SO_2NH_2$. In embodiments, $R^{3D}$ is independently —$NHNH_2$. In embodiments, $R^{3D}$ is independently —$ONH_2$. In embodiments, $R^{3D}$ is independently —NHC=(O)NHNH$_2$. In embodiments, $R^{3D}$ is independently —NHC=(O)NH$_2$. In embodiments, $R^{3D}$ is independently —NHSO$_2$H. In embodiments, $R^{3D}$ is independently —NHC=(O)H. In embodiments, $R^{3D}$ is independently —NHC(O)OH. In embodiments, $R^{3D}$ is independently —NHOH. In embodiments, $R^{3D}$ is independently —$CHF_2$. In embodiments, $R^{3D}$ is independently —$CH_2F$. In embodiments, $R^{3D}$ is independently —$OCF_3$. In embodiments, $R^{3D}$ is independently —$OCHF_2$.

In embodiments, $R^{3D}$ is independently substituted or unsubstituted ($C_1$-$C_5$) alkyl. In embodiments, $R^{3D}$ is independently substituted or unsubstituted 2 to 5 membered heteroalkyl. In embodiments, $R^{3D}$ is independently substituted ($C_1$-$C_5$) alkyl. In embodiments, $R^{3D}$ is independently substituted 2 to 5 membered heteroalkyl. In embodiments, $R^{3D}$ is independently unsubstituted ($C_1$-$C_5$) alkyl. In embodiments, $R^{3D}$ is independently unsubstituted 2 to 5 membered heteroalkyl. In embodiments, $R^{3D}$ is independently substituted or unsubstituted butyl. In embodiments, $R^{3D}$ is independently substituted or unsubstituted butoxy. In embodiments, $R^{3D}$ is independently substituted butyl. In embodiments, $R^{3D}$ is independently substituted butoxy. In embodiments, $R^{3D}$ is independently unsubstituted butyl. In embodiments, $R^{3D}$ is independently unsubstituted butoxy. In embodiments, $R^{3D}$ is independently substituted or unsubstituted propyl. In embodiments, $R^{3D}$ is independently substituted or unsubstituted propoxy. In embodiments, $R^{3D}$ is independently substituted propyl. In embodiments, $R^{3D}$ is independently substituted propoxy. In embodiments, $R^{3D}$ is independently unsubstituted propyl. In embodiments, $R^{3D}$ is independently unsubstituted propoxy. In embodiments, $R^{3D}$ is independently substituted or unsubstituted ethyl. In embodiments, $R^{3D}$ is independently substituted or unsubstituted ethoxy. In embodiments, $R^{3D}$ is independently substituted ethyl. In embodiments, $R^{3D}$ is independently substituted ethoxy. In embodiments, $R^{3D}$ is independently unsubstituted ethyl. In embodiments, $R^{3D}$ is independently unsubstituted ethoxy. In embodiments, $R^{3D}$ is independently substituted or unsubstituted methyl. In embodiments, $R^{3D}$ is independently substituted or unsubstituted methoxy. In embodiments, $R^{3D}$ is independently substituted methyl. In embodiments, $R^{3D}$ is independently substituted methoxy. In embodiments, $R^{3D}$ is independently unsubstituted methyl. In embodiments, $R^{3D}$ is independently unsubstituted methoxy. In embodiments, $R^{3D}$ is independently hydrogen.

$R^{3E}$ is independently hydrogen, halogen, —$CX_3$, —CN, —$SO_nR^{10}$, —$SO_vNR^7R^8$, —$NHNR^7R^8$, —$ONR^7R^8$, —NHC=(O)$NHNR^7R^8$, —NHC=(O)$NR^7R^8$, —N(O)$_m$, —$NR^7R^8$, —C(O)$R^9$, —C(O)—$OR^9$, —C(O)$NR^7R^8$, —$OR^{10}$, —$NR^7SO_2R^{10}$, —$NR^7C$=(O)$R^9$, —$NR^7C(O)OR^9$, —$NR^7OR^9$, —$CHX_2$, —$CH_2X$, —$OCX_3$, —$OCHX_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{3E}$ is hydrogen, oxo, halogen, —$CX^{3E}{}_3$, —$CHX^{3E}{}_2$, —$OCH_2X^{3E}$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{3E}{}_3$, —$OCHX^{3E}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{3E}$ is independently hydrogen, halogen, —$CX^{3E}{}_3$, —$CHX^{3E}{}_2$, —$OCH_2X^{3E}$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{3E}{}_3$, —$OCHX^{3E}{}_2$, $R^{36E}$-substituted or unsubstituted alkyl, $R^{36E}$-substituted or unsubstituted heteroalkyl, $R^{36E}$-substituted or unsubstituted cycloalkyl, $R^{36E}$-substituted or unsubstituted heterocycloalkyl, $R^{36E}$-substituted or unsubstituted aryl, or $R^{36E}$-substituted or unsubstituted heteroaryl. $X^{3E}$ is independently halogen. In embodiments, $X^{3E}$ is independently F or Cl.

$R^{36E}$ is independently oxo, halogen, —$CX^{36E}{}_3$, —$CHX^{36E}{}_2$, —$OCH_2X^{36E}$, —$OCHX^{36E}{}_2$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{36E}{}_3$, —$OCHX^{36E}{}_2$, $R^{37E}$-substituted or unsubstituted alkyl, $R^{37E}$-substituted or unsubstituted heteroalkyl, $R^{37E}$-substituted or unsubstituted cycloalkyl, $R^{37E}$-substituted or unsubstituted heterocycloalkyl, $R^{37E}$-substituted or unsubstituted aryl, or $R^{37E}$-substituted or unsubstituted heteroaryl. $X^{36E}$ is independently halogen. In embodiments, $X^{36E}$ is independently F or Cl.

$R^{37E}$ is independently oxo, halogen, —$CX^{37E}{}_3$, —$CHX^{37E}{}_2$, —$OCH_2X^{37E}$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{37E}{}_3$, —$OCHX^{37E}{}_2$, $R^{38E}$-substituted or unsubstituted alkyl, $R^{38E}$-substituted or unsubstituted heteroalkyl, $R^{38E}$-substituted or unsubstituted cycloalkyl, $R^{38E}$-substituted or unsubstituted heterocycloalkyl, $R^{38E}$-substituted or unsubstituted aryl, or $R^{38E}$-substituted or unsubstituted heteroaryl. $X^{37E}$ is independently halogen. In embodiments, $X^{37E}$ is independently F or Cl.

In embodiments, $R^{3E}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, $OCF_3$, —$OCHF_2$, substituted or unsubstituted ($C_1$-$C_5$) alkyl, or substituted or unsubstituted 2 to 5 membered heteroalkyl. In embodiments, $R^{3E}$ is independently halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, $OCF_3$, —$OCHF_2$, substituted or unsubstituted ($C_1$-$C_5$) alkyl, or substituted or unsubstituted 2 to 5 membered heteroalkyl. In embodiments, $R^{3E}$ is independently halogen. In embodiments, $R^{3E}$ is independently —$CF_3$. In embodiments, $R^{3E}$ is independently —CN. In embodiments, $R^{3E}$ is independently —OH. In embodiments, $R^{3E}$ is independently —$NH_2$. In embodiments, $R^{3E}$ is independently —COOH. In embodiments, $R^{3E}$ is independently —$CONH_2$. In embodiments, $R^{3E}$ is independently —$NO_2$. In embodiments, $R^{3E}$ is independently —SH. In embodiments, $R^{3E}$ is independently —$SO_3H$. In embodiments, $R^{3E}$ is independently —$SO_{4H}$. In embodiments, $R^{3E}$ is independently —$SO_2NH_2$. In embodiments, $R^{3E}$ is independently —$NHNH_2$. In embodiments, $R^{3E}$ is independently —$ONH_2$. In embodiments, $R^{3E}$ is independently —NHC=(O)$NHNH_2$. In embodiments, $R^{3E}$ is independently —NHC=(O)$NH_2$. In embodiments, $R^{3E}$ is independently —$NHSO_2H$. In embodiments, $R^{3E}$ is independently —NHC=(O)H. In embodiments, $R^{3E}$ is independently —NHC(O)OH. In embodiments, $R^{3E}$ is independently —NHOH. In embodiments, $R^{3E}$ is independently —$CHF_2$. In embodiments, $R^{3E}$ is independently —$CH_2F$. In embodiments, $R^{3E}$ is independently —$OCF_3$. In embodiments, $R^{3E}$ is independently —$OCHF_2$.

In embodiments, $R^{3E}$ is independently substituted or unsubstituted ($C_1$-$C_5$) alkyl. In embodiments, $R^{3E}$ is independently substituted or unsubstituted 2 to 5 membered heteroalkyl. In embodiments, $R^{3E}$ is independently substituted ($C_1$-$C_5$) alkyl. In embodiments, $R^{3E}$ is independently substituted 2 to 5 membered heteroalkyl. In embodiments, $R^{3E}$ is independently unsubstituted ($C_1$-$C_5$) alkyl. In embodiments, $R^{3E}$ is independently unsubstituted 2 to 5 membered heteroalkyl. In embodiments, $R^{3E}$ is independently substituted or unsubstituted butyl. In embodiments, $R^{3E}$ is independently substituted or unsubstituted butoxy. In embodiments, $R^{3E}$ is independently substituted butyl. In embodiments, $R^{3E}$ is independently substituted butoxy. In embodiments, $R^{3E}$ is independently unsubstituted butyl. In embodiments, $R^{3E}$ is independently unsubstituted butoxy. In embodiments, $R^{3E}$ is independently substituted or unsubstituted propyl. In embodiments, $R^{3E}$ is independently substituted or unsubstituted propoxy. In embodiments, $R^{3E}$ is independently substituted propyl. In embodiments, $R^{3E}$ is independently substituted propoxy. In embodiments, $R^{3E}$ is independently unsubstituted propyl. In embodiments, $R^{3E}$ is independently unsubstituted propoxy. In embodiments, $R^{3E}$ is independently substituted or unsubstituted ethyl. In embodiments, $R^{3E}$ is independently substituted or unsubstituted ethoxy. In embodiments, $R^{3E}$ is independently substituted ethyl. In embodiments, $R^{3E}$ is independently substituted ethoxy. In embodiments, $R^{3E}$ is independently unsubstituted ethyl. In embodiments, $R^{3E}$ is independently unsubstituted ethoxy. In embodiments, $R^{3E}$ is independently substituted or unsubstituted methyl. In embodiments, $R^{3E}$ is independently substituted or unsubstituted methoxy. In embodiments, $R^{3E}$ is independently substituted methyl. In embodiments, $R^{3E}$ is independently substituted methoxy. In embodiments, $R^{3E}$ is independently unsubstituted methyl. In embodiments, $R^{3E}$ is independently unsubstituted methoxy. In embodiments, $R^{3E}$ is independently hydrogen.

In embodiments, two adjacent $R^3$ substituents (e.g., $R^{3B}$ and $R^{3D}$, $R^{3B}$ and $R^{3A}$, $R^{3A}$ and $R^{3C}$, $R^{3C}$ and $R^{3E}$) may optionally be joined to form a substituted or unsubstituted ($C_3$-$C_{10}$) cycloalkyl or substituted or unsubstituted 3 to 10 membered heterocycloalkyl, substituted or unsubstituted ($C_6$-$C_{10}$) aryl, or substituted or unsubstituted 5 to 10 membered heteroaryl. In embodiments, two adjacent $R^3$ substituents may optionally be joined to form a substituted or unsubstituted ($C_3$-$C_{10}$) cycloalkyl. In embodiments, two adjacent $R^3$ substituents may optionally be joined to form substituted or unsubstituted 3 to 10 membered heterocycloalkyl. In embodiments, two adjacent $R^3$ substituents may optionally be joined to form substituted or unsubstituted ($C_6$-$C_{10}$) aryl. In embodiments, two adjacent $R^3$ substituents may optionally be joined to form substituted or unsubstituted 5 to 10 membered heteroaryl. In embodiments, two adjacent $R^3$ substituents may optionally be joined to form 2,2-dimethyl-1,3-dioxanyl. In embodiments, two adjacent $R^3$ substituents may optionally be joined to form 1,3-dioxanyl. In embodiments, two adjacent $R^3$ substituents may optionally be joined to form 1,3-dioxolanyl. In embodiments, two adjacent $R^3$ substituents may optionally be joined to form 2,2-dimethyl-1,3-dioxolanyl.

Each $R^7$, $R^8$, $R^9$, and $R^{10}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, $OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl.

Each $R^7$ and $R^8$ substituents bonded to the same nitrogen atom may be joined to form a substituted or unsubstituted heterocycloalkyl or substituted or unsubstituted heteroaryl. Each $R^7$ and $R^8$ substituents bonded to the same nitrogen atom may be joined to form an unsubstituted heterocycloalkyl or unsubstituted heteroaryl. Each $R^7$ and $R^8$ substituents bonded to the same nitrogen atom may be joined to form a substituted or unsubstituted 4 to 6 membered heterocycloalkyl or 5 to 6 membered heteroaryl. Each $R^7$ and $R^8$ substituents bonded to the same nitrogen atom may be joined to form an unsubstituted 4 to 6 membered heterocycloalkyl or unsubstituted 5 to 6 membered heteroaryl.

In embodiments, $R^7$ is independently hydrogen, oxo, halogen, —$CX^7_3$, —$CHX^7_2$, —$OCH_2X^7$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^7_3$, —$OCHX^7_2$, $R^{48}$-substituted or unsubstituted alkyl, $R^{48}$-substituted or unsubstituted heteroalkyl, $R^{48}$-substituted or unsubstituted cycloalkyl, $R^{48}$-substituted or unsubstituted heterocycloalkyl, $R^{48}$-substituted or unsubstituted aryl, or $R^{48}$-substituted or unsubstituted heteroaryl. $X^7$ is independently halogen. In embodiments, $X^7$ is independently F or Cl.

$R^{48}$ is independently oxo, halogen, —$CX^{48}_3$, —$CHX^{48}_2$, —$OCH_2X^{48}$, —$OCHX^{48}_2$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{48}_3$, —$OCHX^{48}_2$, $R^{49}$-substituted or unsubstituted alkyl, $R^{49}$-substituted or unsubstituted heteroalkyl, $R^{49}$-substituted or unsubstituted cycloalkyl, $R^{49}$-substituted or unsubstituted heterocycloalkyl, $R^{49}$-substituted or unsubstituted aryl, or $R^{49}$-substituted or unsubstituted heteroaryl. $X^{48}$ is independently halogen. In embodiments, $X^{48}$ is independently F or Cl.

$R^{49}$ is independently oxo, halogen, —$CX^{49}_3$, —$CHX^{49}_2$, —$OCH_2X^{49}$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{49}_3$, —$OCHX^{49}_2$, $R^{50}$-substituted or unsubstituted alkyl, $R^{50}$-substituted or unsubstituted heteroalkyl, $R^{50}$-substituted or unsubstituted cycloalkyl, $R^{50}$-substituted or unsubstituted heterocycloalkyl, $R^{50}$-substituted or unsubstituted aryl, or $R^{50}$-substituted or unsubstituted heteroaryl. $X^{49}$ is independently halogen. In embodiments, $X^{49}$ is independently F or Cl.

In embodiments, $R^8$ is independently hydrogen, oxo, halogen, —$CX^8_3$, —$CHX_2$, —$OCH_2X^8$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^8_3$, —$OCHX^8_2$, $R^{51}$-substituted or unsubstituted alkyl, $R^{51}$-substituted or unsubstituted heteroalkyl, $R^{51}$-substituted or unsubstituted cycloalkyl, $R^{51}$ substituted or unsubstituted heterocycloalkyl, $R^{51}$-substituted or unsubstituted aryl, or $R^{51}$-substituted or unsubstituted heteroaryl. $X^8$ is independently halogen. In embodiments, $X^8$ is independently F or Cl.

$R^{51}$ is independently oxo, halogen, —$CX^{51}_3$, —$CHX^{51}_2$, —$OCH_2X^{51}$, —$OCHX^{51}_2$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{51}_3$, —$OCHX^{51}_2$, $R^{52}$-substituted or unsubstituted alkyl, $R^{52}$-substituted or unsubstituted heteroalkyl, $R^{52}$-substituted or unsubstituted cycloalkyl, $R^{52}$-substituted or unsubstituted heterocycloalkyl, $R^{52}$-substituted or unsubstituted aryl, or $R^{52}$-substituted or unsubstituted heteroaryl. $X^{51}$ is independently halogen. In embodiments, $X^{51}$ is independently F or Cl.

$R^{52}$ is independently oxo, halogen, —$CX^{52}_3$, —$CHX^{52}_2$, —$OCH_2X^{52}$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{52}_3$, —$OCHX^{52}_2$, $R^{53}$-substituted or unsubstituted alkyl, $R^{53}$-substituted or unsubstituted heteroalkyl, $R^{53}$-substituted or unsubstituted cycloalkyl, $R^{53}$-substituted or unsubstituted heterocycloalkyl, $R^{53}$-substituted or unsubstituted aryl, or $R^{53}$-substituted or unsubstituted heteroaryl. $X^{52}$ is independently halogen. In embodiments, $X^{52}$ is independently F or Cl.

In embodiments, $R^9$ is independently hydrogen, oxo, halogen, —$CX^9_3$, —$CHX^9_2$, —$OCH_2X^9$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^9_3$, —$OCHX^9_2$, $R^{54}$-substituted or unsubstituted alkyl, $R^{54}$-substituted or unsubstituted heteroalkyl, $R^{54}$-substituted or unsubstituted cycloalkyl, $R^{54}$-substituted or unsubstituted heterocycloalkyl, $R^{54}$-substituted or unsubstituted aryl, or $R^{54}$-substituted or unsubstituted heteroaryl. $X^9$ is independently halogen. In embodiments, $X^9$ is independently F or Cl.

$R^{54}$ is independently oxo, halogen, —$CX^{54}_3$, —$CHX^{54}_2$, —$OCH_2X^{54}$, —$OCHX^{54}_2$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{54}_3$, —$OCHX^{54}_2$, $R^{55}$-substituted or unsubstituted alkyl, $R^{55}$-substituted or unsubstituted heteroalkyl, $R^{55}$-substituted or unsubstituted cycloalkyl, $R^{55}$-substituted or unsubstituted heterocycloalkyl, $R^{55}$-substituted or unsubstituted aryl, or $R^{55}$-substituted or unsubstituted heteroaryl. $X^{54}$ is independently halogen. In embodiments, $X^{54}$ is independently F or Cl.

$R^{55}$ is independently oxo, halogen, —$CX^{55}_3$, —$CHX^{55}_2$, —$OCH_2X^{55}$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{55}_3$, —$OCHX^{55}_2$, $R^{56}$-substituted or unsubstituted alkyl, $R^{56}$-substituted or unsubstituted heteroalkyl, $R^{56}$-substituted or unsubstituted cycloalkyl, $R^{56}$ substituted or unsubstituted heterocycloalkyl, $R^{56}$-substituted or unsubstituted aryl, or $R^{56}$-substituted or unsubstituted heteroaryl. $X^{55}$ is independently halogen. In embodiments, $X^{55}$ is independently F or Cl.

In embodiments, $R^{10}$ is independently hydrogen, oxo, halogen, —$CX^{10}_3$, —$CHX^{10}_2$, —$OCH_2X^{10}$, —CN, —OH, —$NH_2$, —COOH, —$CONH_2$, —$NO_2$, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{10}_3$, —$OCHX^{10}_2$, $R^{57}$-substituted or unsubstituted alkyl, $R^{57}$-substituted or unsubstituted heteroalkyl, $R^{57}$-substituted or unsubstituted cycloalkyl, $R^{57}$-substituted or unsubstituted heterocycloalkyl, $R^{57}$-substituted or unsubstituted aryl, or $R^{57}$-substituted or unsubstituted heteroaryl. $X^{10}$ is independently halogen. In embodiments, $X^{10}$ is independently F or Cl.

$R^{57}$ is independently oxo, halogen, —$CX^{57}_3$, —$CHX^{57}_2$, —$OCH_2X^{57}$, —$OCHX^{57}_2$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{57}_3$, —$OCHX^{57}_2$, $R^{58}$-substituted or unsubstituted alkyl, $R^{58}$-substituted or unsubstituted heteroalkyl, $R^{58}$-substituted or unsubstituted cycloalkyl, $R^{58}$-substituted or unsubstituted heterocycloalkyl, $R^{58}$-substituted or unsubstituted aryl, or $R^{58}$-substituted or unsubstituted heteroaryl. $X^{57}$ is independently halogen. In embodiments, $X^{57}$ is independently F or Cl.

$R^{58}$ is independently oxo, halogen, —$CX^{58}_3$, —$CHX^{58}_2$, —$OCH_2X^{58}$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{58}_3$, —$OCHX^{58}_2$, $R^{59}$-substituted or unsubstituted alkyl, $R^{59}$-substituted or unsubstituted heteroalkyl, $R^{59}$-substituted or unsubstituted cycloalkyl, $R^{59}$-substituted or unsubstituted heterocycloalkyl, $R^{59}$-substituted or unsubstituted aryl, or $R^{59}$-substituted or unsubstituted heteroaryl. $X^{58}$ is independently halogen. In embodiments, $X^{58}$ is independently F or Cl.

The symbols m and v are independently 1 or 2. The symbol n is independently an integer from 0 to 4. X is independently —Cl, —Br, —I, or —F. In embodiments, X is —Cl. In embodiments, X is —Br. In embodiments, X is —I. In embodiments, X is or —F. In embodiments, $X^a$ is —Cl. In embodiments, $X^a$ is —Br. In embodiments, $X^a$ is —I. In embodiments, $X^a$ is or —F.

In embodiments, Ring B is substituted or unsubstituted cycloalkyl. In embodiments, Ring B is substituted or unsubstituted heterocycloalkyl. In embodiments, Ring B is substituted or unsubstituted aryl. In embodiments, Ring B is substituted or unsubstituted heteroaryl. In embodiments, Ring B is substituted or unsubstituted ($C_3$-$C_{10}$) cycloalkyl, substituted or unsubstituted 3 to 10 membered heterocycloalkyl, substituted or unsubstituted ($C_6$-$C_{10}$) aryl, or substituted or unsubstituted 5 to 10 membered heteroaryl. In embodiments, Ring B is substituted or unsubstituted ($C_3$-$C_{10}$) cycloalkyl. In embodiments, Ring B is substituted or unsubstituted 3 to 10 membered heterocycloalkyl. In embodiments, Ring B is substituted or unsubstituted ($C_6$-$C_{10}$) aryl. In embodiments, Ring B is substituted or unsubstituted 5 to 10 membered heteroaryl. In embodiments, Ring B is substituted or unsubstituted ($C_3$-$C_6$) cycloalkyl. In embodiments, Ring B is substituted or unsubstituted 3 to 6 membered heterocycloalkyl. In embodiments, Ring B is substituted or unsubstituted phenyl. In embodiments, Ring B is substituted or unsubstituted naphthyl. In embodiments, Ring B is substituted or unsubstituted 5 to 9 membered heteroaryl. In embodiments, Ring B is substituted or unsubstituted 5 to 6 membered heteroaryl. In embodiments, Ring B is an unsubstituted 5 to 6 membered heteroaryl. In embodiments, Ring B is substituted or unsubstituted 5 membered heteroaryl. In embodiments, Ring B is a substituted 5 membered heteroaryl. In embodiments, Ring B is an unsubstituted 5 membered heteroaryl.

In embodiments, Ring B is $R^4$-substituted or unsubstituted ($C_3$-$C_{10}$) cycloalkyl, $R^4$-substituted or unsubstituted 5 to 10 membered heterocycloalkyl, $R^4$-substituted or unsubstituted ($C_6$-$C_{10}$) aryl, or $R^4$-substituted or unsubstituted 5 to 10 membered heteroaryl. In embodiments, Ring B is $R^4$-substituted or unsubstituted ($C_3$-$C_{10}$) cycloalkyl or $R^4$-substituted or unsubstituted 5 to 10 membered heterocycloalkyl. In embodiments, Ring B is $R^4$-substituted or unsubstituted ($C_3$-$C_{10}$) cycloalkyl. In embodiments, Ring B is $R^4$-substituted or unsubstituted 3 to 10 membered heterocycloalkyl. In embodiments, Ring B is $R^4$-substituted or unsubstituted ($C_6$-$C_{10}$) aryl. In embodiments, Ring B is $R^4$-substituted or unsubstituted 5 to 10 membered heteroaryl. In embodiments, Ring B is $R^4$-substituted or unsubstituted ($C_3$-$C_6$) cycloalkyl. In embodiments, Ring B is $R^4$-substituted or unsubstituted 3 to 6 membered heterocycloalkyl. In embodiments, Ring B is $R^4$-substituted or unsubstituted phenyl. In embodiments, Ring B is $R^4$-substituted or unsubstituted naphthyl. In embodiments, Ring B is $R^4$-substituted or unsubstituted 5 to 9 membered heteroaryl. In embodiments, Ring B is $R^4$-substituted or unsubstituted 5 to 6 membered heteroaryl. In embodiments, Ring B is $R^4$-substituted or unsubstituted thienyl. In embodiments, Ring B is $R^4$-substituted or unsubstituted phenyl. In embodiments, Ring B is $R^4$-substituted or unsubstituted benzothienyl. In embodiments, Ring B is $R^4$-substituted or unsubstituted naphthyl. In embodiments, Ring B is $R^4$-substituted or unsubstituted benzofuranyl. In embodiments, Ring B is $R^4$-substituted or unsubstituted furanyl. In embodiments, Ring B is $R^4$-substituted or unsubstituted pyrrolyl. In embodiments, Ring B is $R^4$-substituted or unsubstituted 2,3-dihydro-1H-indenyl.

In embodiments, Ring B is substituted cycloalkyl. In embodiments, Ring B is substituted heterocycloalkyl. In embodiments, Ring B is substituted aryl. In embodiments, Ring B is substituted heteroaryl. In embodiments, Ring B is substituted ($C_3$-$C_{10}$) cycloalkyl, substituted 3 to 10 membered heterocycloalkyl, substituted ($C_6$-$C_{10}$) aryl, or substituted 5 to 10 membered heteroaryl. In embodiments, Ring B is substituted ($C_3$-$C_{10}$) cycloalkyl. In embodiments, Ring B is substituted 3 to 10 membered heterocycloalkyl. In embodiments, Ring B is substituted ($C_6$-$C_{10}$) aryl. In embodiments, Ring B is substituted 5 to 10 membered heteroaryl. In embodiments, Ring B is substituted ($C_3$-$C_6$) cycloalkyl. In embodiments, Ring B is substituted 3 to 6 membered heterocycloalkyl. In embodiments, Ring B is substituted phenyl. In embodiments, Ring B is substituted naphthyl. In embodiments, Ring B is substituted 5 to 9 membered heteroaryl. In embodiments, Ring B is substituted 5 to 6 membered heteroaryl. In embodiments, Ring B is $R^4$-substituted ($C_3$-$C_{10}$) cycloalkyl, $R^4$-substituted 5 to 10 membered heterocycloalkyl, $R^4$-substituted ($C_6$-$C_{10}$) aryl, or $R^4$-substituted 5 to 10 membered heteroaryl. In embodiments, Ring B is $R^4$-substituted ($C_3$-$C_{10}$) cycloalkyl or $R^4$-substituted 5 to 10 membered heterocycloalkyl. In embodiments, Ring B is $R^4$-substituted ($C_3$-$C_{10}$) cycloalkyl. In embodiments, Ring B is $R^4$-substituted 3 to 10 membered heterocycloalkyl. In embodiments, Ring B is $R^4$-substituted ($C_6$-$C_{10}$) aryl. In embodiments, Ring B is $R^4$-substituted 5 to 10 membered heteroaryl. In embodiments, Ring B is $R^4$-substituted ($C_3$-$C_6$) cycloalkyl. In embodiments, Ring B is $R^4$-substituted 3 to 6 membered heterocycloalkyl. In embodiments, Ring B is $R^4$-substituted phenyl. In embodiments, Ring B is $R^4$-substituted naphthyl. In embodiments, Ring B is $R^4$-substituted 5 to 9 membered heteroaryl. In embodiments, Ring B is $R^4$-substituted 5 to 6 membered heteroaryl. In embodiments, Ring B is $R^4$-substituted thienyl. In embodiments, Ring B is $R^4$-substituted phenyl. In embodiments, Ring B is $R^4$-substituted benzothienyl. In embodiments, Ring B is $R^4$-substituted naphthyl. In embodiments, Ring B is $R^4$-substituted benzofuranyl. In embodiments, Ring B is $R^4$-substituted furanyl. In embodiments, Ring B is $R^4$-substituted pyrrolyl. In embodiments, Ring B is $R^4$-substituted 2,3-dihydro-1H-indenyl.

In embodiments, Ring B is unsubstituted cycloalkyl. In embodiments, Ring B is unsubstituted heterocycloalkyl. In embodiments, Ring B is unsubstituted aryl. In embodiments, Ring B is unsubstituted heteroaryl. In embodiments, Ring B is unsubstituted ($C_3$-$C_{10}$) cycloalkyl, unsubstituted 3 to 10 membered heterocycloalkyl, unsubstituted ($C_6$-$C_{10}$) aryl, or unsubstituted 5 to 10 membered heteroaryl. In embodiments, Ring B is unsubstituted ($C_3$-$C_{10}$) cycloalkyl. In embodiments, Ring B is unsubstituted 3 to 10 membered heterocycloalkyl. In embodiments, Ring B is unsubstituted ($C_6$-$C_{10}$) aryl. In embodiments, Ring B is unsubstituted 5 to 10 membered heteroaryl. In embodiments, Ring B is unsubstituted ($C_3$-$C_6$) cycloalkyl. In embodiments, Ring B is unsubstituted 3 to 6 membered heterocycloalkyl. In embodiments, Ring B is unsubstituted phenyl. In embodiments, Ring B is unsubstituted naphthyl. In embodiments, Ring B is unsubstituted 5 to 9 membered heteroaryl. In embodiments, Ring B is unsubstituted 5 to 6 membered heteroaryl. In embodiments, Ring B is unsubstituted ($C_3$-$C_{10}$) cycloalkyl, unsubstituted 5 to 10 membered heterocycloalkyl, unsubstituted ($C_6$-$C_{10}$) aryl, or unsubstituted 5 to 10 membered heteroaryl. In embodiments, Ring B is unsubstituted ($C_3$-$C_{10}$) cycloalkyl or unsubstituted 5 to 10 membered heterocycloalkyl. In embodiments, Ring B is unsubstituted ($C_3$-$C_{10}$) cycloalkyl. In embodiments, Ring B is unsubstituted 3 to 10 membered heterocycloalkyl. In embodiments, Ring B is unsubstituted ($C_6$-$C_{10}$) aryl. In embodiments, Ring B is unsubstituted 5 to 10 membered heteroaryl. In embodiments, Ring B is unsubstituted ($C_3$-$C_6$) cycloalkyl. In embodiments, Ring B is unsubstituted 3 to 6 membered heterocycloalkyl. In embodiments, Ring B is unsubstituted phenyl. In embodiments, Ring B is unsubstituted naphthyl. In embodiments, Ring B is unsubstituted 5 to 9 membered heteroaryl. In embodiments, Ring B is unsubstituted 5 to 6 membered heteroaryl. In embodiments, Ring B is unsubstituted thienyl. In embodiments, Ring B is unsubstituted phenyl. In embodiments, Ring B is unsubstituted benzothienyl. In embodiments, Ring B is unsubstituted naphthyl. In embodiments, Ring B is unsubstituted benzofuranyl. In embodiments, Ring B is unsubstituted furanyl. In embodiments, Ring B is unsubstituted pyrrolyl. In embodiments, Ring B is unsubstituted 2,3-dihydro-1H-indenyl. In embodiments, Ring B is unsubstituted phenyl. In embodiments, Ring B is In embodiments, Ring B is

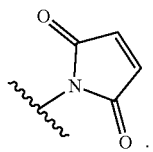 [SMILES: *N1C(=O)C=CC1=O]

In embodiments, Ring B is

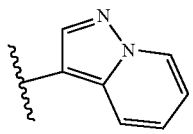

In embodiments, Ring B is

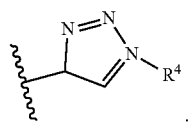

Ring B may be substituted with one $R^4$. Ring B may be substituted with two optionally different $R^4$ substituents. Ring B may be substituted with three optionally different $R^4$ substituents. Ring B may be substituted with four optionally different $R^4$ substituents. Ring B may be substituted with five optionally different $R^4$ substituents. Ring B may be substituted with six optionally different $R^4$ substituents. Ring B may be substituted with seven optionally different $R^4$ substituents. Ring B may be substituted with eight optionally different $R^4$ substituents. Ring B may be substituted with nine optionally different $R^4$ substituents. Ring B may be substituted with ten optionally different $R^4$ substituents.

$R^4$ is independently hydrogen, oxo, halogen, —$CX^a_3$, —CN, —$SO_{n1}R^{14}$, —$SO_{v1}NR^{11}R^{12}$, —$NHNR^{11}R^{12}$, —$ONR^{11}R^{12}$, —NHC=(O)NHNR$^{11}R^{12}$, —NHC=(O)NR$^{11}R^{12}$, —N(O)$^{m1}$, —NR$^{11}R^{12}$, —C(O)R$^{13}$, —C(O)—OR$^{13}$, —C(O)NR$^{11}R^{12}$, —OR$^{14}$, NR$^{11}SO_2R^{14}$, —NR$^{11}$C=(O)R$^{13}$, —NR$^{11}$C(O)OR$^{13}$, —NR$^{11}$OR$^{13}$, —CHX$^a_2$, —CH$_2$X$^a$, —OCX$^a_3$, —OCHX$^a_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^4$ substituents may optionally be joined to form a substituted or unsubstituted cycloalkyl, substituted or unsubstituted heterocycloalkyl, substituted or unsubstituted aryl, or substituted or unsubstituted heteroaryl.

In embodiments, $R^4$ is unsubstituted methyl. In embodiments, $R^4$ is unsubstituted ethyl. In embodiments, $R^4$ is unsubstituted propyl. In embodiments, $R^4$ is unsubstituted methoxy. In embodiments, $R^4$ is unsubstituted ethoxy. In embodiments, $R^4$ is unsubstituted propoxy. In embodiments, $R^4$ is oxo. In embodiments, $R^4$ is unsubstituted phenyl. In embodiments, $R^4$ is unsubstituted benzyl.

In embodiments, $R^4$ is independently hydrogen, oxo, halogen, —$CX^4_3$, —$CHX^4_2$, —$OCH_2X^4$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, —OCX$^4_3$, —OCHX$^4_2$, $R^{39}$-substituted or unsubstituted alkyl, $R^{39}$-substituted or unsubstituted heteroalkyl, $R^{39}$-substituted or unsubstituted cycloalkyl, $R^{39}$-substituted or unsubstituted heterocycloalkyl, $R^{39}$-substituted or unsubstituted aryl, or $R^{39}$-substituted or unsubstituted heteroaryl. $X^4$ is independently halogen. In embodiments, $X^4$ is independently F or Cl.

In embodiments, $R^4$ is $R^{39}$-substituted methyl. In embodiments, $R^4$ is $R^{39}$-substituted ethyl. In embodiments, $R^4$ is or substituted or unsubstituted 2 to 20 membered heteroalkyl. In embodiments, $R^4$ is or substituted or unsubstituted 2 to 20 membered heteroalkyl. In embodiments, $R^4$ is or substituted or unsubstituted 2 to 15 membered heteroalkyl. In embodiments, $R^4$ is

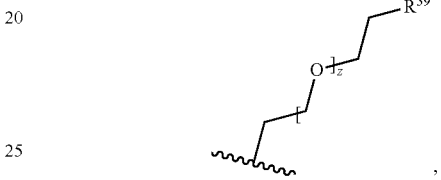

wherein z is an integer from 1 to 10. In embodiments, $R^4$ is

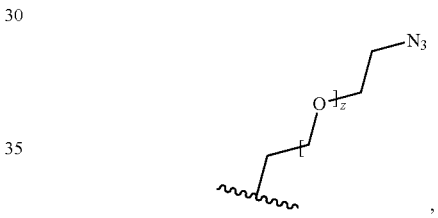

wherein z is an integer from 1 to 10. In embodiments, z is 1. In embodiments, z is 2. In embodiments, z is 3. In embodiments, z is 4. In embodiments, z is 5. In embodiments, z is 6. In embodiments, z is 7. In embodiments, z is 8. In embodiments, z is 9. In embodiments, z is 10. In embodiments, $R^4$ is

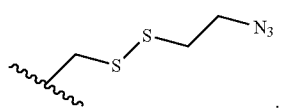 [SMILES: *CSSCCN=[N+]=[N-]]

$R^{39}$ is independently oxo, halogen, —$CX^{39}_3$, —$CHX^{39}_2$, —$OCH_2X^{39}$, —$OCHX^{39}_2$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, —N$_3$, —OCX$^{39}_3$, —OCHX$^{39}_2$, $R^{40}$-substituted or unsubstituted alkyl, $R^{40}$-substituted or unsubstituted heteroalkyl, $R^{40}$-substituted or unsubstituted cycloalkyl, $R^{40}$-substituted or unsubstituted heterocycloalkyl, $R^{40}$-substituted or unsubstituted aryl, or $R^{40}$-substituted or unsubstituted heteroaryl. $X^{39}$ is independently halogen. In embodiments, $X^{39}$ is independently F or Cl.

In embodiments, $R^{39}$ is substituted or unsubstituted ($C_1$-$C_5$) alkyl, substituted or unsubstituted 2 to 5 membered heteroalkyl, substituted or unsubstituted ($C_3$-$C_6$) cycloalkyl, or substituted or unsubstituted 3 to 6 membered heterocycloalkyl substituted or unsubstituted 3 to 6 membered heterocycloalkyl or substituted or unsubstituted 5 to 6 membered heteroaryl. In embodiments, $R^{39}$ is $N_3$. In embodiments, $R^{39}$ is unsubstituted phenyl. In embodiments, $R^{39}$ is unsubstituted benzyl.

$R^{40}$ is independently oxo, halogen, —$CX^{40}_3$, —$CHX^{40}_2$, —$OCH_2X^{40}$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$N_3$, —NHC=(O)$NHNH_2$, —NHC=(O)$NH_2$, —$NHSO_2H$, —NHC=(O)H, —NHC(O)—OH, —NHOH, —$OCX^{40}_3$, —$OCHX^{40}_2$, $R^{41}$-substituted or unsubstituted alkyl, $R^{41}$-substituted or unsubstituted heteroalkyl, $R^{41}$-substituted or unsubstituted cycloalkyl, $R^{41}$-substituted or unsubstituted heterocycloalkyl, $R^{41}$-substituted or unsubstituted aryl, or $R^{41}$-substituted or unsubstituted heteroaryl. $X^{40}$ is independently halogen. In embodiments, $X^{40}$ is independently F or Cl. In embodiments, $R^{40}$ is $N_3$.

In embodiments, $R^4$ is independently oxo, halogen, —$CX^a_3$, —CN, —$SO_nR^{14}$, —$SO_{v1}NR^{11}R^{12}$, —$NHNR^{11}R^{12}$, —$ONR^{11}R^{12}$, —NHC=(O)$NHNR^{11}R^{12}$, —NHC=(O)$NR^{11}R^{12}$, —$N(O)^{m1}$, —$NR^{11}R^{12}$, —$C(O)R^{13}$, —C(O)—$OR^{13}$, —$C(O)NR^{11}R^{12}$, —$OR^{14}$, —$NR^{11}SO_2R^{14}$, —$NR^{11}C$=(O)$R^{13}$, —$NR^{11}C(O)OR^{13}$, —$NR^{11}OR^{13}$, —$CHX^a_2$, —$CH_2X^a$, —$OCX^a_3$, —$OCHX^a_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^4$ is hydrogen. In embodiments, $R^4$ is oxo. In embodiments, $R^4$ is independently halogen. In embodiments, $R^4$ is —$CX^a_3$. In embodiments, $R^4$ is —CN. In embodiments, $R^4$ is —$SO_nR^{14}$. In embodiments, $R^4$ is —$SO_{v1}NR^{11}R^{12}$. In embodiments, $R^4$ is —$NHNR^{11}R^{12}$. In embodiments, $R^4$ is —$ONR^{11}R^{12}$. In embodiments, $R^4$ is —NHC=(O)$NHNR^{11}R^{12}$. In embodiments, $R^4$ is —NHC=(O)$NR^{11}R^{12}$. In embodiments, $R^4$ is —$N(O)_{m1}$. In embodiments, $R^4$ is —$NR^{11}R^{12}$. In embodiments, $R^4$ is —$C(O)R^{13}$. In embodiments, $R^4$ is —C(O)—$OR^{13}$. In embodiments, $R^4$ is —$C(O)NR^{11}R^{12}$. In embodiments, $R^4$ is —$OR^{14}$. In embodiments, $R^4$ is —$NR^{11}SO_2R^{14}$. In embodiments, $R^4$ is —$NR^{11}C$=(O)$R^{13}$. In embodiments, $R^4$ is —$NR^{11}C(O)OR^{13}$. In embodiments, $R^4$ is —$NR^{11}OR^{13}$. In embodiments, $R^4$ is —$CHX^a_2$. In embodiments, $R^4$ is —$CH_2X^a$. In embodiments, $R^4$ is —$OCX^a_3$. In embodiments, $R^4$ is —$OCHX^a_2$.

In embodiments, $R^4$ is substituted or unsubstituted alkyl. In embodiments, $R^4$ is substituted or unsubstituted heteroalkyl. In embodiments, $R^4$ is substituted or unsubstituted cycloalkyl. In embodiments, $R^4$ is substituted or unsubstituted heterocycloalkyl. In embodiments, $R^4$ is substituted or unsubstituted aryl. In embodiments, $R^4$ is substituted or unsubstituted heteroaryl. In embodiments, $R^4$ is substituted alkyl. In embodiments, $R^4$ is substituted heteroalkyl. In embodiments, $R^4$ is substituted cycloalkyl. In embodiments, $R^4$ is substituted heterocycloalkyl. In embodiments, $R^4$ is substituted aryl. In embodiments, $R^4$ is substituted heteroaryl. In embodiments, $R^4$ is unsubstituted alkyl. In embodiments, $R^4$ is unsubstituted heteroalkyl. In embodiments, $R^4$ is unsubstituted cycloalkyl. In embodiments, $R^4$ is unsubstituted heterocycloalkyl. In embodiments, $R^4$ is unsubstituted aryl. In embodiments, $R^4$ is unsubstituted heteroaryl.

In embodiments, $R^4$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, substituted or unsubstituted ($C_1$-$C_5$) alkyl, or substituted or unsubstituted 2 to 5 membered heteroalkyl. In embodiments, $R^4$ is independently halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, substituted or unsubstituted ($C_1$-$C_5$) alkyl, or substituted or unsubstituted 2 to 5 membered heteroalkyl. In embodiments, $R^4$ is methyl.

In embodiments, $R^4$ is independently halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, substituted or unsubstituted ($C_1$-$C_5$) alkyl, or substituted or unsubstituted 2 to 5 membered heteroalkyl. In embodiments, $R^4$ is independently halogen. In embodiments, $R^4$ is independently —$CF_3$. In embodiments, $R^4$ is independently —CN. In embodiments, $R^4$ is independently —OH. In embodiments, $R^4$ is independently —$NH_2$. In embodiments, $R^4$ is independently —COOH. In embodiments, $R^4$ is independently —$CONH_2$. In embodiments, $R^4$ is independently —$NO_2$. In embodiments, $R^4$ is independently —SH. In embodiments, $R^4$ is independently —$SO_3H$. In embodiments, $R^4$ is independently —$SO_4H$. In embodiments, $R^4$ is independently —$SO_2NH_2$. In embodiments, $R^4$ is independently —$NHNH_2$. In embodiments, $R^4$ is independently —$ONH_2$. In embodiments, $R^4$ is independently —NHC=(O)$NHNH_2$. In embodiments, $R^4$ is independently —NHC=(O)$NH_2$. In embodiments, $R^4$ is independently —$NHSO_2H$. In embodiments, $R^4$ is independently —NHC=(O)H. In embodiments, $R^4$ is independently —NHC(O)OH. In embodiments, $R^4$ is independently —NHOH. In embodiments, $R^4$ is independently —$CHF_2$. In embodiments, $R^4$ is independently —$CH_2F$. In embodiments, $R^4$ is independently —$OCF_3$. In embodiments, $R^4$ is independently —$OCHF_2$.

In embodiments, $R^4$ is independently substituted or unsubstituted ($C_1$-$C_5$) alkyl. In embodiments, $R^4$ is independently substituted or unsubstituted 2 to 5 membered heteroalkyl. In embodiments, $R^4$ is independently substituted ($C_1$-$C_5$) alkyl. In embodiments, $R^4$ is independently substituted 2 to 5 membered heteroalkyl. In embodiments, $R^4$ is independently unsubstituted ($C_1$-$C_5$) alkyl. In embodiments, $R^4$ is independently unsubstituted 2 to 5 membered heteroalkyl. In embodiments, $R^4$ is independently substituted or unsubstituted butyl. In embodiments, $R^4$ is independently substituted or unsubstituted butoxy. In embodiments, $R^4$ is independently substituted butyl. In embodiments, $R^4$ is independently substituted butoxy. In embodiments, $R^4$ is independently unsubstituted butyl. In embodiments, $R^4$ is independently unsubstituted butoxy. In embodiments, $R^4$ is independently substituted or unsubstituted propyl. In embodiments, $R^4$ is independently substituted or unsubstituted propoxy. In embodiments, $R^4$ is independently substituted propyl. In embodiments, $R^4$ is independently substituted propoxy. In embodiments, $R^4$ is independently unsubstituted propyl. In embodiments, $R^4$ is independently unsubstituted propoxy. In embodiments, $R^4$ is independently substituted or unsubstituted ethyl. In embodiments, $R^4$ is independently substituted or unsubstituted ethoxy. In embodiments, $R^4$ is independently substituted ethyl. In embodiments, $R^4$ is independently substituted ethoxy. In embodiments, $R^4$ is independently unsubstituted ethyl. In embodiments, $R^4$ is independently unsubstituted ethoxy. In embodiments, $R^4$ is independently substituted or unsubstituted methyl. In embodiments, $R^4$ is independently substituted or unsubstituted methoxy. In embodiments, $R^4$ is independently substituted methyl. In embodiments, $R^4$ is independently substituted methoxy. In embodiments, $R^4$ is independently unsubstituted methyl. In embodiments, $R^4$ is independently unsubstituted methoxy. In embodiments, $R^4$ is independently hydrogen. In embodiments, $R^4$ is independently unsubstituted methoxy. In embodiments, $R^4$ is independently halogen. In embodiments, $R^4$ is F.

In embodiments, two adjacent $R^4$ substituents are joined to form a substituted or unsubstituted cycloalkyl. In embodiments, two adjacent $R^4$ substituents are joined to form a substituted or unsubstituted heterocycloalkyl. In embodiments, two adjacent $R^4$ substituents are joined to form a substituted or unsubstituted aryl. In embodiments, two adjacent $R^4$ substituents are joined to form a substituted or unsubstituted heteroaryl. In embodiments, two adjacent $R^4$ substituents are joined to form a substituted or unsubstituted ($C_3$-$C_6$) cycloalkyl. In embodiments, two adjacent $R^4$ substituents are joined to form a substituted or unsubstituted 3 to 6 membered heterocycloalkyl. In embodiments, two adjacent $R^4$ substituents are joined to form a substituted or unsubstituted ($C_6$-$C_{10}$) aryl. In embodiments, two adjacent $R^4$ substituents are joined to form a substituted or unsubstituted 5 to 10 membered heteroaryl. In embodiments, two adjacent $R^4$ substituents are joined to form a substituted or unsubstituted phenyl. In embodiments, two adjacent $R^4$ substituents are joined to form a substituted or unsubstituted 5 to 9 membered heteroaryl. In embodiments, two adjacent $R^4$ substituents are joined to form a substituted or unsubstituted naphthyl. In embodiments, two adjacent $R^4$ substituents are joined to form a substituted or unsubstituted 5 to 6 membered heteroaryl. In embodiments, two adjacent $R^4$ substituents are joined to form a substituted cycloalkyl. In embodiments, two adjacent $R^4$ substituents are joined to form a substituted heterocycloalkyl. In embodiments, two adjacent $R^4$ substituents are joined to form a substituted aryl. In embodiments, two adjacent $R^4$ substituents are joined to form a substituted heteroaryl. In embodiments, two adjacent $R^4$ substituents are joined to form a substituted ($C_3$-$C_6$) cycloalkyl. In embodiments, two adjacent $R^4$ substituents are joined to form a substituted 3 to 6 membered heterocycloalkyl. In embodiments, two adjacent $R^4$ substituents are joined to form a substituted ($C_6$-$C_{10}$) aryl. In embodiments, two adjacent $R^4$ substituents are joined to form a substituted 5 to 10 membered heteroaryl. In embodiments, two adjacent $R^4$ substituents are joined to form a substituted phenyl. In embodiments, two adjacent $R^4$ substituents are joined to form a substituted 5 to 9 membered heteroaryl. In embodiments, two adjacent $R^4$ substituents are joined to form a substituted naphthyl. In embodiments, two adjacent $R^4$ substituents are joined to form a substituted 5 to 6 membered heteroaryl. In embodiments, two adjacent $R^4$ substituents are joined to form an unsubstituted cycloalkyl. In embodiments, two adjacent $R^4$ substituents are joined to form an unsubstituted heterocycloalkyl. In embodiments, two adjacent $R^4$ substituents are joined to form an unsubstituted aryl. In embodiments, two adjacent $R^4$ substituents are joined to form an unsubstituted heteroaryl. In embodiments, two adjacent $R^4$ substituents are joined to form an unsubstituted ($C_3$-$C_6$) cycloalkyl. In embodiments, two adjacent $R^4$ substituents are joined to form an unsubstituted 3 to 6 membered heterocycloalkyl. In embodiments, two adjacent $R^4$ substituents are joined to form an unsubstituted ($C_6$-$C_{10}$) aryl. In embodiments, two adjacent $R^4$ substituents are joined to form an unsubstituted 5 to 10 membered heteroaryl. In embodiments, two adjacent $R^4$ substituents are joined to form an unsubstituted phenyl. In embodiments, two adjacent $R^4$ substituents are joined to form an unsubstituted 5 to 9 membered heteroaryl. In embodiments, two adjacent $R^4$ substituents are joined to form an unsubstituted naphthyl. In embodiments, two adjacent $R^4$ substituents are joined to form an unsubstituted 5 to 6 membered heteroaryl.

$R^{11}$, $R^{12}$, $R^{13}$, and $R^{14}$ are independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, $OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl; m1 and v1 are independently 1 or 2; n1 is independently an integer from 0 to 4; $X^a$ is independently —Cl, —Br, —I, or —F.

Each $R^{11}$ and $R^{12}$ substituents bonded to the same nitrogen atom may be joined to form a substituted or unsubstituted heterocycloalkyl or substituted or unsubstituted heteroaryl. Each $R^{11}$ and $R^{12}$ substituents bonded to the same nitrogen atom may be joined to form an unsubstituted heterocycloalkyl or unsubstituted heteroaryl. Each $R^{11}$ and $R^{12}$ substituents bonded to the same nitrogen atom may be joined to form a substituted or unsubstituted 4 to 6 membered heterocycloalkyl or substituted or unsubstituted 5 to 6 membered heteroaryl. Each $R^{11}$ and $R^{12}$ substituents bonded to the same nitrogen atom may be joined to form an unsubstituted 4 to 6 membered heterocycloalkyl or unsubstituted 5 to 6 membered heteroaryl.

In embodiments, $R^{11}$ is independently hydrogen, oxo, halogen, —$CX^{11}_3$, —$CHX^{11}_2$, —$OCH_2X^{11}$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{11}_3$, —$OCHX^{11}_2$, $R^{60}$-substituted or unsubstituted alkyl, $R^{60}$-substituted or unsubstituted heteroalkyl, $R^{60}$-substituted or unsubstituted cycloalkyl, $R^{60}$ substituted or unsubstituted heterocycloalkyl, $R^{60}$-substituted or unsubstituted aryl, or $R^{60}$-substituted or unsubstituted heteroaryl. $X^{11}$ is independently halogen. In embodiments, $X^{11}$ is independently F or Cl.

$R^{60}$ is independently oxo, halogen, —$CX^{60}_3$, —$CHX^{60}_2$, —$OCH_2X^{60}$, —$OCHX^{60}_2$, —CN, —OH, —$NH_2$, —COOH, —$CONH_2$, —$NO_2$, —S H, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{60}_3$, —$OCHX^{60}_2$, $R^{61}$-substituted or unsubstituted alkyl, $R^{61}$-substituted or unsubstituted heteroalkyl, $R^{61}$-substituted or unsubstituted cycloalkyl, $R^{61}$-substituted or unsubstituted heterocycloalkyl, $R^{61}$-substituted or unsubstituted aryl, or $R^{61}$-substituted or unsubstituted heteroaryl. $X^{60}$ is independently halogen. In embodiments, $X^{60}$ is independently F or Cl.

$R^{61}$ is independently oxo, halogen, —$CX^{61}_3$, —$CHX^{61}_2$, —$OCH_2X^{61}$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{61}_3$, —$OCHX^{61}_2$, $R^{62}$-substituted or unsubstituted alkyl, $R^{62}$-substituted or unsubstituted heteroalkyl, $R^{62}$-substituted or unsubstituted cycloalkyl, $R^{62}$ substituted or unsubstituted heterocycloalkyl, $R^{62}$-substituted or unsubstituted aryl, or $R^{62}$-substituted or unsubstituted heteroaryl. $X^{61}$ is independently halogen. In embodiments, $X^{61}$ is independently F or Cl.

In embodiments, $R^{12}$ is independently hydrogen, oxo, halogen, —$CX^{12}_3$, —$CHX^{12}_2$, —$OCH_2X^{12}$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{12}_3$, —$OCHX^{12}_2$, $R^{63}$-substituted or unsubstituted alkyl, $R^{63}$-substituted or unsubstituted heteroalkyl, $R^{63}$-substituted or unsubstituted cycloalkyl, $R^{63}$ substituted or unsubstituted heterocycloalkyl, $R^{63}$-substituted or unsubstituted aryl, or $R^{63}$-substituted or unsubstituted heteroaryl. $X^{12}$ is independently halogen. In embodiments, $X^{12}$ is independently F or Cl.

$R^{63}$ is independently oxo, halogen, —$CX^{63}_3$, —$CHX^{63}_2$, —$OCH_2X^{63}$, —$OCHX^{63}_2$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{63}_3$, —$OCHX^{63}_2$, $R^{64}$-substituted or unsubstituted alkyl, $R^{64}$-substituted or unsubstituted heteroalkyl, $R^{64}$-substituted or unsubstituted cycloalkyl, $R^{64}$-substituted or unsubstituted heterocycloalkyl, $R^{64}$-substituted or unsubstituted aryl, or $R^{64}$-substituted or unsubstituted heteroaryl. $X^{63}$ is independently halogen. In embodiments, $X^{63}$ is independently F or Cl.

$R^{64}$ is independently oxo, halogen, —$CX^{64}_3$, —$CHX^{64}_2$, —$OCH_2X^{64}$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{64}_3$, —$OCHX^{64}_2$, $R^{65}$-substituted or unsubstituted alkyl, $R^{65}$-substituted or unsubstituted heteroalkyl, $R^{65}$-substituted or unsubstituted cycloalkyl, $R^{65}$ substituted or unsubstituted heterocycloalkyl, $R^{65}$-substituted or unsubstituted aryl, or $R^{65}$-substituted or unsubstituted heteroaryl. $X^{64}$ is independently halogen. In embodiments, $X^{64}$ is independently F or Cl.

In embodiments, $R^{13}$ is independently hydrogen, oxo, halogen, —$CX^{13}_3$, —$CHX^{13}_2$, —$OCH_2X^{13}$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{13}_3$, —$OCHX^{13}_2$, $R^{66}$-substituted or unsubstituted alkyl, $R^{66}$-substituted or unsubstituted heteroalkyl, $R^{66}$-substituted or unsubstituted cycloalkyl, $R^{66}$ substituted or unsubstituted heterocycloalkyl, $R^{66}$-substituted or unsubstituted aryl, or $R^{66}$-substituted or unsubstituted heteroaryl. $X^{13}$ is independently halogen. In embodiments, $X^{13}$ is independently F or Cl.

$R^{66}$ is independently oxo, halogen, —$CX^{66}_3$, —$CHX^{66}_2$, —$OCH_2X^{66}$, —$OCHX^{66}_2$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{66}_3$, —$OCHX^{66}_2$, $R^{67}$-substituted or unsubstituted alkyl, $R^{67}$-substituted or unsubstituted heteroalkyl, $R^{67}$-substituted or unsubstituted cycloalkyl, $R^{67}$-substituted or unsubstituted heterocycloalkyl, $R^{67}$-substituted or unsubstituted aryl, or $R^{67}$-substituted or unsubstituted heteroaryl. $X^{66}$ is independently halogen. In embodiments, $X^{66}$ is independently F or Cl.

$R^{67}$ is independently oxo, halogen, —$CX^{67}_3$, —$CHX^{67}_2$, —$OCH_2X^{67}$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{67}_3$, —$OCHX^{67}_2$, $R^{68}$-substituted or unsubstituted alkyl, $R^{68}$-substituted or unsubstituted heteroalkyl, $R^{68}$-substituted or unsubstituted cycloalkyl, $R^{68}$ substituted or unsubstituted heterocycloalkyl, $R^{68}$-substituted or unsubstituted aryl, or $R^{68}$-substituted or unsubstituted heteroaryl. $X^{67}$ is independently halogen. In embodiments, $X^{67}$ is independently F or Cl.

In embodiments, $R^{14}$ is independently hydrogen, oxo, halogen, —$CX^{14}_3$, —$CHX^{14}_2$, —$OCH_2X^{14}$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{14}_3$, —$OCHX^{14}_2$, $R^{69}$-substituted or unsubstituted alkyl, $R^{69}$-substituted or unsubstituted heteroalkyl, $R^{69}$-substituted or unsubstituted cycloalkyl, $R^{69}$ substituted or unsubstituted heterocycloalkyl, $R^{69}$-substituted or unsubstituted aryl, or $R^{69}$-substituted or unsubstituted heteroaryl. $X^{14}$ is independently halogen. In embodiments, $X^{14}$ is independently F or Cl.

$R^{69}$ is independently oxo, halogen, —$CX^{69}_3$, —$CHX^{69}_2$, —$OCH_2X^{69}$, —$OCHX^{69}_2$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{69}_3$, —$OCHX^{69}_2$, $R^{70}$-substituted or unsubstituted alkyl, $R^{70}$-substituted or unsubstituted heteroalkyl, $R^{70}$-substituted or unsubstituted cycloalkyl, $R^{70}$-substituted or unsubstituted heterocycloalkyl, $R^{70}$-substituted or unsubstituted aryl, or $R^{70}$-substituted or unsubstituted heteroaryl. $X^{69}$ is independently halogen. In embodiments, $X^{69}$ is independently F or Cl.

$R^{70}$ is independently oxo, halogen, —$CX^{70}_3$, —$CHX^{70}_2$, —$OCH_2X^{70}$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{70}_3$, —$OCHX^{70}_2$, $R^{71}$-substituted or unsubstituted alkyl, $R^{71}$-substituted or unsubstituted heteroalkyl, $R^{71}$-substituted or unsubstituted cycloalkyl, $R^{71}$ substituted or unsubstituted heterocycloalkyl, $R^{71}$-substituted or unsubstituted aryl, or $R^{71}$-substituted or unsubstituted heteroaryl. $X^{70}$ is independently halogen. In embodiments, $X^{70}$ is independently F or Cl.

Each $R^7$, $R^8$, $R^9$, $R^{10}$, $R^{11}$, $R^{12}$, $R^{13}$, and $R^{14}$ may independently be hydrogen, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O) NH_2$, $-NHSO_2H$, $-NHC=(O)H$, $-NHC(O)-OH$, $-NHOH$, $-OCF_3$, $-OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each $R^7$, $R^8$, $R^9$, $R^{10}$, $R^{11}$, $R^{12}$, $R^{13}$, and $R^{14}$ may independently be hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Each $R^7$, $R^8$, $R^9$, $R^{10}$, $R^{11}$, $R^{12}$, $R^{13}$, and $R^{14}$ may independently be hydrogen, unsubstituted alkyl, unsubstituted heteroalkyl, unsubstituted cycloalkyl, unsubstituted heterocycloalkyl, unsubstituted aryl, or unsubstituted heteroaryl. Each $R^7$, $R^8$, $R^9$, $R^{10}$, $R^{11}$, $R^{12}$, $R^{13}$, and $R^{14}$ may independently be hydrogen, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. Each $R^7$, $R^8$, $R^9$, $R^{10}$, $R^{11}$, $R^{12}$, $R^{13}$, and $R^{14}$ may independently be hydrogen, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl.

Each $R^7$, $R^8$, $R^9$, $R^{10}$, $R^{11}$, $R^{12}$, $R^{13}$, and $R^{14}$ may independently be hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$ aryl, or substituted or unsubstituted 5 to 6 membered heteroaryl. Each $R^7$, $R^8$, $R^9$, $R^{10}$, $R^{11}$, $R^{12}$, $R^{13}$, and $R^{14}$ may independently be hydrogen, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted $C_6$ aryl, or unsubstituted 5 to 6 membered heteroaryl.

In embodiments, Ring A is unsubstituted phenyl and Ring B is unsubstituted thienyl. In embodiments, Ring A is para-hydroxy substituted phenyl and Ring B is unsubstituted thienyl. In embodiments, Ring A is para-hydroxy substituted phenyl and Ring B is unsubstituted phenyl. In embodiments, Ring A is para-hydroxy substituted phenyl and Ring B is unsubstituted benzothienyl. In embodiments, Ring A is para-hydroxy substituted phenyl and Ring B is para-methyl substituted phenyl. In embodiments, Ring A is 2-hydroxy pyridin-4-yl and Ring B is unsubstituted thienyl. In embodiments, Ring A is 2-hydroxy pyridin-5-yl and Ring B is unsubstituted thienyl. In embodiments, Ring A is para-hydroxy substituted phenyl and Ring B is unsubstituted napthyl. In embodiments, Ring A is para-hydroxy substituted phenyl and Ring B is unsubstituted 2,3-dihydro-1H-indenyl.

In embodiments, $L^1$ is substituted or unsubstituted ($C_1$-$C_5$) alkylene. In embodiments, $L^1$ is substituted or unsubstituted 2 to 5 membered heteroalkylene. In embodiments, $L^1$ is unsubstituted ($C_1$-$C_3$) alkylene. In embodiments, $L^1$ is $R^{96}$-substituted or unsubstituted $C_1$-$C_5$ alkylene, $R^{96}$-substituted or unsubstituted 2 to 5 membered heteroalkylene. In embodiments, $L^1$ is $R^{96}$-substituted or unsubstituted $C_1$-$C_5$ alkylene. In embodiments, $L^1$ is $R^{96}$-substituted or unsubstituted $C_1$-$C_3$ alkylene. In embodiments, $L^1$ is $R^{96}$-substituted or unsubstituted methylene. In embodiments, $L^1$ is $R^{96}$-substituted or unsubstituted 2 to 5 membered heteroalkylene. In embodiments, $L^1$ is $R^{96}$-substituted or unsubstituted 2 to 3 membered heteroalkylene. In embodiments, $L^1$ is unsubstituted methylene. In embodiments, $L^1$ and $R^1$ are joined to form a substituted or unsubstituted 4 to 8 membered heterocycloalkyl. In embodiments, $L^1$ and $R^1$ are joined to form an $R^{96}$-substituted or unsubstituted 4 to 8 membered heterocycloalkyl. In embodiments, $L^1$ and $R^1$ are joined to form a substituted 4 to 8 membered heterocycloalkyl. In embodiments, $L^1$ and $R^1$ are joined to form an $R^{96}$-substituted 4 to 8 membered heterocycloalkyl. In embodiments, $L^1$ and $R^1$ are joined to form an unsubstituted 4 to 8 membered heterocycloalkyl. In embodiments, $L^1$ and $R^1$ are joined to form a substituted or unsubstituted 4 membered heterocycloalkyl. In embodiments, $L^1$ and $R^1$ are joined to form an $R^{96}$-substituted or unsubstituted 4 membered heterocycloalkyl. In embodiments, $L^9$ and $R^1$ are joined to form a substituted 4 membered heterocycloalkyl. In embodiments, $L^1$ and $R^1$ are joined to form an $R^{96}$ substituted 4 membered heterocycloalkyl. In embodiments, $L^1$ and $R^1$ are joined to form an unsubstituted 4 membered heterocycloalkyl. In embodiments, $L^1$ and $R^1$ are joined to form a substituted or unsubstituted 4 membered heterocycloalkyl. In embodiments, $L^1$ and $R^1$ are joined to form an $R^{96}$-substituted or unsubstituted 5 membered heterocycloalkyl. In embodiments, $L^1$ and $R^1$ are joined to form a substituted 5 membered heterocycloalkyl. In embodiments, L and $R^1$ are joined to form an $R^{96}$-substituted 5 membered heterocycloalkyl. In embodiments, $L^1$ and $R^1$ are joined to form an unsubstituted 5 membered heterocycloalkyl. In embodiments, $L^1$ and R are joined to form a substituted or unsubstituted 4 membered heterocycloalkyl. In embodiments, $L^1$ and $R^1$ are joined to form an $R^{96}$-substituted or unsubstituted 6 membered heterocycloalkyl. In embodiments, $L^1$ and $R^1$ are joined to form a substituted 6 membered heterocycloalkyl. In embodiments, $L^1$ and $R^1$ are joined to form an $R^{96}$-substituted 6 membered heterocycloalkyl. In embodiments, $L^1$ and $R^1$ are joined to form an unsubstituted 6 membered heterocycloalkyl. In embodiments, $L^1$ and $R^1$ are joined to form a substituted or unsubstituted 4 membered heterocycloalkyl. In embodiments, $L^1$ and $R^1$ are joined to form an $R^{96}$-substituted or unsubstituted 7 membered heterocycloalkyl. In embodiments, $L^1$ and $R^1$ are joined to form a substituted 7 membered heterocycloalkyl. In embodiments, $L^1$ and $R^1$ are joined to form an $R^{96}$ substituted 7 membered heterocycloalkyl. In embodiments, $L^1$ and $R^1$ are joined to form an unsubstituted 7 membered heterocycloalkyl. In embodiments, $L^1$ and $R^1$ are joined to form a substituted or unsubstituted 4 membered heterocycloalkyl. In embodiments, $L^1$ and $R^1$ are joined to form an $R^{96}$-substituted or unsubstituted 8 membered heterocycloalkyl. In embodiments, L and $R^1$ are joined to form a substituted 8 membered heterocycloalkyl. In embodiments, $L^1$ and $R^1$ are joined to form an $R^{96}$-substituted 8 membered heterocycloalkyl. In embodiments, $L^1$ and $R^1$ are joined to form an unsubstituted 8 membered heterocycloalkyl.

In embodiments, $L^1$ and $R^2$ are joined to form a substituted or unsubstituted 4 to 8 membered heterocycloalkyl. In embodiments, $L^1$ and $R^2$ are joined to form an $R^{96}$-substituted or unsubstituted 4 to 8 membered heterocycloalkyl. In embodiments, $L^1$ and $R^2$ are joined to form a substituted 4 to 8 membered heterocycloalkyl. In embodiments, $L^1$ and $R^2$ are joined to form an $R^{96}$-substituted 4 to 8 membered heterocycloalkyl. In embodiments, $L^1$ and $R^2$ are joined to form an unsubstituted 4 to 8 membered heterocycloalkyl. In embodiments, $L^1$ and $R^2$ are joined to form a substituted or unsubstituted 4 membered heterocycloalkyl. In embodiments, $L^1$ and $R^2$ are joined to form an $R^{96}$-substituted or unsubstituted 4 membered heterocycloalkyl. In embodiments, $L^1$ and $R^2$ are joined to form a substituted 4 membered heterocycloalkyl. In embodiments, $L^1$ and $R^2$ are joined to form an $R^{96}$-substituted 4 membered heterocycloalkyl. In embodiments, $L^1$ and $R^2$ are joined to form an unsubstituted 4 membered heterocycloalkyl. In embodiments, $L^1$ and $R^2$ are joined to form a substituted or unsubstituted 4 membered heterocycloalkyl. In embodiments, $L^1$ and $R^2$ are joined to form an $R^{96}$-substituted or unsubstituted 5 membered heterocycloalkyl. In embodiments, $L^1$ and $R^2$ are joined to form a substituted 5 membered heterocycloalkyl. In embodiments, $L^1$ and $R^2$ are joined to form an $R^{96}$-substituted 5 membered heterocycloalkyl. In embodiments, $L^1$ and $R^2$ are joined to form an unsubstituted 5 membered heterocycloalkyl. In embodiments, $L^1$ and $R^2$ are joined to form a substituted or unsubstituted 4 membered heterocycloalkyl. In embodiments, $L^1$ and $R^2$ are joined to form an $R^{96}$-substituted or unsubstituted 6 membered heterocycloalkyl. In embodiments, $L^1$ and $R^2$ are joined to form a substituted 6 membered heterocycloalkyl. In embodiments, $L^1$ and $R^2$ are joined to form an $R^{96}$-substituted 6 membered heterocycloalkyl. In embodiments, $L^1$ and $R^2$ are joined to form an unsubstituted 6 membered heterocycloalkyl. In embodiments, $L^1$ and $R^2$ are joined to form a substituted or unsubstituted 4 membered heterocycloalkyl. In embodiments, $L^1$ and $R^2$ are joined to form an $R^{96}$-substituted or unsubstituted 7 membered heterocycloalkyl. In embodiments, L and $R^2$ are joined to form a substituted 7 membered heterocycloalkyl. In embodiments, $L^1$ and $R^2$ are joined to form an $R^{96}$-substituted 7 membered heterocycloalkyl. In embodiments, $L^1$ and $R^2$ are joined to form an unsubstituted 7 membered heterocycloalkyl. In embodiments, $L^1$ and $R^2$ are joined to form a substituted or unsubstituted 4 membered heterocycloalkyl. In embodiments, $L^1$ and $R^2$ are joined to form an $R^{96}$-substituted or unsubstituted 8 membered heterocycloalkyl. In embodiments, $L^1$ and $R^2$ are joined to form a substituted 8 membered heterocycloalkyl. In embodiments, $L^1$ and $R^2$ are joined to form an $R^{96}$-substituted 8 membered heterocycloalkyl. In embodiments, $L^1$ and $R^2$ are joined to form an unsubstituted 8 membered heterocycloalkyl.

In embodiments, $L^1$ is a bond, $R^{96}$-substituted or unsubstituted alkylene, or $R^{96}$-substituted or unsubstituted heteroalkylene.

$R^{96}$ is independently oxo, halogen, $-CX^{96}_3$, $-CHX^{96}_2$, $-OCH_2X^{96}$, $-OCHX^{96}_2$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{96}_3$, $-OCHX^{96}_2$, $R^{97}$-substituted or unsubstituted alkyl, $R^{97}$-substituted or unsubstituted heteroalkyl, $R^{97}$-substituted or unsubstituted cycloalkyl, $R^{97}$-substituted or unsubstituted heterocycloalkyl, $R^{97}$-substituted or unsubstituted aryl, or $R^{97}$-substituted or unsubstituted heteroaryl. $X^{96}$ is independently halogen. In embodiments, $X^{96}$ is independently F or Cl.

$R^{97}$ is independently oxo, halogen, $-CX^{97}_3$, $-CHX^{97}_2$, $-OCH_2X^{97}$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{97}_3$, $-OCHX^{97}_2$, $R^{98}$-substituted or unsubstituted alkyl, $R^{98}$-substituted or unsubstituted heteroalkyl, $R^{98}$-substituted or unsubstituted cycloalkyl, $R^{98}$ substituted or unsubstituted heterocycloalkyl, $R^{98}$-substituted or unsubstituted aryl, or $R^{98}$-substituted or unsubstituted heteroaryl. $X^{97}$ is independently halogen. In embodiments, $X^{97}$ is independently F or Cl.

In embodiments, $L^2$ is a bond, $R^{99}$-substituted or unsubstituted alkylene, or $R^{99}$ substituted or unsubstituted heteroalkylene.

$R^{99}$ is independently oxo, halogen, $-CX^{99}_3$, $-CHX^{99}_2$, $-OCH_2X^{99}$, $-OCHX^{99}_2$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{99}_3$, $-OCHX^{99}_2$, $R^{100}$-substituted or unsubstituted alkyl, $R^{100}$-substituted or unsubstituted heteroalkyl, $R^{100}$-substituted or unsubstituted cycloalkyl, $R^{100}$-substituted or unsubstituted heterocycloalkyl, $R^{100}$-substituted or unsubstituted aryl, or $R^{100}$-substituted or unsubstituted heteroaryl. $X^{99}$ is independently halogen. In embodiments, $X^{99}$ is independently F or Cl.

$R^{100}$ is independently oxo, halogen, $-CX^{100}_3$, $-CHX^{100}_2$, $-OCH_2X^{100}$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{100}_3$, $-OCHX^{100}_2$, $R^{101}$-substituted or unsubstituted alkyl, $R^{101}$-substituted or unsubstituted heteroalkyl, $R^{101}$-substituted or unsubstituted cycloalkyl, $R^{101}$-substituted or unsubstituted heterocycloalkyl, $R^{101}$-substituted or unsubstituted aryl, or $R^{101}$-substituted or unsubstituted heteroaryl. $X^{100}$ is independently halogen. In embodiments, $X^{100}$ is independently F or Cl.

In embodiments, $R^{96}$ is independently oxo, halogen, $-CX^{96}_3$, $-CHX^{96}_2$, $-OCH_2X^{96}$, $-OCHX^{96}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{96}_3$, $-OCHX^{96}_2$, substituted or unsubstituted ($C_1$-$C_5$) alkyl, substituted or unsubstituted 2 to 5 membered heteroalkyl, substituted or unsubstituted ($C_3$-$C_5$) cycloalkyl, substituted or unsubstituted 3 to 5 membered heterocycloalkyl, substituted or unsubstituted phenyl, or substituted or unsubstituted 5 to 6 membered heteroaryl. $X^{96}$ is independently halogen.

In embodiments, $R^1$ is independently hydrogen, oxo, halogen, $-CX^{13}$, $-CHX^{12}$, $-OCH_2X^1$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^1_3$, $-OCHX^1_2$, $R^{30}$-substituted or unsubstituted alkyl, $R^{30}$-substituted or unsubstituted heteroalkyl, $R^{30}$-substituted or unsubstituted cycloalkyl, $R^{30}$ substituted or unsubstituted heterocycloalkyl, $R^{30}$-substituted or unsubstituted aryl, or $R^{30}$-substituted or unsubstituted heteroaryl. $X^1$ is independently halogen. In embodiments, $X^1$ is independently F or Cl.

$R^{30}$ is independently oxo, halogen, $-CX^{30}_3$, $-CHX^{30}_2$, $-OCH_2X^{30}$, $-OCHX^{30}_2$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{30}{}_3$, —OCHX$^{30}{}_2$, R$^{31}$-substituted or unsubstituted alkyl, R$^{31}$-substituted or unsubstituted heteroalkyl, R$^{31}$-substituted or unsubstituted cycloalkyl, R$^{31}$-substituted or unsubstituted heterocycloalkyl, R$^{31}$-substituted or unsubstituted aryl, or R$^{31}$-substituted or unsubstituted heteroaryl. X$^{30}$ is independently halogen. In embodiments, X$^{30}$ is independently F or Cl.

R$^{31}$ is independently oxo, halogen, —CX$^{31}{}_3$, —CHX$^{31}{}_2$, —OCH$_2$X$^{31}$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{31}{}_3$, —OCHX$^{31}{}_2$, R$^{32}$-substituted or unsubstituted alkyl, R$^{32}$-substituted or unsubstituted heteroalkyl, R$^{32}$-substituted or unsubstituted cycloalkyl, R$^{32}$ substituted or unsubstituted heterocycloalkyl, R$^{32}$-substituted or unsubstituted aryl, or R$^{32}$-substituted or unsubstituted heteroaryl. X$^{31}$ is independently halogen. In embodiments, X$^{31}$ is independently F or Cl.

In embodiments, R$^1$ is independently hydrogen, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —CHF$_2$, —CH$_2$F, OCF$_3$, —OCHF$_2$, substituted or unsubstituted (C$_1$-C$_5$) alkyl, substituted or unsubstituted 2 to 5 membered heteroalkyl, substituted or unsubstituted (C$_3$-C$_6$) cycloalkyl, or substituted or unsubstituted 3 to 6 membered heterocycloalkyl. In embodiments, R$^1$ is independently halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —CHF$_2$, —CH$_2$F, OCF$_3$, —OCHF$_2$, substituted or unsubstituted (C$_1$-C$_5$) alkyl, substituted or unsubstituted 2 to 5 membered heteroalkyl, substituted or unsubstituted (C$_3$-C$_6$) cycloalkyl, or substituted or unsubstituted 3 to 6 membered heterocycloalkyl.

In embodiments, R$^1$ is independently halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —CHF$_2$, —CH$_2$F, OCF$_3$, —OCHF$_2$, R$^{30}$-substituted or unsubstituted (C$_1$-C$_5$) alkyl, R$^{30}$-substituted or unsubstituted 2 to 5 membered heteroalkyl, R$^{30}$-substituted or unsubstituted (C$_3$-C$_6$) cycloalkyl, or R$^{30}$-substituted or unsubstituted 3 to 6 membered heterocycloalkyl. In embodiments, R$^1$ is unsubstituted (C$_1$-C$_3$) alkyl. In embodiments, R$^1$ is unsubstituted (C$_1$-C$_2$) alkyl. In embodiments, R$^1$ is R$^{30}$-substituted or unsubstituted (C$_1$-C$_2$) alkyl; R$^{30}$ is independently halogen, —OH, —NH$_2$, —SH, substituted or unsubstituted (C$_1$-C$_3$) alkyl, substituted or unsubstituted 2 to 3 membered heteroalkyl, or substituted or unsubstituted cyclopropyl; and X$^{30}$ is independently halogen. In embodiments, R$^1$ is unsubstituted methyl. In embodiments, R$^1$ is R$^{30}$-substituted or unsubstituted (C$_1$-C$_3$) alkyl or R$^{30}$-substituted or unsubstituted 2 to 3 membered heteroalkyl. In embodiments, R$^1$ is independently hydrogen. In embodiments, R$^1$ is a R$^{30}$-substituted methyl. In embodiments, R$^1$ is a R$^{30}$-substituted ethyl. In embodiments, R$^1$ is R$^{30}$-substituted or unsubstituted 2 to 5 membered heteroalkyl. In embodiments, R$^1$ is R$^{30}$-substituted or unsubstituted 3 membered heteroalkyl. In embodiments, R$^1$ is R$^{30}$-substituted or unsubstituted 2 to 5 membered heteroalkyl. In embodiments, R$^1$ is 9-ethyl-9H-fluorene. In embodiments, R$^1$ is 9-fluoromethoxycarbonyl. In embodiments, R$^1$ is

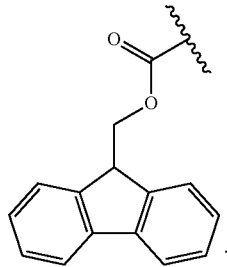 [SMILES: *C(=O)OCC1c2ccccc2-c2ccccc21]

In embodiments, R$^{30}$ is independently oxo, halogen, —CX$^{30}{}_3$, —CHX$^{30}{}_2$, —OCH$_2$X$^{30}$, —OCHX$^{30}{}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{30}{}_3$, —OCHX$^{30}{}_2$, substituted or unsubstituted (C$_1$-C$_5$) alkyl, substituted or unsubstituted 2 to 5 membered heteroalkyl, substituted or unsubstituted (C$_3$-C$_5$) cycloalkyl, substituted or unsubstituted 3 to 5 membered heterocycloalkyl, substituted or unsubstituted phenyl, or substituted or unsubstituted 5 to 6 membered heteroaryl. X$^{30}$ is independently halogen. In embodiments, R$^{30}$ is —Cl. In embodiments, R$^{30}$ is —OH.

In embodiments, R$^{30}$ is independently oxo, halogen, —CX$^{30}{}_3$, —CHX$^{30}{}_2$, —OCH$_2$X$^{30}$, —OCHX$^{30}{}_2$, —CN, —OH, —NH$_2$, —COOH, —CONH$_2$, —NO$_2$, —SH, —SO$_2$NH$_2$, —NHNH$_2$, —ONH$_2$, —NHOH, —OCX$^{30}{}_3$, —OCHX$^{30}{}_2$, substituted or unsubstituted (C$_1$-C$_3$) alkyl, substituted or unsubstituted 2 to 3 membered heteroalkyl, or substituted or unsubstituted cyclopropyl. X$^{30}$ is independently halogen. In embodiments, R$^{30}$ is unsubstituted cyclopropyl. In embodiments, R$^{30}$ is unsubstituted cyclobutyl. In embodiments, R$^{30}$ is unsubstituted cyclopentyl. In embodiments, R$^{30}$ is unsubstituted cyclohexyl. In embodiments, R$^{30}$ is substituted or unsubstituted phenyl. In embodiments, R$^{30}$ is unsubstituted phenyl. In embodiments, R$^{30}$ is unsubstituted benzyl.

In embodiments, R$^{30}$ is independently oxo, halogen, —CX$^{30}{}_3$, —CHX$^{30}{}_2$, —OCH$_2$X$^{30}$, —OCHX$^{30}{}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{30}{}_3$, —OCHX$^{30}{}_2$, substituted or unsubstituted (C$_1$-C$_3$) alkyl, or substituted or unsubstituted 2 to 3 membered heteroalkyl. In embodiments, R$^{30}$ is independently oxo, halogen, —OH, —NH$_2$, —COOH, —CONH$_2$, —NO$_2$, —SH, substituted or unsubstituted (C$_1$-C$_3$) alkyl, or substituted or unsubstituted 2 to 3 membered heteroalkyl. X$^{30}$ is independently halogen.

In embodiments, R$^2$ is independently hydrogen, oxo, halogen, —CX$^2{}_3$, —CHX$^2{}_2$, —OCH$_2$X$^2$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^2{}_3$, —OCHX$^2{}_2$, R$^{33}$-substituted or unsubstituted alkyl, R$^{33}$-substituted or unsubstituted heteroalkyl, R$^{33}$-substituted or unsubstituted cycloalkyl, R$^{33}$-substituted or unsubstituted heterocycloalkyl, R$^{33}$-substituted or unsubstituted aryl, or $R^{33}$-substituted or unsubstituted heteroaryl. $X^2$ is independently halogen. In embodiments, $X^2$ is independently F or Cl.

$R^{33}$ is independently oxo, halogen, —$CX^{33}_3$, —$CHX^{33}_2$, —$OCH_2X^{33}$, —$OCHX^{33}_2$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{33}_3$, —$OCHX^{33}_2$, $R^{34}$-substituted or unsubstituted alkyl, $R^{34}$-substituted or unsubstituted heteroalkyl, $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl. $X^{33}$ is independently halogen. In embodiments, $X^{33}$ is independently F or Cl.

$R^{34}$ is independently oxo, halogen, —$CX^{34}_3$, —$CHX^{34}_2$, —$OCH_2X^{34}$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{34}_3$, —$OCHX^{34}_2$, $R^{35}$-substituted or unsubstituted alkyl, $R^{35}$-substituted or unsubstituted heteroalkyl, $R^{35}$-substituted or unsubstituted cycloalkyl, $R^{35}$-substituted or unsubstituted heterocycloalkyl, $R^{35}$-substituted or unsubstituted aryl, or $R^{35}$-substituted or unsubstituted heteroaryl. $X^{34}$ is independently halogen. In embodiments, $X^{34}$ is independently F or Cl.

In embodiments, $R^2$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, $OCF_3$, —$OCHF_2$, substituted or unsubstituted ($C_1$-$C_5$) alkyl, substituted or unsubstituted 2 to 5 membered heteroalkyl, substituted or unsubstituted ($C_3$-$C_6$) cycloalkyl, or substituted or unsubstituted 3 to 6 membered heterocycloalkyl. In embodiments, $R^2$ is independently halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, $OCF_3$, —$OCHF_2$, substituted or unsubstituted ($C_1$-$C_5$) alkyl, substituted or unsubstituted 2 to 5 membered heteroalkyl, substituted or unsubstituted ($C_3$-$C_6$) cycloalkyl, or substituted or unsubstituted 3 to 6 membered heterocycloalkyl.

In embodiments, $R^2$ is independently halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, $OCF_3$, —$OCHF_2$, $R^{33}$-substituted or unsubstituted ($C_1$-$C_5$) alkyl, $R^{33}$-substituted or unsubstituted 2 to 5 membered heteroalkyl, $R^{33}$-substituted or unsubstituted ($C_3$-$C_6$) cycloalkyl, or $R^{33}$-substituted or unsubstituted 3 to 6 membered heterocycloalkyl. In embodiments, $R^2$ is $R^{33}$-substituted or unsubstituted ($C_1$-$C_3$) alkyl or $R^{33}$ substituted or unsubstituted 2 to 3 membered heteroalkyl. In embodiments, $R^2$ is unsubstituted ($C_1$-$C_3$) alkyl. In embodiments, $R^2$ is unsubstituted ($C_1$-$C_2$) alkyl. In embodiments, $R^2$ is $R^{33}$-substituted or unsubstituted ($C_1$-$C_2$) alkyl; $R^{33}$ is independently halogen, —OH, —$NH_2$, —SH, substituted or unsubstituted ($C_1$-$C_3$) alkyl, substituted or unsubstituted 2 to 3 membered heteroalkyl, or substituted or unsubstituted cyclopropyl. $X^{33}$ is independently halogen. In embodiments, $R^2$ is unsubstituted methyl. In embodiments, $R^2$ is independently hydrogen. In embodiments, $R^2$ is $R^{33}$-substituted or unsubstituted 2 to 5 membered heteroalkyl. In embodiments, $R^2$ is $R^{33}$-substituted or unsubstituted 3 membered heteroalkyl. In embodiments, $R^1$ is $R^{33}$-substituted or unsubstituted 2 to 5 membered heteroalkyl. In embodiments, $R^2$ is 9-ethyl-9H-fluorene. In embodiments, $R^2$ is 9-fluoromethoxycarbonyl. In embodiments, $R^2$ is

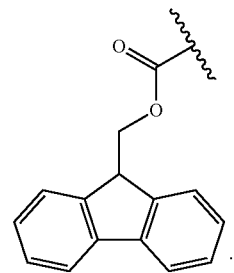 [SMILES: *C(=O)OCC1c2ccccc2-c2ccccc21]

In embodiments, $R^{33}$ is independently oxo, halogen, —$CX^{33}_3$, —$CHX^{30}_2$, —$OCH_2X^{33}$, —$OCHX^{33}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{33}_3$, —$OCHX^{33}_2$, substituted or unsubstituted ($C_1$-$C_5$) alkyl, substituted or unsubstituted 2 to 5 membered heteroalkyl, substituted or unsubstituted ($C_3$-$C_5$) cycloalkyl, substituted or unsubstituted 3 to 5 membered heterocycloalkyl, substituted or unsubstituted phenyl, or substituted or unsubstituted 5 to 6 membered heteroaryl. $X^{33}$ is independently halogen. In embodiments, $R^{33}$ is —Cl. In embodiments, $R^{33}$ is —OH.

In embodiments, $R^{33}$ is independently oxo, halogen, —$CX^{33}_3$, —$CHX^{33}_2$, —$OCH_2X^{33}$, —$OCHX^{33}_2$, —CN, —OH, —$NH_2$, —COOH, —$CONH_2$, —$NO_2$, —SH, —$SO_2NH_2$, —$NHNH_2$, —$ONH_2$, —NHOH, —$OCX^{33}_3$, —$OCHX^{33}_2$, substituted or unsubstituted ($C_1$-$C_3$) alkyl, substituted or unsubstituted 2 to 3 membered heteroalkyl, or substituted or unsubstituted cyclopropyl; and $X^{33}$ is independently halogen. heterocycloalkyl. In embodiments, $R^{33}$ is independently oxo, halogen, —$CX^{33}_3$, —$CHX^{33}_2$, —$OCH_2X^{33}$, —$OCHX^{30}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{33}_3$, —$OCHX^{33}_2$, substituted or unsubstituted ($C_1$-$C_5$) alkyl, substituted or unsubstituted 2 to 5 membered heteroalkyl, substituted or unsubstituted ($C_3$-$C_5$) cycloalkyl, substituted or unsubstituted 3 to 5 membered heterocycloalkyl, substituted or unsubstituted phenyl, or substituted or unsubstituted 5 to 6 membered heteroaryl; and $X^{33}$ is independently halogen. In embodiments, $R^{33}$ is unsubstituted cyclopropyl. In embodiments, $R^{33}$ is unsubstituted cyclobutyl. In embodiments, $R^{33}$ is unsubstituted cyclopentyl. In embodiments, $R^{33}$ is unsubstituted cyclohexyl. In embodiments, $R^{33}$ is substituted or unsubstituted phenyl. In embodiments, $R^{33}$ is unsubstituted phenyl. In embodiments, $R^{33}$ is unsubstituted benzyl.

In embodiments, $R^{33}$ is independently oxo, halogen, —$CX^{33}_3$, —$CHX^{33}_2$, —$OCH_2X^{33}$, —$OCHX^{30}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)NHNH$_2$, —NHC═(O)NH$_2$, —NHSO$_2$H, —NHC═(O)H, —NHC(O)—OH, —NHOH, —OCX$^{33}_3$, —OCHX$^{33}_2$, substituted or unsubstituted (C$_1$-C$_3$) alkyl, or substituted or unsubstituted 2 to 3 membered heteroalkyl; and X$^{33}$ is independently halogen. In embodiments, R$^{33}$ is independently oxo, halogen, —OH, —NH$_2$, —COOH, —CONH$_2$, —NO$_2$, —SH, substituted or unsubstituted (C$_1$-C$_3$) alkyl, or substituted or unsubstituted 2 to 3 membered heteroalkyl; and X$^{33}$ is independently halogen.

In embodiments, L$^1$ and R$^1$ are joined to form a substituted or unsubstituted 4 to 8 membered heterocycloalkyl. In embodiments, L$^1$ and R$^1$ are joined to form a R$^{30}$-substituted or unsubstituted 4 to 8 membered heterocycloalkyl. In embodiments, L$^1$ and R$^2$ are joined to form a substituted or unsubstituted 4 to 8 membered heterocycloalkyl. In embodiments, L$^1$ and R$^2$ are joined to form a R$^{33}$-substituted or unsubstituted 4 to 8 membered heterocycloalkyl.

In embodiments, R$^1$ and R$^2$ are joined to form a substituted or unsubstituted 3 to 6 membered heterocycloalkyl or substituted or unsubstituted 5 to 6 membered heteroaryl. In embodiments, R$^1$ and R$^2$ are joined to form a substituted or unsubstituted 3 to 6 membered heterocycloalkyl. In embodiments, R$^1$ and R$^2$ are joined to form a R$^{30}$-substituted or unsubstituted 3 to 6 membered heterocycloalkyl. In embodiments, R$^1$ and R$^2$ are joined to form a R$^{30}$-substituted or unsubstituted 5 membered heterocycloalkyl.

In embodiments, R$^5$ is substituted or unsubstituted (C$_1$-C$_5$) alkyl or substituted or unsubstituted 2 to 5 membered heteroalkyl. In embodiments, R$^5$ is substituted or unsubstituted (C$_1$-C$_5$) alkyl. In embodiments, R$^5$ is unsubstituted (C$_1$-C$_5$) alkyl. In embodiments, R$^5$ is unsubstituted (C$_1$-C$_3$) alkyl. In embodiments, R$^5$ is unsubstituted methyl. In embodiments, R$^5$ is hydrogen. In embodiments, R$^5$ is propenyl. In embodiments, R$^5$ is ethenyl.

In embodiments, W is O. In embodiments, W is S.

In embodiments, L$^3$ is —N(R$^6$)—. In embodiments, L$^3$ is —CH(R$^6$)—. In embodiments, L$^3$ is a bond. In embodiments, L$^3$ is —O—. In embodiments, L$^3$ is —CH$_2$—. In embodiments, L$^3$ is —NH—.

In embodiments, R$^6$ is hydrogen. In embodiments, R$^6$ is substituted or unsubstituted (C$_1$-C$_5$) alkyl or substituted or unsubstituted 2 to 5 membered heteroalkyl. In embodiments, R$^6$ is substituted or unsubstituted (C$_1$-C$_5$) alkyl. In embodiments, R$^6$ is unsubstituted (C$_1$-C$_5$) alkyl. In embodiments, R$^6$ is unsubstituted (C$_1$-C$_3$) alkyl. In embodiments, R$^6$ is unsubstituted methyl.

In embodiments, R$^6$ is independently hydrogen, oxo, halogen, —CX$^{63}$, —CHX$^{62}$, —OCH$_2$X$^6$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCX$^{63}$, —OCHX$^{62}$, R$^{45}$-substituted or unsubstituted alkyl, R$^{45}$-substituted or unsubstituted heteroalkyl, R$^{45}$-substituted or unsubstituted cycloalkyl, R$^{45}$-substituted or unsubstituted heterocycloalkyl, R$^{45}$-substituted or unsubstituted aryl, or R$^{45}$-substituted or unsubstituted heteroaryl. X$^6$ is independently halogen. In embodiments, X$^6$ is independently F or Cl.

R$^{45}$ is independently oxo, halogen, —CX$^{45}_3$, —CHX$^{45}_2$, —OCH$_2$X$^{45}$, —OCHX$^{45}_2$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCX$^{45}_3$, —OCHX$^{45}_2$, R$^{46}$-substituted or unsubstituted alkyl, R$^{46}$-substituted or unsubstituted heteroalkyl, R$^{46}$-substituted or unsubstituted cycloalkyl, R$^{46}$-substituted or unsubstituted heterocycloalkyl, R$^{46}$-substituted or unsubstituted aryl, or R$^{46}$-substituted or unsubstituted heteroaryl. X$^{45}$ is independently halogen. In embodiments, X$^{45}$ is independently F or Cl.

R$^{46}$ is independently oxo, halogen, —CX$^{46}_3$, —CHX$^{46}_2$, —OCH$_2$X$^{46}$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCX$^{46}_3$, —OCHX$^{46}_2$, R$^{47}$-substituted or unsubstituted alkyl, R$^{47}$-substituted or unsubstituted heteroalkyl, R$^{47}$-substituted or unsubstituted cycloalkyl, R$^{47}$-substituted or unsubstituted heterocycloalkyl, R$^{47}$-substituted or unsubstituted aryl, or R$^{47}$-substituted or unsubstituted heteroaryl. X$^{46}$ is independently halogen. In embodiments, X$^{46}$ is independently F or Cl.

In embodiments, L$^2$ is a bond. In embodiments, L$^2$ is substituted or unsubstituted 2 to 5 membered heteroalkylene. In embodiments, L$^2$ is unsubstituted 2 to 5 membered heteroalkylene. In embodiments, L$^2$ is substituted or unsubstituted (C$_1$-C$_5$) alkylene. In embodiments, L$^2$ is substituted or unsubstituted (C$_2$-C$_5$) alkylene. In embodiments, L$^2$ is unsubstituted (C$_1$-C$_5$) alkylene. In embodiments, L$^2$ is unsubstituted (C$_1$-C$_4$) alkylene. In embodiments, L$^2$ is unsubstituted (C$_1$-C$_3$) alkylene. In embodiments, L$^2$ is unsubstituted (C$_1$-C$_2$) alkylene. In embodiments, L$^2$ is unsubstituted C$_2$ alkylene.

Each X may independently be —F. Each X may independently be —Cl. Each X may independently be —Br. Each X may independently be —I. Each X$^a$ may independently be —F. Each X$^a$ may independently be —Cl. Each X$^a$ may independently be —Br. Each X$^a$ may independently be —I.

Each n1 may independently be 0. Each n1 may independently be 1. Each n1 may independently be 2. Each n1 may independently be 3. Each n1 may independently be 4. Each n may independently be 0. Each n may independently be 1. Each n may independently be 2. Each n may independently be 3. Each n may independently be 4. Each v1 may independently be 0. Each v1 may independently be 1. Each v1 may independently be 2. Each v1 may independently be 3. Each v1 may independently be 4. Each v may independently be 0. Each v may independently be 1. Each v may independently be 2. Each v may independently be 3. Each v2 may independently be 4. Each m1 may independently be 1. Each m1 may independently be 2. Each m may independently be 1. Each m may independently be 2.

In embodiments, the compound has the formula:

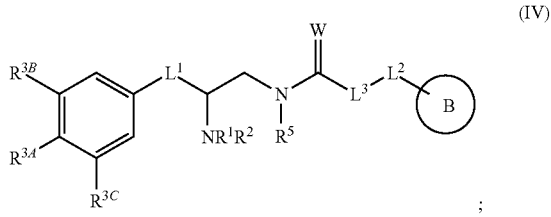

(IV)

wherein R$^1$, R$^2$, R$^{3A}$, R$^{3B}$, R$^{3C}$, R$^5$, L$^1$, L$^2$, L$^3$, W, and Ring B are as described herein (e.g., including in formula I, II, and III, and embodiments thereof). In embodiments, the compound has the formula:

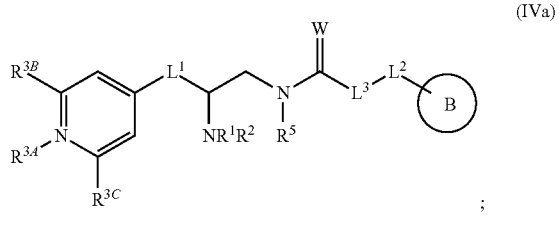

(IVa)

;

wherein $R^1$, $R^2$, $R^{3A}$, $R^{3B}$, $R^{3C}$, $R^5$, $L^1$, $L^2$, $L^3$, W, and Ring B are as described herein (e.g., including in formula I, II, and III, and embodiments thereof). In embodiments, the compound has the formula:

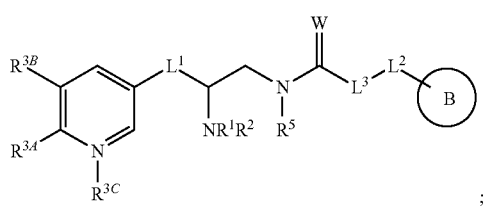

(IVb)

;

wherein $R^1$, $R^2$, $R^{3A}$, $R^{3B}$, $R^{3C}$, $R^5$, $L^1$, $L^2$, $L^3$, W, and Ring B are as described herein (e.g., including in formula I, II, and III, and embodiments thereof).

In embodiments, $R^{3A}$, $R^{3B}$, and $R^{3C}$ are independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, $OCF_3$, —$OCHF_2$, substituted or unsubstituted ($C_1$-$C_5$) alkyl, or substituted or unsubstituted 2 to 5 membered heteroalkyl. In embodiments, $R^{3A}$ is not hydrogen. In embodiments, $R^{3B}$ is not hydrogen. In embodiments, $R^{3C}$ is not hydrogen. In embodiments, $R^{3D}$ is not hydrogen. In embodiments, $R^{3E}$ is not hydrogen. In embodiments, $R^{3A}R^{3B}$, $R^{3C}$, $R^{3D}$, $R^{3E}$ are each independently not halogen.

In embodiments, $R^{3B}$ and $R^{3C}$ are independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, $OCF_3$, —$OCHF_2$, substituted or unsubstituted ($C_1$-$C_5$) alkyl, or substituted or unsubstituted 2 to 5 membered heteroalkyl and $R^{3A}$ is independently halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, $OCF_3$, —$OCHF_2$, substituted or unsubstituted ($C_1$-$C_5$) alkyl, or substituted or unsubstituted 2 to 5 membered heteroalkyl.

In embodiments, the compound has the formula:

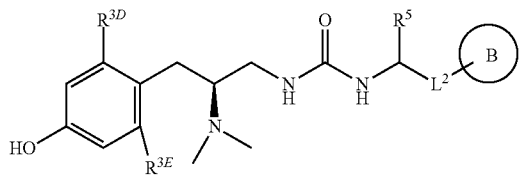

, wherein $R^{3D}$, $R^{3E}$, $R^5$, $L^1$, $L^2$, and Ring B are as described herein.

In embodiments, the compound has the formula:

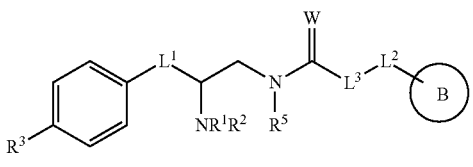

(V)

;

wherein $R^1$, $R^2$, $R^3$, $R^5$, $L^1$, $L^2$, $L^3$, W, and Ring B are as described herein (e.g., including in formula I, II, III, IV, IVa, IVb and embodiments).

In embodiments, $R^3$ is halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, $OCF_3$, —$OCHF_2$, substituted or unsubstituted ($C_1$-$C_5$) alkyl, or substituted or unsubstituted 2 to 5 membered heteroalkyl. In embodiments, $R^3$ is —OH. In embodiments, $R^3$ is not hydrogen.

In embodiments, the compound has the formula:

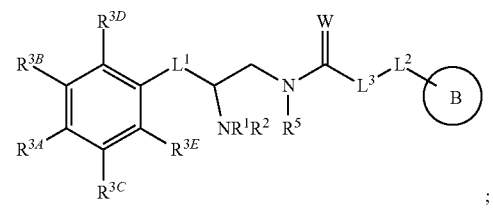

(VI)

;

wherein $R^1$, $R^2$, $R^{3A}$, $R^{3B}$, $R^{3C}$, $R^{3D}$, $R^{3E}$, $R^5$, $L^1$, $L^2$, $L^3$, W, and Ring B are as described herein (e.g., including in formula I, II, III, IV, IVa, IVb and V, and embodiments thereof).

In embodiments, $R^{3A}$, $R^{3B}$, and $R^{3C}$ are independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, $OCF_3$, —$OCHF_2$, substituted or unsubstituted ($C_1$-$C_5$) alkyl, or substituted or unsubstituted 2 to 5 membered heteroalkyl. In embodiments, $R^{3B}$ and $R^{3C}$ are independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —CH$_2$F, OCF$_3$, —OCHF$_2$, substituted or unsubstituted (C$_1$-C$_5$) alkyl, or substituted or unsubstituted 2 to 5 membered heteroalkyl and R$^{3A}$ is independently halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —CHF$_2$, —CH$_2$F, OCF$_3$, —OCHF$_2$, substituted or unsubstituted (C$_1$-C$_5$) alkyl, or substituted or unsubstituted 2 to 5 membered heteroalkyl.

In embodiments, R$^{3D}$ is hydrogen, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —CHF$_2$, —CH$_2$F, OCF$_3$, —OCHF$_2$, substituted or unsubstituted (C$_1$-C$_5$) alkyl, or substituted or unsubstituted 2 to 5 membered heteroalkyl.

In embodiments, R$^{3E}$ is hydrogen halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —CHF$_2$, —CH$_2$F, OCF$_3$, —OCHF$_2$, substituted or unsubstituted (C$_1$-C$_5$) alkyl, or substituted or unsubstituted 2 to 5 membered heteroalkyl.

In embodiments, R$^{3D}$ and R$^{3E}$ are independently unsubstituted (C$_1$-C$_5$) alkyl. In embodiments, R$^{3D}$ and R$^{3E}$ are independently unsubstituted (C$_1$-C$_3$) alkyl. In embodiments, R$^{3D}$ and R$^{3E}$ are independently unsubstituted (C$_1$-C$_2$) alkyl. In embodiments, R$^{3D}$ and R$^{3E}$ are independently unsubstituted methyl.

In embodiments, the compound has the formula:

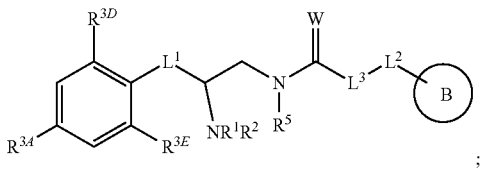

(VII)

wherein R$^1$, R$^2$, R$^{3A}$, R$^{3D}$, R$^{3E}$, R$^5$, L$^1$, L$^2$, L$^3$, W, and Ring B are as described herein (e.g., including in formula I, II, III, IV, IVa, IVb V, and VI, and embodiments thereof).

In embodiments, R$^{3A}$ is —OH. In embodiments, Ring A is unsubstituted phenyl.

In embodiments, the compound has the formula:

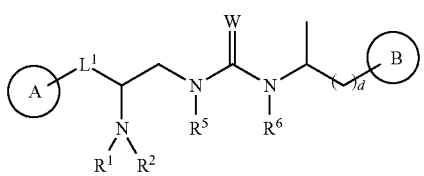

wherein R$^1$, R$^2$, R$^5$, R$^6$, L$^1$, W, Ring A, and Ring B are as described herein (e.g., including in formula I, II, III, IV, IVa, IVb V, VI, and VII, and embodiments thereof) and wherein d is an integer between 0 and 3. In embodiments, the compound has the formula:

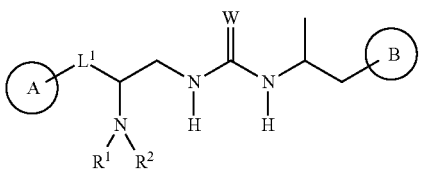

wherein R$^1$, R$^2$, R$^5$, R$^6$, L$^1$, W, Ring A, and Ring B are as described herein (e.g., including in formula I, II, III, IV, IVa, IVb V, VI, and VII, and embodiments thereof).

In embodiments, the compound has the formula:

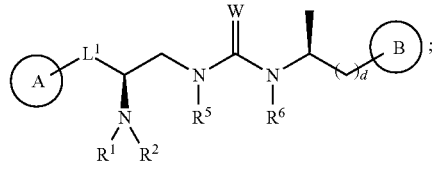

(VIIIa)

wherein R$^1$, R$^2$, R$^5$, R$^6$, L$^1$, W, Ring A, and Ring B are as described herein (e.g., including in formula I, II, III, IV, IVa, IVb V, VI, and VII, and embodiments thereof) and wherein d is an integer between 0 and 3.

In embodiments, the compound has the formula:

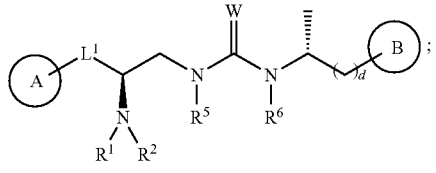

(IX)

wherein R$^1$, R$^2$, R$^5$, R$^6$, L$^1$, W, Ring A, and Ring B are as described herein (e.g., including in formula I, II, III, IV, IVa, IVb V, VI, VII, and VIII, and embodiments thereof) and wherein d is an integer between 0 and 3.

In embodiments, the compound has the formula:

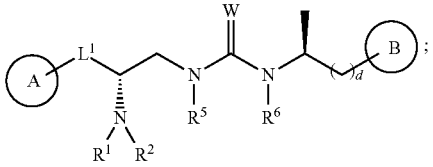

(X)

wherein R$^1$, R$^2$, R$^5$, R$^6$, L$^1$, W, Ring A, and Ring B are as described herein (e.g., including in formula I, II, III, IV, IVa, IVb V, VI, VII, VIII, and IX, and embodiments thereof) and wherein d is an integer between 0 and 3.

In embodiments, the compound has the formula:

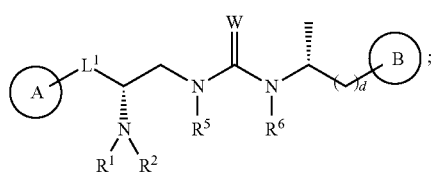
(XI)

wherein $R^1$, $R^2$, $R^5$, $R^6$, $L^1$, W, Ring A, and Ring B are as described herein (e.g., including in formula I, II, III, IV, IVa, IVb V, VI, VII, VIII, IX, and X, and embodiments thereof) and wherein d is an integer between 0 and 3.

In embodiments, the compound has the formula:

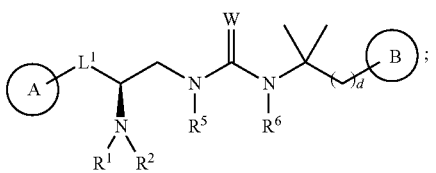
(XII)

wherein $R^1$, $R^2$, $R^5$, $R^6$, $L^1$, W, Ring A, and Ring B are as described herein (e.g., including in formula I, II, III, IV, IVa, IVb V, VI, VII, VIII, IX, X, and XI, and embodiments thereof) and wherein d is an integer between 0 and 3.

In embodiments, the compound has the formula:

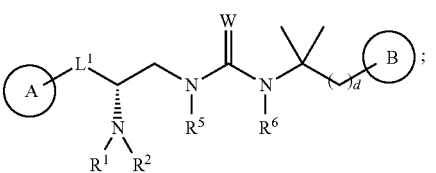
(XIII)

wherein $R^1$, $R^2$, $R^5$, $R^6$, $L^1$, W, Ring A, and Ring B are as described herein (e.g., including in formula I, II, III, IV, IVa, IVb V, VI, VII, VIII, IX, X, XI, and XII, and embodiments thereof) and wherein d is an integer between 0 and 3.

In embodiments, the compound has the formula:

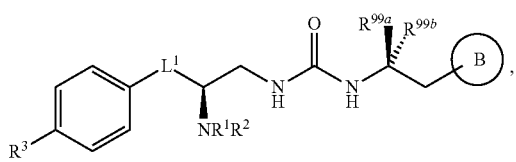
(XIV)

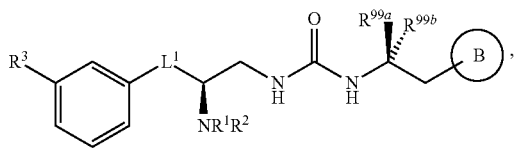
(XV)

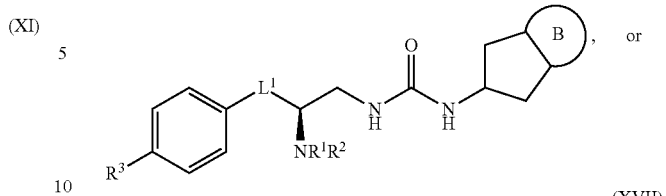
(XVI)

or

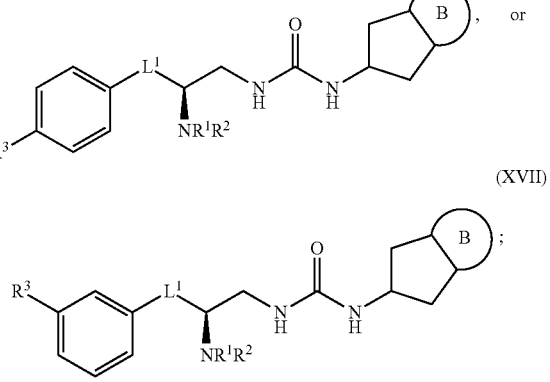
(XVII)

wherein $R^1$, $R^2$, $R^3$, $L^1$, and Ring B are as described herein (e.g., including in formula I, II, III, IV, IVa, IVb V, VI, VII, VIII, IX, X, XI, XII, and XIII, and embodiments thereof).

In embodiments, Ring B is a substituted or unsubstituted phenyl or substituted or unsubstituted 5 to 6 membered heteroaryl; $R^3$ is halogen, —OH, or —$NH_2$; $R^{99a}$ is substituted or unsubstituted ($C_1$-$C_3$) alkyl; and $R^{99b}$ is hydrogen or substituted or unsubstituted ($C_1$-$C_3$) alkyl. In embodiments, Ring B is an unsubstituted phenyl. In embodiments, Ring B is an unsubstituted 5 to 6 membered heteroaryl. In embodiments, Ring B is an unsubstituted 3-thienyl. In embodiments, $R^3$ is —OH. In embodiments, $R^{99a}$ is unsubstituted methyl. In embodiments, $R^{99b}$ is hydrogen. In embodiments, $R^{99b}$ is unsubstituted methyl. In embodiments, $R^1$ and $R^2$ are unsubstituted methyl.

In embodiments, the compound has the formula:

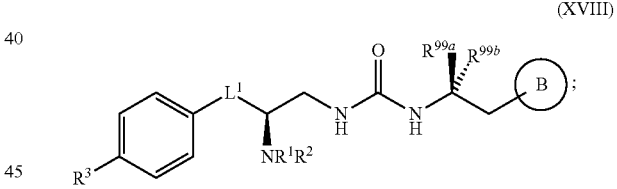
(XVIII)

wherein $R^1$, $R^2$, $R^3$, $L^1$, $R^{99a}$, $R^{99b}$, and Ring B are as described herein (e.g., including in formula I, II, III, IV, IVa, IVb V, VI, VII, VIII, IX, X, XI, XII, XIII, XIV, XV, XVI, and XVII) and embodiments).

In embodiments, the compound has the formula:

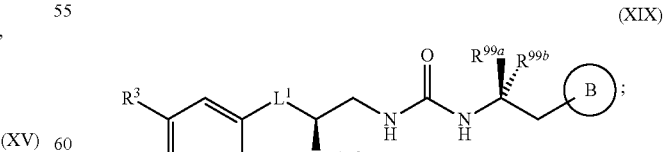
(XIX)

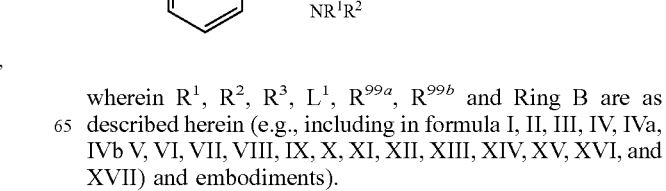

wherein $R^1$, $R^2$, $R^3$, $L^1$, $R^{99a}$, $R^{99b}$ and Ring B are as described herein (e.g., including in formula I, II, III, IV, IVa, IVb V, VI, VII, VIII, IX, X, XI, XII, XIII, XIV, XV, XVI, and XVII) and embodiments).

In embodiments, the compound has the formula:

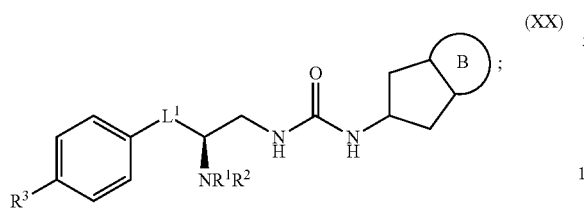

(XX)

wherein $R^1$, $R^2$, $R^3$, $L^1$, $R^{99a}$, $R^{99b}$, and Ring B are as described herein (e.g., including in formula I, II, III, IV, IVa, IVb V, VI, VII, VIII, IX, X, XI, XII, XIII, XIV, XV, XVI, and XVII) and embodiments).

In embodiments, the compound has the formula:

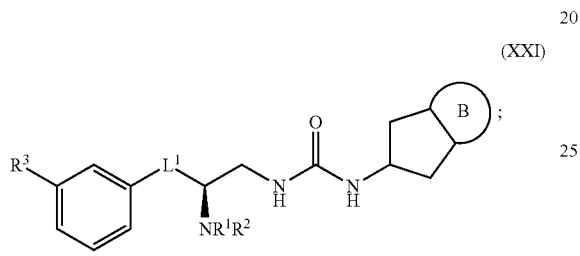

(XXI)

wherein $R^1$, $R^2$, $R^3$, $L^1$, $R^{99a}$, $R^{99b}$, and Ring B are as described herein (e.g., including in formula I, II, III, IV, IVa, IVb V, VI, VII, VIII, IX, X, XI, XII, XIII, XIV, XV, XVI, and XVII) and embodiments).

In embodiments, the compound has the formula:

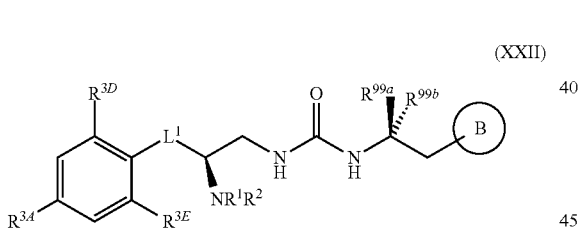

(XXII)

wherein $R^1$, $R^2$, $R^{3A}$, $R^{3D}$, $R^{3E}$, $L^1$, $R^{99a}$, $R^{99b}$, and Ring B are as described herein (e.g., including in formula I, II, III, IV, IVa, IVb V, VI, VII, VIII, IX, X, XI, XII, XIII, XIV, XV, XVI, XVII, XVIII, XIX, XX, and XXI) and embodiments).

In embodiments, Ring B is a substituted or unsubstituted phenyl or substituted or unsubstituted 5 to 6 membered heteroaryl; $R^{3A}$ is halogen, —OH, or —NH$_2$; $R^{3D}$ is unsubstituted ($C_1$-$C_2$) alkyl; $R^{3E}$ is unsubstituted ($C_1$-$C_2$) alkyl; $R^{99a}$ is hydrogen or substituted or unsubstituted ($C_1$-$C_3$) alkyl; $R^{99b}$ is substituted or unsubstituted ($C_1$-$C_3$) alkyl. In embodiments, Ring B is an unsubstituted phenyl. In embodiments, Ring B is an unsubstituted 5 to 6 membered heteroaryl. In embodiments, Ring B is an unsubstituted 3-thienyl. In embodiments, $R^{3A}$ is —OH. In embodiments, $R^{99b}$ is unsubstituted methyl. In embodiments, $R^{99a}$ is hydrogen. In embodiments, $R^{99a}$ is unsubstituted methyl. In embodiments, $R^1$ and $R^2$ are unsubstituted methyl. In embodiments, $R^{3D}$ is unsubstituted methyl. In embodiments, $R^{3E}$ is unsubstituted methyl.

In embodiments, the compound has the formula:

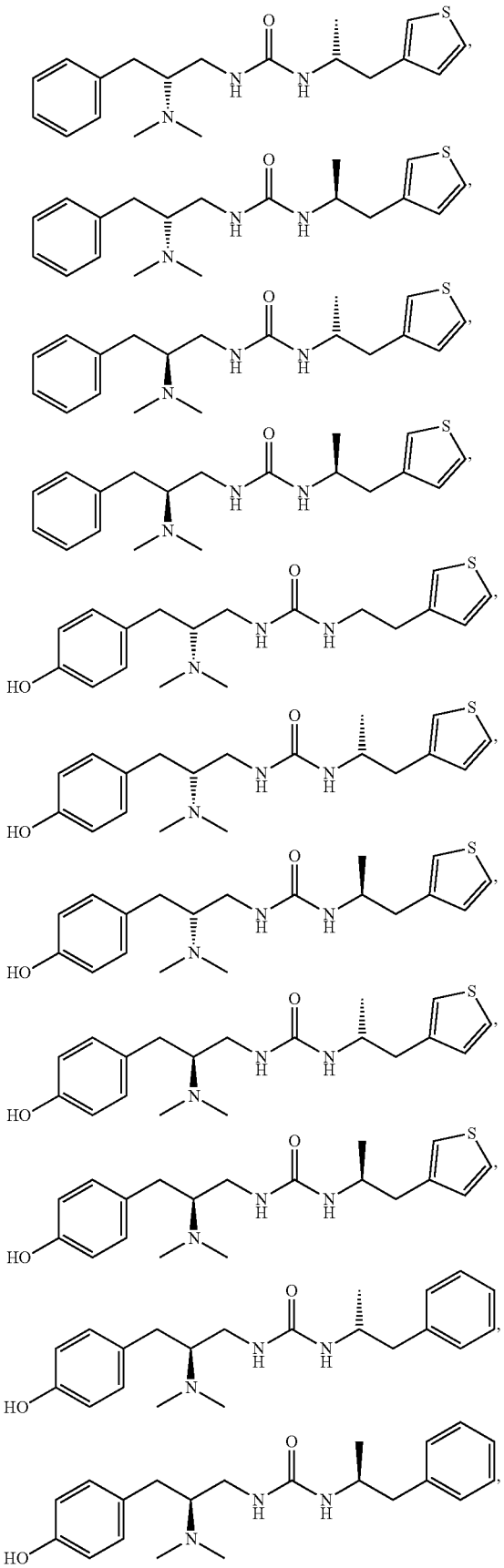

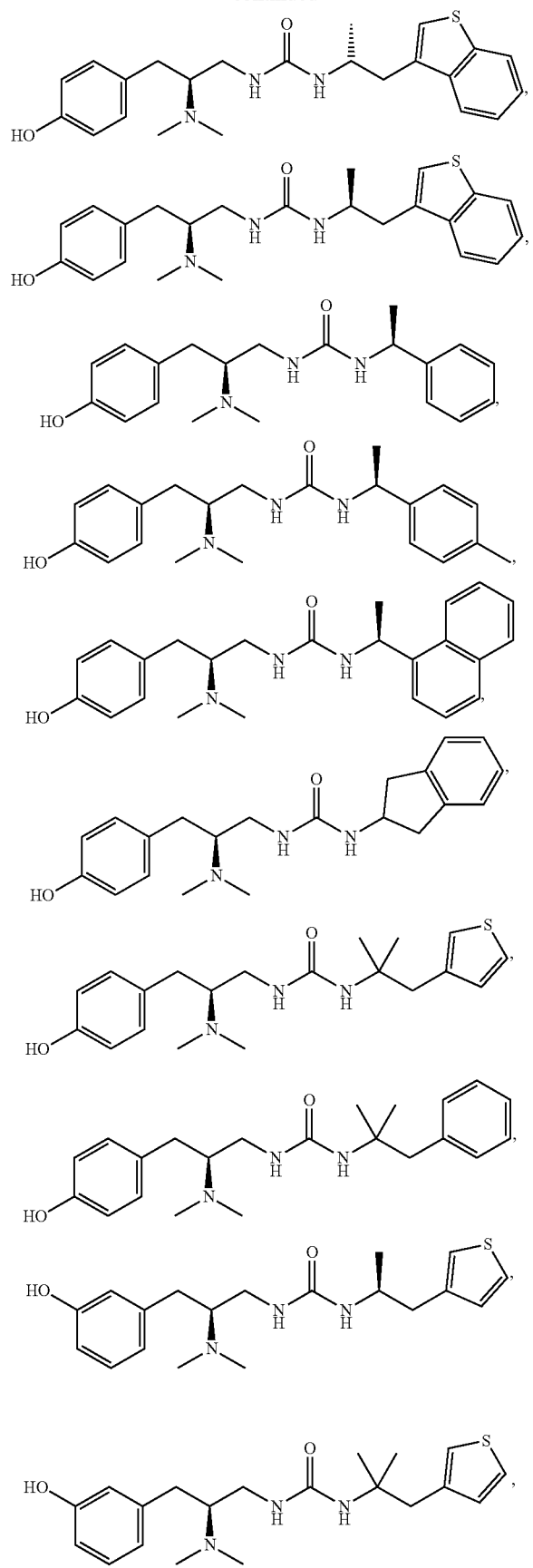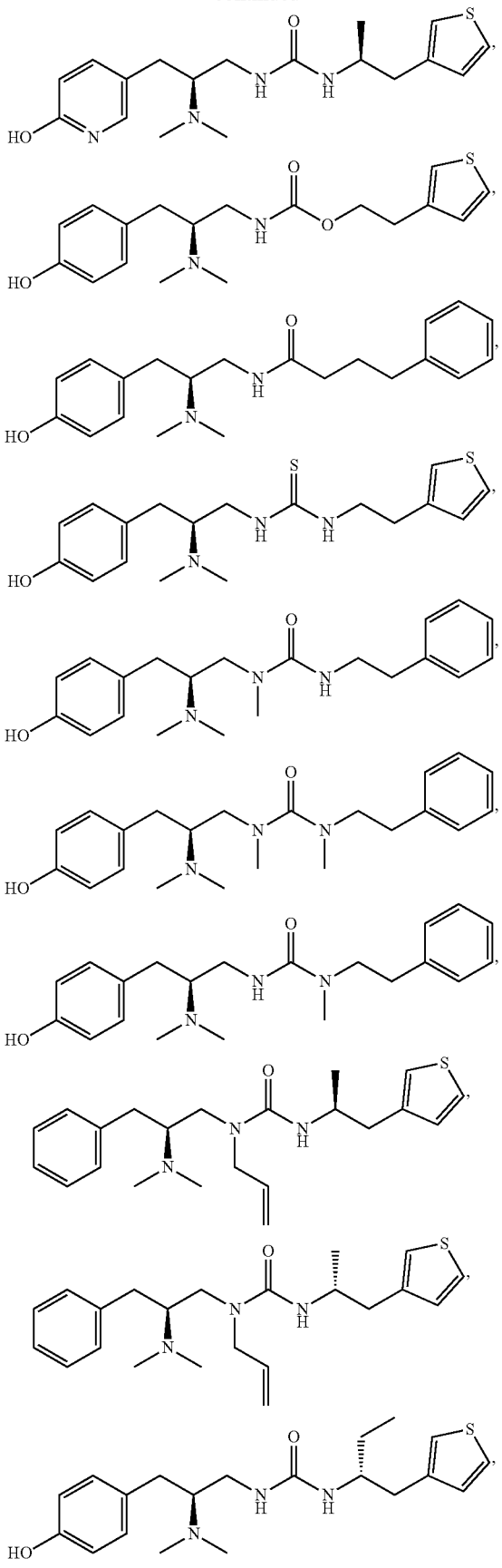

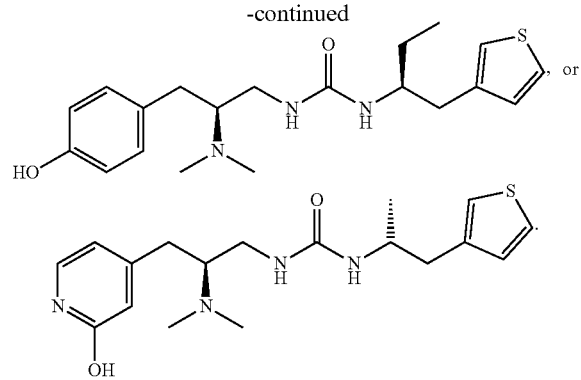
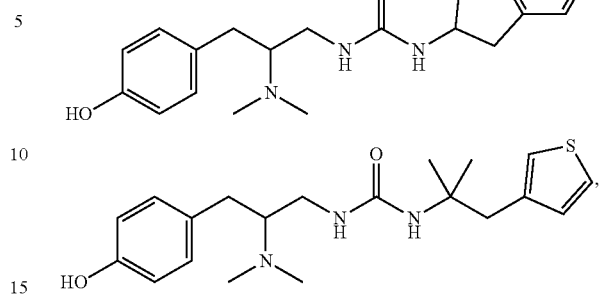
In embodiments, the compound has the formula:
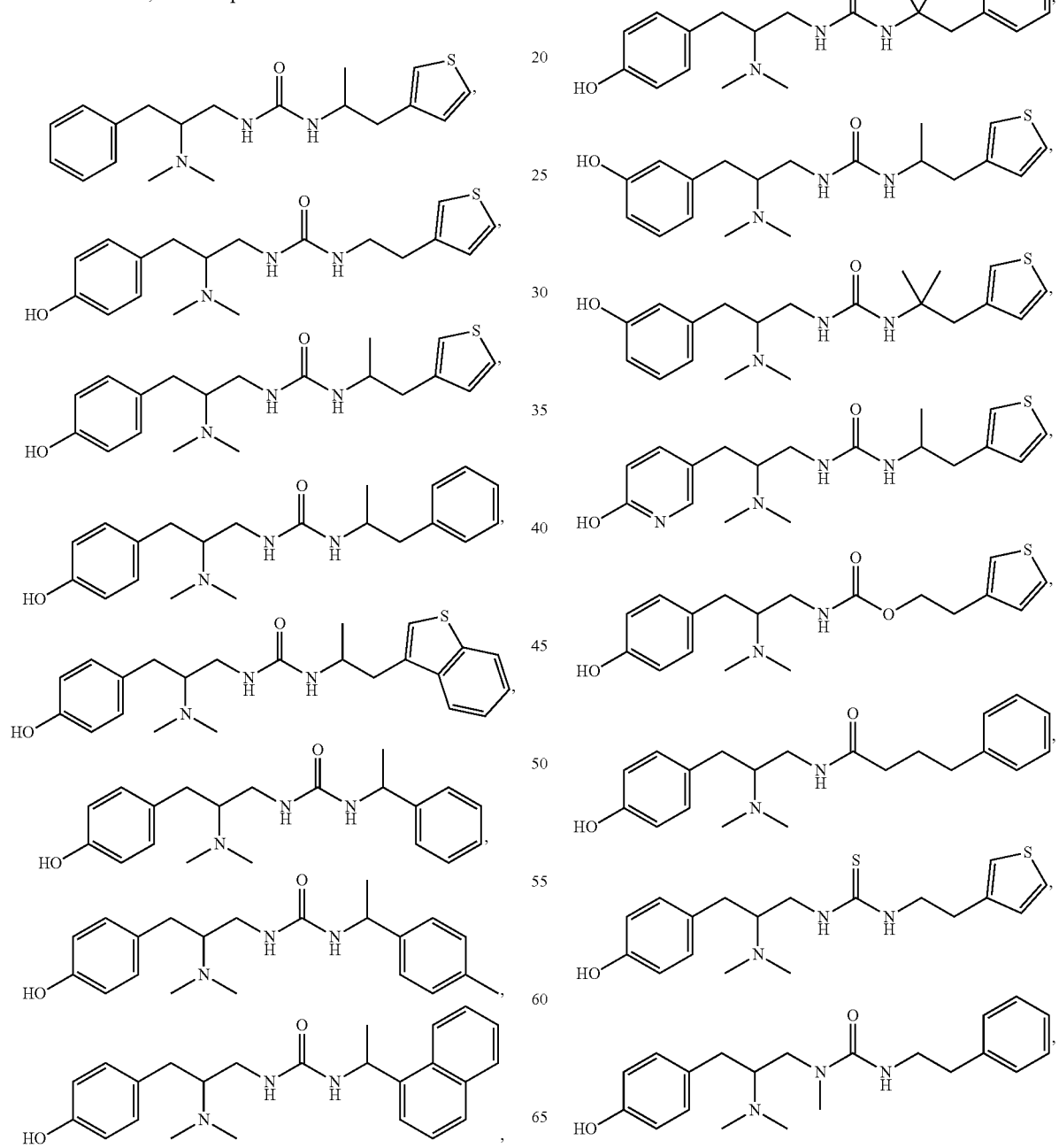

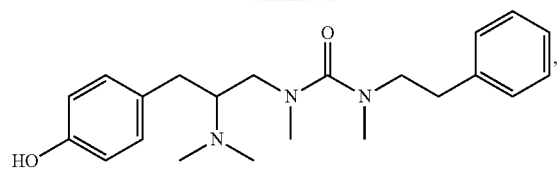
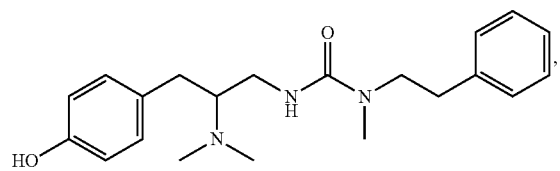
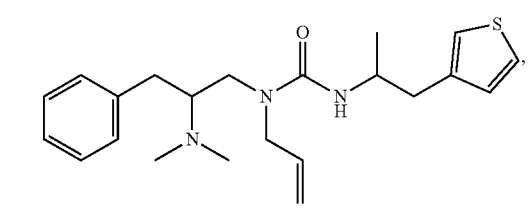
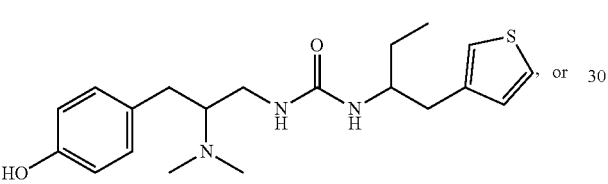
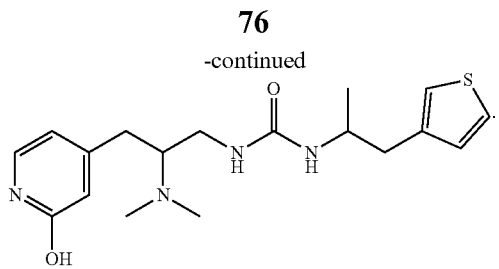
In embodiments, the compound has the formula:
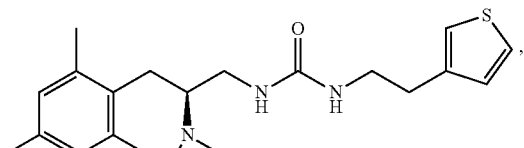
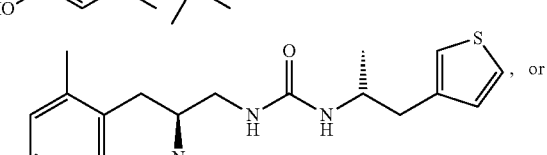
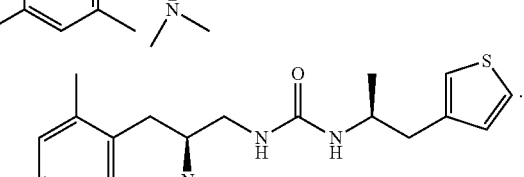
In embodiments, the compound has the formula:
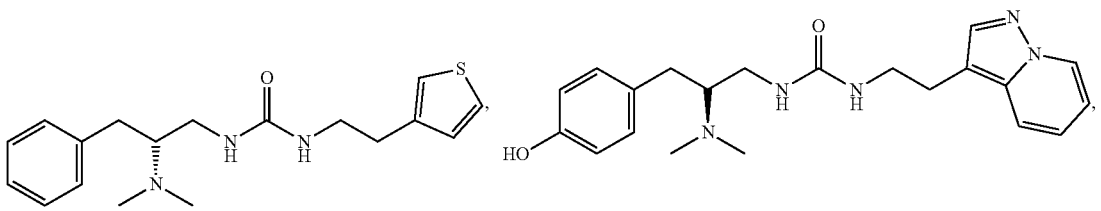
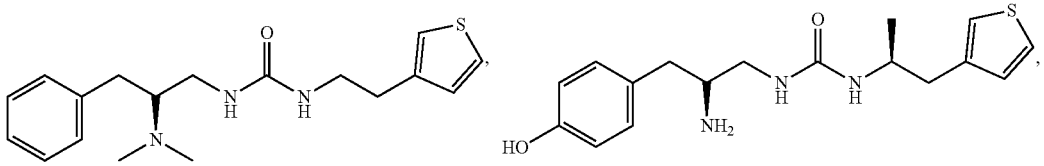
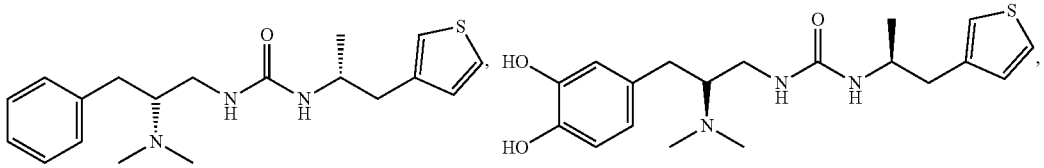
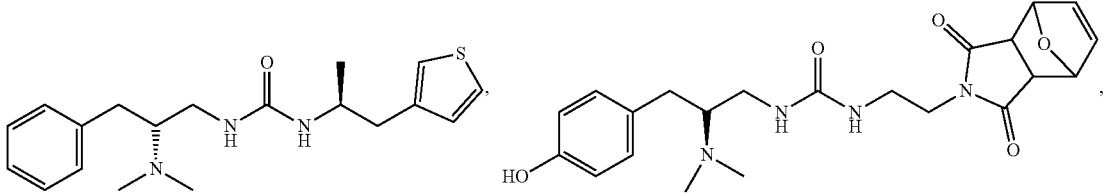

77
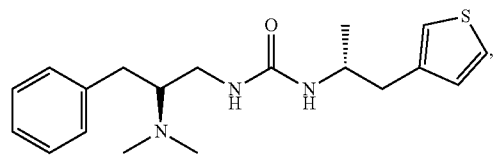
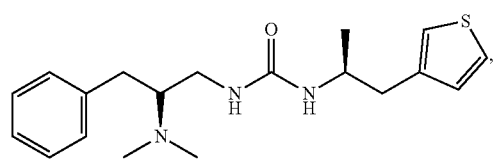
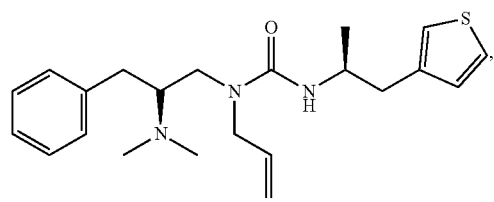
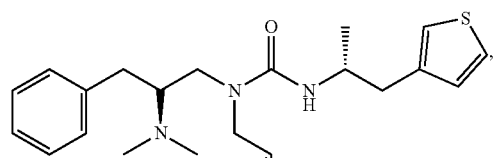
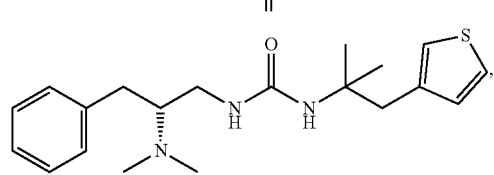
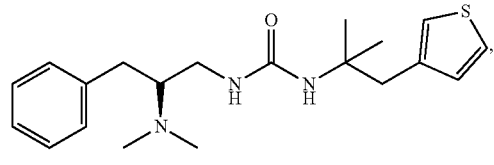
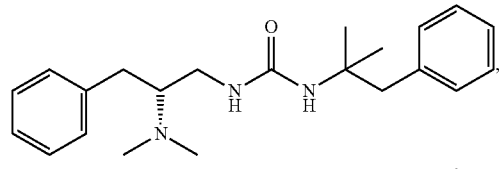
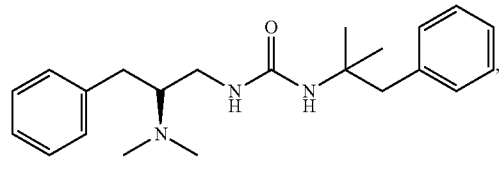
-continued
78
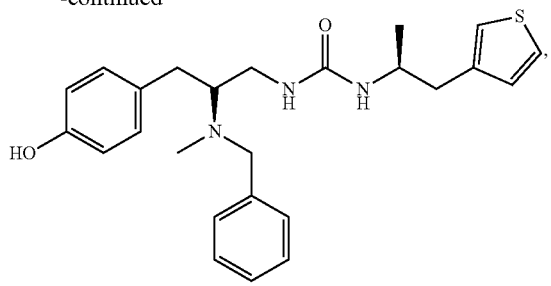
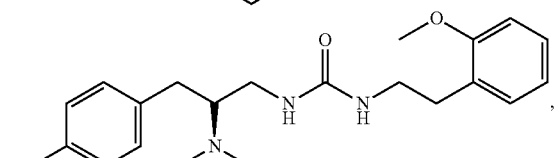
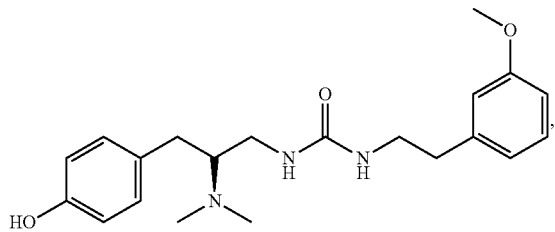
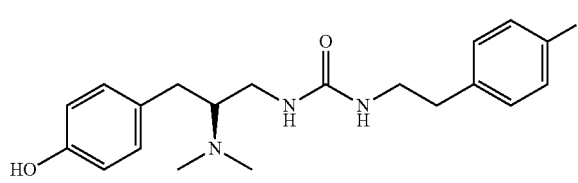
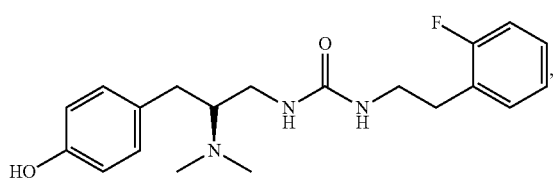
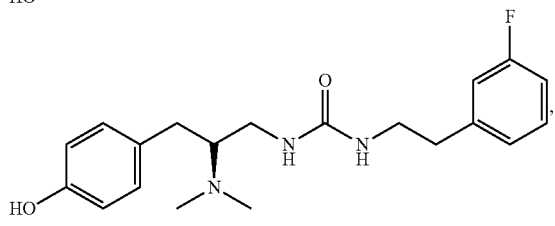
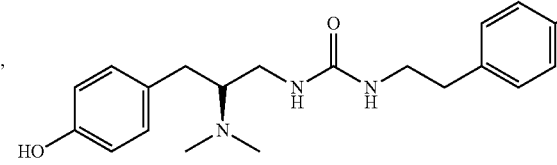
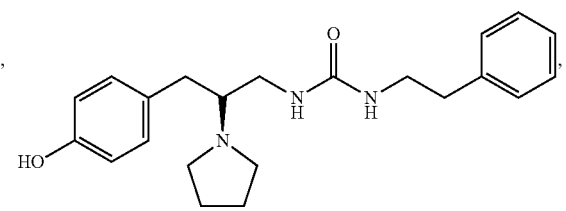

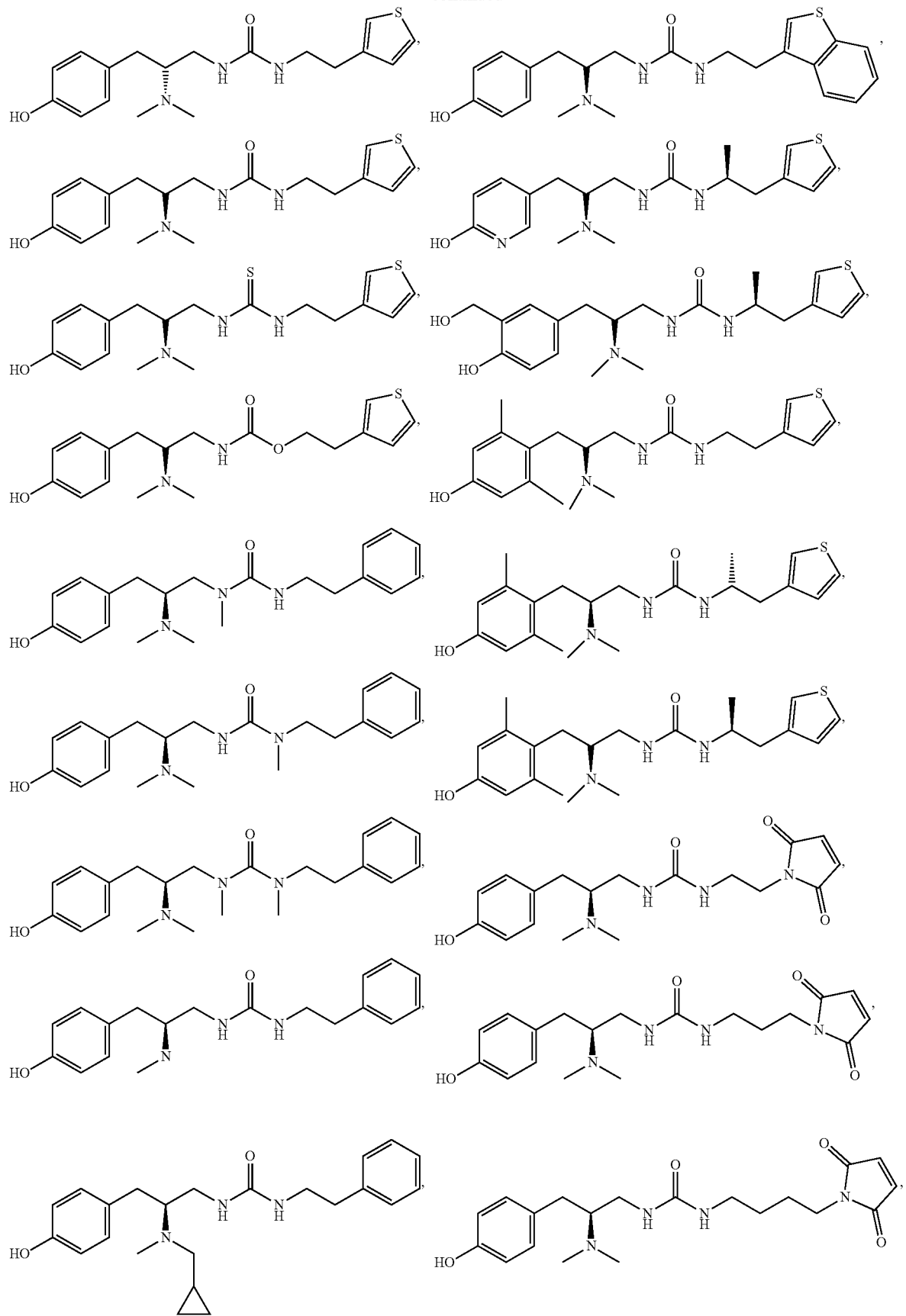

-continued
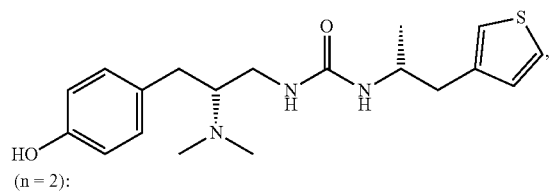
(n = 2):
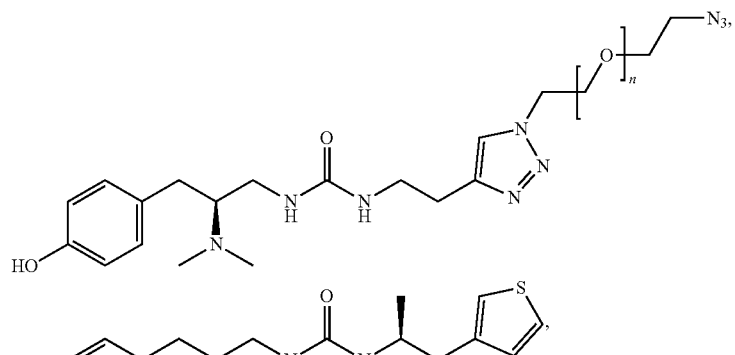
(n = 3):
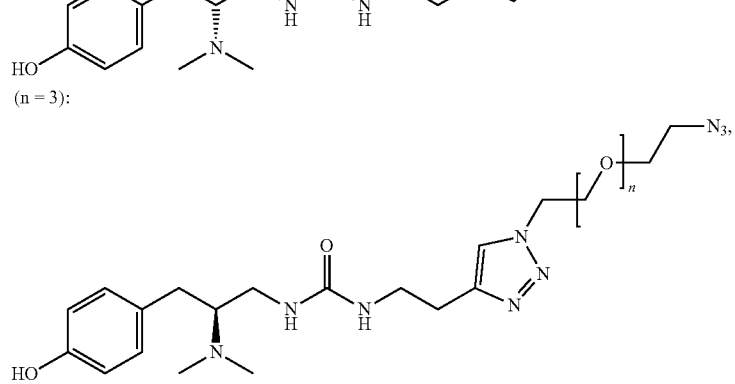
(n = 5):
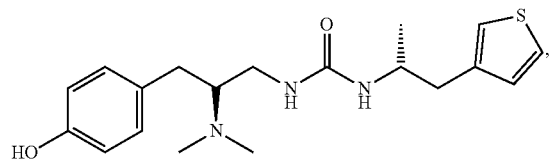
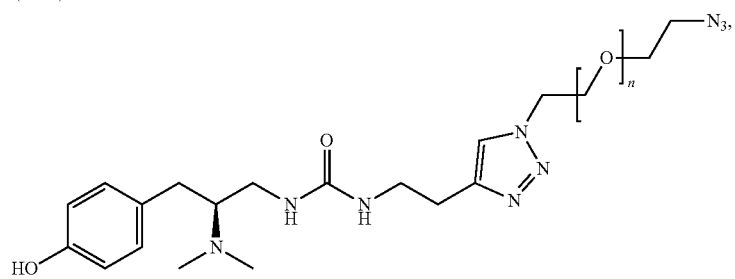
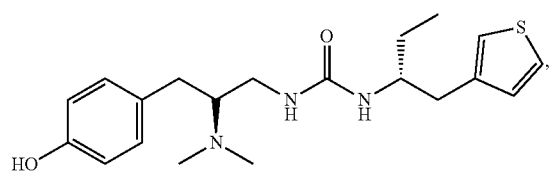

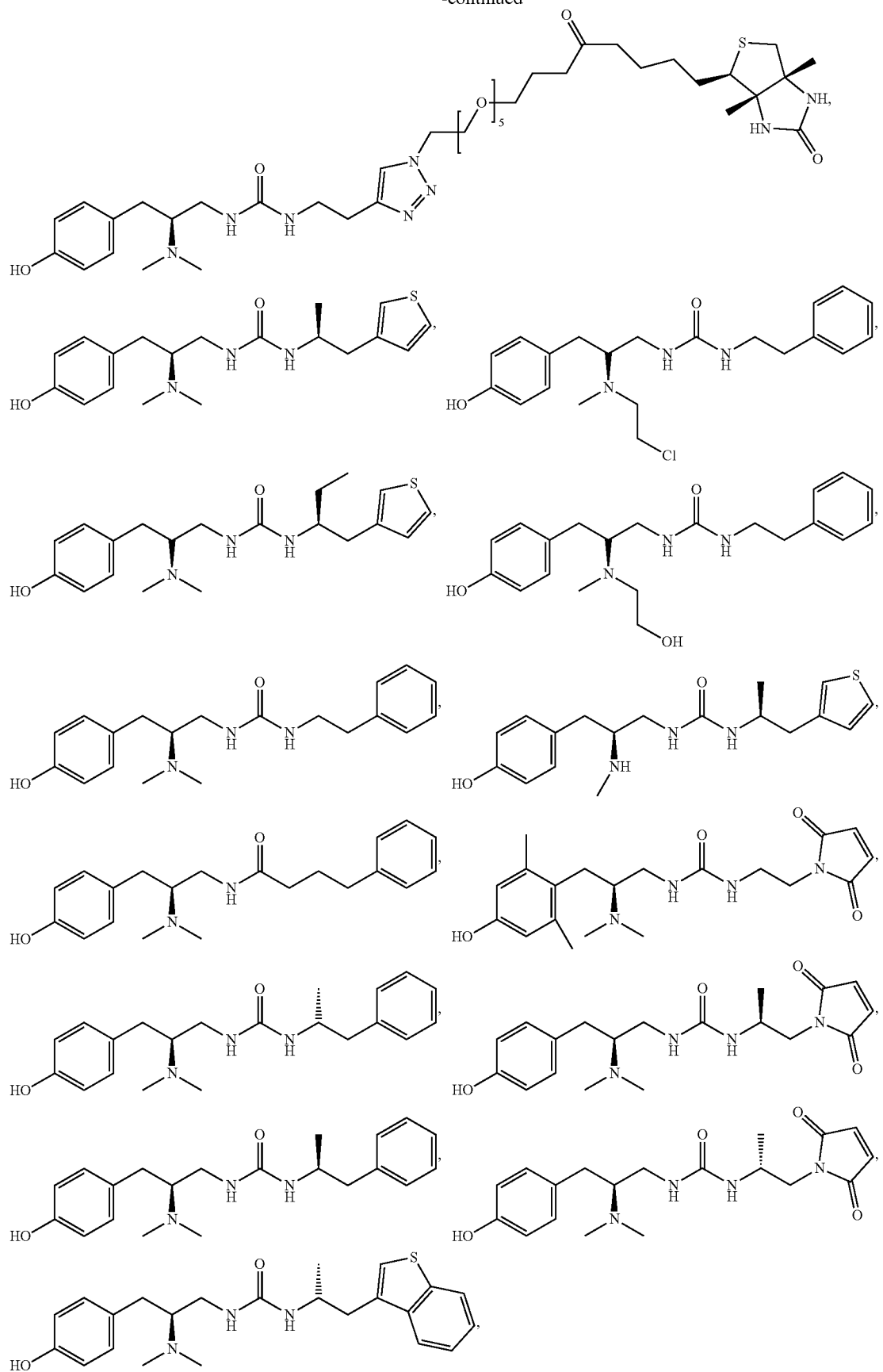

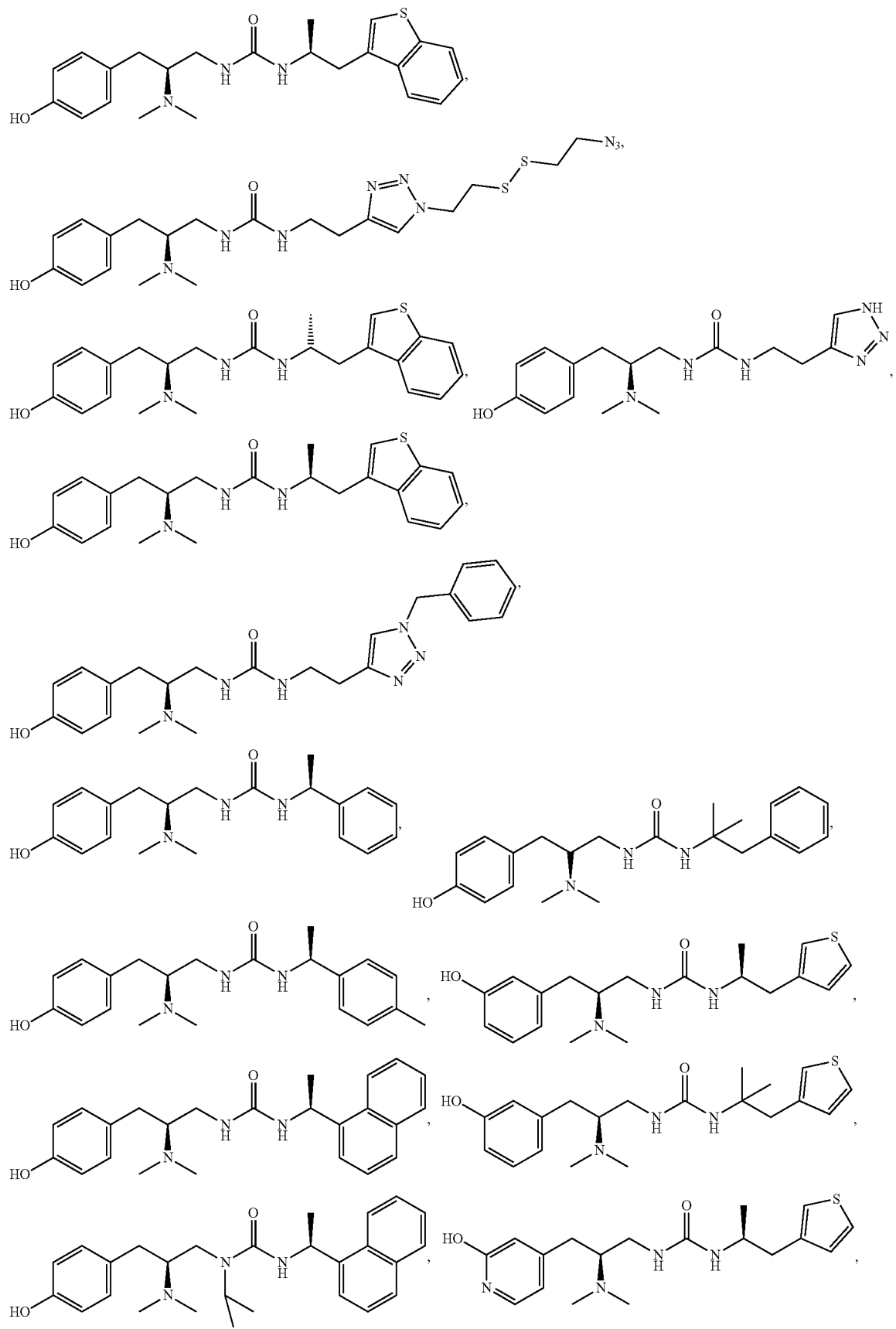

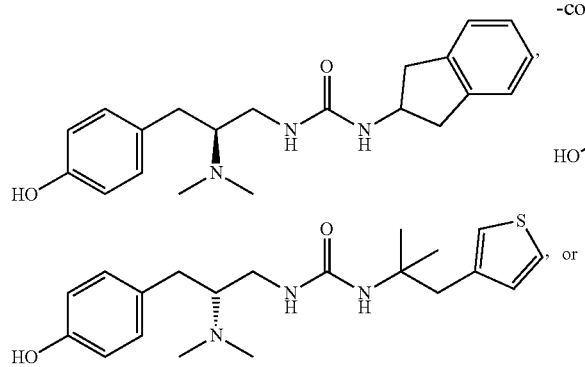

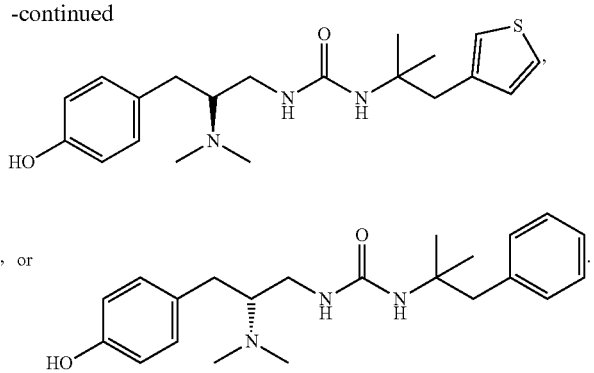

In embodiments, the compound has the formula:

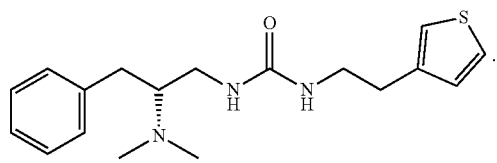

In embodiments, the compound has the formula:

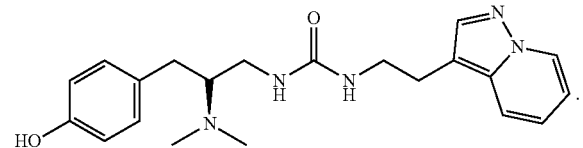

In embodiments, the compound has the formula:

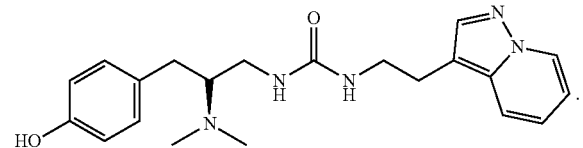

In embodiments, the compound has the formula:

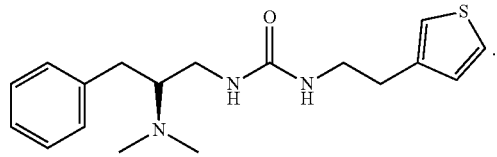

In embodiments, the compound has the formula:

In embodiments, the compound has the formula:

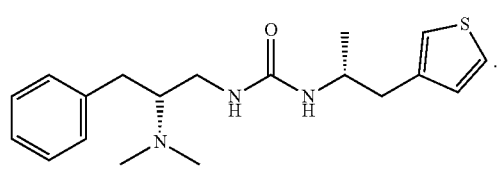

In embodiments, the compound has the formula:

In embodiments, the compound has the formula:

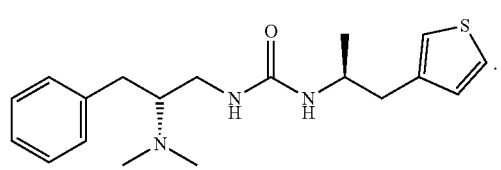

In embodiments, the compound has the formula:

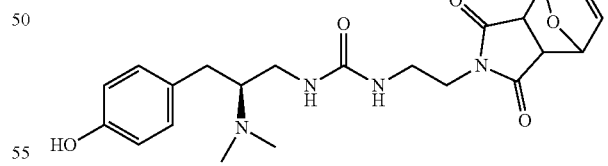

In embodiments, the compound has the formula:

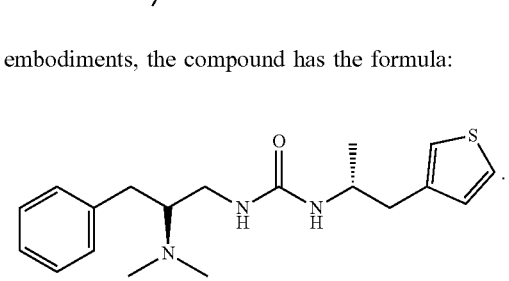

In embodiments, the compound has the formula:

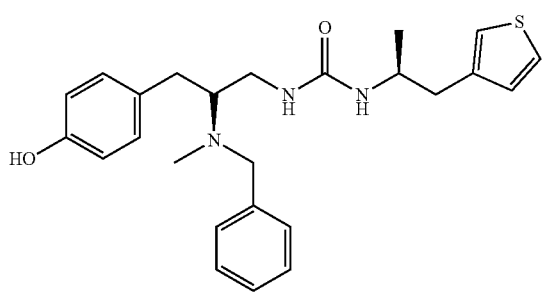

In embodiments, the compound has the formula:

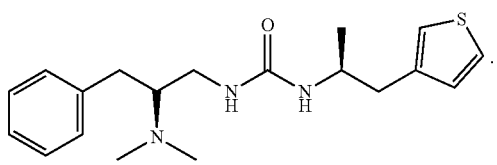

In embodiments, the compound has the formula:

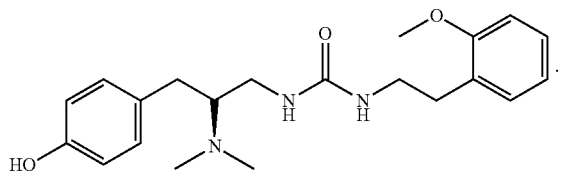

In embodiments, the compound has the formula:

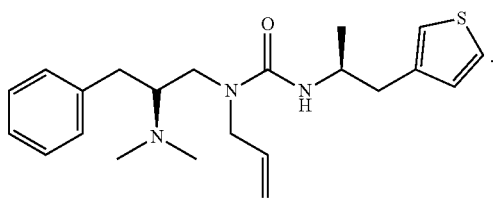

In embodiments, the compound has the formula:

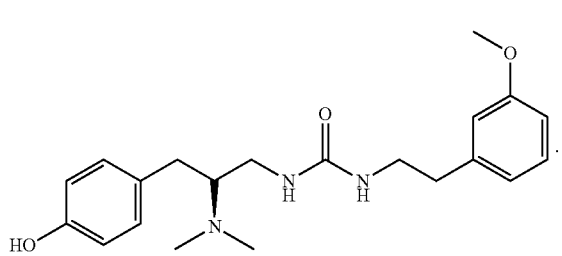

In embodiments, the compound has the formula:

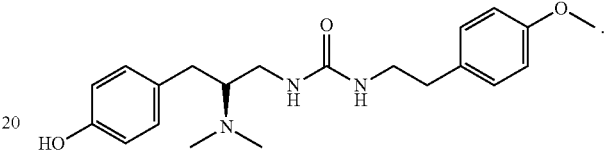

In embodiments, the compound has the formula:

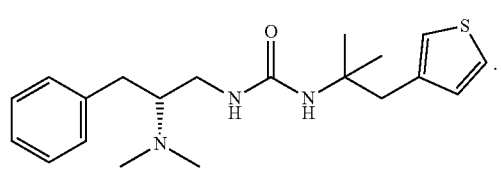

In embodiments, the compound has the formula:

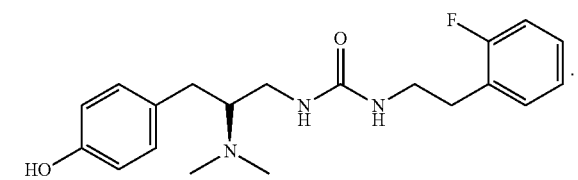

In embodiments, the compound has the formula:

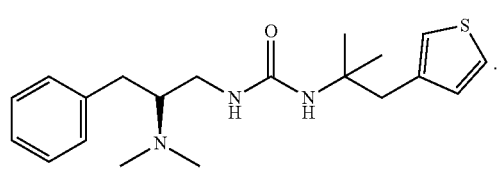

In embodiments, the compound has the formula:

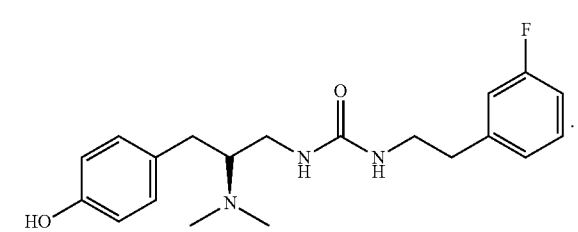

In embodiments, the compound has the formula:

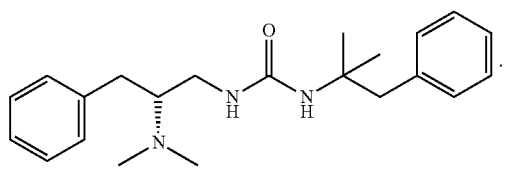

In embodiments, the compound has the formula:

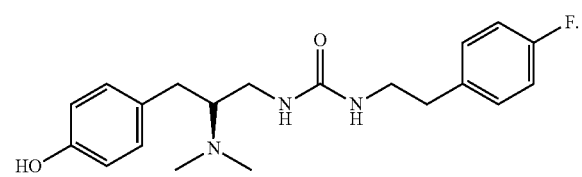

In embodiments, the compound has the formula:

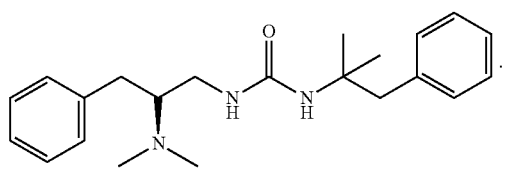

In embodiments, the compound has the formula:

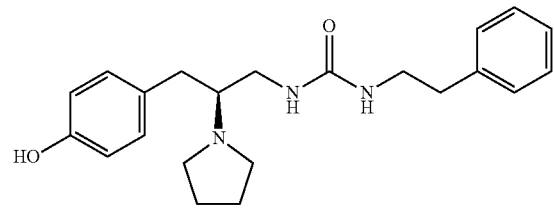

In embodiments, the compound has the formula:

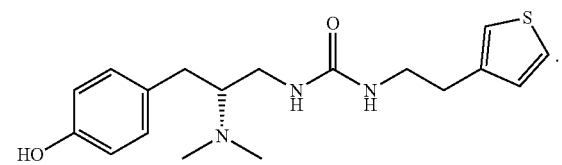

In embodiments, the compound has the formula:

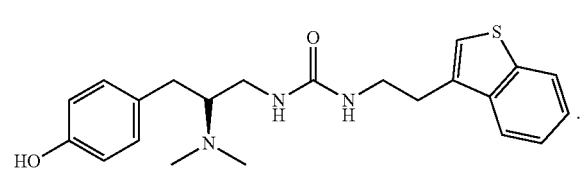

In embodiments, the compound has the formula:

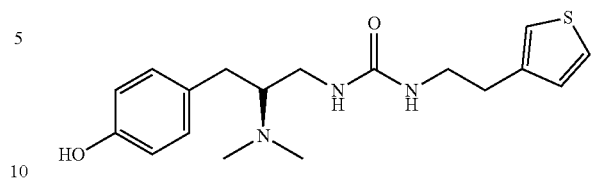

In embodiments, the compound has the formula:

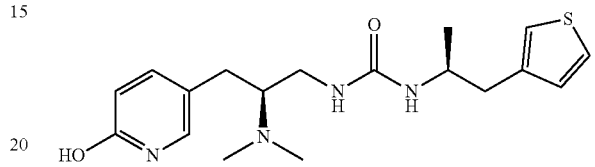

In embodiments, the compound has the formula:

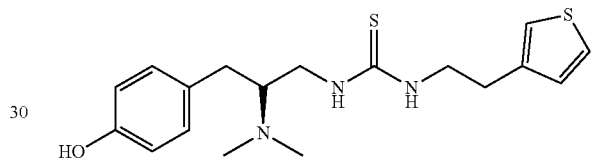

In embodiments, the compound has the formula:

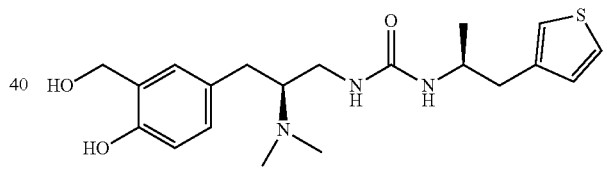

In embodiments, the compound has the formula:

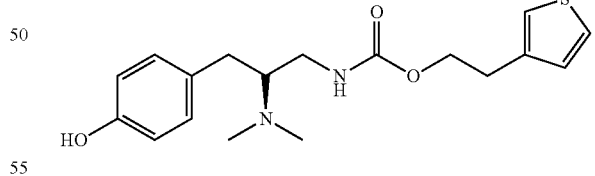

In embodiments, the compound has the formula:

In embodiments, the compound has the formula:

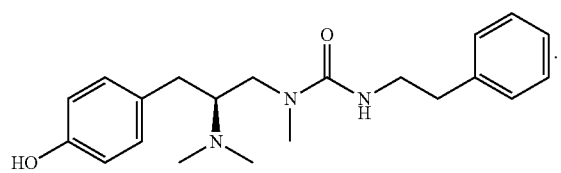

In embodiments, the compound has the formula:


In embodiments, the compound has the formula:

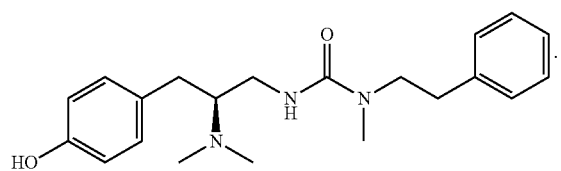

In embodiments, the compound has the formula:


In embodiments, the compound has the formula:

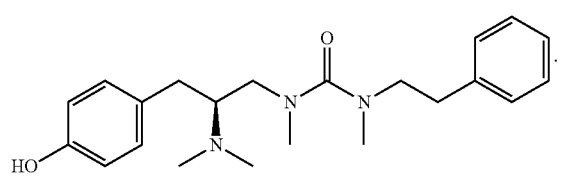

In embodiments, the compound has the formula:

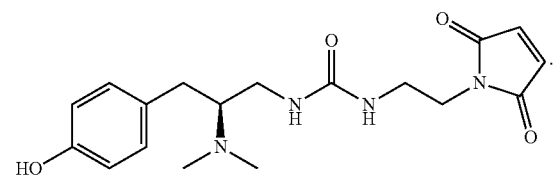

In embodiments, the compound has the formula:

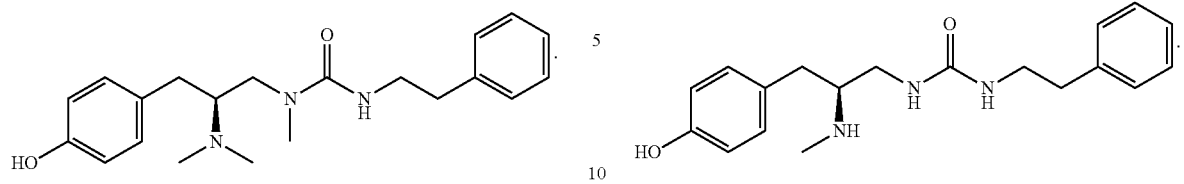

In embodiments, the compound has the formula:

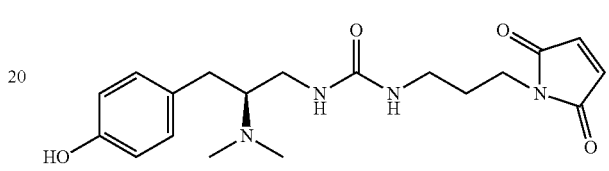

In embodiments, the compound has the formula:

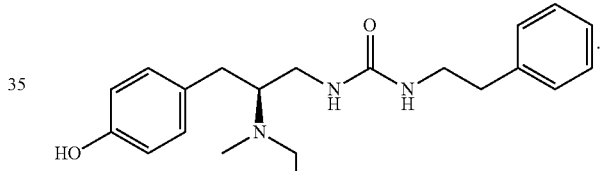

In embodiments, the compound has the formula:

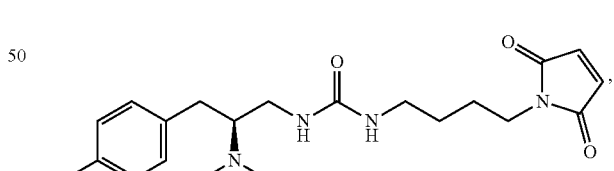

In embodiments, the compound has the formula:

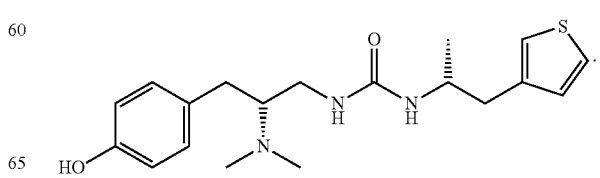

In embodiments, the compound has the formula:
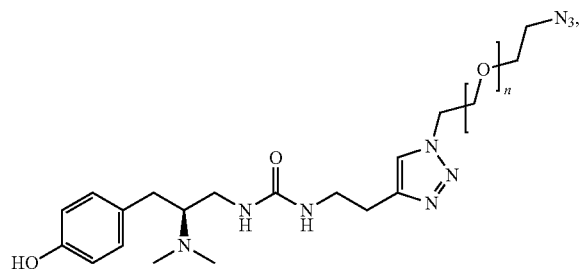
where n is 2. In embodiments, the compound has the formula:
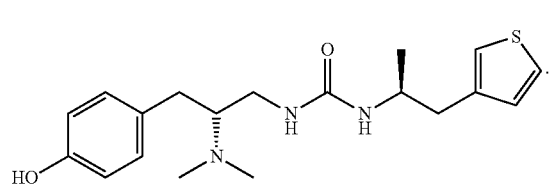
In embodiments the compound has the formula:
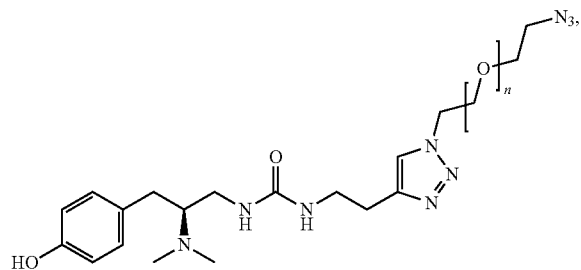
where n is 3. In embodiments, the compound has the formula:
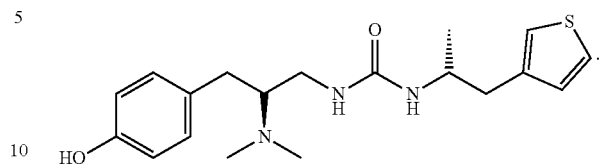
In embodiments, the compound has the formula:
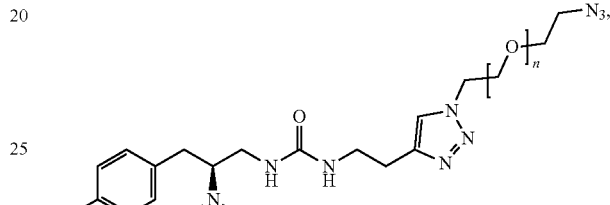
where n is 5. In embodiments, the compound has the formula:
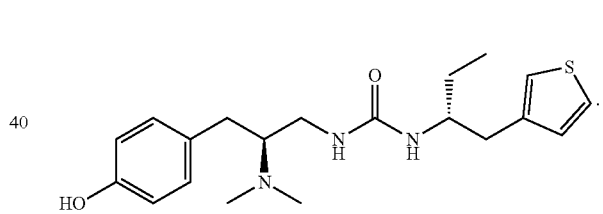
In embodiments, the compound has the formula:
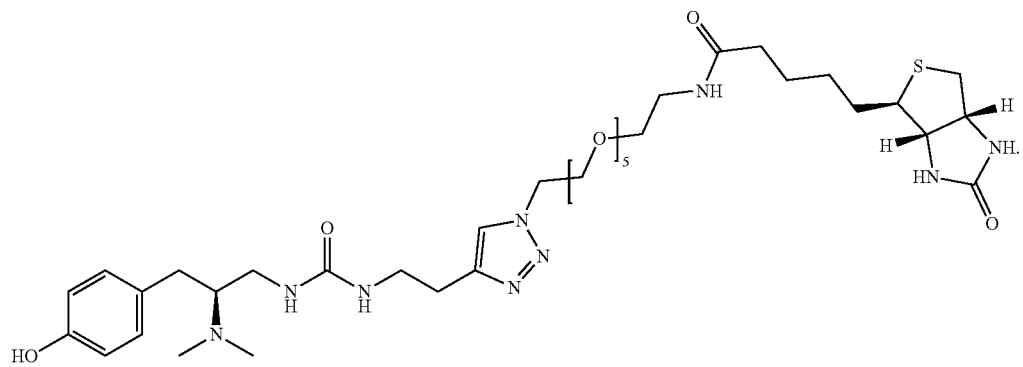

In embodiments, the compound has the formula:

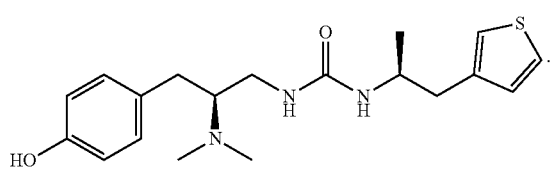 [SMILES: C[C@@H](Cc1ccsc1)NC(=O)NC[C@H](Cc1ccc(O)cc1)N(C)C]

In embodiments, the compound has the formula:

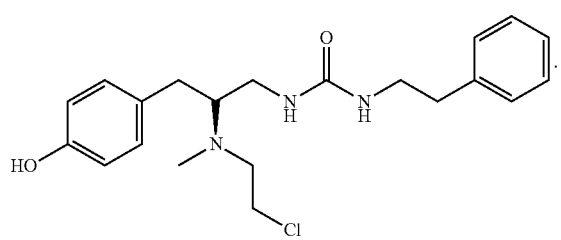

In embodiments, the compound has the formula:

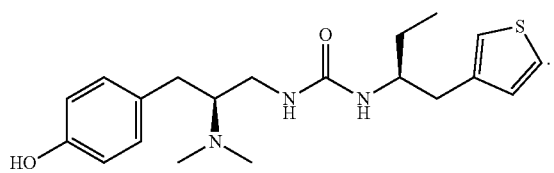 [SMILES: CC[C@@H](Cc1ccsc1)NC(=O)NC[C@H](Cc1ccc(O)cc1)N(C)C]

In embodiments, the compound has the formula:

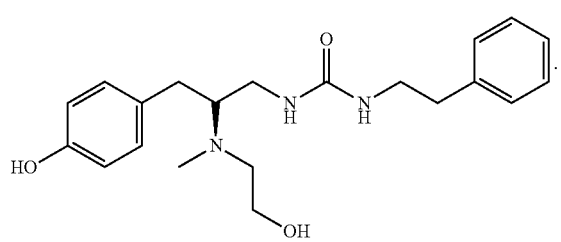

In embodiments, the compound has the formula:

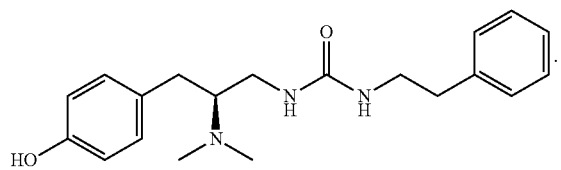 [SMILES: CN(C)[C@H](CNC(=O)NCCc1ccccc1)Cc1ccc(O)cc1]

In embodiments, the compound has the formula:

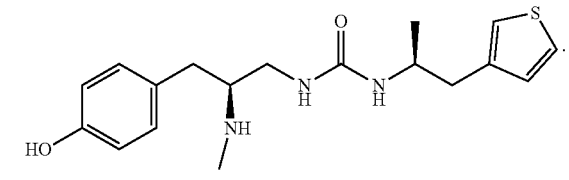 [SMILES: CN[C@H](CNC(=O)N[C@@H](C)Cc1ccsc1)Cc1ccc(O)cc1]

In embodiments, the compound has the formula:

In embodiments, the compound has the formula:

In embodiments, the compound has the formula:

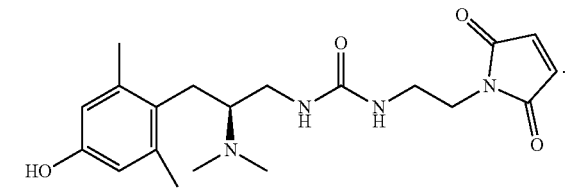 [SMILES: Cc1cc(O)cc(C)c1C[C@@H](CNC(=O)NCCN1C(=O)C=CC1=O)N(C)C]

In embodiments, the compound has the formula:

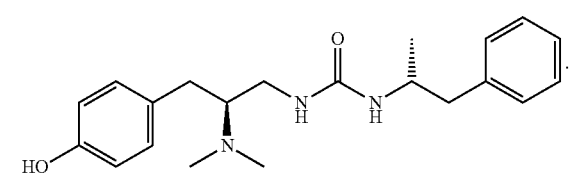

In embodiments, the compound has the formula:

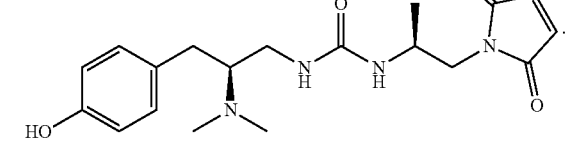

In embodiments, the compound has the formula:

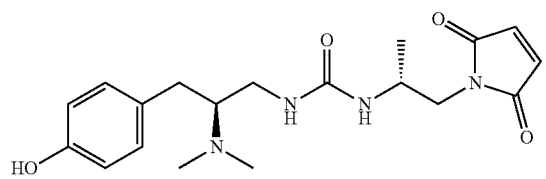

In embodiments, the compound has the formula:

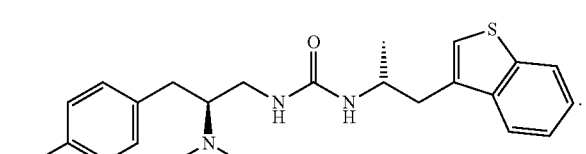

In embodiments, the compound has the formula:

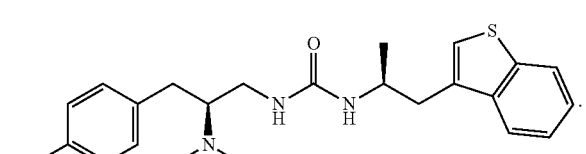

In embodiments, the compound has the formula:

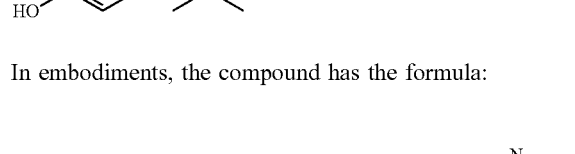

In embodiments, the compound has the formula:

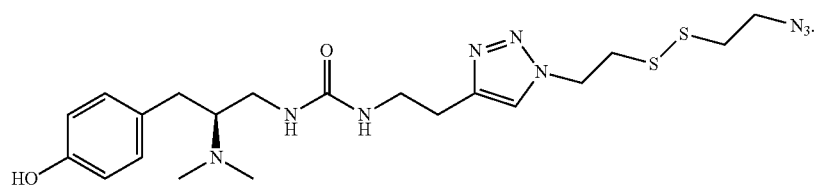

In embodiments, the compound has the formula:

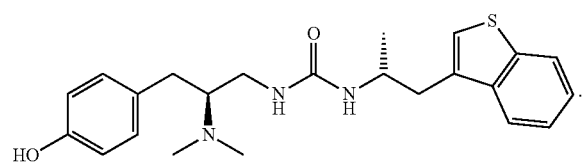

In embodiments, the compound has the formula:

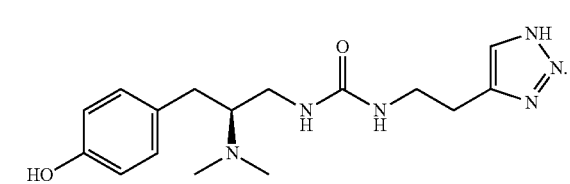 [SMILES: CN(C)[C@H](CNC(=O)NCCc1c[nH]nn1)Cc1ccc(O)cc1]

In embodiments, the compound has the formula:

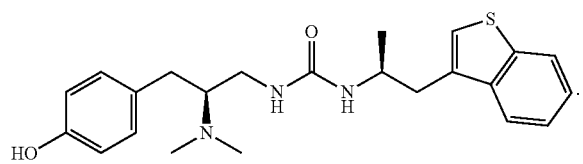 [SMILES: C[C@@H](Cc1csc2ccccc12)NC(=O)NC[C@H](Cc1ccc(O)cc1)N(C)C]

In embodiments, the compound has the formula:

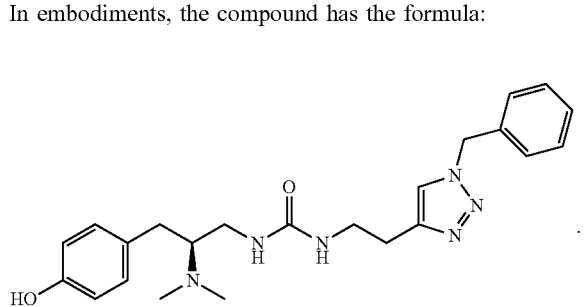

In embodiments, the compound has the formula:

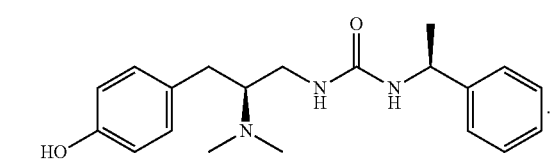 [SMILES: C[C@H](NC(=O)NC[C@H](Cc1ccc(O)cc1)N(C)C)c1ccccc1]

In embodiments, the compound has the formula:

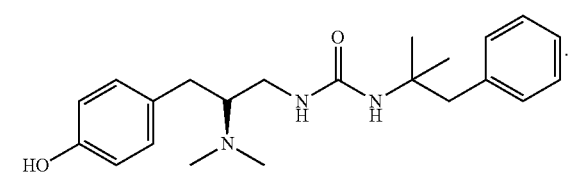

In embodiments, the compound has the formula:

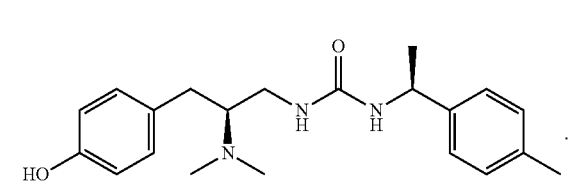 [SMILES: Cc1ccc([C@H](C)NC(=O)NC[C@H](Cc2ccc(O)cc2)N(C)C)cc1]

In embodiments, the compound has the formula:

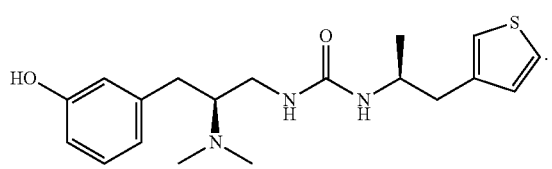 [SMILES: C[C@@H](Cc1ccsc1)NC(=O)NC[C@H](Cc1cccc(O)c1)N(C)C]

In embodiments, the compound has the formula:

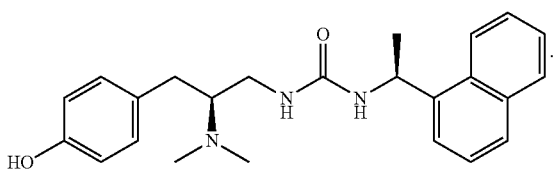 [SMILES: C[C@H](NC(=O)NC[C@H](Cc1ccc(O)cc1)N(C)C)c1cccc2ccccc12]

In embodiments, the compound has the formula:

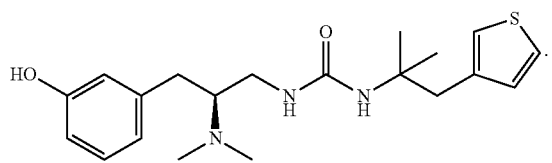 [SMILES: CN(C)[C@H](CNC(=O)NC(C)(C)Cc1ccsc1)Cc1cccc(O)c1]

In embodiments, the compound has the formula:

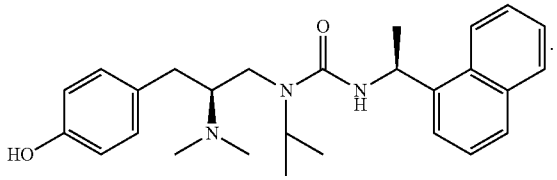 [SMILES: CC(C)N(C[C@H](Cc1ccc(O)cc1)N(C)C)C(=O)N[C@@H](C)c1cccc2ccccc12]

In embodiments, the compound has the formula:

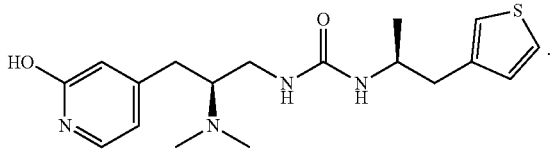 [SMILES: C[C@@H](Cc1ccsc1)NC(=O)NC[C@H](Cc1ccnc(O)c1)N(C)C]

In embodiments, the compound has the formula:

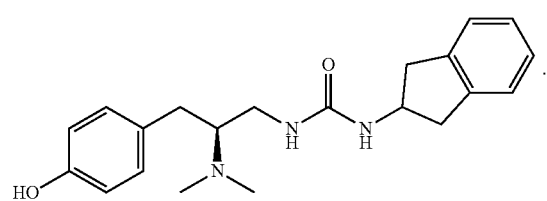 [SMILES: CN(C)[C@H](CNC(=O)NC1Cc2ccccc2C1)Cc1ccc(O)cc1]

In embodiments, the compound has the formula:

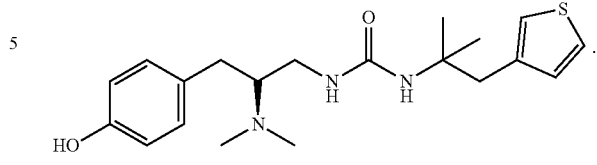

In embodiments. In embodiments, the compound has the formula:

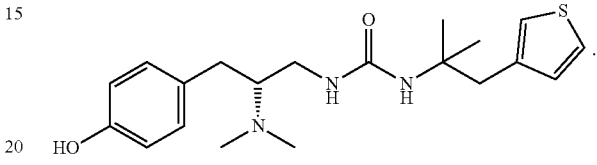

In embodiments, the compound has the formula:

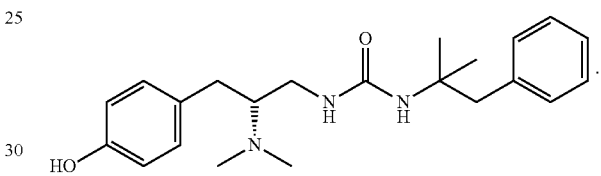

$R^{32}$, $R^{35}$, $R^{38}$, $R^{38A}$, $R^{38B}$, $R^{38C}$, $R^{38D}$, $R^{38E}$, $R^{41}$, $R^{44}$, $R^{47}$, $R^{50}$, $R^{53}$, $R^{56}$, $R^{59}$, $R^{62}$, $R^{65}$, $R^{68}$, $R^{71}$, $R^{98}$, and Riot are independently hydrogen, oxo,
halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl.

In some embodiments, the compound is any one of the compounds described herein (e.g., in an aspect, embodiment, claim, figure, table, or example).

In some embodiments, a compound as described herein may include multiple instances of $R^7$, $R^8$, $R^9$, $R^{10}$, $R^{11}$, $R^{12}$, $R^{13}$, $R^{14}$, $X^a$, X, m1, n1, v1, m, n, v, $R^3$, $R^4$, and/or other variables. In such embodiments, each variable may optional be different and be appropriately labeled to distinguish each group for greater clarity. For example, where each $R^7$, $R^8$, $R^9$, $R^{10}$, $R^{11}$, $R^{12}$, $R^{13}$, $R^{14}$, $X^a$, X, m1, n1, v1, m, n, v, $R^3$, and/or $R^4$, is different, they may be referred to, for example, as $R^{7.1}$, $R^{7.2}$, $R^{7.3}$, $R^{7.4}$, $R^{7.5}$, $R^{7.6}$, $R^{7.7}$, $R^{7.8}$, $R^{7.9}$, $R^{7.10}$, $R^{7.11}$, $R^{7.12}$, $R^{7.13}$, $R^{7.14}$, $R^{7.15}$, $R^{7.16}$, $R^{7.17}$, $R^{7.18}$, $R^{7.19}$, $R^{7.20}$, $R^{7.21}$, $R^{7.22}$, $R^{7.23}$, $R^{7.24}$, $R^{7.25}$, $R^{7.26}$, $R^{7.27}$, $R^{7.28}$, $R^{7.29}$, $R^{7.30}$, $R^{7.31}$, $R^{7.32}$, $R^{7.33}$, $R^{7.34}$, $R^{7.35}$, $R^{7.36}$, $R^{7.37}$, $R^{7.38}$, $R^{7.39}$, $R^{7.40}$, $R^{7.41}$, $R^{7.42}$, $R^{8.1}$, $R^{8.2}$, $R^{8.3}$, $R^{8.4}$, $R^{8.5}$, $R^{8.6}$, $R^{8.7}$, $R^{8.8}$, $R^{8.9}$, $R^{8.10}$, $R^{8.11}$, $R^{8.12}$, $R^{8.13}$, $R^{8.14}$, $R^{8.15}$, $R^{8.16}$, $R^{8.17}$, $R^{8.18}$, $R^{8.19}$, $R^{8.20}$, $R^{8.21}$, $R^{8.22}$, $R^{8.23}$, $R^{8.24}$, $R^{8.25}$, $R^{8.26}$, $R^{8.27}$, $R^{8.28}$, $R^{8.29}$, $R^{8.30}$, $R^{8.31}$, $R^{8.32}$, $R^{8.33}$, $R^{8.34}$, $R^{8.35}$, $R^{8.36}$, $R^{8.37}$, $R^{8.38}$, $R^{8.39}$, $R^{8.40}$, $R^{8.41}$, $R^{8.42}$, $R^{9.1}$, $R^{9.2}$, $R^{9.3}$, $R^{9.4}$, $R^{9.5}$, $R^{9.6}$, $R^{9.7}$, $R^{9.8}$, $R^{9.9}$, $R^{9.10}$, $R^{9.11}$, $R^{9.12}$, $R^{9.13}$, $R^{9.14}$, $R^{9.15}$, $R^{9.16}$, $R^{9.17}$, $R^{9.18}$, $R^{9.19}$, $R^{9.20}$, $R^{9.21}$, $R^{9.22}$, $R^{9.23}$, $R^{9.24}$, $R^{9.25}$, $R^{9.26}$, $R^{9.27}$, $R^{9.28}$, $R^{9.29}$, $R^{9.30}$, $R^{9.31}$, $R^{9.32}$, $R^{9.33}$, $R^{9.34}$, $R^{9.35}$, $R^{9.36}$, $R^{9.37}$, $R^{9.38}$, $R^{9.39}$, $R^{9.40}$, $R^{9.41}$, $R^{9.42}$, $R^{10.1}$, $R^{10.2}$, $R^{10.3}$, $R^{10.14}$, $R^{10.5}$, $R^{10.6}$, $R^{10.7}$, $R^{10.8}$, $R^{10.9}$, $R^{10.10}$, $R^{10.11}$, $R^{10.12}$, $R^{10.13}$, $R^{10.14}$, $R^{10.15}$, $R^{10.16}$, $R^{10.17}$, $R^{10.18}$, $R^{10.19}$, $R^{10.20}$, $R^{10.21}$, $R^{10.22}$, $R^{10.23}$, $R^{10.24}$, $R^{10.25}$, $R^{10.26}$, $R^{10.27}$, $R^{10.28}$, $R^{10.29}$, $R^{10.30}$, $R^{10.31}$, $R^{10.32}$, $R^{10.33}$, $R^{10.34}$, $R^{10.35}$, $R^{10.36}$, $R^{10.37}$, $R^{10.38}$, $R^{10.39}$, $R^{10.40}$, $R^{10.41}$, $R^{10.42}$, $R^{11.1}$, $R^{11.2}$, $R^{11.3}$, $R^{11.4}$, $R^{11.5}$, $R^{11.6}$, $R^{11.7}$, $R^{11.8}$, $R^{11.9}$, $R^{11.10}$, $R^{11.11}$, $R^{11.12}$, $R^{11.13}$, $R^{11.14}$, $R^{11.15}$, $R^{11.16}$, $R^{11.17}$, $R^{11.18}$, $R^{11.19}$, $R^{11.20}$, $R^{11.21}$, $R^{11.22}$, $R^{11.23}$, $R^{11.24}$, $R^{11.25}$, $R^{11.26}$, $R^{11.27}$, $R^{11.28}$, $R^{11.29}$, $R^{11.30}$, $R^{11.31}$, $R^{11.32}$, $R^{11.33}$, $R^{11.34}$, $R^{11.35}$, $R^{11.36}$, $R^{11.37}$, $R^{11.38}$, $R^{11.39}$, $R^{11.40}$, $R^{11.41}$, $R^{11.42}$; $R^{12}$ is assumed by $R^{12.1}$, $R^{12.2}$, $R^{12.3}$, $R^{12.4}$, $R^{12.5}$, $R^{12.6}$, $R^{12.7}$, $R^{12.8}$, $R^{12.9}$, $R^{12.10}$, $R^{12.11}$, $R^{12.12}$, $R^{12.13}$, $R^{12.14}$, $R^{12.15}$, $R^{12.16}$, $R^{12.17}$, $R^{12.18}$, $R^{12.19}$, $R^{12.20}$, $R^{12.21}$, $R^{12.22}$, $R^{12.23}$, $R^{12.24}$, $R^{12.25}$, $R^{12.26}$, $R^{12.27}$, $R^{12.28}$, $R^{12.29}$, $R^{12.30}$, $R^{12.31}$, $R^{12.32}$, $R^{12.33}$, $R^{12.34}$, $R^{12.35}$, $R^{12.36}$, $R^{12.37}$, $R^{12.38}$, $R^{12.39}$, $R^{12.40}$, $R^{12.41}$, $R^{12.42}$; $R^{13}$ is assumed by $R^{13.1}$, $R^{13.2}$, $R^{13.3}$, $R^{13.4}$, $R^{13.5}$, $R^{13.6}$, $R^{13.7}$, $R^{13.8}$, $R^{13.9}$, $R^{13.10}$, $R^{13.11}$, $R^{13.12}$, $R^{13.13}$, $R^{13.14}$, $R^{13.15}$, $R^{13.16}$, $R^{13.17}$, $R^{13.18}$, $R^{13.19}$, $R^{13.20}$, $R^{13.21}$, $R^{13.22}$, $R^{13.23}$, $R^{13.24}$, $R^{13.25}$, $R^{13.26}$, $R^{13.27}$, $R^{13.28}$, $R^{13.29}$, $R^{13.30}$, $R^{13.31}$, $R^{13.32}$, $R^{13.33}$, $R^{13.34}$, $R^{13.35}$, $R^{13.36}$, $R^{13.37}$, $R^{13.38}$, $R^{13.39}$, $R^{13.40}$, $R^{13.41}$, $R^{13.42}$; $R^{14}$ is assumed by $R^{14.1}$, $R^{14.2}$, $R^{14.3}$, $R^{14.4}$, $R^{14.5}$, $R^{14.6}$, $R^{14.7}$, $R^{14.8}$, $R^{14.9}$, $R^{14.10}$, $R^{14.11}$, $R^{14.12}$, $R^{14.13}$, $R^{14.14}$, $R^{14.15}$, $R^{14.16}$, $R^{14.17}$, $R^{14.18}$, $R^{14.19}$, $R^{14.20}$, $R^{14.21}$, $R^{14.22}$, $R^{14.23}$, $R^{14.24}$, $R^{14.25}$, $R^{14.26}$, $R^{14.27}$, $R^{14.28}$, $R^{14.29}$, $R^{14.30}$, $R^{14.31}$, $R^{14.32}$, $R^{14.33}$, $R^{14.34}$, $R^{14.35}$, $R^{14.36}$, $R^{14.37}$, $R^{14.38}$, $R^{14.39}$, $R^{14.40}$, $R^{14.41}$, $R^{14.42}$; $X^a$ is assumed by $X^{a1}$, $X^{a2}$, $X^{a3}$, $X^{a4}$, $X^{a5}$, $X^{a6}$, $X^{a7}$, $X^{a8}$, $X^{a9}$, $X^{a10}$, $X^{a11}$, $X^{a12}$, $X^{a13}$, $X^{a14}$, $X^{a15}$, $X^{a16}$, $X^{a17}$, $X^{a18}$, $X^{a19}$, $X^{a20}$, $X^{a21}$, $X^{a22}$, $X^{a23}$, $X^{a24}$, $X^{a25}$, $X^{a26}$, $X^{a27}$, $X^{a28}$, $X^{a29}$, $X^{a30}$, $X^{a31}$, $X^{a32}$, $X^{a33}$, $X^{a34}$, $X^{a35}$, $X^{a36}$, $X^{a37}$, $X^{a38}$, $X^{a39}$, $X^{a40}$, $X^{a41}$, $X^{a42}$; X is assumed by $X^{-1}$, $X^{-2}$, $X^{-3}$, $X^{-4}$, $X^{-5}$, $X^{-6}$, $X^{-7}$, $X^{-8}$, $X^{-9}$, $X^{-10}$, $X^{-11}$, $X^{-12}$, $X^{-13}$, $X^{-14}$, $X^{-15}$, $X^{-16}$, $X^{-17}$, $X^{-18}$, $X^{-19}$, $X^{-20}$, $X^{-21}$, $X^{-22}$, $X^{-23}$, $X^{-24}$, $X^{-25}$, $X^{-26}$, $X^{-27}$, $X^{-28}$, $X^{-29}$, $X^{-30}$, $X^{-31}$, $X^{-32}$, $X^{-33}$, $X^{-34}$, $X^{-35}$, $X^{-36}$, $X^{-37}$, $X^{-38}$, $X^{-39}$, $X^{-40}$, $X^{-41}$, $X^{-42}$; m1 is assumed by $m1^1$, $m1^2$, $m1^3$, $m1^4$, $m1^5$; n1 is assumed by $n1^1$, $n1^2$, $n1^3$, $n1^4$, $n1^5$; v1 is assumed by $v1^1$, $v1^2$, $v1^3$, $v1^4$, $v1^5$; m is assumed by $m^1$, $m^2$, $m^3$, $m^4$, $m^5$; n is assumed by $n^1$, $n^2$, $n^3$, $n^4$, $n^5$; v is assumed by $v^1$, $v^2$, $v^3$, $v^4$, $v^5$; $R^3$ is assumed by $R^{3.1}$, $R^{3.2}$, $R^{3.3}$, $R^{3.4}$, $R^{3.5}$, $R^{3.6}$, $R^{3.7}$, $R^{3.8}$, $R^{3.9}$, $R^{3.10}$, $R^{3.11}$, $R^{3.12}$, $R^{3.13}$, $R^{3.14}$, $R^{3.15}$, $R^{3.16}$, $R^{3.17}$, $R^{3.18}$, $R^{3.19}$, $R^{3.20}$, $R^{3.21}$, $R^{3.22}$, $R^{3.23}$, $R^{3.24}$, $R^{3.25}$, $R^{3.26}$, $R^{3.27}$, $R^{3.28}$, $R^{3.29}$, $R^{3.30}$, $R^{3.31}$, $R^{3.32}$, $R^{3.33}$, $R^{3.34}$, $R^{3.35}$, $R^{3.36}$, $R^{3.37}$, $R^{3.38}$, $R^{3.39}$, $R^{3.40}$, $R^{3.41}$, $R^{3.42}$; and/or $R^4$ is assumed by $R^{4.1}$, $R^{4.2}$, $R^{4.3}$, $R^{4.4}$, $R^{4.5}$, $R^{4.6}$, $R^{4.7}$, $R^{4.8}$, $R^{4.9}$, $R^{4.10}$, $R^{4.11}$, $R^{4.12}$, $R^{4.13}$, $R^{4.14}$, $R^{4.15}$, $R^{4.16}$, $R^{4.17}$, $R^{4.18}$, $R^{4.19}$, $R^{4.20}$, $R^{4.21}$, $R^{4.22}$, $R^{4.23}$, $R^{4.24}$, $R^{4.25}$, $R^{4.26}$, $R^{4.27}$, $R^{4.28}$, $R^{4.29}$, $R^{4.20}$, $R^{4.31}$, $R^{4.22}$, $R^{4.23}$, $R^{4.24}$, $R^{4.25}$, $R^{4.26}$, $R^{4.27}$, $R^{4.38}$, $R^{4.39}$, $R^{4.40}$, $R^{4.41}$, $R^{4.42}$ The variables used within a definition of $R^7$, $R^8$, $R^9$, $R^{10}$, $R^{11}$, $R^{12}$, $R^{13}$, $R^{14}$, $X^a$, X, m1, n1, v1, m, n, v, $R^3$, $R^4$, and/or other variables that appear at multiple instances and are different may similarly be appropriately labeled to distinguish each group for greater clarity. In some embodiments, the compound is a compound described herein (e.g., in an aspect, embodiment, example, claim, table, scheme, drawing, or figure).

In embodiments, the compound comprises a higher binding affinity for the mu opioid receptor than for the kappa opioid receptor. In embodiments, the compound comprises a greater than 10-fold higher binding affinity for the mu opioid receptor than for the kappa opioid receptor. In embodiments, the compound comprises a greater than 100-fold higher binding affinity for the mu opioid receptor than for the kappa opioid receptor. In embodiments, the compound comprises a higher binding affinity for the mu opioid receptor than for the delta opioid receptor. In embodiments, the compound comprises a greater than 10-fold higher binding affinity for the mu opioid receptor than for the delta opioid receptor. In embodiments, the compound comprises a greater than 100-fold higher binding affinity for the mu opioid receptor than for the delta opioid receptor. In embodiments, the compound comprises a higher binding affinity for the mu opioid receptor than for the nociceptin receptor. In embodiments, the compound comprises a greater than 10-fold higher binding affinity for the mu opioid receptor than for the nociceptin receptor. In embodiments, the compound comprises a greater than 100-fold higher binding affinity for the mu opioid receptor than for the nociceptin receptor.

In embodiments, the compound comprises a greater than 10-fold, 20-fold, 30-fold, 40-fold, 50-fold, 100-fold, 500-fold, or 1000-fold higher binding affinity for the mu opioid receptor than for the kappa opioid receptor. In embodiments, the compound comprises a greater than 10-fold, 20-fold, 30-fold, 40-fold, 50-fold, 100-fold, 500-fold, or 1000-fold higher binding affinity for the mu opioid receptor than for the delta opioid receptor. In embodiments, the compound comprises a greater than 10-fold, 20-fold, 30-fold, 40-fold, 50-fold, 100-fold, 500-fold, or 1000-fold higher binding affinity for the mu opioid receptor than for the nociceptin receptor.

In embodiments, the compound comprises a lower addiction potential than medically used opioids. In embodiments, the compound comprises a lower addiction potential than medically used opiates. In embodiments, the compound comprises a lower addiction potential than morphine. In embodiments, the compound comprises a lower addiction potential than fentanyl. In embodiments, the compound comprises a lower addiction potential than heroin. In embodiments, the compound comprises a lower addiction potential than hydrocodone. In embodiments, the compound comprises a lower addiction potential than oxycodone. In embodiments, the compound comprises a lower addiction potential than morphine derivatives. In embodiments, the compound comprises a lower addiction potential than medically used morphine derivatives. In embodiments, the compound comprises a lower addiction potential than codeine. In embodiments, the compound comprises a lower addiction potential than methadone. In embodiments, the compound comprises a lower addiction potential than hydromorphone. In embodiments, the lowered addiction potential of the compound compared to the opioid is 10-fold. In embodiments, the lowered addiction potential of the compound compared to the opioid is 100-fold. In embodiments, the lowered addiction potential of the compound compared to the opioid is for an identical amount of the compound and the opioid. In embodiments, the lowered addiction potential of the compound compared to the opioid is for an identical level of pain relief.

In embodiments, unless otherwise indicated, a compound described herein is a racemic mixture of all stereoisomers. In embodiments, unless otherwise indicated, a compound described herein is a racemic mixture of all enantiomers. In embodiments, unless otherwise indicated, a compound described herein is a racemic mixture of two opposite stereoisomers. In embodiments, unless otherwise indicated, a compound described herein is a racemic mixture of two opposite enantiomers. In embodiments, unless otherwise indicated, a compound described herein is a single stereoisomer. In embodiments, unless otherwise indicated, a compound described herein is a single enantiomer.

In embodiments, the compound is not:

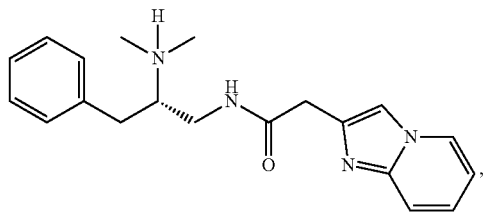

-continued

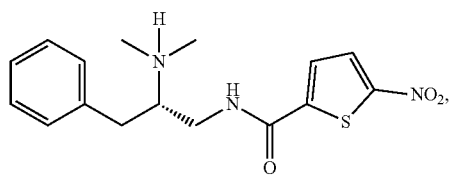

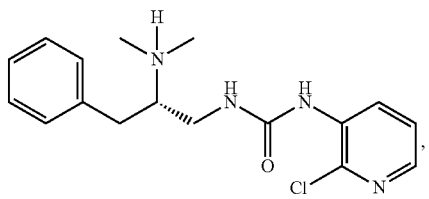

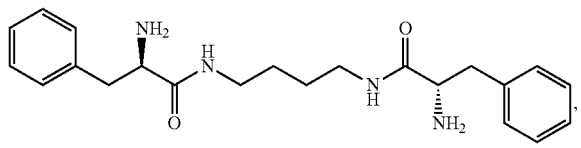

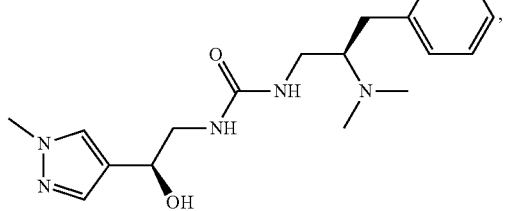

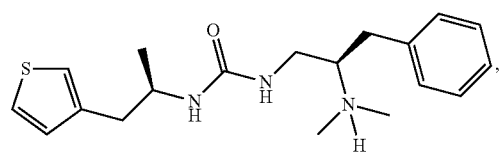

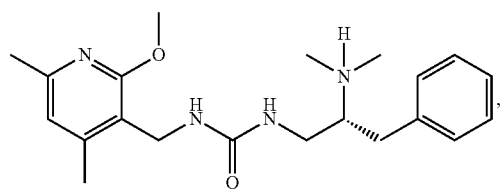

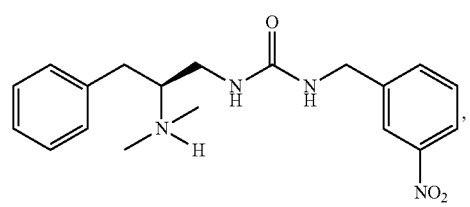

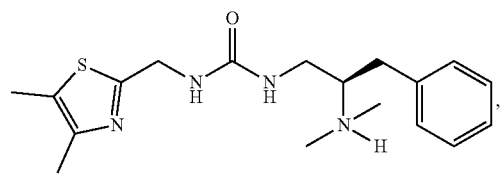

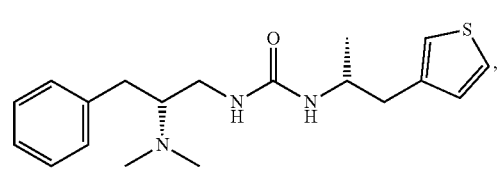

-continued
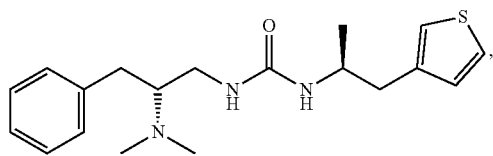,
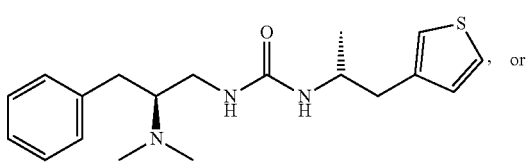, or
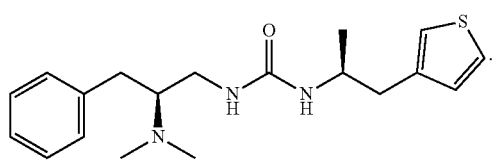.
In embodiments, the compound is not
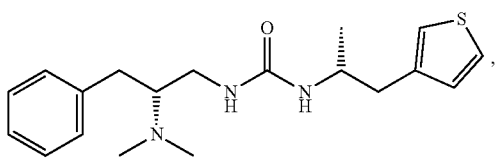,
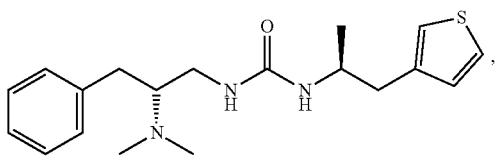,
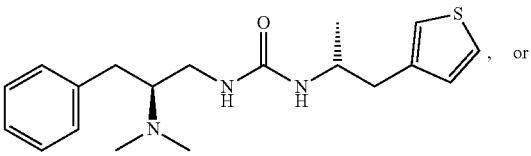, or
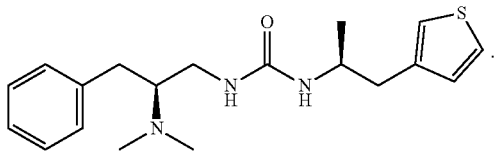 [SMILES: C[C@@H](Cc1ccsc1)NC(=O)NC[C@H](Cc1ccccc1)N(C)C].
In embodiments, the compound is not
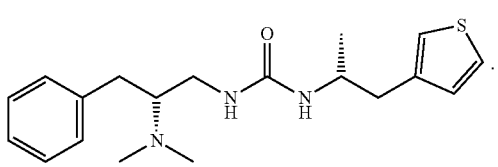.
In embodiments, the compound is not
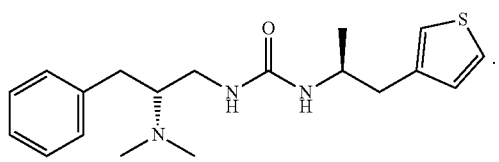.
In embodiments, the compound is not
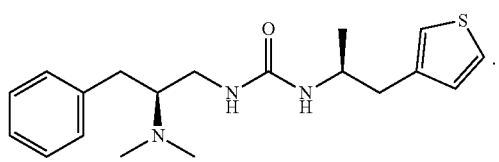.
In embodiments, the compound is not
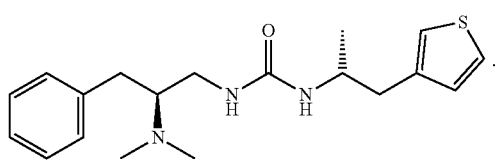.
In embodiments, the compound is not
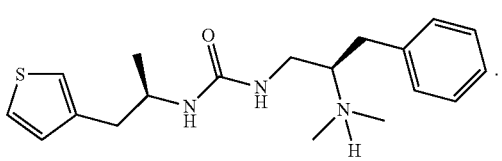.
In embodiments, the compound is not
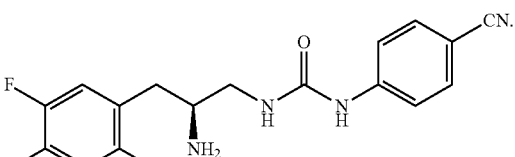
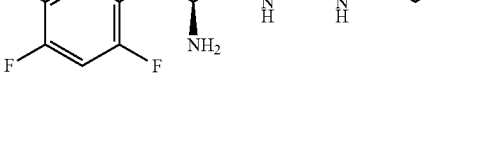.
In embodiments, the compound is not
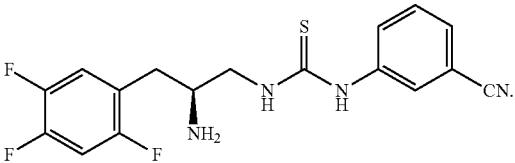 [SMILES: N#Cc1cccc(NC(=S)NC[C@@H](N)Cc2cc(F)c(F)cc2F)c1]

In embodiments, the compound is not

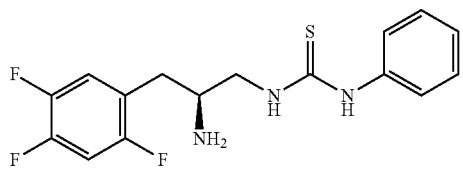

In embodiments, the compound is not

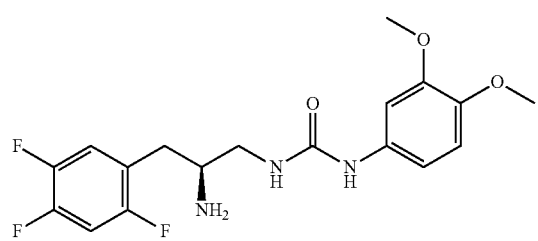

In embodiments, the compound is not

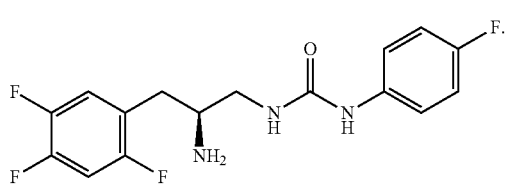 [SMILES: N[C@H](CNC(=O)Nc1ccc(F)cc1)Cc1cc(F)c(F)cc1F]

In embodiments, the compound is not

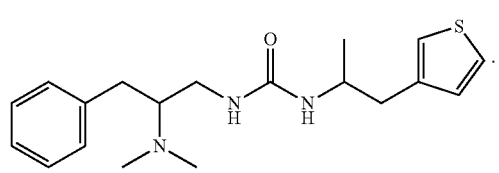 [SMILES: CC(Cc1ccsc1)NC(=O)NCC(Cc1ccccc1)N(C)C]

In embodiments, the compound is not

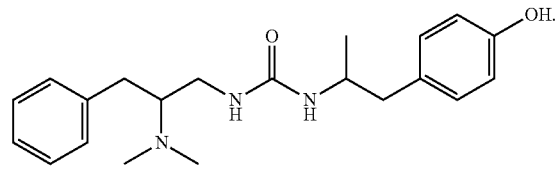 [SMILES: CC(Cc1ccc(O)cc1)NC(=O)NCC(Cc1ccccc1)N(C)C]

In embodiments, the compound is not

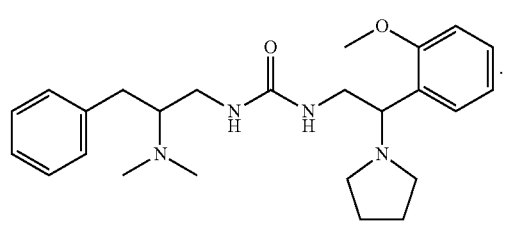 [SMILES: COc1ccccc1C(CNC(=O)NCC(Cc1ccccc1)N(C)C)N1CCCC1]

In embodiments, the compound is not

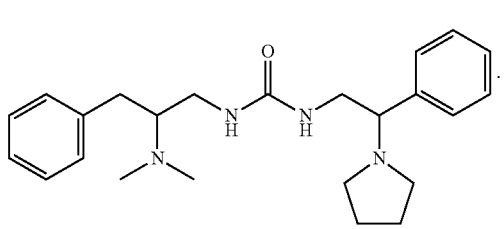 [SMILES: CN(C)C(CNC(=O)NCC(c1ccccc1)N1CCCC1)Cc1ccccc1]

In embodiments, the compound is not

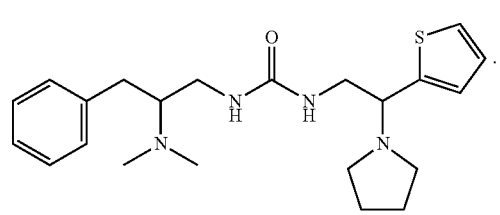 [SMILES: CN(C)C(CNC(=O)NCC(c1cccs1)N1CCCC1)Cc1ccccc1]

In embodiments, the compound is not

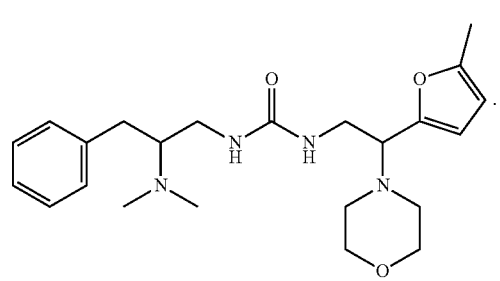 [SMILES: Cc1ccc(C(CNC(=O)NCC(Cc2ccccc2)N(C)C)N2CCOCC2)o1]

In embodiments, the compound is not

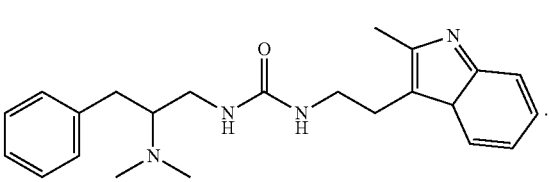 [SMILES: CC1=C(CCNC(=O)NCC(Cc2ccccc2)N(C)C)C2C=CC=CC2=N1]

In embodiments, the compound is not

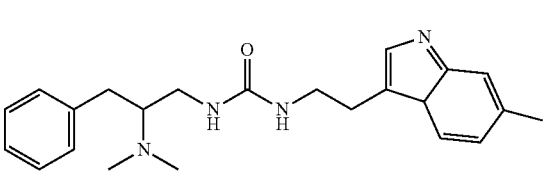

In embodiments, the compound is not

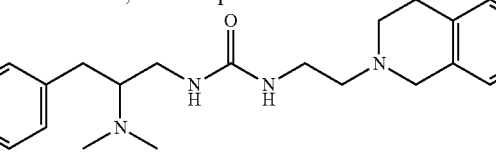

In embodiments, the compound is not

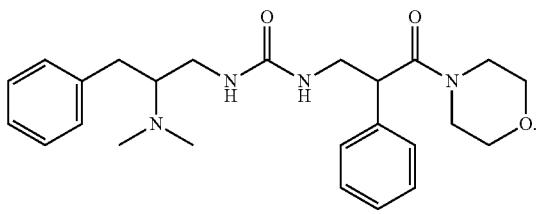 [SMILES: CN(C)C(CNC(=O)NCC(C(=O)N1CCOCC1)c1ccccc1)Cc1ccccc1]

In embodiments, the compound is not

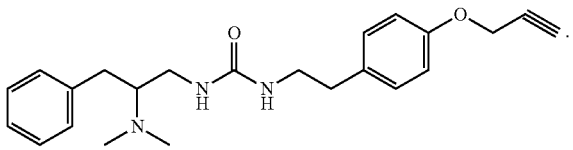 [SMILES: C#CCOc1ccc(CCNC(=O)NCC(Cc2ccccc2)N(C)C)cc1]

In embodiments, the compound is not

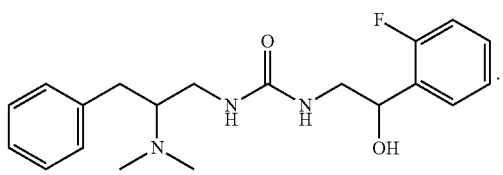 [SMILES: CN(C)C(CNC(=O)NCC(O)c1ccccc1F)Cc1ccccc1]

In embodiments, the compound is not

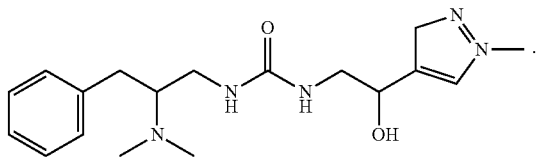

In embodiments, the compound is not

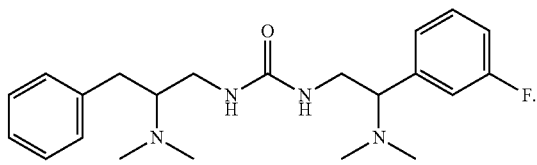 [SMILES: CN(C)C(CNC(=O)NCC(c1cccc(F)c1)N(C)C)Cc1ccccc1]

In embodiments, the compound is not a compound having the formula:

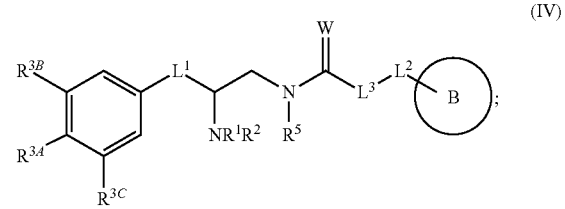

(IV)

wherein $R^1$, $R^2$, $R^{3A}$, $R^{3B}$, $R^{3C}$, $R^5$, $L^1$, $L^2$, $L^3$, W, and Ring B are as described herein (e.g., including in formula I, II, and III, and embodiments thereof). In embodiments, the compound is not a compound wherein $R^{3A}$ is hydrogen. In embodiments, the compound is not a compound wherein Ring B is substituted. In embodiments, the compound is not a compound wherein Ring B is substituted aryl. In embodiments, the compound is not a compound wherein Ring B is substituted heteroaryl. In embodiments, the compound is not a compound wherein Ring B is substituted thienyl. In embodiments, the compound is not a compound wherein Ring B is substituted pyridyl. In embodiments, the compound is not a compound wherein Ring B is substituted phenyl. In embodiments, the compound is not a compound having the formula:

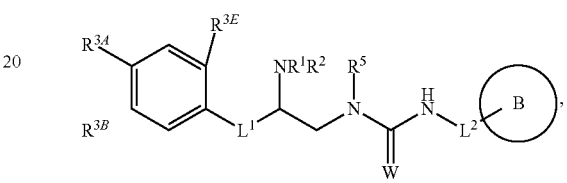

wherein $R^{3A}$, $R^{3B}$, and $R^{3E}$ are independently not halogen.

In embodiments, the compound is not a compound having the formula:

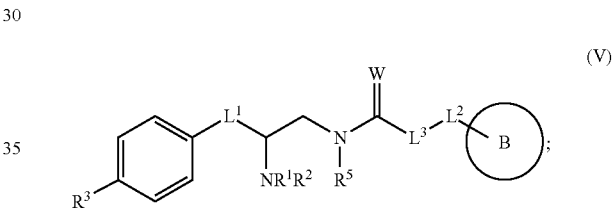

(V)

wherein $R^1$, $R^2$, $R^3$, $R^5$, $L^1$, $L^2$, $L^3$, W, and Ring B are as described herein (e.g., including in formula I, II, III, IV, IVa, IVb and embodiments). In embodiments, the compound is not a compound wherein $R^3$ is hydrogen. In embodiments, the compound is not a compound wherein Ring B is substituted. In embodiments, the compound is not a compound wherein Ring B is substituted aryl. In embodiments, the compound is not a compound wherein Ring B is substituted heteroaryl. In embodiments, the compound is not a compound wherein Ring B is substituted thienyl. In embodiments, the compound is not a compound wherein Ring B is substituted pyridyl. In embodiments, the compound is not a compound wherein Ring B is substituted phenyl.

In embodiments, the compound is not a compound having the formula:

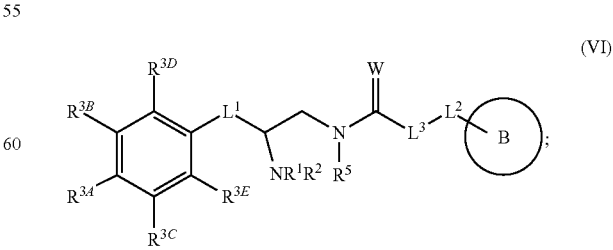

(VI)

wherein $R^1$, $R^2$, $R^{3A}$, $R^{3B}$, $R^{3C}$, $R^{3D}$, $R^{3E}$, $R^5$, $L^1$, $L^2$, $L^3$, W, and Ring B are as described herein (e.g., including in formula I, II, III, IV, IVa, IVb and V, and embodiments thereof). In embodiments, the compound is not a compound wherein $R^{3A}$ is
hydrogen. In embodiments, the compound is not a compound wherein Ring B is substituted. In embodiments, the compound is not a compound wherein Ring B is substituted aryl. In embodiments, the compound is not a compound wherein Ring B is substituted heteroaryl. In embodiments, the compound is not a compound wherein Ring B is substituted thienyl. In embodiments, the compound is not a compound wherein Ring B is substituted pyridyl. In embodiments, the compound is not a compound wherein Ring B is substituted phenyl.

In embodiments, the compound is not a compound having the formula:

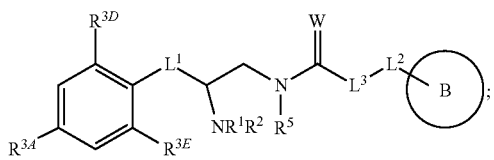

(VII)

wherein $R^1$, $R^2$, $R^{3A}$, $R^{3D}$, $R^{3E}$, $R^5$, $L^1$, $L^2$, $L^3$, W, and Ring B are as described herein (e.g., including in formula I, II, III, IV, IVa, IVb V, and VI, and embodiments thereof). In embodiments, the compound is not a compound wherein $R^{3A}$ is
hydrogen. In embodiments, the compound is not a compound wherein Ring B is substituted. In embodiments, the compound is not a compound wherein Ring B is substituted aryl. In embodiments, the compound is not a compound wherein Ring B is substituted heteroaryl. In embodiments, the compound is not a compound wherein Ring B is substituted thienyl. In embodiments, the compound is not a compound wherein Ring B is substituted pyridyl. In embodiments, the compound is not a compound wherein Ring B is substituted phenyl.

In embodiments, the compound is not a compound having the formula:

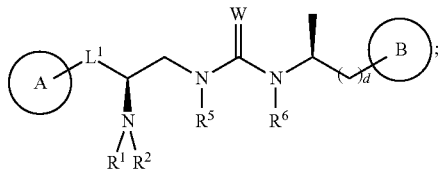

(VIII)

$R^1$, $R^2$, $R^5$, $R^6$, $L^1$, W, Ring A, and Ring B are as described herein (e.g., including in formula I, II, III, IV, IVa, IVb V, VI, and VII, and embodiments thereof) and wherein d is an integer between 0 and 3. In embodiments, the compound is not a compound wherein Ring A is unsubstituted. In embodiments, the compound is not a compound wherein Ring A is unsubstituted aryl. In embodiments, the compound is not a compound wherein Ring A is unsubstituted phenyl. In embodiments, the compound is not a compound wherein Ring B is substituted. In embodiments, the compound is not a compound wherein Ring B is substituted aryl. In embodiments, the compound is not a compound wherein Ring B is substituted heteroaryl. In embodiments, the compound is not a compound wherein Ring B is substituted thienyl. In embodiments, the compound is not a compound wherein Ring B is substituted pyridyl. In embodiments, the compound is not a compound wherein Ring B is substituted phenyl.

In embodiments, the compound is not a compound having the formula:

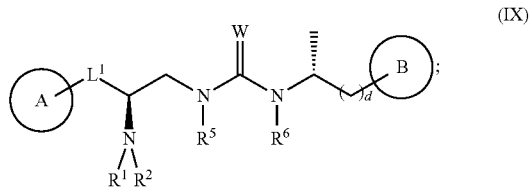

(IX)

wherein $R^1$, $R^2$, $R^5$, $R^6$, $L^1$, W, Ring A, and Ring B are as described herein (e.g., including in formula I, II, III, IV, IVa, IVb V, VI, VII, and VIII, and embodiments thereof) and wherein d is an integer between 0 and 3. In embodiments, the compound is not a compound wherein Ring A is unsubstituted. In embodiments, the compound is not a compound wherein Ring A is unsubstituted aryl. In embodiments, the compound is not a compound wherein Ring A is unsubstituted phenyl. In embodiments, the compound is not a compound wherein Ring B is substituted. In embodiments, the compound is not a compound wherein Ring B is substituted aryl. In embodiments, the compound is not a compound wherein Ring B is substituted heteroaryl. In embodiments, the compound is not a compound wherein Ring B is substituted thienyl. In embodiments, the compound is not a compound wherein Ring B is substituted pyridyl. In embodiments, the compound is not a compound wherein Ring B is substituted phenyl.

In embodiments, the compound is not a compound having the formula:

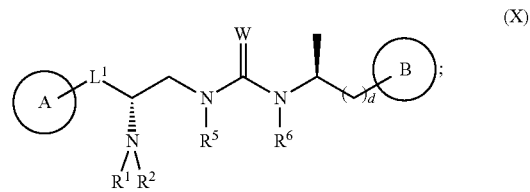

(X)

wherein $R^1$, $R^2$, $R^5$, $R^6$, $L^1$, W, Ring A, and Ring B are as described herein (e.g., including in formula I, II, III, IV, IVa, IVb V, VI, VII, VIII, and IX, and embodiments thereof) and wherein d is an integer between 0 and 3. In embodiments, the compound is not a compound wherein Ring A is unsubstituted. In embodiments, the compound is not a compound wherein Ring A is unsubstituted aryl. In embodiments, the compound is not a compound wherein Ring A is unsubstituted phenyl. In embodiments, the compound is not a compound wherein Ring B is substituted. In embodiments, the compound is not a compound wherein Ring B is substituted aryl. In embodiments, the compound is not a compound wherein Ring B is substituted heteroaryl. In embodiments, the compound is not a compound wherein Ring B is substituted thienyl. In embodiments, the compound is not a compound wherein Ring B is substituted pyridyl. In embodiments, the compound is not a compound wherein Ring B is substituted phenyl.

In embodiments, the compound is not a compound having the formula:

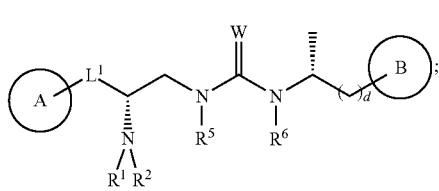
(XI)

wherein $R^1$, $R^2$, $R^5$, $R^6$, $L^1$, W, Ring A, and Ring B are as described herein (e.g., including in formula I, II, III, IV, IVa, IVb V, VI, VII, VIII, IX, and X, and embodiments thereof) and wherein d is an integer between 0 and 3. In embodiments, the compound is not a compound wherein Ring A is unsubstituted. In embodiments, the compound is not a compound wherein Ring A is unsubstituted aryl. In embodiments, the compound is not a compound wherein Ring A is unsubstituted phenyl. In embodiments, the compound is not a compound wherein Ring B is substituted. In embodiments, the compound is not a compound wherein Ring B is substituted aryl. In embodiments, the compound is not a compound wherein Ring B is substituted heteroaryl. In embodiments, the compound is not a compound wherein Ring B is substituted thienyl. In embodiments, the compound is not a compound wherein Ring B is substituted pyridyl. In embodiments, the compound is not a compound wherein Ring B is substituted phenyl.

In embodiments, the compound is not a compound having the formula:

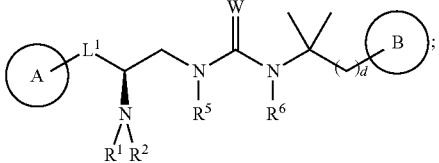
(XII)

wherein $R^1$, $R^2$, $R^5$, $R^6$, $L^1$, W, Ring A, and Ring B are as described herein (e.g., including in formula I, II, III, IV, IVa, IVb V, VI, VII, VIII, IX, X, and XI, and embodiments thereof) and wherein d is an integer between 0 and 3. In embodiments, the compound is not a compound wherein Ring A is unsubstituted. In embodiments, the compound is not a compound wherein Ring A is unsubstituted aryl. In embodiments, the compound is not a compound wherein Ring A is unsubstituted phenyl. In embodiments, the compound is not a compound wherein Ring B is substituted. In embodiments, the compound is not a compound wherein Ring B is substituted aryl. In embodiments, the compound is not a compound wherein Ring B is substituted heteroaryl. In embodiments, the compound is not a compound wherein Ring B is substituted thienyl. In embodiments, the compound is not a compound wherein Ring B is substituted pyridyl. In embodiments, the compound is not a compound wherein Ring B is substituted phenyl.

In embodiments, the compound is not a compound having the formula:

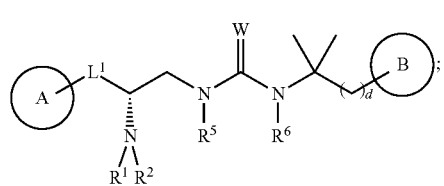
(XIII)

wherein $R^1$, $R^2$, $R^5$, $R^6$, $L^1$, W, Ring A, and Ring B are as described herein (e.g., including in formula I, II, III, IV, IVa, IVb V, VI, VII, VIII, IX, X, XI, and XII, and embodiments thereof) and wherein d is an integer between 0 and 3. In embodiments, the compound is not a compound wherein Ring A is unsubstituted. In embodiments, the compound is not a compound wherein Ring A is unsubstituted aryl. In embodiments, the compound is not a compound wherein Ring A is unsubstituted phenyl. In embodiments, the compound is not a compound wherein Ring B is substituted. In embodiments, the compound is not a compound wherein Ring B is substituted aryl. In embodiments, the compound is not a compound wherein Ring B is substituted heteroaryl. In embodiments, the compound is not a compound wherein Ring B is substituted thienyl. In embodiments, the compound is not a compound wherein Ring B is substituted pyridyl. In embodiments, the compound is not a compound wherein Ring B is substituted phenyl.

In embodiments, the compound is not a compound having the formula:

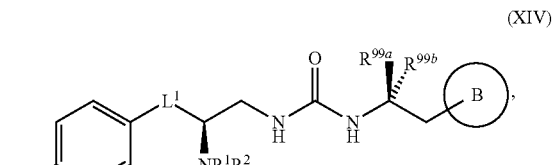
(XIV)

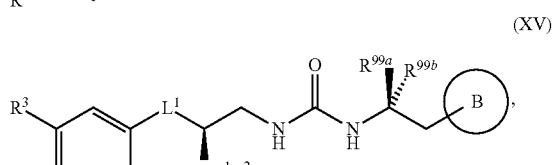
(XV)

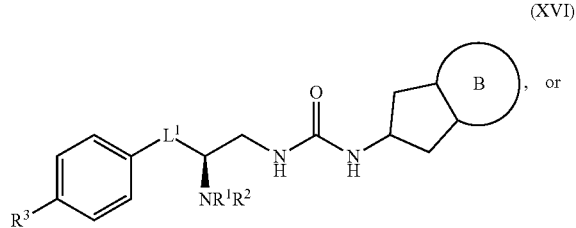
(XVI)

, or

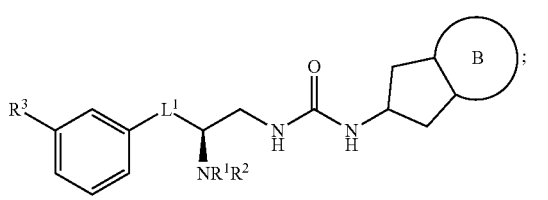
(XVII)

wherein $R^1$, $R^2$, $R^3$, $L^1$, and Ring B are as described herein (e.g., including in formula I, II, III, IV, IVa, IVb V, VI, VII, VIII, IX, X, XI, XII, and XIII, and embodiments thereof). In embodiments, the compound is not a compound wherein $R^3$ is hydrogen. In embodiments, the compound is not a compound wherein $R^3$ is independently halogen. In embodiments, the compound is not a compound wherein Ring B is substituted. In embodiments, the compound is not a compound wherein Ring B is substituted aryl. In embodiments, the compound is not a compound wherein Ring B is substituted heteroaryl. In embodiments, the compound is not a compound wherein Ring B is substituted thienyl. In embodiments, the compound is not a compound wherein Ring B is substituted pyridyl. In embodiments, the compound is not a compound wherein Ring B is substituted phenyl.

In embodiments, the compound is not a compound having the formula:

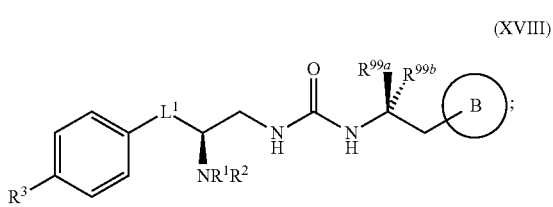

(XVIII)

wherein $R^1$, $R^2$, $R^3$, $L^1$, $R^{99a}$, $R^{99b}$, and Ring B are as described herein (e.g., including in formula I, II, III, IV, IVa, IVb V, VI, VII, VIII, IX, X, XI, XII, XIII, XIV, XV, XVI, and XVII) and embodiments). In embodiments, the compound is not a compound wherein $R^3$ is hydrogen. In embodiments, the compound is not a compound wherein Ring B is substituted. In embodiments, the compound is not a compound wherein Ring B is substituted aryl. In embodiments, the compound is not a compound wherein Ring B is substituted heteroaryl. In embodiments, the compound is not a compound wherein Ring B is substituted thienyl. In embodiments, the compound is not a compound wherein Ring B is substituted pyridyl. In embodiments, the compound is not a compound wherein Ring B is substituted phenyl.

In embodiments, the compound is not a compound having the formula:

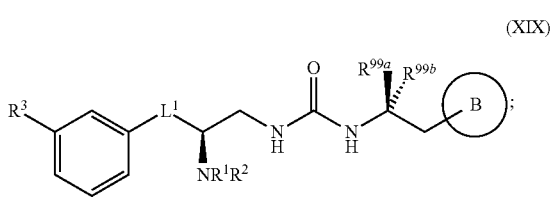

(XIX)

wherein $R^1$, $R^2$, $R^3$, $L^1$, $R^{99a}$, $R^{99b}$, and Ring B are as described herein (e.g., including in formula I, II, III, IV, IVa, IVb V, VI, VII, VIII, IX, X, XI, XII, XIII, XIV, XV, XVI, and XVII) and embodiments). In embodiments, the compound is not a compound wherein $R^3$ is hydrogen. In embodiments, the compound is not a compound wherein Ring B is substituted. In embodiments, the compound is not a compound wherein Ring B is substituted aryl. In embodiments, the compound is not a compound wherein Ring B is substituted heteroaryl. In embodiments, the compound is not a compound wherein Ring B is substituted thienyl. In embodiments, the compound is not a compound wherein Ring B is substituted pyridyl. In embodiments, the compound is not a compound wherein Ring B is substituted phenyl.

In embodiments, the compound is not a compound having the formula:

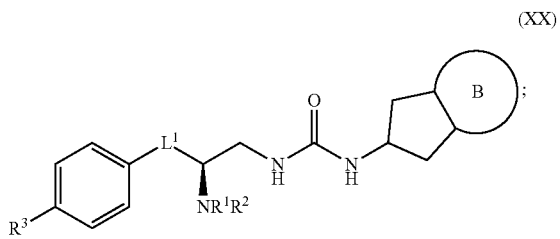

(XX)

wherein $R^1$, $R^2$, $R^3$, $L^1$, $R^{99a}$, $R^{99b}$, and Ring B are as described herein (e.g., including in formula I, II, III, IV, IVa, IVb V, VI, VII, VIII, IX, X, XI, XII, XIII, XIV, XV, XVI, and XVII) and embodiments). In embodiments, the compound is not a compound wherein $R^3$ is hydrogen. In embodiments, the compound is not a compound wherein Ring B is substituted. In embodiments, the compound is not a compound wherein Ring B is substituted aryl. In embodiments, the compound is not a compound wherein Ring B is substituted heteroaryl. In embodiments, the compound is not a compound wherein Ring B is substituted thienyl. In embodiments, the compound is not a compound wherein Ring B is substituted pyridyl. In embodiments, the compound is not a compound wherein Ring B is substituted phenyl.

In embodiments, the compound is not a compound having the formula:

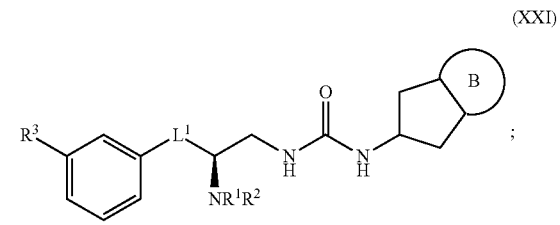

(XXI)

wherein $R^1$, $R^2$, $R^3$, $L^1$, $R^{99a}$, $R^{99b}$, and Ring B are as described herein (e.g., including in formula I, II, III, IV, IVa, IVb V, VI, VII, VIII, IX, X, XI, XII, XIII, XIV, XV, XVI, and XVII) and embodiments). In embodiments, the compound is not a compound wherein $R^3$ is hydrogen. In embodiments, the compound is not a compound wherein Ring B is substituted. In embodiments, the compound is not a compound wherein Ring B is substituted aryl. In embodiments, the compound is not a compound wherein Ring B is substituted heteroaryl. In embodiments, the compound is not a compound wherein Ring B is substituted thienyl. In embodiments, the compound is not a compound wherein Ring B is substituted pyridyl. In embodiments, the compound is not a compound wherein Ring B is substituted phenyl.

In embodiments, the compound is not a compound having the formula:

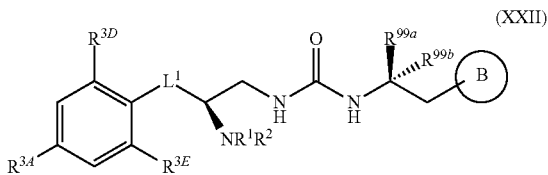

(XXII)

wherein $R^1$, $R^2$, $R^{3A}$, $R^{3D}$, $R^{3E}$, $L^1$, $R^{99a}$, $R^{99b}$, and Ring B are as described herein (e.g., including in formula I, II, III, IV, IVa, IVb V, VI, VII, VIII, IX, X, XI, XII, XIII, XIV, XV, XVI, XVII, XVIII, XIX, XX, and XXI) and embodiments). In embodiments, the compound is not a compound wherein $R^{3A}$ is hydrogen. In embodiments, the compound is not a compound wherein Ring B is substituted. In embodiments, the compound is not a compound wherein Ring B is substituted aryl. In embodiments, the compound is not a compound wherein Ring B is substituted heteroaryl. In embodiments, the compound is not a compound wherein Ring B is substituted thienyl. In embodiments, the compound is not a compound wherein Ring B is substituted pyridyl. In embodiments, the compound is not a compound wherein Ring B is substituted phenyl.

In embodiments, the compound described herein is capable of crossing the blood brain barrier. In embodiments, the compound described herein is a partial agonist of the μOR. In embodiments, the compound described herein is a partial agonist of the μOR. In embodiments, the compound described herein is a partial antagonist of the μOR. Partial agonism is a common term of art, as described in Calvey et. al (Principles and Practice of Pharmacology for Anaesthetists p. 62 (2009)).

III. Pharmaceutical Compositions

In an aspect is provided a pharmaceutical composition including a compound described herein (including in embodiments, examples, figures, or tables) and a pharmaceutically acceptable excipient.

In embodiments, the pharmaceutical composition includes an effective amount of the compound. In embodiments, the pharmaceutical composition includes a therapeutically effective amount of the compound. In embodiments, the pharmaceutical composition includes a second agent (e.g., an additional pain reliever, anti-fibrotic agent, anti-inflammatory agent).

The pharmaceutical compositions may include optical isomers, diastereomers, or pharmaceutically acceptable salts of the modulators disclosed herein. The compound included in the pharmaceutical composition may be covalently attached to a carrier moiety. Alternatively, the compound included in the pharmaceutical composition is not covalently linked to a carrier moiety.

IV. Methods of Treatment

In an aspect is provided a method of treating pain in a subject in need of the treatment, the method including administering an effective amount of a compound described herein (including in embodiments, examples, figures, or tables). An appropriate or effective amount is an amount sufficient to provide the desired therapeutic effect (e.g., treat or alleviate pain or treat or reduce inflammation). Compounds of the invention may be used in combination with other compounds of the invention or with other drugs that may also be useful in the treatment, prevention, or the suppression of pain. In embodiments, the pain is associated with pulmonary edema, kidney stones, minor injuries, wound healing, skin wound healing, vaginitis, candidiasis, lumbar spondylanhrosis, lumbar spondylarthrosis, vascular diseases, migraine headaches, sinus headaches, tension headaches, dental pain, periarteritis *nodosa*, thyroiditis, aplastic anemia, Hodgkin's disease, sclerodoma, rheumatic fever, type I diabetes, type II diabetes, myasthenia gravis, multiple sclerosis, sarcoidosis, nephrotic syndrome, Behcet's syndrome, polymyositis, gingivitis, hypersensitivity, swelling occurring after injury, or myocardial ischemia, or osteoarthritis. In embodiments, the pain is post surgical pain. In embodiments, the compounds described herein are used to treat moderate or severe acute pain. In embodiments, the pain is paroxysmal spontaneous pain, steady pain, allodynia associated with postherpetic neuralgia. In embodiments, the pain is cancer-related pain.

In embodiments, the pain is associated with invasive procedures (e.g., lumbar puncture, biopsy, surgical intervention). In embodiments, the pain is associated with mechanical or metabolic injury to the nervous system, tumor infiltration of nerves or nerve roots, or exposure to chemotherapeutic agents or radiation therapy.

In embodiments, the pain is acute pain (e.g., post surgical pain). In embodiments, the pain is chronic pain. In embodiments, chronic pain is pain that has persisted for at least 1 month. In embodiments, chronic pain is pain that has persisted for at least 2 months. In embodiments, chronic pain is pain that has persisted for at least 3 months. In embodiments, chronic pain is pain that has persisted for at least 4 months. In embodiments, chronic pain is pain that has persisted for at least 5 months. In embodiments, chronic pain is pain that has persisted for at least 6 months. In embodiments, the method does not include an increased risk of respiratory depression. In embodiments, the method does not include respiratory depression. In embodiments, the method does not include an increased risk of constipation. In embodiments, the method does not include constipation. In embodiments, the pain is affective pain. Affective pain may be assessed using an objective psychophysiological measure, subjective ratings, (e.g., the eye-blink component of the startle reflex), or methods described herein (e.g., Example 3). In embodiments, an increased risk indicates an elevated probability of experiencing a symptom (e.g., constipation, respiratory depression). In embodiments, an increased risk is 1%, 2%, 3%, 4%, 5%, 10%, 15%, 25%, 30%, 35%, 40%, 50%, 60%, 70%, 80%, 90%, 100%, 200%, 300%, 400%, 500%, or 1000%. In embodiments, an increased risk is about 1%, 2%, 3%, 4%, 5%, 10%, 15%, 25%, 30%, 35%, 40%, 50%, 60%, 70%, 80%, 90%, 100%, 200%, 300%, 400%, 500%, or about 1000%.

In an aspect is provided a method of treating opioid overdose in a subject in need of the treatment, the method including administering an effective amount of a compound described herein (including in embodiments, examples, figures, or tables).

In an aspect is provided a method of treating addiction in a subject in need of the treatment, the method including administering an effective amount compound described herein (including in embodiments, examples, figures, or tables).

In embodiments, the addiction is opioid addiction. In embodiments, the addiction is heroin addiction. In embodiments, the addiction is oxycodone addiction. In embodiments, the addiction is morphine addiction. In embodiments, the addiction is fentanyl addiction. In embodiments, the addiction is codeine addiction. In embodiments, the addiction is nicotine addiction. In embodiments, the method does not include an increased risk of respiratory depression. In embodiments, the method does not include respiratory depression. In embodiments, the method does not include an increased risk of constipation. In embodiments, the method does not include constipation.

In an aspect is provided a method of treating a psychiatric disorder in a subject in need of the treatment, the method including administering an effective amount of a compound described herein (including in embodiments, examples, figures, or tables).

In embodiments, the psychiatric disorder is depression. In embodiments, the psychiatric disorder is anxiety. In embodiments, the method does not include an increased risk of respiratory depression. In embodiments, the method does not include respiratory depression. In embodiments, the method does not include an increased risk of constipation. In embodiments, the method does not include constipation.

In an aspect is provided a method of treating drug poisoning in a subject in need of the treatment, the method including administering an effective amount of a compound described herein (including in embodiments, examples, figures, or tables).

In embodiments, the drug is an opioid. In embodiments, the drug is an opiate. In embodiments, the drug is heroin. In embodiments, the drug is fentanyl. In embodiments, the drug is morphine. In embodiments, the drug is oxycodone.

The compounds of the invention (i.e. compounds described herein, including in embodiments, examples, figures, tables) can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation or anti-cancer agents).

V. Methods of Modulating Activity

In an aspect is provided a method of modulating the activity of an opioid receptor protein, the method including contacting the opioid receptor protein with an effective amount of a compound described herein (including in embodiments, examples, figures, or tables).

In embodiments, modulating is activating. In embodiments, activating includes a change of 10%, 20%, 30%, 40%, 50%, 60%, 70%, 80%, 90% or greater as compared to a control level. In embodiments, modulating is inhibiting. In embodiments, inhibiting includes a change of 10%, 20%, 30%, 40%, 50%, 60%, 70%, 80%, 90% or greater as compared to a control level can include complete elimination.

In embodiments, the opioid receptor is a human mu opioid receptor.

In embodiments, the method does not include modulating arrestin function. In embodiments, the method does not include increasing arrestin function. In embodiments, the method does not include activating arrestin. In embodiments, the method does not include modulating the activity of a human kappa opioid receptor. In embodiments, the method does not include modulating the activity of a human delta opioid receptor. In embodiments, the method does not include modulating the activity of a human nociceptin receptor.

In embodiments, the method includes modulating human mu opioid receptor function at least 2-fold more than modulating arrestin function. In embodiments, the method includes modulating mu opioid receptor function at least 2-fold more than modulating human kappa opioid receptor function. In embodiments, the method includes modulating mu opioid receptor function at least 2-fold more than modulating human delta opioid receptor function. In embodiments, the method includes modulating mu opioid receptor function at least 2-fold more than modulating human nociceptin receptor function.

In embodiments, the method includes modulating human mu opioid receptor function at least 5-fold more than modulating arrestin function. In embodiments, the method includes modulating mu opioid receptor function at least 5-fold more than modulating human kappa opioid receptor function. In embodiments, the method includes modulating mu opioid receptor function at least 5-fold more than modulating human delta opioid receptor function. In embodiments, the method includes modulating mu opioid receptor function at least 5-fold more than modulating human nociceptin receptor function.

In embodiments, the method includes modulating human mu opioid receptor function at least 10-fold more than modulating arrestin function. In embodiments, the method includes modulating mu opioid receptor function at least 10-fold more than modulating human kappa opioid receptor function. In embodiments, the method includes modulating mu opioid receptor function at least 10-fold more than modulating human delta opioid receptor function. In embodiments, the method includes modulating mu opioid receptor function at least 10-fold more than modulating human nociceptin receptor function.

In embodiments, the method includes modulating human mu opioid receptor function at least 100-fold more than modulating arrestin function. In embodiments, the method includes modulating mu opioid receptor function at least 100-fold more than modulating human kappa opioid receptor function. In embodiments, the method includes modulating mu opioid receptor function at least 100-fold more than modulating human delta opioid receptor function. In embodiments, the method includes modulating mu opioid receptor function at least 100-fold more than modulating human nociceptin receptor function.

In embodiments, the method includes modulating human mu opioid receptor function at least 1000-fold more than modulating arrestin function. In embodiments, the method includes modulating mu opioid receptor function at least 1000-fold more than modulating human kappa opioid receptor function. In embodiments, the method includes modulating mu opioid receptor function at least 1000-fold more than modulating human delta opioid receptor function. In embodiments, the method includes modulating mu opioid receptor function at least 1000-fold more than modulating human nociceptin receptor function.

In embodiments, the method includes modulating human mu opioid receptor function at least 10000-fold more than modulating arrestin function. In embodiments, the method includes modulating mu opioid receptor function at least 10000-fold more than modulating human kappa opioid receptor function. In embodiments, the method includes modulating mu opioid receptor function at least 10000-fold more than modulating human delta opioid receptor function. In embodiments, the method includes modulating mu opioid receptor function at least 10000-fold more than modulating human nociceptin receptor function.

In embodiments, the method includes modulating human mu opioid receptor G protein-mediated function at least 2-fold more than modulating arrestin function. In embodiments, the method includes modulating mu opioid receptor G protein-mediated function at least 2-fold more than modulating human kappa opioid receptor function. In embodiments, the method includes modulating mu opioid receptor G protein-mediated function at least 2-fold more than modulating human delta opioid receptor function. In embodiments, the method includes modulating mu opioid receptor G protein-mediated function at least 2-fold more than modulating human nociceptin receptor function.

In embodiments, the method includes modulating human mu opioid receptor G protein-mediated function at least 5-fold more than modulating arrestin function. In embodiments, the method includes modulating mu opioid receptor G protein-mediated function at least 5-fold more than modulating human kappa opioid receptor function. In embodiments, the method includes modulating mu opioid receptor G protein-mediated function at least 5-fold more than modulating human delta opioid receptor function. In embodiments, the method includes modulating mu opioid receptor G protein-mediated function at least 5-fold more than modulating human nociceptin receptor function.

In embodiments, the method includes modulating human mu opioid G protein-mediated receptor function at least 10-fold more than modulating arrestin function. In embodiments, the method includes modulating mu opioid receptor G protein-mediated function at least 10-fold more than modulating human kappa opioid receptor function. In embodiments, the method includes modulating mu opioid receptor G protein-mediated function at least 10-fold more than modulating human delta opioid receptor function. In embodiments, the method includes modulating mu opioid receptor G protein-mediated function at least 10-fold more than modulating human nociceptin receptor function.

In embodiments, the method includes modulating human mu opioid receptor G protein-mediated function at least 100-fold more than modulating arrestin function. In embodiments, the method includes modulating mu opioid receptor G protein-mediated function at least 100-fold more than modulating human kappa opioid receptor function. In embodiments, the method includes modulating mu opioid receptor G protein-mediated function at least 100-fold more than modulating human delta opioid receptor function. In embodiments, the method includes modulating mu opioid receptor G protein-mediated function at least 100-fold more than modulating human nociceptin receptor function.

In embodiments, the method includes modulating human mu opioid receptor G protein-mediated function at least 1000-fold more than modulating arrestin function. In embodiments, the method includes modulating mu opioid receptor G protein-mediated function at least 1000-fold more than modulating human kappa opioid receptor function. In embodiments, the method includes modulating mu opioid receptor G protein-mediated function at least 1000-fold more than modulating human delta opioid receptor function. In embodiments, the method includes modulating mu opioid receptor G protein-mediated function at least 1000-fold more than modulating human nociceptin receptor function.

In embodiments, the method includes modulating human mu opioid receptor G protein-mediated function at least 10000-fold more than modulating arrestin function. In embodiments, the method includes modulating mu opioid receptor G protein-mediated function at least 10000-fold more than modulating human kappa opioid receptor function. In embodiments, the method includes modulating mu opioid receptor G protein-mediated function at least 10000-fold more than modulating human delta opioid receptor function. In embodiments, the method includes modulating mu opioid receptor G protein-mediated function at least 10000-fold more than modulating human nociceptin receptor function.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example 1. Structure-Based Discovery of Biased μ-Opioid Receptor Analgesics with Reduced Side Effects Opiate addiction, coupled with the potentially lethal side effects of opiates like respiratory depression, has driven optimization campaigns for safer and more effective analgesics since the 19$^{th}$ century. Although the natural products morphine and codeine, and the semi-synthetic drug heroin, were more reliably effective analgesics than raw opium, they retained its liabilities. The classification of opioid receptors into μ, δ, and κ subtypes raised hopes that subtype-specific molecules would escape the liabilities of morphinan-based opiates. Despite the introduction of potent synthetic opioid agonists like methadone and fentanyl and the discovery of endogenous opioid peptides, analgesics without the drawbacks of classic opioids have remained elusive. Recent studies have suggested that opioid-induced analgesia results from μ-opioid receptor (μOR) signaling through the G protein $G_i$, while many side effects, including respiratory depression and constipation, may be conferred via β-arrestin pathway signaling. Agonists specific to the μOR and biased toward the $G_i$ signaling pathway are therefore sought both as therapeutic leads and as molecular probes to understand μOR signaling.

The determination of the crystal structures of the μ, δ, κ, and nociceptin opioid receptors provided an opportunity to seek new μOR agonists via structure-based approaches. We thus targeted the μOR for structure-based docking, seeking ligands with new chemotypes. We reasoned that such new chemotypes might confer signaling properties with new biological effects.

We docked over 3 million commercially available lead-like compounds against the orthosteric pocket of inactive μOR, prioritizing interactions both with known affinity determinants and interactions with putative specificity residues that differ among the four opioid receptor subtypes. For each compound, an average of 1.3 million configurations was evaluated for complementarity to the receptor using the physics-based energy function in DOCK3.6. The top ranking molecules were inspected for features not explicitly captured in the scoring-function. We manually examined the top 2500 (0.08%) of the docking-ranked list for their novelty, their interactions with key polar residues such as Asp147$^{3.32}$ (superscripts indicate Ballesteros-Weinstein numbering), while deprioritizing molecules with strained internal interactions. Ultimately, 23 high-scoring molecules with ranks ranging from 237 to 2095 out of the over 3 million docked were selected for testing (FIG. 1E). Compared to the 5,215 μOR ligands annotated in ChEMBL16, these docking hits had Extended Connectivity Fingerprint 4 (ECFP4) based Tanimoto coefficients ($T_c$) ranging from 0.28 to 0.31, which is consistent with the exploration of novel scaffolds. Of the 23 tested, seven had μOR binding affinities ($K_i$) ranging from 2.3 μM to 14 μM, as observed in Table 1.

TABLE 1

Molecules with μOR activity identified in the initial screen.

| Cmpd | Structure | Rank | $T_c{}^a$ | μOR $K_i$ (μM) |
|---|---|---|---|---|
| 1 | 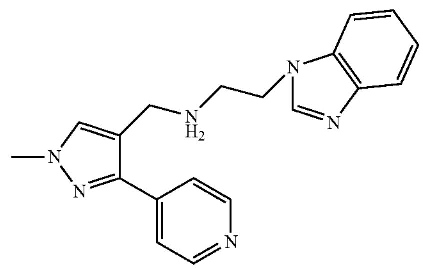 [SMILES: Cn1cc(CNCCn2cnc3ccccc32)c(-c2ccncc2)n1] | 467 | 0.28 | 7.2 |
| 2 | 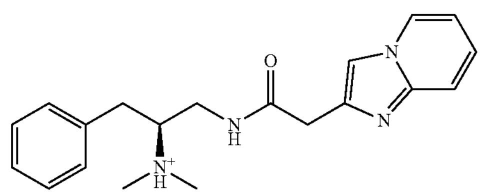 | 358 | 0.28 | 5.8 |
| 3 | 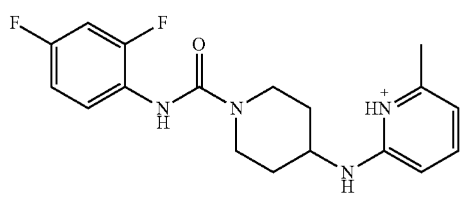 [SMILES: Cc1cccc(NC2CCN(C(=O)Nc3ccc(F)cc3F)CC2)n1] | 1281 | 0.30 | 13.8 |
| 4 | 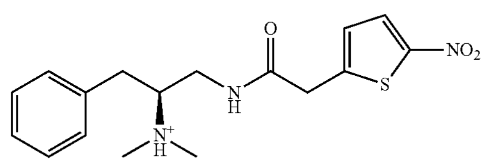 | 1465 | 0.30 | 2.3 |
| 5 | 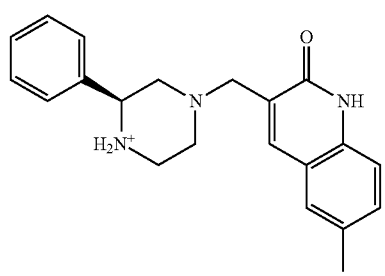 [SMILES: Cc1ccc2[nH]c(=O)c(CN3CC[NH2+][C@@H](c4ccccc4)C3)cc2c1] | 2418 | 0.31 | 4.7 |
| 6 | 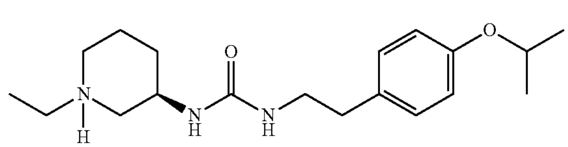 | 2211 | 0.30 | 10.0 |
| 7 | 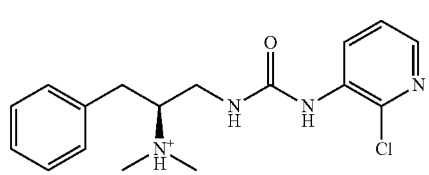 | 1140 | 0.30 | 2.5 |

$^a$The ECFP_4 Tanimoto similarity ($T_c$) to the most similar μOR ligand in ChEMBL16.

The new ligands are predicted to engage the μOR in new ways (FIGS. 2A-2H). Most opioid ligands use a cationic amine to ion pair with Asp147[3.32], a canonical interaction observed in structures of the μOR, δOR, KOR, and nociceptin receptor bound to ligands of different scaffolds. As anticipated, the docked ligands recapitulated this interaction. Much less precedence exists for the formation of an additional hydrogen bond with this anchor aspartate, often mediated in the docking poses by a urea amide. In embodiments, the new ligands with the urea carbonyl is modeled to hydrogen-bond with Tyr148[3.33], while the rest of the ligands often occupy sites unexplored by morphinans. To our knowledge, the double hydrogen bond coordination of Asp147[3.32] modeled in the docking poses has not been anticipated or observed for opioid ligands previously.

Despite the structural novelty of the initial docking hits, in embodiments their affinities were low. To enhance affinity and selectivity, we docked 500 analogs of compounds 4, 5 and 7 that retained the key recognition groups but added packing substituents or extended further toward the extracellular side of the receptor, where the opioid receptors are more variable. Of the 15 top-scoring analogs that were tested, seven had $K_i$ values between 87 nM and 4.7 μM (Table 2).

TABLE 2

Analogs tested at the μOR.

| Cmpd | Structure | Docking Score | $T_c^a$ | μOR $K_i$ (μM) | κOR $K_i$ (μM) | μOR $G_i$ EC50 (μM) |
|---|---|---|---|---|---|---|
| 8 | (structure) | −42.08 | 0.31 | 0.82 | 0.46 | 6.6 |
| 9 | (structure) | −48.30 | 0.31 | <50% | 1.36 | ND |
| 10 | (structure) | −51.73 | 0.31 | 4.75 | <50% | ND |
| 11 | (structure) | −46.79 | 0.35 | 1.86 | <50% | ND |
| 12 | (structure) | −51.88 | 0.35 | 0.042 | 0.46 | 0.18 |
| 13 | (structure) | −51.22 | 0.35 | 0.550 | 1.02 | 3.1 |

TABLE 2-continued

Analogs tested at the μOR.

| Cmpd | Structure | Docking Score | $T_c{}^a$ | μOR $K_i$ (μM) | κOR $K_i$ (μM) | μOR $G_i$ EC50 (μM) |
|---|---|---|---|---|---|---|
| 14 | 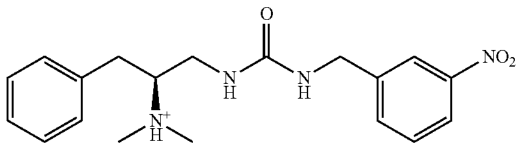 | −50.42 | 0.37 | 0.087 | 0.51 | 0.44 |
| 15 | 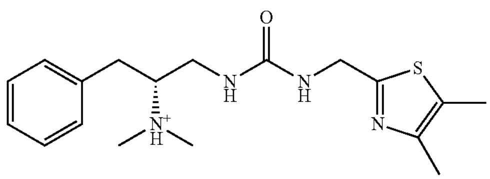 | −43.17 | 0.37 | 0.130 | <50% | ND |

$^a$The ECFP_4 Tanimoto similarity ($T_c$) to the most similar μOR ligand in ChEMBL16.
ND = not detectable under these experimental conditions.

Encouragingly, several were specific for the μOR over KOR (12-15, Table 2). We then investigated the more potent analogs for signaling potency and efficacy. Although the structure we docked against was the inactive state of the μOR, compounds 8 and 12-14 activated $G_{i/o}$(Table 2). Intriguingly, compound 12 (FIG. 3B) strongly activated $G_{i/o}$ with low levels of β-arrestin2 recruitment.

Figure 3A:
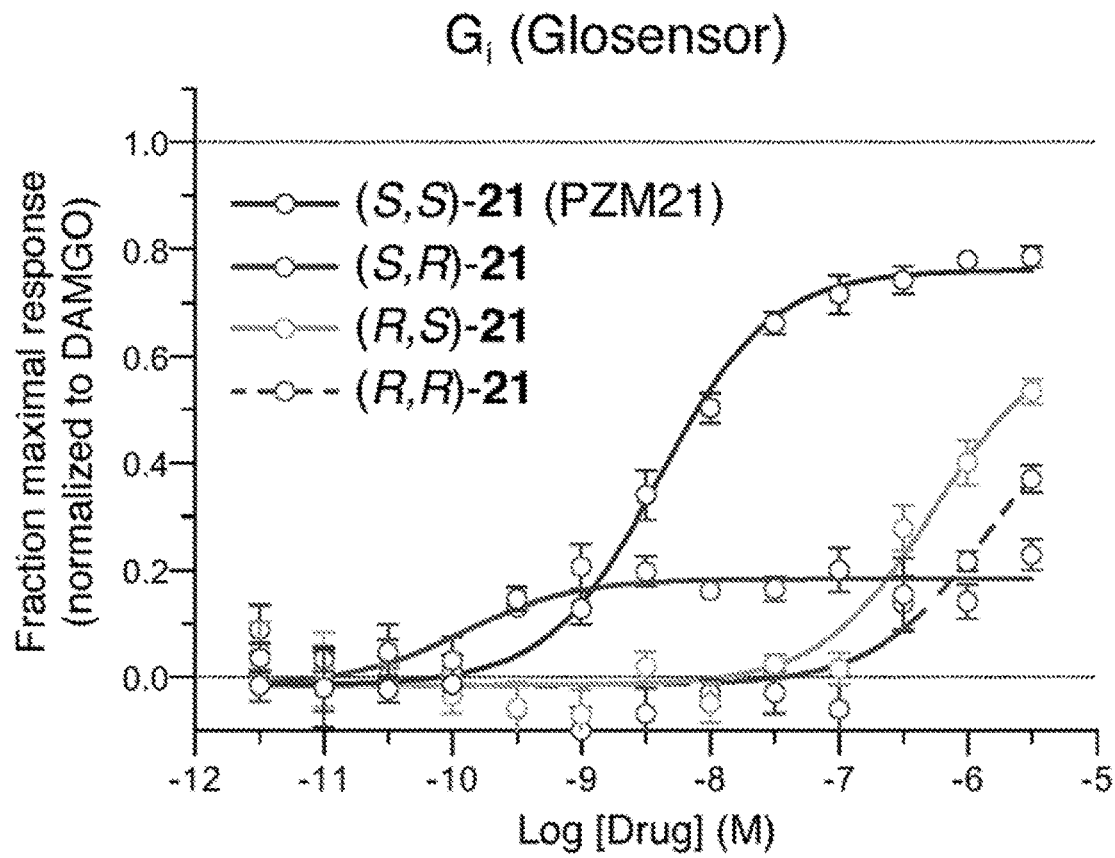
FIGS. 3A-3B. Variation of the chiral centers in compound PZM21 results in large changes in efficacy and potency. Notably, (S,R)-21 is a more potent partial agonist of the μOR as compared to (S,S)-21 (PZM21). Structure-activity relationship of compound 12 and 21 stereoisomers with affinities displayed as pKi values and agonist potency and efficacy in a $G_{i/o}$ Glosensor assay.
Figure 3B:
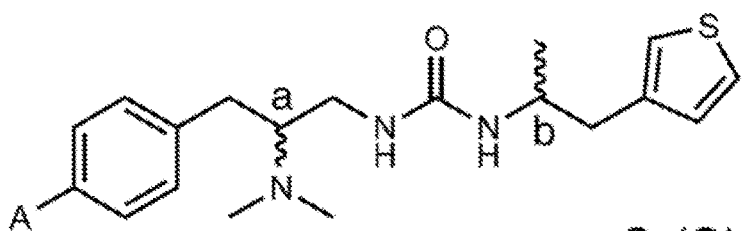

To optimize compound 12, we synthesized stereochemically pure isomers and introduced a phenolic hydroxyl (FIG. 3B). The synthesis of the (S,S) stereoisomer of 12 improved affinity ($K_i$) to 4.8 nM and had an signaling $EC_{50}$ of 65 nM; it was the most potent and efficacious $G_{i/o}$ signaling agonist among the four isomers. The phenolic hydroxyl, introduced to make compound (S,S)-21, was designed to exploit a water-mediated hydrogen bond with His297$^{6.52}$, an interaction observed in the structure of μOR in complex with β-FNA and in other structures of the δOR and KOR. This hydroxyl was readily accommodated in the docked μOR-12 complex, improving the predicted docking energy. Compound (S,S)-21 had an $EC_{50}$ of 4.6 nM in a $G_{i/o}$ activation assay, with 76% efficacy, and a $K_i$ of 1.1 nM in radioligand binding assays (Table 3), an improvement of 40-fold versus 12.

TABLE 3

Binding and signaling properties of compounds 12 and PZM21.

| | 12 | PZM21 |
|---|---|---|
| $K_i$ (nM) | | |
| μOR | 42 | 1.1 |
| δOR | N.A. | 506 |
| κOR | 464 | 18 |
| nociceptin | ND | ND |
| $G_{i/o}$ (Glosensor) $EC_{50}$ (nM) | $E_{max}$ (%) | | |
| μOR | 180 | 88 | 4.6 | 77 |
| δOR | ND | 1900 | 78 |

TABLE 3-continued

Binding and signaling properties of compounds 12 and PZM21.

| | 12 | PZM21 |
|---|---|---|
| κOR | ND | ND |
| nociceptin | 1400 | 43 | ND |
| Arrestin recruitment (PathHunter) $EC_{50}$ (nM) | $E_{max}$ (%) | | |
| μOR | 940 | 9.4 | ND |

ND = not detectable under these experimental conditions.

The other three stereoisomers of (S,S)-21 activity is observed in FIG. 3B suggesting a specific stereochemical requirement for both potency and efficacy in agreement with the docked poses of (S,S)-21 to the inactive and active structures of OR. We refer to (S,S)-21 as compound PZM21 henceforth.

Figure 4:
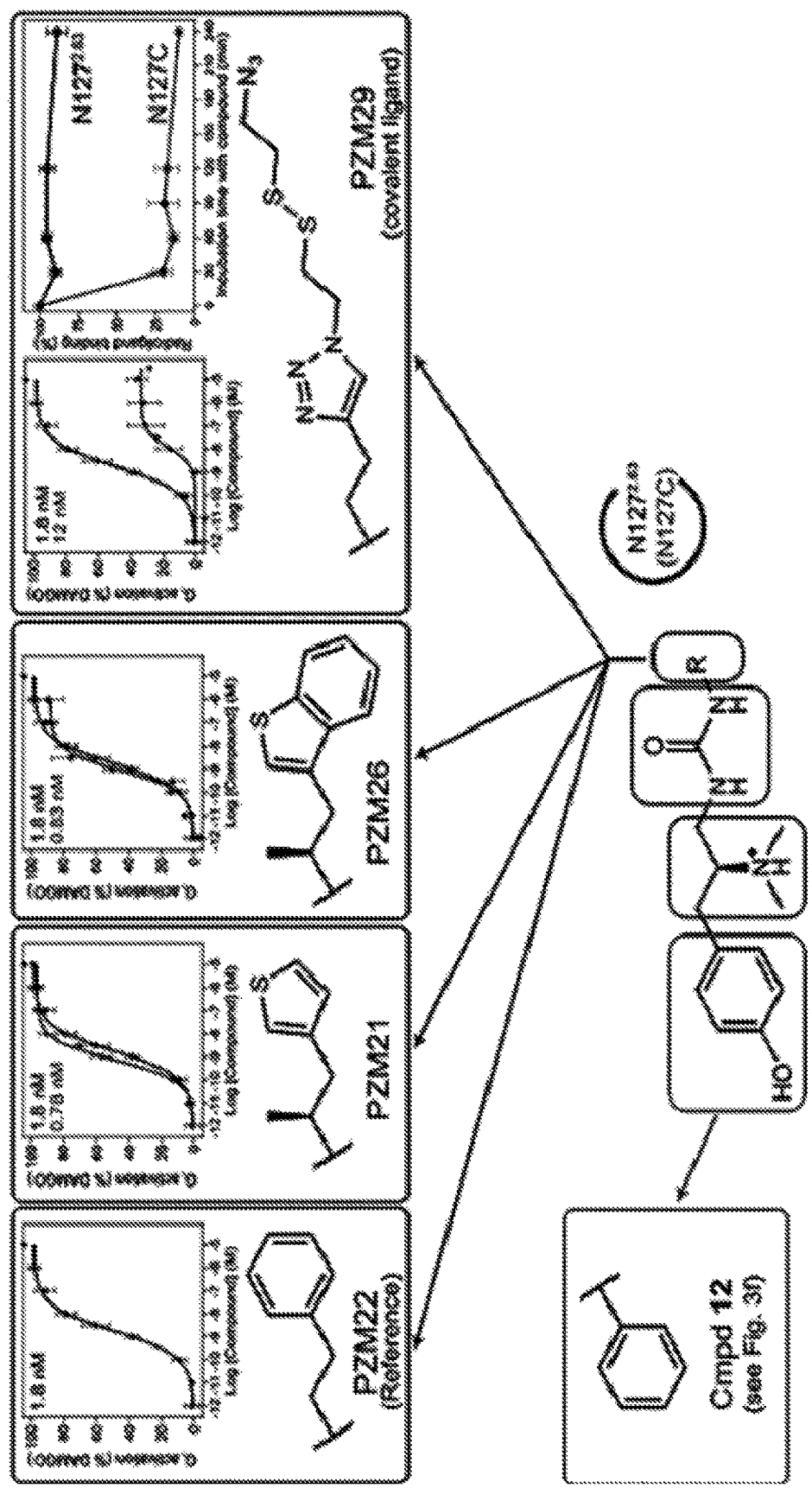
FIG. 4. Eight analogs were synthesized to probe the binding orientation of PZM21 and their efficacy as agonists were tested in a $G_{i/o}$ signaling assay. Analogs were compared to a parent reference compound (PZM22) with similar efficacy and potency to PZM21. The covalent compound PZM29 binds to the µOR:N127C variant irreversibly, as evidenced by wash-resistant inhibition of radioligand binding.

Because PZM21 was discovered against the inactive structure of μOR, its docked complex to active μOR retains ambiguities. To investigate this further, more detailed docking and molecular dynamics simulations were conducted. The resulting model was tested by synthesizing molecules that perturbed or exploited specific modeled interactions (FIG. 4). Neutralization of charge by amidation (compound PZM28) decreases potency by 1000-fold, supporting a key ionic interaction between the PZM21 tertiary amine and Asp147$^{3.32}$ (FIG. 4). Compound PZM27, which adds steric bulk to the tertiary amine, was synthesized to disrupt putative hydrophobic interactions between the N-methyl group and Met151$^{3.36}$ and Trp293$^{6.48}$ consistent with its 30-fold loss of potency and decreased efficacy (FIG. 4). Compounds PZM23, PZM24, and PZM25, which were synthesized to disrupt hydrogen bonding interactions in the model between the urea and Asp147$^{3.32}$, Tyr326$^{7.43}$ and Gln124$^{2.60}$, lose between 30 and 230-fold potency despite their decreased solvation penalties (FIG. 4). These key ionic and hydrogen-bonding interactions are maintained in 3 μs of molecular dynamics simulations of PZM21 in complex with active μOR, as are interactions between the phenolic hydroxyl and the bridging waters to His297$^{6.52}$, further supporting their relevance to the modeled pose (FIG. 4). The thiophene of PZM21, modeled to fit in the more open specificity region of the μOR, can be replaced with a larger benzothiophene without loss of potency (FIG. 4). Interactions of the thiophene with residues that differ among the opioid receptor sub-types may contribute to PZM21 specificity. More compellingly, the simulations and docking predict that the PZM21 thiophene comes within 6 Å of $Asn127^{2.63}$ in the active μOR. To probe this experimentally, we synthesized an irreversible version of PZM21 (compound PZM29) designed to form a covalent bond with μOR engineered with an Asn127Cys (N127C) mutation. Compound PZM29 binds irreversibly to this mutant but not the wild-type receptor and retains its efficacy as an agonist, supporting the overall orientation of PZM21 as modeled and simulated in the orthosteric μOR site.

Figure 5:
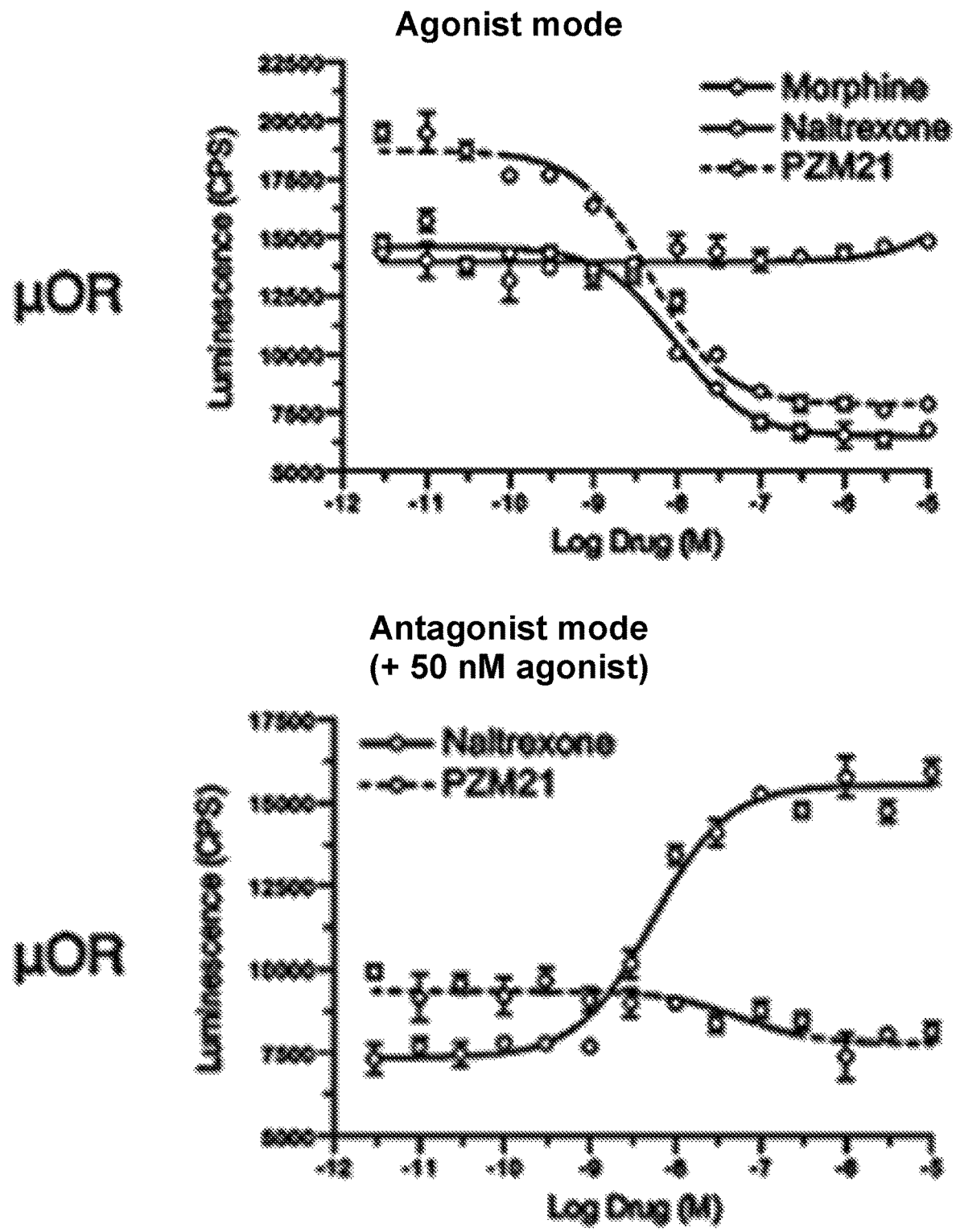
FIG. 5. Signaling properties of PZM21 at the opioid receptors. Displayed are raw luminescence data from a $G_{i/o}$ Glosensor assay. In agonist mode, agonists induce a decrease in luminescence signal while inverse agonists increase signal by decreasing basal signaling. For each opioid receptor, a prototypical well-characterized agonist and antagonist were used to validate the assay. In antagonist mode, a competition reaction is performed with 50 nM agonist and an escalating amount of tested drug. Here, true antagonists increase the observed signal, consistent with their ability to compete with the agonist but not induce $G_i$ signaling.

PZM21 had no detectable KOR or nociceptin receptor agonist activity, while it is a 500-fold weaker δOR agonist (FIG. 5 and Table 3), making it a selective μOR agonist. Indeed, PZM21 is an antagonist at KOR ($K_i$ of 18 nM) (FIG. 5 and Table 3). To investigate specificity more broadly, PZM21 was counter-screened for agonism against 316 other GPCRs. Activity at 10 μM was observed at several peptide and protein receptors; however, no potent activity was confirmed with a full dose-response experiment at these receptors. PZM21 therefore has high agonist specificity among GPCRs. PZM21 was also tested for inhibition of the hERG ion channel and the dopamine, norepinephrine, and serotonin neurotransmitter transporters. At hERG, PZM21 had an $IC_{50}$ between 2 to 4 μM, which is 500-1000-fold weaker than its potency as a μOR agonist. Its inhibition of the neurotransmitter transporters, which are also analgesia targets, was even weaker with $IC_{50}$ values ranging from 7.8 to 34 μM. Thus, PZM21 is a potent, selective, and efficacious opioid agonist.

Figure 6A:
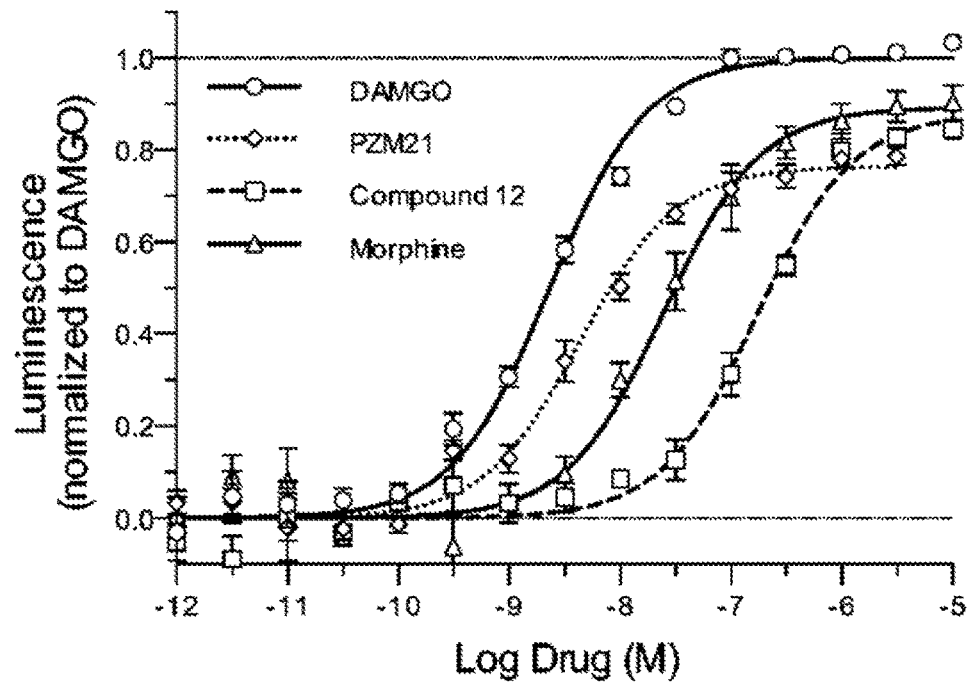
FIGS. 6A-6B. Biased signaling for PZM21 and compound 12. $G_{i/o}$ signaling assay shows robust µOR agonist activity for PZM21 and compound 12 with undetectable β-arrestin2 recruitment in the PathHunter assay.
Figure 6B:
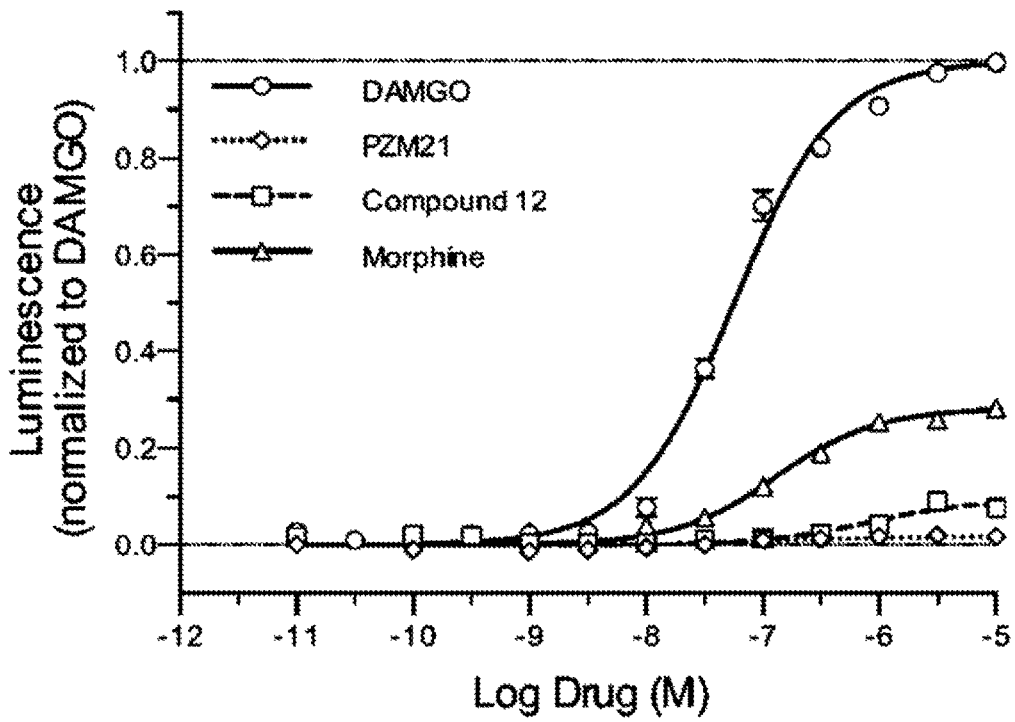

A major goal of this study was to find new chemotypes that might display biased signaling and perhaps, unlike canonical opioid drugs, have more favorable in vivo profiles. Signaling by PZM21 and other μOR agonists appears to be mediated primarily by the heterotrimeric G protein $G_{i/o}$, as its effect on cAMP levels were eliminated by pertussis toxin and no activity was observed in a calcium release assay (FIGS. 6A-6B). A maximal concentration of PZM21 led to no detectable β-arrestin2 recruitment in the PathHunter assay (DiscoverRx) and a minimal level of μOR internalization compared to DAMGO and morphine (FIGS. 6A-6B). β-arrestin2 recruitment was too low to even permit a formal calculation of bias. Since β-arrestin recruitment can depend on the expression level of G protein-coupled receptor kinase 2 (GRK2), we also investigated $G_{i/o}$ signaling and arrestin recruitment in cells co-transfected with this kinase. Even in the presence of over-expressed GRK2, PZM21 still has weak arrestin recruitment efficacy compared to DAMGO and even to morphine. In fact, the signaling bias of PZM21 was undistinguishable from TRV130, a $G_i$ biased opioid agonist now in Phase III clinical trials, whereas its G protein-bias substantially exceeded that of herkinorin, which has also been purported to be a $G_i$-biased agonist. An intriguing distinction in these signaling studies is the lack of agonist activity of PZM21 at KOR. While PZM21 is an 18 nM antagonist of this receptor, the other biased agonist, TRV130, activates KOR with similar potency to morphine. Additionally, despite having similar levels of signaling bias, in modeling studies TRV130 and PZM21 appear to engage the μOR in distinct ways.

Figure 7:
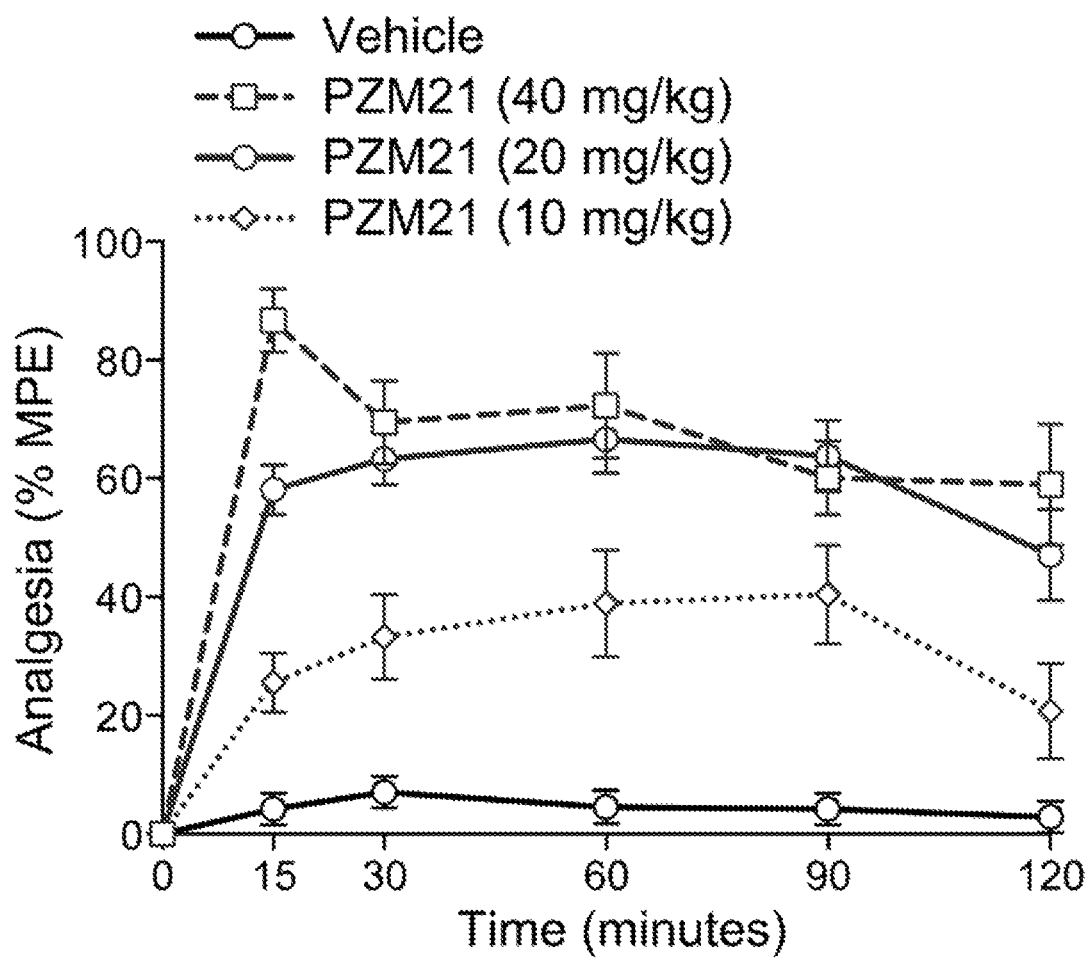
FIG. 7. Dose-dependent analgesia conferred by PZM21 in a hot-plate assay. Latency of withdrawal to noxious stimuli is shown as percentage of the maximal possible effect (% MPE).
Figure 8:
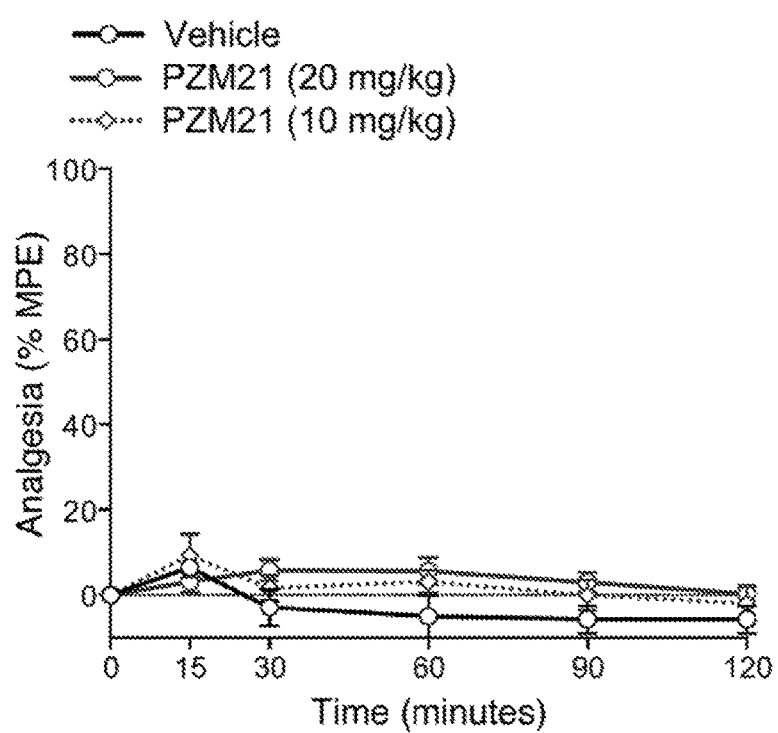
FIG. 8. PZM21 shows no activity in a tail flick assay, unlike previously characterized effects seen with classical opioids.
Figure 9A:
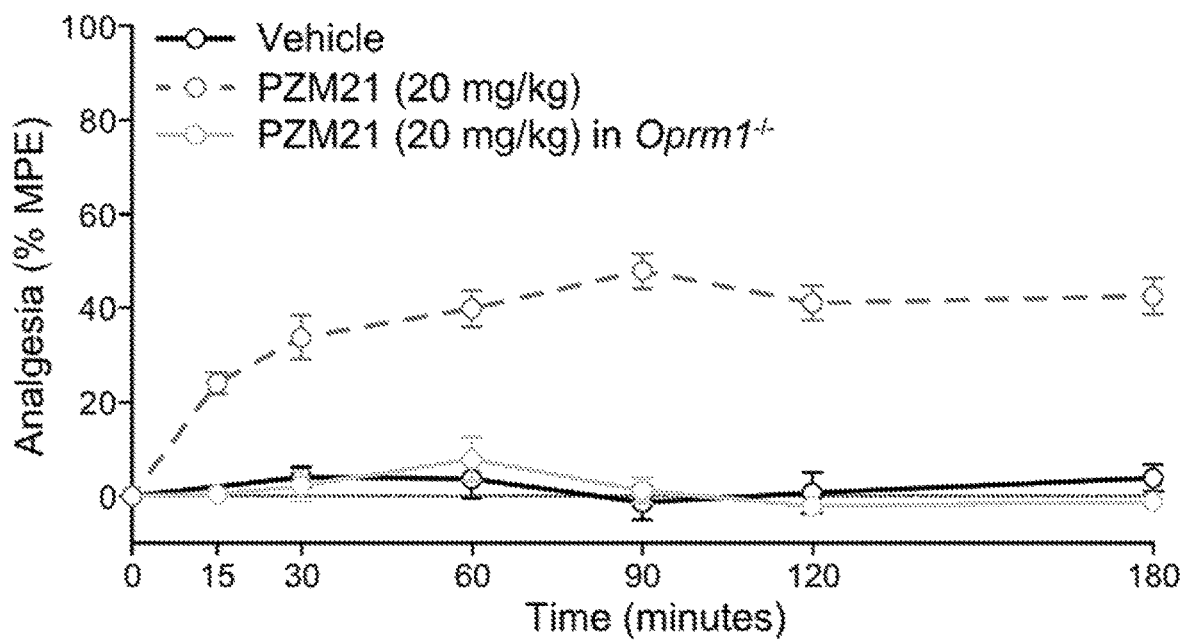
FIGS. 9A-9B. Analgesic responses measured in the hot-plate assay were subcategorized into either affective or reflexive behaviors and scored separately. Unlike classical opioids like morphine, PZM21 only modulates the affective component of pain.
Figure 9B:
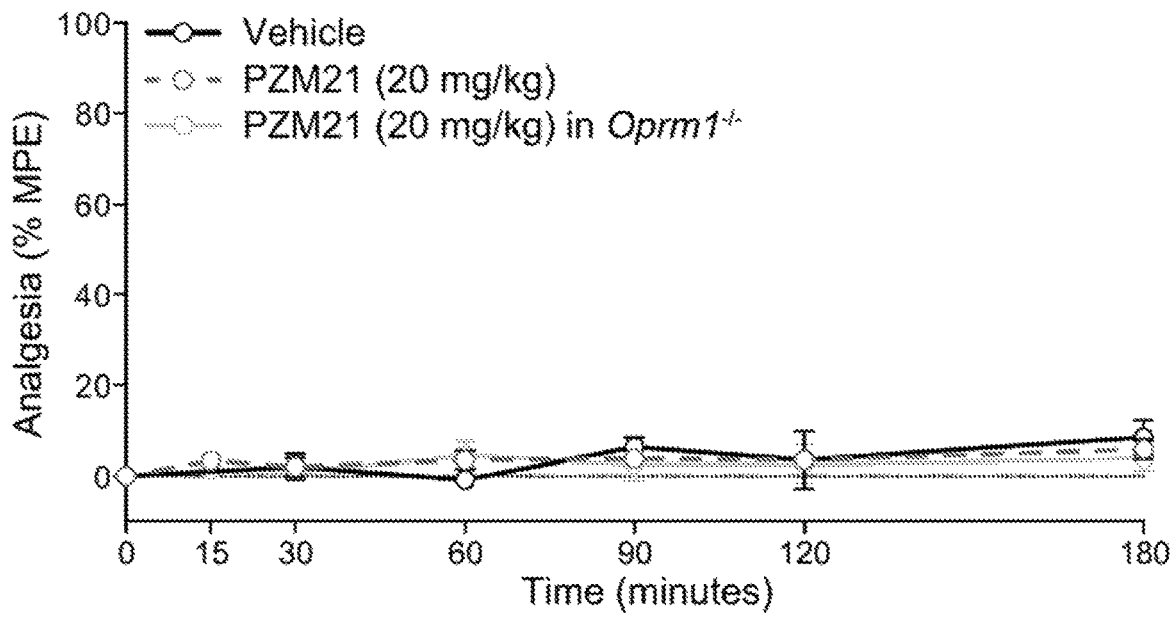

Consistent with its μOR agonist activity, PZM21 displayed dose-dependent analgesia in a mouse hot-plate assay, with a percent maximal possible effect (% MPE) of 87% reached 15 minutes after administration of the highest dose of drug tested (FIG. 7). The highest dose of morphine tested plateaued at 92% after 30 minutes. Intriguingly, we observed no analgesic effect for PZM21 in the tail-flick assay (FIG. 8). Such a distinction is unprecedented among opioid analgesics. The hot-plate experiment assesses analgesia at both higher-level central nervous system (CNS) brain and spinal nociceptive circuits, while the tail flick experiment is more specific for spinal reflexive responses. Subcategorizing the behavioral responses in the hot-plate experiment as either affective (CNS mediated) or reflexive (spinally mediated) showed that, unlike morphine, PZM21 solely confers analgesia to the affective component of pain. Though separation of these two analgesic pathways is unique to PZM21 among known opioid analgesics, it has been observed by selective chemogenetic activation or toxin-induced inactivation of CNS neurons in rodents. Indeed, PZM21 is also active in a formalin injection nociception assay, likely from supraspinal activation of descending inhibitory circuits. PZM21 analgesia results from μOR activation in vivo as genetic knockout of the μOR completely ablates the observed analgesic response in the hot-plate assay (FIG. 9A). Meanwhile, PZM21 is relatively stable to metabolism by mouse liver microsomes, with only 8% metabolism over one hour. Signaling experiments with the resulting metabolite pool show no evidence of a metabolite with more potent activation of the OR, confirming that the observed analgesic activity results primarily from the originally administered dose of PZM21.

Figure 10:
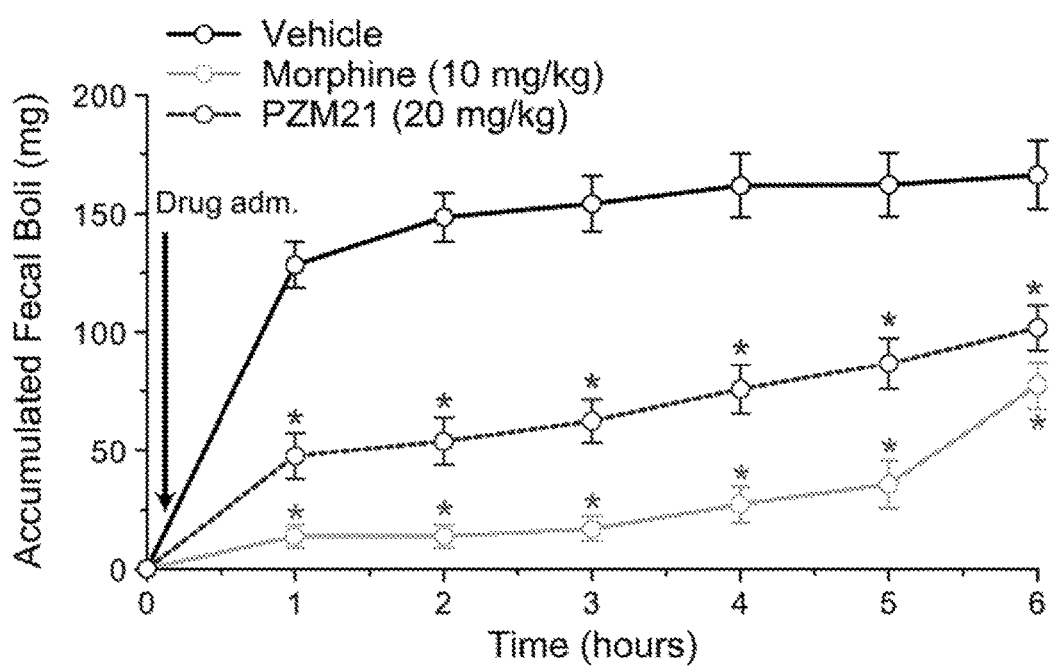
FIG. 10. PZM21 shows reduced constipatory effects as compared to morphine.
Figure 11:
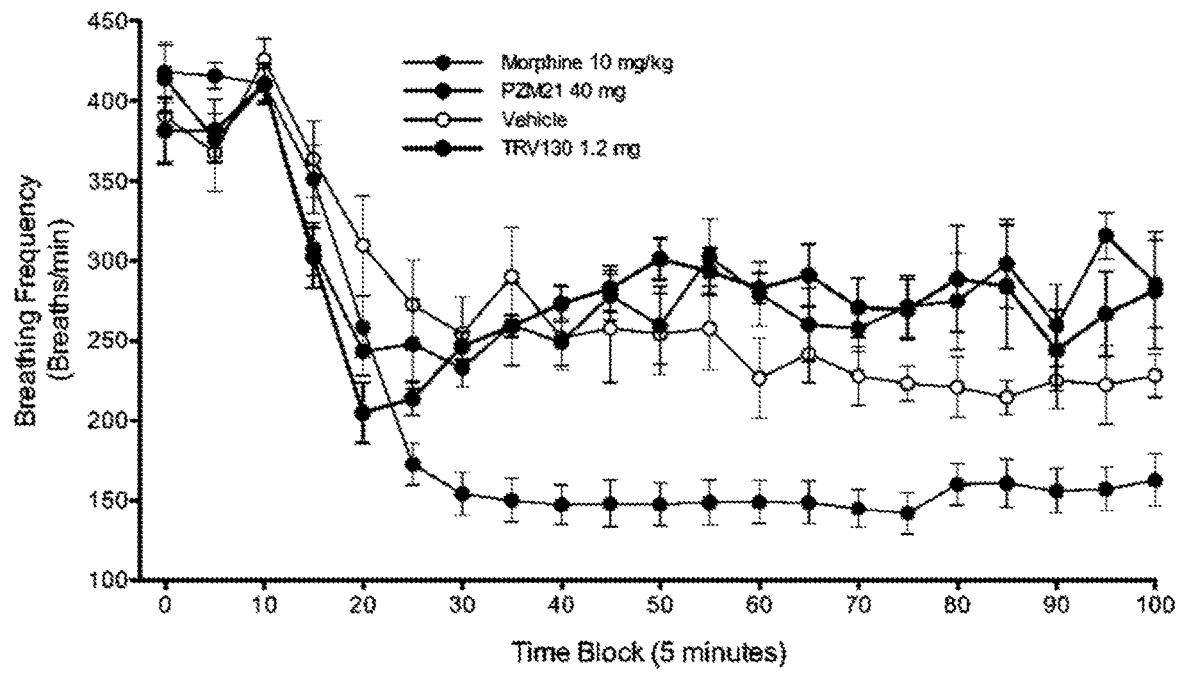
FIG. 11. Unlike morphine and TRV130, PZM21 has no effect on respiratory frequency and is statistically similar to vehicle for all times tested after administration of drug.

Based on previous genetic studies with arrestin knockout mice and pharmacological studies with biased compounds, we anticipated that PZM21 would confer longer-lasting analgesia with decreased respiratory depression and constipation—both key dose limiting side effects of classic opioid agonists. Analgesia induced by PZM21 lasts up to 180 minutes, substantially longer than that induced by a maximal dose of morphine and the biased agonist TRV130 (FIG. 7). Whereas PZM21 does reduce defecation, its constipation effect is substantially less than morphine (FIG. 10). Respiratory depression was investigated by dosing unrestrained mice with equianalgesic doses of PZM21, TRV130 and morphine (40 mg/kg, 1.2 mg/kg, and 10 mg/kg, respectively), and measuring respiration by whole body plethysmography. While morphine profoundly depressed respiration frequency, PZM21 was undistinguishable from vehicle (FIG. 11). By comparison, TRV130 significantly depresses respiration at 15 minutes, correlating with its peak analgesic response. Although respiratory depression by OR may be partially mediated by activation of G-protein coupled inwardly-rectifying potassium channels (GIRKs), systemically infused opioids can decrease respiratory frequency even in GIRK-/- mice[38], consistent with the G protein independent signaling mechanisms first suggested by the arrestin knockout studies. The rapid respiratory depression observed for morphine and TRV130 may reflect GIRK activation. At later time points, however, PZM21 induces minimal respiratory depression despite providing robust analgesia. Conversely, morphine induces a prolonged course of respiratory depression that does not subside with resolution of the analgesic response at 90 minutes. This dissociation in analgesia and respiratory depression at later time points may reflect differential recruitment of β-arrestin2. Taken together, these studies support minimal β-arrestin2 signaling in vivo by PZM21.

Figure 12A:
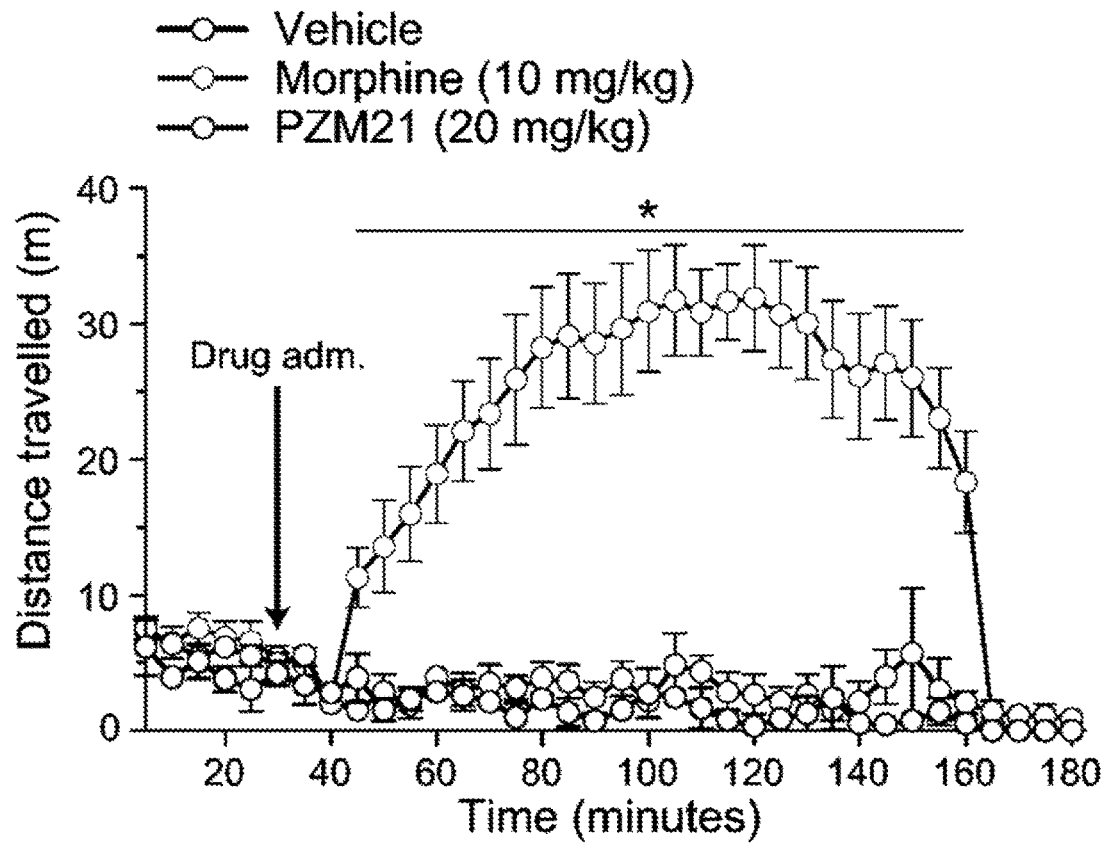
FIGS. 12A-12B. Unlike morphine PZM21 does not induce open field locomotion, suggesting decreased activation of dopaminergic reward circuits.
Figure 12B:
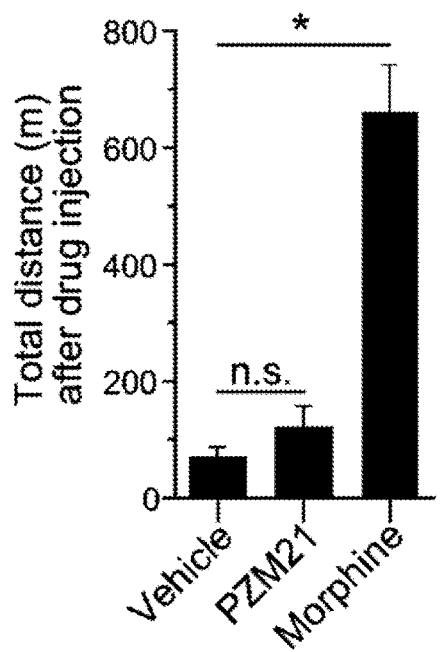
Figure 13:
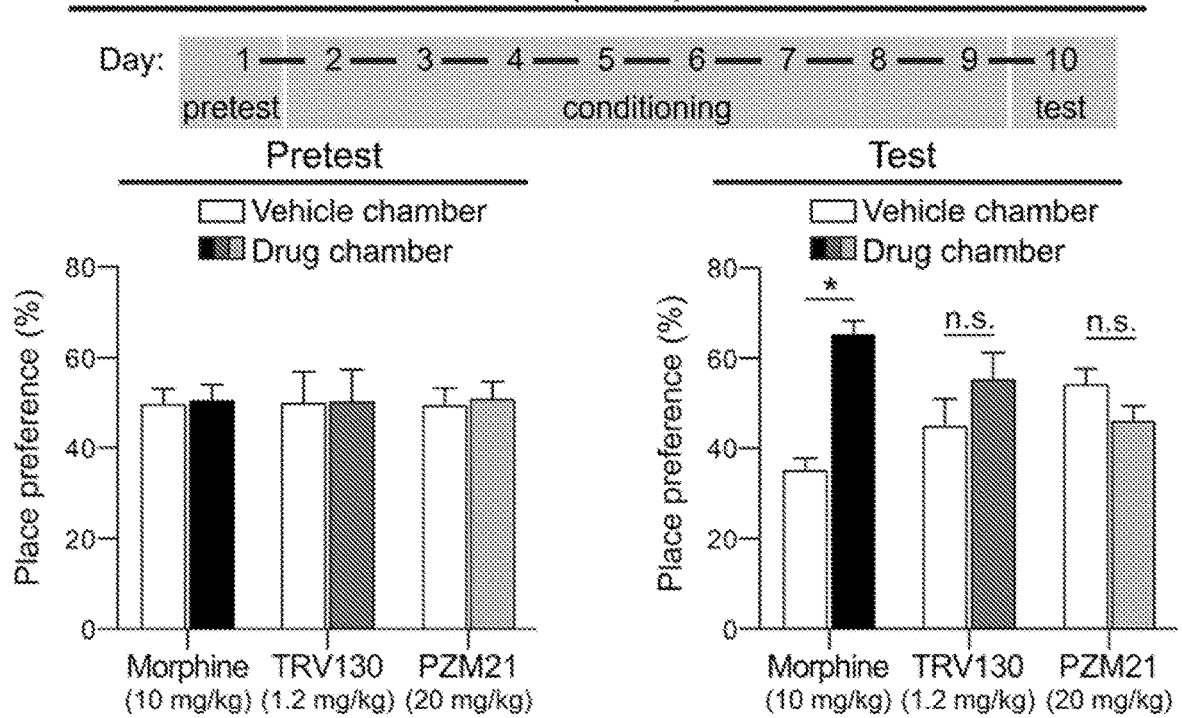
FIG. 13. PZM21 does not induce conditioned place preference and therefore has lower reinforcing activity as compared to morphine. This may suggest that PZM21 and analogous molecules have decreased liability for addiction.
Figure 14:
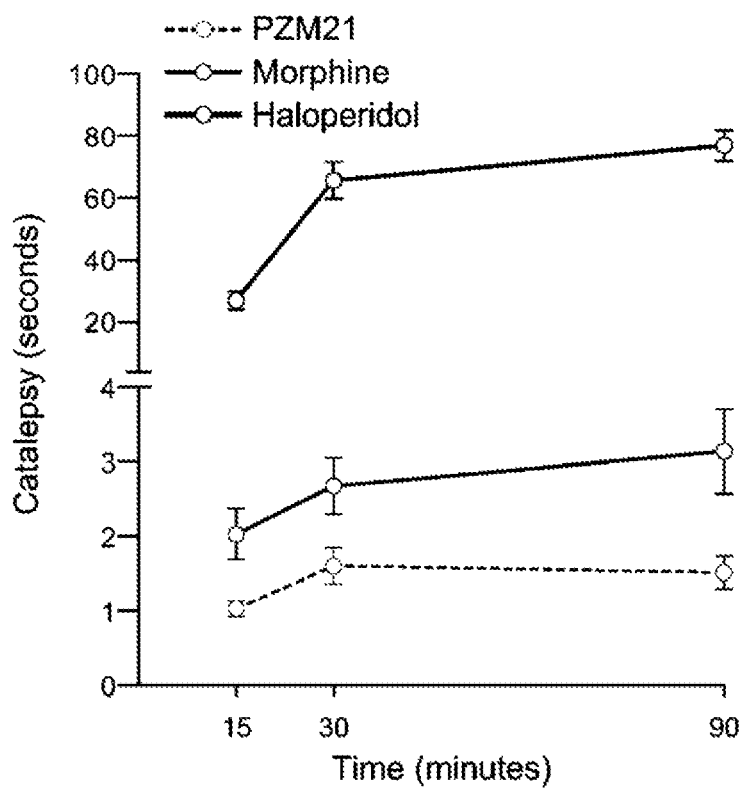
FIG. 14. PZM21 does not induce cataleptic behavior.

A major liability of current opioid analgesics is reinforcement and addiction, which are both postulated to be mediated—at least in part—by activation of the dopaminergic reward circuits. A biomarker for such activation in mice is an acute hyperlocomotive response, reflecting mesolimbic dopaminergic activation. Whereas morphine induced mouse hyperlocomotion in an open field assay (FIGS. 12A-12B), a close-to equianalgesic dose of PZM21 had no apparent effect on locomotion versus vehicle. The decreased distance traveled does not reflect a cataleptic effect of the molecule. Consistent with decreased activation of reward circuits, administration of PZM21 also does not induce a conditioned place preference response (FIG. 13), unlike morphine and other opioids. Though TRV130 does trend more toward inducing place preference, its activity is also not significant relative to vehicle; this lack of conditioned place preference for both biased agonists may support a role for G protein bias in the lack of opioid-induced reinforcing behavior. The differences between morphine and PZM21 in conditioned place preference do not simply reflect dissimilarities in CNS penetration between the two drugs, as a substantial fraction of PZM21 crosses the blood brain barrier.

Biased signaling through G protein and arrestin pathways reflects the stabilization of conformations over 30 Å from the orthosteric site where PZM21 binds.

This study supports a structure-based approach for GPCR ligand discovery. This method can reliably identify entirely new scaffolds and chemotypes. These new chemotypes may stabilize receptor conformations not explored previously and thereby generate novel biological effects. With a novel chemotype in hand, the docked structure provides a straight-forward strategy for optimization. Here, we were able to optimize an initial docking hit, compound 7, 1000-fold to the final lead molecule, PZM21, by evaluating approximately 50 molecules. Though this campaign was inspired by existing μOR biased agonists like TRV130, the structure-based approach led to a compound with novel properties which are structurally distinct compared to previously explored opioid ligands, with not only substantial signaling bias but also unexpected opioid receptor selectivity. These features have contributed to favorable biological effects, with long lasting analgesia coupled to apparent elimination of respiratory depression, specificity for central over reflex analgesia, lack of locomotor potentiation and conditioned place preference, and hence a reduced potential for opioid-induced reinforcement for PZM21 and molecules like it. The selectivity, potency, and biased signaling of PZM21 make it a tool molecule of a sort previously unavailable to interrogate μOR signaling.

Example 2. Syntheses Conditions

Synthesis of enantiopure 12 and PZM21: The stereochemically pure isomers of 12 and PZM21 were synthesized from corresponding (R)- and (S)-amino acid amides, which were either commercially available or readily prepared from the corresponding acid or ester. The primary amino group was dimethylated using an excess of aqueous formaldehyde and sodium triacetoxyborohydride in aqueous acetonitrile. The carboxamides 16a,b were converted to primary amines by treatment with borane-tetrahydrofurane complex under reflux yielding the diamines 17a,b. Henry reaction of thiophene-3-carbaldehyde with nitroethane afforded the nitropropene derivative 18, which was converted into the racemic alkylamine 19. Activation with 4-nitrophenyl chloroformate yielded the carbamates 20, which were coupled with the enantiopure primary amines 17a,b to achieve diastereomeric mixtures of the corresponding ureas 12 and 21. HPLC separation using a semi-preparative Chiralpak AS-H column gave the overall eight pure stereoisomers of 12 and 21 including PZM21.

To determine the absolute configuration of the final products and efficiently prepare PZM21, we synthesized enantiomerically enriched carbamate 20, coupled it with the corresponding primary amines. For enantiomeric enrichment, we performed chiral resolution of the racemic primary amine 19 via repetitive crystallization with di-p-anisoyl-(S)-tartaric acid. After triple crystallization, we obtained 19 enriched in dextrorotatory enantiomer ($[\alpha]_D^{25}=+20.5$ 0). The corresponding (R)-acetamide has been previously characterized as dextrorotatory ($[\alpha]_D 20=+49.8°$), so enantiomerically enriched 19 was treated with acetic anhydride and triethylamine, and the specific rotation of the product was measured. Based on the value of specific rotation of the resulting acetamide ($[\alpha]_D 21=-46.6°$), we assigned the absolute configuration of the major isomer to be (S). (S)-enriched 20 was used for synthesis of the final urea derivatives and absolute configuration of diastereomers in pairs was assigned based on the equality of retention time in chiral HPLC.

Synthesis of structural analogs PZM22-29: Structural analogs of PZM21 were synthesized starting from stereochemically pure L-tyrosine amide (30) or L-tyrosine methylamide (31) (see scheme 2). N-methylation or N-benzylation and subsequent N-methylation followed by amide reduction led to the respective diamines 35-37. Coupling with the nitrophenyl carbamates 42-44 resulted in the phenethyl ureas PZM22-25 and compound 38, and the benzothiophene analog PZM26. The N-benzyl protected derivative 38 was converted into the respective secondary amine 39 by catalytic hydrogenation. This intermediate was used to introduce additional substituents leading to the N-cyclopropylmethyl derivative PZM27 and the N-formyl derivative PZM28.

The disulfide functionalized PZM21 analog PZM29 could be prepared starting from the dimethylamine 35. Coupling with the N-butynylimidazole-1-carboxamide 45 led to the alkynyl functionalized urea 46. Copper catalyzed cycloaddition with bis(2-azidoethyl) disulfide resulted in the desired triazole derivative PZM29.

Scheme 1 (below). Syntheses of stereochemically pure 12 and 21. Reactants and conditions: i) $CH_2O$, $NaBH(OAc)_3$, acetonitrile/water, rt, 15-30 min, 77-98%; ii) 1M $BH_3$.THF, reflux, 20 h, 48-95%; iii) nitroethane, HCOOH/ethanolamine, 90° C., 7 h, 82%; iv) 1M $LiAlH_4$, reflux, 30 min, 56%; v) 4-nitrophenyl chloroformate, triethylamine, THF, 0° C. to rt, 6 h, 75%; vi) corresponding primary amine, DMF, rt, 20 h, 70-98%.

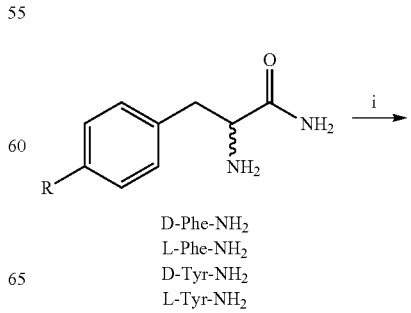

D-Phe-NH$_2$
L-Phe-NH$_2$
D-Tyr-NH$_2$
L-Tyr-NH$_2$

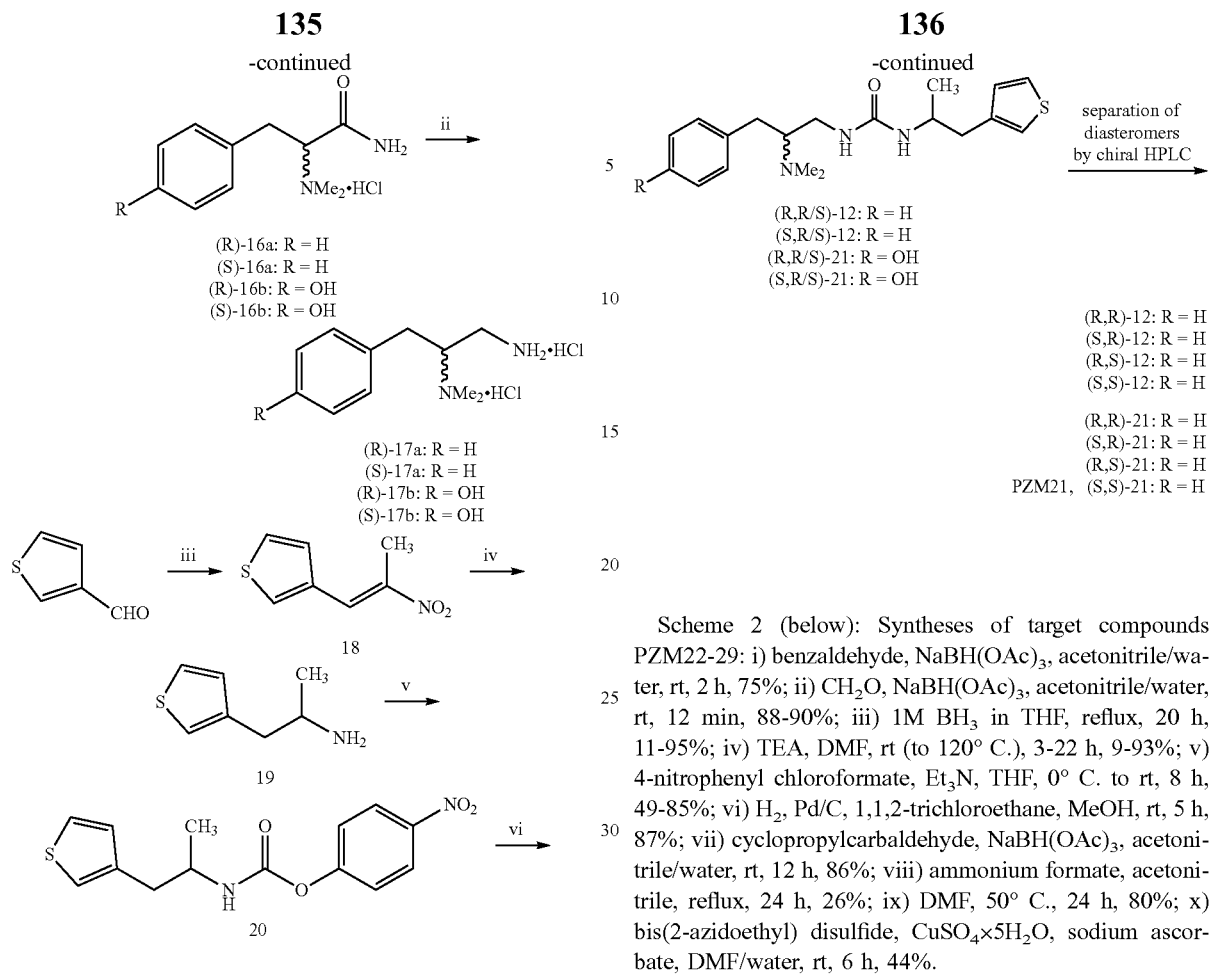

Scheme 2 (below): Syntheses of target compounds PZM22-29: i) benzaldehyde, NaBH(OAc)₃, acetonitrile/water, rt, 2 h, 75%; ii) CH₂O, NaBH(OAc)₃, acetonitrile/water, rt, 12 min, 88-90%; iii) 1M BH₃ in THF, reflux, 20 h, 11-95%; iv) TEA, DMF, rt (to 120° C.), 3-22 h, 9-93%; v) 4-nitrophenyl chloroformate, Et₃N, THF, 0° C. to rt, 8 h, 49-85%; vi) H₂, Pd/C, 1,1,2-trichloroethane, MeOH, rt, 5 h, 87%; vii) cyclopropylcarbaldehyde, NaBH(OAc)₃, acetonitrile/water, rt, 12 h, 86%; viii) ammonium formate, acetonitrile, reflux, 24 h, 26%; ix) DMF, 50° C., 24 h, 80%; x) bis(2-azidoethyl) disulfide, CuSO₄×5H₂O, sodium ascorbate, DMF/water, rt, 6 h, 44%.

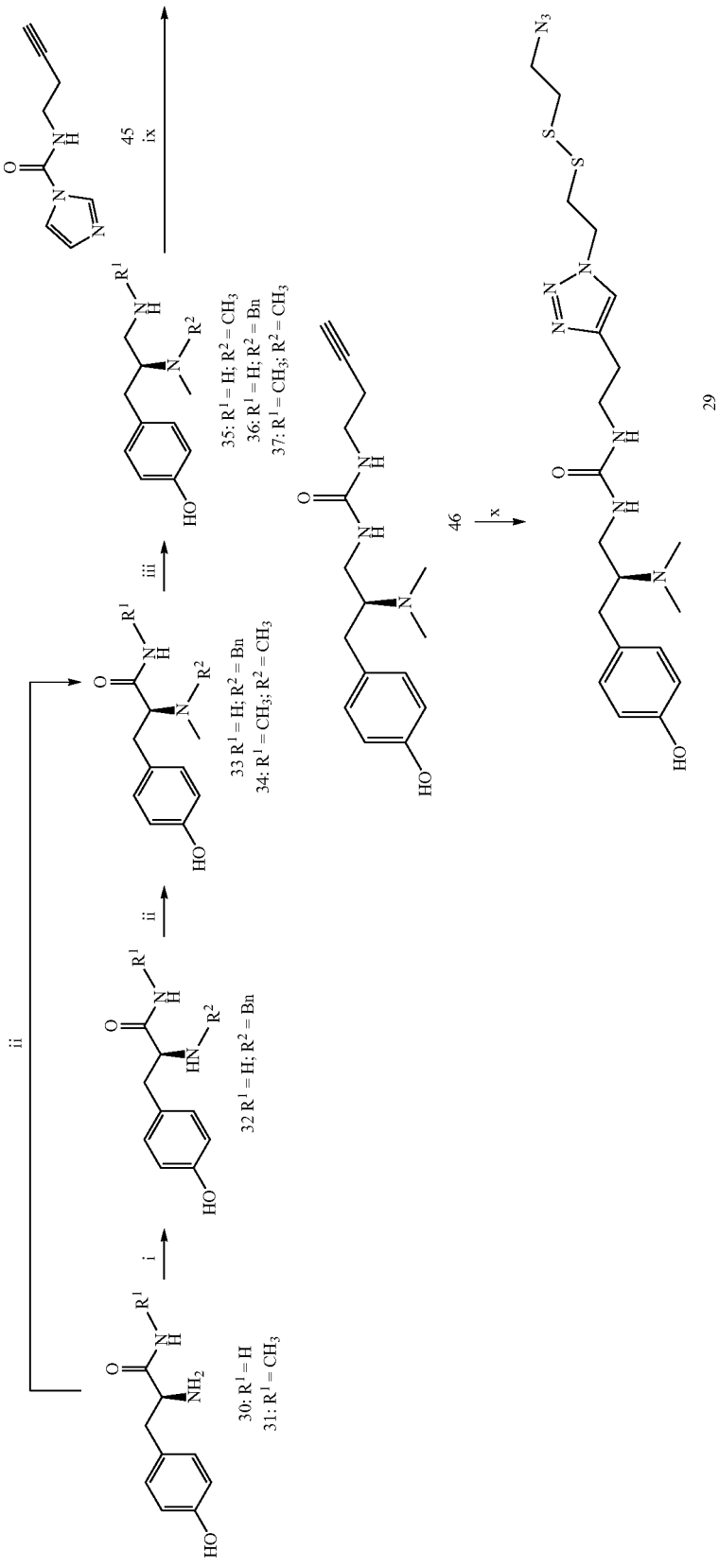

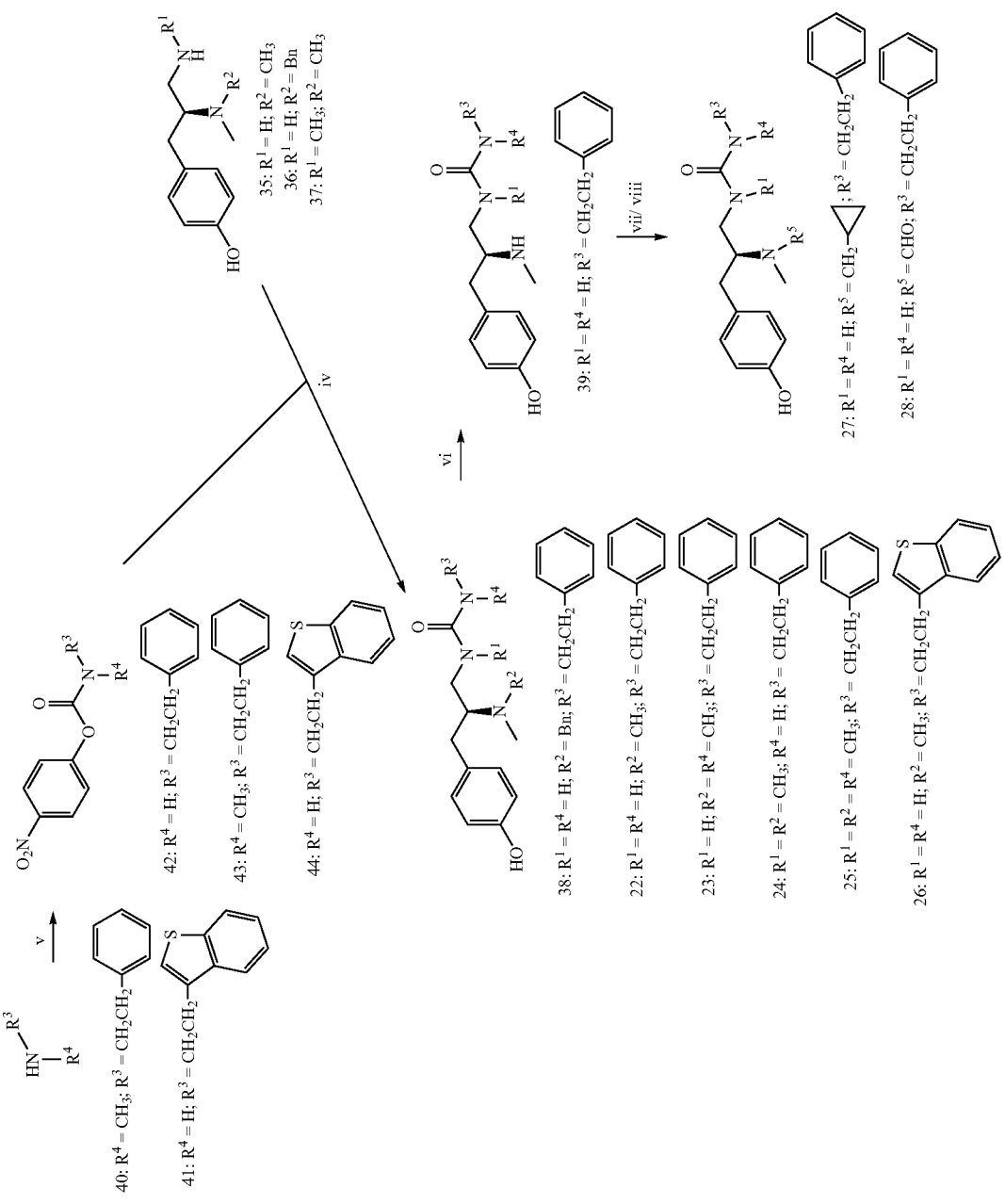

All chemicals and solvents were purchased from Sigma Aldrich, Acros, or Alfa Aesar and were used without additional purification. Anhydrous solvents were of the highest commercially available grade and were stored over molecular sieves under a nitrogen atmosphere.

Flash chromatography was performed on Merck silica gel 60 (40-63 μm) as stationary phase under positive pressure of dry nitrogen gas. Dry column vacuum chromatography was performed on Alfa Aesar TLC high purity grade silica gel without binder (12 μm) as a stationary phase and Florisil® (100-200 mesh) or celite for sample preparation. Elution was performed under negative pressure from water aspirator. Preparative chiral HPLC was performed on Agilent 1100 HPLC system with UV detection (λ=254 nm and λ=210 nm) using Chiralpak® AS-H semi-preparative column (250×10 mm, 5 μm) with eluent specified for each particular compound. Purification by preparative RP-HPLC was performed on Agilent 1100 preparative series, column: Zorbax Eclipse XDB-C8 PrepHT (21.2×150 mm, 5 μm [C8]), flow rate: 10 mL/min, employing solvent system as specified below.

HR-ESIMS analyses were conducted on a Bruker Daltonik microTOF II or a Bruker maXis MS in the laboratory of the Chair of Bioinorganic Chemistry, Friedrich Alexander Universität. HPLC-MS and HPLC purity analyses were performed with an Agilent binary gradient system using UV detection (λ=254 nm) in combination with ChemStation software. The Zorbax Eclipse XDB-C8 (4.6 mm×150 mm, 5 μm) column was used with a flow rate of 0.5 mL/min in reversed phase mode (eluent: MeOH/H$_2$O+0.1% HCOOH, 10% to 100% in 21 min, 100% 3 min). Mass detection was conducted with a Bruker Esquire 2000 ion-trap mass spectrometer using APCI or ESI ionization source or with Bruker amaZon SL mass spectrometer in combination with a Agilent 1100 or Dionex Ultimate 3000 UHPLC system; respectively. $^1$H, and 13C spectra were recorded on a Brucker Avance 360 or a Brucker Avance 600 FT-NMR-Spectrometer. Chemical shifts were calculated as ppm relative to TMS ($^1$H) or solvent signal ($^{13}$C) as internal standards.

(R)-2-Amino-3-phenylpropanamide hydrochloride D-Phe-NH$_2$

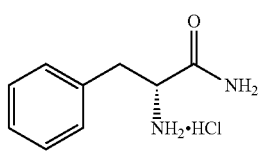

Dry ammonia gas was bubbled through the ice-cold solution of D-phenylalanine methyl ester hydrochloride (1.01 g, 4.7 mmol) in anhydrous methanol (12 mL) for 25 min. Then the flask was sealed and the mixture was allowed to warm up to the ambient temperature and stirred for 20 h (progress of the conversion was monitored by TLC). After the consumption of the starting material, the reaction mixture was purged with dry nitrogen gas (10 min) and the solvent was removed under reduced pressure. The white solid residue was suspended in boiling ethanol (30 mL), filtered and the precipitate was washed with ethanol (5 mL). Combined filtrate and washing were concentrated under reduced pressure. The white solid residue was dried under high vacuum. Yield: 0.89 g (95%). LCMS(ESI+): t$_R$=9.0 min, purity: 99%; m/z: no molecular ion. $^1$H NMR (360 MHz, DMSO-d$_6$) δ 8.27 (br. s., 3H), 7.99 (s, 1H), 7.49 (s, 1H), 7.18-7.41 (m, 5H), 3.97 (t, J=6.8 Hz, 1H), 3.12 (dd, J=14.0, 6.5 Hz, 1H), 3.05 (dd, J=14.0, 7.0 Hz, 1H).1H NMR (360 MHz, DMSO-d$_6$, exchange with D$_2$O) δ 7.21-7.40 (m, 5H), 3.97 (t, J=6.8 Hz, 1H), 3.11 (dd, J=14.1, 6.3 Hz, 1H), 3.03 (dd, J=14.1, 7.2 Hz, 1H).13C NMR (91 MHz, DMSO-d$_6$) δ 169.6, 135.2, 129.5 (2C), 128.4 (2C), 127.0, 53.4, 36.6. HR-EIMS: found 164.0950; calcd. 164.0950 for C$_9$H$_{12}$N$_2$O ([M−HCl]$^+$). [α]$_D^{24}$=−17.4° (c 5, H$_2$O).

(S)-2-Amino-3-phenylpropanamide hydrochloride D-Phe-NH$_2$

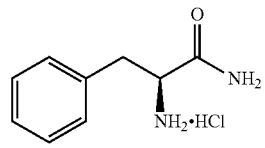

(S)-2-Amino-3-phenylpropanamide hydrochloride was synthesized following the synthetic protocol for (R)-2-amino-3-phenylpropanamide hydrochloride. From L-phenylalanine methyl ester hydrochloride (1.02 g, 4.7 mmol) the desired product was obtained as a white solid (0.89 g, 94%). LCMS(ESI+): t$_R$=9.0 min, purity: 99%; m/z: no molecular ion. $^1$H NMR (360 MHz, DMSO-d$_6$) δ 8.24 (br. s., 3H), 8.00 (br. s., 1H), 7.48 (br. s., 1H), 7.18-7.37 (m, 5H), 3.97 (t, J=6.7 Hz, 1H), 3.11 (dd, J=14.0, 6.5 Hz, 1H), 3.05 (dd, J=13.9, 7.1 Hz, 1H). $^1$H NMR (360 MHz, DMSO-d$_6$, exchange with D$_2$O) δ 7.21-7.40 (m, 5H), 3.96 (dd, J=7.3, 6.4 Hz, 1H), 3.10 (dd, J=14.0, 6.4 Hz, 1H), 3.01 (dd, J=14.0, 7.3 Hz, 1H). 13C NMR (91 MHz, DMSO-d$_6$) δ 169.7, 135.2, 129.5 (2C), 128.4 (2C), 127.0, 53.4, 36.7. [α]$_D^{22}$=+17.5° (c 0.9, H$_2$O).

(R)-2-(Dimethylamino)-3-phenylpropanamide (R)-16a

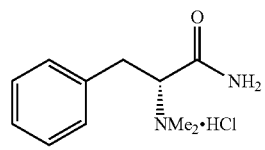

37% Aqueous formaldehyde (2 mL, 27 mmol) was added to a suspension of (R)-2-amino-3-phenylpropanamide hydrochloride (0.39 g, 1.94 mmol) in acetonitrile (10 mL), followed by addition of sodium triacetoxyborohydride (1.65 g, 7.8 mmol). After 30 min of vigorous stirring the reaction was quenched with 1N NaOH, basified to pH>10, and extracted with ethyl acetate (3×20 mL). Combined organic layers were dried over anhydrous Na$_2$SO$_4$, filtered and concentrated under reduced pressure. The crude free base was dissolved in isopropanol (1.5 mL) and hydrochloride salt was precipitated via addition of 2N HCl in diethyl ether (1.5 mL, 3 mmol) and dilution with diethyl ether (10 mL). The slurry was filtered and the white solid was washed with diethyl ether (2×5 mL). The product was obtained as a white solid (0.34 g, 77%) after drying under high vacuum. LCMS (ESI+): t$_R$=10.7 min, purity: n/a (220 nm); m/z found: 193.4; calcd. 193.2 ([M-Cl]$^+$). 1H NMR (360 MHz, DMSO-d$_6$) δ 11.13 (br. s., 1H), 7.92 (s, 1H), 7.61 (s, 1H), 7.19-7.38 (m, 5H), 4.05 (dd, J=10.9, 4.0 Hz, 1H), 3.31 (dd, J=12.9, 3.9 Hz, 1H), 3.07 (dd, J=12.9, 11.0 Hz, 1H), 2.82 (s, 6H). 13C NMR (91 MHz, DMSO-d$_6$) δ 167.0, 135.1, 129.2 (2C), 128.4 (2C), 127.0, 66.9, 33.5. (NHMe$_2$ signals are overlapping with DMSO signal). [α]$_D^{23}$=−71.0° (c 0.7, H$_2$O). HR-EIMS: found 192.1261; calcd. 192.1263 for C$_{11}$H$_{16}$N$_2$O (M$^+$).

(S)-2-(Dimethylamino)-3-phenylpropanamide (S)-16a

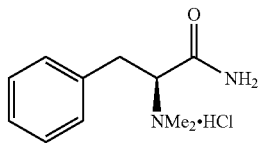

(S)-16a was synthesized following the protocol described for (R)-16a. From (S)-2-amino-3-phenylpropanamide hydrochloride (0.39 g, 1.94 mmol), 37% formaldehyde (1.44 mL, 19.4 mmol), and sodium triacetoxyborohydride (1.64 g, 7.8 mmol) the desired product was obtained as a white solid (0.36 g, 80%). LCMS(ESI+): t$_R$=10.7 min, purity: n/a (220 nm); m/z found: 193.4; calcd. 193.2 ([M-Cl]$^+$). $^1$H NMR (360 MHz, DMSO-d$_6$) δ 11.08 (br. s., 1H), 7.89 (br. s., 1H), 7.58 (br. s., 1H), 7.15-7.43 (m, 5H), 4.02 (dd, J=10.7, 3.9 Hz, 1H), 3.22-3.29 (m, 1H), 3.06 (dd, J=12.8, 10.8 Hz, 1H), 2.80 (s, 6H). $^1$H NMR (360 MHz, DMSO-d$_6$, exchange with D$_2$O) δ 7.19-7.39 (m, 5H), 4.02 (dd, J=10.6, 4.3 Hz, 1H), 3.28 (dd, J=12.9, 4.3 Hz, 1H), 3.05 (dd, J=13.0, 10.6 Hz, 1H), 2.82 (s, 6H). [α]$_D^{23}$=+71.4° (c 0.7, H$_2$O).

(R)-2-(Dimethylamino)-3-(4-hydroxyphenyl)propanamide hydrochloride (R)-16b

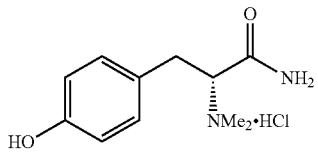

To a suspension of D-tyrosinamide (0.50 g, 2.3 mmol) in acetonitrile/water (9:1 v/v, 7 mL), 37% aqueous formaldehyde (2.0 mL, 27 mmol) was added followed by sodium triacetoxyborohydride (2.35 g, 11.1 mmol). The mixture was stirred for 15 min at an ambient temperature and then quenched by saturated NaHCO$_3$ (8 mL). The pH was adjusted to 8 by addition of 5% aqueous Na$_2$CO$_3$, and the mixture was extracted with isopropanol/ethyl acetate (1:3 v/v, 4×25 mL). Combined organic layers were dried over anhydrous Na$_2$SO$_4$, filtered, and concentrated under reduced pressure. The residue was dissolved in isopropanol (7 mL) and treated with 37% aqueous HCl (0.25 mL). The solution was concentrated to 2-3 mL, the product was precipitated by diethyl ether (15 mL) and filtered. White solid was washed with diethyl ether (2×10 mL) and dried under high vacuum. Yield: 0.54 g (96%). TLC (NH$_4$OH/MeOH/CHCl$_3$ 2.5:22.5:75): R$_f$=0.62 (KMnO$_4$ stain). LCMS (ESI+): t$_R$=6.1-7.1 min, purity: 97% (254 nm); m/z found: 209.3, calcd.: 209.3 ([M-Cl]$^+$). $^1$H NMR (600 MHz, DMSO-d$_6$) δ 11.10 (br. s., 1H), 9.43 (s, 1H), 7.91 (s, 1H), 7.59 (s, 1H), 7.02 (d, J=8.3 Hz, 2H), 6.71 (d, J=8.3 Hz, 2H), 3.96 (dd, J=10.9, 4.1 Hz, 1H), 3.17 (dd, J=13.0, 4.0 Hz, 1H), 2.95 (dd, J=12.9, 10.9 Hz, 1H), 2.79 (s, 6H). $^1$H NMR (600 MHz, D$_2$O) δ 7.20 (d, J=8.5 Hz, 2H), 6.91 (d, J=8.3 Hz, 2H), 4.04 (dd, J=10.8, 5.1 Hz, 1H), 3.42 (dd, J=13.0, 5.1 Hz, 1H), 2.87-3.17 (m, 7H). $^{13}$C NMR (91 MHz, DMSO-d$_6$) δ 167.3, 156.4, 130.1 (2C), 124.9, 115.3 (2C), 67.1, 32.7. $^{13}$C NMR (91 MHz, D$_2$O, acetone as internal standard) δ 170.5, 155.7, 131.4 (2C), 126.0, 116.4 (2C), 70.1, 42.4 (2C), 34.0. HR-EIMS: m/z found: 209.1291, calcd.: 209.1290 for C$_{11}$H$_{17}$N$_2$O$_2$ ([M-Cl]$^+$). [α]$_D^{26}$=−55.7° (c 0.5, MeOH).

(S)-2-(Dimethylamino)-3-(4-hydroxyphenyl)propanamide hydrochloride (S)-16b

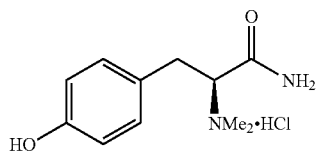

(S)-16b was synthesized following the synthetic protocol for (R)-16b. From L-tyrosinamide (0.54 g, 3.0 mmol), 37% aqueous formaldehyde (2.5 mL, 33 mmol), and sodium triacetoxyborohydride (2.9 g, 13.5 mmol) the desired product was obtained (0.57 g, 78%) as a white solid. LCMS (ESI+): t$_R$=6.1-7.1 min, purity: 98% (254 nm); m/z found: 209.3, calcd.: 209.3 ([M-Cl]$^+$). $^1$H NMR (360 MHz, DMSO-d$_6$) δ 10.99 (br. s., 1H), 9.39 (br. s., 1H), 7.88 (s, 1H), 7.58 (s, 1H), 7.02 (d, J=8.6 Hz, 2H), 6.71 (d, J=8.6 Hz, 2H), 3.95 (dd, J=10.8, 3.9 Hz, 1 H), 3.17 (dd, J=13.0, 3.9 Hz, 1H), 2.95 (dd, J=13.0, 10.8 Hz, 1H), 2.79 (s, 6H). $^1$H NMR (360 MHz, DMSO-d$_6$, exchange with D$_2$O) δ 7.04 (d, J=8.4 Hz, 2H), 6.71 (d, J=8.5 Hz, 2H), 3.95 (dd, J=10.4, 4.5 Hz, 1H), 3.17 (dd, J=13.2, 4.5 Hz, 1H), 2.93 (dd, J=13.1, 10.6 Hz, 1H), 2.82 (d, J=7.7 Hz, 6H). 13C NMR (91 MHz, DMSO-d$_6$) δ 167.2, 156.3, 130.1 (2C), 124.8, 115.2 (2 C), 67.1, 32.6. HR-EIMS: found 208.1214; calcd. 208.1212 for C$_{11}$H$_{16}$N$_2$O$_2$ ([M-HCl]$^+$). [α]$_D^{26}$=+58.6° (c 0.59, MeOH).

(R)—N$^2$,N$^2$-dimethyl-3-phenylpropane-1,2-diamine dihydrochloride (R)-17a

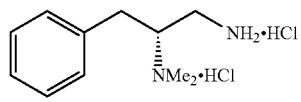

1M Borane-tetrahydrofurane complex (8.5 mL, 8.5 mmol) was slowly added to a suspension of (R)-16a (0.32 g, 1.40 mmol) in anhydrous THF (5 mL) under cooling with ice bath under nitrogen atmosphere. The mixture was refluxed for 20 h and then quenched by slow addition of anhydrous methanol (15 mL). The solvent was removed under reduced pressure and the dilution/evaporation sequence was repeated twice. The obtained oily residue was dissolved in isopropanol (5 mL) and 2N HCl in diethyl ether (1.4 mL, 2.8 mmol) was added, followed by dilution with diethyl ether (50 mL). The slurry was sonicated and filtered. Free-flowing white solid was obtained (0.25 g, 72%) after drying under high vacuum. TLC (NH$_4$OH/MeOH/CHCl$_3$ 1.5:13.5:85): R$_f$ (prod)=0.22. LCMS(ESI+): t$_R$=9.0 min, purity: n/a (220 nm); m/z found: 179.4; calcd. 179.3 ([M–H-2Cl]+). 1H NMR (360 MHz, DMSO-d6) δ 11.15 (br. s., 1H), 8.56 (br. s., 3H), 7.18-7.44 (m, 5H), 3.78-4.00 (m, 1H), 3.32-3.48 (m, 1H), 3.27 (dd, J=13.9, 3.9 Hz, 1H), 2.69-2.99 (m, 8H). 13C NMR (91 MHz, DMSO-d6) δ 135.7, 129.4 (2C), 128.8 (2C), 127.2, 64.1, 36.8, 30.8. $[\alpha]_D^{23}$=+12.5° (c 1.1, H2O). HR-ESIMS: found 179.1540; calcd. 179.1543 for $C_{11}H_{19}N_2$ ([M-Cl—HCl]+).

(S)—$N^2,N^2$-dimethyl-3-phenylpropane-1,2-diamine dihydrochloride (S)-17a

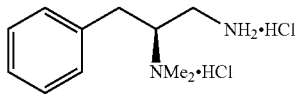

(S)-17a was synthesized following the protocol for (R)-17a. From (S)-16a (0.32 g, 1.40 mmol) and 1M borane-tetrahydrofurane complex (8.5 mL, 8.5 mmol) the desired product was obtained as a free-flowing white solid (0.143 g, 48%) after additional purification by dry-column vacuum chromatography (gradient elution with NH4OH/MeOH/CHCl3 from 1:9:90 to 2:18:80). LCMS(ESI+): $t_R$=9.0 min, purity: n/a (220 nm); m/z found: 179.4; calcd. 179.3 ([M–H-2Cl]+). 1H NMR (360 MHz, DMSO-d6) δ 11.16 (br. s., 1H), 8.58 (br. s., 3H), 7.11-7.49 (m, 5H), 3.82-3.98 (m, 1H), 3.37-3.48 (m, 1H), 3.28 (dd, J=14.1, 3.9 Hz, 1H), 2.73-2.96 (m, 8H). 1H NMR (360 MHz, DMSO-d6, exchange with D2O) δ 7.25-7.47 (m, 5H), 3.79-3.95 (m, 1H), 3.43 (dd, J=14.6, 8.8 Hz, 1H), 3.26 (dd, J=14.6, 4.3 Hz, 1H), 2.77-2.98 (m, 8H). [α]D23=–13.7° (c 0.9, H2O).

(R)-4-[3-Amino-2-(dimethylamino)propyl]phenol dihydrochloride (R)-17b

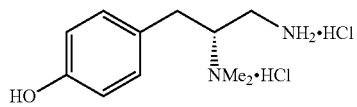

1M Borane-tetrahydrofurane complex (12.0 mL, 12.0 mmol) was slowly added to suspension of (R)-16b (0.45 mg, 1.85 mmol) in anhydrous THF (5 mL) under cooling with ice bath. The mixture was refluxed for 15 h under nitrogen atmosphere and then quenched with anhydrous methanol (10 mL dropwise, gas release). The solvent was removed under reduced pressure and dilution-evaporation sequence was repeated with anhydrous methanol (2×10 mL). The residue was resuspended in methanol (10 mL) with addition of 37% aqueous HCl (0.2 mL), concentrated under reduced pressure, diluted with ethanol and evaporated again (repeated twice). The residue was suspended in diethyl ether (ca. 5 mL), sonicated, and filtered. The product was washed with acetone (3×10 mL). Yield: 0.46 g (93%) of a white solid after drying under high vacuum. TLC (NH4OH/MeOH/CHCl3 2.5:22.5:75): $R_f$=0.23 (KMnO4 stain). LCMS(ESI+): $t_R$=5.0 min, purity: 95%; m/z found: 195.4, calcd.: 195.3 ([M-2Cl-H]+). 1H NMR (360 MHz, DMSO-d6) δ 11.10 (br. s., 1H), 9.49 (br. s., 1H), 8.58 (br. s., 3H), 7.13 (d, J=8.4 Hz, 2H), 6.77 (d, J=8.4 Hz, 2H), 3.63-3.92 (m, 1H), 3.21-3.50 (m, 1H), 3.07-3.20 (m, 1H), 2.80 (br. m, 6H), 2.57-2.74 (m, 2H). 1H NMR (360 MHz, DMSO-d6, exchange with D2O) δ 7.15 (d, J=8.4 Hz, 2H), 6.78 (d, J=8.4 Hz, 2H), 3.72 (br. s., 1H), 3.36 (dd, J=14.0, 7.6 Hz, 1H), 3.11 (dd, J=14.0, 4.1 Hz, 1H), 2.58-2.96 (m, 8H). 13C NMR (91 MHz, DMSO-d6) δ 156.5, 130.2 (2C), 125.3, 115.5 (2C), 64.4, 36.6, 30.1. $[\alpha]_D^{25}$=+5.1° (c 0.96, H2O).

(S)-4-[3-Amino-2-(dimethylamino)propyl]phenol dihydrochloride (S)-17b

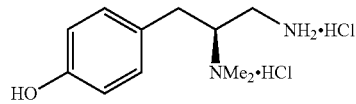

(S)-17b was synthesized following the synthetic protocol for (R)-17b. From (S)-16b (0.46 g, 1.89 mmol) and 1M borane-tetrahydrofurane complex (11.5 mL, 11.5 mmol) the desired product was obtained as a white solid (0.23 g, 46%) after additional purification by washing with acetonitrile (5 mL). LCMS(ESI+): $t_R$=4.3-4.9 min, purity: 95%; m/z found: 195.4, calcd.: 195.3 ([M-2Cl-H]+). 1H NMR (360 MHz, DMSO-d6) δ 11.13 (br. s., 1H), 9.52 (br. s., 1H), 8.63 (br. s., 3H), 7.14 (d, J=8.5 Hz, 2H), 6.78 (d, J=8.5 Hz, 2H), 3.68-4.00 (m, 1H), 3.24-3.56 (m, 1H), 3.16 (dd, J=14.3, 3.7 Hz, 1H), 2.80-2.94 (m, 6H), 2.67-2.79 (m, 2H). 1H NMR (600 MHz, DMSO-d6, exchange with D2O) δ 7.14 (d, J=8.5 Hz, 2H), 6.77 (d, J=8.5 Hz, 2H), 3.80 (br. s., 1H), 3.34-3.39 (m, 1H), 3.14 (dd, J=14.0, 3.5 Hz, 1H), 2.76-2.95 (m, 7H), 2.66-2.75 (m, 1H). 13C NMR (91 MHz, DMSO-d6) δ 156.5, 130.2 (2C), 125.3, 115.5 (2C), 64.3, 36.6, 30.1. 13C NMR (91 MHz, D2O, MeOH as external standard) δ 155.4, 130.7 (2C), 125.0, 116.3 (2C), 64.4, 39.9 (2C), 37.2, 31.8. [ ]D24=–10.1° (c 0.47, H2O). HR-ESIMS: m/z found 195.1498; calcd. 195.1492 for $C_{11}H_{19}N_2O$ ([M-Cl—HCl]+).

(E)-3-(2-Nitroprop-1-en-1-yl)thiophene 18

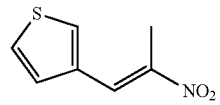

Nitroethane (13 ml, 0.18 mmol) and thiophene-3-carbaldehyde (3.9 ml, 45 mmol) were added to an ice-cold mixture of formic acid (7.5 mL, 0.20 mol) and ethanolamine (8.5 mL, 0.14 mol). The reaction mixture was heated to 85-90° C. and stirred for 7 h. The resulting solution was poured into cold water (300 mL), and the slurry was filtered. The precipitated product was washed with water (3×50 mL) yielding yellow solid (7.4 g, 98%). From two batches, 8.4 g of the crude product was recrystallized from ethanol/water (4:1 v/v) yielding yellow crystalline solid (7.0 g, 83%). LCMS (ESI+): $t_R$=19.5 min, purity: 98% (254 nm); no molecular ion. 1H NMR (360 MHz, CDCl3) δ 8.08 (br. s, 1H), 7.60 (m, J=3.0, 1.3 Hz, 1H), 7.44 (ddd, J=5.1, 3.0, 0.5 Hz, 1H), 7.28 (ddd, J=5.1, 1.3, 0.4 Hz, 1H), 2.50 (d, J=0.9 Hz, 3H). 13C NMR (151 MHz, CDCl3) δ 146.2, 133.7, 129.9, 128.2, 127.5, 127.0, 14.2. HR-EIMS: m/z found: 169.0197, calcd.: 169.0197 for $C_7H_7NO_2S$ ([M]+).

(RS)-1-(Thiophen-3-yl)propan-2-amine 19a

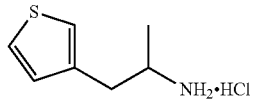

The solution of 18 (6.9 g, 41 mmol) in anhydrous THF (30 mL) was added dropwise to 1M LiAlH$_4$ in THF (200 mL, 200 mmol) at a rate adjusted to keep the mixture under a gentle reflux. After complete addition of the starting material, the reaction mixture was refluxed for 30 min, cooled to 0° C., and Na$_2$SO$_4$.10H$_2$O was slowly added until the mixture solidified. The resulting slurry was diluted with water, followed by additional Na$_2$SO$_4$.10H$_2$O (2×0.5 g). The suspension was stirred for 15 min at ice bath and then filtered through Celite; the filter cake was washed thoroughly with ethyl acetate (total volume 500 mL). The yellow filtrate was concentrated under reduced pressure and the brown residue was dissolved in diethyl ether (100 mL). Ether solution was extracted with 1N HCl (3×100 mL). Combined aqueous layers were basified with 25% aqueous NH$_3$, and back-extracted with ethyl acetate (3×100 mL). Combined organic layers were dried over anhydrous Na$_2$SO$_4$, filtered and concentrated under reduced pressure. The brown residue was dissolved in diethyl ether (50 mL), cooled to 0° C. and the product was precipitated by 2N HCl in diethyl ether (15 mL, 30 mmol) and filtered off. The precipitate was recrystallized from acetonitrile (ca. 100 mL), washed with cold acetone, and dried under high vacuum. Yield: 4.02 g (56%) as gray crystalline solid. LCMS (ESI+): $t_R$=12.3 min, purity: 98% (254 nm); m/z found: 142.3, calcd.: 142.2 ([M-Cl]$^+$). 1H NMR (600 MHz, DMSO-d$_6$) δ 8.18 (br. s., 3H), 7.52 (dd, J=4.9, 2.8 Hz, 1H), 7.32 (dddd, J=2.8, 1.3, 1.0, 0.6 Hz, 1H), 7.04 (dd, J=4.9, 1.3 Hz, 1H), 3.38-3.47 (m, 1H), 3.01 (ddd, J=14.0, 4.9, 1.0 Hz, 1H), 2.76 (ddd, J=14.0, 9.1, 0.6 Hz, 1H), 1.13 (d, J=6.4 Hz, 3H). 13C NMR (151 MHz, DMSO-d$_6$) δ 136.8, 128.5, 126.4, 122.9, 47.3, 34.6, 17.7. HR-EIMS: m/z found: 142.0689, calcd.: 142.0690 for C$_7$H$_{12}$NS ([M-Cl]$^+$).

(S)-1-(Thiophen-3-yl)propan-2-amine (S)-19a (Chiral Resolution)

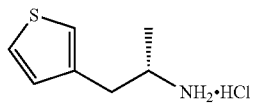

Racemic 19 (1.05 g, 5.9 mmol) was dissolved in water (40 mL), the solution was basified by 25% aq. NH$_3$, and extracted with chloroform (3×40 mL). Combined organic layers were dried over anhydrous Na$_2$SO$_4$, filtered and concentrated under reduced pressure. The liquid residue was dissolved in ethanol (10 mL) and added to a hot solution of di-p-anisoyl-D-tartaric acid (2.5 g, 5.9 mmol) in acetonitrile (20 mL). White precipitate formed immediately. The slurry was diluted with water (10 mL) and heated to the boiling point. Ethanol was added in small portions until all the solids dissolved. Seeding crystals (~5 mg) were added and the solution was allowed to cool down to ambient temperature. Crystalline precipitate was filtered off and washed with acetonitrile (2×6 mL). Washings were combined with mother liquor, heated to boiling and the solution was allowed to cool down to ambient temperature in an open beaker. The crystals from the first crop were dissolved in 1N NaOH (25 mL) and the solution was extracted by chloroform (3×15 mL). Combined extracts were dried over anhydrous Na$_2$SO$_4$, filtered and concentrated under reduced pressure. The residue was dissolved in diethyl ether (30 mL) and hydrochloride salt was precipitated by adding excess of 2M HCl in diethyl ether. The solvent was removed under reduced pressure and the resulting white solid was dried under high vacuum, yielding a white solid (0.45 g). Specific optical rotation of the first crop (converted to hydrochloride) $[\alpha]21_D$=+15.5° (c 1.25, H$_2$O). The 2$^{nd}$ crop of crystals formed as a voluminous precipitate after two days of standing in the open beaker. It was collected by filtration and washed with acetonitrile (3×3 mL). Then the diastereomeric salt was converted to hydrochloride as described above. White crystalline solid (0.32 g) was obtained. Specific optical rotation $[\alpha]^{21}_D$=-13.0° (H$_2$O, 20.4° C., c 0.92).

Crystals from the first crop (0.45 g, 2.5 mmol) were converted to free amine as described above, and dissolved in ethanol (10 mL). The solution was mixed with di-p-anisoyl-D-tartaric acid (1.05 g, 2.5 mmol) and acetonitrile (10 mL). Total amount of 120 mL of water-ethanol (3:1 v/v) was added to completely dissolve the solids under heating to boiling point. The hot solution was left in an open Erlenmeyer flask for crystallization at 4° C. After 20 h precipitated crystals were collected by filtration, washed with acetonitrile (2×4 mL) and dried by suction. Di-p-anisoyl-D-tartrate salt was converted to hydrochloride as described above. Yield: 0.32 g (60% after double crystallization). $[\alpha]_D^{22}$=+19.2° (c 0.94, H$_2$O). Triple crystallization delivers the product with $[\alpha]_D^{25}$=+20.5° (c 0.52, H$_2$O). Absolute configuration was established by acylation of enantiomerically enriched amine with acetic anhydride and comparing measured optical rotation to published data.

(S)—N-[1-(Thiophen-3-yl)propan-2-yl]acetamide (S)—N—Ac-19a

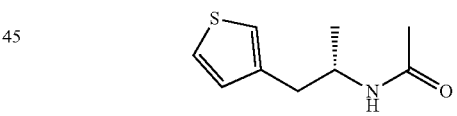

Acetic anhydride (30 μL, 0.32 mmol) was slowly added to a solution of (S)-19 (50 mg, 0.28 mmol) and triethylamine (80 μL, 0.57 mmol) in chloroform (1.5 mL). The mixture was stirred for 3 hrs at ambient temperature. Then the mixture was diluted with chloroform (3 mL), washed with saturated NaHCO$_3$ (3×3 mL) and brine (3 mL), dried over anhydrous Na$_2$SO$_4$, filtered, and concentrated under reduced pressure. The residue was dried under high vacuum yielding white crystalline product (49 mg, 95%). LCMS(ESI+): $t_R$=20.0 min, purity: 97%; m/z found: 184.3; calcd. 184.3 ([M+H]$^+$). 1H NMR (360 MHz, CDCl$_3$) δ 7.27 (dd, J=4.9, 3.0 Hz, 1H), 6.96-7.02 (m, 1H), 6.94 (dd, J=4.9, 1.2 Hz, 1H), 5.26 (br. s., 1H), 4.26 (dquind, J=8.3, 6.6, 5.9 Hz, 1H), 2.83 (dd, J=14.3, 5.9 Hz, 1H), 2.79 (dd, J=14.2, 6.6 Hz, 1H), 1.93 (s, 3H), 1.12 (d, J=6.7 Hz, 3H). 13C NMR (91 MHz, CDCl$_3$) δ 169.3, 138.1, 128.8, 125.6, 122.0, 45.5, 36.7, 23.5, 20.2. HR-EIMS: found 183.0718; calcd. 183.0718 for C$_9$H$_{13}$NOS (M$^+$). $[\alpha]_D^{21}$=-46.6° (c 1.0, CHCl$_3$). Based on literature

4-Nitrophenyl (RS)-[1-(thiophen-3-yl)propan-2-yl] carbamate 20

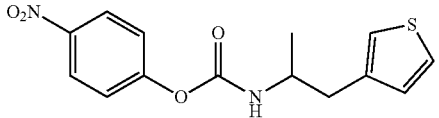 [SMILES: CC(Cc1ccsc1)NC(=O)Oc1ccc([N+](=O)[O-])cc1]

A 25 mL Schlenk flask was charged with racemic 19 (0.20 g, 1.13 mmol) and triethylamine (0.32 mL, 2.3 mmol) in anhydrous THF (5 mL) under nitrogen atmosphere and cooling with ice bath. A solution of 4-nitrophenyl chloroformate (0.23 g, 1.13 mmol) in anhydrous THF (2 mL) was added dropwise followed by a rinse with anhydrous THF (1 mL). The reaction mixture was allowed to warm up to an ambient temperature and stirred for 6 h. Then the slurry was diluted with dichloromethane (20 mL) and filtered. The filtrate was washed with saturated aqueous $NaHCO_3$ (3×15 mL) and brine (15 mL), dried over anhydrous $Na_2SO_4$, filtered and concentrated under reduced pressure. The crude residue was purified by flash chromatography (100% dichloromethane) yielding desired product as a white foam (0.26 g, 75%). TLC: (ethyl acetate/hexane 4:6): $R_f$=0.64. LCMS (ESI+): $t_R$=20.4 min, purity: 96%; m/z found: 329.3, calcd.: 329.3 ([M+Na]$^+$). $^1$H NMR (600 MHz, $CDCl_3$) δ 8.20-8.26 (m, 2H), 7.31 (dd, J=4.7, 3.0 Hz, 1H), 7.24-7.29 (m, 2H), 7.05 (ddt, J=2.9, 1.4, 0.8, Hz, 1H), 6.98 (dd, J=4.9, 1.1 Hz, 1H), 4.98 (d, J=7.7 Hz, 1H), 4.07 (dqt, J=7.6, 6.7, 6.4 Hz, 1H), 2.90 (d, J=6.4 Hz, 2H), 1.25 (d, J=6.7 Hz, 3H). 13C NMR (91 MHz, $CDCl_3$) δ 155.9, 152.3, 144.7, 137.6, 128.6, 125.9, 125.1 (2C), 122.3, 121.9 (2C), 48.0, 37.0, 20.3. HR-EIMS: m/z found: 306.0674, calcd.: 306.0674 for $C_{14}H_{14}N_2O_4S$ (M$^+$).

4-Nitrophenyl (S)-[1-(thiophen-3-yl)propan-2-yl] carbamate (S)-19

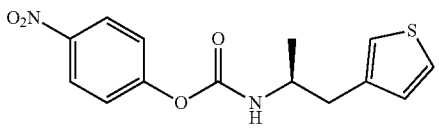 [SMILES: C[C@@H](Cc1ccsc1)NC(=O)Oc1ccc([N+](=O)[O-])cc1]

(S)-20 was synthesized following the protocol for racemic 20, using enantiomerically enriched (S)-19 as starting material. Spectral characteristics were the same as for the racemic compound. LCMS(ESI+): $t_R$=20.4 min, purity: 98%; m/z found: 329.3, calcd.: 329.3 ([M+Na]$^+$). $^1$H NMR (360 MHz, $CDCl_3$) δ 8.20-8.26 (m, 2H), 7.31 (dd, J=4.9, 3.0 Hz, 1H), 7.24-7.29 (m, 2H), 7.05 (ddt, J=2.9, 1.4, 0.8, Hz, 1H), 6.98 (dd, J=4.9, 1.3 Hz, 1H), 4.96 (d, J=7.6 Hz, 1H), 4.07 (dqt, J=7.6, 6.7, 6.4 Hz, 1H), 2.90 (d, J=6.4 Hz, 2H), 1.26 (d, J=6.7 Hz, 3 H). 13C NMR (91 MHz, $CDCl_3$) δ 155.9, 152.3, 144.7, 137.6, 128.6, 125.9, 125.1 (2C), 122.3, 121.9 (2C), 48.0, 37.0, 20.3. $[α]_D^{22}$=−44.9° (c 0.5, $CHCl_3$).

data ($[α]_D^{20}$=+49.8° for (R)-enantiomer; c 0.5, $CHCl_3$), the absolute configuration was assigned to be (S) for the product and the amine precursor.

1-[(R)-2-(Dimethylamino)-3-phenylpropyl]-3-[(RS)-1-(thiophen-3-yl)propan-2-yl]urea (R,RS)-12

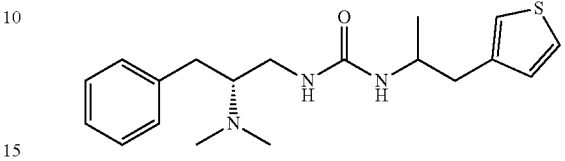

Triethylamine (50 μL, 0.36 mmol) was added to a suspension of (R)-17a (85 mg, 0.34 mmol) and racemic 20 (104 mg, 0.34 mmol) in anhydrous DMF (1 mL) under nitrogen atmosphere. The mixture was stirred at ambient temperature for 20 h and then diluted with isopropanol/ethyl acetate (1:3 v/v, 20 mL), washed with 1N NaOH (5×15 mL), and extracted with 0.1N HCl (3×20 mL). Combined aqueous extracts were basified with carbonate buffer to pH 9 and back-extracted with ethyl acetate (3×25 mL). Combined organic layers were dried over anhydrous $Na_2SO_4$, filtered and concentrated under reduced pressure. No further purification was required. The product was obtained as a colorless oil (107 mg, 92%). TLC ($NH_4OH$/MeOH/$CHCl_3$ 1:9:90): $R_f$=0.50. Diastereomers were separated by semi-preparative HPLC (AS-H chiral column, 0.1% diethyl amine in isopropanol/hexane 50:50, 6 mL/min, 6 min).

1-[(R)-2-(Dimethylamino)-3-phenylpropyl]-3-[(R)-1-(thiophen-3-yl)propan-2-yl]urea (R,R)-12

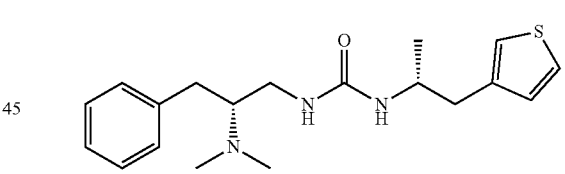

Chiral HPLC: AS-H column, 0.1% diethyl amine in isopropanol/hexane 50:50, 6 mL/min, 6 min: $t_R$=4.3 min. LCMS(ESI+): $t_R$=21.3 min, purity: 99%; m/z found: 346.6; calcd. 346.5 ([M+H]$^+$). 1H NMR (360 MHz, $CDCl_3$) δ 7.24 (dd, J=4.9, 3.0 Hz, 1H), 7.07-7.32 (m, 5H), 6.94-6.99 (m, 1H), 6.92 (dd, J=4.9, 1.2 Hz, 1H), 4.88 (d, J=5.8 Hz, 1H), 4.37 (d, J=7.7 Hz, 1H), 3.96 (dquind, J=8.1, 6.7, 5.4 Hz, 1H), 3.20 (ddd, J=12.8, 6.9, 4.2 Hz, 1H), 2.95 (dd, J=13.3, 3.6 Hz, 1H), 2.91 (ddd, J=12.8, 10.0, 2.0 Hz, 1H), 2.80 (dd, J=14.0, 5.3 Hz, 1H), 2.76 (tt, J=10.0, 4.0 Hz, 1H), 2.72 (dd, J=14.0, 7.0 Hz, 1H), 2.31 (s, 6H), 2.31 (dd, J=13.3, 10.0 Hz, 1H), 1.07 (d, J=6.6 Hz, 3H). 13C NMR (91 MHz, $CDCl_3$) δ 157.7, 139.4, 138.6, 129.0 (2C), 129.0, 128.6 (2C), 126.2, 125.3, 121.9, 65.4, 46.4, 40.7, 40.1 (2C), 37.5, 31.5, 20.7. $[α]_{D25}$=−1.5° (c 0.42, $CHCl_3$). HR-ESIMS: found 346.1952, calcd. 346.1948 for $C_{19}H_{28}N_3OS$ ([M+H]$^+$).

1-[(R)-2-(Dimethylamino)-3-phenylpropyl]-3-[(S)-1-(thiophen-3-yl)propan-2-yl]urea (R,S)-12

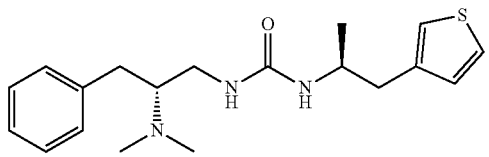 [SMILES: C[C@@H](Cc1ccsc1)NC(=O)NC[C@@H](Cc1ccccc1)N(C)C]

Chiral HPLC: AS-H column, 0.1% diethyl amine in isopropanol/hexane 50:50, 6 mL/min, 6 min: $t_R$=5.3 min. LCMS(ESI+): $t_R$=20.6 min, purity: 99%; m/z found: 346.7; calcd. 346.5 ([M+H]$^+$). 1H NMR (600 MHz, CDCl$_3$) δ 7.26-7.30 (m, 2H), 7.23 (dd, J=4.9, 3.0 Hz, 1H), 7.17-7.21 (m, 1H), 7.12-7.15 (m, 2H), 6.94-6.96 (m, 1H), 6.92 (dd, J=4.9, 1.3 Hz, 1H), 4.90 (br. d, J=5.8 Hz, 1H), 4.46 (br. s., 1H), 3.98 (dquind, J=8.1, 6.6, 5.4 Hz, 1H), 3.18 (ddd, J=13.0, 6.8, 4.3 Hz, 1H), 2.94 (dd, J=13.3, 3.6 Hz, 1H), 2.91 (ddd, J=13.3, 10.0, 1.4 Hz, 1H), 2.79 (dd, J=14.0, 5.5 Hz, 1H), 2.74 (tt, J=10.0, 4.0 Hz, 1H), 2.73 (dd, J=14.0, 6.8 Hz, 1H), 2.31 (s, 6H), 2.29 (dd, J=13.4, 10.3 Hz, 1H), 1.07 (d, J=6.6 Hz, 3H). $[\alpha]_D^{23}$=−16.2° (c 0.46, CHCl$_3$). The absolute configuration at 1-(thiophen-3-yl)propan-2-yl substituent was established by synthesizing the final product with enantiomerically enriched (S)-20 of known configuration, and comparing the retention time of the resulting product with the retention time of diastereomers in the chiral HPLC.

1-[(S)-2-(Dimethylamino)-3-phenylpropyl]-3-[(RS)-1-(thiophen-3-yl)propan-2-yl]urea (S,RS)-12

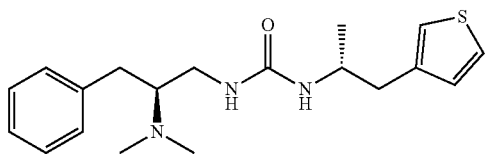 [SMILES: C[C@H](Cc1ccsc1)NC(=O)NC[C@H](Cc1ccccc1)N(C)C]

(S,RS)-12 was synthesized following the protocol for (R,RS)-12. From (S)-17a (85 mg, 0.34 mmol), racemic 20 (109 mg, 0.36 mmol), and triethylamine (55 μL, 0.40 mmol) the desired product was obtained as a colorless oil (109 mg, 93%). Diastereomers were separated by semi-preparative HPLC (AS-H chiral column, 0.1% diethyl amine in isopropanol/hexane 10:90, 11 mL/min, 8.5 min).

1-[(S)-2-(Dimethylamino)-3-phenylpropyl]-3-[(R)-1-(thiophen-3-yl)propan-2-yl]urea (S,R)-12

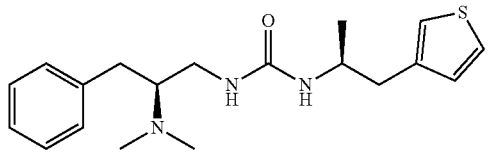 [SMILES: C[C@@H](Cc1ccsc1)NC(=O)NC[C@H](Cc1ccccc1)N(C)C]

Chiral HPLC: AS-H column, 0.1% diethyl amine in isopropanol/hexane 10:90, 11 mL/min, 108 bar, 8.5 min: $t_R$=4.9 min. LCMS(ESI+): $t_R$=20.6 min, purity: 99%; m/z found: 346.7; calcd. 346.5 ([M+H]$^+$). 1H NMR (360 MHz, CDCl$_3$) δ 7.22 (dd, J=4.9, 3.0 Hz, 1H), 7.08-7.32 (m, 5H), 6.93-6.96 (m, 1H), 6.92 (dd, J=4.9, 1.3 Hz, 1H), 4.89 (br. d, J=5.6 Hz, 1H), 4.46 (br. d, J=6.2 Hz, 1H), 3.97 (dquind, J=8.1, 6.6, 5.4 Hz, 1H), 3.18 (ddd, J=13.0, 6.8, 4.3 Hz, 1H), 2.94 (dd, J=13.3, 3.6 Hz, 1H), 2.91 (ddd, J=13.3, 10.0, 1.4 Hz, 1H), 2.80 (dd, J=14.3, 5.7 Hz, 1H), 2.74 (tt, J=10.0, 4.0 Hz, 1H), 2.72 (dd, J=14.0, 6.8 Hz, 1H), 2.31 (s, 6H), 2.29 (dd, J=13.3, 10.0 Hz, 1H), 1.07 (d, J=6.6 Hz, 3H). 13C NMR (91 MHz, CDCl$_3$) δ 157.7, 139.3, 138.6, 129.0 (2C), 129.0, 128.6 (2C), 126.2, 125.2, 121.9, 65.7, 46.3, 40.6, 40.1 (2C), 37.5, 31.4, 20.7.$[\alpha]_D^{29}$=+16.7° (c 0.44, CHCl$_3$). HR-ES-IMS: found 346.1950, calcd. 346.1948 for $C_{19}H_{28}N_3OS$ ([M+H]$^+$).

1-[(S)-2-(Dimethylamino)-3-phenylpropyl]-3-[(S)-1-(thiophen-3-yl)propan-2-yl]urea (S,S)-12

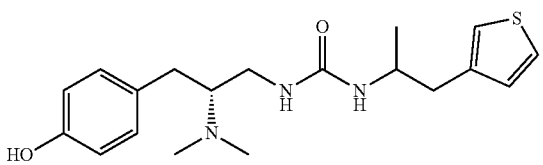 [SMILES: CC(Cc1ccsc1)NC(=O)NC[C@@H](Cc1ccc(O)cc1)N(C)C]

Chiral HPLC: AS-H column, 0.1% diethyl amine in isopropanol/hexane 10:90, 11 mL/min, 8.5 min: $t_R$=6.5 min. LCMS(ESI+): $t_R$=21.3 min, purity: 99%; m/z found: 346.6; calcd. 346.5 ([M+H]$^+$). $^1$H NMR (600 MHz, CDCl$_3$) δ 7.26-7.29 (m, 2H), 7.23 (dd, J=4.9, 2.9 Hz, 1H), 7.17-7.21 (m, 1H), 7.12-7.16 (m, 2H), 6.94-6.97 (m, 1H), 6.92 (dd, J=4.9, 1.3 Hz, 1H), 4.91 (br. d, J=5.9 Hz, 1H), 4.42 (br. s., 1H), 3.96 (dquind, J=8.1, 6.6, 6.6, 6.6, 6.6, 5.4 Hz, 1H), 3.19 (ddd, J=12.8, 6.9, 4.2 Hz, 1H), 2.94 (dd, J=13.3, 3.6 Hz, 1H), 2.91 (ddd, J=12.8, 10.0, 2.0 Hz, 1H), 2.80 (dd, J=14.0, 5.4 Hz, 1H), 2.75 (tt, J=10.0, 4.1 Hz, 1H), 2.72 (dd, J=14.1, 6.9 Hz, 1H), 2.30 (s, 6H), 2.30 (dd, J=13.3, 10.0 Hz, 1H), 1.07 (d, J=6.7 Hz, 3H). $[\alpha]_D^{23}$=+3.5° (c 0.70, CHCl$_3$).

1-[(R)-2-(Dimethylamino)-3-(4-hydroxyphenyl)propyl]-3-((RS)-1-(thiophen-3-yl)propan-2-yl)urea (R,RS)-21

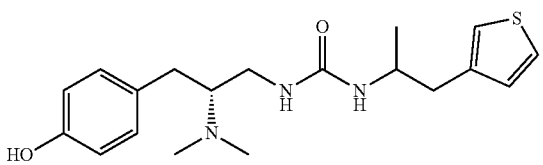 [SMILES: CC(Cc1ccsc1)NC(=O)NC[C@@H](Cc1ccc(O)cc1)N(C)C]

To a suspension of (R)-17b (102 mg, 0.382 mmol) in acetonitrile (3 mL), triethylamine (0.16 mL, 1.15 mmol) was added. The flask was sealed and heated to 60° C. Solution of racemic 20 (117 mg, 0.382 mmol) in acetonitrile (3 mL) was added. The mixture immediately turned yellow. The temperature was increased to 80° C. The mixture was stirred for 2 h and then filtered through a cotton pad and concentrated under reduced pressure. The residue was suspended in 33% isopropanol/ethyl acetate (9 mL) and washed with carbonate buffer (pH 9, 5×5 mL). Organic layer was extracted with 0.1N HCl (3×5 mL). Combined acidic aqueous layers were basified with carbonate buffer to pH 9 and back-extracted with ethyl acetate (3×10 mL). Combined organic layers were dried over Na$_2$SO$_4$, filtered and concentrated under reduced pressure. The crude residue was purified by dry-column vacuum chromatography (gradient elution with NH$_4$OH/MeOH/CHCl$_3$ from 0.5:4.5:95 to 1.5:13.5:85). Yield: 94 mg (68%) as a white solid after trituration with hexane. LCMS (ESI+): t$_R$=19.0 min, purity: 98%; m/z found: 362.6, calcd.: 362.5 ([M+H]$^+$). 1H NMR (—HCl) (360 MHz, DMSO-d$_6$) δ 10.27 (br. s., 1H), 9.31 (br. s., 1H), 7.42 (ddd, J=4.9, 3.0, 1.9 Hz, 1H), 7.15 (d, J=2.8 Hz, 1H), 7.08 (d, J=7.9 Hz, 2H), 6.96 (dd, J=4.9, 1.2 Hz, 1H), 6.72 (d, J=8.4 Hz, 2H), 5.99-6.37 (m, 2H), 3.79 (dt, J=13.3, 6.7 Hz, 1H), 2.87-3.26 (m, 4H), 2.53-2.85 (m, 9H), 0.97 (d, J=6.6 Hz, 3H). 13C NMR (91 MHz, DMSO-d$_6$) δ 157.7, 155.9, 139.2, 130.0 (2C), 128.8, 125.3, 121.6, 115.2 (2C), 79.1, 66.5 (br. s, 2C), 45.8, 37.7, 36.9, 30.8, 20.7. Diastereomers were separated by semi-preparative HPLC (AS-H chiral column, 0.1% diethyl amine in isopropanol/hexane 50:50, 8 mL/min, 8.5 min).

1-[(R)-2-(Dimethylamino)-3-(4-hydroxyphenyl)propyl]-3-((R)-1-(thiophen-3-yl)propan-2-yl)urea (R,R)-21

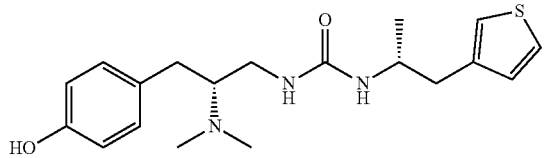 [SMILES: C[C@H](Cc1ccsc1)NC(=O)NC[C@@H](Cc1ccc(O)cc1)N(C)C]

Chiral HPLC: AS-H column, 0.1% diethyl amine in isopropanol/hexane 50:50, 8 mL/min: t$_R$=4.2 min. LCMS (ESI+): t$_R$=19.0 min, purity: 98%; m/z found: 362.7, calcd.: 362.5 ([M+H]$^+$). 1H NMR (600 MHz, CDCl$_3$) δ 7.23 (dd, J=4.9, 3.0 Hz, 1H), 6.97-7.00 (m, 1H), 6.96 (d, J=8.3 Hz, 2H), 6.94 (dd, J=4.9, 1.0 Hz, 1H), 6.76 (d, J=8.4 Hz, 2H), 5.13 (br. s., 1H), 4.53 (br. s., 1H), 3.97 (spt, J=6.7 Hz, 1H), 3.31 (m, J=12.7 Hz, 1H), 2.91 (dd, J=12.7, 10.2 Hz, 1H), 2.87 (dd, J=13.4, 3.2 Hz, 1H), 2.80 (dd, J=13.9, 5.4 Hz, 1H), 2.72 (dd, J=14.1, 6.9 Hz, 1H), 2.64-2.72 (m, 1H), 2.33 (s, 6H), 2.25 (dd, J=13.2, 10.7 Hz, 1H), 1.08 (d, J=6.6 Hz, 3H). [α]$_D^{23}$=−30.4° (c 0.39, CHCl$_3$).

1-[(R)-2-(Dimethylamino)-3-(4-hydroxyphenyl)propyl]-3-((S)-1-(thiophen-3-yl)propan-2-yl)urea (R,S)-21

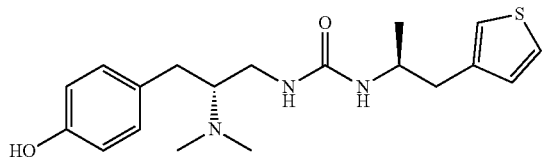 [SMILES: C[C@@H](Cc1ccsc1)NC(=O)NC[C@@H](Cc1ccc(O)cc1)N(C)C]

Chiral HPLC: AS-H column, 0.1% diethyl amine in isopropanol/hexane 50:50, 8 mL/min: t$_R$=6.3 min. LCMS (ESI+): t$_R$=19.0 min, purity: 98%; m/z found: 362.7, calcd.: 362.5 ([M+H]$^+$). $^1$H NMR (600 MHz, CDCl$_3$) δ 7.23 (dd, J=4.9, 2.9 Hz, 1H), 6.96-6.99 (m, 1H), 6.95 (d, J=8.4 Hz, 2H), 6.93 (dd, J=4.9, 1.0 Hz, 1H), 6.76 (d, J=8.4 Hz, 2H), 5.12 (br. s., 1H), 4.59 (br. s., 1H), 3.97 (spt, J=6.7 Hz, 1H), 3.29 (s, 1H), 2.91 (dd, J=12.9, 10.2 Hz, 1H), 2.86 (dd, J=13.4, 3.3 Hz, 1H), 2.80 (dd, J=14.0, 5.7 Hz, 1H), 2.73 (dd, J=14.0, 6.9 Hz, 1H), 2.68 (tt, J=10.2, 3.8 Hz, 1H), 2.33 (s, 6H), 2.24 (dd, J=13.3, 10.7 Hz, 1H), 1.08 (d, J=6.5 Hz, 3H). [α]$_D^{30}$=−34.1° (c 0.28, CHCl$_3$). The absolute configuration at 1-(thiophen-3-yl)propan-2-yl substituent was established by synthesizing the final product with enantiomerically enriched (S)-20 of known configuration, and comparing the retention time of the resulting product with the retention time of diastereomers in the chiral HPLC.

1-[(S)-2-(Dimethylamino)-3-(4-hydroxyphenyl)propyl]-3-((RS)-1-(thiophen-3-yl)propan-2-yl)urea (S,RS)-21

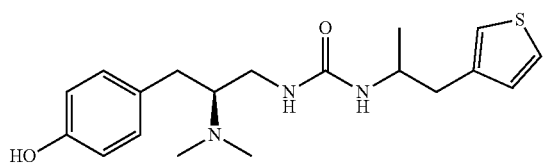 [SMILES: CC(Cc1ccsc1)NC(=O)NC[C@H](Cc1ccc(O)cc1)N(C)C]

Triethylamine (0.16 mL, 1.15 mmol) was slowly added to a suspension of (S)-17b (106 mg, 0.40 mmol) and racemic 20 (121 mg, 0.40 mmol) in anhydrous DMF (2.5 mL) under nitrogen atmosphere. The mixture was stirred for 20 h at ambient temperature, and then diluted with isopropanol/ethyl acetate (1:3 v/v, 12 mL). The organic layer was washed with carbonate buffer (pH 9, 5×5 mL) and extracted with 0.1N HCl (3×5 mL). Combined acidic aqueous layers were basified with carbonate buffer to pH 9 and back-extracted with ethyl acetate (3×10 mL). Combined organic layers were dried over anhydrous Na$_2$SO$_4$, filtered and concentrated under reduced pressure. Further purification of the crude yellow oil was accomplished by dry-column vacuum chromatography (gradient elution with NH$_4$OH/MeOH/CHCl$_3$ from 0.7:6.3:93 to 1:9:90), yielding the desired product (100 mg, 70%) as a white solid after trituration with hexane. Diastereomers were separated by semi-preparative HPLC (AS-H chiral column, 0.1% diethyl amine in isopropanol/hexane 35:65, 7 mL/min, 9 min).

1-[(S)-2-(Dimethylamino)-3-(4-hydroxyphenyl)propyl]-3-((S)-1-(thiophen-3-yl)propan-2-yl)urea PZM21

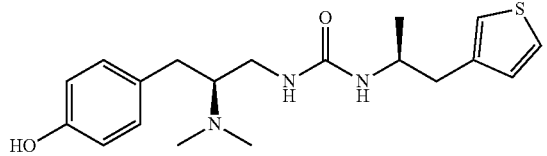 [SMILES: C[C@@H](Cc1ccsc1)NC(=O)NC[C@H](Cc1ccc(O)cc1)N(C)C]

Chiral HPLC: AS-H column, 0.1% diethyl amine in isopropanol/hexane 35:65, 7 mL/min, 9 min: t$_R$=7.1 min. The stereoisomeric purity was determined to be >99%. LCMS(ESI+): t$_R$=19.0 min, purity: 99%; m/z found: 362.7, calcd.: 362.5 ([M+H]$^+$). 1H NMR (360 MHz, CDCl$_3$) δ ppm 7.22 (dd, J=4.9, 3.0 Hz, 1H), 6.95-6.97 (m, 1H), 6.94 (d, J=8.5 Hz, 2H), 6.92 (dd, J=4.9, 1.2 Hz, 1H), 6.76 (d, J=8.4 Hz, 2H), 5.18 (br. d, J=5.2 Hz, 1H), 4.70 (br. s., 1H), 3.95 (spt, J=6.8 Hz, 1H), 3.29 (ddd, J=13.2, 6.6, 4.0 Hz, 1H), 2.91

(ddd, J=13.3, 9.7, 2.2 Hz, 1H), 2.85 (dd, J=13.3, 3.3 Hz, 1H), 2.79 (dd, J=14.1, 5.4 Hz, 1H), 2.70 (dd, J=14.1, 6.6 Hz, 1H), 2.66 (m, J=9.7, 6.6, 3.3 Hz, 1H), 2.31 (s, 6H), 2.23 (dd, J=13.3, 10.6 Hz, 1H), 1.07 (d, J=6.8 Hz, 3H). 13C NMR (91 MHz, CDCl$_3$) δ ppm 158.2, 155.6, 138.5, 129.9 (2C), 129.4, 128.9, 125.3, 122.0, 115.7 (2C), 65.7, 46.6, 40.4, 40.1 (2C), 37.5, 30.4, 20.6. [α]$D_{23}$=+40.3° (c 1.0, CHCl$_3$). HR-ESIMS: m/z found 362.1901; calcd. 362.1897 for $C_{19}H_{28}N_3O_2S$ ([M+H]$^+$).

1-[(S)-2-(Dimethylamino)-3-(4-hydroxyphenyl)propyl]-3-((R)-1-(thiophen-3-yl)propan-2-yl)urea (S,R)-21

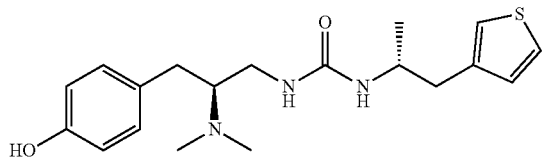 [SMILES: C[C@H](Cc1ccsc1)NC(=O)NC[C@H](Cc1ccc(O)cc1)N(C)C]

Chiral HPLC: AS-H column, 0.1% diethyl amine in isopropanol/hexane 35:65, 7 mL/min, 9 min: t$_R$=5.4 min. LCMS(ESI+): t$_R$=19.0 min, purity: 99%; m/z found: 362.7, calcd.: 362.5 ([M+H]$^+$). $^1$H NMR (600 MHz, CDCl$_3$) δ 7.22 (dd, J=4.8, 2.9 Hz, 1H), 6.96-6.98 (m, 1H), 6.94 (d, J=8.1 Hz, 2H), 6.93 (dd, J=4.8, 1.0 Hz, 1H), 6.76 (d, J=8.1 Hz, 2H), 5.13 (br. d, J=6.1 Hz, 1H), 4.67 (br. s, 1H), 3.96 (spt, J=6.7 Hz, 1H), 3.23-3.33 (m, 1H), 2.91 (ddd, J=13.3, 9.8, 2.2 Hz, 1H), 2.85 (dd, J=13.2, 3.2 Hz, 1H), 2.80 (dd, J=14.2, 5.5 Hz, 1H), 2.72 (dd, J=14.2, 7.0 Hz, 1H), 2.66 (tt, J=10.2, 3.8 Hz, 1H), 2.31 (s, 6H), 2.23 (dd, J=13.3, 10.7 Hz, 1H), 1.07 (d, J=6.6 Hz, 3H). 13C NMR (91 MHz, CDCl$_3$) δ 158.1, 155.4, 138.5, 129.9 (2C), 129.6, 129.0, 125.3, 122.0, 115.7 (2C), 65.9, 46.6, 40.4, 40.1 (2C), 37.5, 30.4, 20.7. [α]$_D^{25}$=+32.2° (c 0.58, CHCl$_3$). HR-ESIMS: m/z found 362.1901; calcd. 362.1897 for $C_{19}H_{28}N_3O_2S$ ([M+H]$^+$). The absolute configuration at 1-(thiophen-3-yl)propan-2-yl substituent was established by synthesizing the final product with enantiomerically enriched (S)-20 of known configuration, and comparing the retention time of the resulting product with the retention time of diastereomers in the chiral HPLC.

(S)-1-(2-(Dimethylamino)-3-(4-hydroxyphenyl)propyl)-3-phenethylurea×HCOOH PZM22

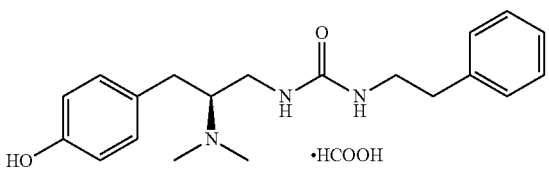 [SMILES: CN(C)[C@H](CNC(=O)NCCc1ccccc1)Cc1ccc(O)cc1 ; "·HCOOH"]

Compound 35 (72 mg, 0.27 mmol) was suspended in dry DMF (2.5 mL) in a microwave tube. Triethylamine (20 μL, 0.14 mmol)) and 4-nitrophenyl phenethylcarbamate (42) (70 mg, 0.24 mmol)) were added and the mixture was stirred at room temperature under argon atmosphere for 3 hours. Then, the solution was diluted with isopropanol/EtOAc (1:3) and washed with a saturated aqueous solution of NaHCO$_3$. The organic layer was extracted with 0.1N HCl-solution and the aqueous extracts were adjusted to pH 9 with saturated aqueous NaHCO$_3$/Na$_2$CO$_3$ solution and finally extracted with EtOAc. The organic layers were dried (Na$_2$SO$_4$), filtered under reduced pressure. The residue was purified by preparative HPLC (acetonitrile in 0.1% and concentrated aqueous HCOOH, 5% to 30% acetonitrile in 13 min) to give pure PZM22 as a white powder in 37% yield (34.6 mg) after lyophilisation. LCMS (ESI+) t$_R$=4.2-4.8 min, m/z found 342.2, calcd 342.2 [M+H]$^+$. HR EIMS m/z found 342.2186, calcd 342.2176 for $C_{20}H_{27}N_3O_2$ [M+H]$^+$. Purity: 99%. $^1$H NMR (600 MHz, DMSO) δ 8.29 (s, 1H), 7.29-7.24 (m, 2H), 7.20-7.15 (m, 3H), 6.99-6.93 (m, 2H), 6.70-6.65 (m, 2H), 6.11 (t, J=5.6 Hz, 1H), 5.71-5.63 (m, 1H), 3.16 (dd, J=13.4, 6.0 Hz, 2H), 3.09-3.04 (m, 1H), 2.84-2.76 (m, 2H), 2.71 (dd, J=13.5, 4.2 Hz, 1H), 2.63 (t, J=7.3 Hz, 2H), 2.59-2.54 (m, 1H), 2.25 (s, 6H), 2.19 (dd, J=13.5, 9.3 Hz, 1H). 13C NMR (91 MHz, DMSO) δ 157.75, 155.32, 139.72, 129.97, 129.70 (2C), 128.54 (2C), 128.17 (2C), 125.84, 115.01 (2C), 65.38, 40.79, 39.96 (2C), 39.14, 36.12, 30.30.

(S)-3-(2-(Dimethylamino)-3-(4-hydroxyphenyl)propyl)-1-methyl-1-phenethylurea×HCOOH PZM23

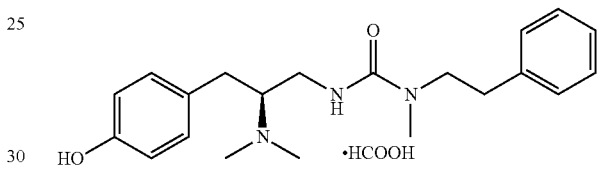

PZM23 was prepared as described for PZM22 using (S)-4-[3-amino-2-(dimethylamino)propyl]phenol (35) (50.9 mg, 0.26 mmol) and 4-nitrophenyl methyl(phenethyl)carbamate (43) (90.0 mg, 0.30 mmol) as starting materials. The reaction mixture was stirred 8 h at 120° C. Purification by preparative HPLC (acetonitrile in 0.1% aqueous HCOOH, 5% to 45% acetonitrile in 13 min) gave the pure product in 9% yield (9.1 mg). LCMS (ESI+) t$_R$=4.4-4.9 min, m/z found 356.0, calcd 356.2 [M+H]$^+$. HR EIMS m/z found 356.2344, calcd 356.2333 for $C_{21}H_{29}N_3O_2$ [M+H]$^+$. Purity: 98%. $^1$H NMR (600 MHz, DMSO) δ 8.45 (s, 1H), 7.30-7.24 (m, 2H), 7.23-7.15 (m, 3H), 7.00-6.92 (m, 2H), 6.69-6.63 (m, 2H), 5.75-5.65 (m, 1H), 3.34-3.30 (m, 2H), 3.00-2.95 (m, 2H), 2.74-2.63 (m, 7H), 2.27 (dd, J=9.2, 4.1 Hz, 1H), 2.24 (s, 6H). 13C NMR (151 MHz, DMSO) δ 157.66, 155.78, 139.86, 130.83, 130.17 (2C), 129.15 (2C), 128.74 (2C), 126.46, 115.44 (2C), 65.35, 50.36, 40.53, 40.13 (2C), 34.58, 34.13, 31.68.

(S)-1-(2-(Dimethylamino)-3-(4-hydroxyphenyl)propyl)-1-methyl-3-phenethylurea×HCOOH PZM24

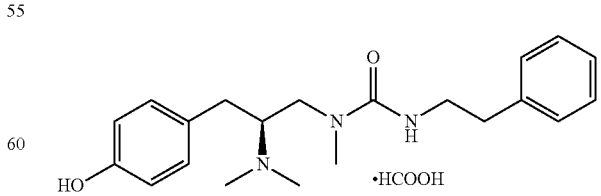

PZM24 was prepared as described for PZM22 using (S)-4-(2-(dimethylamino)-3-(methylamino)propyl)phenol (37) (15.0 mg, 72.0 μmol) and 4-nitrophenyl phenethylcarbamate (42) (18.7 mg, 66.0 μmol) as starting materials. After purification by preparative HPLC (acetonitrile in 0.1% aqueous HCOOH, 5% to 47% acetonitrile in 13 min) the pure compound (10.3 mg, 39%) was obtained. LCMS (ESI+) $t_R$=3.3-4.2 min, m/z found 356.0, calcd 356.2 [M+H]$^+$. HR EIMS m/z found 356.2338, calcd 356.2333 for $C_{21}H_{29}N_3O_2$ [M+H]$^+$. Purity: 99%. 1H NMR (600 MHz, DMSO) δ 8.37 (s, 1H), 7.30-7.25 (m, 2H), 7.21-7.15 (m, 3H), 6.99-6.92 (m, 2H), 6.69-6.62 (m, 2H), 6.48-6.37 (m, 1H), 3.32 (dd, J=14.5, 8.1 Hz, 1H), 3.20 (ddd, J=9.2, 7.0, 1.6 Hz, 2H), 2.94 (dd, J=14.5, 4.7 Hz, 1H), 2.83-2.77 (m, 1H), 2.72-2.63 (m, 3H), 2.55 (s, 3H), 2.25-2.15 (m, 7H). 13C NMR (91 MHz, DMSO) δ 157.97, 155.27, 139.85, 130.19, 129.66 (2C), 128.55 (2C), 128.18 (2C), 125.82, 115.01 (2C), 64.60, 48.12, 41.77, 40.04 (2C), 36.01, 34.06, 31.00, 30.62.

(S)-1-(2-(Dimethylamino)-3-(4-hydroxyphenyl)propyl)-1,3-dimethyl-3-phenethylurea×HCOOH
PZM25

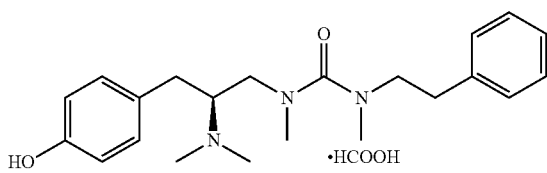 [SMILES: CN(CCc1ccccc1)C(=O)N(C)C[C@H](Cc1ccc(O)cc1)N(C)C ; "·HCOOH"]

PZM25 was prepared as described for PZM22 using (S)-4-(2-(dimethylamino)-3-(methylamino)propyl)phenol (37) (20.0 mg, 96.0 μmol) and 4-nitrophenyl methyl(phenethyl)carbamate (43) (52.5 mg, 0.18 mmol) as starting materials. The reaction mixture was stirred 4 h at 120° C. after it had been stirred for 18 hr at ambient temperature. Purification by preparative HPLC (acetonitrile in 0.1% aqueous HCOOH, 5% to 48% acetonitrile in 14 min) gave the pure product in 20% yield (7.8 mg). LCMS (ESI+) $t_R$=4.2-4.8 min, m/z found 370.0, calcd 370.2 [M+H]$^+$. HR EIMS m/z found 370.2495, calcd 370.2489 for $C_{22}H_{31}N_3O_2$ [M+H]$^+$. Purity: 100%. 1H NMR (600 MHz, DMSO) δ 8.39 (s, 1H), 7.29-7.25 (m, 2H), 7.21-7.16 (m, 3H), 6.98-6.93 (m, 2H), 6.67-6.63 (m, 2H), 3.26 (dd, J=13.7, 8.5 Hz, 1H), 3.23-3.14 (m, 2H), 2.88 (dd, J=13.8, 5.3 Hz, 1H), 2.86-2.80 (m, 1H), 2.78-2.70 (m, 2H), 2.66-2.60 (m, 4H), 2.60 (s, 3H), 2.19 (s, 6H), 2.18-2.14 (m, 1H). 13C NMR (151 MHz, DMSO) δ 163.97, 155.29, 139.52, 130.27, 129.63 (2C), 128.59 (2C), 128.24 (2C), 125.96, 114.98 (2C), 63.10, 51.58, 49.30, 40.07, 40.04, 36.88, 36.32, 33.16, 31.36.

1-((S)-1-(Benzo[b]thiophen-3-yl)propan-2-yl)-3-((S)-2-(dimethylamino)-3-(4-hydroxyphenyl)propyl)urea×HCOOH PZM26

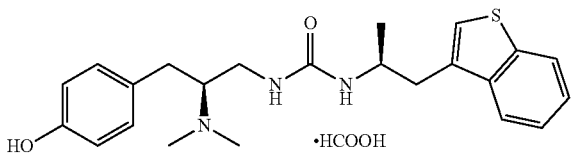 [SMILES: C[C@@H](Cc1csc2ccccc12)NC(=O)NC[C@H](Cc1ccc(O)cc1)N(C)C ; "·HCOOH"]

PZM26 was prepared as described for PZM22 using (S)-4-[3-amino-2-(dimethylamino)propyl]phenol (35) (25.0 mg, 0.13 mmol) and 4-nitrophenyl (1-(benzo[b]thiophen-3-yl)propan-2-yl)carbamate (44) (43.3 mg, 0.12 mmol) as starting materials. Yield: 31.7 mg (57%). Diastereomers were separated by semi-preparative HPLC (AS-H chiral column, 0.1% diethyl amine in isopropanol/hexane 15:85, 12 mL/min, 25 min, $t_R$ (1-((R)-1-(benzo[b]thiophen-3-yl)propan-2-yl)-3-((S)-2-(dimethylamino)-3-(4-hydroxyphenyl)propyl)urea×HCOOH): 12.5 min, $t_R$ (1-((S)-1-(benzo[b]thiophen-3-yl)propan-2-yl)-3-((S)-2-(dimethylamino)-3-(4-hydroxyphenyl)propyl)urea×HCOOH (PZM26)): 18.5 min). The pure compound was obtained after additional purification by preparative HPLC (acetonitrile in 0.1% aqueous HCOOH, 5% to 74% acetonitrile in 10 min). LCMS (ESI+) $t_R$=5.3-6.4 min, m/z found 412.2, calcd 412.2 [M+H]$^+$, HR EIMS m/z found 412.2062, calcd 412.2053 for $C_{23}H_{29}N_3O_2S$ [M+H]$^+$. Purity: 96%. $^1$H NMR (600 MHz, CDCl$_3$) δ 8.62 (s, 1H), 7.90-7.86 (m, 1H), 7.85-7.81 (m, 1H), 7.37-7.29 (m, 2H), 7.16 (s, 1H), 6.97-6.92 (m, 2H), 6.78-6.74 (m, 2H), 5.72 (s, 1H), 4.85 (s, 1H), 4.17 (dp, J=13.5, 6.7 Hz, 1H), 3.34 (d, J=13.2 Hz, 1H), 3.12 (dd, J=14.2, 5.4 Hz, 1H), 2.98 (dd, J=13.3, 9.6 Hz, 1H), 2.93-2.80 (m, 3H), 2.40 (s, 6H), 2.38-2.31 (m, 1H), 1.12 (d, J=6.6 Hz, 3H). 13C NMR (91 MHz, DMSO) δ 158.17, 156.17, 139.48, 138.92, 133.52, 130.08 (2C), 124.06, 123.86, 123.23, 122.73, 121.90, 115.35 (2C), 66.86, 45.19, 40.51, 39.92 (2C), 37.69, 35.54, 30.65, 20.41.

(S)-1-(2-((Cyclopropylmethyl)(methyl)amino)-3-(4-hydroxyphenyl)propyl)-3-phenethylurea×CF$_3$COOH
PZM27

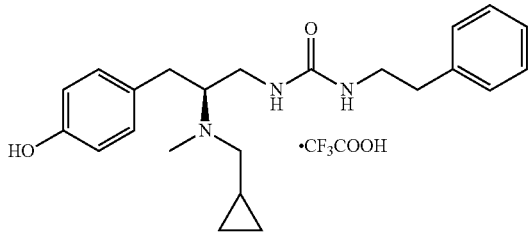 [SMILES: CN(CC1CC1)[C@H](CNC(=O)NCCc1ccccc1)Cc1ccc(O)cc1 ; "·CF3COOH"]

To compound 39 (23.9 mg, 0.07 mmol) in 3 mL of a 9:1 (v/v) mixture of acetonitrile/H$_2$O (3 mL), AcOH (10 μL), cyclopropylcarboxaldehyde (55 μL, 0.73 mmol) and sodium triacetoxyborohydride (155 mg, 0.73 mmol) were added consecutively. After stirring for 12 h at ambient temperature the reaction was quenched with a saturated aqueous solution of NaHCO$_3$ and adjusted to pH 8-9 with saturated aqueous NaHCO$_3$/Na$_2$CO$_3$ solution. The mixture was extracted with EtOAc, organic layers were dried (Na$_2$SO$_4$), filtered and evaporated. The residue was purified by preparative HPLC (acetonitrile in 0.1% aqueous CF$_3$COOH, 10% to 65% acetonitrile in 10 min) to give the product as a white powder (31.1 mg, 86%) after lyophilisation. LCMS (ESI+) $t_R$=4.8-5.5 min, m/z found 382.25, calcd 382.25 [M+H]$^+$. HR EIMS m/z found 382.2496, calcd 382.2489 for $C_{23}H_{31}N_3O_2$ [M+H]$^+$. Purity: 100%. $^1$H NMR (3:2 isomer ratio, 600 MHz, D$_2$O) δ 7.39-7.31 (m, 2H), 7.31-7.23 (m, 3H), 7.22-7.15 (m, 2H), 6.96-6.86 (m, 2H), 3.82-3.71 (m, 1H), 3.49 (dd, J=15.3, 7.1 Hz), 3.40 (dd, J=15.5, 8.1 Hz, 1H), 3.32 (t, J=6.5 Hz, 2H), 3.27-3.15 (m, 2H), 3.09-2.97 (m, 2H), 2.95 (dd, J=13.2, 7.6 Hz), 2.90 (s, 1H), 2.87 (s, 2H), 2.82 (dd, J=14.3, 9.1 Hz), 2.78-2.69 (m, 3H), 1.12-1.00 (m, 1H), 0.79-0.66 (m, 2H), 0.44-0.30 (m, 2H). 13C NMR (3:2 isomer ratio, 151 MHz, DMSO) δ 159.88, 158.81, 156.30, 156.28, 139.46, 139.36, 130.23, 130.14, 128.58, 128.57, 128.27, 128.26, 126.17, 126.06, 126.03, 126.01, 115.49, 115.44, 66.81, 66.75, 58.19, 56.08, 41.16, 41.03, 38.34, 37.56, 35.92, 35.85, 37.47, 34.92, 31.19, 29.89, 6.34, 6.11, 4.70, 4.14, 3.97, 3.44.

(S)—N-(1-(4-Hydroxyphenyl)-3-(3-phenethylureido)propan-2-yl)-N-methylformamide PZM28

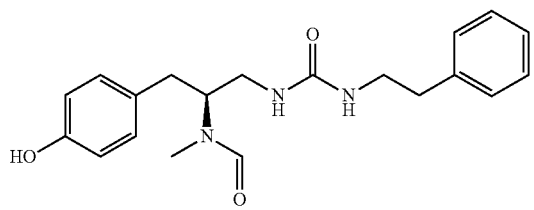 [SMILES: CN(C=O)[C@H](CNC(=O)NCCc1ccccc1)Cc1ccc(O)cc1]

(S)-1-(3-(4-Hydroxyphenyl)-2-(methylamino)propyl)-3-phenethylurea (39) (14.7 mg, 45.0 μmol) was dissolved in a microwave tube in dry acetonitrile (1 mL). Ammonium formate (14.2 mg, 0.23 mmol) was added and the reaction mixture was stirred at reflux temperature for 24 h. Then the solvent was evaporated and the obtained residue was purified by flash chromatography ($CH_2Cl_2$/MeOH 20:1) to give the compound as a mixture of cis-/trans-isomers in 26% yield (4.2 mg). LCMS (ESI+) $t_R$=5.7-6.4 min, m/z found 356.21, calcd 356.20 [M+H]$^+$. HR EIMS m/z found 356.1968 and 378.1793, calcd 356.1969 and 378.1788 for $C_{20}H_{25}N_3O_3$ [M+H]$^+$ and [M+Na]$^+$, respectively. Purity: 95%. 1H NMR (2:1 isomer ratio, 500 MHz, CDCl$_3$) δ 7.86 (s, 1H), 7.47 (s, 1H), 7.41 (s, 1H), 7.29-7.10 (m, 5H), 6.99-6.98 (m, 1H), 6.92-6.90 (m, 1H), 6.75-6.71 (m, 2H), 5.14-4.54 (m, 2H), 3.67-3.58 (m, 2H), 3.42-3.38 (m, 2H), 3.22-3.05 (m, 1H), 2.82-2.55 (m, 7H). $^{13}$C NMR (2:1 isomer ratio, 125 MHz, CDCl$_3$) δ 164.39, 163.85, 158.29, 158.24, 155.57, 155.33, 139.06, 129.74, 128.81, 128.55, 128.20, 127.88, 126.38, 115.78, 115.58, 61.13, 41.57, 41.40, 40.67, 40.49, 36.33, 36.29, 35.38, 34.76, 30.82, 29.67.

(S)-1-(2-(1-(2-((2-Azidoethyl)disulfanyl)ethyl)-1H-1,2,3-triazol-4-yl)ethyl)-3-(2-(dimethylamino)-3-(4-hydroxyphenyl)propyl)urea×CF$_3$COOH PZM29

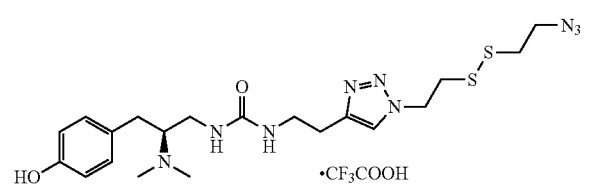 [SMILES: CN(C)[C@H](CNC(=O)NCCc1cn(CCSSCCN=[N+]=[N-])nn1)Cc1ccc(O)cc1 ; "·CF3COOH"]

PZM29 was synthesized via CuAAc reaction: (S)-1-(But-3-yn-1-yl)-3-(2-(dimethylamino)-3-(4-hydroxyphenyl)propyl)urea (46) (31.5 mg, 0.11 mmol), CuSO$_4$×5H$_2$O (7.10 mg, 28.4 μmol), sodium ascorbate (8.10 mg, 41.0 μmol) and bis(2-azidoethyl) disulfide (46.3 mg, 0.23 mmol) were dissolved in of DMF/H$_2$O (1.2 mL, 2:1 (v/v)) and stirred at room temperature for 6 h. The reaction mixture was quenched with 0.1M EDTA-solution, adjusted to pH 8-9 with saturated aqueous NaHCO$_3$/Na$_2$CO$_3$ solution and extracted with EtOAc. Combined organic layers were dried (Na$_2$SO$_4$), filtered and concentrated under reduced pressure. The residue was purified by preparative HPLC (acetonitrile in 0.1% aqueous CF$_3$COOH, 5% to 50% acetonitrile in 12 min) to give the pure product in 44% (29 mg) yield. LCMS (ESI+) $t_R$=3.5-4.5 min, m/z found 494.1, calcd 494.2 [M+H]$^+$. HR EIMS m/z found 494.2110, calcd 494.2115 for $C_{20}H_{31}N_9O_2S_2$ [M+H]$^+$. Purity: 98%. 1H NMR (600 MHz, DMSO) δ 9.64 (s, 1H), 9.37 (s, 1H), 7.92 (s, 1H), 7.18-7.01 (m, 2H), 6.80-6.67 (m, 2H), 6.38 (s, 2H), 4.61 (t, J=6.6 Hz, 2H), 3.59 (t, J=6.4 Hz, 2H), 3.49-3.40 (m, 1H), 3.32-3.25 (m, 3H), 3.23 (t, J=6.6 Hz, 2H), 3.21-3.12 (m, 1H), 3.00 (dd, J=13.8, 3.5 Hz, 1H), 2.95 (t, J=6.4 Hz, 2H), 2.88 (d, J=4.9 Hz, 3H), 2.81 (d, J=4.9 Hz, 3H), 2.74 (t, J=7.3 Hz, 2H), 2.60 (dd, J=13.7, 10.7 Hz, 1H). $^{13}$C NMR (151 MHz, DMSO) δ 158.76, 156.28, 144.50, 130.19 (2C), 126.14, 122.50, 115.44 (2C), 67.14, 49.11, 47.90, 40.90, 40.06, 38.32, 37.85, 37.20, 36.70, 30.56, 26.22.

(S)-2-(Benzylamino)-3-(4-hydroxyphenyl)propanamide 32

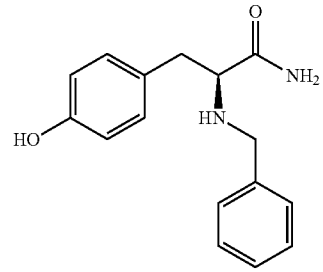 [SMILES: NC(=O)[C@H](Cc1ccc(O)cc1)NCc1ccccc1]

To a suspension of L-tyrosinamide (30) (0.80 g, 4.47 mmol) in a 9:1 (v/v) mixture of acetonitrile/H$_2$O (19 mL), AcOH (0.40 mL), benzaldehyde (0.47 g, 4.44 mmol) and sodium triacetoxyborohydride (2.82 g, 13.3 mmol) were added. The reaction mixture was stirred for 2 hours and quenched with a saturated aqueous solution of NaHCO$_3$. The pH was adjusted to pH 8-9 by saturated aqueous NaHCO$_3$/Na$_2$CO$_3$ solution and extracted with isopropanol/EtOAc (1:3). The organic layers were dried (Na$_2$SO$_4$), filtered and evaporated. The product (901 mg, 75%) was obtained as a white solid after purification by flash chromatography (CH$_2$Cl$_2$/MeOH/NH$_3$ 15:1:0.1). LCMS (ESI+) m/z found 271.0, calcd 271.1 [M+H]$^+$.

(S)-2-(Benzyl(methyl)amino)-3-(4-hydroxyphenyl)propanamide 33

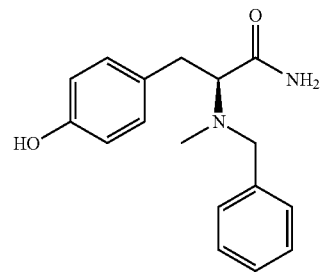 [SMILES: CN(Cc1ccccc1)[C@@H](Cc1ccc(O)cc1)C(N)=O]

Compound 33 was prepared as described for compound (R)-16b. Starting from (S)-2-(benzylamino)-3-(4-hydroxyphenyl)propanamide (32) (0.80 g, 2.96 mmol), 37% aqueous formaldehyde (1.20 mL, 14.8 mmol) and sodium triacetoxyborohydride (1.88 g, 8.88 mmol), the product was obtained (0.76 g, 90%) as a white solid after purification by flash chromatography (CH$_2$Cl$_2$/MeOH/NH$_3$ 20:1:0.1). LCMS (ESI+) m/z found 285.0, calcd 285.2 [M+H]$^+$.

(S)-2-(Dimethylamino)-3-(4-hydroxyphenyl)-N-methylpropanamide 34

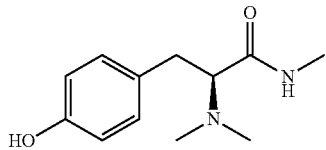 [SMILES: CNC(=O)[C@H](Cc1ccc(O)cc1)N(C)C]

Compound 34 was prepared as described for compound (R)-16b. Starting from (S)-2-amino-3-(4-hydroxyphenyl)-N-methylpropanamide (31) (0.40 g, 2.06 mmol), 37% aqueous formaldehyde (1.54 mL, 20.6 mmol) and sodium triacetoxyborohydride (2.20 g, 10.3 mmol) the pure product was obtained (0.40 g, 88%) as a white solid after purification by flash chromatography (CH$_2$Cl$_2$/MeOH/NH$_3$ 9:1:0.1). LCMS (ESI+) m/z found 222.92, calcd 223.14 [M+H]$^+$.

(S)-4-[3-Amino-2-(dimethylamino)propyl]phenol 35

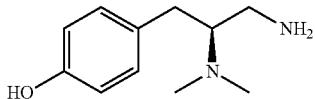

Compound 35 was synthesized following the synthetic protocol for (S)-17b. Starting from (S)-16b (4.10 g, 16.8 mmol) and 1M borane-tetrahydrofurane complex (102 mL, 103 mmol), the product was obtained as a yellowish white foam (3.10 g, 95%) after flash chromatography (CH$_2$Cl$_2$/MeOH/NH$_3$ 9:1:0.1). LCMS (ESI+) m/z found 194.90, calcd 195.15 [M+H]$^+$.

(S)-4-(3-Amino-2-(benzyl(methyl)amino)propyl)phenol 36

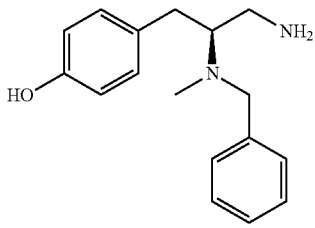 [SMILES: CN(Cc1ccccc1)[C@H](CN)Cc1ccc(O)cc1]

Compound 36 was synthesized as described for compound 35 using (S)-2-(benzyl(methyl)amino)-3-(4-hydroxyphenyl)propanamide (0.70 g, 2.46 mmol) as starting material. 36 (0.52 g, 78%) was obtained after purification by flash chromatography (CH$_2$Cl$_2$/MeOH/NH$_3$ 9:1:0.1). LCMS (ESI+) m/z found 271.03, calcd 271.18 [M+H]$^+$.

(S)-4-(2-(Dimethylamino)-3-(methylamino)propyl)phenol 37

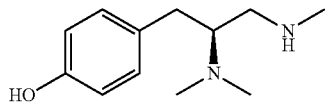

Compound 37 was prepared as described for compound 35 using (S)-2-(dimethylamino)-3-(4-hydroxyphenyl)-N-methylpropanamide (34) (0.38 g, 1.71 mmol) as starting material. The product was obtained after purification by flash chromatography (CH$_2$Cl$_2$/MeOH/NH$_3$ 9:1:0.1) in 11% (38.2 mg) yield. LCMS (ESI+) m/z found 208.89, calcd 209.16 [M+H]$^+$.

(S)-1-(2-(Benzyl(methyl)amino)-3-(4-hydroxyphenyl)propyl)-3-phenethylurea 38

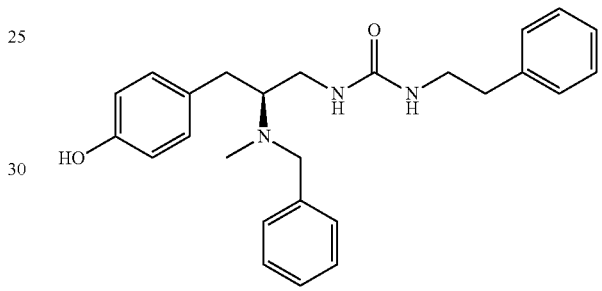

Compound 38 was prepared as described for PZM22 using (S)-4-(3-amino-2-(benzyl(methyl)amino)propyl)phenol (36) (0.1 g, 0.42 mmol) and 4-nitrophenyl phenethylcarbamate (42) (0.10 g, 0.35 mmol) as starting materials. Pure product was obtained after flash chromatography (CH$_2$Cl$_2$/MeOH/NH$_3$ 50:1:0.1→40:1:0.1→30:1:0.1) in 93% (0.14 g) yield. LCMS (ESI+) m/z found 418.22, calcd 418.25 [M+H]$^+$.

(S)-1-(3-(4-Hydroxyphenyl)-2-(methylamino)propyl)-3-phenethylurea 39

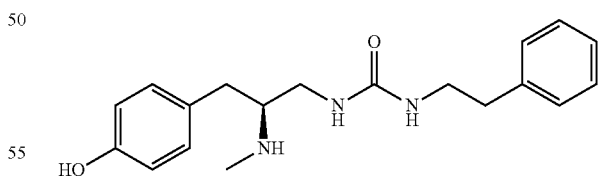

Compound 38 (0.12 g, 0.30 mmol) was dissolved in MeOH (10 mL) in a Schlenk flask and stirred under N$_2$ atmosphere. 1,1,2-Trichloroethane (27 µL, 0.30 mmol) and 10% Pd—C were added and the mixture was stirred for 5 h under H$_2$ atmosphere at ambient temperature. The suspension was filtered through celite, the filtrate was evaporated and the residue was purified by flash chromatography (CH$_2$Cl$_2$/MeOH/NH$_3$ 15:1:0.1) to give pure 39 in 87% (81.3 mg) yield. LCMS (ESI+) m/z found 328.15, calcd 328.20 [M+H]$^+$.

4-Nitrophenyl methyl(phenethyl)carbamate 43

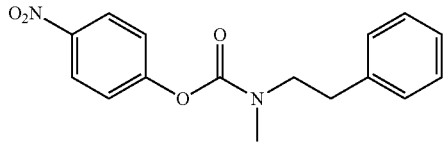 [SMILES: CN(CCc1ccccc1)C(=O)Oc1ccc([N+](=O)[O-])cc1]

4-Nitrophenyl chloroformate (0.32 g, 1.56 mmol) in a Schlenk flask was solved in dry THF (4 mL) and stirred under $N_2$ atmosphere in an ice-water-bath. A mixture of N-methyl-(β-phenylethyl) amine (40) (0.20 g, 1.48 mmol) and triethylamine (0.41 mL, 2.96 mmol) in dry THF (5 mL) was added dropwise. The reaction mixture was allowed to warm up to room temperature and was stirred for 8 h. The mixture was diluted with dichloromethane, filtered and the filtrate was washed with saturated aqueous $NaHCO_3$ and brine. The organic layer was dried ($Na_2SO_4$), filtered and concentrated under reduced pressure. The residue was purified by flash chromatography (100% dichloromethane) to give the product as a white solid (85%, 0.38 g) after trituration with hexane. LCMS (ESI+) m/z found 300.84, calcd 301.12 $[M+H]^+$.

4-Nitrophenyl (1-(benzo[b]thiophen-3-yl)propan-2-yl)carbamate 44

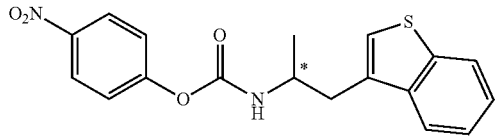 [SMILES: CC(Cc1csc2ccccc12)NC(=O)Oc1ccc([N+](=O)[O-])cc1]

Compound 44 was prepared as described for compound 43 using 1-(1-benzothiophen-3-yl)propan-2-amine hydrochloride (0.11 g, 0.49 mmol), 4-nitrophenyl chloroformate (97.5 mg, 0.49 mmol) and triethylamine (0.14 mL, 0.97 mmol) as starting materials. Pure 44 was obtained after purification by flash chromatography (100% dichloromethane). Yield: 84.7 mg (49%) as a white solid after trituration with hexane. LCMS (ESI+) m/z found 357.13, calcd 357.09 $[M+H]^+$.

(S)-1-(But-3-yn-1-yl)-3-(2-(dimethylamino)-3-(4-hydroxyphenyl)propyl)urea 46

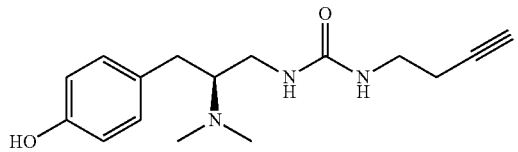 [SMILES: C#CCCNC(=O)NC[C@H](Cc1ccc(O)cc1)N(C)C]

N-3-Butyn-1-yl-1H-imidazole-1-carboxamide (45) (0.33 g, 2.01 mmol) and (S)-4-[3-amino-2-(dimethylamino)propyl]phenol (35) (0.50 g, 2.57 mmol) were solved in dry DMF (10 mL) and stirred for 24 h under Ar atmosphere at 50° C. $H_2O$ was added and the mixture was lyophilisated. After purification by flash chromatography ($CH_2Cl_2$/MeOH/ $NH_3$ 9:1:0.1) the product was obtained as a white solid (0.47 g, 80%). LCMS (ESI+) m/z found 290.05, calcd 290.19 $[M+H]^+$

Overview of Molecular Dynamics Simulations

| µOR structure | His297$^{6.52}$ protonation state | Simulation size (# total atoms) | Length of each simulation | Total simulation time |
|---|---|---|---|---|
| Inactive | δN (HID) | 101,161 | 350 ns; 450 ns; 350 ns | 2.0 µs |
| Inactive | εN (HIE) | 101,167 | 400 ns; 450 ns | |
| Active | δN (HID) | 101,473 | 950 ns; 900 ns; 950 ns | 3.6 µs |
| Active | εN (HIE) | 101,476 | 1000 ns; 950 ns; 950 ns | |

Example 3. Methods

Molecular Docking and Analog Selection:

The inactive state µ-opioid receptor structure (PDB: 4DKL) was used as input for receptor preparation with DOCK Blaster (http://blaster.docking.org). Forty-five matching spheres were used based on a truncated version of the crystallized ligand. The covalent bond and linker region of the antagonist 3-funaltrexamine were removed for sphere generation. The ligand sampling parameters were set with bin size, bin size overlap, and distance tolerances of 0.4 Å, 0.1 Å, and 1.5 Å, respectively, for both the matching spheres and for the docked molecules. Ligand poses were scored by summing the receptor-ligand electrostatics and van der Waals interaction energy corrected for ligand desolvation. Receptor atom partial chargers were used from the united atom AMBER force field except for Lys233 and Tyr326, where the dipole moment was increased. Over 3 million commercially available molecules from the ZINC (http://zinc.docking.org) lead-like set were docked into the receptor using DOCK3.6 (http://dock.compbio.ucsf.edu). Among the top ranking 0.08% of molecules were inspected and 23 were selected for experimental testing in the primary screen.

For a secondary screen, analogs of the top three hits from the primary screen (Compounds 4, 5 and 7) with a similarity of greater than 0.7 (as defined in the ZINC search facility) were identified in the ZINC database. Additionally, substructure searches were performed using the scaffolds of each of these three compounds. The searches yielded 500 purchasable compounds, which were then docked as in the primary screen. Analogs were manually inspected for interactions and selected for further experimental testing.

Radioligand Binding Studies:

For a primary screen of selected molecules, binding to µOR was assessed by measuring competition against the radioligand $^3$H-diprenorphine ($^3$H-DPN). Each compound was initially tested at 20 µM and was incubated with $^3$H-DPN at a concentration equal to the $K_d$ (0.4 nM) of the radioligand in µOR containing Sf9 insect cell membranes. The reaction contained 40 fmol of µOR and was incubated in a buffer of 20 mM HEPES pH 7.5, 100 mM sodium chloride, and 0.1% bovine serum albumin for 1 hour at 25° C. To separate free from bound radioligand, reactions were rapidly filtered over Whatman GF/B filters with the aid of a Brandel harvester and $^3$H-DPN counts were measured by liquid scintillation. Compounds with more than 25% of $^3$H-DPN radioactivity were further tested in full dose-response to determine the affinity ($K_i$) in HEK293 membranes. Subsequently, the 15 analogs were tested in full dose-response for affinity at the µOR and the κOR by the National Institutes of Mental Health Psychoactive Drug Screen Program (PDSP), as were the affinities of compounds 12, PZM21, and their stereoisomers at the µOR, δOR, κOR and nociception receptor.

Radioligand depletion assays to test the irreversible binding of compound PZM29 were performed as described previously. Human embryonic kidney 293 (HEK 293) cells were transiently transfected with µOR or the cysteine mutant µOR:N127C using the Mirus TransIT-293 transfection reagent (MoBiTec, Goettingen, Germany), grown for 48 hrs, harvested, and homogenates were prepared as described. For radioligand depletion experiments, homogenates were pre-incubated in TRIS buffer (50 mM Tris at pH 7.4) at a protein concentration of 50-100 g/mL or 70-120 µg/mL for µOR and OR:N127C, respectively and the covalent ligand (at 5 µM) for different time intervals. Incubation was stopped by centrifugation and reversibly bound ligand was washed three times (resuspension in buffer for 30 min and subsequent centrifugation). Membranes were then used for radioligand binding experiments with $^3$H-diprenorphine (final concentration: 0.7 nM, specific activity: 30 Ci/mmol, purchased from Biotrend, Cologne, Germany) to determine specific binding at the µOR ($B_{max}$=4000-6500 fmol/mg protein, $K_D$=0.25-0.45 nM) and the µOR:N127C receptor ($B_{max}$=1300-6000 fmol/mg protein, $K_D$=0.18-0.25 nM), respectively as described. Non-specific binding was determined in the presence of 10 µM naloxone. For data analysis, the radioactivity counts were normalized to values where 100% represents effect of buffer and 0% represents non-specific binding. Five independent experiments, each done in quadruplicate, were performed and the resulting values were calculated and pooled to a mean curve which is displayed.

GTPγS Binding Experiments:

The [$^{35}$S]-GTPγS binding assay was performed with membrane preparations from HEK 293 cells coexpressing the human µOR and the PTX insensitive G-protein subunits $G\alpha_{o1}$ or $G\alpha_{i2}$. Cells were transiently transfected using the Mirus TransIT-293 transfection reagent (MoBiTec, Goettingen, Germany), grown for 48 hrs, harvested and homogenates were prepared as described. The receptor expression level ($B_{max}$) and $K_D$ values were determined in saturation experiments with $^3$H-diprenorphine (specific activity: 30 Ci/mmol, purchased from Biotrend, Cologne, Germany) ($B_{max}$=3700±980 fmol/mg protein, $K_D$=0.30±0.093 nM for µOR+$G\alpha_{o1}$ or $B_{max}$=5800±2000 fmol/mg, $K_D$=0.46±0.095 nM for µOR+$G\alpha_{i2}$, respectively). The assay was carried out in 96-well plates with a final volume of 200 µL. In each well, 10 µM GDP, the compounds (0.1 pM to 100 µM final concentration) and the membranes (30 µg/mL final protein concentration) were incubated for 30 min at 37° C. in incubation buffer containing 20 mM HEPES, 10 mM $MgCl_2.6H_2O$ and 70 mg/L saponin. After the addition of 0.1 nM [$^{35}$S]-GTPγS (specific activity 1250 Ci/mmol, PerkinElmer, Rodgau, Germany) incubation was continued at 37° C. for further 30 min or 75 min for µOR+$G\alpha_{o1}$ or µOR+$G\alpha_{i2}$, respectively. Incubation was stopped by filtration through Whatman GF/B filters soaked with ice cold PBS. Bound radioactivity was measured by scintillation measurement as described previously.

Data analysis was performed by normalizing the radioactivity counts (ccpms) to values when 0% represents the non-stimulated receptor and 100% the maximum effect of morphine or DAMGO. Dose-response curves were calculated by non-linear regression in GraphPad Prism 6.0. Mean values±S.E.M. for $EC_{50}$ and $E_{max}$ values were derived from 3-12 individual experiments each done in triplicate.

$G_{i/o}$ Induced cAMP Inhibition:

To measure µOR $G_{i/o}$-mediated cAMP inhibition, HEK293T cells were co-transfected using calcium phosphate in a 1:1 ratio with human µOR and a split-luciferase based cAMP biosensor (pGloSensor™-22F; Promega). For experiments including GRK2 co-expression, cells were transfected with 1 µg/15-cm dish of GRK2. After at least 24 hours, transfected cells were washed with phosphate buffered saline (PBS) and trypsin was used to dissociate the cells. Cells were centrifuged, resuspended in plating media (1% dialyzed FBS in DMEM), plated at a density of 15,000-20,000 cells per 40 µl per well in poly-lysine coated 384-well white clear bottom cell culture plates, and incubated at 37° C. with 5% $CO_2$ overnight. For inactivation of pertussis-toxin (PTX) $G\alpha_{i/o}$ experiments, cells were plated with 100 ng/mL final concentration PTX. The next day, drug dilutions were prepared in fresh assay buffer (20 mM HEPES, 1×HBSS, 0.1% bovine serum album (BSA), and 0.01% ascorbic acid, pH 7.4) at 3× drug concentration. Plates were decanted and 20 µL per well of drug buffer (20 mM HEPES, 1×HBSS, pH 7.4) was added to each well. Drug addition to 384 well plates was performed by FLIPR adding 10 uL of drug per well for a total volume of 30 µL. Plates were allowed to incubate for exactly 15 minutes in the dark at room temperature. To stimulate endogenous cAMP via β adrenergic-$G_s$ activation, 10 µL of 4× isoproterenol (200 nM final concentration) diluted in drug buffer supplemented with GloSensor assay substrate was added per well. Cells were again incubated in the dark at room temperature for 15 minutes, and luminescence intensity was quantified using a Wallac TriLux microbeta (Perkin Elmer) luminescence counter. Data were normalized to DAMGO-induced cAMP inhibition and analyzed using nonlinear regression in GraphPad Prism 6.0 (Graphpad Software Inc., San Diego, Calif.).

Determination of functional activity of PZM21-29 for SAR studies was performed using a BRET-based cAMP accumulation assay. HEK-293T cells were transiently co-transfected with pcDNA3L-His-CAMYEL42 (purchased from ATCC via LCG Standards, Wesel, Germany) and human µOR a cDNA ratio of 2:2 using Mirus TransIT-293 transfection reagent. 24 hours post-transfection, cells were seeded into white half-area 96-well plates at 20×10$^4$ cells/well and grown overnight. On the following day, phenol red free medium was removed and replaced by Phosphate Buffered Saline (PBS) and cells were serum starved for 1 hour before treatment. The assay was started by adding 10 µL coelenterazine h (Progmega, Mannheim, Germany) to each well to yield a final concentration of 5 µM. After 5 minute incubation, compounds were added in PBS containing forskolin (final concentration 10 µM). Reads of the plates started 15 minutes after agonist addition. BRET readings were collected using a CLARIOstar plate reader (BMG LabTech, Ortenberg, Germany). Emission signals from *Renilla* Luciferase and YFP were measured simultaneously using a BRET1 filter set (475-30 nm/535-30 nm). BRET ratios (emission at 535-30 nm/emission at 475-30 nm) were calculated and dose-response curves were fitted by nonlinear regression using GraphPad Prism 6.0. Curves were normalized to basal BRET ratio obtained from dPBS and the maximum effect of morphine and DAMGO. Each curve is derived from three to five independent experiments each done in duplicate.

Calcium Release:

Calcium release was measured using a FLIPR$^{TETRA}$ fluorescence imaging plate reader (Molecular Devices). Calcium release experiments were run in parallel to Gi/o Glosensor experiments with the same HEKT cells transfected with µOR, except cells for FLIPR were plated in poly-lysine coated 384-well black clear bottom cell culture plates. Cells were incubated at 37° C. with 5% $CO_2$ overnight, and next day, media was decanted and replaced with Fluo-4 direct calcium dye (Life Technologies) made up in HBSS with 20 mM HEPES, pH 7.4. Dye was incubated for 1 hour at 37° C. Afterwards, cells were equilibrated to room temperature, and fluorescence in each well was read for the initial 10 seconds to establish a baseline. Afterwards, 10 µL of drug (3×) was added per well and the maximum-fold increase in fluorescence was determined as fold-over-baseline. Drug solutions used for the FLIPR assay were exactly the same as used for Gi/o Glosensor experiments. To activate endogenous $G_q$-coupled receptors as a positive control for calcium release, TFLLR-$NH_2$ (10 µM, PAR-1 selective agonist) was used.

Receptor Internalization:

Internalization was measured using the eXpress DiscoveRx PathHunter GPCR internalization assay utilizing split β-galactosidase complementation. Briefly, cryopreserved U2OS cells expressing the human µOR were thawed rapidly and plated in supplied medium and 96-well culture plates. Next day, cells were stimulated with drugs (10×) and allowed to incubate for 90 minutes at 37° C. with 5% $CO_2$. Afterwards, substrate was added to cells and chemiluminescence was measured on a TriLux (Perkin Elmer) plate counter. Data were normalized to DAMGO and analyzed using Graphpad Prism 6.0.

β-Arrestin Recruitment Assays:

β-Arrestin recruitment was measured by either the PathHunter enzyme complementation assay (DiscoveRx) or by previously described bioluminescence resonance energy transfer (BRET) methods. Assays using DiscoveRx PathHunter eXpress OPRM1 CHO-K1 Beta-Arrestin GPCR Assays were conducted exactly as instructed by the manufacturer. Briefly, supplied cryopreserved cells were thawed and resuspended in the supplied medium, and plated in the furnished 96-well plates. Next day, 10× dilutions of agonist (prepared in HBSS and 20 mM HEPES, pH 7.4) were added to the cells and incubated for 90 minutes. Next, the detection reagents were reconstituted, mixed at the appropriate ratio, and added to the cells. After 60 min, luminescence per well was measured on a TriLux (Perkin-Elmer) plate counter. Data were normalized to DAMGO and analyzed using the sigmoidal dose-response function built into GraphPad Prism 6.0.

To measure µOR mediated β-Arrestin recruitment by BRET in the presence or absence of GRK2 co-expression, HEK293T cells were co-transfected in a 1:1:15 ratio with human µOR containing C-terminal *renilla* luciferase (RLuc8), GRK2, and Venus-tagged N-terminal β-arrestin2, respectively. In the case of experiments where GRK2 expression was varied, pcDNA3.1 was substituted for GRK2 to maintain the same concentration of DNA transfected. After at least 24 hours, transfected cells were plated in poly-lysine coated 96-well white clear bottom cell culture plates in plating media at a density of 125,000-250,000 cells per 200 µl per well and incubated overnight. The next day, media was decanted and cells were washed twice with 60 µL of drug buffer and incubated at room temperature for at least 10 minutes prior to drug stimulation. 30 µL of drug (3λ) was added per well and incubated for at least 30 minutes in the dark. Then, 10 µL of the RLuc substrate, coelenterazine H (Promega, 5 µM final concentration) was added per well, and plates were read for both luminescence at 485 nm and fluorescent eYFP emission at 530 nm for 1 second per well using a Mithras LB940 microplate reader. The ratio of eYFP/RLuc was calculated per well and the net BRET ratio was calculated by substracting the eYFP/RLuc per well from the eYFP/RLuc ratio without Venus-Arrestin present. Data were normalized to DAMGO-induced stimulation and analyzed using nonlinear regression in GraphPad Prism 6.0.

Ligand Bias Calculation:

Multiple approaches have been described to quantitate ligand bias, including operational models, intrinsic relative activity models, and allosteric models. In the absence of GRK2, we observe no β-arrestin2 recruitment for PZM21 and TRV130. This prevents a quantitative assessment of bias by the operational model. In the case where GRK2 is overexpressed, we observe arrestin recruitment for PZM21 and TRV130. In this case, we utilize the operational model to calculate ligand bias and display equiactive bias plots for comparison of ligand efficacy for distinct signaling pathways. The Glosensor $G_{i/o}$, DiscoverX PathHunter β-arrestin, or net BRET concentration response curves were fit to the Black-Leff operational model to determine transduction coefficients ($_T/K_A$). Compound bias factors are expressed after normalization against the prototypical opioid agonist DAMGO used as a reference. Bias factors are expressed as the value of $\Delta\Delta \log(_T/K_A)$.

Assessment of Off-Target PZM21 Activity:

To identify potential off-target activity of PZM21, we utilized the National Institutes of Mental Health Psychoactive Drug Screen Program. Compound PZM21 was first tested for activity against 320 non-olfactory GPCRs using the PRESTO-Tango GPCRome screening β-arrestin recruitment assay. We used 10 µM PZM21 and activity at each receptor was measured in quadruplicate. Potential positive receptor hits were defined as those that increase the relative luminescence value by two fold. Positive hits were subsequently re-tested in full dose-response mode to determine whether the luminescence signal titrates with increasing concentrations of PZM21. A number of false positive hits were discounted by this approach. PZM21 inhibition of hERG channel was performed as described previously[55] and neurotransmitter transporter assays were determined used the Molecular Devices Neurotransmitter Assay Kit (Molecular Devices).

In Vivo Studies:

Adult male C57BL/6J obtained from Jackson Laboratories (Bar Harbor, Me.) were used to investigate behavioral responses, respiratory effects, and hyperlocomotion induced by PZM21 and compared with morphine or vehicle (0.9% sodium chloride). For µOR knockout animals, Oprm1−/− mice (B6.129S2-Oprm1tm1Kff/J) were obtained from Jackson Laboratories. All drugs were dissolved in vehicle and injected subcutaneously. Each study incorporated more than 7 mice. Behavioral studies were conducted at the University of North Carolina following the National Institutes of Health's guidelines for care and use of animals and with approved mouse protocols from the institutional animal care and use committees.

Measurement of Analgesia:

Analgesia-like responses in were measured as previously described using a hotplate analgesia meter with dimensions of 29.2×26.7 cm with mice restricted to a cylinder 8.9 cm in diameter and 15.2 cm high (IITC Life Sciences, Woodland Hills, Calif.). Response was measured by recording the latency to lick, flutter, or splay hind paw(s), or an attempt to jump out of the apparatus at 55° C., with a maximum cutoff time of 30 s. Once a response was observed or the cutoff time had elapsed, the subject was immediately removed from the hotplate and placed back in its home cage. The animals were acclimated to the hotplate, while cool, and a baseline analgesic response time was acquired several hours before drug treatment and testing. Mice were injected with either vehicle, morphine (5 mg/kg or 10 mg/kg), TRV130 (1.2 mg/kg) or PZM21 (10 mg/kg, 20 mg/kg, or 40 mg/kg). After injection of drug, the analgesic effect expressed as percentage maximum possible effect (% MPE) was measured at 15, 30, 60, 90, and 120 minutes after drug treatment. If animals did not display hind paw lick, splay, or flutter, they were removed from the trial. Additionally, if animals attempted to jump out of the plate or urinated on the hotplate they were removed from the trial. To assess analgesia by the tail-flick assay, a tail flick analgesia meter (Columbus Instruments, Columbus, Ohio). Mice were gently immobilized with a cotton towel and the tail base was placed on a radiant light source emitting a constant temperature of 56° C. The tail withdrawal latency was measured at similar time points as the hot-plate assay after administration of vehicle, morphine or PZM21. The cutoff time for the heat source was set at 10 seconds to avoid tissue damage. Analgesic response times were measured similar to the hot plate assay.

Analgesia in µOR knockout mice and subcategorization of affective/reflexive pain: Oprm1−/− and wild-type C57Bl/6J mice (male; 8-11 weeks) were acclimated to the testing environment and thermal-plate equipment for three non-consecutive days between 11 A.M. and 1 P.M. prior to any pharmacological studies. Acclimation was achieved by individually confining mice within an enclosed semi-transparent red plastic cylinder (10 cm D×15 cm H) on a raised metal-mesh rack (61 cm H) for 30 minutes, and then exposing each mouse to the thermal-plate equipment (non-heated; floor dimensions, 16.5×16.5 cm; Bioseb), while confined within a clear plastic chamber (16 L×16 W×30 H cm). Acclimation exposure to the thermal plate lasted for 30 seconds, and exposure was repeated after 30 minutes to mimic the test day conditions. The testing environment had an average ambient temperature of 22.6° C. and illumination of 309 lux from overhead fluorescence lighting. The same male experimenter (G.C.) was present throughout the entire duration of habituation and testing to exclude possible olfaction-induced alterations in sensory thresholds.

Cutaneous application of a noxious stimulus, or time spent on a hot plate apparatus can broadly elicit several distinct behavioral responses: 1. Withdrawal reflexes: rapid reflexive retraction or digit splaying of the paw, 2. Affective-motivational responses: directed licking and biting of the paw, and/or a motivational response characterized by jumping away from the heated floor plate. Paw withdrawal reflexes are classically measured in studies of hypersensitivity, and involve simple spinal cord and brainstem circuits. In contrast, affective responses are complex, non-stereotyped behaviors requiring processing by limbic and cortical circuits in the brain, the appearance of which indicates the subject's motivation and arousal to make the unpleasant sensation cease by licking the affected tissue, or seeking an escape route. To distinguish between potential differential analgesic effects of PZM21, mice were placed on the heated apparatus (52.5° C.), and the latency to exhibition of the first sign of a hindpaw reflexive withdraw, and the first sign of an affective response was recorded. A maximum exposure cutoff of 30 seconds was set to reduce tissue damage. Mice were injected with either vehicle, morphine (10 mg/kg), or PZM21 (20 mg/kg). After injection of drug, the analgesic effect on either reflex or attending responses was expressed as percentage maximum possible effect (% MPE), and was measured at −30 (baseline), 15, 30, 60, 90, 120, and 180 minutes relative to drug treatment.

Formalin Injection Assay:

Analgesia to formalin injection was carried out as described previously[66]. Mice were first habituated for 20 minutes to the testing environment which included a home cage without bedding, food, and water. After habituation, vehicle, morphine (10 mg/kg), or PZM21 (40 mg/kg) was injected subcutaneously. This was followed by injection of 20 µL of 1% formalin in 0.9% saline under the skin of the dorsal surface of the right hindpaw. Animals were returned to their home cage and behavioral responses were recorded for one hour. Nociception was estimated by measuring the cumulative time spent by animals licking the formalin-injected paw. As opioids classically display two phases of analgesic action, nociceptive behavior was measured during both the early phase (0 to 5 minutes) and the late phase (20 to 30 minutes).

Mouse Plethysmography:

Respiration data was collected using a whole body plethysmography system (Buxco Electronics Inc, Wilmington, N.C.) as described[67]. This method measures respiratory frequency, tidal volume, peak flows, inspiratory time, and expiratory time in conscious and unrestrained mice. Briefly, Buxco airflow transducers were attached to each plethysmography chamber and a constant flow rate was maintained for all chambers. Each chamber was calibrated to its attached transducer prior to the experiment. Animals were first habituated to the clear plexiglass chambers for 10 minutes. Respiratory parameters were recorded for 10 minutes to establish a baseline prior to injection of vehicle, morphine (10 mg/kg), TRV130 (1.2 mg/kg) or PZM21 (20 mg/kg or 40 mg/kg). Respiratory parameters were then collected on unrestrained mice for 100 minutes post drug injection. To decrease respiratory variability induced by anxiety, mice were shielded from view of other animals and experimenter.

Accumulated Fecal Boli Quantification:

To measure constipatory effects of morphine and PZM21, we assessed the total accumulated fecal boli as described previously. Briefly, mice were injected with vehicle, morphine (10 mg/kg) or PZM21 (20 mg/kg) and placed within a plexiglass chamber (5 cm×8 cm×8 cm) positioned on a mesh screen. Mice were maintained without food or water for 6 hours. Fecal boli were collected underneath the mesh on a paper towel and the cumulative mass was measured every hour for six hours.

Open Field Locomotor Response:

A photocell-equipped automated open field chamber (40 cm×40 cm×30 cm; Versamax system, Accuscan Instruments) contained inside sound-attenuating boxes was used to assess locomotor activity. Baseline ambulation of freely moving mice was monitored over 30 minutes, followed by injection with vehicle, morphine (10 mg/kg) or PZM21 (20 mg/kg). Locomotor activity was monitored for another 150 minutes.

Conditioned Place Preference:

A three-chambered conditioned place preference apparatus (Med-Associates, St. Albans, Vt.) consisting of white or black chambers (16.8×12.7×12.7 cm each) with uniquely textured white mesh or black rod floors and separated by a neutral central chamber (7.2×12.7×12.7 cm) was used for conditioned place preference testing. On day 1 (preconditioning day), mice were placed in the central chamber and allowed to explore freely for 30 minutes. Time spent in each compartment was used to estimate baseline chamber preferences and mice showing specific chamber bias more than 70% were not studied further. On days 2-9 (conditioning days) mice were injected with either vehicle or drug and paired with either the white mesh or the black rod chambers.

All mice received vehicle on days 2, 4, 6, 8 and drug on days 3, 5, 7, 9. On day 10 (test day), mice were again placed in the central chamber as on day 1 and allowed to explore freely for 30 minutes. Time spent in each chamber was expressed as percentage preference.

Cataleptic Effect:

Drug induced catalepsy was measured in mice using the bar test, which includes a horizontally placed 3 mm diameter wooden bar fixed 4 cm above the floor. Mice were habituated with the bar and the environment for 20 minutes before subcutaneous injection of either haloperidol (2 mg/kg), morphine (10 mg/kg), or PZM21 (20 mg/kg). To measure catalepsy, both forepaws were gently placed on the bar and the length of time during which each mouse remained in the initial position was measured. The effect was measured at 15, 30 and 90 minutes after drug injection. Maximum cut-off time for each challenge was 90 seconds.

Pharmacokinetics of PZM21:

Studies were performed by the Preclinical Therapeutics Core and the Drug Studies Unit at the University of California San Francisco. Ten mice were injected subcutaneously with 20 mg/kg of PZM21. At each time point, 1 mL of blood was collected from three mice and the serum concentration of PZM21 determined by liquid chromatography-mass spectrometry (LC/MS). Mice were subsequently sacrificed and entire brains were homogenized for determination of PZM21 concentrations by LC/MS. All studies were performed with approved mouse protocols from the institutional animal care and use committees.

Metabolism of PZM21:

Metabolism experiments were performed as described previously. In brief, pooled microsomes from male mouse liver (CD-1) were purchased (Sigma Aldrich) and stored at −75° C. until required. NADPH was purchased (Carl Roth) and stored at −8° C. The incubation reactions were carried out in polyethylene caps (Eppendorf, 1.5 mL) at 37° C. The incubation mixture contained PZM21 (80 µM) or positive controls (imipramine and rotigotine), pooled liver microsomes (0.5 mg of microsomal protein/mL of incubation mixture) and Tris-$MgCl_2$ buffer (48 mM Tris, 4.8 mM $MgCl_2$, pH 7.4). The final incubation volume was 0.5 mL. Microsomal reactions were initiated by addition of 50 µL of enzyme cofactor solution NADPH (final concentration of 1 mM). At 0, 15, 30 and 60 min the enzymatic reactions were terminated by addition of 500 µL of ice-cold acetonitrile (containing 8 µM internal standard), and precipitated protein was removed by centrifugation (15,000 rcf for 3 min). The supernatant was analyzed by HPLC/MS (binary solvent system, eluent acetonitrile in 0.1% aqueous formic acid, 10-40% acetonitrile in 8 min, 40-95% acetonitrile in 1 min, 95% acetonitrile for 1 min, flow rate of 0.3 mL/min). The experiments were repeated in three independent experiments. Parallel control incubations were conducted in the absence of cofactor solution to determine unspecific binding to matrix. Substrate remaining and metabolite formation was calculated as a mean value±SEM of three independent experiments by comparing AUC of metabolites and substrate after predetermined incubation time to AUC of substrate at time 0, estimating a similar ionization rate, corrected by a factor calculated from the AUC of internal standard at each time point.

Chemical Synthesis:

The stereochemically pure isomers of 12 and PZM21 were synthesized from corresponding (R)- and (S)-amino acid amides, which were either commercially available or readily prepared from the corresponding acid or ester (see Example 2). The primary amino group was dimethylated using an excess of aqueous formaldehyde and sodium triacetoxyborohydride in aqueous acetonitrile. The carboxamides 16a,b were converted to primary amines by treatment with borane-tetrahydrofurane complex under reflux yielding the diamines 17a,b. Henry reaction of thiophene-3-carbaldehyde with nitroethane afforded the nitropropene derivative 18, which was converted into the racemic alkylamine 19. Activation with 4-nitrophenyl chloroformate yielded the carbamates 20, which were coupled with the enantiopure primary amines 17a,b to achieve diastereomeric mixtures of the corresponding ureas 12 and 21. HPLC separation using a semi-preparative Chiralpak AS-H column gave the overall eight pure stereoisomers of 12 and 21 including PZM21.

To determine the absolute configuration of the final products and efficiently prepare PZM21, we synthesized enantiomerically enriched carbamate 20, coupled it with the corresponding primary amines. For enantiomeric enrichment, we performed chiral resolution of the racemic primary amine 19 via repetitive crystallization with di-p-anisoyl-(S)-tartaric acid. After triple crystallization, we obtained 19 enriched in dextrorotatory enantiomer ($[\alpha]_D^{25}$=+20.5 0). The corresponding (R)-acetamide has been previously characterized as dextrorotatory ($[\alpha]_D^{20}$=+49.8°), so enantiomerically enriched 19 was treated with acetic anhydride and triethylamine, and the specific rotation of the product was measured. Based on the value of specific rotation of the resulting acetamide ($[\alpha]_D^{21}$=−46.6°), we assigned the absolute configuration of the major isomer to be (S). (S)-enriched 20 was used for synthesis of the final urea derivatives and absolute configuration of diastereomers in pairs was assigned based on the equality of retention time in chiral HPLC. A full description of the synthetic routes and analytical data of the compounds 12, PZM21 and its analogs PZM22-29 are presented in Example 2.

Detailed Modeling of PZM21 and TRV130 Binding Poses:

PZM21 was docked to the inactive state µOR structure using DOCK3.6 as described for the primary screen, with the exception that the forty-five matching spheres used were generated based on the docked pose of compound 12. The resulting ligand-receptor complex was further optimized through minimization with the AMBER protein force field and the GAFF ligand force field supplemented with AM1-BCC charges. Docking of PZM21 and TRV130 to the active state OR structure (PDB: 5C1M) was also performed with DOCK3.6 with parameters as described above. The amino-terminus of the active state OR, which forms a lid over the orthosteric binding site (residues Gly52-Met65) was removed prior to receptor preparation. Matching spheres were generated based on the pose of PZM21 in the inactive state. The resulting complexes were then minimized with AMBER. PZM21's pose in the active state µOR structure was further refined using Glide (Schrödinger) in XP mode.

Molecular dynamics simulations were based on crystal structures of µOR in the inactive- and active-state conformation (PDB: 4DKL and 5CM1, respectively). In both cases, all non-receptor residues (T4 lysozyme in the inactive state and Nb39 in the active state) were removed. For the active state, amino-terminal residues were removed as for docking studies above. Initial coordinates of PZM21 were generated by molecular docking as described above. The receptor was simulated with two tautomers of $His297^{6.52}$, either in the neutral Ndelta or the Neplison state. The µOR-PZM21 complex was embedded in a lipid bilayer consisting of dioleoylphosphatidylcholine (DOPC) molecules as described previously. The charges of the inactive- and active-state simulation systems were neutralized by adding 11 and 14 chloride ions, respectively. To carry out MD simulations, the GROMACS simulation package was used as described previously. Briefly, the general AMBER force field (GAFF) was used for PZM21 and the lipids and the AMBER force field ff99SB for the receptor. Parameters for PZM21 were assigned using antechamber, and charges were calculated using Gaussian09 (Gaussian, Inc.) at the HF/6-31(d,p) level and the RESP procedure according to the literature. During the simulations, PZM21 was protonated at its tertiary amine and simulated as a cation. The SPC/E water model was used, and the simulations were carried out at 310 K. Analysis of the trajectories was performed using the GROMACS simulation package. Each simulation in a given condition was initiated from identical coordinates, but with initial atom velocities assigned independently and randomly. An overview of the simulation systems and their simulation times is shown in Example 2.

TABLE 4

Receptor binding and activation data—opioid receptor ligands

| compound | humanDOR [3H]dyprenorphine | hKOR [3H]dyprenorphine | hMOR [3H]dyprenorphine | hMOR + $G_{qi5}$ IP accumulation assay |
|---|---|---|---|---|
| phenyl substituted ligands | | | | |

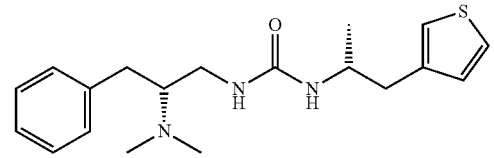

BD 127 DR

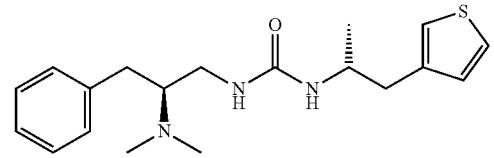

BD 127 DS

| BD 127DR 33446 | (2) 12000 ± 15000 | (2) 5000 ± 2700 | | (2) 2900 ± 1500 |
| BD 127DS 33445 | (2) 11000 ± 8800 | (2) 3100 ± 280 | | (2) 2400 ± 2000 |

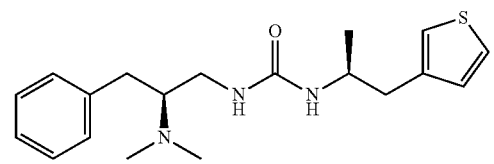 [SMILES: C[C@@H](Cc1ccsc1)NC(=O)NC[C@H](Cc1ccccc1)N(C)C]

BD 127 LR

BD 127 LS (S,S)-12
120 nM MOR agonist

| BD 127LR 33448 | (3) 1800 ± 150 | (3) 1300 ± 300 | | (3) 380 ± 96 |
| BD 127LS | (2) 2800 ± 1800 | (2) 1000 ± 520 | | (2) 140 ± 84 |

TABLE 4-continued
Receptor binding and activation data—opioid receptor ligands
| compound | humanDOR [3H]dyprenorphine | hKOR [3H]dyprenorphine | hMOR [3H]dyprenorphine | hMOR + $G_{qi5}$ IP accumulation assay |
|---|---|---|---|---|
| 33447 | | | | |
4-hydroxyphenyl substituted ligands
(23)
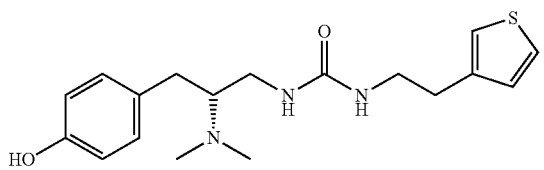
DD 16
58 nM MOR agonist
| DD 16 | (3) 330 ± 160 | (3) 150 ± 35 | (6) 43 ± 11 | |
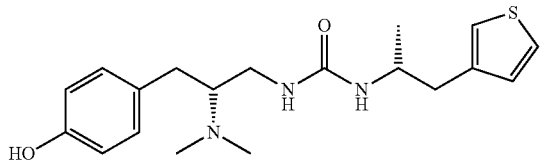
BD 122 DR
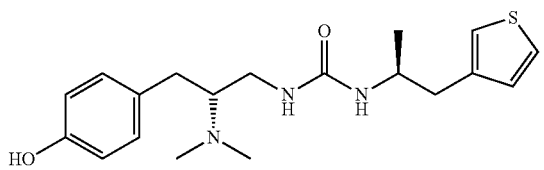
BD 122 DS
| BD 122DR 33175 | (2) 4100 ± 2200 | (2) 3100 ± 280 | (2) 290 ± 150 | |
| BD 122DS 33176 | (2) 4800 ± 3300 | (2) 2300 ± 2300 | (2) 480 ± 57 | |
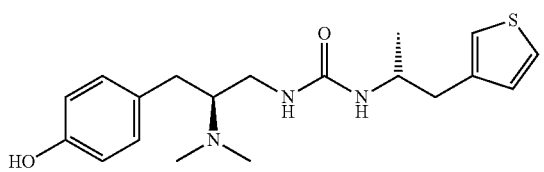
BD 122 LR
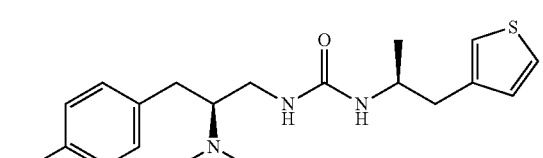
BD 122 LS
(S,S)-21
| BD 122LR 33444 | (4) 88 ± 16 | (4) 190 ± 23 | (4) 42 ± 11 | (2) $EC_{50}$: 47 nM a: 17% |
| BD 122LS 33443 | (3) 470 ± 98 | (3) 33 ± 5.6 | (3) 36 ± 8.2 | (3) $EC_{50}$: 37 nM a: 73% |

TABLE 4-continued

Receptor binding and activation data—opioid receptor ligands

| compound | humanDOR [3H]dyprenorphine | hKOR [3H]dyprenorphine | hMOR [3H]dyprenorphine | hMOR + $G_{qi5}$ IP accumulation assay |
|---|---|---|---|---|

DD 61L-A

DD 61L-B

| DD 61L-A | (2) 91 ± 28 | (2) 67 ± 23 | (2) 81 ± 18 | |
| DD 61L-B | (2) 360 ± 64 | (2) 37 ± 26 | (2) 42 ± 5.0 | |

DD 63LR

DD 63LS

| DD 63L-RS diastereomeric mixture | (2) 44 ± 1.4 | (2) 14 ± 0.71 | (2) 16 ± 1.4 | |

DD 53 LS

DD 51 LS

| DD 53LS | (2) 180 ± 71 | (2) 22 ± 13 | (2) 28 ± 18 | |
| DD 51LS | (3) 700 ± 150 | (3) 180 ± 47 | (3) 150 ± 11 | |

TABLE 4-continued

Receptor binding and activation data—opioid receptor ligands

| compound | humanDOR [3H]dyprenorphine | hKOR [3H]dyprenorphine | hMOR [3H]dyprenorphine | hMOR + $G_{qi5}$ IP accumulation assay |
|---|---|---|---|---|

*[Structure of DD 50 LS]*

*[Structure of DD 57L]*

| DD 50LS | (3) 570 ± 270 | (3) 71 ± 17 | (3) 84 ± 20 | |
| DD 57L | (2) 74 ± 51 | (2) 40 ± 9.2 | (2) 8.3 ± 3.8 | |

*[Structure of DD 32L]*

*[Structure of DD 33L]*

| DD 32L | (4) 650 ± 130 | (4) 46 ± 5.3 | (4) 38 ± 8.9 | |
| DD 33L | (3) 920 ± 240 | (3) 91 ± 14 | (3) 46 ± 11 | |

3-hydroxyphenyl substituted ligands

*[Structure of DD 47 LS]*

*[Structure of DD 46L]*

| DD 47LS | (4) 350 ± 78 | (4) 46 ± 6.7 | (4) 34 ± 2.2 | |
| DD 46L | (3) 190 ± 12 | (3) 32 ± 4.3 | (3) 25 ± 9.0 | |

TABLE 4-continued

Receptor binding and activation data—opioid receptor ligands

| compound | humanDOR [3H]dyprenorphine | hKOR [3H]dyprenorphine | hMOR [3H]dyprenorphine | hMOR + $G_{qi5}$ IP accumulation assay |
|---|---|---|---|---|
| 2,6-dimethyl-4-hydroxyphenyl substituted ligands | | | | |

DD 34L

| DD 34L | (3) 51 ± 4.8 | (3) 27 ± 3.2 | (3) 6.2 ± 0.85 | (2) $EC_{50}$: — nM a: <5% |

(22)

BD 131 LR

BD 131 LS

| BD 131LR | (4) 17 ± 6.5 | (4) 12 ± 0.90 | (4) 4.1 ± 0.97 | (2) $EC_{50}$: — nM @ 10 μM a: 10% |
| BD 131LS | (3) 85 ± 30 | (3) 6.5 ± 2.1 | (3) 12 ± 1.7 | (2) $EC_{50}$: — nM a: <5% |

| hydroxypyridyl substituted ligands | | | | |

DD xxy

DD xxz

| DD xxy | | | | |
| DD xxz | | | | |

$K_i$ values [nM±SD] for two individual experiments or $K_i$ in [nM±SEM] derived from (n) independent experiments all done in triplicate. $EC_{50}$ [nM] and efficacy a [% morphine] from combined curves derived from IP accumulation experiments (n) in triplicate.

TABLE 5A

| Assay | Compound | | | | | | | | |
|---|---|---|---|---|---|---|---|---|---|
| | DAMGO | PZM21 | DD90 | DD184 | DD108 | DD102 | DD109 | DD63L-B | DD61L-B |
| Arrestin EC50 nM | 353 | 91.96 | 53.46 | No Activity | 4713 | 1984 | No Activity | 397.2 | 84.09 |
| Arrestin pEC50 | 6.45 | 7.036 | 7.272 | N/D | 5.327 | 5.703 | N/D | 6.401 | 7.075 |
| Arrestin pEC50 SEM | 0.05 | 0.1901 | 0.3081 | N/D | 0.05503 | 0.1039 | N/D | 0.09686 | 0.187 |
| Arrestin Emax % DAMGO | 100 | 15 | 5 | No Activity | 120 | 30 | No Activity | 38 | 12 |
| Arrestin Emax SEM | 2.8 | 1.307 | 0.6839 | N/D | 6.78 | 2.483 | N/D | 2.034 | 0.9993 |
| Arrestin + GRK2 EC50 nM | 42 | 107.5 | 144.3 | No Activity | 1491 | 1499 | No Activity | 82.06 | 278.1 |
| Arrestin + GRK2 pEC50 | 7.37 | 6.969 | 6.841 | N/D | 5.826 | 5.824 | N/D | 7.086 | 6.556 |
| Arrestin + GRK2 pEC50 SEM | 0.04 | 0.06272 | 0.09356 | N/D | 0.02826 | 0.06056 | N/D | 0.04359 | 0.06909 |
| Arrestin + GRK2 Emax % DAMGO | 100 | 76 | 31 | No Activity | 118 | 61 | No Activity | 92 | 79 |
| Arrestin + GRK2 Emax SEM | 1.7 | 2.205 | 1.404 | N/D | 2.441 | 2.711 | N/D | 2.1 | 2.874 |
| Gi/o EC50 nM | 3.16 | 10.12 | 4.252 | 558.6 | 35.07 | 37.93 | No Activity | 5.697 | 35.46 |
| Gi/o pEC50 | 8.50 | 7.995 | 8.371 | 6.253 | 7.455 | 7.421 | N/D | 8.244 | 7.45 |
| Gi/o pEC50 SEM | 0.09 | 0.1518 | 0.09051 | 0.3179 | 0.1215 | 0.1012 | N/D | 0.06386 | 0.1509 |
| Gi/o Emax % DAMGO | 100 | 74 | 76 | 40 | 86 | 76 | No Activity | 88 | 84 |
| Gi/o Emax SEM | 2.9 | 4.178 | 2.392 | 7.081 | 4.292 | 3.203 | N/D | 1.995 | 4.56 |

N/D: Not Determined

TABLE 5B

| Assay | Cmpd No. | | | | | | | | |
|---|---|---|---|---|---|---|---|---|---|
| | DD88B | DD47 LS | DD131 | DD16 | DD32L | DD33L | DD81 | DD53LS | DD57L |
| Arrestin EC50 nM | 15.48 | 357.5 | 229.7 | 410 | 5.227 | No Activity | 24.91 | 67.92 | No Activity |
| Arrestin pEC50 | 7.81 | 6.447 | 6.639 | 6.387 | 8.282 | N/D | 7.604 | 7.168 | N/D |
| Arrestin pEC50 SEM | 0.3934 | 0.1681 | 0.1864 | 0.3349 | 0.7404 | N/D | 0.4664 | 0.3609 | N/D |
| Arrestin Emax % DAMGO | 5 | 12 | 11 | 5 | 3 | No Activity | 3 | 5 | No Activity |
| Arrestin Emax SEM | 0.754 | 1.059 | 1.03 | 1.016 | 0.6845 | N/D | 0.5225 | 0.8031 | N/D |
| Arrestin + GRK2 EC50 nM | 100.8 | 210.9 | 213.4 | 143.6 | 49.39 | 133.7 | 67.07 | 87.36 | No Activity |
| Arrestin + GRK2 pEC50 | 6.997 | 6.676 | 6.671 | 6.843 | 7.306 | 6.874 | 7.173 | 7.059 | N/D |
| Arrestin + GRK2 pEC50 SEM | 0.09398 | 0.07638 | 0.0846 | 0.09999 | 0.1503 | 0.1712 | 0.1367 | 0.09247 | N/D |
| Arrestin + GRK2 Emax % DAMGO | 45 | 70 | 45 | 33 | 24 | 14 | 27 | 33 | No Activity |
| Arrestin + GRK2 Emax SEM | 1.94 | 2.714 | 1.932 | 1.598 | 1.522 | 1.152 | 1.636 | 1.359 | N/D |
| Gi/o EC50 nM | 9.239 | 16.98 | 7.94 | 7.554 | 23.49 | 98.06 | 15.11 | 3.078 | No Activity |
| Gi/o pEC50 | 8.034 | 7.77 | 8.1 | 8.122 | 7.629 | 7.008 | 7.821 | 8.512 | N/D |
| Gi/o pEC50 SEM | 0.1238 | 0.1336 | 0.1918 | 0.1493 | 0.1864 | 0.2297 | 0.4286 | 0.1265 | N/D |
| Gi/o Emax % DAMGO | 67 | 73 | 57 | 60 | 52 | 61 | 22 | 63 | No Activity |
| Gi/o Emax SEM | 3.062 | 3.768 | 3.987 | 3.222 | 3.831 | 5.569 | 3.508 | 2.715 | N/D |

N/D: Not Determined

TABLE 5C

Ligands for Table 5A and 5B.

DAMGO

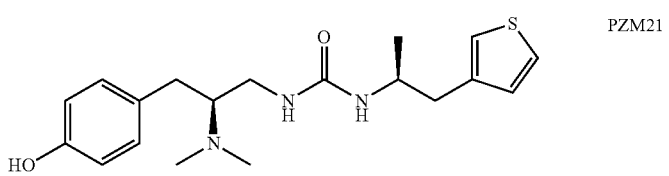

PZM21

TABLE 5C-continued
Ligands for Table 5A and 5B.
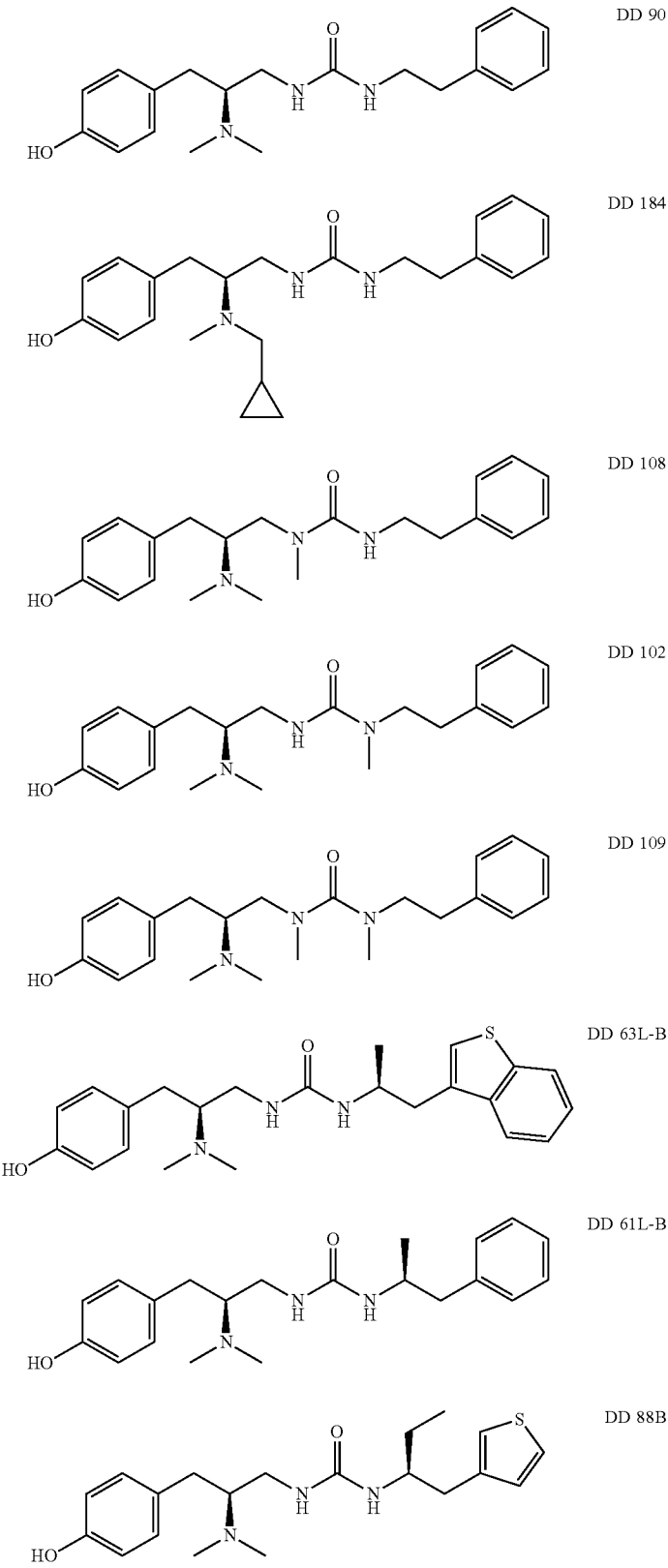

TABLE 5C-continued
Ligands for Table 5A and 5B.
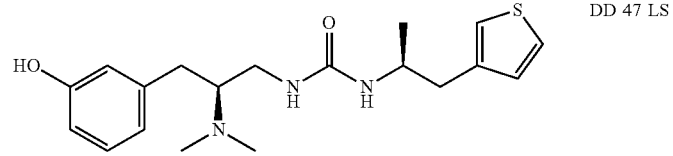
DD 47 LS
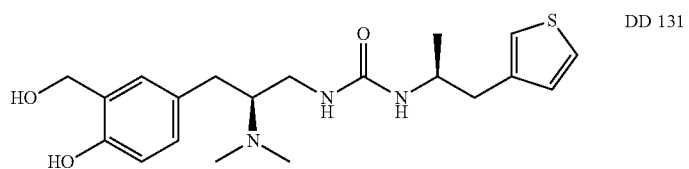
DD 131
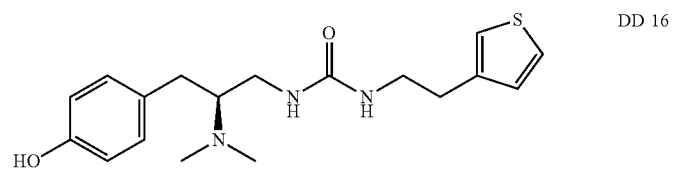
DD 16
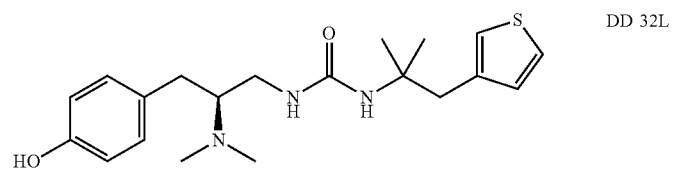
DD 32L
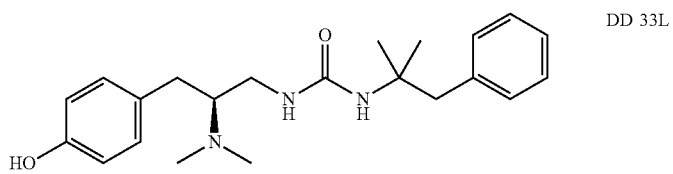
DD 33L
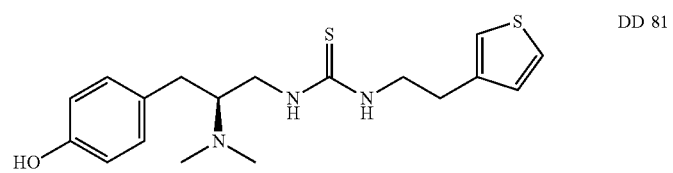
DD 81
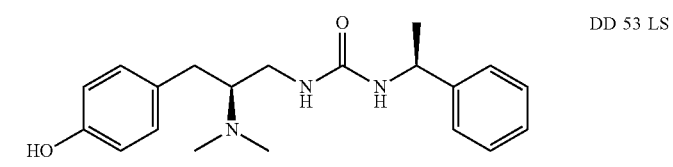
DD 53 LS
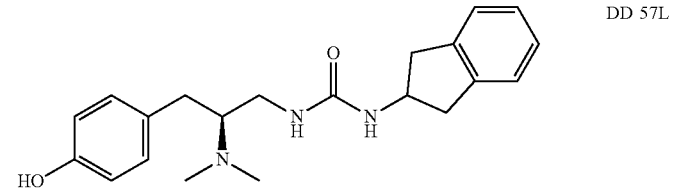
DD 57L

Example 4. Additional Characterization and Syntheses

Method A: General Method for Synthesis of Urea Compounds

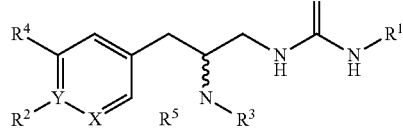

Compound 35 ($R^2$=OH, $R^3$=R=CH$_3$, $R^4$=H, X=Y=C) [or (R)-17a ($R^2$=H, $R^3$=$R^5$=CH$_3$, $R^4$=H, X=Y=C)/(S)-17a ($R^2$=H, $R^3$=$R^5$=CH$_3$, $R^4$=H, X=Y=C)/(R)-17b ($R^2$=OH, $R^3$=$R^5$=CH$_3$, $R^4$=H, X=Y=C), (S)-DD45 ($R^2$=H, $R^3$=$R^5$=CH$_3$, $R^4$=OH, X=Y=C), (S)-DD74 ($R^3$=$R^5$=CH$_3$, $R^4$=OH, X=C, Y=N), (S)-DD76 ($R^2$=OH, $R^3$=$R^5$=CH$_3$, $R^4$=H, X=N, Y=C), (S)-DD122 ((S)-3-(2,2-dimethyl-4H-benzo[d][1,3]dioxin-6-yl)-$N^2$,$N^2$-dimethylpropane-1,2-diamine), (S)-DDLM18 ((S)-3-(2,2-dimethylbenzo[d][1,3]dioxol-5-yl)-$N^2$,$N^2$-dimethylpropane-1,2-diamine), (S)-DDLM12 ((S)-4-(3-amino-2-(pyrrolidin-1-yl)propyl)phenol), (S)-DD195 ($R^2$=OH, $R^3$=H, R=CH$_3$, $R^4$=H, X=Y=C), 36 ($R^2$=OH, $R^3$=Bn, $R^5$=CH$_3$, $R^4$=H, X=Y=C), (S)-DD199 ($R^2$=OH, $R^3$=H, $R^5$=Fmoc, $R^4$=H, X=Y=C)] (1.2 eq) was suspended in dry DMF in a microwave tube. Triethylamine (0.6 eq) and 4-nitrophenyl-$R^1$-carbamate (1 eq) were added and the mixture was stirred at room temperature under argon atmosphere for 3-20 hours. Then, the solution was diluted with isopropanol/EtOAc (1:3) and washed with a saturated aqueous solution of NaHCO$_3$. The organic layer was extracted with 0.1N HCl-solution and the aqueous extracts were adjusted to pH 9 with saturated aqueous NaHCO$_3$/Na$_2$CO$_3$ solution and finally extracted with EtOAc. The organic layers were dried (Na$_2$SO$_4$), filtered and concentrated under reduced pressure. The residue was purified by preparative HPLC giving the corresponding formates or trifluoroacetates.

Compounds Synthesized Following Method A (S)-1-(2-(dimethylamino)-3-phenylpropyl)-3-(2-(thiophen-3-yl)ethyl)urea (DD18)

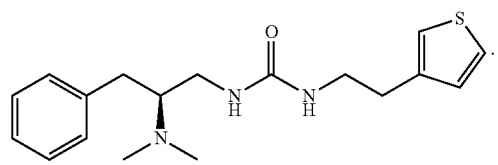 [SMILES: CN(C)[C@H](CNC(=O)NCCc1ccsc1)Cc1ccccc1]

Yield: 42%. LCMS (ESI+): $t_R$=14.0-14.3 min, m/z found 332.7, m/z calcd 332.2 [M+H]$^+$.

(R)-1-(2-(dimethylamino)-3-phenylpropyl)-3-(2-(thiophen-3-yl)ethyl)urea (DD17)

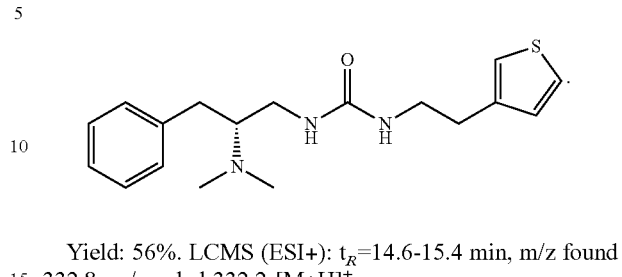

Yield: 56%. LCMS (ESI+): $t_R$=14.6-15.4 min, m/z found 332.8, m/z calcd 332.2 [M+H]$^+$.

(S)-1-(2-(dimethylamino)-3-(4-hydroxyphenyl)propyl)-3-(2-(thiophen-3-yl)ethyl)urea (DD16)

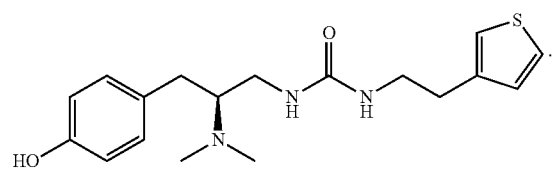 [SMILES: CN(C)[C@H](CNC(=O)NCCc1ccsc1)Cc1ccc(O)cc1]

Yield: 40%. LCMS (ESI+): $t_R$=14.0-14.3 min, m/z found 348.8, m/z calcd 348.2 [M+H]$^+$.

(R)-1-(2-(dimethylamino)-3-(4-hydroxyphenyl)propyl)-3-(2-(thiophen-3-yl)ethyl)urea (DD15)

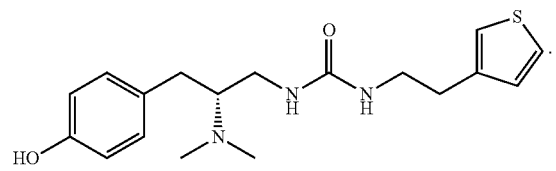 [SMILES: CN(C)[C@@H](CNC(=O)NCCc1ccsc1)Cc1ccc(O)cc1]

Yield: 47%. LCMS (ESI+): $t_R$=13.3-14.2 min, m/z found 348.7, m/z calcd 348.2 [M+H]$^+$.

(S)-1-(2-(dimethylamino)-3-(4-hydroxyphenyl)propyl)-3-(2-methyl-1-(thiophen-3-yl)propan-2-yl)urea (DD32L)

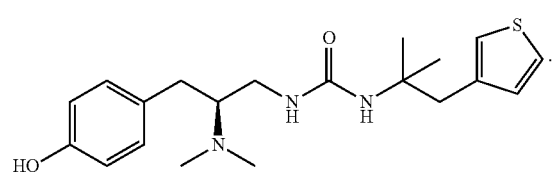 [SMILES: CN(C)[C@H](CNC(=O)NC(C)(C)Cc1ccsc1)Cc1ccc(O)cc1]

Yield: 50%. LCMS (ESI+): $t_R$=9.5-9.8 min, m/z found 376.7, m/z calcd 376.2 [M+H]$^+$.

191

(R)-1-(2-(dimethylamino)-3-(4-hydroxyphenyl)propyl)-3-(2-methyl-1-(thiophen-3-yl)propan-2-yl)urea (DD32D)

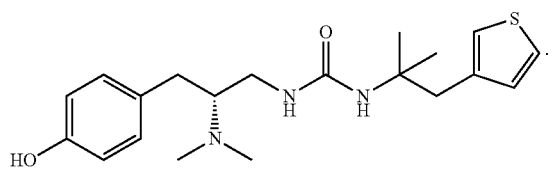 [SMILES: CN(C)[C@@H](CNC(=O)NC(C)(C)Cc1ccsc1)Cc1ccc(O)cc1]

Yield: 54%. LCMS (ESI+): $t_R$=1.2-15.8 min, m/z found 376.7, m/z calcd 376.2 [M+H]$^+$.

(S)-1-(2-(dimethylamino)-3-phenylpropyl)-3-(2-methyl-1-(thiophen-3-yl)propan-2-yl)urea (DD35L)

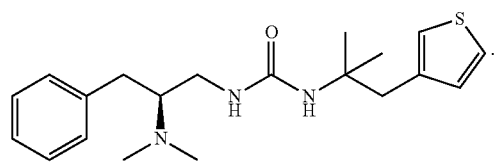 [SMILES: CN(C)[C@H](CNC(=O)NC(C)(C)Cc1ccsc1)Cc1ccccc1]

Yield: 56%. LCMS (ESI+): $t_R$=15.1-16.8 min, m/z found 360.7, m/z calcd 360.2 [M+H]$^+$ (R)-1-(2-(dimethylamino)-3-phenylpropyl)-3-(2-methyl-1-(thiophen-3-yl)propan-2-yl)urea (DD35D)

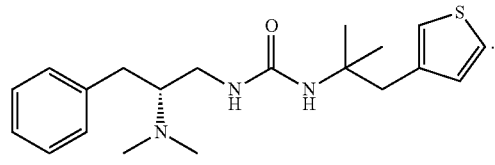 [SMILES: CN(C)[C@@H](CNC(=O)NC(C)(C)Cc1ccsc1)Cc1ccccc1]

Yield: 45%. LCMS (ESI+): $t_R$=15.2-17.0 min, m/z found 360.8, m/z calcd 360.2 [M+H]$^+$.

(S)-1-(2-(dimethylamino)-3-(4-hydroxyphenyl)propyl)-3-(2-methyl-1-phenylpropan-2-yl)urea (DD33L)

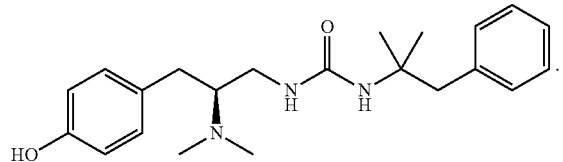 [SMILES: CN(C)[C@H](CNC(=O)NC(C)(C)Cc1ccccc1)Cc1ccc(O)cc1]

Yield: 27%. LCMS (ESI+): $t_R$=15.2-16.0 min, m/z found 370.8, m/z calcd 370.2 [M+H]$^+$.

192

(R)-1-(2-(dimethylamino)-3-(4-hydroxyphenyl)propyl)-3-(2-methyl-1-phenylpropan-2-yl)urea (DD33D)

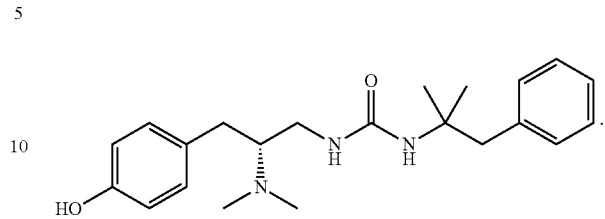

Yield: 17%. LCMS (ESI+): $t_R$=13.6-14.8 min, m/z found 370.8, m/z calcd 370.2 [M+H]$^+$.

(S)-1-(2-(dimethylamino)-3-phenylpropyl)-3-(2-methyl-1-phenylpropan-2-yl)urea (DD36L)

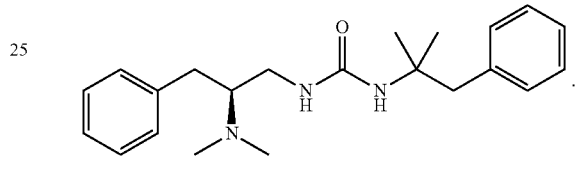

Yield: 48%. LCMS (ESI+): $t_R$=17.4-18.2 min, m/z found 354.6, m/z calcd 354.3 [M+H]$^+$.

(R)-1-(2-(dimethylamino)-3-phenylpropyl)-3-(2-methyl-1-phenylpropan-2-yl)urea (DD36D)

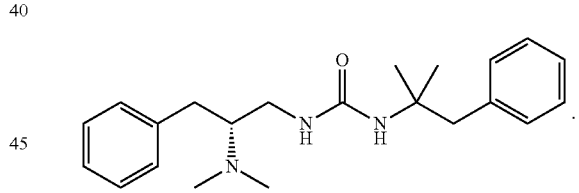

Yield: 23%. LCMS (ESI+): $t_R$=16.6-17.8 min, m/z found 354.9, m/z calcd 354.3 [M+H]$^+$ 1-((S)-2-(dimethylamino)-3-(3-hydroxyphenyl)propyl)-3-((S)-1-(thiophen-3-yl)propan-2-yl)urea (DD47LS)

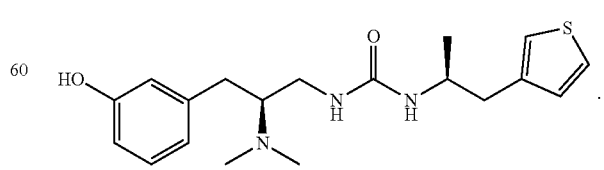

Yield: 59%. LCMS (ESI+): $t_R$=15.0-15.2 min, m/z found 362.7, m/z calcd 362.2 [M+H]$^+$.

193

(S)-1-(2-(dimethylamino)-3-(3-hydroxyphenyl)propyl)-3-(2-methyl-1-(thiophen-3-yl)propan-2-yl)urea (DD46L)

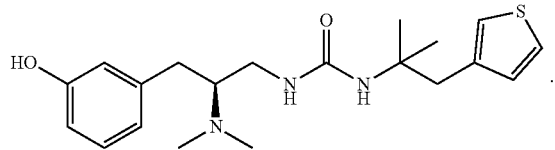 [SMILES: CN(C)[C@H](CNC(=O)NC(C)(C)Cc1ccsc1)Cc1cccc(O)c1]

Yield: 72%. LCMS (ESI+): $t_R$=15.9-16.9 min, m/z found 376.7, m/z calcd 376.2 [M+H]$^+$.

1-((S)-2-(dimethylamino)-3-(4-hydroxyphenyl)propyl)-3-((S)-1-phenylethyl)urea (DD53LS)

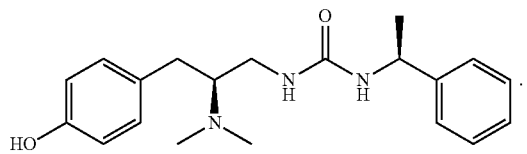 [SMILES: C[C@H](NC(=O)NC[C@H](Cc1ccc(O)cc1)N(C)C)c1ccccc1]

Yield: 22%. LCMS (ESI+): $t_R$=10.7-15.0 min, m/z found 342.7, m/z calcd 342.2 [M+H]$^+$.

1-((S)-2-(dimethylamino)-3-(4-hydroxyphenyl)propyl)-3-((S)-1-(p-tolyl)ethyl)urea (DD51LS)

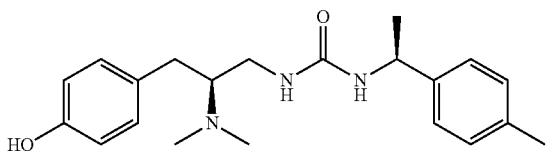

Yield: 30%. LCMS (ESI+): $t_R$=9.8-10.0 min, m/z found 356.7, m/z calcd 356.2 [M+H]$^+$.

1-((S)-2-(dimethylamino)-3-(4-hydroxyphenyl)propyl)-3-((S)-1-(naphthalen-1-yl)ethyl)urea (DD50LS)

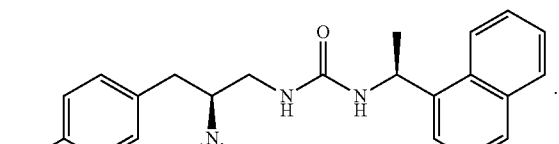

Yield: 31%. LCMS (ESI+): $t_R$=16.3-16.7 min, m/z found 392.8, m/z calcd 392.2 [M+H]$^+$.

194

(S)-1-(2,3-dihydro-1H-inden-2-yl)-3-(2-(dimethylamino)-3-(4-hydroxyphenyl)propyl)urea (DD57L)

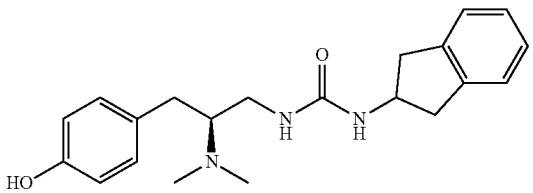

Yield: 84%. LCMS (ESI+): $t_R$=9.6-9.9 min, m/z found 354.6, m/z calcd 354.2 [M+H]$^+$.

1-((S)-2-(dimethylamino)-3-(4-hydroxyphenyl)propyl)-3-((R)-1-phenylpropan-2-yl)urea (DD61LA)

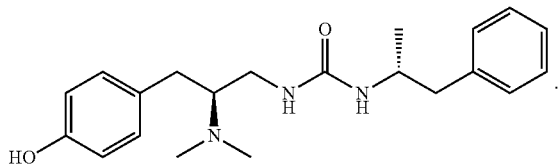 [SMILES: C[C@H](Cc1ccccc1)NC(=O)NC[C@H](Cc1ccc(O)cc1)N(C)C]

Yield: 39%. LCMS (ESI+): $t_R$=9.6-9.9 min, m/z found 356.6, m/z calcd 356.2 [M+H]$^+$. Chiral HPLC: AS-H column, 0.1% diethyl amine in isopropanol/hexane 15:85, 9 mL/min, 25 min: $t_R$=14.2 min.

1-((S)-2-(dimethylamino)-3-(4-hydroxyphenyl)propyl)-3-((S)-1-phenylpropan-2-yl)urea (DD61LB)

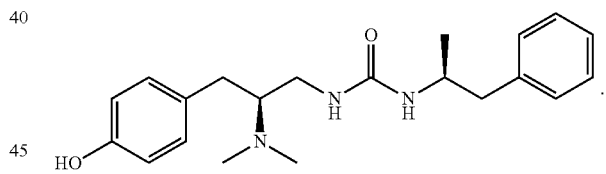

Yield: 39%. LCMS (ESI+): $t_R$=9.6-9.9 min, m/z found 356.6, m/z calcd 356.2 [M+H]$^+$. Chiral HPLC: AS-H column, 0.1% diethyl amine in isopropanol/hexane 15:85, 9 mL/min, 25 min: $t_R$=21.2 min.

1-((S)-2-(dimethylamino)-3-(6-hydroxypyridin-3-yl)propyl)-3-((S)-1-(thiophen-3-yl)propan-2-yl)urea (DD78)

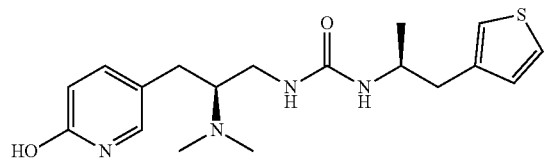

Yield: 20%. LCMS (ESI+): $t_R$=1.0-1.8 min, m/z found 363.0, m/z calcd 363.2 [M+H]$^+$.

1-((S)-2-(dimethylamino)-3-(2-hydroxypyridin-4-yl)
propyl)-3-((S)-1-(thiophen-3-yl)propan-2-yl)urea
(DD79)

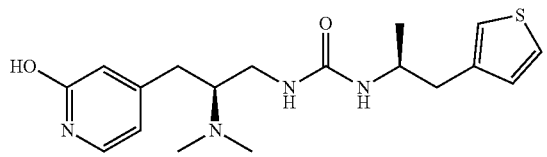

Yield: 20%. LCMS (ESI+): $t_R$=0.8-1.8 min, m/z found 363.0, m/z calcd 363.2 [M+H]$^+$ 1-((S)-2-(dimethylamino)-3-(4-hydroxyphenyl)propyl)-3-((R)-1-(thiophen-3-yl)butan-2-yl)urea
(DD88A)

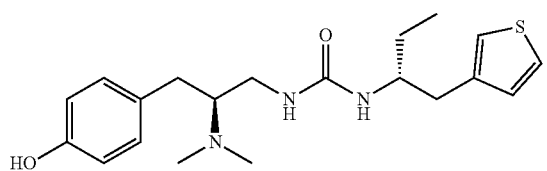

Yield: 41%. LCMS (ESI+): $t_R$=3.9-4.5 min, m/z found 376.0, m/z calcd 376.2 [M+H]$^+$. Chiral HPLC: AS-H column, 0.1% diethyl amine in isopropanol/hexane 15:85, 5 mL/min, 28 min: $t_R$=6.6 min.

1-((S)-2-(dimethylamino)-3-(4-hydroxyphenyl)propyl)-3-((S)-1-(thiophen-3-yl)butan-2-yl)urea
(DD88B)

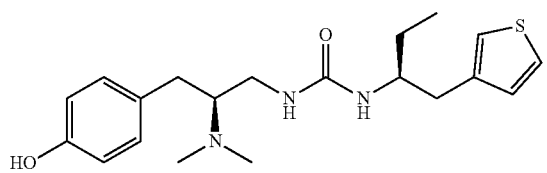

Yield: 41%. LCMS (ESI+): $t_R$=4.1-4.6 min, m/z found 376.0, m/z calcd 376.2 [M+H]$^+$. Chiral HPLC: AS-H column, 0.1% diethyl amine in isopropanol/hexane 15:85, 5 mL/min, 28 min: $t_R$=15.1 min.

1-((S)-3-(2,2-dimethyl-4H-benzo[d][1,3]dioxin-6-yl)-2-(dimethylamino)propyl)-3-((S)-1-(thiophen-3-yl)propan-2-yl)urea (DD127)

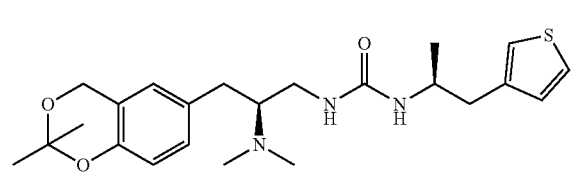

Yield: 64%. LCMS (ESI+): $t_R$=5.6-6.2 min, m/z found 432.1 m/z calcd 432.2 [M+H]$^+$.

1-((S)-2-(dimethylamino)-3-(4-hydroxyphenyl)propyl)-3-(2-(1,3-dioxo-1,3,3a,4,7,7a-hexahydro-2H-4,7-epoxyisoindol-2-yl)ethyl)urea (DD137)

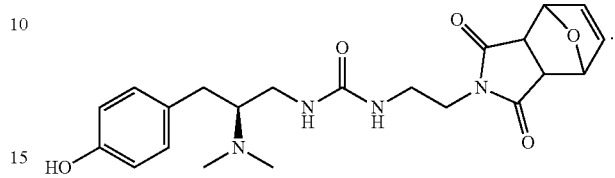

Yield: 34%. LCMS (ESI+): $t_R$=0.7-1.2 min, m/z found 429.1, m/z calcd 429.2 [M+H]$^+$.

1-((S)-2-(dimethylamino)-3-(4-hydroxyphenyl)propyl)-3-(3-(1,3-dioxo-1,3,3a,4,7,7a-hexahydro-2H-4,7-epoxyisoindol-2-yl)propyl)urea (DD135)

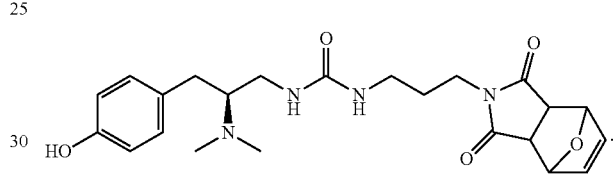

Yield: 42%. LCMS (ESI+): $t_R$=0.6-1.4 min, m/z found 443.1, m/z calcd 443.2 [M+H]$^+$.

1-((S)-2-(dimethylamino)-3-(4-hydroxyphenyl)propyl)-3-(4-(1,3-dioxo-1,3,3a,4,7,7a-hexahydro-2H-4,7-epoxyisoindol-2-yl)butyl)urea (DD136)

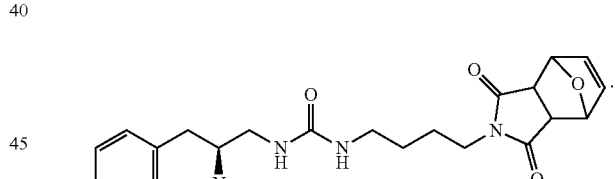

Yield: 30%. LCMS (ESI+): $t_R$=0.6-1.5 min, m/z found 457.1, m/z calcd 457.2 [M+H]$^+$.

1-((S)-2-(dimethylamino)-3-(4-hydroxyphenyl)propyl)-3-((2S)-1-(1,3-dioxo-1,3,3a,4,7,7a-hexahydro-2H-4,7-epoxyisoindol-2-yl)propan-2-yl)urea (DD157)

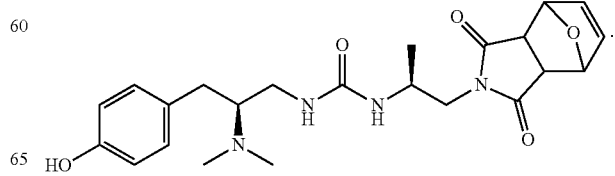

Yield: 65%. LCMS (ESI+): $t_R$=0.5-1.6 min, m/z found 443.1, m/z calcd 443.2 [M+H]$^+$.

1-((S)-2-(dimethylamino)-3-(4-hydroxyphenyl)propyl)-3-((2R)-1-(1,3-dioxo-1,3,3a,4,7,7a-hexahydro-2H-4,7-epoxyisoindol-2-yl)propan-2-yl)urea (DD175)

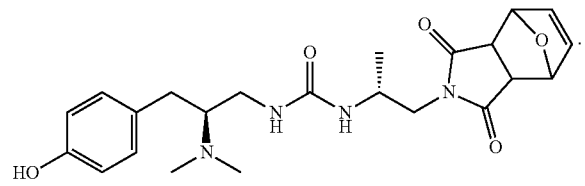 [SMILES: C[C@H](CN1C(=O)C2C3C=CC(O3)C2C1=O)NC(=O)NC[C@H](Cc1ccc(O)cc1)N(C)C]

Yield: 73%. LCMS (ESI+): $t_R$=0.7-1.4 min, m/z found 443.2, m/z calcd 443.2 [M+H]$^+$.

1-((S)-3-(4-hydroxyphenyl)-2-(methylamino)propyl)-3-((S)-1-(thiophen-3-yl)propan-2-yl)urea (DD196)

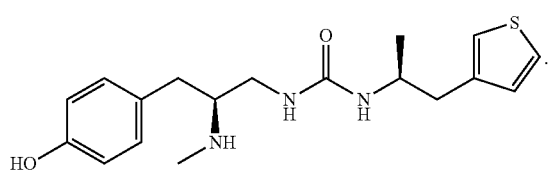 [SMILES: CN[C@H](CNC(=O)N[C@@H](C)Cc1ccsc1)Cc1ccc(O)cc1]

Yield: 26%. LCMS (ESI+): $t_R$=2.9-4.0 min, m/z found 348.2, m/z calcd 348.2 [M+H]$^+$ 1-((S)-2-(benzyl(methyl)amino)-3-(4-hydroxyphenyl)propyl)-3-((S)-1-(thiophen-3-yl)propan-2-yl)urea (DD187)

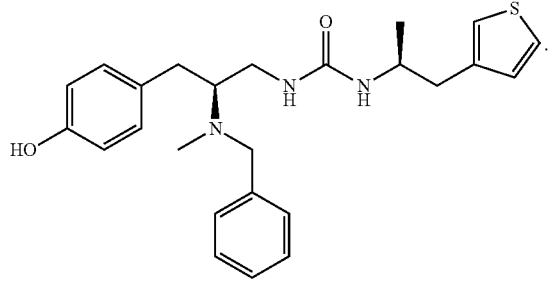 [SMILES: C[C@@H](Cc1ccsc1)NC(=O)NC[C@H](Cc1ccc(O)cc1)N(C)Cc1ccccc1]

Yield: 92%. LCMS (ESI+): $t_R$=5.3-6.7 min, m/z found 438.2, m/z calcd 438.2 [M+H]$^+$.

(S)-1-(2-(dimethylamino)-3-(4-hydroxyphenyl)propyl)-3-(2-fluorophenethyl)urea (DDLM-08)

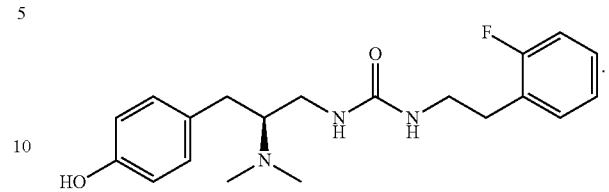

Yield: 79%. LCMS (ESI+): $t_R$=2.6-5.5 min, m/z found 360.2, m/z calcd 360.2 [M+H]$^+$.

(S)-1-(2-(dimethylamino)-3-(4-hydroxyphenyl)propyl)-3-(3-fluorophenethyl)urea (DDLM-10)

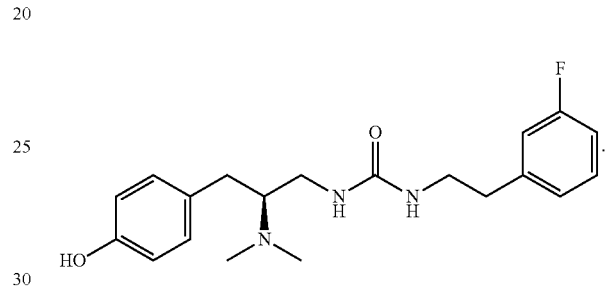

Yield: 40%. LCMS (ESI+): $t_R$=1.8-3.8 min, m/z found 360.2, m/z calcd 360.2 [M+H]$^+$.

(S)-1-(2-(dimethylamino)-3-(4-hydroxyphenyl)propyl)-3-(4-fluorophenethyl)urea (DDLM-15)

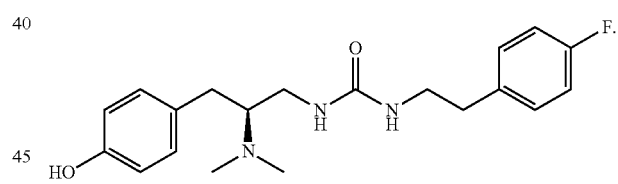

Yield: 44%. LCMS (ESI+): $t_R$=0.6-4.9 min, m/z found 360.2, m/z calcd 360.2 [M+H]$^+$.

(S)-1-(3-(4-hydroxyphenyl)-2-(pyrrolidin-1-yl)propyl)-3-phenethylurea (DDLM-14)

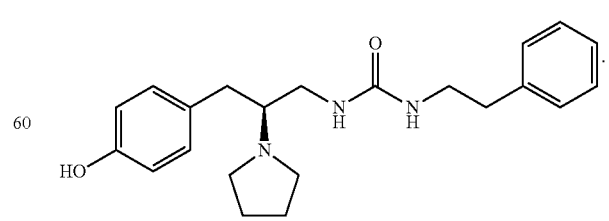

Yield: 28%. LCMS (ESI+): $t_R$=2.0-5.3 min, m/z found 368.2, m/z calcd 368.2 [M+H]$^+$.

(S)-1-(2-(dimethylamino)-3-(4-hydroxyphenyl)pro-
pyl)-3-(2-(pyrazolo[1,5-a]pyridin-3-yl)ethyl)urea
(DD208)

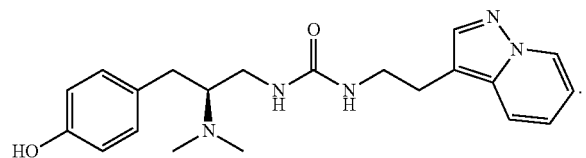 [SMILES: CN(C)[C@H](CNC(=O)NCCc1cnn2ccccc12)Cc1ccc(O)cc1]

Yield: 38%. LCMS (ESI+): $t_R$=0.9-2.8 min, m/z found 382.2, m/z calcd 382.2 [M+H]$^+$.

(S)-1-(2-(dimethylamino)-3-(4-hydroxyphenyl)pro-
pyl)-3-(4-fluoro-2-methoxyphenethyl)urea (DD214)

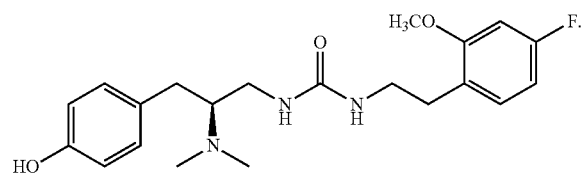 [SMILES: COc1cc(F)ccc1CCNC(=O)NC[C@H](Cc1ccc(O)cc1)N(C)C]

(9H-fluoren-9-yl)methyl ((S)-1-(4-hydroxyphenyl)-
3-(3-((S)-1-(thiophen-3-yl)propan-2-yl)ureido)pro-
pan-2-yl)carbamate (DD202)

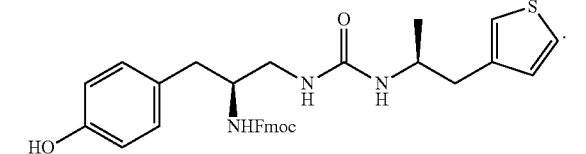

Yield: 34%. LCMS (ESI+): $t_R$=7.6-8.7 min, m/z found 578.2, m/z calcd 578.2 [M+H]$^+$.

1-((S)-2-(dimethylamino)-3-(2,2-dimethylbenzo[d]
[1,3]dioxol-5-yl)propyl)-3-((S)-1-(thiophen-3-yl)
propan-2-yl)urea (DDLM19)

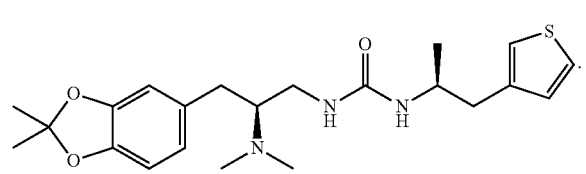 [SMILES: C[C@@H](Cc1ccsc1)NC(=O)NC[C@H](Cc1ccc2c(c1)OC(C)(C)O2)N(C)C]

Yield: 72%. LCMS (ESI+): $t_R$=5.4-6.9 min, m/z found 418.2, m/z calcd 418.2 [M+H]$^+$.

1-((S)-2-(dimethylamino)-3-(4-hydroxy-2,6-dimeth-
ylphenyl)propyl)-3-(1-(thiophen-3-yl)propan-2-yl)
urea (BD131L-RS)

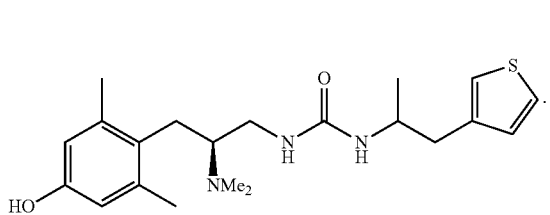 [SMILES: Cc1cc(O)cc(C)c1C[C@@H](CNC(=O)NC(C)Cc1ccsc1)N(C)C]

A 20 mL microwave vial was charged with [BD130-L] (0.30 g, 1.01 mmol) and triethylamine (0.15 mL, 1.08 mmol) in anhydrous DMF (2 mL) under nitrogen atmosphere. A solution of [(S)-20] (0.11 g, 0.36 mmol) and [20] (0.20 g, 0.65 mmol) in DMF (2.5 mL) was added. The mixture was stirred at ambient temperature for 20 h. Then the reaction mixture was diluted by 25% iPrOH in EtOAc (25 mL) and washed with carbonate buffer (pH 9, 3×15 mL). Aqueous washings were back-extracted with EtOAc (15 mL). Combined organic layers were extracted with 0.1 N HCl (3×25 mL). Combined aqueous layers were basified with carbonate buffer to pH 9 and extracted with 25% iPrOH in EtOAc (3×50 mL). Combined organic layers were dried over anhydrous $Na_2SO_4$, filtered and concentrated under reduced pressure. The residue was purified by dry-column vacuum chromatography ($NH_4OH$/MeOH/$CHCl_3$ 0.9:8.1:91).

Diastereomers were separated by preparative HPLC (Chiralpak IC, 0.1% diethylamine in iPrOH/0.1% diethylamine in hexane 30:70, 10 mL/min, 114 bar). Yield: 129 mg of BD131LS (48%); 53 mg of BD131LR (42%). TLC ($NH_4OH$/MeOH/$CHCl_3$ 1.2:10.8:88) $R_f$=0.47 ($KMnO_4$ stain).

1-((S)-2-(dimethylamino)-3-(4-hydroxy-2,6-dimeth-
ylphenyl)propyl)-3-((S)-1-(thiophen-3-yl)propan-2-
yl)urea (BD131-LS)

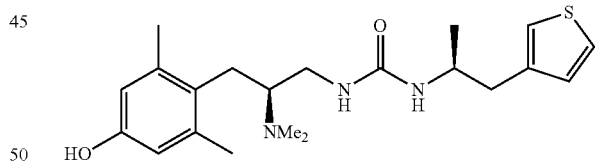

Chiral HPLC: Chiralpak IC column, 0.1% diethylamine in iPrOH/0.1% diethylamine in hexane 30:70, 10 mL/min, 114 bar, 6 min: $t_R$=3.0 min. LCMS (STANDESI): $t_R$=2.9 min, purity: 98% (254 nm); m/z found 390.7, calcd. 390.6 for $C_{13}H_{23}N_2O$ [M-Cl]$^+$. $^1$H NMR (360 MHz, $CDCl_3$) δ ppm 7.23 (dd, J=4.9, 3.0 Hz, 1H), 6.95-6.99 (m, 1H), 6.93 (dd, J=4.9, 1.2 Hz, 1H), 6.49 (s, 2H), 5.03 (br. d, J=6.2 Hz, 1H), 4.39 (br. d, J=7.7 Hz, 1H), 3.94 (spt, J=6.6 Hz, 1H), 3.09 (ddd, J=12.8, 6.8, 4.2 Hz, 1H), 2.97 (ddd, J=12.4, 10.0, 1.7 Hz, 1H), 2.80 (dd, J=14.0, 5.2 Hz, 1H), 2.69-2.84 (m, 2H), 2.71 (dd, J=14.0, 6.9 Hz, 1H), 2.50 (dd, J=13.1, 10.9 Hz, 1H), 2.37 (s, 6H), 2.25 (s, 6H), 1.07 (d, J=6.6 Hz, 3H). $^{13}$C NMR (91 MHz, $CDCl_3$) d ppm 157.9, 154.4, 138.5, 137.7 (2C), 129.0, 126.4, 125.3, 122.0, 115.6 (2C), 63.3, 46.6, 40.3, 39.8 (2C), 37.5, 23.2, 20.7, 20.6 (2C). HR- ESIMS: m/z found 390.2219; calcd. 390.2210 for $C_{21}H_{32}N_3O_2S$ ([M+H]$^+$). [α]$_D^{24}$=+22.9° (c 0.59, CHCl$_3$).

1-((S)-2-(dimethylamino)-3-(4-hydroxy-2,6-dimethylphenyl)propyl)-3-((R)-1-(thiophen-3-yl)propan-2-yl)urea (BD131-LR)

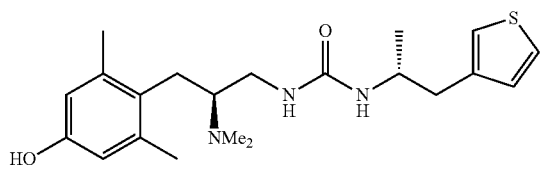 [SMILES: Cc1cc(O)cc(C)c1C[C@@H](CNC(=O)N[C@H](C)Cc1ccsc1)N(C)C]

Chiral HPLC: Chiralpak IC column, 0.1% diethylamine in iPrOH/0.1% diethylamine in hexane 30:70, 10 mL/min, 114 bar, 6 min: $t_R$=4.5 min. LCMS (STANDESI): $t_R$=2.9 min, purity: 98% (254 nm); m/z found 390.7, calcd. 390.6 for $C_{13}H_{23}N_2O$ [M-Cl]$^+$. 1H NMR (360 MHz, CDCl$_3$) δ ppm 7.22 (dd, J=4.9, 3.0 Hz, 1H), 6.94-6.98 (m, 1H), 6.92 (dd, J=4.9, 1.3 Hz, 1H), 6.49 (s, 2H), 5.04 (br. d, J=5.5 Hz, 1H), 4.49 (br. d, J=6.2 Hz, 1H), 3.94 (spt, J=6.8 Hz, 1H), 3.09 (ddd, J=12.5, 6.9, 4.4 Hz, 1H), 2.98 (ddd, J=12.4, 10.0, 1.7 Hz, 1H), 2.80 (dd, J=14.0, 4.5 Hz, 1H), 2.71-2.79 (m, 2H), 2.71 (dd, J=14.0, 7.0 Hz, 1H), 2.50 (dd, J=13.2, 11.0 Hz, 1H), 2.38 (s, 6H), 2.24 (s, 6H), 1.06 (d, J=6.6 Hz, 3H). $^{13}$C NMR (91 MHz, CDCl$_3$) d ppm 157.9, 154.4, 138.6, 137.7 (2C), 129.0, 126.3, 125.3, 121.9, 115.6 (2C), 63.6, 46.6, 40.1, 39.8 (2C), 37.5, 23.2, 20.6, 20.6 (2C). HR-ESIMS: m/z found 390.2219; calcd. 390.2210 for $C_{21}H_{32}N_3O_2S$ ([M+H]$^+$). [α]$_D^{24}$=+32.8° (c 0.48, CHCl$_3$).

1-((S)-2-(dimethylamino)-3-(4-hydroxy-2,6-dimethylphenyl)propyl)-3-(2-(1,3-dioxo-1,3,3a,4,7,7a-hexahydro-2H-4,7-epoxyisoindol-2-yl)ethyl)urea (DD140)

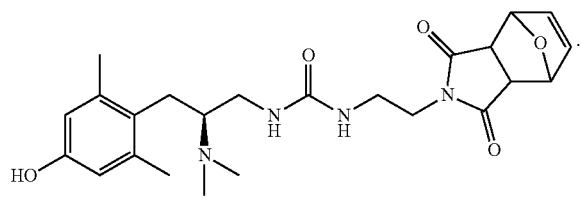 [SMILES: Cc1cc(O)cc(C)c1C[C@@H](CNC(=O)NCCN1C(=O)C2C3C=CC(O3)C2C1=O)N(C)C]

DD140 was synthesized according the procedure for BD131L-RS using BD130-L and DD126 as starting materials. Yield: 59%. LCMS (ESI+): $t_R$=0.6-1.4 min, m/z found 457.1, m/z calcd 457.2 [M+H]$^+$.

(S)-1-(2-(dimethylamino)-3-(4-hydroxy-2,6-dimethylphenyl)propyl)-3-(2-(thiophen-3-yl)ethyl)urea (DD34L)

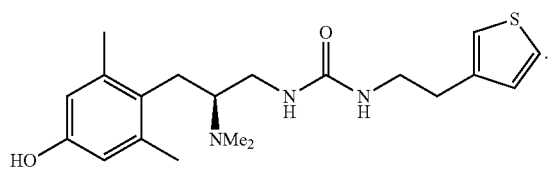

DD34L was synthesized according the procedure for BD131L-RS using BD130-L and DD14 as starting materials. Yield: 48%. LCMS (ESI+): $t_R$=9.3-10.4 min, m/z found 376.7, m/z calcd 376.2 [M+H]$^+$.

1-((S)-2-(dimethylamino)-3-(4-hydroxyphenyl)propyl)-1-isopropyl-3-((S)-1-(naphthalen-1-yl)ethyl)urea (DD50NP)

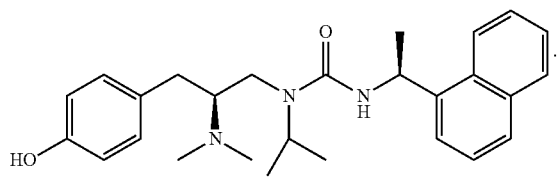 [SMILES: CC(C)N(C[C@H](Cc1ccc(O)cc1)N(C)C)C(=O)N[C@@H](C)c1cccc2ccccc12]

DD50NP was synthesized according Method A using DD27NP ((S)-4-(2-(dimethylamino)-3-(isopropylamino)propyl)phenol) and DD49-S as starting materials. Yield: 17%. LCMS (ESI+): $t_R$=10.5-10.7 min, m/z found 434.9, m/z calcd 434.3 [M+H]$^+$.

Method B: Alternative Method for Synthesis of Urea Compounds

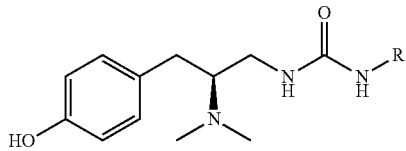

DD180 was weighed in a microwave tube and solved in dry DMF. R—NH$_2$ was added, the tube sealed and the reaction mixture stirred at 70° C. overnight under inert atmosphere. H$_2$O demin. was added and the mixture lyophilisated. The crude product was purified by preparative HPLC giving the corresponding formates or trifluoroacetates.

Compounds Synthesized Following Method B (S)-1-(2-(dimethylamino)-3-(4-hydroxyphenyl)propyl)-3-(2-methoxyphenethyl)urea (DD198)

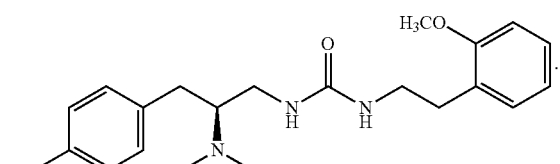

Yield: 21%. LCMS (ESI+): $t_R$=3.0-4.4 min, m/z found 372.1, m/z calcd 372.2 [M+H]$^+$.

(S)-1-(2-(dimethylamino)-3-(4-hydroxyphenyl)propyl)-3-(3-methoxyphenethyl)urea (DD200)

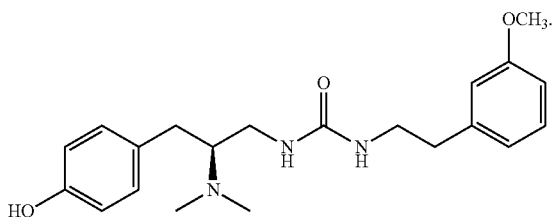 [SMILES: COc1cccc(CCNC(=O)NC[C@H](Cc2ccc(O)cc2)N(C)C)c1]

Yield: 20%. LCMS (ESI+): $t_R$=3.5-4.6 min, m/z found 372.2, m/z calcd 372.2 [M+H]⁺.

(S)-1-(2-(dimethylamino)-3-(4-hydroxyphenyl)propyl)-3-(4-methoxyphenethyl)urea (DD201)

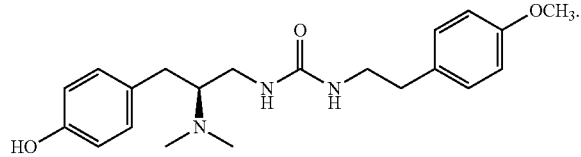 [SMILES: COc1ccc(CCNC(=O)NC[C@H](Cc2ccc(O)cc2)N(C)C)cc1]

Yield: 27%. LCMS (ESI+): $t_R$=2.7-4.1 min, m/z found 372.2, m/z calcd 372.2 [M+H]⁺.

(S)-1-(2-(benzo[b]thiophen-3-yl)ethyl)-3-(2-(dimethylamino)-3-(4-hydroxyphenyl)propyl)urea (DD203)

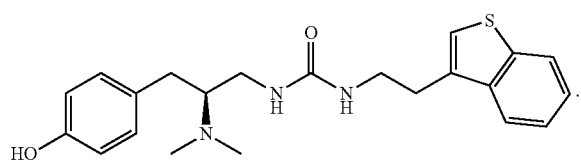 [SMILES: CN(C)[C@H](CNC(=O)NCCc1csc2ccccc12)Cc1ccc(O)cc1]

Yield: 25%. LCMS (ESI+): $t_R$=5.1-5.7 min, m/z found 398.1, m/z calcd 398.2 [M+H]⁺.

1-allyl-1-((S)-2-(dimethylamino)-3-phenylpropyl)-3-(1-(thiophen-3-yl)propan-2-yl)urea (DD93AB)

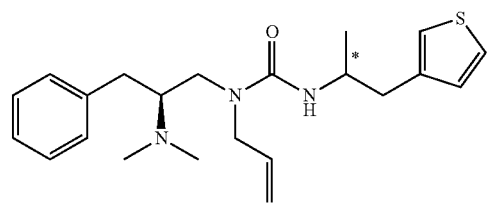

(S, R/S)-12 (1 eq) and Sodium Hydride (60% suspension in oil, 21.5 eq) were weighed in a microwave tube and suspended in dry THF. The mixture was stirred in an ice-water-bath and 1,3-Dibromopropan (5 eq) was slowly added. The reaction vessel was allowed to warm up to room temperature and stirred overnight. Then the mixture was stirred at reflux temperature for 8 h. The reaction mixture was quenched by addition of ice. The suspension was diluted with CHCl₃, washed with sat. NaHCO₃ solution and extracted with 0.1N HCl. Combined aqueous extracts were basified with 0.1N NaOH to pH>10 and back-extracted with ethyl acetate. Combined organic layers were dried over anhydrous Na₂SO₄, filtered and concentrated under reduced pressure. Purification and separation of diastereomeres was performed using flash chromatography. Yield: 54%. LCMS (ESI+): $t_R$=5.7-6.0 min or 6.0-6.2 min, m/z found 386.1, m/z calcd 386.2 [M+H]⁺.

(S)—N-(2-(dimethylamino)-3-(4-hydroxyphenyl)propyl)-4-phenylbutanamide (DD91)

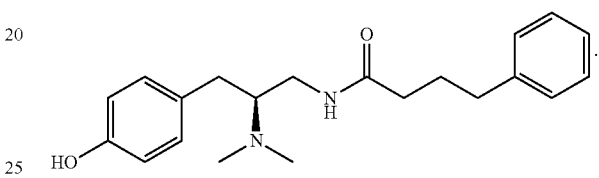

4-Phenylbutanoic acid (1 eq) in a Schlenk flask was solved in dry DMF and stirred under N₂ atmosphere in an ice-water-bath. DIPEA (1.2 eq), HATU (1.1 eq) and then 35 (1.1 eq) were added. The mixture was allowed to warm up to room temperature and was stirred for 15 h. Water was added and the aqueous mixture was extracted with EtOAc. The organic layer was washed with sat. NaHCO₃ solution and H₂O dem. The organic layer was dried (Na₂SO₄), filtered and concentrated under reduced pressure. The residue was purified by preparative HPLC. Yield: 17%. LCMS (ESI+): $t_R$=4.8-5.2 min, m/z found 341.2, m/z calcd 341.2 [M+H]⁺.

(S)-1-(2-(dimethylamino)-3-(4-hydroxyphenyl)propyl)-3-(2-(thiophen-3-yl)ethyl)thiourea (DD81)

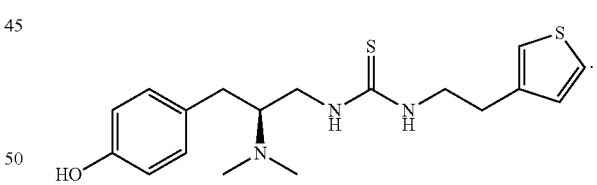

3-(2-isothiocyanatoethyl)thiophene (4.5 eq) in a microwave tube solved in dichloromethane was stirred in an ice-water-bath. 35 (1 eq) and TEA (2.2 eq) solved in dry DMF were added slowly. The mixture was allowed to warm up to room temperature and stirred for 7 h. The solvent was then evaporated, the residue diluted with isopropanol/EtOAc (1:3) and washed with a saturated aqueous solution of NaHCO₃. The organic layer was extracted with 0.1N HCl-solution and the aqueous extracts were adjusted to pH 9 with saturated aqueous NaHCO₃/Na₂CO₃ solution and finally extracted with EtOAc. The organic layers were dried (Na₂SO₄), filtered and concentrated under reduced pressure. The residue was purified by preparative HPLC. Yield: 20%. LCMS (ESI+): $t_R$=9.3-9.8 min, m/z found 364.5, m/z calcd 364.2 [M+H]⁺.

2-(thiophen-3-yl)ethyl (S)-(2-(dimethylamino)-3-(4-hydroxyphenyl)propyl)carbamate (DD77)

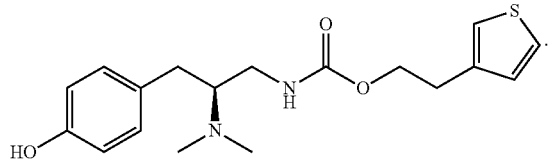 [SMILES: CN(C)[C@H](CNC(=O)OCCc1ccsc1)Cc1ccc(O)cc1]

DD77 was synthesized according Method A using 4-nitrophenyl (2-(thiophen-3-yl)ethyl) carbonate (1 eq) and compound 35 as starting materials. Yield: 58%. LCMS (ESI+): $t_R$=8.7-9.5 min, m/z found 349.5, m/z calcd 349.2 [M+H]$^+$.

(S)-1-(2-((2-chloroethyl)(methyl)amino)-3-(4-hydroxyphenyl)propyl)-3-phenethylurea (DD185)

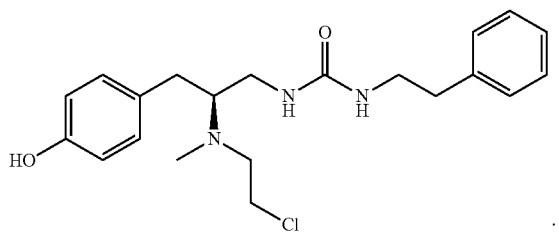 [SMILES: CN(CCCl)[C@H](CNC(=O)NCCc1ccccc1)Cc1ccc(O)cc1]

Compound 39 was solved in dichloroethane. An high excess of sodium triacetoxyborohydride was added and subsequently a high excess of chloroacetaldehyde (50 wt. %). After 10 minutes of vigorous stirring, the reaction was cooled in an ice-water-bath and quenched with sat. NaHCO$_3$ solution and extracted with dichloromethane. Combined organic layers were dried over anhydrous Na$_2$SO$_4$, filtered and concentrated under reduced pressure. The residue was purified by preparative HPLC giving the corresponding trifluoroacetate. Yield: 54%. LCMS (ESI+): $t_R$=3.5-4.9 min, m/z found 390.2, m/z calcd 390.2 [M+H]$^+$.

(S)-1-(2-((2-hydroxyethyl)(methyl)amino)-3-(4-hydroxyphenyl)propyl)-3-phenethylurea (DD186)

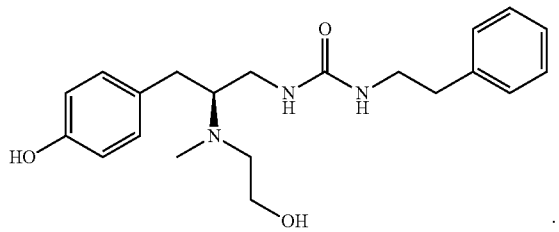 [SMILES: CN(CCO)[C@H](CNC(=O)NCCc1ccccc1)Cc1ccc(O)cc1]

DD182 was dissolved in EtOH in a Schlenk flask and stirred under N$_2$ atmosphere. 10% Pd—C were added and the mixture was stirred for 5 h under H$_2$ atmosphere at ambient temperature. The suspension was filtered through celite, the filtrate was evaporated and the residue was purified by preparative HPLC giving the corresponding formate. Yield: 60%. LCMS (ESI+): $t_R$=1.3-3.1 min, m/z found 372.2, m/z calcd 372.2 [M+H]$^+$

1-((S)-2-(dimethylamino)-3-(4-hydroxy-3-(hydroxymethyl)phenyl)propyl)-3-((S)-1-(thiophen-3-yl)propan-2-yl)urea (DD131)

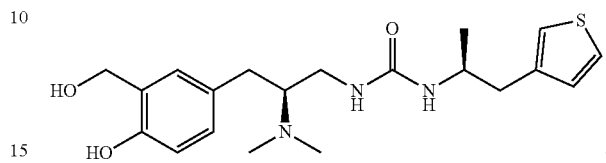

DD127 was solved in a mixture of MeOH/TFA (1:1) and stirred under inert atmosphere at room temperature for 16 h. The solvent was evaporated, the residue diluted with water, lyophilisated and purified by preparative HPLC giving the corresponding trifluoroacetate. Yield: 48%. LCMS (ESI+): $t_R$=2.7-3.5 min, m/z found 392.1, m/z calcd 392.2 [M+H]$^+$.

Method C: CuAAc-Reaction

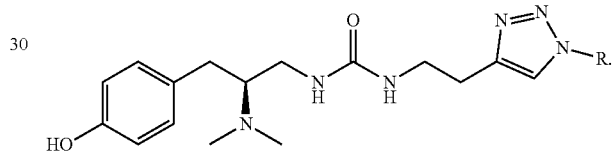

(S)-1-(But-3-yn-1-yl)-3-(2-(dimethylamino)-3-(4-hydroxyphenyl)propyl)urea (46) (1 eq), CuSO$_4$×5H$_2$O (0.2 eq), sodium ascorbate (0.5 eq) and R—N$_3$ (2-5 eq) were dissolved in a mixture of DMF/H$_2$O (2:1 (v/v)) and stirred at room temperature for 6 h. The reaction mixture was quenched with 0.1M EDTA-solution, adjusted to pH 2-3 with 0.1 N HCl and washed with DCM (3×). Then the aqueous phase was adjusted to pH 8-9 with saturated aqueous NaHCO$_3$/Na$_2$CO$_3$ solution and extracted with EtOAc. Combined organic layers were dried (Na$_2$SO$_4$), filtered and concentrated under reduced pressure. The residue was purified by preparative HPLC.

Compounds Synthesized Following Method C

(S)-1-(2-(1-benzyl-1H-1,2,3-triazol-4-yl)ethyl)-3-(2-(dimethylamino)-3-(4-hydroxyphenyl)propyl)urea (DD154)

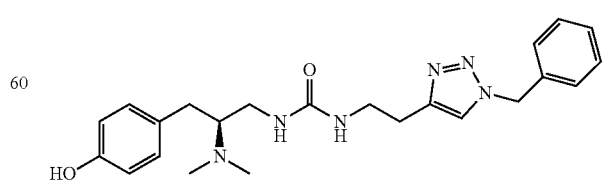

Yield: 78%. LCMS (ESI+): $t_R$=2.2-4.1 min, m/z found 423.2, m/z calcd 423.2 [M+H]$^+$.

(S)-1-(2-(1-(2-(2-(2-azidoethoxy)ethoxy)ethyl)-1H-1,2,3-triazol-4-yl)ethyl)-3-(2-(dimethylamino)-3-(4-hydroxyphenyl)propyl)urea (DD161)
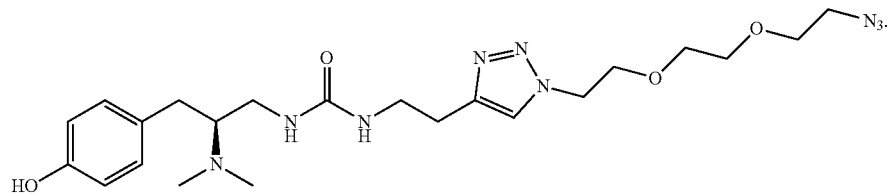 [SMILES: CN(C)[C@H](CNC(=O)NCCc1cn(CCOCCOCCN=[N+]=[N-])nn1)Cc1ccc(O)cc1]
Yield: 21%. LCMS (ESI+): $t_R$=0.6-1.8 min, m/z found 490.2, m/z calcd 490.3 [M+H]$^+$.
(S)-1-(2-(1-(2-(2-(2-(2-azidoethoxy)ethoxy)ethoxy)ethyl)-1H-1,2,3-triazol-4-yl)ethyl)-3-(2-(dimethylamino)-3-(4-hydroxyphenyl)propyl)urea (DD165)
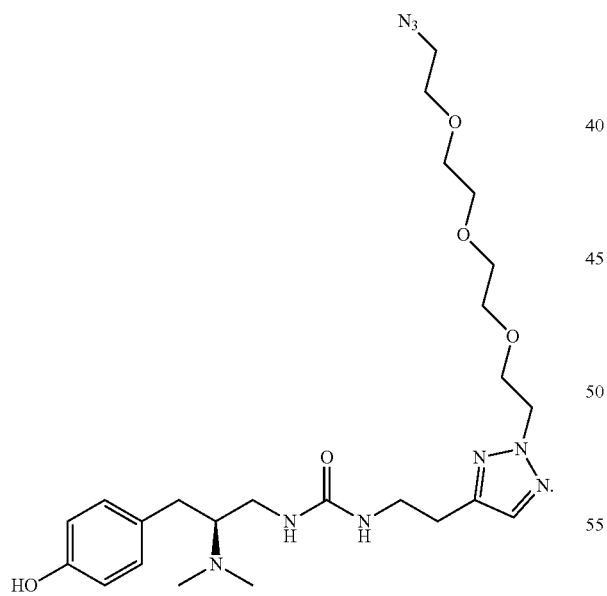
Yield: 21%. LCMS (ESI+): $t_R$=0.6-2.1 min, m/z found 534.2, m/z calcd 534.3 [M+H]$^+$.

209
S)-1-(2-(1-(17-azido-3,6,9,12,15-pentaoxaheptade-cyl)-1H-1,2,3-triazol-4-yl)ethyl)-3-(2-(dimethyl-amino)-3-(4-hydroxyphenyl)propyl)urea (DD168)
210
N-(17-(4-(2-(3-((S)-2-(dimethylamino)-3-(4-hydroxyphenyl)propyl)ureido)ethyl)-1H-1,2,3-triazol-1-yl)-3,6,9,12,15-pentaoxaheptadecyl)-5-((3aS,4S,6aR)-2-oxohexahydro-1H-thieno[3,4-d]imidazol-4-yl)pentanamide (DD170)
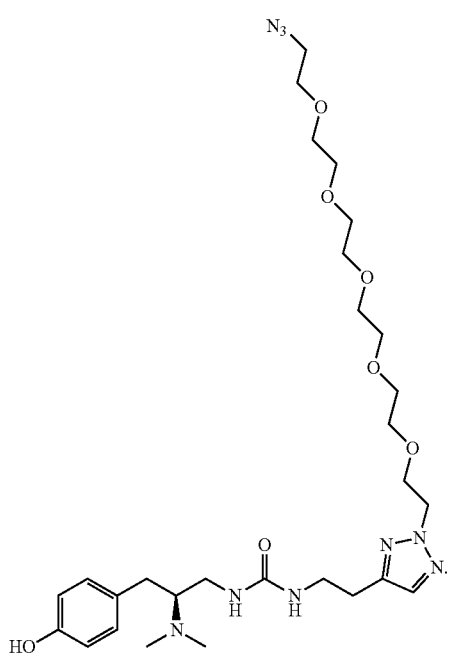 [SMILES: CN(C)[C@H](CNC(=O)NCCc1cnn(CCOCCOCCOCCOCCOCCN=[N+]=[N-])n1)Cc1ccc(O)cc1]
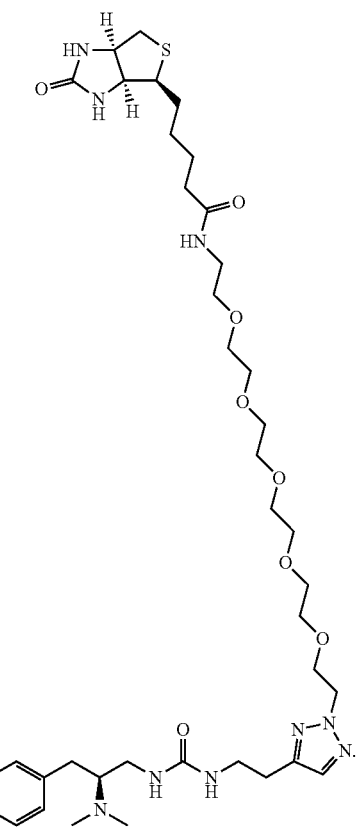
Yield: 23%. LCMS (ESI+): $t_R$=0.7-4.0 min, m/z found 622.3, m/z calcd 622.4 [M+H]$^+$.
Yield: 52%. LCMS (ESI+): $t_R$=4.4-4.8 min, m/z found 822.5, m/z calcd 822.5 [M+H]$^+$.

Method D: Retro-Diels-Alder

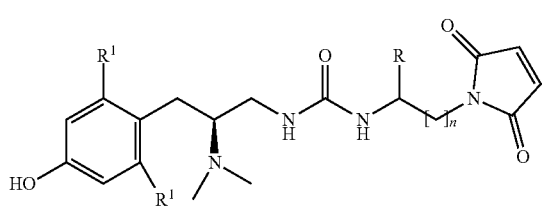

Compounds DD135, DD136, DD137, DD140, DD157 and DD175 were weighed in a microwave tube and suspended in toluene. The tube was sealed and the mixture stirred at reflux temperature for 8 h. The solvent was evaporated and the product was obtained after purification by preparative HPLC giving the corresponding trifluoroacetates.

Compounds Synthesized Following Method D (S)-1-(2-(dimethylamino)-3-(4-hydroxyphenyl)propyl)-3-(2-(2,5-dioxo-2,5-dihydro-1H-pyrrol-1-yl)ethyl)urea (DD120)

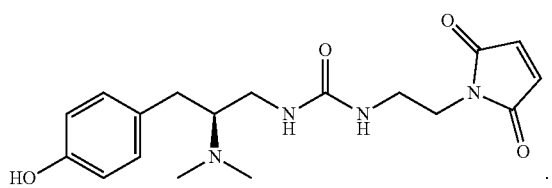 [SMILES: CN(C)[C@H](CNC(=O)NCCN1C(=O)C=CC1=O)Cc1ccc(O)cc1]

Yield: 20%. LCMS (ESI+): $t_R$=0.7-1.2 min, m/z found 361.1, m/z calcd 361.2 [M+H]$^+$.

(S)-1-(2-(dimethylamino)-3-(4-hydroxyphenyl)propyl)-3-(3-(2,5-dioxo-2,5-dihydro-1H-pyrrol-1-yl)propyl)urea (DD138)

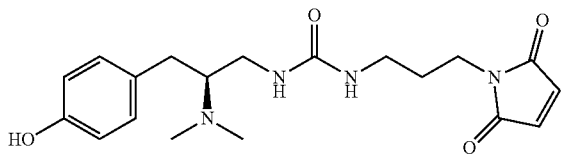

Yield: 20%. LCMS (ESI+): $t_R$=0.6-1.6 min, m/z found 375.1, m/z calcd 375.2 [M+H]$^+$.

(S)-1-(2-(dimethylamino)-3-(4-hydroxyphenyl)propyl)-3-(4-(2,5-dioxo-2,5-dihydro-1H-pyrrol-1-yl)butyl)urea (DD139)

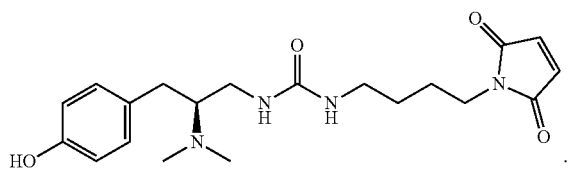 [SMILES: CN(C)[C@H](CNC(=O)NCCCCN1C(=O)C=CC1=O)Cc1ccc(O)cc1]

Yield: 45%. LCMS (ESI+): $t_R$=1.0-1.5 min, m/z found 389.1, m/z calcd 389.2 [M+H]$^+$.

1-((S)-2-(dimethylamino)-3-(4-hydroxyphenyl)propyl)-3-((S)-1-(2,5-dioxo-2,5-dihydro-1H-pyrrol-1-yl)propan-2-yl)urea (DD158)

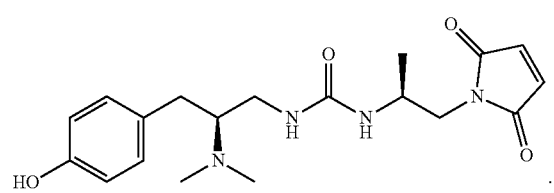 [SMILES: C[C@@H](CN1C(=O)C=CC1=O)NC(=O)NC[C@H](Cc1ccc(O)cc1)N(C)C]

Yield: 51%. LCMS (ESI+): $t_R$=0.7-1.5 min, m/z found 375.1, m/z calcd 375.2 [M+H]$^+$.

1-((S)-2-(dimethylamino)-3-(4-hydroxyphenyl)propyl)-3-((R)-1-(2,5-dioxo-2,5-dihydro-1H-pyrrol-1-yl)propan-2-yl)urea (DD179)

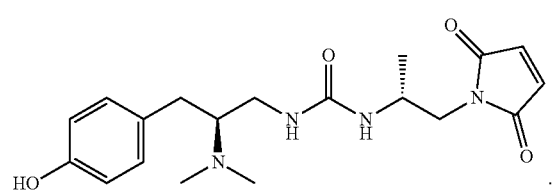 [SMILES: C[C@H](CN1C(=O)C=CC1=O)NC(=O)NC[C@H](Cc1ccc(O)cc1)N(C)C]

Yield: 56%. LCMS (ESI+): $t_R$=0.8-1.6 min, m/z found 375.1, m/z calcd 375.2 [M+H]$^+$.

(S)-1-(2-(dimethylamino)-3-(4-hydroxy-2,6-dimethylphenyl)propyl)-3-(2-(2,5-dioxo-2,5-dihydro-1H-pyrrol-1-yl)ethyl)urea (DD144)

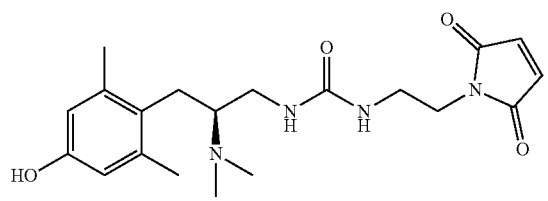

Yield: 67%. LCMS (ESI+): $t_R$=0.8-1.5 min, m/z found 389.1, m/z calcd 389.2 [M+H]$^+$.

1-((S)-3-(3,4-dihydroxyphenyl)-2-(dimethylamino)propyl)-3-((S)-1-(thiophen-3-yl)propan-2-yl)urea (DDLM20)

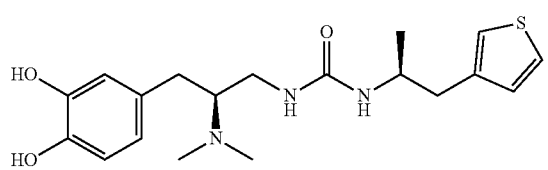

DDLM19 was stirred in 1M HCl solution for 4 h at 65° C. The mixture was diluted with water, lyophilisated and purified by preparative HPLC giving the corresponding trifluoroacetate. Yield: 75%. LCMS (ESI+): $t_R$=2.3-3.3 min, m/z found 378.1, m/z calcd 378.2 [M+H]$^+$.

1-((S)-2-amino-3-(4-hydroxyphenyl)propyl)-3-((S)-1-(thiophen-3-yl)propan-2-yl)urea (DD206)

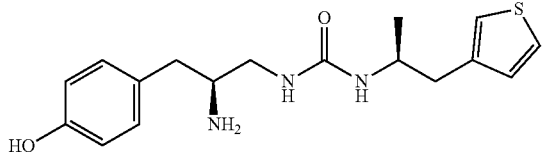

DD202 was stirred in 25% piperidine in DMF for 0.5 h. The mixture was diluted with MeOH and the solvent evaporated. Purification by preparative HPLC gave the corresponding formate as a white powder. Yield: 60%. LCMS (ESI+): $t_R$=2.1-4.6 min, m/z found 334.1, m/z calcd 334.2 [M+H]$^+$.

Method E: General Method for N-Debenzylation

Benzylated compound (1 eq) was dissolved in MeOH in a Schlenk flask and stirred under $N_2$ atmosphere. 1,1,2-Trichloroethane (2 eq) and 10% Pd—C were added and the mixture was stirred for 2-5 h under $H_2$ atmosphere at ambient temperature. The suspension was filtered through celite, the filtrate was evaporated and the residue was purified by flash chromatography or preparative HPLC.

Compounds Synthesized Following Method E (S)-1-(2-(1H-1,2,3-triazol-4-yl)ethyl)-3-(2-(dimethylamino)-3-(4-hydroxyphenyl)propyl)urea (DD156)

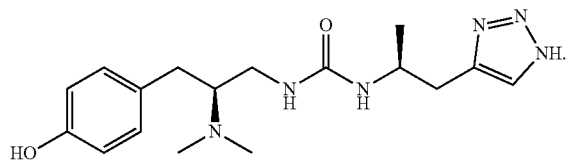 [SMILES: C[C@@H](Cc1c[nH]nn1)NC(=O)NC[C@H](Cc1ccc(O)cc1)N(C)C]

Yield: 57%. LCMS (ESI+): $t_R$=0.8-1.2 min, m/z found 333.1, m/z calcd 333.2 [M+H]$^+$.

(S)-4-(3-amino-2-(methylamino)propyl)phenol (DD195)

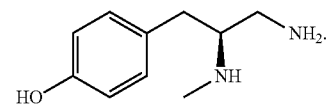

(S)-1-(2-((2-(benzyloxy)ethyl)(methyl)amino)-3-(4-hydroxyphenyl)propyl)-3-phenethylurea (DD182)

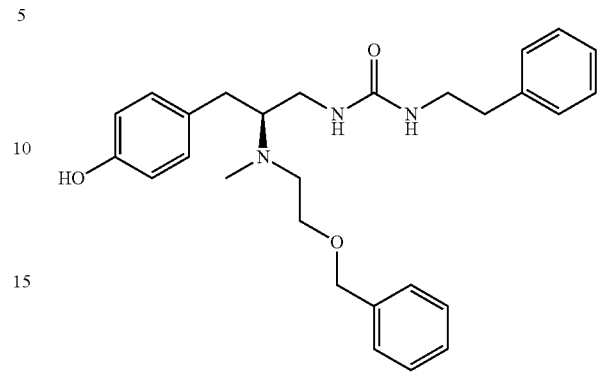

Compound 39 (1 eq) was weighed in a microwave tube and solved in dry DMF. NaHCO$_3$ (6.1 eq) and 2-(benzyloxy)ethyl methanesulfonate (6.5 eq) were added, the tube sealed and the mixture stirred at 100° C. for 15 h under inert atmosphere. The mixture was the diluted with EtOAc and washed with sat. NaHCO$_3$ solution. The organic layer was dried (Na$_2$SO$_4$), filtered and concentrated under reduced pressure. The residue was purified by flash chromatography. Yield: 50%. LCMS (ESI+): $t_R$=5.8-6.7 min, m/z found 462.3, m/z calcd 462.3 [M+H]$^+$.

Method F: General Method for Synthesis of 4-Nitrophenyl-R$^1$-Carbamates

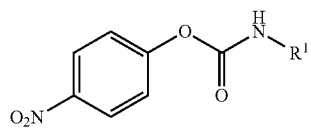

4-Nitrophenyl chloroformate (2 eq) in a Schlenk flask was solved in dry THF and stirred under $N_2$ atmosphere in an ice-water-bath. A mixture of R$^1$—NH$_2$ (1 eq) and triethylamine (1-2 eq) in dry THF was added dropwise. The reaction mixture was allowed to warm up to room temperature and was stirred for 3-8 h. The mixture was diluted with dichloromethane, filtered and the filtrate was washed with saturated aqueous NaHCO$_3$ and brine. The organic layer was dried (Na$_2$SO$_4$), filtered and concentrated under reduced pressure. The residue was purified by flash chromatography (100% dichloromethane) to give the product as a white solid after trituration with hexane.

Compounds Synthesized Following Method F

4-Nitrophenyl (2-(thiophen-3-yl)ethyl)carbamate (DD14)

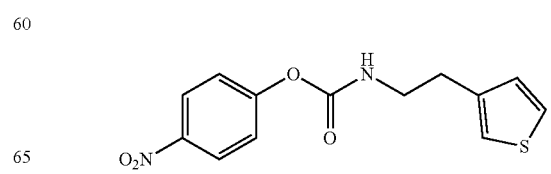

4-nitrophenyl (2-methyl-1-(thiophen-3-yl)propan-2-yl)carbamate (DD24)

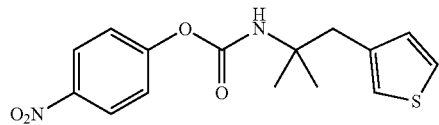 [SMILES: O=C(NCCc1ccsc1)Oc1ccc([N+](=O)[O-])cc1]

4-nitrophenyl (S)-(1-phenylethyl)carbamate (DD52)

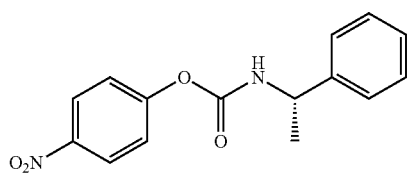

4-nitrophenyl (S)-(1-(naphthalen-1-yl)ethyl)carbamate (DD49)

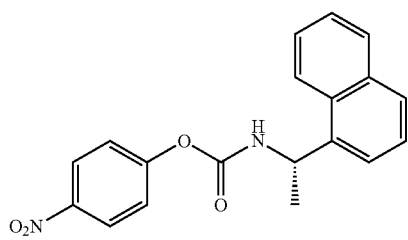

4-nitrophenyl (S)-(1-(p-tolyl)ethyl)carbamate (DD48)

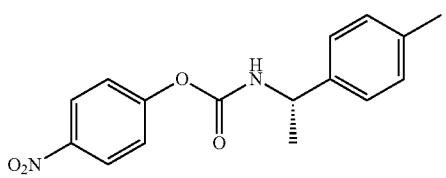

4-nitrophenyl (2,3-dihydro-1H-inden-2-yl)carbamate (DD56)

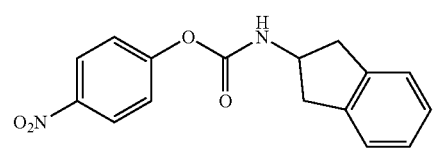

4-nitrophenyl (2-(pyrazolo[1,5-a]pyridin-3-yl)ethyl)carbamate (AU-10)

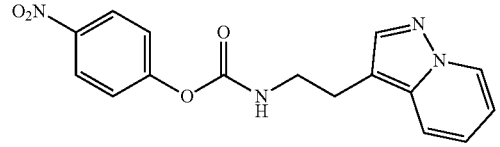

4-nitrophenyl (1-(thiophen-3-yl)butan-2-yl)carbamate (DD87)

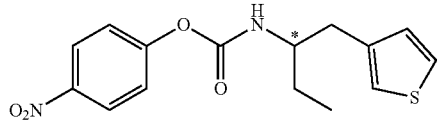

4-nitrophenyl ((2S)-1-(1,3-dioxo-1,3,3a,4,7,7a-hexahydro-2H-4,7-epoxyisoindol-2-yl)propan-2-yl)carbamate (DD153)

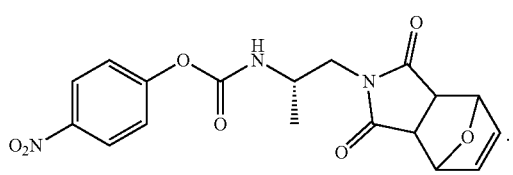 [SMILES: C[C@@H](CN1C(=O)C2C3C=CC(O3)C2C1=O)NC(=O)Oc1ccc([N+](=O)[O-])cc1]

4-nitrophenyl (4-(1,3-dioxo-1,3,3a,4,7,7a-hexahydro-2H-4,7-epoxyisoindol-2-yl)butyl)carbamate (DD134)

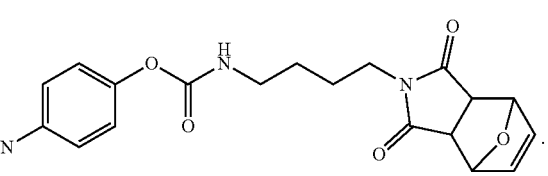

4-nitrophenyl (2-(1,3-dioxo-1,3,3a,4,7,7a-hexahydro-2H-4,7-epoxyisoindol-2-yl)ethyl)carbamate (DD126)

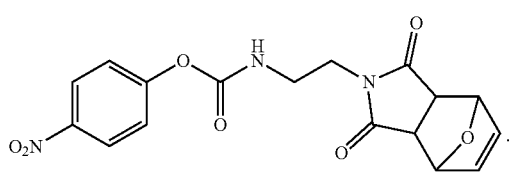 [SMILES: O=C(NCCN1C(=O)C2C3C=CC(O3)C2C1=O)Oc1ccc([N+](=O)[O-])cc1]

4-nitrophenyl (3-(1,3-dioxo-1,3,3a,4,7,7a-hexa-hydro-2H-4,7-epoxyisoindol-2-yl)propyl)carbamate (DD133)

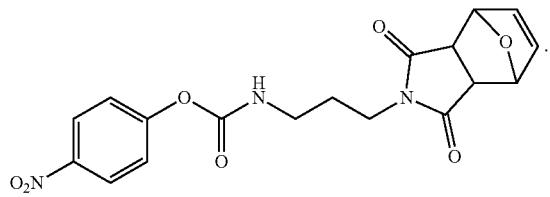 [SMILES: O=C(NCCCN1C(=O)C2C3C=CC(O3)C2C1=O)Oc1ccc([N+](=O)[O-])cc1]

4-nitrophenyl ((2R)-1-(1,3-dioxo-1,3,3a,4,7,7a-hexa-hydro-2H-4,7-epoxyisoindol-2-yl)propan-2-yl)carbamate (DD173)

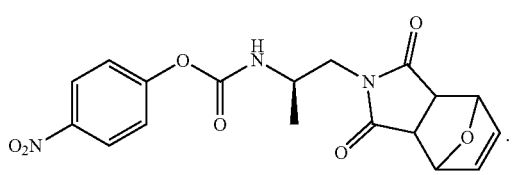 [SMILES: C[C@H](CN1C(=O)C2C3C=CC(O3)C2C1=O)NC(=O)Oc1ccc([N+](=O)[O-])cc1]

(S)—N-(2-(dimethylamino)-3-(4-hydroxyphenyl)propyl)-1H-imidazole-1-carboxamide (DD180)

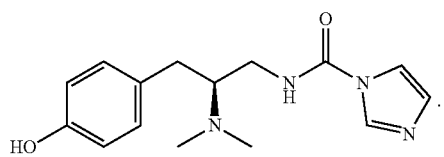 [SMILES: CN(C)[C@H](CNC(=O)n1ccnc1)Cc1ccc(O)cc1]

Compound 35 (1 eq) in a Schlenk flask was solved in dry DMF and stirred under $N_2$ atmosphere in an ice-water-bath. A mixture of CDI (1 eq) in dry DMF was added dropwise. The reaction mixture was allowed to warm up to room temperature and was stirred overnight. $H_2O$ demin. was added and the mixture lyophilisated. The product was used in the following steps without further purification.

Method G: Reduction of Amides

1M Borane-tetrahydrofurane complex (6.1 eq) was slowly added to suspension of Amide (1 eq) in anhydrous THF under cooling with ice bath. The mixture was refluxed for 15 h (except for DD199 stirring at room temperature) under nitrogen atmosphere and then quenched with anhydrous methanol on ice. The mixture was refluxed again for 1 h. The solvent was then removed under reduced pressure and dilution-evaporation sequence was repeated with anhydrous methanol. The residue was resuspended in methanol with addition of 37% aqueous HCl (except for DD122 and DDLM18) and concentrated under reduced pressure, diluted with ethanol and evaporated again (repeated twice). Purification either by HCl salt formation and/or flash chromatography.

Compounds Synthesized Following Method G (S)-4-(3-amino-2-(dimethylamino)propyl)pyridin-2-ol (DD74)

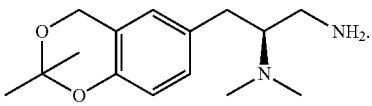

(S)-5-(3-amino-2-(dimethylamino)propyl)pyridin-2-ol (DD76)

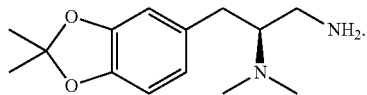 [SMILES: CN(C)[C@H](CN)Cc1ccc2c(c1)OC(C)(C)O2]

(S)-3-(2,2-dimethyl-4H-benzo[d][1,3]dioxin-6-yl)-$N^2,N^2$-dimethylpropane-1,2-diamine (DD122)

(S)-3-(2,2-dimethylbenzo[d][1,3]dioxol-5-yl)-$N^2,N^2$-dimethylpropane-1,2-diamine (DDLM18)

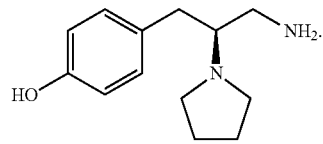 [SMILES: NC[C@H](Cc1ccc(O)cc1)N1CCCC1]

(S)-4-(3-amino-2-(pyrrolidin-1-yl)propyl)phenol (DDLM12)

(S)-3-(3-amino-2-(dimethylamino)propyl)phenol (DD45)

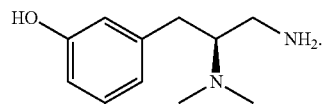

219
(9H-fluoren-9-yl)methyl (S)-(1-amino-3-(4-hydroxyphenyl)propan-2-yl)carbamate (DD199)

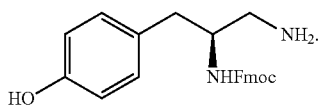

Method H: Reductive Methylation of Primary Amines

To a suspension of amino amides (1 eq) in acetonitrile/water (9:1 v/v), 37% aqueous formaldehyde (10 eq) was added followed by sodium triacetoxyborohydride (5 eq). The mixture was stirred for 10 min at an ambient temperature and then quenched by saturated $NaHCO_3$. The pH was adjusted to 8-9 by addition of sat. $NaHCO_3/Na_2CO_3$ solution, and the mixture was extracted with isopropanol/ethyl acetate (1:3 v/v). Combined organic layers were dried over anhydrous $Na_2SO_4$, filtered, and concentrated under reduced pressure. The residue was purified by flash chromatography.

Compounds Synthesized Following Method H (S)-3-(2,2-dimethyl-4H-benzo[d][1,3]dioxin-6-yl)-2-(dimethylamino)propanamide (DD117)

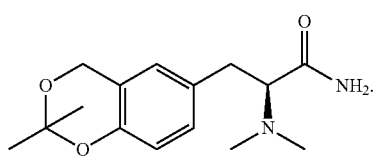

(S)-2-(dimethylamino)-3-(2,2-dimethylbenzo[d][1,3]dioxol-5-yl)propanamide (DDLM17)

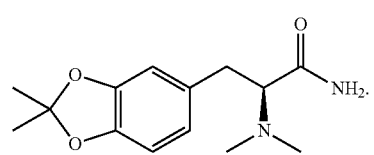 [SMILES: CN(C)[C@@H](Cc1ccc2c(c1)OC(C)(C)O2)C(N)=O]

(S)-2-(dimethylamino)-3-(2-hydroxypyridin-4-yl)propanamide (DD71)

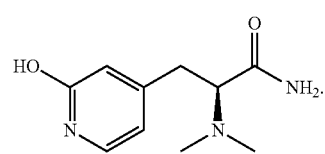

220
(S)-2-(dimethylamino)-3-(6-hydroxypyridin-3-yl)propanamide (DD72)

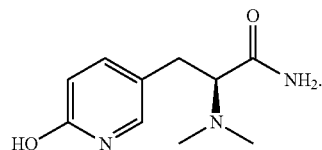

(S)-2-(dimethylamino)-3-(3-hydroxyphenyl)propanamide (DD42)

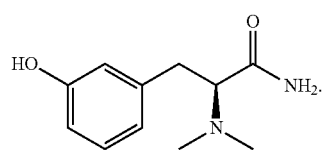

Method I: Aminolysis of carboxylic acid esters

Carboxylic acid esters (1 eq) were solved in dry methanol and stirred at −10° C. in an acetone-ice-bath. Dry ammonia gas was bubbled through the solution for 30 minutes at −10° C. and the solution was then allowed to warm up to room temperature and stirred overnight. After full conversion of starting material the solvent was evaporated and dried under high vacuum overnight. No further purification was required.

Compounds Synthesized Following Method I (S)-2-amino-3-(2-hydroxypyridin-4-yl)propanamide (DD68)

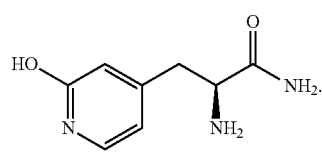 [SMILES: NC(=O)[C@@H](N)Cc1ccnc(O)c1]

(S)-2-amino-3-(6-hydroxypyridin-3-yl)propanamide (DD69)

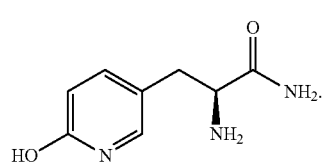 [SMILES: NC(=O)[C@@H](N)Cc1ccc(O)nc1]

Method J: Amidation of Carboxlic Acids

Carboxylic acids (acetonide- and fmoc-protected, 1 eq) was solved in acetonitrile. EEDQ (1.1 eq) and subsequently NH$_4$HCO$_3$ (3 eq) were added. The mixture was stirred at room temperature for 20 h. Then the precipitate was filtered off, washed with H$_2$O dem. and chloroform. Combined filtrates were washed with 5% NaHCO$_3$ solution and the combined organic layers were dried over anhydrous Na$_2$SO$_4$, filtered, and concentrated under reduced pressure. The residue was purified by flash chromatography.

Compounds Synthesized Following Method J (9H-fluoren-9-yl)methyl (S)-(1-amino-3-(2,2-dimethyl-4H-benzo[d][1,3]dioxin-6-yl)-1-oxopropan-2-yl)carbamate (DD112)

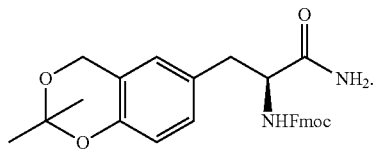

(9H-fluoren-9-yl)methyl (S)-(1-amino-3-(2,2-dimethylbenzo[d][1,3]dioxol-5-yl)-1-oxopropan-2-yl)carbamate (DDLM11)

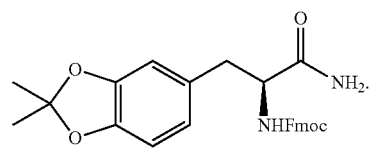

(S)-2-amino-3-(2,2-dimethyl-4H-benzo[d][1,3]dioxin-6-yl)propanamide (DD116)

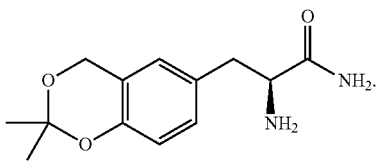 [SMILES: CC1(C)OCc2cc(C[C@H](N)C(N)=O)ccc2O1]

DD112 (1 eq) was solved in dichloromethane, DBU (2.5 eq) was added and the mixture was stirred for 2.5 h at room temperature. The solvent was evaporated and the residue purified by flash chromatography. Yield: 76%.

(S)-2-amino-3-(2,2-dimethylbenzo[d][1,3]dioxol-5-yl)propanamide (DDLM16)

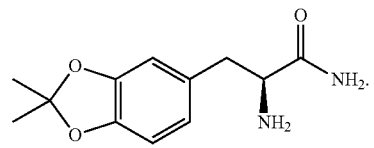 [SMILES: CC1(C)Oc2ccc(C[C@H](N)C(N)=O)cc2O1]

DDLM11 (1 eq) was stirred in 25% piperidine in DMF for 75 min. The mixture was diluted with MeOH and the solvent evaporated. The residue was purified by flash chromatography. Yield: 70%

2-((R)-2-aminopropyl)-3a,4,7,7a-tetrahydro-1H-4,7-epoxyisoindole-1,3(2H)-dione (DD 172

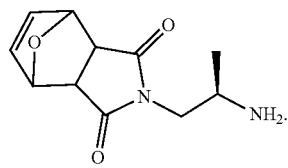 [SMILES: C[C@@H](N)CN1C(=O)C2C3C=CC(O3)C2C1=O]

tert-butyl (R)-(1-aminopropan-2-yl)carbamate hydrochloride (1 eq) in a microwave tube was solved in MeOH. Na$_2$CO$_3$ (2 eq) and TBAB (0.26 eq) was added and the mixture was stirred in an ice-water-bath. 3a,4,7,7a-tetrahydro-4,7-epoxyisobenzofuran-1,3-dione (1 eq) in a flask, suspended in MeOH was also stirred in an ice-water-bath for 10 minutes and then slowly added to the reaction mixture. The mixture was allowed to warm up to room temperature and stirred for 1 h. DMS (1.5 eq) was added, the tube sealed and the mixture was stirred at 70° C. overnight. Then the mixture was allowed to cool to room temperature, chloroform and 0.1 N NaOH was added, the layers separated and the aqueous phase washed with chloroform. Combined organic layers were washed with 0.1 N NaOH, 0.1 N HCl and brine and the dried over anhydrous Na$_2$SO$_4$, filtered, and concentrated under reduced pressure. The residue was solved in dichloromethane/TFA (10:1) at 0° C. The mixture was allowed to warm up to room temperature and then stirred for 3 h. It was diluted with MeOH and the solvent evaporated. The residue was solved in sat. NaHCO$_3$ solution, the pH adjusted with NH$_{3conc.}$ to 10 and extracted with chloroform (10×). Combined organic layers were dried over anhydrous Na$_2$SO$_4$, filtered, and concentrated under reduced pressure. Yield: 52%

2-((S)-2-aminopropyl)-3a,4,7,7a-tetrahydro-1H-4,7-epoxyisoindole-1,3(2H)-dione (DD151)

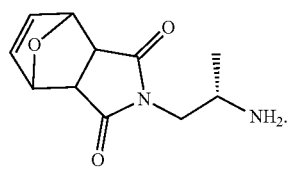 [SMILES: C[C@H](N)CN1C(=O)C2C3C=CC(O3)C2C1=O]

DD151 was synthesized as described for DD172, using tert-butyl (S)-(1-aminopropan-2-yl)carbamate (1 eq) and 3a,4,7,7a-tetrahydro-4,7-epoxyisobenzofuran-1,3-dione (1 eq) as starting materials. Yield: 10%.

(S)-3-(4-hydroxyphenyl)-2-(pyrrolidin-1-yl)propanamide (DDLM5)

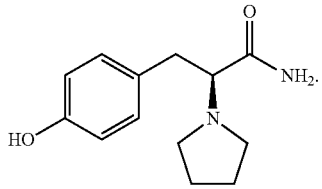 [SMILES: NC(=O)[C@H](Cc1ccc(O)cc1)N1CCCC1]

L-Tyrosinamide (1 eq) was solved in dry DMF in a microwave tube. 1,4-dibromobutane was added, the tube sealed and the mixture stirred for 5 h at room temperature and for 15 h at 50° C. under inert atmosphere. DDLM5×HBr precipitated and could be filtered off and subsequently purified by flash chromatography. Yield: 35%

BD128-L:

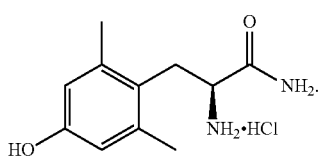

A mixture of Boc-L-Dmt-OH (0.62 g, 2.0 mmol), pyridine (0.16 mL, 2.0 mmol), di-tert-butyl dicarbonate (1.0 mL, 4.3 mmol), and ammonium bicarbonate (0.32 g, 4.1 mmol) in anhydrous dioxane (5 mL) was sealed in a microwave tube and stirred vigorously for 4 h at ambient temperature. Then the mixture was filtered and the precipitate was washed with ethyl acetate (2×2 mL). The filtrate was concentrated under reduced pressure and the obtained residue was redissolved in EtOAc (20 mL) and washed with 0.1 N HCl (2×15 mL), saturated aqueous NaHCO$_3$ (2×10 mL) and saturated aqueous NaCl (10 mL). Organic layer was dried over anhydrous Na$_2$SO$_4$, filtered and the solvent was removed under reduced pressure. White solid residue was dissolved in 2N HCl in diethyl ether (10.0 mL, 20.0 mmol), sonicated, and stirred for 20 h at ambient temperature. After 20 h the product precipitated. The slurry was filtered and the precipitate was washed with diethyl ether (2×10 mL). The white solid was dried under high vacuum yielding 0.474 g (97%) of the desired product. It was used in the next step without further purification.

TLC (NH$_4$OH/MeOH/CHCl$_3$ 2:18:80): R$_f$ (prod)=0.46 (ninhydrin stain). LCMS: t$_R$=9.9 min, purity: 96%; m/z found: 231.4; calcd. 231.3 ([M+Na]$^+$). $^1$H NMR (600 MHz, DMSO-d$_6$) d ppm 9.10 (br. s., 1H), 8.42 (br. s., 3H), 7.36 (s, 1H), 7.35 (s, 1H), 6.41 (s, 2H), 3.65 (dquin, J=11.0, 5.3 Hz, 1H), 2.98 (dd, J=13.8, 11.0 Hz, 1H), 2.90 (ddd, J=13.8, 5.3, 3.0 Hz, 1 H), 2.19 (s, 6H). $^1$H NMR (600 MHz, DMSO-d$_6$, exchange with D$_2$O) d ppm 7.40 (s, 1H), 7.34 (s, 1H), 6.42 (s, 2H), 3.66 (dd, J=10.8, 4.7 Hz, 1H), 2.99 (dd, J=13.8, 10.8 Hz, 1H), 2.87 (dd, J=13.8, 4.7 Hz, 1H), 2.19 (s, 6H)$^{13}$C NMR (151 MHz, DMSO-d$_6$) δ ppm 170.2, 155.6, 138.4 (2C), 122.2, 114.9 (2C), 51.6, 30.5, 20.0 (2C). [α]$_D^{25}$=+83.9° (c 0.38, H$_2$O).

BD129-L:

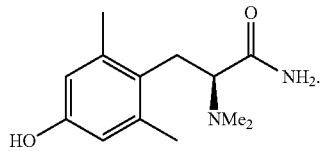

BD128L (474 mg, 1.94 mmol) was suspended in a mixture of MeCN (15 mL) and water (2.5 mL). To the mixture 37% aqueous formaldehyde (1.5 mL, 20 mmol) was added, followed by sodium triacetoxyborohydride (1.65 g, 7.8 mmol). The mixture was stirred at ambient temperature for 15 min. The reaction was quenched with saturated aqueous NaHCO$_3$ (15 mL, gas release). The layers were separated. pH of aqueous layer was adjusted to 8 by addition of solid Na$_2$CO$_3$, it was filtered and extracted by 20% iPrOH in EA (3×15 mL). Combined organic layers were dried over anhydrous Na$_2$SO$_4$, filtered and concentrated under reduced pressure yielding white solid (450 mg, 98%) after drying under high vacuum. The product was obtained and characterized as free base since it was easier to handle in this form.

TLC (NH$_4$OH/MeOH/CHCl$_3$ 1.5:13.5:85): R$_f$ (prod)=0.49 (KMnO$_4$ stain). LCMS (STANDESI): t$_R$=2.9 min, purity: 99% (254 nm); m/z found 237.5, calcd. 237.3 for C$_{13}$H$_{21}$N$_2$O$_2$ [M+H]$^+$. $^1$H NMR (600 MHz, DMSO-d$_6$) δ ppm 8.91 (br. s., 1H), 7.06 (br. s., 1H), 6.74 (br. s., 1H), 6.35 (s, 2H), 3.00 (dd, J=9.3, 3.6 Hz, 1H), 2.94 (dd, J=13.4, 9.3 Hz, 1H), 2.56 (dd, J=13.4, 3.6 Hz, 1H), 2.27 (s, 6H), 2.19 (s, 6H). $^1$H NMR (600 MHz, DMSO-d$_6$, exchange with D$_2$O) d ppm 6.36 (s, 2H), 3.01 (dd, J=9.4, 3.8 Hz, 1H), 2.95 (dd, J=13.4, 9.3 Hz, 1H), 2.57 (dd, J=13.4, 3.8 Hz, 1H), 2.27 (s, 6H), 2.19 (s, 6H). $^{13}$C NMR (151 MHz, DMSO-d$_6$) d ppm 172.3, 154.7, 137.6 (2C), 126.5, 114.7 (2C), 67.1, 41.8 (2C), 28.9, 20.1 (2C). HRESI-MS: m/z found: 237.1597, calcd. 237.1598 for C$_{13}$H$_{21}$N$_2$O$_2$ ([M+H]$^+$). [α]$_D^{25}$=+57.9° (c 0.51, MeOH).

BD130-L:

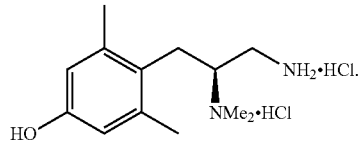

In a screw-cap tube to a suspension of crude BD129L (0.43 g, 1.84 mmol) in anhydrous THF (3 mL) borane tetrahydrofurane complex (13 mL, 13 mmol) was added at ambient temperature. The reaction tube was sealed and the mixture was vigourously stirred at 65-70° C. for 20 h. Then the reaction was quenched with MeOH, concentrated under reduced pressure, and dilution-concentration sequence was repeated twice more and the resulting yellow residue was dried under high vacuum. Then the crude product was diluted with EtOH (25 mL), 36% aqueous HCl was added (3 mL) and the mixture was concentrated under reduced pressure, dilution-concentration sequence was repeated twice more with EtOH. The resulting white solid was dissolved in hot EtOH (15 mL), filtered and the filtrate was concentrated under reduced pressure. The residue was suspended in acetone (15 mL), filtered, the solids were washed with additional acetone (15 mL) and dried under high vacuum. Yield: 0.40 g (98%).

TLC (NH₄OH/MeOH/CHCl₃ 3:27:70) $R_f$=0.50 (KMnO₄ and nynhydrin stain). LCMS (STANDESI): $t_R$=2.9 min, purity: 99% (254 nm); m/z found 223.5, calcd. 223.3 for $C_{13}H_{23}N_2O$ [M–H–2Cl]⁺. ¹H NMR (600 MHz, DMSO-d₆) δ ppm 11.10 (br. s., 1H), 9.27 (br. s., 1H), 8.45 (s, 3H), 6.49 (s, 2H), 3.89 (br. s., 1H), 3.55 (br. s., 1H), 3.12 (d, J=13.2 Hz, 1H), 2.78-3.08 (m, 6H), 2.69 (t, J=13.1 Hz, 1H), 2.57 (d, J=14.0 Hz, 1H), 2.23 (s, 6H). HRESI-MS: m/z found: 223.1802; calcd. 223.1805 for $C_{13}H_{23}N_2O$ ([M-Cl—H]⁺). $[\alpha]_D^{26}$=–4.3° (c 0.52, H₂O).

PZM Analogs

| Compound | binding affinity $K_i$ [nM]—number of independent experiments (n) | | | |
|---|---|---|---|---|
| | MM1 (MOR N127C) | hMOR | hKOR | hDOR |
| Morphine | (5) 32 | (15) 52 | (10) 1200 | (10) 1800 |
| Naloxone | (8) 3.7 | (21) 4.1 | (26) 23 | (20) 57 |
| DAMGO | (5) 25 | | (5) 3300 | (5) 980 |
| TRV 130 | (3) 27 | | | |

-continued

| Compound | binding affinity K$_i$ [nM]—number of independent experiments (n) | | | |
|---|---|---|---|---|
| | MM1 (MOR N127C) | hMOR | hKOR | hDOR |
| DD 17 | | (2) 4200 | (2) 8100 | (2) 25000 |
| DD 18 | | (2) 350 | (2) 3100 | (2) 4500 |
| BD 127DR | | (2) 2900 | (2) 5000 | (2) 12000 |
| BD 127DS | | (2) 2400 | (2) 3100 | (2) 11000 |
| BD 127LR | | (3) 380 | (3) 1300 | (3) 1800 |
| BD 127LS | | (2) 140 | (2) 1000 | (2) 2800 |
| DD 93A | | (3) 3200 | (2) 1700 | (3) ~15000 |

| Compound | MM1 (MOR N127C) | hMOR | hKOR | hDOR |
|---|---|---|---|---|
| DD 93B | | (4) 4100 | (3) 3100 | (4) ~15000 |
| 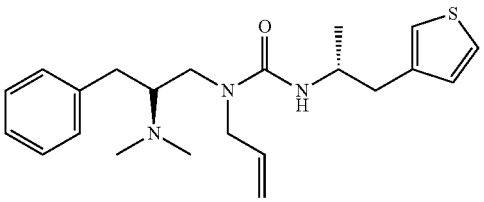 | | | | |
| DD 35D | | (2) 180 | (2) 960 | (2) 2400 |
| 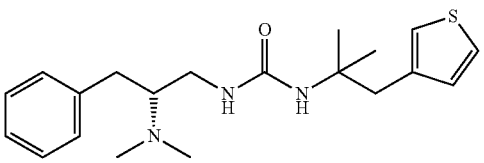 | | | | |
| DD 35L | | (2) 210 | (2) 790 | (2) 3000 |
| 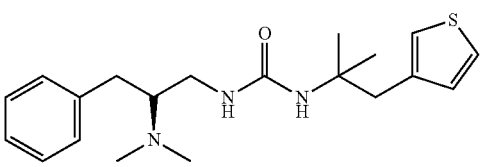 | | | | |
| DD 36D | | (2) 640 | (2) 1100 | (2) 1000 |
| 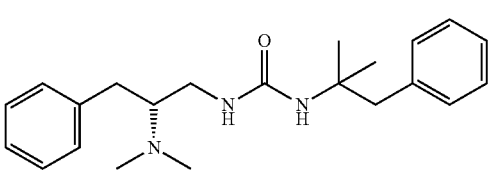 | | | | |
| DD 36L | | (2) 490 | (3) 930 | (3) 3300 |
| 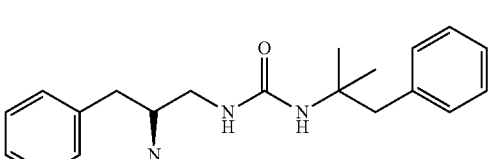 | | | | |
| DD 15 | | (2) 1500 | (2) 5200 | (2) 11000 |
| 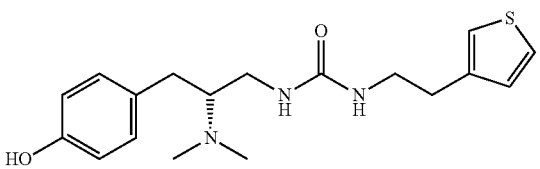 | | | | |

-continued

| Compound | MM1 (MOR N127C) | hMOR | hKOR | hDOR |
|---|---|---|---|---|
| DD 16 | | (6) 43 | (3) 150 | (3) 330 |
| DD 81 | | (6) 29 | (4) 86 | (4) 70 |
| DD 77 | | (5) 170 | (3) 190 | (3) 570 |
| DD 108 | | (7) 610 | (2) 340 | (2) 1700 |
| DD 102 | | (5) 320 | (2) 160 | (2) 1200 |
| DD 109 | | (7) 490 | (2) 220 | (2) 4200 |

-continued

| Compound | binding affinity $K_i$ [nM]—number of independent experiments (n) | | | |
|---|---|---|---|---|
| | MM1 (MOR N127C) | hMOR | hKOR | hDOR |
| DD 181 | | (3) 290 | | |
| DD 184 | | (3) 760 | | |
| BD 122DR | | (2) 290 | (2) 3100 | (2) 4100 |
| BD 122DS | | (2) 480 | (2) 2300 | (2) 4800 |
| BD 122LR | | (4) 42 | (4) 190 | (4) 88 |
| DD 88A R configuration according to $R_T$ | | (4) 96 | (2) 60 | (2) 470 |

-continued

| Compound | binding affinity $K_i$ [nM]—number of independent experiments (n) | | | |
| --- | --- | --- | --- | --- |
| | MM1 (MOR N127C) | hMOR | hKOR | hDOR |
| BD 122LS (PZM21) | (3) 46 | (8) 37 | (2) 18 | (2) 1000 |
| DD 88B<br>S configuration according to $R_T$ | | (4) 41 | (4) 4.5 | (4) 570 |
| DD 90 | | (5) 47 | (2) 45 | (2) 250 |
| DD 91 | | (7) 72 | (2) 100 | (3) 370 |
| DD 61L-A<br>R configuration according to $R_T$ | | (2) 81 | (2) 67 | (2) 91 |
| DD 61L-B<br>S configuration according to $R_T$ | | (2) 42 | (2) 37 | (2) 360 |

-continued

| Compound | binding affinity K$_i$ [nM]—number of independent experiments (n) | | | |
|---|---|---|---|---|
| | MM1 (MOR N127C) | hMOR | hKOR | hDOR |
| DD 63L-RS Diastereomers Equal mixture of | | (2) 14 | (2) 19 | (2) 44 |
| and | | | | |
| DD 63L-LA R configuration according to R$_T$ | | (3) 43 | (3) 67 | (3) 83 |
| DD 63L-LB S configuration according to R$_T$ | | (3) 8.3 | (3) 22 | (3) 110 |
| DD 53 LS | | (3) 38 | (3) 35 | (3) 590 |
| DD 51 LS | | (3) 150 | (3) 180 | (3) 700 |

-continued
| Compound | MM1 (MOR N127C) | hMOR | hKOR | hDOR |
|---|---|---|---|---|
| DD 50 LS | | (4) 85 | (4) 74 | (4) 540 |
| 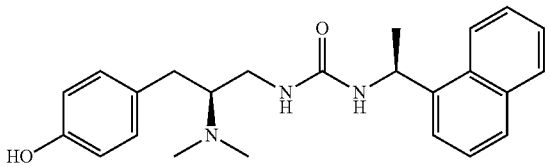 [SMILES: C[C@H](NC(=O)NC[C@H](Cc1ccc(O)cc1)N(C)C)c1cccc2ccccc12] | | | | |
| DD 50 NP | | (1) 400 | (1) 920 | (1) 570 |
| 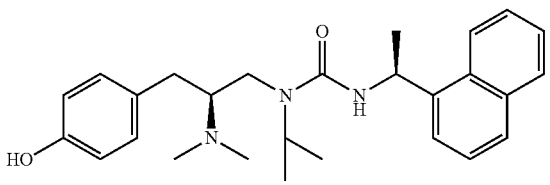 [SMILES: CC(C)N(C[C@H](Cc1ccc(O)cc1)N(C)C)C(=O)N[C@@H](C)c1cccc2ccccc12] | | | | |
| DD 57L | | (3) 7.7 | (3) 51 | (3) 56 |
| 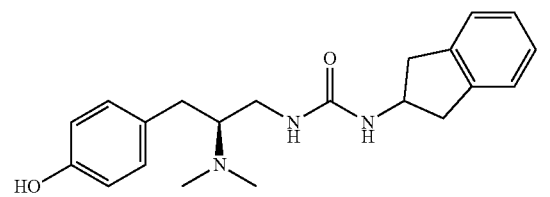 [SMILES: CN(C)[C@H](CNC(=O)NC1Cc2ccccc2C1)Cc1ccc(O)cc1] | | | | |
| DD 32D | | (3) 310 | (3) 1300 | (3) 2900 |
| 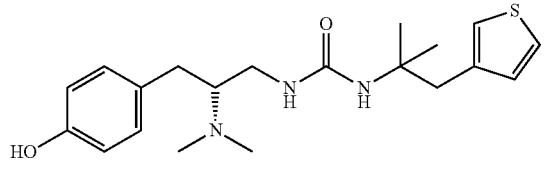 | | | | |
| DD 32L | | (4) 38 | (4) 46 | (4) 650 |
| 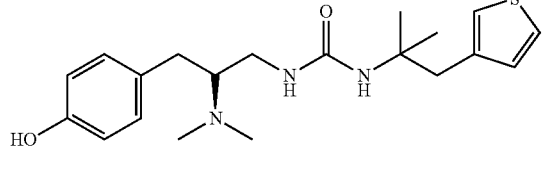 | | | | |
| DD 33D | | (3) 460 | (3) 1500 | (3) 3600 |
| 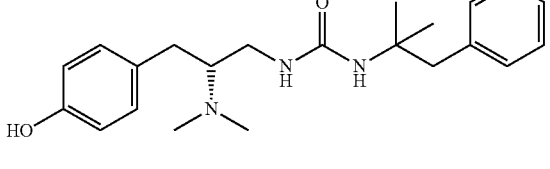 | | | | |

-continued

| Compound | MM1 (MOR N127C) | hMOR | hKOR | hDOR |
|---|---|---|---|---|
| DD 33L | | (3) 46 | (3) 91 | (3) 920 |
| DD 47LS | | (3) 34 | (4) 46 | (4) 350 |
| DD 46L | | (3) 25 | (3) 32 | (3) 190 |
| DD 79 I | | (3) 210 | (3) 1200 | (3) 4100 |
| DD 78 | 3800 | (1) 4600 | (2) 12000 | (3) >20000 |
| DD 131 | | (2) 66 | (2) 86 | (2) 1500 | binding affinity $K_i$ [nM]—number of independent experiments (n)

-continued
| Compound | binding affinity K$_i$ [nM]—number of independent experiments (n) | | | |
| --- | --- | --- | --- | --- |
| | MM1 (MOR N127C) | hMOR | hKOR | hDOR |
| DD 34L (ANTAGONIST) | | (3) 6.2 | (3) 27 | (3) 51 |
| 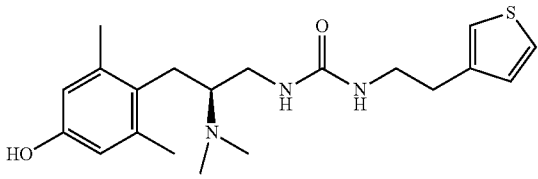 [SMILES: Cc1cc(O)cc(C)c1C[C@@H](CNC(=O)NCCc1ccsc1)N(C)C] | | | | |
| BD 131LR | | (4) 4.1 | (4) 12 | (4) 17 |
| 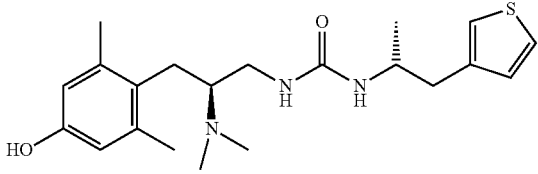 | | | | |
| BD 131LS | | (3) 12 | (3) 6.5 | (3) 85 |
| 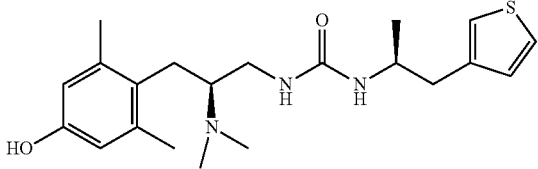 [SMILES: Cc1cc(O)cc(C)c1C[C@@H](CNC(=O)N[C@@H](C)Cc1ccsc1)N(C)C] | | | | |
| DD 120 D1 (covalent compound) | (4) 3.7 | (9) 240 | (3) 600 | (3) 450 |
| 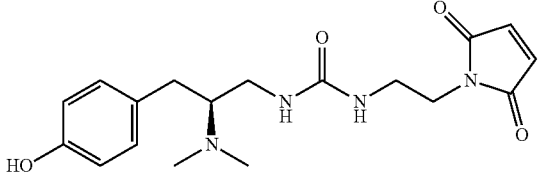 [SMILES: CN(C)[C@H](CNC(=O)NCCN1C(=O)C=CC1=O)Cc1ccc(O)cc1] | | | | |
| DD 138 | (2) 4.7 | (3) 580 | (3) 450 | (3) 3100 |
| 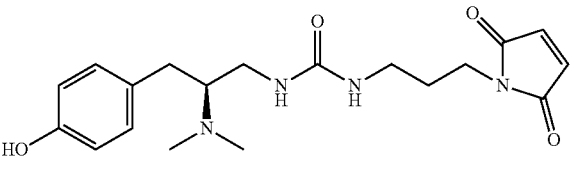 [SMILES: CN(C)[C@H](CNC(=O)NCCCN1C(=O)C=CC1=O)Cc1ccc(O)cc1] | | | | |
| DD 139 | (5) 5.9 | (3) 1000 | (2) 760 | (3) 4900 |
| 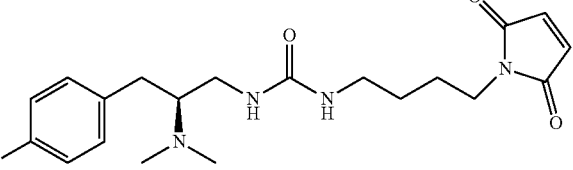 | | | | |

-continued

| Compound | binding affinity $K_i$ [nM]—number of independent experiments (n) | | | |
| --- | --- | --- | --- | --- |
| | MM1 (MOR N127C) | hMOR | hKOR | hDOR |
| DD 144 (ANTAGONIST, Covalent) | (3) 0.93 | (3) 18 | (2) 200 | (2) 150 |
| DD 158 | (3) 5.6 | (4) 410 | (2) 1200 | (2) 860 |
| DD 179 | (4) 0.13 + 290 | (4) 90 | (2) 690 | (2) 210 |
| DD 159 | (4) 34 | (4) 420 | (2) 1500 | (2) 3900 |
| DD 156 | (2) 630 | (2) 960 | (2) 1400 | (2) 4700 |
| DD 154 | | (3) 200 | (2) 1400 | (3) 580 |

-continued
| Compound | binding affinity $K_i$ [nM]—number of independent experiments (n) | | | |
|---|---|---|---|---|
| | MM1 (MOR N127C) | hMOR | hKOR | hDOR |
| DD 161 (n = 2) | | (4) 4700 | (3) 1200 | (2) 3000 |
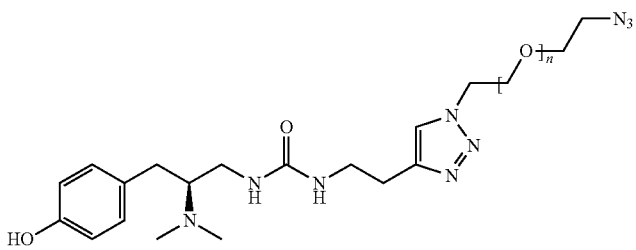
| | | | | |
|---|---|---|---|---|
| DD 165 (n = 3) | | (5) 3500 | (2) 2900 | (3) 3900 |
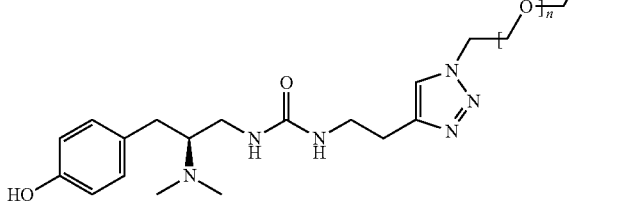
| | | | | |
|---|---|---|---|---|
| DD 168 (n = 5) | | (2) 13000 | | |
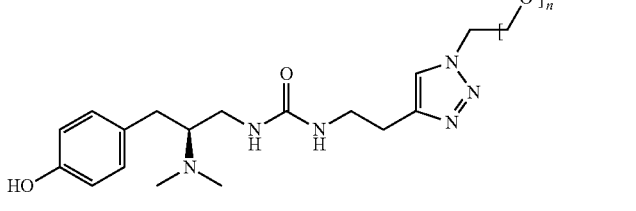
| | | | | |
|---|---|---|---|---|
| DD 170 (biotin tag) | | (2) 13000 | | |
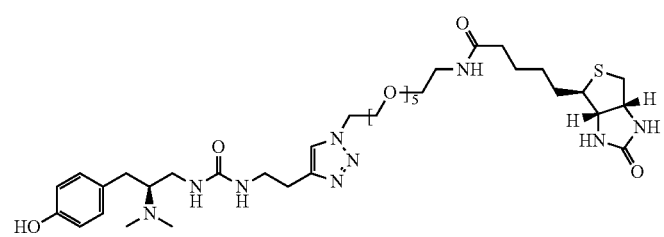
| | | | | |
|---|---|---|---|---|
| DD185 | (4) 47 | (4) 47 | (2) 250 | (2) 360 |
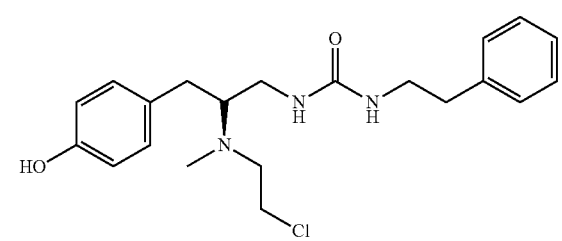

-continued

| Compound | MM1 (MOR N127C) | hMOR | hKOR | hDOR |
|---|---|---|---|---|
| DD186 | | (2) 970 | (2) 1300 | (2) 1800 |
| DD196 | | (2) 81 | (2) 240 | (3) 700 |
| DD187 | | (2) 220 | (2) 210 | (2) 720 |
| DD198 | | (3) 22 | (3) 140 | (3) 150 |
| DD200 | | (2) 110 | (2) 1300 | (2) 220 | binding affinity K$_i$ [nM]—number of independent experiments (n)

-continued

| Compound | binding affinity K_i [nM]—number of independent experiments (n) | | | |
| --- | --- | --- | --- | --- |
| | MM1 (MOR N127C) | hMOR | hKOR | hDOR |
| DD201 | | (2) 330 | (2) 1500 | (2) 10000 |
| DDLM-08 | | (3) 43 | (3) 440 | (2) 53 |
| DDLM-10 | | (3) 36 | (3) 170 | (2) 250 |
| DDLM-15 | | (3) 27 | (3) 190 | (1) 250 |
| DDLM-14 | | (3) 660 | (3) 770 | (3) 1500 |
| DD203 | | | | |

| Compound | binding affinity $K_i$ [nM]—number of independent experiments (n) | | | |
|---|---|---|---|---|
| | MM1 (MOR N127C) | hMOR | hKOR | hDOR |
| DD208 | | | | |
| DD206 | | | | |
| DDLM20 | | | | |
| DD 137 | (3) 2300 | (2) 8200 | (2) 36000 | |

EMBODIMENTS

Embodiment 1

A compound having the formula:

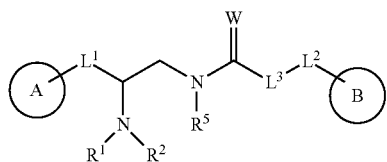

wherein, W is O or S; Ring A is independently substituted or unsubstituted aryl or substituted or unsubstituted heteroaryl; Ring B is independently substituted or unsubstituted cycloalkyl, substituted or unsubstituted heterocycloalkyl, substituted or unsubstituted aryl, or substituted or unsubstituted heteroaryl; $L^1$ and $L^2$ are independently a bond, substituted or unsubstituted ($C_1$-$C_5$) alkylene, or substituted or unsubstituted 2 to 5 membered heteroalkylene; $R^1$ and $R^2$ are independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, $OCF_3$, —$OCHF_2$, substituted or unsubstituted ($C_1$-$C_5$) alkyl, substituted or unsubstituted 2 to 5 membered heteroalkyl, substituted or unsubstituted ($C_3$-$C_6$) cycloalkyl, or substituted or unsubstituted 3 to 6 membered heterocycloalkyl; $R^1$ and $R^2$ may optionally be joined to form a substituted or unsubstituted 3 to 6 membered heterocycloalkyl or substituted or unsubstituted 5 to 6 membered heteroaryl; $L^1$ and $R^1$ may optionally be joined to form a substituted or unsubstituted 4 to 8 membered heterocycloalkyl; $L^1$ and $R^2$ may optionally be joined to form a substituted or unsubstituted 4 to 8 membered heterocycloalkyl; $L^3$ is a bond, —O—, —N($R^6$)—, or —$CH_2$—; $R^5$ is hydrogen, —$CF_3$, —CN, —COOH, —$CONH_2$, —$CHF_2$, —$CH_2F$, substituted or unsubstituted ($C_1$-$C_5$) alkyl, or substituted or unsubstituted 2 to 5 membered heteroalkyl; and $R^6$ is hydrogen, —CF$_3$, —CN, —COOH, —CONH$_2$, —CHF$_2$, —CH$_2$F, substituted or unsubstituted (C$_1$-C$_5$) alkyl, or substituted or unsubstituted 2 to 5 membered heteroalkyl.

Embodiment 2

The compound of embodiment 1, having the formula:

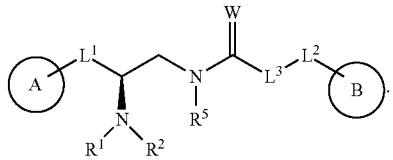

Embodiment 3

The compound of embodiment 1, having the formula:

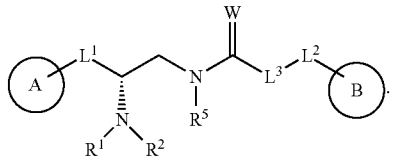

Embodiment 4

The compound of one of embodiments 1 to 3, wherein Ring A is substituted or unsubstituted (C$_6$-C$_{10}$) aryl or substituted or unsubstituted 5 to 10 membered heteroaryl.

Embodiment 5

The compound of one of embodiments 1 to 3, wherein Ring A is R$^3$-substituted or unsubstituted (C$_6$-C$_{10}$) aryl or R$^3$-substituted or unsubstituted 5 to 10 membered heteroaryl; R$^3$ is independently hydrogen, halogen, —CX$_3$, —CN, —SO$_n$R$^{10}$, —SO$_2$NR$^7$R$^8$, —NHNR$^7$R$^8$, —ONR$^7$R$^8$, —NHC=(O)NHNR$^7$R$^8$, —NHC=(O)NR$^7$R$^8$, —N(O)$_m$, —NR$^7$R$^8$, —C(O)R$^9$, —C(O)—OR$^9$, —C(O)NR$^7$R$^8$, —OR$^{10}$, —NR$^7$SO$_2$R$^{10}$, —NR$^7$C=(O)R$^9$, —NR$^7$C(O)OR$^9$, —NR$^7$OR$^9$, —CHX$_2$, —CH$_2$X, —OCX$_3$, —OCHX$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; Two adjacent R$^3$ substituents may optionally be joined to form a substituted or unsubstituted cycloalkyl, substituted or unsubstituted heterocycloalkyl, substituted or unsubstituted aryl, or substituted or unsubstituted heteroaryl; R$^7$, R$^8$, R$^9$, and R$^{10}$ are independently hydrogen, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —CHF$_2$, —CH$_2$F, OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^7$ and R$^8$ substituents bonded to the same nitrogen atom may optionally be joined to form a substituted or unsubstituted heterocycloalkyl or substituted or unsubstituted heteroaryl; m and v are independently 1 or 2; n is independently an integer from 0 to 4; X is independently —Cl, —Br, —I, or —F.

Embodiment 6

The compound of embodiment 5, wherein Ring A is R$^3$-substituted or unsubstituted (C$_6$-C$_{10}$) aryl.

Embodiment 7

The compound of embodiment 5, wherein Ring A is R$^3$-substituted or unsubstituted phenyl.

Embodiment 8

The compound of one of embodiments 5 to 7, wherein R$^3$ is independently hydrogen, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —CHF$_2$, —CH$_2$F, OCF$_3$, —OCHF$_2$, substituted or unsubstituted (C$_1$-C$_5$) alkyl, or substituted or unsubstituted 2 to 5 membered heteroalkyl.

Embodiment 9

The compound of one of embodiments 5 to 7, wherein R$^3$ is —OH.

Embodiment 10

The compound of one of embodiments 1 to 9, having the formula:

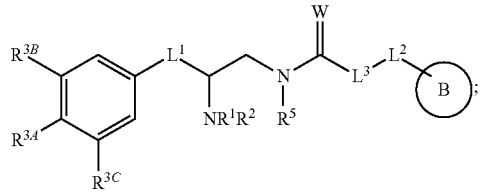

wherein R$^{3A}$, R$^{3B}$, and R$^{3C}$ are independently hydrogen, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —CHF$_2$, —CH$_2$F, OCF$_3$, —OCHF$_2$, substituted or unsubstituted (C$_1$-C$_5$) alkyl, or substituted or unsubstituted 2 to 5 membered heteroalkyl.

Embodiment 11

The compound of one of embodiments 1 to 9, having the formula:

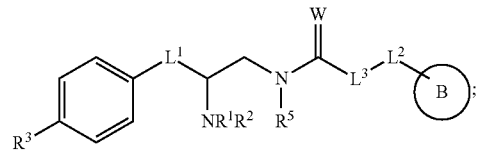

wherein R³ is
halogen, —CF₃, —CN, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)OH, —NHOH, —CHF₂, —CH₂F, OCF₃, —OCHF₂, substituted or unsubstituted (C₁-C₅) alkyl, or substituted or unsubstituted 2 to 5 membered heteroalkyl.

Embodiment 12

The compound of embodiment 11, wherein R³ is —OH.

Embodiment 13

The compound of one of embodiments 1 to 9, having the formula:

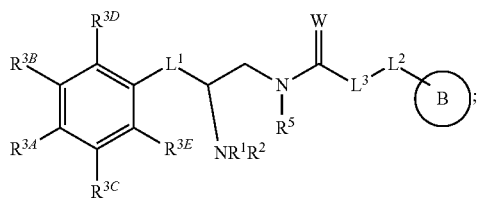

wherein $R^{3A}$, $R^{3B}$, and $R^{3C}$ are independently
halogen, —CF₃, —CN, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)OH, —NHOH, —CHF₂, —CH₂F, OCF₃, —OCHF₂, substituted or unsubstituted (C₁-C₅) alkyl, or substituted or unsubstituted 2 to 5 membered heteroalkyl; $R^{3D}$ is hydrogen, halogen, —CF₃, —CN, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)OH, —NHOH, —CHF₂, —CH₂F, OCF₃, —OCHF₂, substituted or unsubstituted (C₁-C₅) alkyl, or substituted or unsubstituted 2 to 5 membered heteroalkyl; $R^{3E}$ is hydrogen halogen, —CF₃, —CN, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)OH, —NHOH, —CHF₂, —CH₂F, OCF₃, —OCHF₂, substituted or unsubstituted (C₁-C₅) alkyl, or substituted or unsubstituted 2 to 5 membered heteroalkyl; and z is an integer between 0 and 3.

Embodiment 14

The compound of embodiment 13, wherein $R^{3D}$ and $R^{3E}$ are independently unsubstituted (C₁-C₅) alkyl.

Embodiment 15

The compound of embodiment 13, wherein $R^{3D}$ and $R^{3E}$ are independently unsubstituted (C₁-C₃) alkyl.

Embodiment 16

The compound of embodiment 13, wherein $R^{3D}$ and $R^{3E}$ are independently unsubstituted (C₁-C₂) alkyl.

Embodiment 17

The compound of embodiment 13, wherein $R^{3D}$ and $R^{3E}$ are independently unsubstituted methyl.

Embodiment 18

The compound of embodiment 13, having the formula:

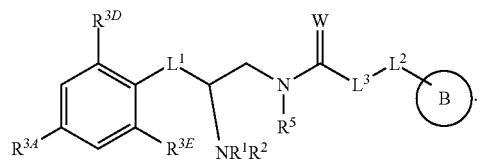

Embodiment 19

The compound of embodiment 18, wherein $R^{3A}$ is —OH.

Embodiment 20

The compound of embodiment 5, wherein Ring A is unsubstituted phenyl.

Embodiment 21

The compound of one of embodiments 1 to 20, wherein Ring B is substituted or unsubstituted (C₃-C₁₀) cycloalkyl or substituted or unsubstituted 3 to 10 membered heterocycloalkyl, substituted or unsubstituted (C₆-C₁₀) aryl, or substituted or unsubstituted 5 to 10 membered heteroaryl.

Embodiment 22

The compound of one of embodiments 1 to 20, wherein Ring B is R⁴-substituted or unsubstituted (C₃-C₁₀) cycloalkyl, R⁴-substituted or unsubstituted 5 to 10 membered heterocycloalkyl, R⁴-substituted or unsubstituted (C₆-C₁₀) aryl, or R⁴-substituted or unsubstituted 5 to 10 membered heteroaryl; R⁴ is independently oxo,
halogen, —CX$^a$₃, —CN, —SO$_{n1}$R¹⁴, —SO$_{v1}$NR¹¹R¹², —NHNR¹¹R¹², —ONR¹¹R¹², —NHC=(O)NHNR¹¹R¹², —NHC=(O)NR¹¹R¹², —N(O)$_{m1}$, —NR¹¹R¹², —C(O)R¹³, —C(O)—OR¹³, —C(O)NR¹¹R¹², —OR¹⁴, NRSO₂R¹⁴, —NR¹¹C=(O)R¹³, —NR¹¹C(O)OR¹³, —NR¹¹OR¹³, —CHX₂, —CH₂X, —OCX₃, —OCHX₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R⁴ substituents may optionally be joined to form a substituted or unsubstituted cycloalkyl, substituted or unsubstituted heterocycloalkyl, substituted or unsubstituted aryl, or substituted or unsubstituted heteroaryl; R¹¹, R¹², R¹³, and R¹⁴ are independently hydrogen,
halogen, —CF₃, —CN, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)OH, —NHOH, —CHF₂, —CH₂F, OCF₃, —OCHF₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R¹¹ and $R^{12}$ substituents bonded to the same nitrogen atom may optionally be joined to form a substituted or unsubstituted heterocycloalkyl or substituted or unsubstituted heteroaryl; m1 and v1 are independently 1 or 2; n1 is independently an integer from 0 to 4; $X^a$ is independently —Cl, —Br, —I, or —F.

Embodiment 23

The compound of embodiment 22, wherein Ring B is $R^4$-substituted or unsubstituted $(C_3-C_{10})$ cycloalkyl.

Embodiment 24

The compound of embodiment 22, wherein Ring B is $R^4$-substituted or unsubstituted 3 to 10 membered heterocycloalkyl.

Embodiment 25

The compound of embodiment 22, wherein Ring B is $R^4$-substituted or unsubstituted $(C_6-C_{10})$ aryl.

Embodiment 26

The compound of embodiment 22, wherein Ring B is $R^4$-substituted or unsubstituted 5 to 10 membered heteroaryl.

Embodiment 27

The compound of embodiment 22, wherein Ring B is $R^4$-substituted or unsubstituted thienyl, $R^4$-substituted or unsubstituted phenyl, $R^4$-substituted or unsubstituted benzothienyl, $R^4$-substituted or unsubstituted naphthyl, $R^4$-substituted or unsubstituted benzofuranyl, $R^4$-substituted or unsubstituted furanyl, $R^4$-substituted or unsubstituted pyrrolyl, or $R^4$-substituted or unsubstituted 2,3-dihydro-1H-indenyl.

Embodiment 28

The compound of one of embodiments 1 to 3, wherein Ring A is unsubstituted phenyl and Ring B is unsubstituted thienyl; Ring A is para-hydroxy substituted phenyl and Ring B is unsubstituted thienyl; Ring A is para-hydroxy substituted phenyl and Ring B is unsubstituted phenyl; Ring A is para-hydroxy substituted phenyl and Ring B is unsubstituted benzothienyl; Ring A is para-hydroxy substituted phenyl and Ring B is para-methyl substituted phenyl; Ring A is 2-hydroxy pyridin-4-yl and Ring B is unsubstituted thienyl; Ring A is 2-hydroxy pyridin-5-yl and Ring B is unsubstituted thienyl; Ring A is para-hydroxy substituted phenyl and Ring B is unsubstituted napthtyl; or Ring A is para-hydroxy substituted phenyl and Ring B is unsubstituted 2,3-dihydro-1H-indenyl.

Embodiment 29

The compound of one of embodiments 22 to 28, wherein $R^4$ is independently halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)OH, —NHOH, —$CHF_2$, —$CH_2F$, $OCF_3$, —$OCHF_2$, substituted or unsubstituted $(C_1-C_5)$ alkyl, or substituted or unsubstituted 2 to 5 membered heteroalkyl.

Embodiment 30

The compound of one of embodiments 22 to 28, wherein $R^4$ is methyl.

Embodiment 31

The compound of embodiment 22, wherein Ring B is unsubstituted phenyl.

Embodiment 32

The compound of one of embodiments 1 to 31, wherein $L^1$ is substituted or unsubstituted $(C_1-C_5)$ alkylene.

Embodiment 33

The compound of one of embodiments 1 to 31, wherein $L^1$ is substituted or unsubstituted 2 to 5 membered heteroalkylene.

Embodiment 34

The compound of one of embodiments 1 to 31, wherein $L^1$ is unsubstituted $(C_1-C_3)$ alkylene.

Embodiment 35

The compound of one of embodiments 1 to 31, wherein $L^1$ is $R^{96}$-substituted or unsubstituted $C_1-C_5$ alkylene, $R^{96}$-substituted or unsubstituted 2 to 5 membered heteroalkylene; $R^{96}$ is independently oxo, halogen, —$CX^{96}_3$, —$CHX^{96}_2$, —$OCH_2X^{96}$, —$OCHX^{96}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, —$OCX^{96}_3$, —$OCHX^{96}_2$, substituted or unsubstituted $(C_1-C_5)$ alkyl, substituted or unsubstituted 2 to 5 membered heteroalkyl, substituted or unsubstituted $(C_3-C_5)$ cycloalkyl, substituted or unsubstituted 3 to 5 membered heterocycloalkyl, substituted or unsubstituted phenyl, or substituted or unsubstituted 5 to 6 membered heteroaryl; and $X^{96}$ is halogen.

Embodiment 36

The compound of one of embodiments 1 to 31, wherein $L^1$ is $R^{96}$-substituted or unsubstituted $C_1-C_5$ alkylene; $R^{96}$ is independently oxo, halogen, —$CX^{96}_3$, —$CHX^{96}_2$, —$OCH_2X^{96}$, —$OCHX^{96}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, —$OCX^{96}_3$, —$OCHX^{96}_2$, substituted or unsubstituted $(C_1-C_5)$ alkyl, substituted or unsubstituted 2 to 5 membered heteroalkyl, substituted or unsubstituted $(C_3-C_5)$ cycloalkyl, substituted or unsubstituted 3 to 5 membered heterocycloalkyl, substituted or unsubstituted phenyl, or substituted or unsubstituted 5 to 6 membered heteroaryl; and $X^{96}$ is halogen.

Embodiment 37

The compound of one of embodiments 1 to 31, wherein $L^1$ is $R^{96}$-substituted or unsubstituted $C_1-C_3$ alkylene; $R^{96}$ is independently oxo,

Embodiment 38

The compound of one of embodiments 1 to 31, wherein $L^1$ is $R^{96}$-substituted or unsubstituted methylene; $R^{96}$ is independently oxo, halogen, $-CX^{96}_3$, $-CHX^{96}_2$, $-OCH_2X^{96}$, $-OCHX^{96}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{96}_3$, $-OCHX^{96}_2$, substituted or unsubstituted ($C_1$-$C_5$) alkyl, substituted or unsubstituted 2 to 5 membered heteroalkyl, substituted or unsubstituted ($C_3$-$C_5$) cycloalkyl, substituted or unsubstituted 3 to 5 membered heterocycloalkyl, substituted or unsubstituted phenyl, or substituted or unsubstituted 5 to 6 membered heteroaryl; and $X^{96}$ is halogen.

Embodiment 39

The compound of one of embodiments 1 to 31, wherein $L^1$ is $R^{96}$-substituted or unsubstituted 2 to 5 membered heteroalkylene; $R^{96}$ is independently oxo, halogen, $-CX^{96}_3$, $-CHX^{96}_2$, $-OCH_2X^{96}$, $-OCHX^{96}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{96}_3$, $-OCHX^{96}_2$, substituted or unsubstituted ($C_1$-$C_5$) alkyl, substituted or unsubstituted 2 to 5 membered heteroalkyl, substituted or unsubstituted ($C_3$-$C_5$) cycloalkyl, substituted or unsubstituted 3 to 5 membered heterocycloalkyl, substituted or unsubstituted phenyl, or substituted or unsubstituted 5 to 6 membered heteroaryl; and $X^{96}$ is halogen.

Embodiment 40

The compound of one of embodiments 1 to 31, wherein $L^1$ is $R^{96}$-substituted or unsubstituted 2 to 3 membered heteroalkylene; $R^{96}$ is independently oxo, halogen, $-CX^{96}_3$, $-CHX^{96}_2$, $-OCH_2X^{96}$, $-OCHX^{96}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{96}_3$, $-OCHX^{96}_2$, substituted or unsubstituted ($C_1$-$C_5$) alkyl, substituted or unsubstituted 2 to 5 membered heteroalkyl, substituted or unsubstituted ($C_3$-$C_5$) cycloalkyl, substituted or unsubstituted 3 to 5 membered heterocycloalkyl, substituted or unsubstituted phenyl, or substituted or unsubstituted 5 to 6 membered heteroaryl; and $X^{96}$ is halogen.

Embodiment 41

The compound of one of embodiments 1 to 31, wherein $L^1$ is unsubstituted methylene.

Embodiment 42

The compound of one of embodiments 1 to 41, wherein $R^1$ is unsubstituted ($C_1$-$C_3$) alkyl.

Embodiment 43

The compound of one of embodiments 1 to 41, wherein $R^1$ is unsubstituted ($C_1$-$C_2$) alkyl.

Embodiment 44

The compound of one of embodiments 1 to 41, wherein $R^1$ is independently hydrogen, halogen, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-CHF_2$, $-CH_2F$, $OCF_3$, $-OCHF_2$, substituted or unsubstituted ($C_1$-$C_5$) alkyl, substituted or unsubstituted 2 to 5 membered heteroalkyl, substituted or unsubstituted ($C_3$-$C_6$) cycloalkyl, or substituted or unsubstituted 3 to 6 membered heterocycloalkyl.

Embodiment 45

The compound of one of embodiments 1 to 41, wherein $R^1$ is independently halogen, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-CHF_2$, $-CH_2F$, $OCF_3$, $-OCHF_2$, substituted or unsubstituted ($C_1$-$C_5$) alkyl, substituted or unsubstituted 2 to 5 membered heteroalkyl, substituted or unsubstituted ($C_3$-$C_6$) cycloalkyl, or substituted or unsubstituted 3 to 6 membered heterocycloalkyl.

Embodiment 46

The compound of one of embodiments 1 to 41, wherein $R^1$ is independently halogen, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-CHF_2$, $-CH_2F$, $OCF_3$, $-OCHF_2$, $R^{30}$-substituted or unsubstituted ($C_1$-$C_5$) alkyl, $R^{30}$-substituted or unsubstituted 2 to 5 membered heteroalkyl, $R^{30}$-substituted or unsubstituted ($C_3$-$C_6$) cycloalkyl, or $R^{30}$-substituted or unsubstituted 3 to 6 membered heterocycloalkyl; $R^{30}$ is independently oxo, halogen, $-CX^{30}_3$, $-CHX^{30}_2$, $-OCH_2X^{30}$, $-OCHX^{30}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{30}_3$, $-OCHX^{30}_2$, substituted or unsubstituted ($C_1$-$C_5$) alkyl, substituted or unsubstituted 2 to 5 membered heteroalkyl, substituted or unsubstituted ($C_3$-$C_5$) cycloalkyl, substituted or unsubstituted 3 to 5 membered heterocycloalkyl, substituted or unsubstituted phenyl, or substituted or unsubstituted 5 to 6 membered heteroaryl; and $X^{30}$ is halogen.

Embodiment 47

The compound of one of embodiments 1 to 41, wherein $R^1$ is $R^{30}$-substituted or unsubstituted ($C_1$-$C_3$) alkyl or $R^{30}$-substituted or unsubstituted 2 to 3 membered heteroalkyl; $R^{30}$ is independently oxo, halogen, —CX$^{30}_3$, —CHX$^{30}_2$, —OCH$_2$X$^{30}$, —OCHX$^{30}_2$, —CN, —OH, —NH$_2$, —COOH, —CONH$_2$, —NO$_2$, —SH, —SO$_2$NH$_2$, —NHNH$_2$, —ONH$_2$, —NHOH, —OCX$^{30}_3$, —OCHX$^{30}_2$, substituted or unsubstituted (C$_1$-C$_3$) alkyl, substituted or unsubstituted 2 to 3 membered heteroalkyl, or substituted or unsubstituted cyclopropyl; and X$^{30}$ is halogen.

Embodiment 48

The compound of one of embodiments 1 to 41, wherein R$^1$ is R$^{30}$-substituted or unsubstituted (C$_1$-C$_2$) alkyl; R$^{30}$ is independently halogen, —OH, —NH$_2$, —SH, substituted or unsubstituted (C$_1$-C$_3$) alkyl, substituted or unsubstituted 2 to 3 membered heteroalkyl, or substituted or unsubstituted cyclopropyl; and X$^{30}$ is halogen.

Embodiment 49

The compound of one of embodiments 1 to 41, wherein R$^1$ is unsubstituted methyl.

Embodiment 50

The compound of one of embodiments 1 to 49, wherein R$^2$ is unsubstituted (C$_1$-C$_3$) alkyl.

Embodiment 51

The compound of one of embodiments 1 to 49, wherein R$^2$ is unsubstituted (C$_1$-C$_2$) alkyl.

Embodiment 52

The compound of one of embodiments 1 to 49, wherein R$^2$ is independently hydrogen, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —CHF$_2$, —CH$_2$F, OCF$_3$, —OCHF$_2$, substituted or unsubstituted (C$_1$-C$_5$) alkyl, substituted or unsubstituted 2 to 5 membered heteroalkyl, substituted or unsubstituted (C$_3$-C$_6$) cycloalkyl, or substituted or unsubstituted 3 to 6 membered heterocycloalkyl.

Embodiment 53

The compound of one of embodiments 1 to 49, wherein R$^2$ is independently halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —CHF$_2$, —CH$_2$F, OCF$_3$, —OCHF$_2$, substituted or unsubstituted (C$_1$-C$_5$) alkyl, substituted or unsubstituted 2 to 5 membered heteroalkyl, substituted or unsubstituted (C$_3$-C$_6$) cycloalkyl, or substituted or unsubstituted 3 to 6 membered heterocycloalkyl.

Embodiment 54

The compound of one of embodiments 1 to 49, wherein R$^2$ is independently halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC (O)OH, —NHOH, —CHF$_2$, —CH$_2$F, OCF$_3$, —OCHF$_2$, R$^{33}$-substituted or unsubstituted (C$_1$-C$_5$) alkyl, R$^{33}$-substituted or unsubstituted 2 to 5 membered heteroalkyl, R$^{33}$-substituted or unsubstituted (C$_3$-C$_6$) cycloalkyl, or R$^{33}$-substituted or unsubstituted 3 to 6 membered heterocycloalkyl; R$^{33}$ is independently oxo,
halogen, —CX$^{33}_3$, —CHX$^{30}_2$, —OCH$_2$X$^{33}$, —OCHX$^{33}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{33}_3$, —OCHX$^{33}_2$, substituted or unsubstituted (C$_1$-C$_5$) alkyl, substituted or unsubstituted 2 to 5 membered heteroalkyl, substituted or unsubstituted (C$_3$-C$_5$) cycloalkyl, substituted or unsubstituted 3 to 5 membered heterocycloalkyl, substituted or unsubstituted phenyl, or substituted or unsubstituted 5 to 6 membered heteroaryl; and X$^{33}$ is halogen.

Embodiment 55

The compound of one of embodiments 1 to 49, wherein R$^2$ is R$^{33}$-substituted or unsubstituted (C$_1$-C$_3$) alkyl or R$^{33}$-substituted or unsubstituted 2 to 3 membered heteroalkyl; R$^{33}$ is independently oxo,
halogen, —CX$^{33}_3$, —CHX$^{33}_2$, —OCH$_2$X$^{33}$, —OCHX$^{33}_2$, —CN, —OH, —NH$_2$, —COOH, —CONH$_2$, —NO$_2$, —SH, —SO$_2$NH$_2$, —NHNH$_2$, —ONH$_2$, —NHOH, —OCX$^{33}_3$, —OCHX$^{33}_2$, substituted or unsubstituted (C$_1$-C$_3$) alkyl, substituted or unsubstituted 2 to 3 membered heteroalkyl, or substituted or unsubstituted cyclopropyl; and X$^{33}$ is halogen.

Embodiment 56

The compound of one of embodiments 1 to 49, wherein R$^2$ is R$^{33}$-substituted or unsubstituted (C$_1$-C$_2$) alkyl; R$^{33}$ is independently halogen, —OH, —NH$_2$, —SH, substituted or unsubstituted (C$_1$-C$_3$) alkyl, substituted or unsubstituted 2 to 3 membered heteroalkyl, or substituted or unsubstituted cyclopropyl; and X$^{33}$ is halogen.

Embodiment 57

The compound of one of embodiments 1 to 49, wherein R$^2$ is unsubstituted methyl.

Embodiment 58

The compound of one of embodiments 1 to 31, wherein L$^1$ and R$^1$ are joined to form a substituted or unsubstituted 4 to 8 membered heterocycloalkyl.

Embodiment 59

The compound of one of embodiments 1 to 31, wherein L$^1$ and R$^1$ are joined to form a R$^{30}$-substituted or unsubstituted 4 to 8 membered heterocycloalkyl; R$^{30}$ is independently oxo,
halogen, —CX$^{30}_3$, —CHX$^{30}_2$, —OCH$_2$X$^{30}$, —OCHX$^{30}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{30}_3$, —OCHX$^{30}_2$, substituted or unsubstituted (C$_1$-C$_5$) alkyl, substituted or unsubstituted 2 to 5 membered heteroalkyl, substituted or unsubstituted (C$_3$-C$_5$) cycloalkyl, substituted or unsubstituted 3 to 5 membered heterocycloalkyl, substituted or unsubstituted phenyl, or substituted or unsubstituted 5 to 6 membered heteroaryl; and X$^{30}$ is halogen.

Embodiment 60

The compound of one of embodiments 1 to 31, wherein $L^1$ and $R^1$ are joined to form a $R^{30}$-substituted or unsubstituted 4 to 8 membered heterocycloalkyl; $R^{30}$ is independently oxo, halogen, $-CX^{30}{}_3$, $-CHX^{30}{}_2$, $-OCH_2X^{30}$, $-OCHX^{30}{}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{30}{}_3$, $-OCHX^{30}{}_2$, substituted or unsubstituted ($C_1$-$C_3$) alkyl, or substituted or unsubstituted 2 to 3 membered heteroalkyl; and $X^{30}$ is halogen.

Embodiment 61

The compound of one of embodiments 1 to 31, wherein $L^1$ and $R^1$ are joined to form a $R^{30}$-substituted or unsubstituted 4 to 8 membered heterocycloalkyl; $R^{30}$ is independently oxo, halogen, $-OH$, $-NH_2$, $-COOH$, $-CONH_2$, $-NO_2$, $-SH$, substituted or unsubstituted ($C_1$-$C_3$) alkyl, or substituted or unsubstituted 2 to 3 membered heteroalkyl; and $X^{30}$ is halogen.

Embodiment 62

The compound of one of embodiments 1 to 31, wherein $L^1$ and $R^2$ are joined to form a substituted or unsubstituted 4 to 8 membered heterocycloalkyl.

Embodiment 63

The compound of one of embodiments 1 to 31, wherein $L^1$ and $R^2$ are joined to form a $R^{33}$-substituted or unsubstituted 4 to 8 membered heterocycloalkyl; $R^{33}$ is independently oxo, halogen, $-CX^{33}{}_3$, $-CHX^{33}{}_2$, $-OCH_2X^{33}$, $-OCHX^{30}{}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{33}{}_3$, $-OCHX^{33}{}_2$, substituted or unsubstituted ($C_1$-$C_5$) alkyl, substituted or unsubstituted 2 to 5 membered heteroalkyl, substituted or unsubstituted ($C_3$-$C_5$) cycloalkyl, substituted or unsubstituted 3 to 5 membered heterocycloalkyl, substituted or unsubstituted phenyl, or substituted or unsubstituted 5 to 6 membered heteroaryl; and $X^{33}$ is halogen.

Embodiment 64

The compound of one of embodiments 1 to 31, wherein $L^1$ and $R^2$ are joined to form a $R^{33}$-substituted or unsubstituted 4 to 8 membered heterocycloalkyl; $R^{33}$ is independently oxo, halogen, $-CX^{33}{}_3$, $-CHX^{33}{}_2$, $-OCH_2X^{33}$, $-OCHX^{30}{}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{33}{}_3$, $-OCHX^{33}{}_2$, substituted or unsubstituted ($C_1$-$C_3$) alkyl, or substituted or unsubstituted 2 to 3 membered heteroalkyl; and $X^{33}$ is halogen.

Embodiment 65

The compound of one of embodiments 1 to 31, wherein $L^1$ and $R^2$ are joined to form a $R^{33}$-substituted or unsubstituted 4 to 8 membered heterocycloalkyl; $R^{33}$ is independently oxo, halogen, $-OH$, $-NH_2$, $-COOH$, $-CONH_2$, $-NO_2$, $-SH$, substituted or unsubstituted ($C_1$-$C_3$) alkyl, or substituted or unsubstituted 2 to 3 membered heteroalkyl; and $X^{33}$ is halogen.

Embodiment 66

The compound of one of embodiments 1 to 31, wherein $R^1$ and $R^2$ are joined to form a substituted or unsubstituted 3 to 6 membered heterocycloalkyl or substituted or unsubstituted 5 to 6 membered heteroaryl.

Embodiment 67

The compound of one of embodiments 1 to 31, wherein $R^1$ and $R^2$ are joined to form a substituted or unsubstituted 3 to 6 membered heterocycloalkyl.

Embodiment 68

The compound of one of embodiments 1 to 31, wherein $R^1$ and $R^2$ are joined to form a $R^{30}$-substituted or unsubstituted 3 to 6 membered heterocycloalkyl; $R^{30}$ is independently oxo, halogen, $-CX^{30}{}_3$, $-CHX^{30}{}_2$, $-OCH_2X^{30}$, $-OCHX^{30}{}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{30}{}_3$, $-OCHX^{30}{}_2$, substituted or unsubstituted ($C_1$-$C_5$) alkyl, substituted or unsubstituted 2 to 5 membered heteroalkyl, substituted or unsubstituted ($C_3$-$C_5$) cycloalkyl, substituted or unsubstituted 3 to 5 membered heterocycloalkyl, substituted or unsubstituted phenyl, or substituted or unsubstituted 5 to 6 membered heteroaryl; and $X^{30}$ is halogen.

Embodiment 69

The compound of one of embodiments 1 to 31, wherein $R^1$ and $R^2$ are joined to form a $R^{30}$-substituted or unsubstituted 3 to 6 membered heterocycloalkyl; $R^{30}$ is independently oxo, halogen, $-CX^{30}{}_3$, $-CHX^{30}{}_2$, $-OCH_2X^{30}$, $-OCHX^{30}{}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{30}{}_3$, $-OCHX^{30}{}_2$, substituted or unsubstituted ($C_1$-$C_3$) alkyl, or substituted or unsubstituted 2 to 3 membered heteroalkyl; and $X^{30}$ is halogen.

Embodiment 70

The compound of one of embodiments 1 to 69, wherein $R^5$ is substituted or unsubstituted ($C_1$-$C_5$) alkyl or substituted or unsubstituted 2 to 5 membered heteroalkyl.

Embodiment 71

The compound of one of embodiments 1 to 69, wherein $R^5$ is substituted or unsubstituted ($C_1$-$C_5$) alkyl.

Embodiment 72

The compound of one of embodiments 1 to 69, wherein $R^5$ is unsubstituted ($C_1$-$C_5$) alkyl.

Embodiment 73

The compound of one of embodiments 1 to 69, wherein $R^5$ is unsubstituted $(C_1-C_3)$ alkyl.

Embodiment 74

The compound of one of embodiments 1 to 69, wherein $R^5$ is unsubstituted methyl.

Embodiment 75

The compound of one of embodiments 1 to 69, wherein $R^5$ is hydrogen.

Embodiment 76

The compound of one of embodiments 1 to 75, wherein W is O.

Embodiment 77

The compound of one of embodiments 1 to 75, wherein W is S.

Embodiment 78

The compound of one of embodiments 1 to 77, wherein $L^3$ is —N($R^6$)—.

Embodiment 79

The compound of one of embodiments 1 to 78, wherein $R^6$ is hydrogen.

Embodiment 80

The compound of one of embodiments 1 to 78, wherein $R^6$ is substituted or unsubstituted $(C_1-C_5)$ alkyl or substituted or unsubstituted 2 to 5 membered heteroalkyl.

Embodiment 81

The compound of one of embodiments 1 to 78, wherein $R^6$ is substituted or unsubstituted $(C_1-C_5)$ alkyl.

Embodiment 82

The compound of one of embodiments 1 to 78, wherein $R^6$ is unsubstituted $(C_1-C_5)$ alkyl.

Embodiment 83

The compound of one of embodiments 1 to 78, wherein $R^6$ is unsubstituted $(C_1-C_3)$ alkyl.

Embodiment 84

The compound of one of embodiments 1 to 78, wherein $R^6$ is unsubstituted methyl.

Embodiment 85

The compound of one of embodiments 1 to 77, wherein $L^3$ is a bond.

Embodiment 86

The compound of one of embodiments 1 to 77, wherein $L^3$ is —O—.

Embodiment 87

The compound of one of embodiments 1 to 77, wherein $L^3$ is —$CH_2$—.

Embodiment 88

The compound of one of embodiments 1 to 87, wherein $L^2$ is a bond.

Embodiment 89

The compound of one of embodiments 1 to 87, wherein $L^2$ is substituted or unsubstituted 2 to 5 membered heteroalkylene.

Embodiment 90

The compound of one of embodiments 1 to 87, wherein $L^2$ is unsubstituted 2 to 5 membered heteroalkylene.

Embodiment 91

The compound of one of embodiments 1 to 87, wherein $L^2$ is substituted or unsubstituted $(C_1-C_5)$ alkylene.

Embodiment 92

The compound of one of embodiments 1 to 87, wherein $L^2$ is unsubstituted $(C_1-C_5)$ alkylene.

Embodiment 93

The compound of one of embodiments 1 to 87, wherein $L^2$ is unsubstituted $(C_1-C_4)$ alkylene.

Embodiment 94

The compound of one of embodiments 1 to 87, wherein $L^2$ is unsubstituted $(C_1-C_3)$ alkylene.

Embodiment 95

The compound of one of embodiments 1 to 87, wherein $L^2$ is unsubstituted $(C_1-C_2)$ alkylene.

Embodiment 96

The compound of one of embodiments 1 to 84, having the formula:

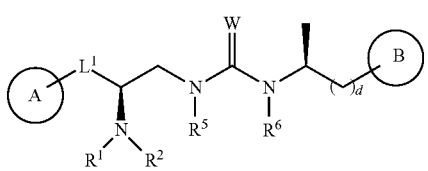

wherein d is an integer between 0 and 3.

Embodiment 97

The compound of one of embodiments 1 to 84, having the formula:

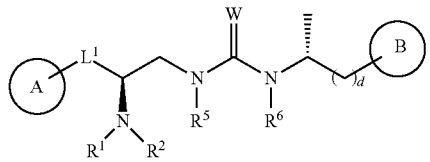

wherein d is an integer between 0 and 3.

Embodiment 98

The compound of one of embodiments 1 to 84, having the formula:

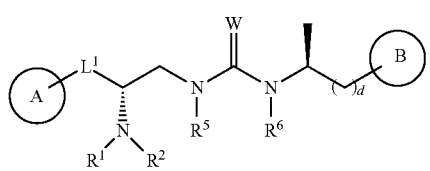

wherein d is an integer between 0 and 3.

Embodiment 99

The compound of one of embodiments 1 to 84, having the formula:

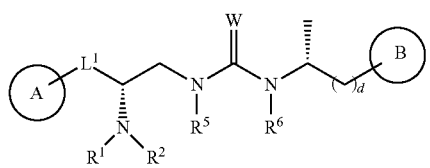

wherein d is an integer between 0 and 3.

Embodiment 100

The compound of one of embodiments 1 to 84, having the formula:

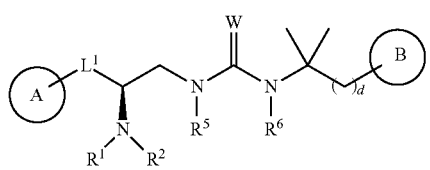

wherein d is an integer between 0 and 3.

Embodiment 101

The compound of one of embodiments 1 to 84, having the formula:

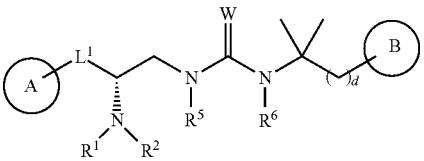

wherein d is an integer between 0 and 3.

Embodiment 102

The compound of embodiment 1, having the formula:

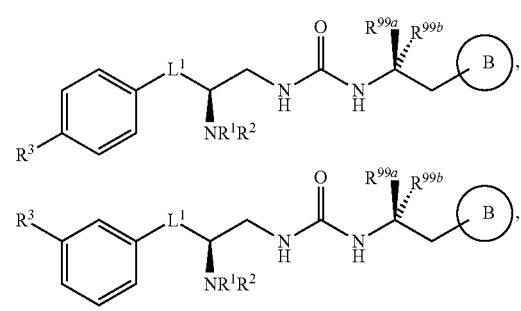

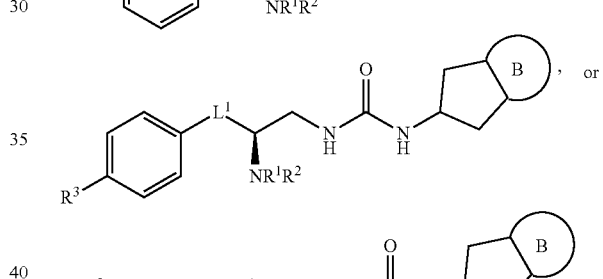

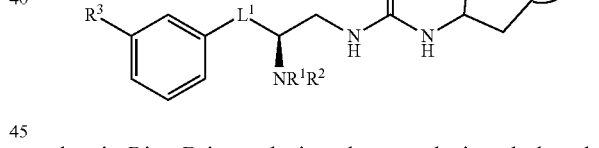

wherein Ring B is a substituted or unsubstituted phenyl or substituted or unsubstituted 5 to 6 membered heteroaryl; $R^3$ is halogen, —OH, or —NH$_2$; $R^{99a}$ is substituted or unsubstituted ($C_1$-$C_3$) alkyl; and $R^{99b}$ is hydrogen or substituted or unsubstituted ($C_1$-$C_3$) alkyl.

Embodiment 103

The compound of embodiment 102, wherein Ring B is an unsubstituted phenyl.

Embodiment 104

The compound of embodiment 102, wherein Ring B is an unsubstituted 5 to 6 membered heteroaryl.

Embodiment 105

The compound of embodiment 102, wherein Ring B is an unsubstituted 3-thienyl.

Embodiment 106

The compound of one of embodiments 102 to 105, wherein $R^3$ is —OH.

Embodiment 107

The compound of one of embodiments 102 to 106, wherein $R^{99a}$ is unsubstituted methyl.

Embodiment 108

The compound of one of embodiments 102 to 107, wherein $R^{99b}$ is hydrogen.

Embodiment 109

The compound of one of embodiments 102 to 107, wherein $R^{99b}$ is unsubstituted methyl.

Embodiment 110

The compound of one of embodiments 102 to 109, wherein $R^1$ and $R^2$ are unsubstituted methyl.

Embodiment 111

The compound of one of embodiments 102 to 110, having the formula

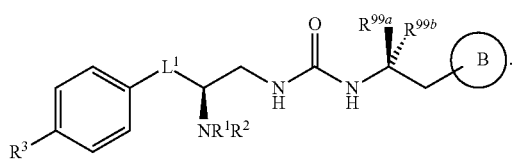

Embodiment 112

The compound of one of embodiments 102 to 110, having the formula

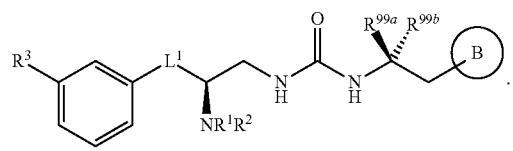

Embodiment 113

The compound of one of embodiments 102 to 110, having the formula

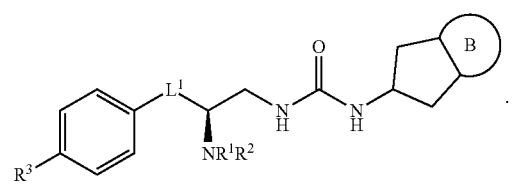

Embodiment 114

The compound of one of embodiments 102 to 110, having the formula

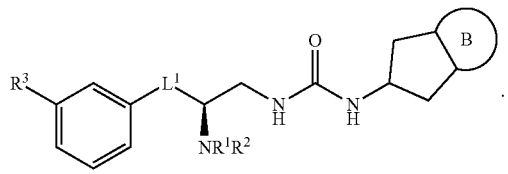

Embodiment 115

The compound of embodiment 1, having the formula:

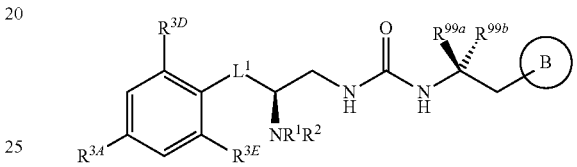

wherein Ring B is a substituted or unsubstituted phenyl or substituted or unsubstituted 5 to 6 membered heteroaryl; $R^{3A}$ is halogen, —OH, or —NH$_2$; $R^{3D}$ is unsubstituted ($C_1$-$C_2$) alkyl; $R^{3E}$ is unsubstituted ($C_1$-$C_2$) alkyl; $R^{99a}$ is hydrogen or substituted or unsubstituted ($C_1$-$C_3$) alkyl; and $R^{99b}$ is substituted or unsubstituted ($C_1$-$C_3$) alkyl.

Embodiment 116

The compound of embodiment 115, wherein Ring B is an unsubstituted phenyl.

Embodiment 117

The compound of embodiment 115, wherein Ring B is an unsubstituted 5 to 6 membered heteroaryl.

Embodiment 118

The compound of embodiment 115, wherein Ring B is an unsubstituted 3-thienyl.

Embodiment 119

The compound of one of embodiments 115 to 118, wherein $R^{3A}$ is —OH.

Embodiment 120

The compound of one of embodiments 115 to 119, wherein $R^{99b}$ is unsubstituted methyl.

Embodiment 121

The compound of one of embodiments 115 to 120, wherein $R^{99a}$ is hydrogen.

Embodiment 122

The compound of one of embodiments 115 to 120, wherein $R^{99a}$ is unsubstituted methyl.

Embodiment 123
The compound of one of embodiments 115 to 122, wherein $R^1$ and $R^2$ are unsubstituted methyl.
Embodiment 124
The compound of one of embodiments 115 to 123, wherein $R^{3D}$ is unsubstituted methyl.
Embodiment 125
The compound of one of embodiments 115 to 124, wherein $R^{3E}$ is unsubstituted methyl.
Embodiment 126
The compound of embodiment 1, having the formula:
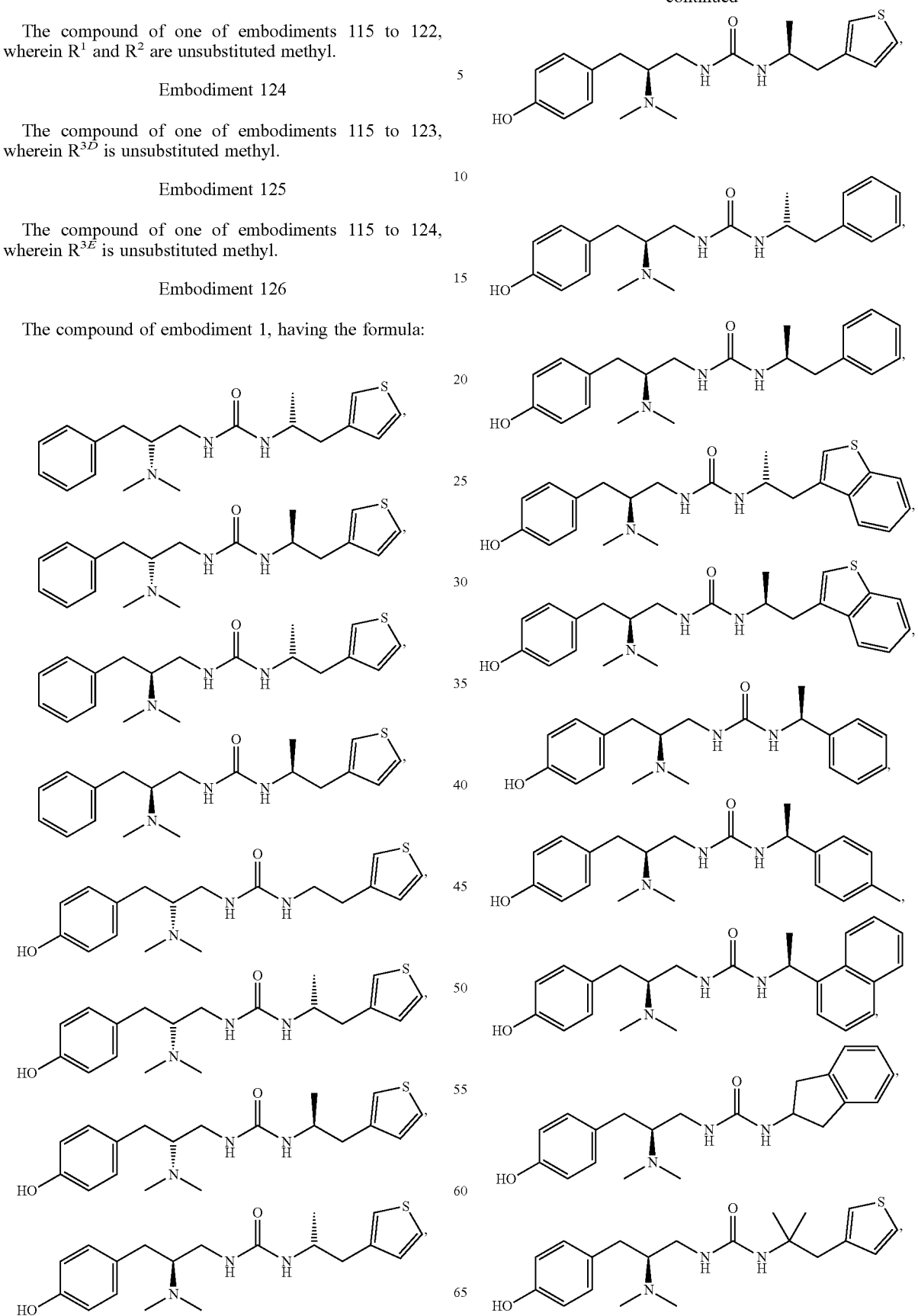

275
-continued
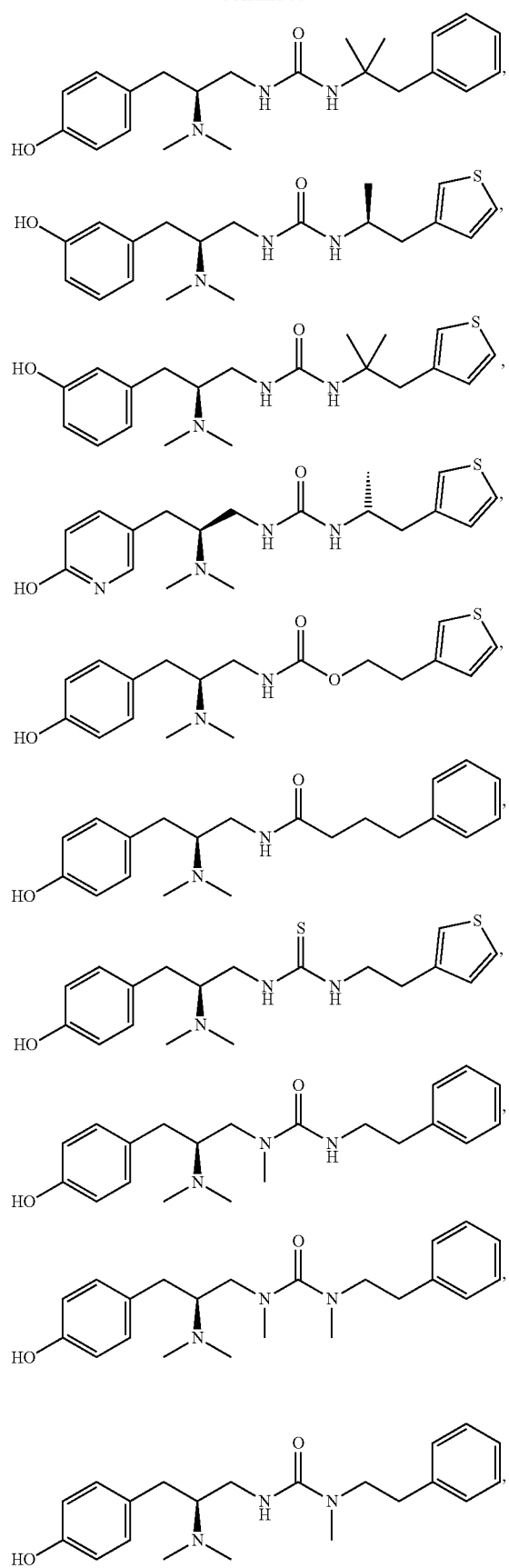
276
-continued
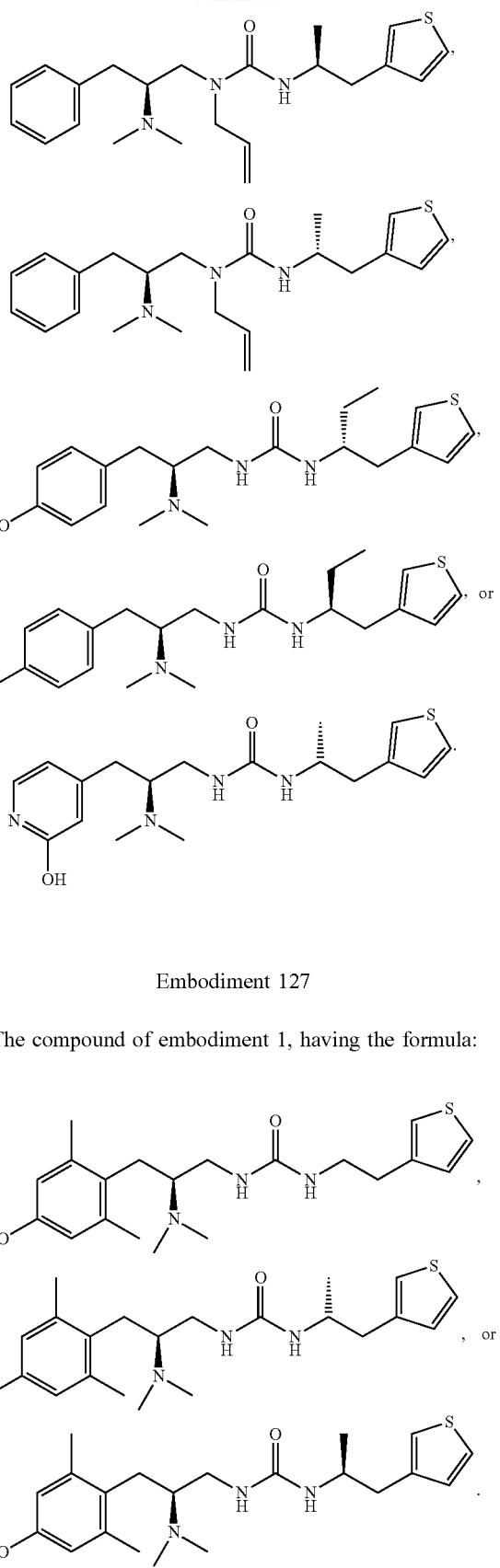
Embodiment 127
The compound of embodiment 1, having the formula:

Embodiment 128

The compound of one of embodiments 1 to 127, wherein the compound is not

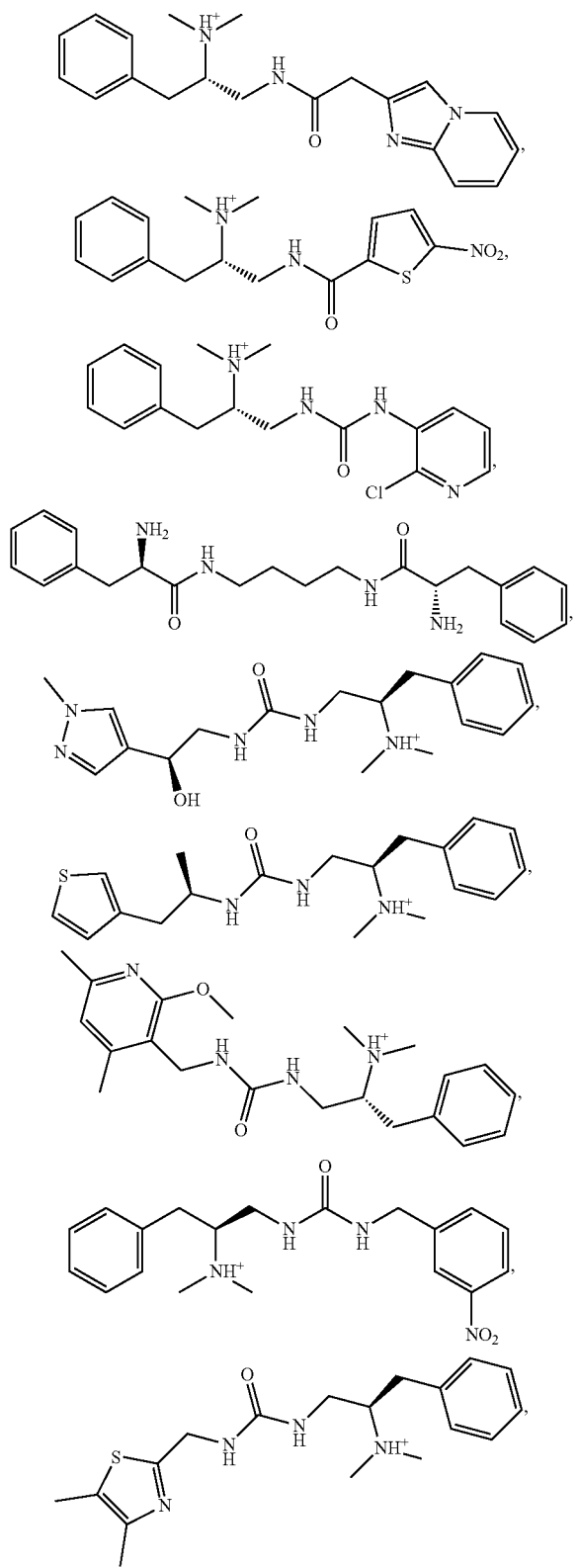

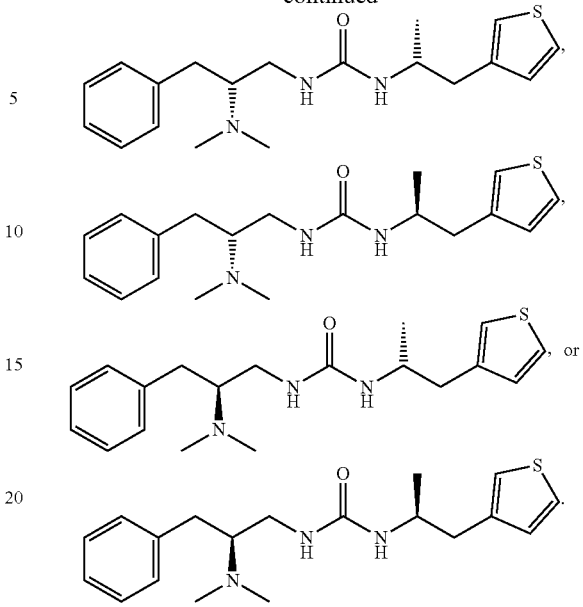

, or

Embodiment 129

A compound of one of embodiments 1 to 128 having a lower binding affinity for the mu opioid receptor than for the kappa opioid receptor.

Embodiment 130

A compound of one of embodiments 1 to 128 having greater than 10-fold lower binding affinity for the mu opioid receptor than for the kappa opioid receptor.

Embodiment 131

A compound of one of embodiments 1 to 128 having greater than 100-fold lower binding affinity for the mu opioid receptor than for the kappa opioid receptor.

Embodiment 132

A compound of one of embodiments 1 to 131 having a lower binding affinity for the mu opioid receptor than for the delta opioid receptor.

Embodiment 133

A compound of one of embodiments 1 to 131 having greater than 10-fold lower binding affinity for the mu opioid receptor than for the delta opioid receptor.

Embodiment 134

A compound of one of embodiments 1 to 131 having greater than 100-fold lower binding affinity for the mu opioid receptor than for the delta opioid receptor.

Embodiment 135

A compound of one of embodiments 1 to 134 having a lower binding affinity for the mu opioid receptor than for the nociceptin receptor.

Embodiment 136

A compound of one of embodiments 1 to 134 having greater than 10-fold lower binding affinity for the mu opioid receptor than for the nociceptin receptor.

Embodiment 137

A compound of one of embodiments 1 to 134 having greater than 100-fold lower binding affinity for the mu opioid receptor than for the nociceptin receptor.

Embodiment 138

A compound of one of embodiments 1 to 137 having a lower addiction potential than other medically used opioids.

Embodiment 139

A compound of one of embodiments 1 to 137 having a lower addiction potential than other medically used opiate.

Embodiment 140

A compound of one of embodiments 1 to 137 having a lower addiction potential than morphine.

Embodiment 141

A compound of one of embodiments 1 to 137 having a lower addiction potential than heroin.

Embodiment 142

A compound of one of embodiments 1 to 137 having a lower addiction potential than oxycodone.

Embodiment 143

A compound of one of embodiments 1 to 137 having a lower addiction potential than fentanyl.

Embodiment 144

A compound of one of embodiments 1 to 137 having a lower addiction potential than hydrocodone.

Embodiment 145

A compound of one of embodiments 1 to 137 having a lower addiction potential than hydromorphone.

Embodiment 146

A compound of one of embodiments 1 to 137 having a lower addiction potential than methadone.

Embodiment 147

A compound of one of embodiments 1 to 137 having a lower addiction potential than oxymorphone.

Embodiment 148

A pharmaceutical composition comprising a pharmaceutically acceptable excipient and a compound of one of embodiments 1 to 147.

Embodiment 149

A method of treating pain in a subject in need of said treatment, said method comprising administering an effective amount of a compound of one of embodiments 1 to 12, 20 to 114, 126, and 128 to 147, to said subject.

Embodiment 150

The method of embodiment 149, wherein said pain is acute pain.

Embodiment 151

The method of embodiment 149, wherein pain is chronic pain.

Embodiment 152

The method of one of embodiments 149 to 151, wherein said method does not comprise an increased risk of respiratory depression.

Embodiment 153

The method of one of embodiments 149 to 151, wherein said method does not comprise respiratory depression.

Embodiment 154

The method of one of embodiments 149 to 151, wherein said method does not comprise an increased risk of constipation.

Embodiment 155

The method of one of embodiments 149 to 151, wherein said method does not comprise constipation.

Embodiment 156

A method of treating opioid overdose in a subject in need of said treatment, said method comprising administering an effective amount of a compound of one of embodiments 1 to 8, 10, 13 to 101, 115 to 125, and 127 to 147, to said subject.

Embodiment 157

A method of treating addiction in a subject in need of said treatment, said method comprising administering an effective amount compound of one of embodiments 1 to 12, 30 to 114, 126, and 128 to 147, to said subject.

Embodiment 158

The method of embodiment 157, wherein said addiction is opioid addiction.

Embodiment 159

The method of embodiment 157, wherein said addiction is nicotine addiction.

Embodiment 160

The method of one of embodiments 157 to 159, wherein said method does not comprise an increased risk of respiratory depression.

Embodiment 161

The method of one of embodiments 157 to 159, wherein said method does not comprise respiratory depression.

Embodiment 162

The method of one of embodiments 157 to 159, wherein said method does not comprise an increased risk of constipation.

Embodiment 163

The method of one of embodiments 157 to 159, wherein said method does not comprise constipation.

Embodiment 164

A method of treating a psychiatric disorder in a subject in need of said treatment, said method comprising administering an effective amount of a compound of one of embodiments 1 to 12, 20 to 114, 126, and 128 to 147, to said subject.

Embodiment 165

The method of embodiment 164, wherein said psychiatric disorder is depression.

Embodiment 166

The method of embodiment 164, wherein said psychiatric disorder is anxiety.

Embodiment 167

The method of one of embodiments 164 to 166, wherein said method does not comprise an increased risk of respiratory depression.

Embodiment 168

The method of one of embodiments 164 to 166, wherein said method does not comprise respiratory depression.

Embodiment 169

The method of one of embodiments 164 to 166, wherein said method does not comprise an increased risk of constipation.

Embodiment 170

The method of one of embodiments 164 to 166, wherein said method does not comprise constipation.

Embodiment 171

A method of modulating the activity of an opioid receptor protein, said method comprising contacting said opioid receptor protein with an effective amount of a compound of one of embodiments 1 to 147.

Embodiment 172

The method of embodiment 171, wherein said opioid receptor is a human mu opioid receptor.

Embodiment 173

The method of one of embodiments 171 to 172, wherein modulating is activating.

Embodiment 174

The method of one of embodiments 171 to 172, wherein modulating is inhibiting.

Embodiment 175

The method of one of embodiments 171 to 174, wherein said method does not comprise modulating arrestin function.

Embodiment 176

The method of one of embodiments 171 to 175, wherein said method does not comprise modulating the activity of a human kappa opioid receptor.

Embodiment 177

The method of one of embodiments 171 to 176, wherein said method does not comprise modulating the activity of a human delta opioid receptor.

Embodiment 178

The method of one of embodiments 171 to 177, wherein said method does not comprise modulating the activity of a human nociceptin receptor.

Additional Embodiments

Embodiment N1

A compound having the formula:

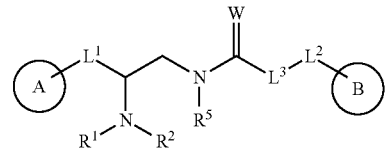

wherein, W is O or S; Ring A is substituted or unsubstituted aryl or substituted or unsubstituted heteroaryl; Ring B is substituted or unsubstituted cycloalkyl, substituted or unsubstituted heterocycloalkyl, substituted or unsubstituted aryl, or substituted or unsubstituted heteroaryl; $L^1$ and $L^2$ are independently a bond, substituted or unsubstituted ($C_1$-$C_5$) alkylene, or substituted or unsubstituted 2 to 5 membered heteroalkylene; $R^1$ and $R^2$ are independently hydrogen, halogen, —$CF_3$, —CN, —OH, —$NH_2$, —COOH, —$CONH_2$, —$NO_2$, —SH, —$SO_3$H, —$SO_4$H, —$SO_2NH_2$, —$NHNH_2$, —$ONH_2$, —NHC=(O)$NHNH_2$, —NHC=(O) $NH_2$, —$NHSO_2$H, —NHC=(O)H, —NHC(O)OH, —NHOH, —$CHF_2$, —$CH_2$F, $OCF_3$, —$OCHF_2$, substituted or unsubstituted ($C_1$-$C_5$) alkyl, substituted or unsubstituted 2 to 5 membered heteroalkyl, substituted or unsubstituted ($C_3$-$C_6$) cycloalkyl, or substituted or unsubstituted 3 to 6 membered heterocycloalkyl; $R^1$ and $R^2$ may optionally be joined to form a substituted or unsubstituted 3 to 6 membered heterocycloalkyl or substituted or unsubstituted 5 to 6 membered heteroaryl; $L^1$ and $R^1$ may optionally be joined to form a substituted or unsubstituted 4 to 8 membered heterocycloalkyl; $L^1$ and $R^2$ may optionally be joined to form a substituted or unsubstituted 4 to 8 membered heterocycloalkyl; $L^3$ is a bond, —O—, —N($R^6$)—, or —$CH_2$—; $R^5$ is hydrogen, —$CF_3$, —CN, —COOH, —$CONH_2$, —$CHF_2$, —$CH_2F$, substituted or unsubstituted ($C_1$-$C_5$) alkyl, or substituted or unsubstituted 2 to 5 membered heteroalkyl; and $R^6$ is hydrogen, —$CF_3$, —CN, —COOH, —$CONH_2$, —$CHF_2$, —$CH_2F$, substituted or unsubstituted ($C_1$-$C_5$) alkyl, or substituted or unsubstituted 2 to 5 membered heteroalkyl.

Embodiment N2

The compound of embodiment N1, wherein Ring A is substituted or unsubstituted ($C_6$-$C_{10}$) aryl or substituted or unsubstituted 5 to 10 membered heteroaryl.

Embodiment N3

The compound of embodiment N1, wherein Ring A is $R^3$-substituted or unsubstituted ($C_6$-$C_{10}$) aryl or $R^3$-substituted or unsubstituted 5 to 10 membered heteroaryl; $R^3$ is independently hydrogen, halogen, —$CX_3$, —CN, —$SO_nR^1$, —$SO_vNR^7R^8$, —$NHNR^7R^8$, —$ONR^7R^8$, —NHC=(O)$NHNR^7R^8$, —NHC=(O)$NR^7R^8$, —N(O)$_m$, —$NR^7R^8$, —C(O)$R^9$, —C(O)—$OR^9$, —C(O)$NR^7R^8$, —$OR^{10}$, —$NR^7SO_2R$, —$NR^7C$=(O)$R^9$, —$NR^7C(O)OR^9$, —$NR^7OR^9$, —$CHX_2$, —$CH_2X$, —$OCX_3$, —$OCHX_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl; $R^7$, $R^8$, $R^9$, and $R^{10}$ are independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, $OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; m and v are independently 1 or 2; n is independently an integer from 0 to 4; and X is independently —Cl, —Br, —I, or —F.

Embodiment N4

The compound of embodiment N3, wherein Ring A is $R^3$-substituted or unsubstituted phenyl.

Embodiment N5

The compound of embodiment N3 or N4, wherein $R^3$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, $OCF_3$, —$OCHF_2$, substituted or unsubstituted ($C_1$-$C_5$) alkyl, or substituted or unsubstituted 2 to 5 membered heteroalkyl.

Embodiment N6

The compound of any one of embodiments N1 to N5, having the formula:

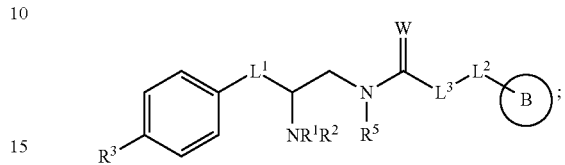

wherein
$R^3$ is halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, $OCF_3$, —$OCHF_2$, substituted or unsubstituted ($C_1$-$C_5$) alkyl, or substituted or unsubstituted 2 to 5 membered heteroalkyl.

Embodiment N7

The compound of any one of embodiments N1 to N5, having the formula:

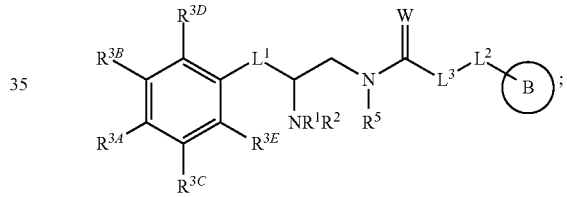

wherein $R^{3A}$, $R^{3B}$, and $R^{3C}$ are independently halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, $OCF_3$, —$OCHF_2$, substituted or unsubstituted ($C_1$-$C_5$) alkyl, or substituted or unsubstituted 2 to 5 membered heteroalkyl;
$R^{3D}$ is hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, $OCF_3$, —$OCHF_2$, substituted or unsubstituted ($C_1$-$C_5$) alkyl, or substituted or unsubstituted 2 to 5 membered heteroalkyl;
$R^{3E}$ is hydrogen halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, $OCF_3$, —$OCHF_2$, substituted or unsubstituted ($C_1$-$C_5$) alkyl, or substituted or unsubstituted 2 to 5 membered heteroalkyl.

Embodiment N8

The compound of embodiment N7, wherein $R^{3D}$ and $R^{3E}$ are independently unsubstituted ($C_1$-$C_3$) alkyl.

Embodiment N9

The compound of embodiment N7, wherein $R^{3D}$ and $R^{3E}$ are independently unsubstituted methyl.

Embodiment N10

The compound of any one of embodiments N1 to N5, having the formula:

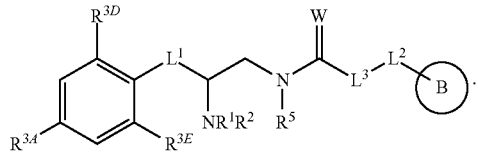

Embodiment N11

The compound of any one of embodiments N1 to N10, wherein Ring B is substituted or unsubstituted $(C_3-C_{10})$ cycloalkyl or substituted or unsubstituted 3 to 10 membered heterocycloalkyl, substituted or unsubstituted $(C_6-C_{10})$ aryl, or substituted or unsubstituted 5 to 10 membered heteroaryl.

Embodiment N12

The compound of any one of embodiments N1 to N10, wherein Ring B is $R^4$-substituted or unsubstituted $(C_3-C_{10})$ cycloalkyl, $R^4$-substituted or unsubstituted 5 to 10 membered heterocycloalkyl, $R^4$-substituted or unsubstituted $(C_6-C_{10})$ aryl, or $R^4$-substituted or unsubstituted 5 to 10 membered heteroaryl; $R^4$ is independently oxo, halogen, $-CX^a{}_3$, $-CN$, $-SO_{n1}R^{14}$, $-SO_{v1}NR^{11}R^{12}$, $-NHNR^{11}R^{12}$, $-ONR^{11}R^{12}$, $-NHC=(O)NHNR^{11}R^{12}$, $-NHC=(O)NR^{11}R^{12}$, $-N(O)_{m1}$, $-NR^{11}R^{12}$, $-C(O)R^{13}$, $-C(O)-OR^{13}$, $-C(O)NR^{11}R^{12}$, $-OR^{14}$, $-NR^{11}SO_2R^{14}$, $-NR^{11}C=(O)R^{13}$, $-NR^{11}C(O)OR^{13}$, $-NR^{11}OR^{13}$, $-CHX_2$, $-CH_2X$, $-OCX_3$, $-OCHX_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^4$ substituents may optionally be joined to form a substituted or unsubstituted cycloalkyl, substituted or unsubstituted heterocycloalkyl, substituted or unsubstituted aryl, or substituted or unsubstituted heteroaryl; $R^{11}$, $R^{12}$, $R^{13}$, and $R^{14}$ are independently hydrogen, halogen, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-CHF_2$, $-CH_2F$, $OCF_3$, $-OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl; m1 and v1 are independently 1 or 2; n1 is independently an integer from 0 to 4; and
$X^a$ is independently $-Cl$, $-Br$, $-I$, or $-F$.

Embodiment N13

The compound of any one of embodiments N1 to N10, wherein Ring B is $R^4$-substituted or unsubstituted thienyl, $R^4$-substituted or unsubstituted phenyl, $R^4$-substituted or unsubstituted benzothienyl, $R^4$-substituted or unsubstituted naphthyl, $R^4$-substituted or unsubstituted benzofuranyl, $R^4$-substituted or unsubstituted furanyl, $R^4$-substituted or unsubstituted pyrrolyl, or $R^4$-substituted or unsubstituted 2,3-dihydro-1H-indenyl.

Embodiment N14

The compound of any one of embodiments N1 to N10, wherein
Ring A is unsubstituted phenyl and Ring B is unsubstituted thienyl;
Ring A is para-hydroxy substituted phenyl and Ring B is unsubstituted thienyl;
Ring A is para-hydroxy substituted phenyl and Ring B is unsubstituted phenyl;
Ring A is para-hydroxy substituted phenyl and Ring B is unsubstituted benzothienyl;
Ring A is para-hydroxy substituted phenyl and Ring B is para-methyl substituted phenyl;
Ring A is 2-hydroxy pyridin-4-yl and Ring B is unsubstituted thienyl;
Ring A is 2-hydroxy pyridin-5-yl and Ring B is unsubstituted thienyl;
Ring A is para-hydroxy substituted phenyl and Ring B is unsubstituted napththyl; or
Ring A is para-hydroxy substituted phenyl and Ring B is unsubstituted 2,3-dihydro-1H-indenyl.

Embodiment N15

The compound of any one of embodiments N1 to N10, wherein Ring B is unsubstituted phenyl.

Embodiment N16

The compound of any one of embodiments N1 to N15, wherein $L^1$ is $R^{96}$-substituted or unsubstituted $C_1$-$C_5$ alkylene, $R^{96}$-substituted or unsubstituted 2 to 5 membered heteroalkylene; $R^{96}$ is independently oxo, halogen, $-CX^{96}{}_3$, $-CHX^{96}{}_2$, $-OCH_2X^{96}$, $-OCHX^{96}{}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{96}{}_3$, $-OCHX^{96}{}_2$, substituted or unsubstituted $(C_1-C_5)$ alkyl, substituted or unsubstituted 2 to 5 membered heteroalkyl, substituted or unsubstituted $(C_3-C_5)$ cycloalkyl, substituted or unsubstituted 3 to 5 membered heterocycloalkyl, substituted or unsubstituted phenyl, or substituted or unsubstituted 5 to 6 membered heteroaryl; and $X^{96}$ is halogen.

Embodiment N17

The compound of any one of embodiments N1 to N15, wherein $L^1$ is $R^{96}$-substituted or unsubstituted methylene.

Embodiment N18

The compound of any one of embodiments N1 to N17, wherein $R^1$ is unsubstituted $(C_1-C_2)$ alkyl.

Embodiment N19

The compound of any one of embodiments N1 to N17, wherein $R^1$ is independently hydrogen, halogen, $-CF_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —CHF$_2$, —CH$_2$F, OCF$_3$, —OCHF$_2$, substituted or unsubstituted (C$_1$-C$_5$) alkyl, substituted or unsubstituted 2 to 5 membered heteroalkyl, substituted or unsubstituted (C$_3$-C$_6$) cycloalkyl, or substituted or unsubstituted 3 to 6 membered heterocycloalkyl.

Embodiment N20

The compound of any one of embodiments N1 to N19, wherein R$^2$ is unsubstituted (C$_1$-C$_2$) alkyl.

Embodiment N21

The compound of any one of embodiments N1 to N19, wherein R$^2$ is independently hydrogen, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —CHF$_2$, —CH$_2$F, OCF$_3$, —OCHF$_2$, substituted or unsubstituted (C$_1$-C$_5$) alkyl, substituted or unsubstituted 2 to 5 membered heteroalkyl, substituted or unsubstituted (C$_3$-C$_6$) cycloalkyl, or substituted or unsubstituted 3 to 6 membered heterocycloalkyl.

Embodiment N22

The compound of any one of embodiments N1 to N17, wherein R$^1$ and R$^2$ are joined to form a substituted or unsubstituted 3 to 6 membered heterocycloalkyl or substituted or unsubstituted 5 to 6 membered heteroaryl.

Embodiment N23

The compound of any one of embodiments N1 to N22, wherein R$^5$ is hydrogen, substituted or unsubstituted (C$_1$-C$_5$) alkyl or substituted or unsubstituted 2 to 5 membered heteroalkyl.

Embodiment N24

The compound of any one of embodiments N1 to N23, wherein W is O.

Embodiment N25

The compound of any one of embodiments N1 to N24, wherein L$^3$ is —N(R$^6$)—.

Embodiment N26

The compound of any one of embodiments N1 to N25, wherein R$^6$ is hydrogen, substituted or unsubstituted (C$_1$-C$_5$) alkyl or substituted or unsubstituted 2 to 5 membered heteroalkyl.

Embodiment N27

The compound of any one of embodiments N1 to N26, wherein L$^2$ is substituted or unsubstituted (C$_1$-C$_3$) alkylene, or substituted or unsubstituted 2 to 5 membered heteroalkylene.

Embodiment N28

The compound of embodiment N1, having the formula:

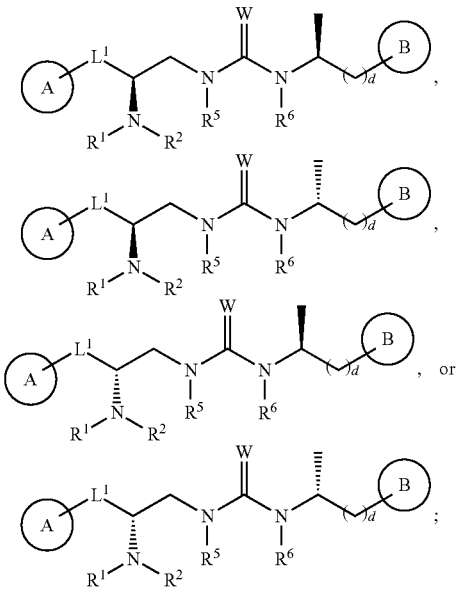

wherein d is an integer between 0 and 3.

Embodiment N29

The compound of embodiment N1, having the formula:

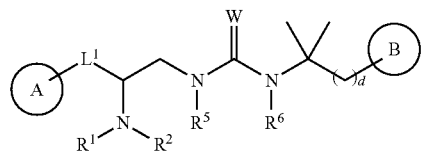

R$^1$, R$^2$ wherein d is an integer between 0 and 3.

Embodiment N30

The compound of embodiment N1, having the formula:

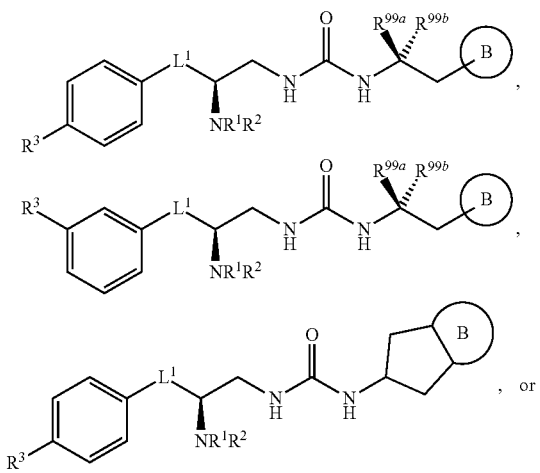

289

-continued

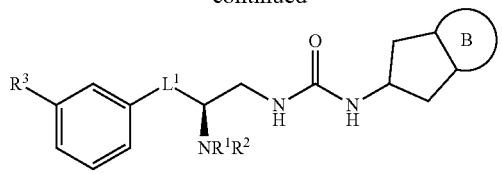

wherein Ring B is a substituted or unsubstituted phenyl or substituted or unsubstituted 5 to 6 membered heteroaryl; $R^3$ is halogen, —OH, or —NH$_2$; $R^{99a}$ is substituted or unsubstituted (C$_1$-C$_3$) alkyl; and $R^{99b}$ is hydrogen or substituted or unsubstituted (C$_1$-C$_3$) alkyl.

Embodiment N31

The compound of any one of embodiments N1 to N30, wherein Ring B is an unsubstituted 3-thienyl.

Embodiment N32

The compound of embodiment N1, having the formula:

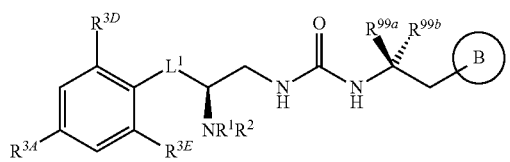

wherein Ring B is a substituted or unsubstituted phenyl or substituted or unsubstituted 5 to 6 membered heteroaryl; $R^{3A}$ is halogen, —OH, or —NH$_2$; $R^{3D}$ is unsubstituted (C$_1$-C$_2$) alkyl; $R^{3E}$ is unsubstituted (C$_1$-C$_2$) alkyl; $R^{99a}$ is hydrogen or substituted or unsubstituted (C$_1$-C$_3$) alkyl; $R^{99b}$ is substituted or unsubstituted (C$_1$-C$_3$) alkyl.

Embodiment N33

The compound of embodiment N1, having the formula:

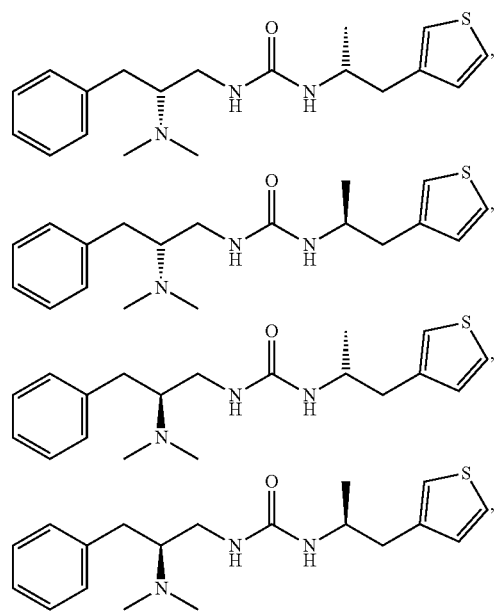

290

-continued

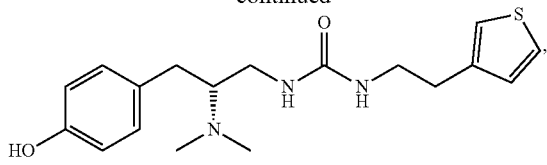

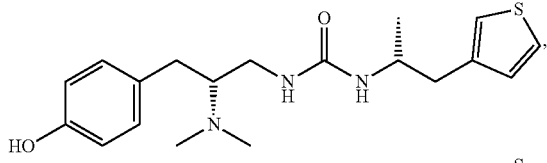

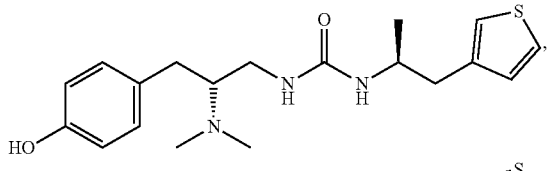

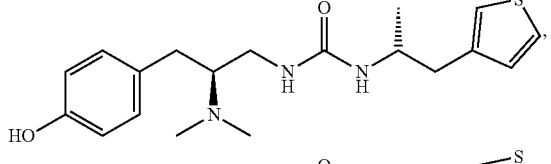

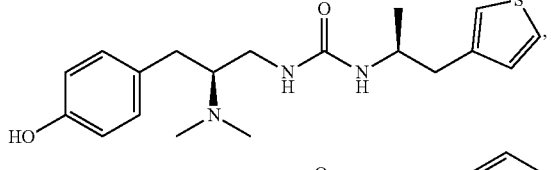

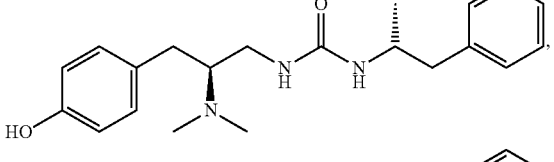

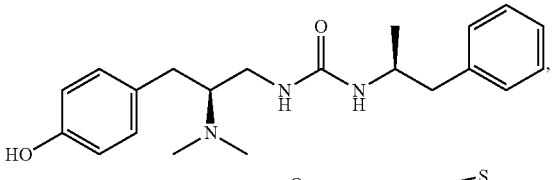

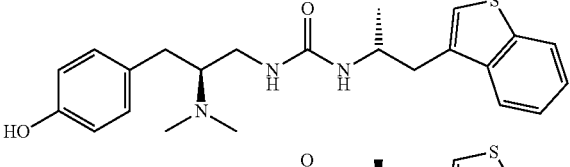

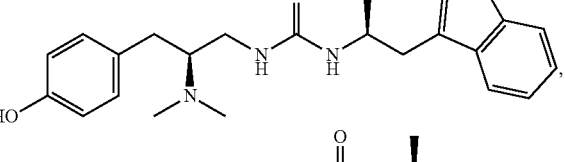

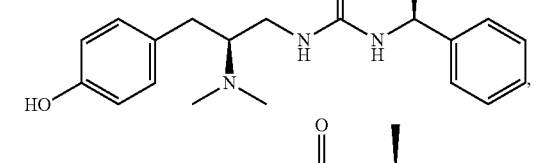

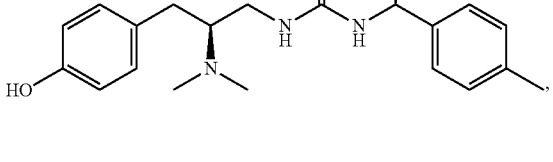

-continued
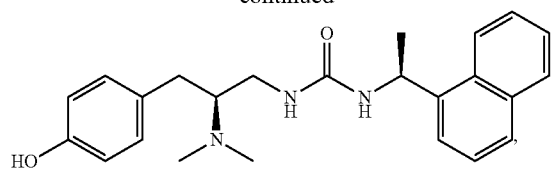
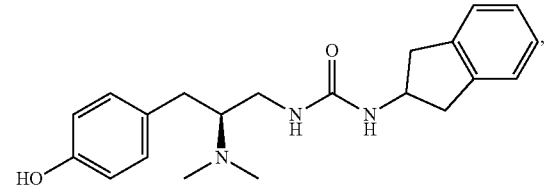
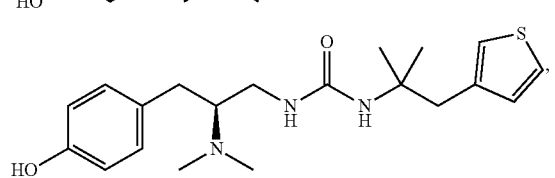
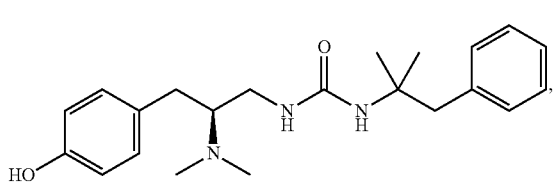
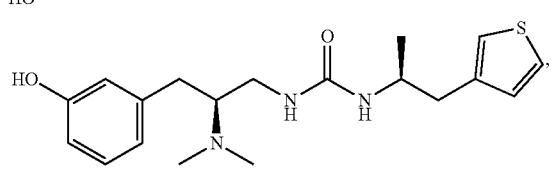
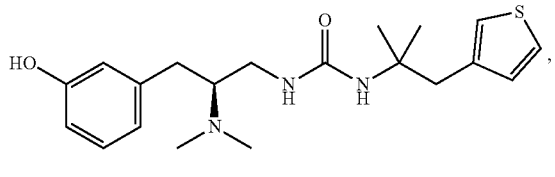
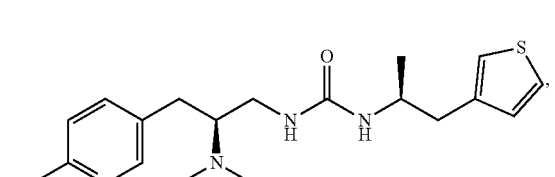
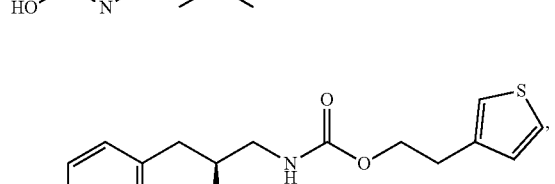
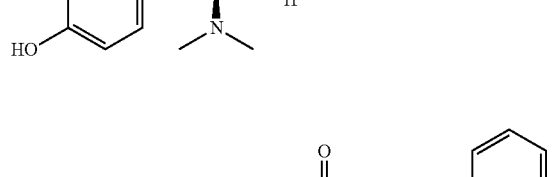
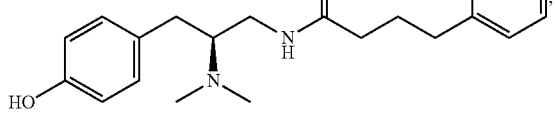
-continued
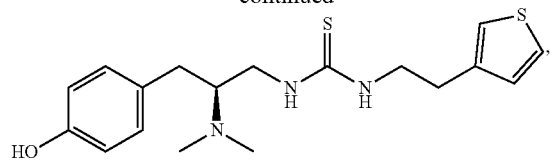
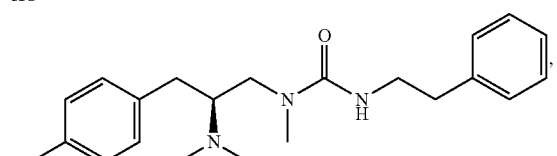
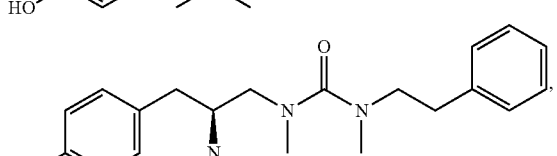
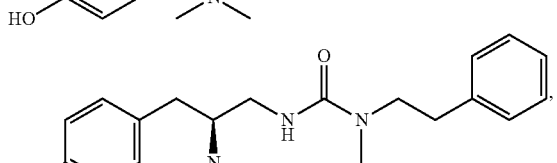
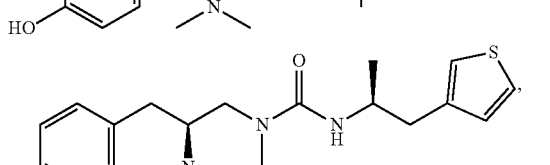
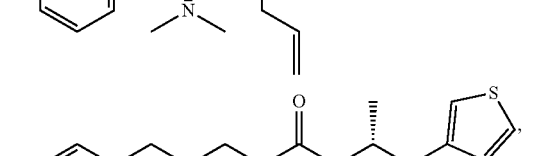
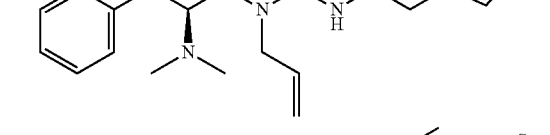
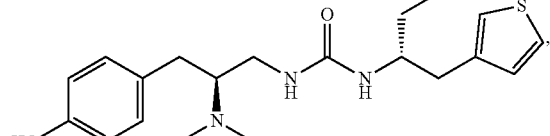
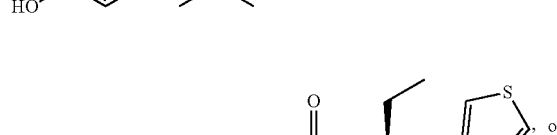
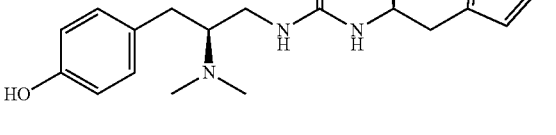 or
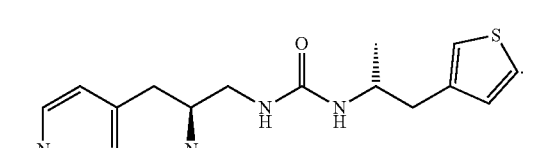

Embodiment N34

The compound of embodiment N1, having the formula:

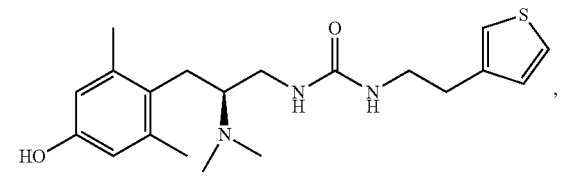

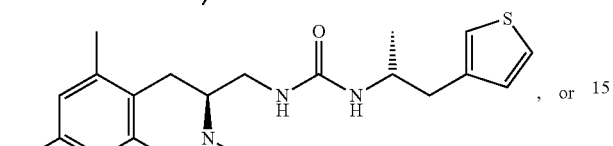, or

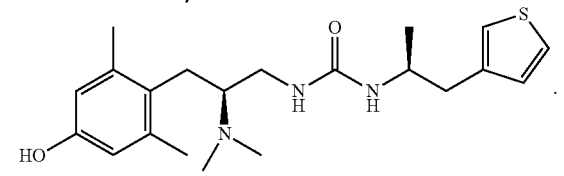

Embodiment N35

The compound of embodiment N1, wherein the compound is

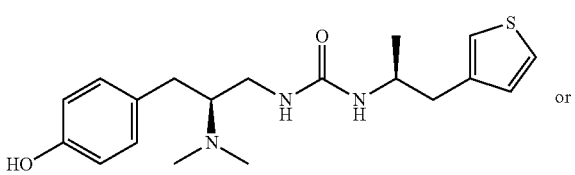 or

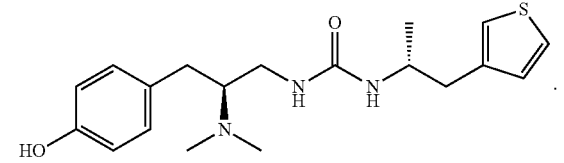.

Embodiment N36

The compound of any one of embodiments N1 to N35, having a higher binding affinity for the mu opioid receptor than for the kappa opioid receptor.

Embodiment N37

The compound of any one of embodiments N1 to N35, having a higher binding affinity for the mu opioid receptor than for the delta opioid receptor.

Embodiment N38

The compound of any one of embodiments N1 to N35, having a higher binding affinity for the mu opioid receptor than for the nociceptin receptor.

Embodiment N39

The compound of any one of embodiments N1 to N35, having a lower addiction potential than other medically used opioids or opiates.

Embodiment N40

The compound of any one of embodiments N1 to N35, having a lower addiction potential than morphine, heroin, oxycodone, fentanyl, hydrocodone, hydromorphone, methadone, or oxymorphone.

Embodiment N41

A pharmaceutical composition comprising a pharmaceutically acceptable excipient and a compound of one of embodiments N1 to N40.

Embodiment N42

A method of treating pain in a subject in need of said treatment, said method comprising administering an effective amount of a compound of one of embodiments N1 to N6, N11 to N31, N33, or N35 to N40, to said subject.

Embodiment N43

The method of embodiment N42, wherein said method does not comprise an increased risk of respiratory depression or constipation.

Embodiment N44

A method of treating opioid overdose in a subject in need of said treatment, said method comprising administering an effective amount of a compound of one of embodiments N1 to N5, N7 to N29, N32, or N34 to N40, to said subject.

Embodiment N45

A method of treating addiction in a subject in need of said treatment, said method comprising administering an effective amount compound of one of embodiments N1 to N6, N11 to N31, N33, or N35 to N40, to said subject.

Embodiment N46

A method of treating a psychiatric disorder in a subject in need of said treatment, said method comprising administering an effective amount of a compound of one of embodiments N1 to N6, N11 to N31, N33, or N35 to N40, to said subject.

Embodiment N47

A method of modulating the activity of an opioid receptor protein, said method comprising contacting said opioid receptor protein with an effective amount of a compound of one of embodiments N1 to N40.

Embodiment N48

The method of embodiment N47, wherein said method does not comprise modulating arrestin function.

Embodiment N49

The compound of embodiment 1, wherein the compound is not

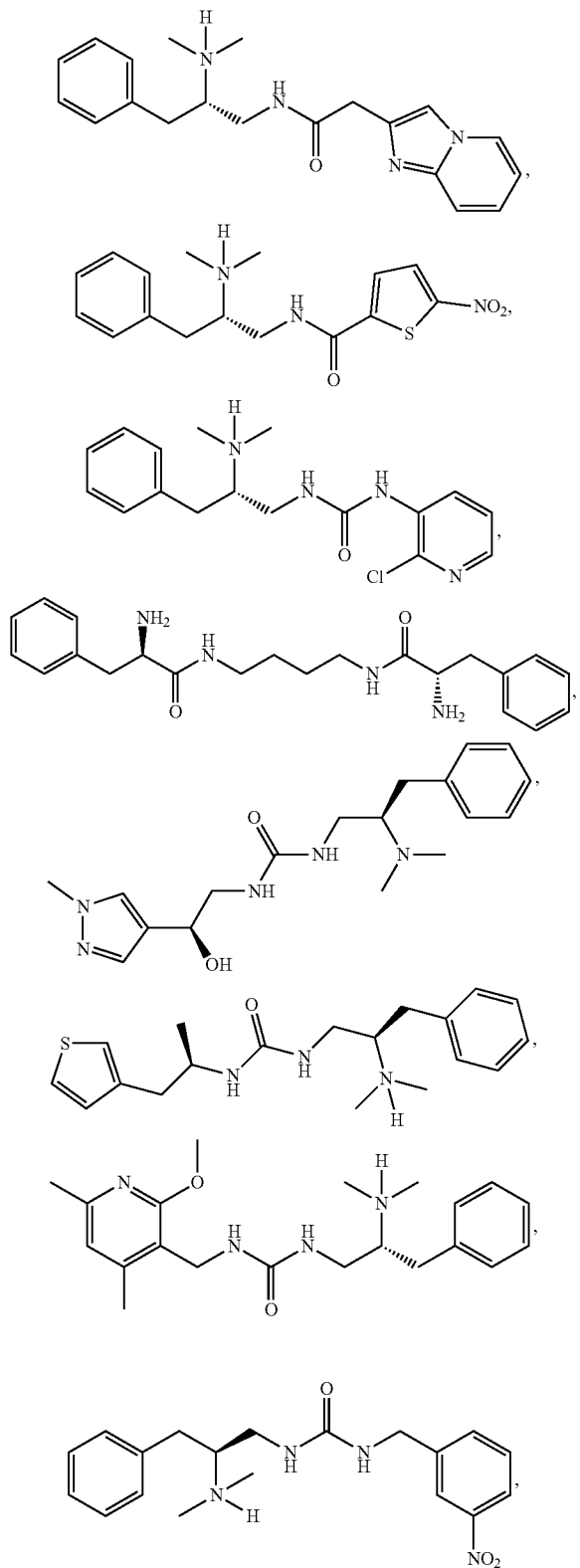

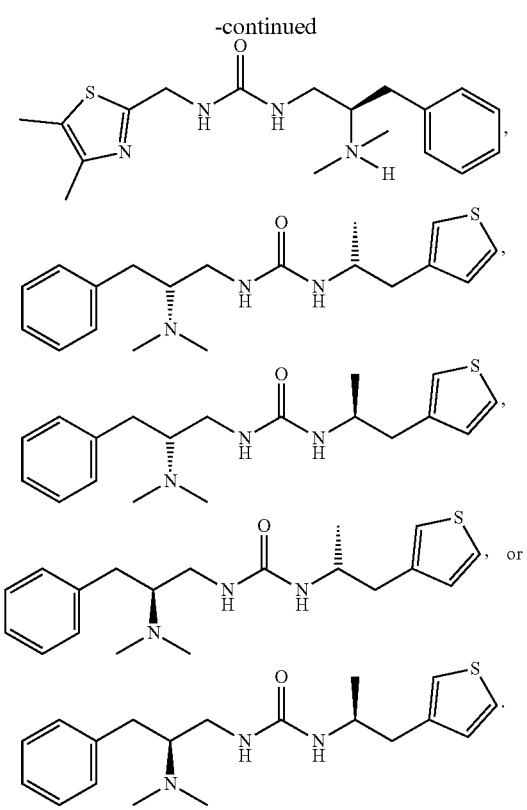

What is claimed is:
1. A compound having the formula:

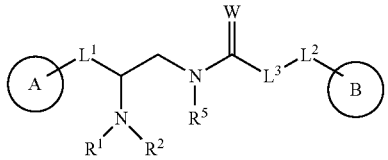

wherein,
W is O or S;
Ring A is independently R³-substituted or unsubstituted phenyl or R³-substituted or unsubstituted pyridinyl;
Ring B is independently R⁴-substituted or unsubstituted thienyl, R⁴-substituted or unsubstituted phenyl, R⁴-substituted or unsubstituted benzothienyl, R⁴-substituted or unsubstituted naphthyl, R⁴-substituted or unsubstituted benzofuranyl, R⁴-substituted or unsubstituted furanyl, R⁴-substituted or unsubstituted pyrrolyl-2,5-dione, or R⁴-substituted or unsubstituted 2,3-dihydro-1H-indenyl;
L¹ is independently a bond or an unsubstituted (C₁-C₅) alkylene;
L² is an unsubstituted (C₁-C₅) alkylene;
R¹ and R² are independently hydrogen, halogen, —CF₃, —CN, —OH, —NH₂, —COOH, —CONH₂, —NO₂, —SH, —SO₃H, —SO₄H, —SO2NH₂, —NHNH₂, —ONH₂, NHC═(O)NHNH₂, NHC═(O)NH₂, —NHSO₂H, —NHC═(O)H, —NHC(O)OH, —NHOH, —CHF₂, —CH₂F, —OCF₃, —OCHF₂, substituted or unsubstituted (C₁-C₅) alkyl, substituted or unsubstituted 2 to 5 membered heteroalkyl, substituted or unsubstituted (C₃-C₆) cycloalkyl, or substituted or unsubstituted 3 to 6 membered heterocycloalkyl; or $R^1$ and $R^2$ may optionally be joined to form a substituted or unsubstituted 3 to 6 membered heterocycloalkyl or substituted or unsubstituted 5 to 6 membered heteroaryl;

$L^1$ and $R^1$ may optionally be joined to form a substituted or unsubstituted 4 to 8 membered heterocycloalkyl;

$L^1$ and $R^2$ may optionally be joined to form a substituted or unsubstituted 4 to 8 membered heterocycloalkyl;

$L^3$ is —N($R^6$)—;

$R^3$ is independently hydrogen, —$CX_3$, $CHX_2$, $CH_2X$, —CN, —$SO_nR^{10}$, —$SO_vNR^7R^8$, —$NHNR^7R^8$, —$ONR^7R^8$, —NHC=(O)NHN$R^7R^8$, —NHC=(O)N$R^7R^8$, —N(O)$_m$, —$NR^7R^8$, —C(O)$R^9$, —C(O)—$OR^9$, —C(O)N$R^7R^8$, —$OR^{10}$, —$NR^7SO_2R^{10}$, —$NR_7$C=(O)$R^9$, —$NR^7$C(O)$OR^9$, —$NR^7OR^9$, —$CHX_2$, —$CH_2X$, —$OCX_3$, —$OCHX_2$, substituted or unsubstituted alkyl, unsubstituted heteroalkyl, unsubstituted cycloalkyl, unsubstituted heterocycloalkyl, unsubstituted aryl, or unsubstituted heteroaryl; or two adjacent $R^3$ substituents may optionally be joined to form an unsubstituted cycloalkyl, unsubstituted heterocycloalkyl, unsubstituted aryl, or unsubstituted heteroaryl;

$R^4$ is independently hydrogen, halogen, —$CX^a_3$, —CN, —$SO_{n1}R^{14}$, —$SO_{v1}NR^{11}R^{12}$, —$NHNR^{11}R^{12}$, —$ONR^{11}R^{12}$, —NHC=(O)NHN$R^{11}R^{12}$, —NHC=(O)N$R^{11}R^{12}$, —N(O)$_{m1}$, —$NR^{11}R^{12}$, —C(O)$R^{13}$, —C(O) —$OR^{13}$, α, —$OR^{14}$, —$NR^{11}SO_2R^{14}$, —$NR^{14}$C=(O)$R^{13}$, —$NR^{11}$C(O)$OR^{13}$, —$NR^{11}OR^{13}$, —$CHX^2$, —$CH_2X$, —$OCX_3$, —$OCHX_2$, oxo, substituted or unsubstituted alkyl, substituted or unsubstituted heteroalkyl, unsubstituted cycloalkyl, unsubstituted heterocycloalkyl, unsubstituted aryl, or unsubstituted heteroaryl; or two adjacent $R^4$ substituents may optionally be joined to form an unsubstituted cycloalkyl, unsubstituted heterocycloalkyl, unsubstituted aryl, or unsubstituted heteroaryl;

$R^5$ is independently hydrogen, —$CF_3$, —CN, —COOH, —$CONH_2$, —$CHF_2$, —$CH_2F$, substituted or unsubstituted ($C_1$-$C_5$) alkyl, or substituted or unsubstituted 2 to 5 membered heteroalkyl;

$R^6$ is hydrogen, —$CF_3$, —CN, —COOH, —$CONH_2$, —$CHF_2$, —$CH_2F$, substituted or unsubstituted ($C_1$-$C_5$) alkyl, or substituted or unsubstituted 2 to 5 membered heteroalkyl $R^{10}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NH$NH_2$, —NHC=(O)$NH_2$, —$NHSO_2H$, —NHC=(O)H, —NHC(O)OH, —NHOH, —$CHF_2$, —$CH_2F$, $OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or $R^7$ and $R^8$ substituents bonded to the same nitrogen atom may optionally be joined to form a substituted or unsubstituted heterocycloalkyl or substituted or unsubstituted heteroaryl;

$R^7$ and $R^8$ are independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NH$NH_2$—NHC=(O)$NH_2$, —$NHSO_2H$, —NHC=(O)H, —NHC(O)OH, —NHOH, —$CHF_2$, —$CH_2F$, $OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted heteroaryl, $R^9$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NH$NH_2$, —NHC=(O)$NH_2$, —$NHSO_2H$, —NHC=(O)H, —NHC(O)OH, —NHOH, —$CHF_2$, —$CH_2F$, $OCF_3$, —$OCHF_2$, substituted or unsubstituted alkyl, substituted or unsubstituted heteroalkyl, substituted or unsubstituted cycloalkyl, substituted or unsubstituted heterocycloalkyl, unsubstituted aryl, or substituted or unsubstituted heteroaryl;

$R^{11}$, $R^{12}$, $R^{13}$, and $R^{14}$ are independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NH$NH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl;

m, m1, v, and v1 are independently 1 or 2;

n and n1 are independently an integer from 0 to 4; and

X and $X^a$ are independently —Cl, —Br, —I, or —F.

2. The compound of claim 1, wherein Ring A is $R^3$-substituted or unsubstituted phenyl.

3. The compound of claim 1, wherein $R^3$ is independently hydrogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NH$NH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, substituted or unsubstituted ($C_1$-$C_5$) alkyl, or unsubstituted 2 to 5 membered heteroalkyl.

4. The compound of claim 1, having the formula:

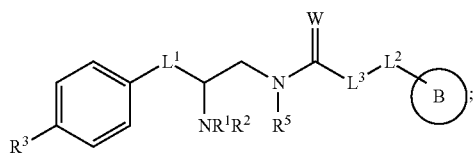

wherein $R^3$ is, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NH$NH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, or substituted or unsubstituted ($C_1$-$C_5$) alkyl, or unsubstituted 2 to 5 membered heteroalkyl.

5. The compound of claim 1, having the formula:

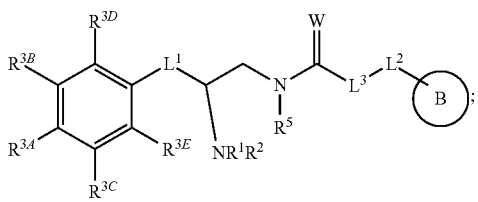

wherein $R^{3A}$, $R^{3B}$, and $R^{3C}$ are independently $CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, $OCF_3$, —$OCHF_2$, substituted or unsubstituted ($C_1$-$C_5$) alkyl, or unsubstituted 2 to 5 membered heteroalkyl;

$R^{3D}$ is hydrogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, substituted or unsubstituted ($C_1$-$C_5$) alkyl, or unsubstituted 2 to 5 membered heteroalkyl; and $R^{3E}$ is hydrogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, $OCF_3$, —$OCHF_2$, substituted or unsubstituted ($C_1$-$C_5$) alkyl, or unsubstituted 2 to 5 membered heteroalkyl.

6. The compound of claim 5, wherein $R^{3D}$ and $R^{3E}$ are independently unsubstituted ($C_1$-$C_3$) alkyl.

7. The compound of claim 5, wherein $R^{3D}$ and $R^{3E}$ are independently unsubstituted methyl.

8. The compound of claim 5, having the formula:

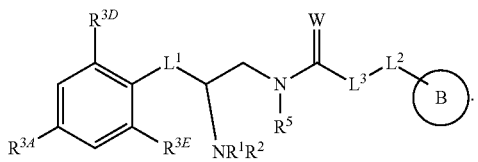

9. The compound of claim 1, wherein

Ring A is unsubstituted phenyl and Ring B is unsubstituted thienyl;

Ring A is para-hydroxy substituted phenyl and Ring B is unsubstituted thienyl;

Ring A is para-hydroxy substituted phenyl and Ring B is unsubstituted phenyl;

Ring A is para-hydroxy substituted phenyl and Ring B is unsubstituted benzothienyl;

Ring A is para-hydroxy substituted phenyl and Ring B is para-methyl substituted phenyl;

Ring A is 2-hydroxy pyridin-4-yl and Ring B is unsubstituted thienyl;

Ring A is 2-hydroxy pyridin-5-yl and Ring B is unsubstituted thienyl;

Ring A is para-hydroxy substituted phenyl and Ring B is unsubstituted napththyl; or Ring A is para-hydroxy substituted phenyl and Ring B is unsubstituted 2,3-dihydro-1H-indenyl.

10. The compound of claim 1, wherein Ring B is unsubstituted phenyl.

11. The compound of claim 1, wherein $R^1$ is unsubstituted ($C_1$-$C_2$) alkyl.

12. The compound of claim 1, wherein $R^1$ is independently hydrogen, substituted or unsubstituted ($C_1$-$C_5$) alkyl, substituted or unsubstituted 2 to 5 membered heteroalkyl, substituted or unsubstituted ($C_3$-$C_6$) cycloalkyl, or substituted or unsubstituted 3 to 6 membered heterocycloalkyl.

13. The compound of claim 1, wherein $R^2$ is unsubstituted ($C_1$-$C_2$) alkyl.

14. The compound of claim 1, wherein $R^2$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, substituted or unsubstituted ($C_1$-$C_5$) alkyl, substituted or unsubstituted 2 to 5 membered heteroalkyl, substituted or unsubstituted ($C_3$-$C_6$) cycloalkyl, or substituted or unsubstituted 3 to 6 membered heterocycloalkyl.

15. The compound of claim 1, wherein $R^5$ is hydrogen, substituted or unsubstituted ($C_1$-$C_5$) alkyl or substituted or unsubstituted 2 to 5 membered heteroalkyl.

16. The compound of claim 1, wherein W is O.

17. The compound of claim 1, wherein $R^6$ is hydrogen, substituted B or unsubstituted ($C_1$-$C_5$) alkyl or substituted or unsubstituted 2 to 5 membered heteroalkyl.

18. The compound of claim 1, wherein $L^2$ is unsubstituted ($C_1$-$C_3$) alkylene.

19. The compound of claim 1, having the formula:

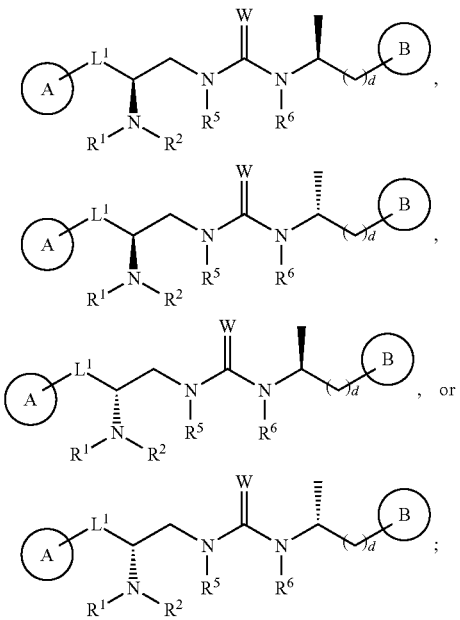

wherein d is an integer between 0 and 3.

20. The compound of claim 1, having the formula:

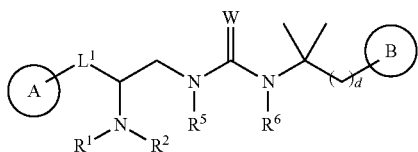

wherein d is an integer between 0 and 3.

21. The compound of claim 1, having the formula:

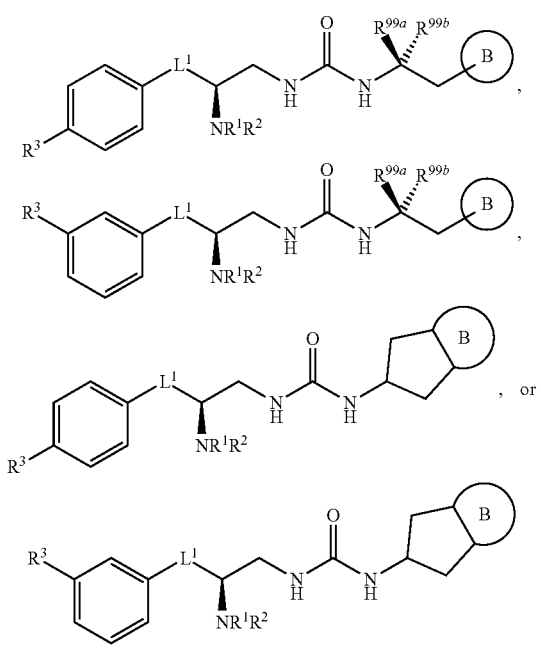

wherein:
Ring B is a substituted or unsubstituted phenyl or substituted or unsubstituted thienyl, substituted or unsubstituted benzothienyl, substituted or unsubstituted benzofuranyl, substituted or unsubstituted furanyl, substituted or unsubstituted pyrrolyl-2,5-dione, substituted or unsubstituted 2,3-dihydro-1H-indenyl, substituted or unsubstituted 1H-1,2,3-triazolyl, or substituted or unsubstituted pyrazolo[1,5-a]pyridinyl;
$R^3$ is —OH, or —NH$_2$;
$R^{99a}$ is substituted or unsubstituted (C$_1$-C$_3$) alkyl; and
$R^{99b}$ is hydrogen or substituted or unsubstituted (C$_1$-C$_3$) alkyl.

22. The compound of claim 21, wherein Ring B is an unsubstituted 3-thienyl.

23. The compound of claim 1, having the formula:

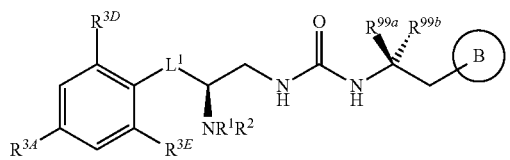

wherein:
Ring B is a substituted or unsubstituted phenyl or substituted or unsubstituted thienyl, substituted or unsubstituted benzothienyl, substituted or unsubstituted benzofuranyl, substituted or unsubstituted furanyl, substituted or unsubstituted pyrrolyl-2,5-dione, substituted or unsubstituted 2,3-dihydro-1H-indenyl, substituted or unsubstituted 1H-1,2,3-triazolyl, or substituted or unsubstituted pyrazolo[1,5-a]pyridinyl;

$R^{3A}$ is —OH, or —NH$_2$;
$R^{3D}$ is unsubstituted (C$_1$-C$_2$) alkyl;
$R^{3E}$ is unsubstituted (CL-C2) alkyl;
$R^{99a}$ is hydrogen or substituted or unsubstituted (C$_1$-C$_3$) alkyl; and
$R^{99b}$ is substituted or unsubstituted (C$_1$-C$_3$) alkyl.

24. The compound of claim 1, having the formula:

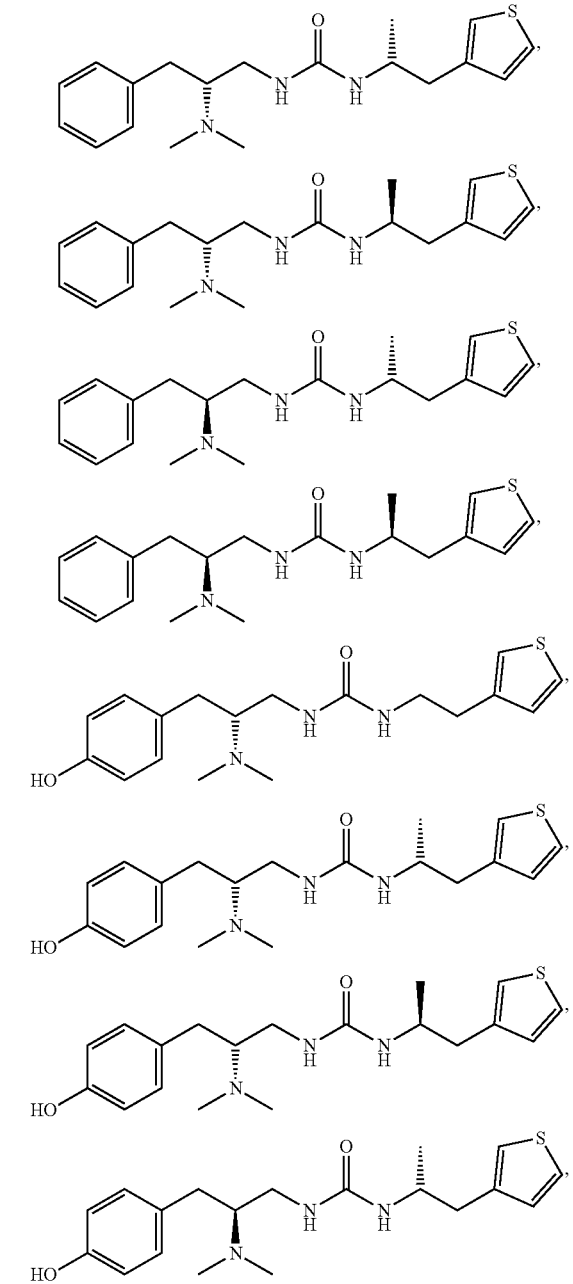

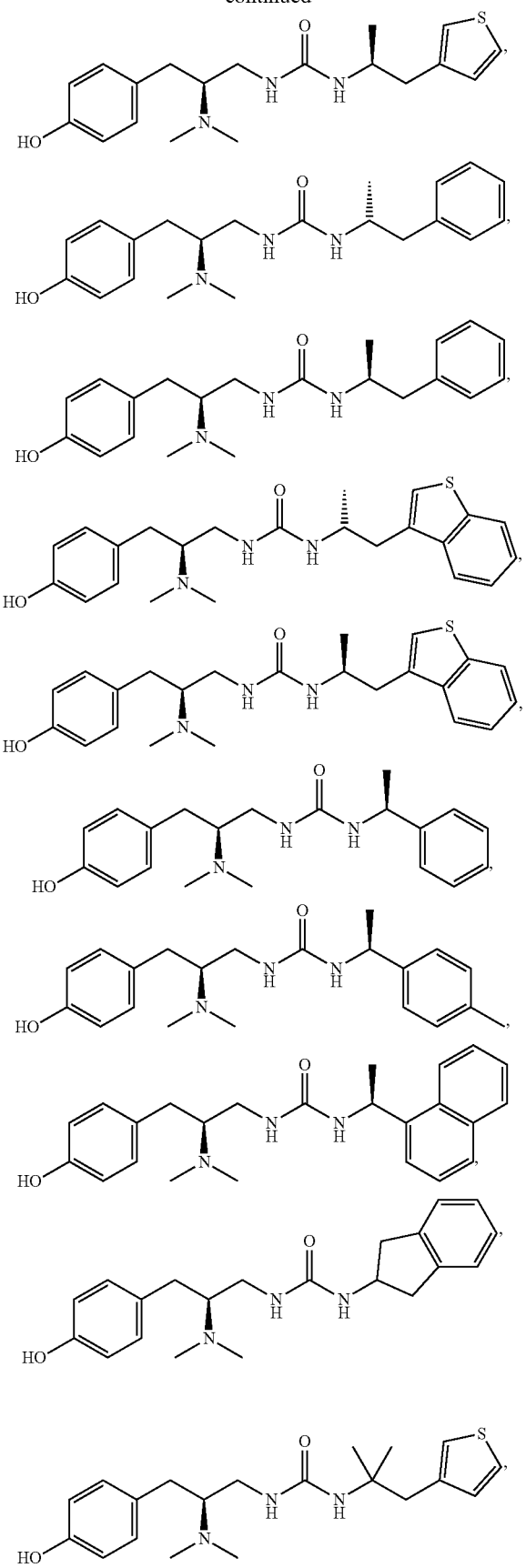
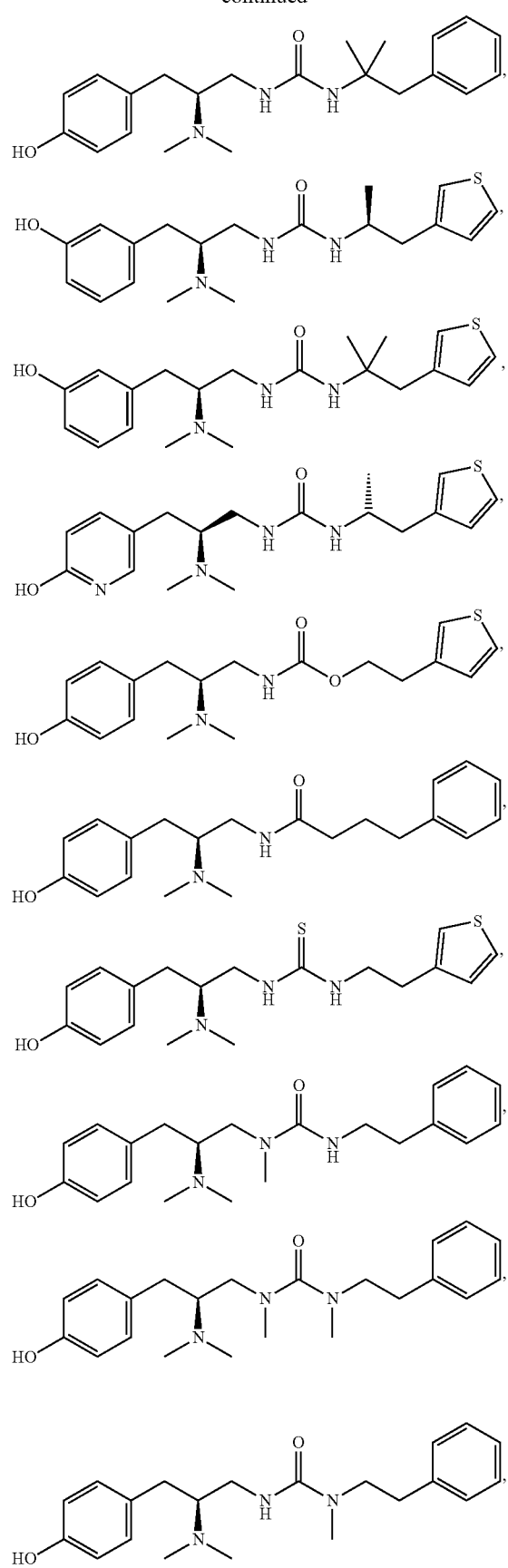

-continued

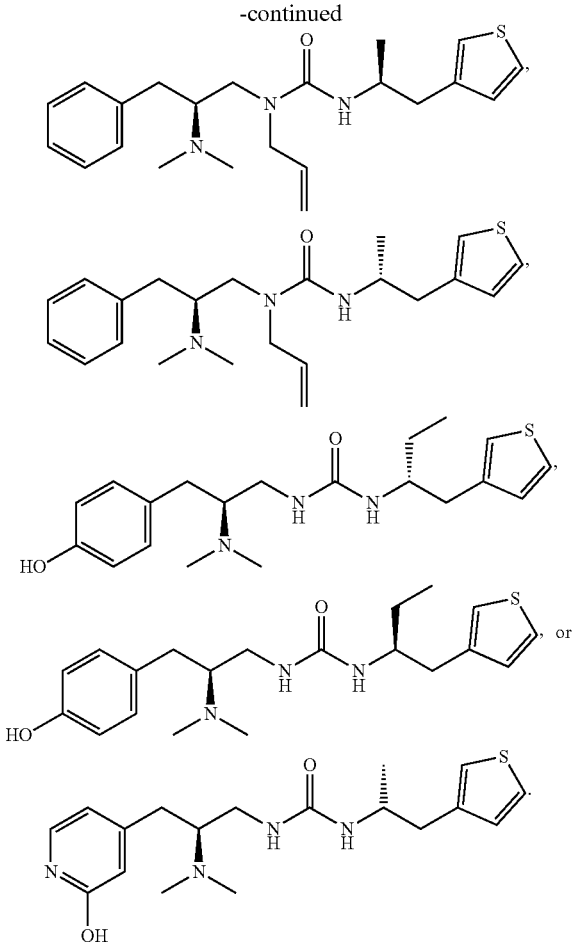

25. The compound of claim 1, having the formula:

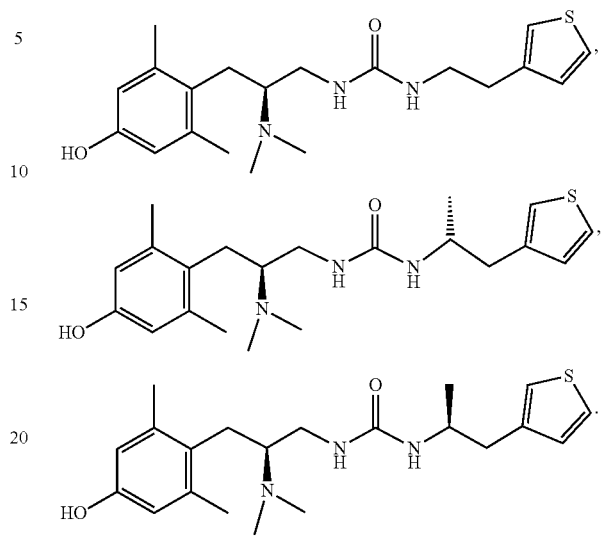

26. A compound of claim 1, having a higher binding affinity for the mu opioid receptor than for the kappa opioid receptor, wherein ring A is a substituted or unsubstituted phenyl.

27. A compound of claim 1, having a higher binding affinity for the mu opioid receptor than for the delta opioid receptor, wherein ring A is a substituted or unsubstituted phenyl.

28. A pharmaceutical composition comprising a pharmaceutically acceptable excipient and a compound of claim 1.

* * * * *

UNITED STATES PATENT AND TRADEMARK OFFICE
CERTIFICATE OF CORRECTION

PATENT NO. : 10,702,498 B2  
APPLICATION NO. : 15/743079  
DATED : July 7, 2020  
INVENTOR(S) : Brian K. Shoichet et al.

Page 1 of 1

It is certified that error appears in the above-identified patent and that said Letters Patent is hereby corrected as shown below:

In the Claims

Column 297, Line 28, Claim 1 the "$\alpha$" should be replaced with "-C(O)NR$^{11}$R$^{12}$" in the definition of R$^4$.

Signed and Sealed this  
Fifteenth Day of March, 2022

Drew Hirshfeld  
*Performing the Functions and Duties of the*  
*Under Secretary of Commerce for Intellectual Property and*  
*Director of the United States Patent and Trademark Office*